US007527952B2

(12) United States Patent
Wilson et al.

(10) Patent No.: US 7,527,952 B2
(45) Date of Patent: May 5, 2009

(54) **CRYSTALS OF INOSINE MONOPHOSPHATE DEHYDROGENASE/OXIDIZED INOSINE MONOPHOSPHATE THIOMIDATE INTERMEDIATE/MYCOPHENOLIC ACID (IIMPDH/XMP*/MPA)**

(75) Inventors: Keith P. Wilson, La Jolla, CA (US); Michael D. Sintchak, Winchester, MA (US); Mark Andrew Fleming, Winchester, MA (US); David M. Armistead, Sudbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/645,289

(22) Filed: Dec. 21, 2006

(65) Prior Publication Data

US 2007/0124083 A1  May 31, 2007

Related U.S. Application Data

(62) Division of application No. 09/678,016, filed on Oct. 2, 2000, now Pat. No. 7,216,041, which is a division of application No. 08/640,164, filed on Apr. 30, 1996, now Pat. No. 6,128,582.

(51) Int. Cl.
*C12P 21/06* (2006.01)
*C12N 9/04* (2006.01)
(52) U.S. Cl. ..................................... 435/190; 435/69.1
(58) Field of Classification Search ........................ None
See application file for complete search history.

(56) References Cited

U.S. PATENT DOCUMENTS

| 4,833,233 | A | 5/1989 | Carter |
| 5,353,236 | A | 10/1994 | Subbiah |
| 5,380,879 | A | 1/1995 | Sjogren |
| 5,444,072 | A | 8/1995 | Patterson et al. |
| 5,557,535 | A | 9/1996 | Srinivasan et al. |
| 5,932,600 | A | 8/1999 | Saunders et al. |
| 6,826,488 | B1 * | 11/2004 | Collart et al. ................. 702/27 |
| 7,083,961 | B1 * | 8/2006 | Luecke et al. ............... 435/189 |

FOREIGN PATENT DOCUMENTS

| WO | WO 90/01545 | 2/1990 |
| WO | WO 94/01105 | 1/1994 |
| WO | WO 94/12184 | 6/1994 |
| WO | WO 94/17185 | 8/1994 |
| WO | WO 94/25860 | 11/1994 |

OTHER PUBLICATIONS

Balbes et al., "A Perspective of Modern Methods in Computer-Aided Drug Design," *Reviews in Computational Chemistry*, K.B. Lipkowitz and D.B. Boyd, Eds., VCH Publishers, New York, 5:337-379 (1994).
Bartlett et al., "CAVEAT: A Program to Facilitate the Structure-Derived Design of Biologically Active Molecules," *Molecular Rec-*
*ognition in Chemical and Biological Problems*, S.M. Roberts, Ed., Royal Society of Chemistry, Special Publication No. 78:182-196 (1989).
Böhm, "The Computer Program LUDI: A New Method For The De Novo Design of Enzyme Inhibitors," *Journal of Computer-Aided Molecular Design*, 6:61-78 (1992).
Bryan, "Protein Engineering," *Biotech. Adv.*, 5:221-234 (1987).
Campbell et al., "Diffraction, in Biological Spectroscopy," The Benjamin/Cummings Publishing Company, Inc., Menlo Park, CA, pp. 299-326 (1984).
Cohen et al., "Molecular Modeling Software and Methods for Medicinal Chemistry," *Journal of Medicinal Chemistry*, 33(3):883-894 (1990).
Eisen et al., "HOOK: A Program for Finding Novel Molecular Architectures that Satisfy the Chemical and Steric Requirements of a Macromolecule Binding Site," *Proteins Struct. Funct. Genet.*, 19:199-221 (1994).
Gillet et al., "SPROUT: A Program for Structure Generation," *J. Comp. Aid. Molec. Design*, 7:127-153 (1993).
Goodford, "A Computational Procedure for Determining Energetically Favorable Binding Sites on Biologically Important Macromolecules," *J. Med. Chem.*, 28:849-857 (1985).
Goodsell et al., "Automated Docking of Substrates to Proteins by Simulated Annealing," *Proteins Struct. Funct. Genet.*, 8:195-202 (1990).
Gregory et al., "Treatment With Rapamycin and Mycophenolic Acid Reduces Arterial Intimal Thickening Produced by Mechanical Injury and Allows Endothelial Replacement," *Transplantation*, 59(5):655-661 (1995).
Guida, "Software for Structure-Based Drug Design," *Curr. Opin. Struct. Biology*, 4:777-781 (1994).
Hansch et al., "Comparison of the Inhibition of *Escherichia coli* and *Lactobacillus casei* Dihydrofolate Reductase by 2,4-diamino-5-(substituted-benzyl) pyrimidines; quantitative Structure-Activity Relationships, X-Ray Crystallography and Computer Graphics in Structure-Activity Analysis," *Chemical Abstracts*, 97:298f: 29 (1982); *Journal of Medicinal Chemistry*, 25:777-84 (1982).

(Continued)

*Primary Examiner*—Marianne P Allen
(74) *Attorney, Agent, or Firm*—Ropes & Gray LLP; James F. Haley, Jr.; Raymond M. Doss

(57) ABSTRACT

The present invention relates to a data storage medium encoded with the corresponding structure coordinates of molecules and molecular complexes which comprise the active site binding pockets of IMPDH. Such data storage material is capable of displaying such molecules and molecular complexes, or their structural homologues, as a graphical three-dimensional representation on a computer screen. This invention also relates to methods of using the structure coordinates to solve the structure of homologous proteins or protein complexes. In addition, this invention relates to methods of using the structure coordinates to screen and design compounds, including inhibitory compounds, that bind to IMPDH or homologues thereof. This invention also relates to molecules and molecular complexes which comprise the active site binding pockets of IMPDH or close structural homologues of the active site binding pockets. This invention also relates to compounds and pharmaceutical compositions which are inhibitors of IMPDH.

2 Claims, 118 Drawing Sheets

OTHER PUBLICATIONS

Huete-Pérez, et al., "Identification of the IMP Binding Site in the IMP Dehydrogenase From *Tritrichomonas foetus*," *Biochemistry*, 34:13889-13894 (1995).

Jancarik et al., "Sparse Matrix Sampling: A Screening Method for Crystallization of Proteins," *J. Appl. Cryst.*, 24:409-411 (1991).

Kajihara et al., "Protein Modelling Using a Chimera Reference Protein Derived From Exons," *Protein Eng.*, 6:615-620 (1993).

Kuntz et al., "A Geometric Approach to Macromolecule-Ligand Interactions," *J. Mol. Biol.*, 161:269-288 (1982).

Lauri et al., "CAVEAT: A Program to Facilitate the Design of Organic Molecules," *J. Comp. Aid. Molec. Design*, 8:51-66 (1994).

Li et al., "A comparison by QSAR Crystallography and Computer Graphics of the Inhibition of Various Dihydrofolate Reductases b 5-(x-benzyl)-2,4-diaminopyrimidines," *Chemical Abstracts*, 98:17257a:28 (1983); *Quantitative Structure Activity Relationships Pharmacol. Chem. Bil.*, 1:1-7 (1982).

Makara et al., "Nuclear Magnetic Resonance and Molecular Modeling Study on Mycophenolic Acid: Implications for Binding to Inosine Monophosphate Dehydrogenase," *J. Med. Chem.*, 39:1236-1242 (1996).

Martin, "3D Database Searching In Drug Design," *Journal of Medicinal Chemistry*, 35(12):2145-54 (1992).

Miranker et al., M., "Functionality Maps of Binding Sites: A Multiple Copy Simultaneous Search Method," *Proteins Struct. Funct. Genet.*, 11:29-34 (1991).

Meng et al., "Automated Docking with Grid-Based Energy Evaluation," *Journal of Computational Chemistry*, 13:505-524 (1992).

Montero et al., "Demonstration of Induction of Erythrocyte Inosine Monophospate Dehydrogenase Activity in Ribavirin-Treated Patients Using a High Performance Liquid Chromatography Linked Method," *Clinica Chimica Acta*, 238:169-178 (1995).

Moon et al., "Computer Design of Bioactive Molecules: A method for Receptor-Based De Novo Ligand Design," *Proteins, Structure, Functions, and Genetics*, 11:314-328 (1991).

Morris, "New Small Molecule Immunosuppressants for Transplantation: Review of Essential Concepts," *The Journal of Heart and Lung Transplantation*, 12:S275-S286 (1993).

Musil et al., "The Refined 2.15 Å X-Ray Crystal Structure of Human Liver Cathepsin B: the Structural Basis for its Specificity," *EMBO J.*, 10(9):2321-2330 (1991).

Navia et al., "Use of Structural Information in Drug Design," *Current Opinion in Structural Biology*, 2:202-210 (1992).

Nishibata et al., "Automatic Creation of Drug Candidate Structures Based on Receptor Structure. Starting Point for Artificial Lead Generation," *Tetrahedron*, 47:8985-8990 (1991).

Russell et al., "Rational Modification of Enzyme Catalysis by Engineering Surface Charge," *Nature*, 328:496-500 (1987).

Sielecki et al., "Structure of Recombinant Human Renin, a Target for Cardiovascular-Active Drugs, at 2.5 Å Resolution," *Science*, 243:1346-1351 (1989).

Sintchak et al., "Structure and Mechanism of Inosine Monophosphate Dehydrogenase in Complex with the Immunosuppressant Mycophenolic Acid," *Cell*, 85:921-930 (1996).

Uhlin et al., "Crystallization and Crystallographic Investigations of Ribonucleotide Reductase Protein R1 From *Escherichia coli*," *FEBS Lett.*, 336(1):148-152 (1993).

Whitby et al., "Preliminary X-Ray Crystallographic Analysis of Tritrichomonas foetus Inosine-5'-Monophosphate Dehydrogenase," *Proteins: Structure, Function, and Genetics*, 23:598-603 (1995).

Wright et al., "Structure of Subtilisin BPN' at 2.5 Å Resolution," *Nature*, 221:235-242 (1969).

* cited by examiner

FIG. 1A-1

IMPDH COORDINATES

| | | Atom Type | Residue | # | X | Y | Z | OCC | B |
|---|---|---|---|---|---|---|---|---|---|
| ATOM | 1 | CB | ALA | 17 | 72.558 | 49.267 | 65.109 | 1.00 | 22.70 |
| ATOM | 2 | C | ALA | 17 | 71.313 | 51.476 | 65.238 | 1.00 | 26.93 |
| ATOM | 3 | O | ALA | 17 | 70.825 | 51.262 | 64.127 | 1.00 | 29.36 |
| ATOM | 4 | N | ALA | 17 | 71.028 | 49.819 | 66.975 | 1.00 | 26.46 |
| ATOM | 5 | CA | ALA | 17 | 72.022 | 50.375 | 66.030 | 1.00 | 26.18 |
| ATOM | 6 | N | LEU | 18 | 71.234 | 52.650 | 65.852 | 1.00 | 25.12 |
| ATOM | 7 | CA | LEU | 18 | 70.583 | 53.798 | 65.245 | 1.00 | 23.77 |
| ATOM | 8 | CB | LEU | 18 | 69.314 | 54.098 | 66.036 | 1.00 | 24.11 |
| ATOM | 9 | CG | LEU | 18 | 68.112 | 54.653 | 65.285 | 1.00 | 25.97 |
| ATOM | 10 | CD1 | LEU | 18 | 67.670 | 53.647 | 64.234 | 1.00 | 20.03 |
| ATOM | 11 | CD2 | LEU | 18 | 66.998 | 54.949 | 66.278 | 1.00 | 24.01 |
| ATOM | 12 | C | LEU | 18 | 71.549 | 54.973 | 65.364 | 1.00 | 22.96 |
| ATOM | 13 | O | LEU | 18 | 72.234 | 55.092 | 66.376 | 1.00 | 24.55 |
| ATOM | 14 | N | THR | 19 | 71.657 | 55.805 | 64.334 | 1.00 | 20.50 |
| ATOM | 15 | CA | THR | 19 | 72.555 | 56.953 | 64.418 | 1.00 | 19.77 |
| ATOM | 16 | CB | THR | 19 | 73.040 | 57.451 | 63.032 | 1.00 | 19.66 |
| ATOM | 17 | OG1 | THR | 19 | 71.942 | 57.976 | 62.285 | 1.00 | 24.22 |
| ATOM | 18 | CG2 | THR | 19 | 73.681 | 56.329 | 62.254 | 1.00 | 21.13 |
| ATOM | 19 | C | THR | 19 | 71.856 | 58.108 | 65.118 | 1.00 | 20.76 |
| ATOM | 20 | O | THR | 19 | 70.625 | 58.138 | 65.196 | 1.00 | 23.20 |
| ATOM | 21 | N | ALA | 20 | 72.644 | 59.064 | 65.604 | 1.00 | 20.04 |
| ATOM | 22 | CA | ALA | 20 | 72.129 | 60.244 | 66.286 | 1.00 | 17.52 |
| ATOM | 23 | CB | ALA | 20 | 73.277 | 61.136 | 66.727 | 1.00 | 16.35 |
| ATOM | 24 | C | ALA | 20 | 71.188 | 61.011 | 65.370 | 1.00 | 17.21 |
| ATOM | 25 | O | ALA | 20 | 70.121 | 61.445 | 65.789 | 1.00 | 18.45 |
| ATOM | 26 | N | GLN | 21 | 71.586 | 61.168 | 64.114 | 1.00 | 18.11 |
| ATOM | 27 | CA | GLN | 21 | 70.768 | 61.865 | 63.132 | 1.00 | 17.57 |
| ATOM | 28 | CB | GLN | 21 | 71.445 | 61.795 | 61.759 | 1.00 | 19.03 |
| ATOM | 29 | CG | GLN | 21 | 70.925 | 62.768 | 60.699 | 1.00 | 23.41 |
| ATOM | 30 | CD | GLN | 21 | 69.630 | 62.324 | 60.040 | 1.00 | 31.00 |
| ATOM | 31 | OE1 | GLN | 21 | 69.245 | 61.155 | 60.105 | 1.00 | 34.26 |
| ATOM | 32 | NE2 | GLN | 21 | 68.957 | 63.260 | 59.381 | 1.00 | 36.22 |
| ATOM | 33 | C | GLN | 21 | 69.383 | 61.210 | 63.093 | 1.00 | 17.94 |
| ATOM | 34 | O | GLN | 21 | 68.374 | 61.895 | 63.181 | 1.00 | 20.56 |
| ATOM | 35 | N | GLN | 22 | 69.340 | 59.883 | 63.025 | 1.00 | 15.31 |
| ATOM | 36 | CA | GLN | 22 | 68.072 | 59.155 | 62.976 | 1.00 | 14.95 |
| ATOM | 37 | CB | GLN | 22 | 68.316 | 57.682 | 62.671 | 1.00 | 14.56 |
| ATOM | 38 | CG | GLN | 22 | 68.906 | 57.446 | 61.307 | 1.00 | 19.65 |
| ATOM | 39 | CD | GLN | 22 | 69.475 | 56.058 | 61.166 | 1.00 | 28.31 |
| ATOM | 40 | OE1 | GLN | 22 | 69.911 | 55.447 | 62.146 | 1.00 | 29.91 |
| ATOM | 41 | NE2 | GLN | 22 | 69.499 | 55.554 | 59.939 | 1.00 | 34.86 |
| ATOM | 42 | C | GLN | 22 | 67.284 | 59.251 | 64.265 | 1.00 | 14.40 |
| ATOM | 43 | O | GLN | 22 | 66.104 | 59.559 | 64.260 | 1.00 | 17.28 |
| ATOM | 44 | N | LEU | 23 | 67.961 | 58.997 | 65.369 | 1.00 | 13.72 |
| ATOM | 45 | CA | LEU | 23 | 67.360 | 59.019 | 66.686 | 1.00 | 13.86 |
| ATOM | 46 | CB | LEU | 23 | 68.430 | 58.644 | 67.719 | 1.00 | 10.46 |
| ATOM | 47 | CG | LEU | 23 | 68.090 | 58.588 | 69.210 | 1.00 | 10.45 |
| ATOM | 48 | CD1 | LEU | 23 | 67.222 | 57.399 | 69.478 | 1.00 | 13.28 |
| ATOM | 49 | CD2 | LEU | 23 | 69.354 | 58.489 | 70.036 | 1.00 | 9.21 |
| ATOM | 50 | C | LEU | 23 | 66.698 | 60.343 | 67.072 | 1.00 | 17.33 |
| ATOM | 51 | O | LEU | 23 | 65.552 | 60.353 | 67.517 | 1.00 | 17.38 |
| ATOM | 52 | N | PHE | 24 | 67.417 | 61.454 | 66.894 | 1.00 | 22.11 |
| ATOM | 53 | CA | PHE | 24 | 66.926 | 62.781 | 67.282 | 1.00 | 23.93 |
| ATOM | 54 | CB | PHE | 24 | 68.060 | 63.626 | 67.870 | 1.00 | 18.72 |
| ATOM | 55 | CG | PHE | 24 | 68.688 | 63.017 | 69.084 | 1.00 | 18.19 |
| ATOM | 56 | CD1 | PHE | 24 | 68.056 | 63.098 | 70.321 | 1.00 | 16.51 |

FIG. 1A-2

| | | | | | | | | |
|---|---|---|---|---|---|---|---|---|
| ATOM | 57 | CD2 | PHE | 24 | 69.849 | 62.270 | 68.975 | 1.00 | 16.34 |
| ATOM | 58 | CE1 | PHE | 24 | 68.573 | 62.445 | 71.422 | 1.00 | 16.81 |
| ATOM | 59 | CE2 | PHE | 24 | 70.373 | 61.614 | 70.070 | 1.00 | 17.36 |
| ATOM | 60 | CZ | PHE | 24 | 69.732 | 61.695 | 71.295 | 1.00 | 20.29 |
| ATOM | 61 | C | PHE | 24 | 66.228 | 63.569 | 66.212 | 1.00 | 28.47 |
| ATOM | 62 | O | PHE | 24 | 66.123 | 64.788 | 66.308 | 1.00 | 30.83 |
| ATOM | 63 | N | ASN | 25 | 65.728 | 62.886 | 65.197 | 1.00 | 31.66 |
| ATOM | 64 | CA | ASN | 25 | 65.039 | 63.585 | 64.130 | 1.00 | 35.39 |
| ATOM | 65 | CB | ASN | 25 | 65.970 | 63.788 | 62.926 | 1.00 | 37.11 |
| ATOM | 66 | CG | ASN | 25 | 66.984 | 64.917 | 63.156 | 1.00 | 32.50 |
| ATOM | 67 | OD1 | ASN | 25 | 66.630 | 66.090 | 63.117 | 1.00 | 34.46 |
| ATOM | 68 | ND2 | ASN | 25 | 68.235 | 64.562 | 63.402 | 1.00 | 24.11 |
| ATOM | 69 | C | ASN | 25 | 63.752 | 62.868 | 63.767 | 1.00 | 37.00 |
| ATOM | 70 | O | ASN | 25 | 63.416 | 62.689 | 62.593 | 1.00 | 37.37 |
| ATOM | 71 | N | CYS | 26 | 63.053 | 62.447 | 64.821 | 1.00 | 38.09 |
| ATOM | 72 | CA | CYS | 26 | 61.768 | 61.759 | 64.725 | 1.00 | 39.40 |
| ATOM | 73 | CB | CYS | 26 | 61.902 | 60.316 | 65.197 | 1.00 | 41.92 |
| ATOM | 74 | SG | CYS | 26 | 63.069 | 59.371 | 64.233 | 1.00 | 54.81 |
| ATOM | 75 | C | CYS | 26 | 60.701 | 62.474 | 65.566 | 1.00 | 39.10 |
| ATOM | 76 | O | CYS | 26 | 59.562 | 62.020 | 65.636 | 1.00 | 40.50 |
| ATOM | 77 | N | GLY | 27 | 61.092 | 63.563 | 66.232 | 1.00 | 37.42 |
| ATOM | 78 | CA | GLY | 27 | 60.169 | 64.345 | 67.044 | 1.00 | 34.99 |
| ATOM | 79 | C | GLY | 27 | 59.622 | 63.721 | 68.319 | 1.00 | 33.08 |
| ATOM | 80 | O | GLY | 27 | 58.602 | 64.171 | 68.843 | 1.00 | 33.66 |
| ATOM | 81 | N | ASP | 28 | 60.324 | 62.731 | 68.857 | 1.00 | 29.48 |
| ATOM | 82 | CA | ASP | 28 | 59.872 | 62.053 | 70.061 | 1.00 | 26.13 |
| ATOM | 83 | CB | ASP | 28 | 60.518 | 60.669 | 70.156 | 1.00 | 31.57 |
| ATOM | 84 | CG | ASP | 28 | 60.062 | 59.717 | 69.058 | 1.00 | 37.50 |
| ATOM | 85 | OD1 | ASP | 28 | 59.113 | 60.055 | 68.313 | 1.00 | 42.70 |
| ATOM | 86 | OD2 | ASP | 28 | 60.651 | 58.615 | 68.949 | 1.00 | 40.12 |
| ATOM | 87 | C | ASP | 28 | 60.107 | 62.803 | 71.368 | 1.00 | 24.31 |
| ATOM | 88 | O | ASP | 28 | 59.607 | 62.382 | 72.405 | 1.00 | 26.33 |
| ATOM | 89 | N | GLY | 29 | 60.879 | 63.885 | 71.340 | 1.00 | 20.96 |
| ATOM | 90 | CA | GLY | 29 | 61.152 | 64.622 | 72.564 | 1.00 | 17.97 |
| ATOM | 91 | C | GLY | 29 | 61.908 | 63.793 | 73.597 | 1.00 | 19.01 |
| ATOM | 92 | O | GLY | 29 | 61.468 | 63.660 | 74.748 | 1.00 | 21.20 |
| ATOM | 93 | N | LEU | 30 | 63.065 | 63.261 | 73.197 | 1.00 | 17.09 |
| ATOM | 94 | CA | LEU | 30 | 63.892 | 62.416 | 74.057 | 1.00 | 12.60 |
| ATOM | 95 | CB | LEU | 30 | 64.817 | 61.547 | 73.212 | 1.00 | 9.93 |
| ATOM | 96 | CG | LEU | 30 | 64.233 | 60.723 | 72.068 | 1.00 | 10.94 |
| ATOM | 97 | CD1 | LEU | 30 | 65.388 | 60.127 | 71.284 | 1.00 | 9.88 |
| ATOM | 98 | CD2 | LEU | 30 | 63.302 | 59.628 | 72.598 | 1.00 | 11.80 |
| ATOM | 99 | C | LEU | 30 | 64.762 | 63.194 | 75.021 | 1.00 | 13.15 |
| ATOM | 100 | O | LEU | 30 | 65.039 | 64.376 | 74.824 | 1.00 | 12.25 |
| ATOM | 101 | N | THR | 31 | 65.290 | 62.474 | 75.998 | 1.00 | 12.92 |
| ATOM | 102 | CA | THR | 31 | 66.164 | 63.037 | 77.006 | 1.00 | 16.46 |
| ATOM | 103 | CB | THR | 31 | 65.392 | 63.352 | 78.279 | 1.00 | 22.29 |
| ATOM | 104 | OG1 | THR | 31 | 64.263 | 64.164 | 77.961 | 1.00 | 33.50 |
| ATOM | 105 | CG2 | THR | 31 | 66.253 | 64.121 | 79.219 | 1.00 | 25.29 |
| ATOM | 106 | C | THR | 31 | 67.204 | 61.969 | 77.318 | 1.00 | 16.75 |
| ATOM | 107 | O | THR | 31 | 67.076 | 60.831 | 76.863 | 1.00 | 18.24 |
| ATOM | 108 | N | TYR | 32 | 68.207 | 62.328 | 78.113 | 1.00 | 14.54 |
| ATOM | 109 | CA | TYR | 32 | 69.281 | 61.418 | 78.493 | 1.00 | 13.73 |
| ATOM | 110 | CB | TYR | 32 | 70.114 | 62.029 | 79.623 | 1.00 | 14.15 |
| ATOM | 111 | CG | TYR | 32 | 70.778 | 63.348 | 79.275 | 1.00 | 13.25 |
| ATOM | 112 | CD1 | TYR | 32 | 71.485 | 63.498 | 78.087 | 1.00 | 11.60 |
| ATOM | 113 | CE1 | TYR | 32 | 72.102 | 64.696 | 77.770 | 1.00 | 11.18 |
| ATOM | 114 | CD2 | TYR | 32 | 70.708 | 64.443 | 80.143 | 1.00 | 9.67 |
| ATOM | 115 | CE2 | TYR | 32 | 71.323 | 65.641 | 79.831 | 1.00 | 5.87 |

FIG. 1A-3

| ATOM | 116 | CZ | TYR | 32 | 72.020 | 65.759 | 78.645 | 1.00 | 9.04 |
| --- | --- | --- | --- | --- | --- | --- | --- | --- | --- |
| ATOM | 117 | OH | TYR | 32 | 72.646 | 66.936 | 78.322 | 1.00 | 12.17 |
| ATOM | 118 | C | TYR | 32 | 68.836 | 60.014 | 78.895 | 1.00 | 14.12 |
| ATOM | 119 | O | TYR | 32 | 69.377 | 59.028 | 78.412 | 1.00 | 15.71 |
| ATOM | 120 | N | ASN | 33 | 67.844 | 59.919 | 79.770 | 1.00 | 13.11 |
| ATOM | 121 | CA | ASN | 33 | 67.371 | 58.614 | 80.217 | 1.00 | 11.54 |
| ATOM | 122 | CB | ASN | 33 | 66.496 | 58.768 | 81.462 | 1.00 | 11.83 |
| ATOM | 123 | CG | ASN | 33 | 67.311 | 59.056 | 82.713 | 1.00 | 17.66 |
| ATOM | 124 | OD1 | ASN | 33 | 68.541 | 59.127 | 82.665 | 1.00 | 23.03 |
| ATOM | 125 | ND2 | ASN | 33 | 66.634 | 59.216 | 83.840 | 1.00 | 20.22 |
| ATOM | 126 | C | ASN | 33 | 66.628 | 57.803 | 79.162 | 1.00 | 9.67 |
| ATOM | 127 | O | ASN | 33 | 66.382 | 56.632 | 79.359 | 1.00 | 11.34 |
| ATOM | 128 | N | ASP | 34 | 66.314 | 58.411 | 78.027 | 1.00 | 10.31 |
| ATOM | 129 | CA | ASP | 34 | 65.565 | 57.730 | 76.980 | 1.00 | 9.62 |
| ATOM | 130 | CB | ASP | 34 | 64.693 | 58.723 | 76.202 | 1.00 | 7.60 |
| ATOM | 131 | CG | ASP | 34 | 63.702 | 59.452 | 77.080 | 1.00 | 10.75 |
| ATOM | 132 | OD1 | ASP | 34 | 62.884 | 58.790 | 77.743 | 1.00 | 16.59 |
| ATOM | 133 | OD2 | ASP | 34 | 63.728 | 60.695 | 77.105 | 1.00 | 16.20 |
| ATOM | 134 | C | ASP | 34 | 66.410 | 56.951 | 75.996 | 1.00 | 10.82 |
| ATOM | 135 | O | ASP | 34 | 65.857 | 56.330 | 75.088 | 1.00 | 12.67 |
| ATOM | 136 | N | PHE | 35 | 67.732 | 56.997 | 76.119 | 1.00 | 10.03 |
| ATOM | 137 | CA | PHE | 35 | 68.566 | 56.251 | 75.180 | 1.00 | 11.20 |
| ATOM | 138 | CB | PHE | 35 | 68.809 | 57.065 | 73.905 | 1.00 | 8.60 |
| ATOM | 139 | CG | PHE | 35 | 69.723 | 58.235 | 74.093 | 1.00 | 5.90 |
| ATOM | 140 | CD1 | PHE | 35 | 69.222 | 59.467 | 74.457 | 1.00 | 2.20 |
| ATOM | 141 | CD2 | PHE | 35 | 71.095 | 58.094 | 73.916 | 1.00 | 9.58 |
| ATOM | 142 | CE1 | PHE | 35 | 70.059 | 60.547 | 74.628 | 1.00 | 5.47 |
| ATOM | 143 | CE2 | PHE | 35 | 71.944 | 59.166 | 74.085 | 1.00 | 8.35 |
| ATOM | 144 | CZ | PHE | 35 | 71.423 | 60.399 | 74.450 | 1.00 | 10.50 |
| ATOM | 145 | C | PHE | 35 | 69.892 | 55.758 | 75.748 | 1.00 | 12.61 |
| ATOM | 146 | O | PHE | 35 | 70.284 | 56.119 | 76.859 | 1.00 | 13.92 |
| ATOM | 147 | N | LEU | 36 | 70.568 | 54.917 | 74.972 | 1.00 | 14.59 |
| ATOM | 148 | CA | LEU | 36 | 71.863 | 54.348 | 75.346 | 1.00 | 14.60 |
| ATOM | 149 | CB | LEU | 36 | 71.712 | 52.852 | 75.647 | 1.00 | 15.42 |
| ATOM | 150 | CG | LEU | 36 | 71.050 | 52.471 | 76.958 | 1.00 | 15.98 |
| ATOM | 151 | CD1 | LEU | 36 | 70.772 | 50.996 | 76.982 | 1.00 | 12.63 |
| ATOM | 152 | CD2 | LEU | 36 | 71.943 | 52.880 | 78.105 | 1.00 | 19.66 |
| ATOM | 153 | C | LEU | 36 | 72.825 | 54.475 | 74.183 | 1.00 | 13.79 |
| ATOM | 154 | O | LEU | 36 | 72.402 | 54.693 | 73.046 | 1.00 | 15.53 |
| ATOM | 155 | N | ILE | 37 | 74.117 | 54.370 | 74.468 | 1.00 | 13.37 |
| ATOM | 156 | CA | ILE | 37 | 75.114 | 54.398 | 73.412 | 1.00 | 11.78 |
| ATOM | 157 | CB | ILE | 37 | 76.301 | 55.330 | 73.708 | 1.00 | 12.62 |
| ATOM | 158 | CG2 | ILE | 37 | 77.117 | 55.521 | 72.432 | 1.00 | 9.76 |
| ATOM | 159 | CG1 | ILE | 37 | 75.818 | 56.695 | 74.204 | 1.00 | 9.90 |
| ATOM | 160 | CD1 | ILE | 37 | 76.942 | 57.594 | 74.695 | 1.00 | 3.11 |
| ATOM | 161 | C | ILE | 37 | 75.616 | 52.963 | 73.403 | 1.00 | 11.63 |
| ATOM | 162 | O | ILE | 37 | 75.927 | 52.406 | 74.464 | 1.00 | 9.34 |
| ATOM | 163 | N | LEU | 38 | 75.605 | 52.347 | 72.225 | 1.00 | 12.19 |
| ATOM | 164 | CA | LEU | 38 | 76.048 | 50.964 | 72.067 | 1.00 | 12.98 |
| ATOM | 165 | CB | LEU | 38 | 75.474 | 50.372 | 70.778 | 1.00 | 12.87 |
| ATOM | 166 | CG | LEU | 38 | 74.129 | 49.627 | 70.830 | 1.00 | 9.25 |
| ATOM | 167 | CD1 | LEU | 38 | 73.238 | 50.120 | 71.943 | 1.00 | 7.47 |
| ATOM | 168 | CD2 | LEU | 38 | 73.445 | 49.763 | 69.494 | 1.00 | 3.33 |
| ATOM | 169 | C | LEU | 38 | 77.572 | 50.880 | 72.067 | 1.00 | 16.00 |
| ATOM | 170 | O | LEU | 38 | 78.244 | 51.672 | 71.402 | 1.00 | 18.83 |
| ATOM | 171 | N | PRO | 39 | 78.134 | 49.894 | 72.803 | 1.00 | 14.92 |
| ATOM | 172 | CD | PRO | 39 | 77.416 | 48.835 | 73.528 | 1.00 | 16.09 |
| ATOM | 173 | CA | PRO | 39 | 79.578 | 49.702 | 72.899 | 1.00 | 14.01 |
| ATOM | 174 | CB | PRO | 39 | 79.688 | 48.579 | 73.928 | 1.00 | 14.77 |

FIG. 1A-4

| | | | | | | | | |
|---|---|---|---|---|---|---|---|---|
| ATOM | 175 | CG | PRO | 39 | 78.470 | 47.778 | 73.672 | 1.00 | 16.81 |
| ATOM | 176 | C | PRO | 39 | 80.247 | 49.339 | 71.574 | 1.00 | 15.63 |
| ATOM | 177 | O | PRO | 39 | 79.639 | 48.687 | 70.713 | 1.00 | 15.28 |
| ATOM | 178 | N | GLY | 40 | 81.513 | 49.736 | 71.439 | 1.00 | 14.98 |
| ATOM | 179 | CA | GLY | 40 | 82.262 | 49.470 | 70.230 | 1.00 | 12.21 |
| ATOM | 180 | C | GLY | 40 | 83.409 | 48.495 | 70.399 | 1.00 | 13.01 |
| ATOM | 181 | O | GLY | 40 | 83.224 | 47.389 | 70.919 | 1.00 | 12.38 |
| ATOM | 182 | N | TYR | 41 | 84.583 | 48.892 | 69.904 | 1.00 | 13.42 |
| ATOM | 183 | CA | TYR | 41 | 85.794 | 48.077 | 69.957 | 1.00 | 13.37 |
| ATOM | 184 | CB | TYR | 41 | 86.353 | 47.862 | 68.551 | 1.00 | 13.51 |
| ATOM | 185 | CG | TYR | 41 | 87.638 | 47.069 | 68.546 | 1.00 | 21.45 |
| ATOM | 186 | CD1 | TYR | 41 | 87.680 | 45.770 | 69.050 | 1.00 | 24.36 |
| ATOM | 187 | CE1 | TYR | 41 | 88.863 | 45.046 | 69.069 | 1.00 | 28.32 |
| ATOM | 188 | CD2 | TYR | 41 | 88.818 | 47.625 | 68.064 | 1.00 | 26.04 |
| ATOM | 189 | CE2 | TYR | 41 | 90.013 | 46.910 | 68.082 | 1.00 | 25.88 |
| ATOM | 190 | CZ | TYR | 41 | 90.029 | 45.623 | 68.585 | 1.00 | 27.54 |
| ATOM | 191 | OH | TYR | 41 | 91.211 | 44.917 | 68.607 | 1.00 | 29.43 |
| ATOM | 192 | C | TYR | 41 | 86.861 | 48.731 | 70.824 | 1.00 | 14.08 |
| ATOM | 193 | O | TYR | 41 | 87.248 | 49.878 | 70.588 | 1.00 | 14.99 |
| ATOM | 194 | N | ILE | 42 | 87.381 | 47.980 | 71.785 | 1.00 | 14.83 |
| ATOM | 195 | CA | ILE | 42 | 88.390 | 48.518 | 72.691 | 1.00 | 16.98 |
| ATOM | 196 | CB | ILE | 42 | 88.076 | 48.131 | 74.151 | 1.00 | 17.07 |
| ATOM | 197 | CG2 | ILE | 42 | 89.107 | 48.739 | 75.098 | 1.00 | 14.32 |
| ATOM | 198 | CG1 | ILE | 42 | 86.650 | 48.568 | 74.507 | 1.00 | 16.63 |
| ATOM | 199 | CD1 | ILE | 42 | 86.157 | 48.016 | 75.818 | 1.00 | 15.82 |
| ATOM | 200 | C | ILE | 42 | 89.795 | 48.048 | 72.352 | 1.00 | 18.11 |
| ATOM | 201 | O | ILE | 42 | 90.060 | 46.844 | 72.285 | 1.00 | 19.16 |
| ATOM | 202 | N | ASP | 43 | 90.692 | 49.000 | 72.129 | 1.00 | 17.76 |
| ATOM | 203 | CA | ASP | 43 | 92.082 | 48.683 | 71.826 | 1.00 | 20.06 |
| ATOM | 204 | CB | ASP | 43 | 92.331 | 48.676 | 70.312 | 1.00 | 20.24 |
| ATOM | 205 | CG | ASP | 43 | 92.245 | 50.056 | 69.682 | 1.00 | 23.30 |
| ATOM | 206 | OD1 | ASP | 43 | 91.509 | 50.936 | 70.186 | 1.00 | 23.90 |
| ATOM | 207 | OD2 | ASP | 43 | 92.915 | 50.248 | 68.648 | 1.00 | 25.65 |
| ATOM | 208 | C | ASP | 43 | 93.016 | 49.659 | 72.540 | 1.00 | 20.53 |
| ATOM | 209 | O | ASP | 43 | 94.110 | 49.955 | 72.071 | 1.00 | 21.86 |
| ATOM | 210 | N | PHE | 44 | 92.564 | 50.152 | 73.685 | 1.00 | 19.12 |
| ATOM | 211 | CA | PHE | 44 | 93.323 | 51.091 | 74.488 | 1.00 | 19.11 |
| ATOM | 212 | CB | PHE | 44 | 93.219 | 52.509 | 73.910 | 1.00 | 22.06 |
| ATOM | 213 | CG | PHE | 44 | 91.816 | 53.051 | 73.883 | 1.00 | 26.32 |
| ATOM | 214 | CD1 | PHE | 44 | 90.925 | 52.675 | 72.871 | 1.00 | 23.08 |
| ATOM | 215 | CD2 | PHE | 44 | 91.367 | 53.904 | 74.890 | 1.00 | 26.77 |
| ATOM | 216 | CE1 | PHE | 44 | 89.612 | 53.131 | 72.866 | 1.00 | 19.60 |
| ATOM | 217 | CE2 | PHE | 44 | 90.053 | 54.363 | 74.893 | 1.00 | 27.23 |
| ATOM | 218 | CZ | PHE | 44 | 89.174 | 53.974 | 73.875 | 1.00 | 23.92 |
| ATOM | 219 | C | PHE | 44 | 92.716 | 51.039 | 75.881 | 1.00 | 19.64 |
| ATOM | 220 | O | PHE | 44 | 91.666 | 50.418 | 76.085 | 1.00 | 19.73 |
| ATOM | 221 | N | THR | 45 | 93.359 | 51.699 | 76.834 | 1.00 | 19.57 |
| ATOM | 222 | CA | THR | 45 | 92.871 | 51.699 | 78.203 | 1.00 | 20.17 |
| ATOM | 223 | CB | THR | 45 | 94.015 | 51.487 | 79.185 | 1.00 | 21.18 |
| ATOM | 224 | OG1 | THR | 45 | 95.014 | 52.488 | 78.966 | 1.00 | 25.33 |
| ATOM | 225 | CG2 | THR | 45 | 94.623 | 50.113 | 78.988 | 1.00 | 18.41 |
| ATOM | 226 | C | THR | 45 | 92.144 | 52.985 | 78.560 | 1.00 | 18.54 |
| ATOM | 227 | O | THR | 45 | 92.360 | 54.024 | 77.944 | 1.00 | 18.57 |
| ATOM | 228 | N | ALA | 46 | 91.310 | 52.914 | 79.589 | 1.00 | 17.69 |
| ATOM | 229 | CA | ALA | 46 | 90.541 | 54.066 | 80.030 | 1.00 | 17.75 |
| ATOM | 230 | CB | ALA | 46 | 89.709 | 53.719 | 81.253 | 1.00 | 13.85 |
| ATOM | 231 | C | ALA | 46 | 91.441 | 55.251 | 80.315 | 1.00 | 18.75 |
| ATOM | 232 | O | ALA | 46 | 91.138 | 56.367 | 79.917 | 1.00 | 20.63 |
| ATOM | 233 | N | ASP | 47 | 92.582 | 55.001 | 80.944 | 1.00 | 20.24 |

FIG. 1A-5

| ATOM | 234 | CA | ASP | 47 | 93.504 | 56.088 | 81.268 | 1.00 | 21.37 |
|---|---|---|---|---|---|---|---|---|---|
| ATOM | 235 | CB | ASP | 47 | 94.580 | 55.645 | 82.278 | 1.00 | 25.83 |
| ATOM | 236 | CG | ASP | 47 | 95.352 | 54.403 | 81.837 | 1.00 | 35.96 |
| ATOM | 237 | OD1 | ASP | 47 | 96.462 | 54.556 | 81.274 | 1.00 | 38.06 |
| ATOM | 238 | OD2 | ASP | 47 | 94.870 | 53.269 | 82.091 | 1.00 | 42.93 |
| ATOM | 239 | C | ASP | 47 | 94.129 | 56.778 | 80.060 | 1.00 | 19.38 |
| ATOM | 240 | O | ASP | 47 | 94.754 | 57.822 | 80.196 | 1.00 | 19.83 |
| ATOM | 241 | N | GLN | 48 | 93.920 | 56.222 | 78.874 | 1.00 | 18.14 |
| ATOM | 242 | CA | GLN | 48 | 94.477 | 56.808 | 77.665 | 1.00 | 18.72 |
| ATOM | 243 | CB | GLN | 48 | 94.867 | 55.713 | 76.667 | 1.00 | 20.43 |
| ATOM | 244 | CG | GLN | 48 | 96.117 | 54.922 | 77.038 | 1.00 | 25.96 |
| ATOM | 245 | CD | GLN | 48 | 96.606 | 54.032 | 75.900 | 1.00 | 31.16 |
| ATOM | 246 | OE1 | GLN | 48 | 97.052 | 54.519 | 74.857 | 1.00 | 30.37 |
| ATOM | 247 | NE2 | GLN | 48 | 96.520 | 52.721 | 76.096 | 1.00 | 33.58 |
| ATOM | 248 | C | GLN | 48 | 93.510 | 57.772 | 77.000 | 1.00 | 20.23 |
| ATOM | 249 | O | GLN | 48 | 93.840 | 58.387 | 75.985 | 1.00 | 22.71 |
| ATOM | 250 | N | VAL | 49 | 92.311 | 57.896 | 77.558 | 1.00 | 20.36 |
| ATOM | 251 | CA | VAL | 49 | 91.286 | 58.771 | 76.997 | 1.00 | 18.46 |
| ATOM | 252 | CB | VAL | 49 | 89.878 | 58.347 | 77.489 | 1.00 | 19.19 |
| ATOM | 253 | CG1 | VAL | 49 | 88.826 | 59.354 | 77.039 | 1.00 | 22.83 |
| ATOM | 254 | CG2 | VAL | 49 | 89.545 | 56.957 | 76.964 | 1.00 | 17.01 |
| ATOM | 255 | C | VAL | 49 | 91.540 | 60.240 | 77.315 | 1.00 | 15.71 |
| ATOM | 256 | O | VAL | 49 | 91.771 | 60.601 | 78.465 | 1.00 | 16.81 |
| ATOM | 257 | N | ASP | 50 | 91.482 | 61.083 | 76.291 | 1.00 | 14.39 |
| ATOM | 258 | CA | ASP | 50 | 91.711 | 62.514 | 76.455 | 1.00 | 14.04 |
| ATOM | 259 | CB | ASP | 50 | 92.620 | 63.027 | 75.338 | 1.00 | 11.59 |
| ATOM | 260 | CG | ASP | 50 | 92.982 | 64.500 | 75.497 | 1.00 | 15.45 |
| ATOM | 261 | OD1 | ASP | 50 | 93.099 | 65.001 | 76.641 | 1.00 | 19.60 |
| ATOM | 262 | OD2 | ASP | 50 | 93.166 | 65.160 | 74.460 | 1.00 | 18.29 |
| ATOM | 263 | C | ASP | 50 | 90.396 | 63.299 | 76.466 | 1.00 | 13.17 |
| ATOM | 264 | O | ASP | 50 | 89.600 | 63.207 | 75.529 | 1.00 | 14.97 |
| ATOM | 265 | N | LEU | 51 | 90.199 | 64.101 | 77.508 | 1.00 | 11.28 |
| ATOM | 266 | CA | LEU | 51 | 88.989 | 64.899 | 77.658 | 1.00 | 10.04 |
| ATOM | 267 | CB | LEU | 51 | 88.452 | 64.770 | 79.080 | 1.00 | 8.54 |
| ATOM | 268 | CG | LEU | 51 | 88.308 | 63.399 | 79.734 | 1.00 | 5.22 |
| ATOM | 269 | CD1 | LEU | 51 | 87.731 | 63.609 | 81.122 | 1.00 | 3.10 |
| ATOM | 270 | CD2 | LEU | 51 | 87.404 | 62.485 | 78.912 | 1.00 | 8.97 |
| ATOM | 271 | C | LEU | 51 | 89.153 | 66.390 | 77.337 | 1.00 | 10.78 |
| ATOM | 272 | O | LEU | 51 | 88.289 | 67.187 | 77.688 | 1.00 | 12.28 |
| ATOM | 273 | N | THR | 52 | 90.247 | 66.776 | 76.688 | 1.00 | 12.96 |
| ATOM | 274 | CA | THR | 52 | 90.476 | 68.181 | 76.347 | 1.00 | 12.08 |
| ATOM | 275 | CB | THR | 52 | 91.721 | 68.340 | 75.469 | 1.00 | 12.55 |
| ATOM | 276 | OG1 | THR | 52 | 92.867 | 67.868 | 76.191 | 1.00 | 10.40 |
| ATOM | 277 | CG2 | THR | 52 | 91.930 | 69.795 | 75.090 | 1.00 | 15.12 |
| ATOM | 278 | C | THR | 52 | 89.254 | 68.722 | 75.627 | 1.00 | 11.99 |
| ATOM | 279 | O | THR | 52 | 88.798 | 68.142 | 74.644 | 1.00 | 13.13 |
| ATOM | 280 | N | SER | 53 | 88.731 | 69.837 | 76.120 | 1.00 | 11.60 |
| ATOM | 281 | CA | SER | 53 | 87.530 | 70.412 | 75.548 | 1.00 | 11.26 |
| ATOM | 282 | CB | SER | 53 | 86.325 | 69.983 | 76.377 | 1.00 | 13.37 |
| ATOM | 283 | OG | SER | 53 | 86.159 | 68.577 | 76.326 | 1.00 | 17.69 |
| ATOM | 284 | C | SER | 53 | 87.554 | 71.922 | 75.445 | 1.00 | 11.98 |
| ATOM | 285 | O | SER | 53 | 88.144 | 72.607 | 76.276 | 1.00 | 13.12 |
| ATOM | 286 | N | ALA | 54 | 86.894 | 72.435 | 74.416 | 1.00 | 11.95 |
| ATOM | 287 | CA | ALA | 54 | 86.817 | 73.864 | 74.173 | 1.00 | 12.45 |
| ATOM | 288 | CB | ALA | 54 | 86.566 | 74.122 | 72.693 | 1.00 | 8.03 |
| ATOM | 289 | C | ALA | 54 | 85.699 | 74.486 | 74.997 | 1.00 | 15.40 |
| ATOM | 290 | O | ALA | 54 | 84.527 | 74.138 | 74.821 | 1.00 | 17.45 |
| ATOM | 291 | N | LEU | 55 | 86.056 | 75.371 | 75.920 | 1.00 | 15.11 |
| ATOM | 292 | CA | LEU | 55 | 85.052 | 76.052 | 76.722 | 1.00 | 15.35 |

FIG. 1A-6

| ATOM | 293 | CB | LEU | 55 | 85.679 | 76.793 | 77.905 | 1.00 | 11.75 |
| ATOM | 294 | CG | LEU | 55 | 84.652 | 77.545 | 78.753 | 1.00 | 5.59 |
| ATOM | 295 | CD1 | LEU | 55 | 83.821 | 76.562 | 79.548 | 1.00 | 2.00 |
| ATOM | 296 | CD2 | LEU | 55 | 85.338 | 78.506 | 79.685 | 1.00 | 7.88 |
| ATOM | 297 | C | LEU | 55 | 84.398 | 77.062 | 75.795 | 1.00 | 16.99 |
| ATOM | 298 | O | LEU | 55 | 83.183 | 77.132 | 75.703 | 1.00 | 19.02 |
| ATOM | 299 | N | THR | 56 | 85.216 | 77.843 | 75.102 | 1.00 | 17.95 |
| ATOM | 300 | CA | THR | 56 | 84.707 | 78.844 | 74.179 | 1.00 | 18.88 |
| ATOM | 301 | CB | THR | 56 | 84.709 | 80.275 | 74.804 | 1.00 | 16.13 |
| ATOM | 302 | OG1 | THR | 56 | 86.054 | 80.712 | 75.017 | 1.00 | 14.10 |
| ATOM | 303 | CG2 | THR | 56 | 83.970 | 80.300 | 76.145 | 1.00 | 16.08 |
| ATOM | 304 | C | THR | 56 | 85.614 | 78.815 | 72.955 | 1.00 | 20.87 |
| ATOM | 305 | O | THR | 56 | 86.517 | 77.980 | 72.869 | 1.00 | 23.00 |
| ATOM | 306 | N | LYS | 57 | 85.371 | 79.718 | 72.011 | 1.00 | 21.01 |
| ATOM | 307 | CA | LYS | 57 | 86.174 | 79.799 | 70.805 | 1.00 | 20.04 |
| ATOM | 308 | CB | LYS | 57 | 85.741 | 80.986 | 69.955 | 1.00 | 18.70 |
| ATOM | 309 | CG | LYS | 57 | 84.745 | 80.615 | 68.891 | 1.00 | 21.51 |
| ATOM | 310 | CD | LYS | 57 | 84.338 | 81.805 | 68.056 | 1.00 | 23.91 |
| ATOM | 311 | CE | LYS | 57 | 83.449 | 81.350 | 66.915 | 1.00 | 32.96 |
| ATOM | 312 | NZ | LYS | 57 | 82.765 | 82.469 | 66.212 | 1.00 | 36.85 |
| ATOM | 313 | C | LYS | 57 | 87.661 | 79.894 | 71.089 | 1.00 | 22.00 |
| ATOM | 314 | O | LYS | 57 | 88.469 | 79.549 | 70.238 | 1.00 | 25.73 |
| ATOM | 315 | N | LYS | 58 | 88.033 | 80.380 | 72.267 | 1.00 | 22.39 |
| ATOM | 316 | CA | LYS | 58 | 89.444 | 80.490 | 72.598 | 1.00 | 23.85 |
| ATOM | 317 | CB | LYS | 58 | 89.927 | 81.933 | 72.445 | 1.00 | 25.83 |
| ATOM | 318 | CG | LYS | 58 | 89.896 | 82.442 | 71.001 | 1.00 | 28.99 |
| ATOM | 319 | CD | LYS | 58 | 90.874 | 83.590 | 70.769 | 1.00 | 34.75 |
| ATOM | 320 | CE | LYS | 58 | 90.656 | 84.733 | 71.755 | 1.00 | 42.57 |
| ATOM | 321 | NZ | LYS | 58 | 91.646 | 85.843 | 71.599 | 1.00 | 44.82 |
| ATOM | 322 | C | LYS | 58 | 89.847 | 79.921 | 73.958 | 1.00 | 25.84 |
| ATOM | 323 | O | LYS | 58 | 91.034 | 79.809 | 74.240 | 1.00 | 28.83 |
| ATOM | 324 | N | ILE | 59 | 88.882 | 79.596 | 74.817 | 1.00 | 24.95 |
| ATOM | 325 | CA | ILE | 59 | 89.207 | 79.005 | 76.118 | 1.00 | 21.26 |
| ATOM | 326 | CB | ILE | 59 | 88.186 | 79.373 | 77.215 | 1.00 | 19.15 |
| ATOM | 327 | CG2 | ILE | 59 | 88.599 | 78.744 | 78.536 | 1.00 | 18.36 |
| ATOM | 328 | CG1 | ILE | 59 | 88.030 | 80.892 | 77.345 | 1.00 | 13.94 |
| ATOM | 329 | CD1 | ILE | 59 | 89.012 | 81.556 | 78.261 | 1.00 | 10.28 |
| ATOM | 330 | C | ILE | 59 | 89.120 | 77.494 | 75.934 | 1.00 | 23.50 |
| ATOM | 331 | O | ILE | 59 | 88.112 | 76.979 | 75.445 | 1.00 | 24.71 |
| ATOM | 332 | N | THR | 60 | 90.163 | 76.784 | 76.335 | 1.00 | 22.69 |
| ATOM | 333 | CA | THR | 60 | 90.182 | 75.337 | 76.211 | 1.00 | 22.98 |
| ATOM | 334 | CB | THR | 60 | 91.067 | 74.904 | 75.028 | 1.00 | 26.30 |
| ATOM | 335 | OG1 | THR | 60 | 90.432 | 75.296 | 73.803 | 1.00 | 30.53 |
| ATOM | 336 | CG2 | THR | 60 | 91.283 | 73.398 | 75.026 | 1.00 | 27.27 |
| ATOM | 337 | C | THR | 60 | 90.664 | 74.716 | 77.518 | 1.00 | 22.51 |
| ATOM | 338 | O | THR | 60 | 91.712 | 75.080 | 78.038 | 1.00 | 25.19 |
| ATOM | 339 | N | LEU | 61 | 89.865 | 73.806 | 78.057 | 1.00 | 20.62 |
| ATOM | 340 | CA | LEU | 61 | 90.165 | 73.150 | 79.316 | 1.00 | 16.73 |
| ATOM | 341 | CB | LEU | 61 | 88.910 | 73.162 | 80.190 | 1.00 | 14.48 |
| ATOM | 342 | CG | LEU | 61 | 88.062 | 74.436 | 80.112 | 1.00 | 9.39 |
| ATOM | 343 | CD1 | LEU | 61 | 86.663 | 74.190 | 80.668 | 1.00 | 9.35 |
| ATOM | 344 | CD2 | LEU | 61 | 88.766 | 75.570 | 80.834 | 1.00 | 2.85 |
| ATOM | 345 | C | LEU | 61 | 90.597 | 71.714 | 79.072 | 1.00 | 16.25 |
| ATOM | 346 | O | LEU | 61 | 90.453 | 71.189 | 77.968 | 1.00 | 15.53 |
| ATOM | 347 | N | LYS | 62 | 91.111 | 71.075 | 80.113 | 1.00 | 17.42 |
| ATOM | 348 | CA | LYS | 62 | 91.550 | 69.695 | 80.017 | 1.00 | 20.31 |
| ATOM | 349 | CB | LYS | 62 | 92.624 | 69.379 | 81.061 | 1.00 | 23.11 |
| ATOM | 350 | CG | LYS | 62 | 93.910 | 70.206 | 80.915 | 1.00 | 31.56 |
| ATOM | 351 | CD | LYS | 62 | 94.470 | 70.167 | 79.492 | 1.00 | 36.67 |

FIG. 1A-7

| | | | | | | | | | |
|---|---|---|---|---|---|---|---|---|---|
| ATOM | 352 | CE | LYS | 62 | 94.867 | 68.753 | 79.074 | 1.00 | 40.37 |
| ATOM | 353 | NZ | LYS | 62 | 95.167 | 68.655 | 77.613 | 1.00 | 41.00 |
| ATOM | 354 | C | LYS | 62 | 90.360 | 68.773 | 80.190 | 1.00 | 22.22 |
| ATOM | 355 | O | LYS | 62 | 90.378 | 67.642 | 79.718 | 1.00 | 24.32 |
| ATOM | 356 | N | THR | 63 | 89.322 | 69.262 | 80.863 | 1.00 | 24.24 |
| ATOM | 357 | CA | THR | 63 | 88.106 | 68.485 | 81.093 | 1.00 | 22.98 |
| ATOM | 358 | CB | THR | 63 | 87.927 | 68.142 | 82.581 | 1.00 | 22.74 |
| ATOM | 359 | OG1 | THR | 63 | 87.737 | 69.344 | 83.327 | 1.00 | 28.60 |
| ATOM | 360 | CG2 | THR | 63 | 89.146 | 67.422 | 83.117 | 1.00 | 22.14 |
| ATOM | 361 | C | THR | 63 | 86.913 | 69.312 | 80.621 | 1.00 | 22.76 |
| ATOM | 362 | O | THR | 63 | 86.993 | 70.541 | 80.523 | 1.00 | 24.77 |
| ATOM | 363 | N | PRO | 64 | 85.788 | 68.656 | 80.321 | 1.00 | 21.21 |
| ATOM | 364 | CD | PRO | 64 | 85.600 | 67.195 | 80.223 | 1.00 | 20.66 |
| ATOM | 365 | CA | PRO | 64 | 84.597 | 69.367 | 79.858 | 1.00 | 19.26 |
| ATOM | 366 | CB | PRO | 64 | 83.938 | 68.321 | 78.974 | 1.00 | 20.57 |
| ATOM | 367 | CG | PRO | 64 | 84.162 | 67.063 | 79.773 | 1.00 | 17.12 |
| ATOM | 368 | C | PRO | 64 | 83.669 | 69.750 | 81.004 | 1.00 | 18.03 |
| ATOM | 369 | O | PRO | 64 | 82.466 | 69.859 | 80.819 | 1.00 | 18.92 |
| ATOM | 370 | N | LEU | 65 | 84.220 | 69.984 | 82.181 | 1.00 | 17.42 |
| ATOM | 371 | CA | LEU | 65 | 83.388 | 70.281 | 83.331 | 1.00 | 17.61 |
| ATOM | 372 | CB | LEU | 65 | 83.877 | 69.442 | 84.518 | 1.00 | 16.50 |
| ATOM | 373 | CG | LEU | 65 | 84.124 | 67.954 | 84.216 | 1.00 | 11.41 |
| ATOM | 374 | CD1 | LEU | 65 | 84.753 | 67.288 | 85.403 | 1.00 | 10.97 |
| ATOM | 375 | CD2 | LEU | 65 | 82.840 | 67.245 | 83.834 | 1.00 | 9.50 |
| ATOM | 376 | C | LEU | 65 | 83.326 | 71.769 | 83.679 | 1.00 | 18.70 |
| ATOM | 377 | O | LEU | 65 | 84.331 | 72.472 | 83.605 | 1.00 | 19.19 |
| ATOM | 378 | N | VAL | 66 | 82.145 | 72.234 | 84.081 | 1.00 | 16.36 |
| ATOM | 379 | CA | VAL | 66 | 81.926 | 73.638 | 84.429 | 1.00 | 15.28 |
| ATOM | 380 | CB | VAL | 66 | 81.328 | 74.418 | 83.206 | 1.00 | 14.14 |
| ATOM | 381 | CG1 | VAL | 66 | 81.133 | 75.878 | 83.547 | 1.00 | 13.24 |
| ATOM | 382 | CG2 | VAL | 66 | 82.221 | 74.291 | 81.985 | 1.00 | 12.95 |
| ATOM | 383 | C | VAL | 66 | 80.927 | 73.740 | 85.595 | 1.00 | 14.30 |
| ATOM | 384 | O | VAL | 66 | 79.938 | 73.018 | 85.624 | 1.00 | 15.07 |
| ATOM | 385 | N | SER | 67 | 81.189 | 74.605 | 86.569 | 1.00 | 13.41 |
| ATOM | 386 | CA | SER | 67 | 80.262 | 74.767 | 87.683 | 1.00 | 13.36 |
| ATOM | 387 | CB | SER | 67 | 80.995 | 75.037 | 88.999 | 1.00 | 10.98 |
| ATOM | 388 | OG | SER | 67 | 81.834 | 76.166 | 88.910 | 1.00 | 14.86 |
| ATOM | 389 | C | SER | 67 | 79.322 | 75.909 | 87.330 | 1.00 | 14.70 |
| ATOM | 390 | O | SER | 67 | 79.742 | 76.930 | 86.783 | 1.00 | 15.74 |
| ATOM | 391 | N | SER | 68 | 78.041 | 75.718 | 87.610 | 1.00 | 15.87 |
| ATOM | 392 | CA | SER | 68 | 77.022 | 76.706 | 87.293 | 1.00 | 16.05 |
| ATOM | 393 | CB | SER | 68 | 75.639 | 76.067 | 87.443 | 1.00 | 18.67 |
| ATOM | 394 | OG | SER | 68 | 74.602 | 77.004 | 87.194 | 1.00 | 21.96 |
| ATOM | 395 | C | SER | 68 | 77.080 | 77.993 | 88.106 | 1.00 | 16.26 |
| ATOM | 396 | O | SER | 68 | 77.445 | 77.995 | 89.283 | 1.00 | 16.76 |
| ATOM | 397 | N | PRO | 69 | 76.699 | 79.116 | 87.483 | 1.00 | 16.03 |
| ATOM | 398 | CD | PRO | 69 | 76.396 | 79.279 | 86.052 | 1.00 | 15.90 |
| ATOM | 399 | CA | PRO | 69 | 76.699 | 80.411 | 88.169 | 1.00 | 15.65 |
| ATOM | 400 | CB | PRO | 69 | 76.592 | 81.414 | 87.014 | 1.00 | 15.49 |
| ATOM | 401 | CG | PRO | 69 | 76.975 | 80.626 | 85.778 | 1.00 | 17.02 |
| ATOM | 402 | C | PRO | 69 | 75.445 | 80.475 | 89.063 | 1.00 | 16.27 |
| ATOM | 403 | O | PRO | 69 | 74.384 | 80.927 | 88.625 | 1.00 | 13.16 |
| ATOM | 404 | N | MET | 70 | 75.553 | 79.981 | 90.295 | 1.00 | 17.24 |
| ATOM | 405 | CA | MET | 70 | 74.423 | 79.975 | 91.215 | 1.00 | 18.66 |
| ATOM | 406 | CB | MET | 70 | 73.724 | 78.611 | 91.180 | 1.00 | 20.15 |
| ATOM | 407 | CG | MET | 70 | 73.116 | 78.255 | 89.831 | 1.00 | 20.32 |
| ATOM | 408 | SD | MET | 70 | 72.490 | 76.578 | 89.729 | 1.00 | 18.83 |
| ATOM | 409 | CE | MET | 70 | 70.886 | 76.796 | 90.447 | 1.00 | 22.16 |
| ATOM | 410 | C | MET | 70 | 74.868 | 80.270 | 92.633 | 1.00 | 19.79 |

FIG. 1A-8

| ATOM | 411 | O | MET | 70 | 75.992 | 79.965 | 93.004 | 1.00 | 20.13 |
|---|---|---|---|---|---|---|---|---|---|
| ATOM | 412 | N | ASP | 71 | 73.958 | 80.827 | 93.427 | 1.00 | 23.75 |
| ATOM | 413 | CA | ASP | 71 | 74.194 | 81.184 | 94.832 | 1.00 | 24.77 |
| ATOM | 414 | CB | ASP | 71 | 72.863 | 81.499 | 95.539 | 1.00 | 29.35 |
| ATOM | 415 | CG | ASP | 71 | 72.367 | 82.882 | 95.265 | 1.00 | 38.41 |
| ATOM | 416 | OD1 | ASP | 71 | 73.156 | 83.834 | 95.406 | 1.00 | 47.71 |
| ATOM | 417 | OD2 | ASP | 71 | 71.177 | 83.021 | 94.930 | 1.00 | 44.52 |
| ATOM | 418 | C | ASP | 71 | 74.842 | 80.080 | 95.643 | 1.00 | 22.82 |
| ATOM | 419 | O | ASP | 71 | 75.774 | 80.331 | 96.404 | 1.00 | 23.85 |
| ATOM | 420 | N | THR | 72 | 74.293 | 78.875 | 95.508 | 1.00 | 19.87 |
| ATOM | 421 | CA | THR | 72 | 74.746 | 77.713 | 96.258 | 1.00 | 17.82 |
| ATOM | 422 | CB | THR | 72 | 73.531 | 76.878 | 96.711 | 1.00 | 14.30 |
| ATOM | 423 | OG1 | THR | 72 | 72.808 | 76.423 | 95.562 | 1.00 | 13.27 |
| ATOM | 424 | CG2 | THR | 72 | 72.608 | 77.713 | 97.557 | 1.00 | 12.15 |
| ATOM | 425 | C | THR | 72 | 75.725 | 76.792 | 95.534 | 1.00 | 17.18 |
| ATOM | 426 | O | THR | 72 | 75.864 | 75.623 | 95.898 | 1.00 | 18.53 |
| ATOM | 427 | N | VAL | 73 | 76.394 | 77.291 | 94.504 | 1.00 | 14.78 |
| ATOM | 428 | CA | VAL | 73 | 77.317 | 76.440 | 93.786 | 1.00 | 13.05 |
| ATOM | 429 | CB | VAL | 73 | 76.773 | 76.032 | 92.388 | 1.00 | 10.97 |
| ATOM | 430 | CG1 | VAL | 73 | 77.717 | 75.035 | 91.741 | 1.00 | 9.58 |
| ATOM | 431 | CG2 | VAL | 73 | 75.365 | 75.434 | 92.482 | 1.00 | 8.96 |
| ATOM | 432 | C | VAL | 73 | 78.661 | 77.111 | 93.589 | 1.00 | 16.49 |
| ATOM | 433 | O | VAL | 73 | 79.675 | 76.677 | 94.160 | 1.00 | 15.55 |
| ATOM | 434 | N | THR | 74 | 78.650 | 78.223 | 92.860 | 1.00 | 17.15 |
| ATOM | 435 | CA | THR | 74 | 79.894 | 78.896 | 92.539 | 1.00 | 18.39 |
| ATOM | 436 | CB | THR | 74 | 80.096 | 78.965 | 91.011 | 1.00 | 17.98 |
| ATOM | 437 | OG1 | THR | 74 | 79.847 | 77.675 | 90.436 | 1.00 | 24.62 |
| ATOM | 438 | CG2 | THR | 74 | 81.531 | 79.368 | 90.675 | 1.00 | 19.70 |
| ATOM | 439 | C | THR | 74 | 80.253 | 80.257 | 93.116 | 1.00 | 18.82 |
| ATOM | 440 | O | THR | 74 | 79.606 | 81.274 | 92.847 | 1.00 | 20.11 |
| ATOM | 441 | N | GLU | 75 | 81.354 | 80.247 | 93.854 | 1.00 | 18.87 |
| ATOM | 442 | CA | GLU | 75 | 81.969 | 81.425 | 94.439 | 1.00 | 18.61 |
| ATOM | 443 | CB | GLU | 75 | 81.534 | 81.645 | 95.886 | 1.00 | 14.35 |
| ATOM | 444 | CG | GLU | 75 | 80.255 | 82.451 | 95.967 | 1.00 | 15.80 |
| ATOM | 445 | CD | GLU | 75 | 79.843 | 82.834 | 97.379 | 1.00 | 21.75 |
| ATOM | 446 | OE1 | GLU | 75 | 80.413 | 82.310 | 98.363 | 1.00 | 26.31 |
| ATOM | 447 | OE2 | GLU | 75 | 78.917 | 83.664 | 97.505 | 1.00 | 20.92 |
| ATOM | 448 | C | GLU | 75 | 83.469 | 81.131 | 94.301 | 1.00 | 19.83 |
| ATOM | 449 | O | GLU | 75 | 83.847 | 80.171 | 93.619 | 1.00 | 19.89 |
| ATOM | 450 | N | ALA | 76 | 84.326 | 81.934 | 94.919 | 1.00 | 20.57 |
| ATOM | 451 | CA | ALA | 76 | 85.762 | 81.724 | 94.787 | 1.00 | 18.25 |
| ATOM | 452 | CB | ALA | 76 | 86.517 | 82.637 | 95.713 | 1.00 | 22.39 |
| ATOM | 453 | C | ALA | 76 | 86.178 | 80.278 | 95.008 | 1.00 | 17.57 |
| ATOM | 454 | O | ALA | 76 | 86.733 | 79.652 | 94.110 | 1.00 | 18.52 |
| ATOM | 455 | N | GLY | 77 | 85.845 | 79.739 | 96.177 | 1.00 | 16.64 |
| ATOM | 456 | CA | GLY | 77 | 86.203 | 78.372 | 96.513 | 1.00 | 16.11 |
| ATOM | 457 | C | GLY | 77 | 85.960 | 77.364 | 95.406 | 1.00 | 18.32 |
| ATOM | 458 | O | GLY | 77 | 86.870 | 76.624 | 95.036 | 1.00 | 20.06 |
| ATOM | 459 | N | MET | 78 | 84.744 | 77.345 | 94.866 | 1.00 | 19.25 |
| ATOM | 460 | CA | MET | 78 | 84.381 | 76.420 | 93.797 | 1.00 | 17.27 |
| ATOM | 461 | CB | MET | 78 | 82.878 | 76.495 | 93.501 | 1.00 | 14.83 |
| ATOM | 462 | CG | MET | 78 | 82.379 | 75.543 | 92.416 | 1.00 | 9.04 |
| ATOM | 463 | SD | MET | 78 | 82.630 | 73.797 | 92.794 | 1.00 | 9.74 |
| ATOM | 464 | CE | MET | 78 | 81.306 | 73.505 | 93.947 | 1.00 | 4.67 |
| ATOM | 465 | C | MET | 78 | 85.174 | 76.725 | 92.539 | 1.00 | 18.93 |
| ATOM | 466 | O | MET | 78 | 85.817 | 75.835 | 91.985 | 1.00 | 20.73 |
| ATOM | 467 | N | ALA | 79 | 85.173 | 77.990 | 92.122 | 1.00 | 19.92 |
| ATOM | 468 | CA | ALA | 79 | 85.890 | 78.412 | 90.916 | 1.00 | 18.97 |
| ATOM | 469 | CB | ALA | 79 | 85.761 | 79.919 | 90.715 | 1.00 | 17.50 |

FIG. 1A-9

| ATOM | 470 | C | ALA | 79 | 87.357 | 78.002 | 90.955 | 1.00 | 19.41 |
|------|-----|------|-----|----|--------|--------|--------|------|-------|
| ATOM | 471 | O | ALA | 79 | 87.912 | 77.573 | 89.949 | 1.00 | 21.40 |
| ATOM | 472 | N | ILE | 80 | 87.977 | 78.106 | 92.125 | 1.00 | 20.17 |
| ATOM | 473 | CA | ILE | 80 | 89.383 | 77.739 | 92.281 | 1.00 | 20.16 |
| ATOM | 474 | CB | ILE | 80 | 89.964 | 78.235 | 93.641 | 1.00 | 18.57 |
| ATOM | 475 | CG2 | ILE | 80 | 91.349 | 77.658 | 93.885 | 1.00 | 16.92 |
| ATOM | 476 | CG1 | ILE | 80 | 90.034 | 79.758 | 93.662 | 1.00 | 19.76 |
| ATOM | 477 | CD1 | ILE | 80 | 90.403 | 80.338 | 95.011 | 1.00 | 22.90 |
| ATOM | 478 | C | ILE | 80 | 89.547 | 76.228 | 92.188 | 1.00 | 19.90 |
| ATOM | 479 | O | ILE | 80 | 90.330 | 75.740 | 91.381 | 1.00 | 19.26 |
| ATOM | 480 | N | ALA | 81 | 88.773 | 75.496 | 92.984 | 1.00 | 20.78 |
| ATOM | 481 | CA | ALA | 81 | 88.850 | 74.038 | 93.014 | 1.00 | 21.41 |
| ATOM | 482 | CB | ALA | 81 | 87.876 | 73.479 | 94.027 | 1.00 | 22.18 |
| ATOM | 483 | C | ALA | 81 | 88.586 | 73.439 | 91.653 | 1.00 | 22.24 |
| ATOM | 484 | O | ALA | 81 | 89.308 | 72.544 | 91.210 | 1.00 | 25.18 |
| ATOM | 485 | N | MET | 82 | 87.576 | 73.971 | 90.977 | 1.00 | 21.26 |
| ATOM | 486 | CA | MET | 82 | 87.187 | 73.506 | 89.653 | 1.00 | 20.10 |
| ATOM | 487 | CB | MET | 82 | 85.905 | 74.220 | 89.215 | 1.00 | 20.89 |
| ATOM | 488 | CG | MET | 82 | 85.096 | 73.499 | 88.147 | 1.00 | 22.31 |
| ATOM | 489 | SD | MET | 82 | 84.241 | 72.058 | 88.768 | 1.00 | 17.73 |
| ATOM | 490 | CE | MET | 82 | 83.598 | 72.738 | 90.224 | 1.00 | 16.02 |
| ATOM | 491 | C | MET | 82 | 88.307 | 73.740 | 88.628 | 1.00 | 18.83 |
| ATOM | 492 | O | MET | 82 | 88.535 | 72.905 | 87.754 | 1.00 | 19.46 |
| ATOM | 493 | N | ALA | 83 | 88.992 | 74.877 | 88.723 | 1.00 | 18.24 |
| ATOM | 494 | CA | ALA | 83 | 90.082 | 75.184 | 87.801 | 1.00 | 17.87 |
| ATOM | 495 | CB | ALA | 83 | 90.501 | 76.642 | 87.925 | 1.00 | 13.75 |
| ATOM | 496 | C | ALA | 83 | 91.267 | 74.269 | 88.072 | 1.00 | 18.76 |
| ATOM | 497 | O | ALA | 83 | 91.869 | 73.732 | 87.143 | 1.00 | 18.19 |
| ATOM | 498 | N | LEU | 84 | 91.568 | 74.060 | 89.352 | 1.00 | 19.47 |
| ATOM | 499 | CA | LEU | 84 | 92.687 | 73.213 | 89.754 | 1.00 | 19.62 |
| ATOM | 500 | CB | LEU | 84 | 92.864 | 73.216 | 91.282 | 1.00 | 17.06 |
| ATOM | 501 | CG | LEU | 84 | 93.341 | 74.485 | 92.011 | 1.00 | 14.41 |
| ATOM | 502 | CD1 | LEU | 84 | 93.302 | 74.256 | 93.508 | 1.00 | 9.31 |
| ATOM | 503 | CD2 | LEU | 84 | 94.742 | 74.893 | 91.579 | 1.00 | 10.69 |
| ATOM | 504 | C | LEU | 84 | 92.518 | 71.778 | 89.268 | 1.00 | 22.34 |
| ATOM | 505 | O | LEU | 84 | 93.503 | 71.089 | 88.986 | 1.00 | 24.52 |
| ATOM | 506 | N | THR | 85 | 91.276 | 71.321 | 89.160 | 1.00 | 22.85 |
| ATOM | 507 | CA | THR | 85 | 91.030 | 69.954 | 88.734 | 1.00 | 19.74 |
| ATOM | 508 | CB | THR | 85 | 89.824 | 69.343 | 89.481 | 1.00 | 17.66 |
| ATOM | 509 | OG1 | THR | 85 | 88.669 | 70.165 | 89.301 | 1.00 | 16.20 |
| ATOM | 510 | CG2 | THR | 85 | 90.137 | 69.242 | 90.962 | 1.00 | 13.32 |
| ATOM | 511 | C | THR | 85 | 90.927 | 69.748 | 87.232 | 1.00 | 19.88 |
| ATOM | 512 | O | THR | 85 | 90.970 | 68.612 | 86.758 | 1.00 | 23.55 |
| ATOM | 513 | N | GLY | 86 | 90.816 | 70.830 | 86.473 | 1.00 | 18.94 |
| ATOM | 514 | CA | GLY | 86 | 90.744 | 70.689 | 85.030 | 1.00 | 16.63 |
| ATOM | 515 | C | GLY | 86 | 89.580 | 71.388 | 84.362 | 1.00 | 18.45 |
| ATOM | 516 | O | GLY | 86 | 89.538 | 71.457 | 83.129 | 1.00 | 21.10 |
| ATOM | 517 | N | GLY | 87 | 88.615 | 71.852 | 85.151 | 1.00 | 16.36 |
| ATOM | 518 | CA | GLY | 87 | 87.462 | 72.534 | 84.596 | 1.00 | 13.99 |
| ATOM | 519 | C | GLY | 87 | 87.530 | 74.029 | 84.820 | 1.00 | 14.34 |
| ATOM | 520 | O | GLY | 87 | 88.616 | 74.606 | 84.784 | 1.00 | 16.64 |
| ATOM | 521 | N | ILE | 88 | 86.381 | 74.659 | 85.051 | 1.00 | 13.64 |
| ATOM | 522 | CA | ILE | 88 | 86.315 | 76.097 | 85.292 | 1.00 | 14.14 |
| ATOM | 523 | CB | ILE | 88 | 86.337 | 76.910 | 83.957 | 1.00 | 13.53 |
| ATOM | 524 | CG2 | ILE | 88 | 85.019 | 76.758 | 83.207 | 1.00 | 13.51 |
| ATOM | 525 | CG1 | ILE | 88 | 86.596 | 78.398 | 84.233 | 1.00 | 12.85 |
| ATOM | 526 | CD1 | ILE | 88 | 86.774 | 79.248 | 82.974 | 1.00 | 7.87 |
| ATOM | 527 | C | ILE | 88 | 85.033 | 76.404 | 86.062 | 1.00 | 16.48 |
| ATOM | 528 | O | ILE | 88 | 84.130 | 75.564 | 86.142 | 1.00 | 18.54 |

FIG. 1A-10

| ATOM | 529 | N | GLY | 89 | 84.962 | 77.591 | 86.652 | 1.00 | 15.46 |
| --- | --- | --- | --- | --- | --- | --- | --- | --- | --- |
| ATOM | 530 | CA | GLY | 89 | 83.775 | 77.965 | 87.389 | 1.00 | 14.33 |
| ATOM | 531 | C | GLY | 89 | 83.293 | 79.336 | 86.965 | 1.00 | 15.78 |
| ATOM | 532 | O | GLY | 89 | 84.073 | 80.128 | 86.430 | 1.00 | 16.51 |
| ATOM | 533 | N | PHE | 90 | 81.997 | 79.584 | 87.145 | 1.00 | 15.87 |
| ATOM | 534 | CA | PHE | 90 | 81.370 | 80.858 | 86.820 | 1.00 | 13.02 |
| ATOM | 535 | CB | PHE | 90 | 80.302 | 80.671 | 85.748 | 1.00 | 10.44 |
| ATOM | 536 | CG | PHE | 90 | 80.849 | 80.519 | 84.366 | 1.00 | 7.78 |
| ATOM | 537 | CD1 | PHE | 90 | 81.236 | 79.271 | 83.889 | 1.00 | 7.49 |
| ATOM | 538 | CD2 | PHE | 90 | 81.002 | 81.627 | 83.543 | 1.00 | 2.32 |
| ATOM | 539 | CE1 | PHE | 90 | 81.765 | 79.133 | 82.608 | 1.00 | 2.11 |
| ATOM | 540 | CE2 | PHE | 90 | 81.529 | 81.492 | 82.264 | 1.00 | 2.00 |
| ATOM | 541 | CZ | PHE | 90 | 81.911 | 80.244 | 81.803 | 1.00 | 2.00 |
| ATOM | 542 | C | PHE | 90 | 80.734 | 81.412 | 88.092 | 1.00 | 14.14 |
| ATOM | 543 | O | PHE | 90 | 79.793 | 80.824 | 88.630 | 1.00 | 16.10 |
| ATOM | 544 | N | ILE | 91 | 81.259 | 82.530 | 88.586 | 1.00 | 14.53 |
| ATOM | 545 | CA | ILE | 91 | 80.740 | 83.147 | 89.810 | 1.00 | 12.62 |
| ATOM | 546 | CB | ILE | 91 | 81.640 | 84.310 | 90.299 | 1.00 | 10.72 |
| ATOM | 547 | CG2 | ILE | 91 | 81.243 | 84.711 | 91.712 | 1.00 | 9.90 |
| ATOM | 548 | CG1 | ILE | 91 | 83.123 | 83.921 | 90.241 | 1.00 | 11.39 |
| ATOM | 549 | CD1 | ILE | 91 | 83.527 | 82.815 | 91.181 | 1.00 | 13.02 |
| ATOM | 550 | C | ILE | 91 | 79.343 | 83.704 | 89.556 | 1.00 | 12.28 |
| ATOM | 551 | O | ILE | 91 | 79.072 | 84.264 | 88.494 | 1.00 | 13.30 |
| ATOM | 552 | N | HIS | 92 | 78.458 | 83.546 | 90.531 | 1.00 | 13.70 |
| ATOM | 553 | CA | HIS | 92 | 77.093 | 84.044 | 90.407 | 1.00 | 13.81 |
| ATOM | 554 | CB | HIS | 92 | 76.191 | 83.431 | 91.488 | 1.00 | 13.49 |
| ATOM | 555 | CG | HIS | 92 | 76.413 | 83.993 | 92.859 | 1.00 | 11.95 |
| ATOM | 556 | CD2 | HIS | 92 | 75.949 | 85.118 | 93.448 | 1.00 | 10.24 |
| ATOM | 557 | ND1 | HIS | 92 | 77.183 | 83.358 | 93.808 | 1.00 | 16.02 |
| ATOM | 558 | CE1 | HIS | 92 | 77.183 | 84.063 | 94.924 | 1.00 | 12.53 |
| ATOM | 559 | NE2 | HIS | 92 | 76.442 | 85.137 | 94.731 | 1.00 | 14.71 |
| ATOM | 560 | C | HIS | 92 | 77.088 | 85.567 | 90.527 | 1.00 | 13.18 |
| ATOM | 561 | O | HIS | 92 | 78.006 | 86.150 | 91.087 | 1.00 | 13.75 |
| ATOM | 562 | N | HIS | 93 | 76.043 | 86.205 | 90.020 | 1.00 | 13.84 |
| ATOM | 563 | CA | HIS | 93 | 75.943 | 87.653 | 90.095 | 1.00 | 14.71 |
| ATOM | 564 | CB | HIS | 93 | 75.788 | 88.276 | 88.705 | 1.00 | 17.81 |
| ATOM | 565 | CG | HIS | 93 | 74.533 | 87.885 | 87.985 | 1.00 | 23.00 |
| ATOM | 566 | CD2 | HIS | 93 | 74.158 | 86.718 | 87.411 | 1.00 | 27.41 |
| ATOM | 567 | ND1 | HIS | 93 | 73.509 | 88.776 | 87.749 | 1.00 | 25.59 |
| ATOM | 568 | CE1 | HIS | 93 | 72.559 | 88.175 | 87.055 | 1.00 | 27.85 |
| ATOM | 569 | NE2 | HIS | 93 | 72.926 | 86.926 | 86.836 | 1.00 | 24.93 |
| ATOM | 570 | C | HIS | 93 | 74.831 | 88.105 | 91.025 | 1.00 | 14.74 |
| ATOM | 571 | O | HIS | 93 | 74.359 | 89.228 | 90.945 | 1.00 | 15.99 |
| ATOM | 572 | N | ASN | 94 | 74.381 | 87.201 | 91.885 | 1.00 | 17.54 |
| ATOM | 573 | CA | ASN | 94 | 73.340 | 87.516 | 92.860 | 1.00 | 18.66 |
| ATOM | 574 | CB | ASN | 94 | 72.566 | 86.249 | 93.225 | 1.00 | 20.67 |
| ATOM | 575 | CG | ASN | 94 | 71.413 | 86.516 | 94.175 | 1.00 | 22.98 |
| ATOM | 576 | OD1 | ASN | 94 | 71.278 | 85.849 | 95.199 | 1.00 | 27.48 |
| ATOM | 577 | ND2 | ASN | 94 | 70.552 | 87.456 | 93.819 | 1.00 | 19.79 |
| ATOM | 578 | C | ASN | 94 | 74.056 | 88.067 | 94.088 | 1.00 | 19.98 |
| ATOM | 579 | O | ASN | 94 | 73.932 | 87.526 | 95.189 | 1.00 | 19.74 |
| ATOM | 580 | N | CYS | 95 | 74.852 | 89.113 | 93.863 | 1.00 | 19.29 |
| ATOM | 581 | CA | CYS | 95 | 75.637 | 89.783 | 94.896 | 1.00 | 20.12 |
| ATOM | 582 | CB | CYS | 95 | 76.902 | 88.986 | 95.182 | 1.00 | 20.79 |
| ATOM | 583 | SG | CYS | 95 | 77.831 | 88.599 | 93.694 | 1.00 | 23.06 |
| ATOM | 584 | C | CYS | 95 | 76.014 | 91.152 | 94.343 | 1.00 | 22.11 |
| ATOM | 585 | O | CYS | 95 | 75.616 | 91.490 | 93.228 | 1.00 | 24.36 |
| ATOM | 586 | N | THR | 96 | 76.745 | 91.954 | 95.115 | 1.00 | 21.65 |
| ATOM | 587 | CA | THR | 96 | 77.145 | 93.277 | 94.639 | 1.00 | 22.63 |

FIG. 1A-11

| ATOM | 588 | CB | THR | 96 | 77.634 | 94.193 | 95.778 | 1.00 | 24.51 |
| --- | --- | --- | --- | --- | --- | --- | --- | --- | --- |
| ATOM | 589 | OG1 | THR | 96 | 78.672 | 93.540 | 96.520 | 1.00 | 29.99 |
| ATOM | 590 | CG2 | THR | 96 | 76.494 | 94.560 | 96.709 | 1.00 | 27.18 |
| ATOM | 591 | C | THR | 96 | 78.271 | 93.155 | 93.628 | 1.00 | 22.82 |
| ATOM | 592 | O | THR | 96 | 79.039 | 92.191 | 93.654 | 1.00 | 23.49 |
| ATOM | 593 | N | PRO | 97 | 78.378 | 94.128 | 92.710 | 1.00 | 23.91 |
| ATOM | 594 | CD | PRO | 97 | 77.427 | 95.220 | 92.438 | 1.00 | 23.87 |
| ATOM | 595 | CA | PRO | 97 | 79.440 | 94.099 | 91.702 | 1.00 | 23.66 |
| ATOM | 596 | CB | PRO | 97 | 79.250 | 95.433 | 90.989 | 1.00 | 22.66 |
| ATOM | 597 | CG | PRO | 97 | 77.769 | 95.597 | 91.009 | 1.00 | 22.97 |
| ATOM | 598 | C | PRO | 97 | 80.798 | 94.013 | 92.391 | 1.00 | 25.33 |
| ATOM | 599 | O | PRO | 97 | 81.704 | 93.328 | 91.914 | 1.00 | 25.86 |
| ATOM | 600 | N | GLU | 98 | 80.906 | 94.687 | 93.536 | 1.00 | 26.55 |
| ATOM | 601 | CA | GLU | 98 | 82.126 | 94.703 | 94.344 | 1.00 | 28.76 |
| ATOM | 602 | CB | GLU | 98 | 81.952 | 95.621 | 95.564 | 1.00 | 29.88 |
| ATOM | 603 | CG | GLU | 98 | 81.732 | 97.096 | 95.255 | 1.00 | 38.55 |
| ATOM | 604 | CD | GLU | 98 | 80.297 | 97.439 | 94.870 | 1.00 | 41.59 |
| ATOM | 605 | OE1 | GLU | 98 | 79.373 | 97.094 | 95.641 | 1.00 | 39.58 |
| ATOM | 606 | OE2 | GLU | 98 | 80.100 | 98.084 | 93.811 | 1.00 | 43.89 |
| ATOM | 607 | C | GLU | 98 | 82.469 | 93.288 | 94.835 | 1.00 | 30.16 |
| ATOM | 608 | O | GLU | 98 | 83.596 | 92.795 | 94.653 | 1.00 | 31.09 |
| ATOM | 609 | N | PHE | 99 | 81.478 | 92.645 | 95.449 | 1.00 | 28.04 |
| ATOM | 610 | CA | PHE | 99 | 81.619 | 91.302 | 95.989 | 1.00 | 24.81 |
| ATOM | 611 | CB | PHE | 99 | 80.301 | 90.871 | 96.619 | 1.00 | 23.36 |
| ATOM | 612 | CG | PHE | 99 | 80.334 | 89.502 | 97.235 | 1.00 | 24.63 |
| ATOM | 613 | CD1 | PHE | 99 | 80.695 | 89.335 | 98.563 | 1.00 | 26.18 |
| ATOM | 614 | CD2 | PHE | 99 | 79.951 | 88.384 | 96.502 | 1.00 | 21.79 |
| ATOM | 615 | CE1 | PHE | 99 | 80.668 | 88.075 | 99.159 | 1.00 | 26.07 |
| ATOM | 616 | CE2 | PHE | 99 | 79.922 | 87.132 | 97.088 | 1.00 | 20.62 |
| ATOM | 617 | CZ | PHE | 99 | 80.282 | 86.975 | 98.422 | 1.00 | 22.53 |
| ATOM | 618 | C | PHE | 99 | 82.004 | 90.322 | 94.905 | 1.00 | 23.00 |
| ATOM | 619 | O | PHE | 99 | 82.969 | 89.577 | 95.052 | 1.00 | 23.86 |
| ATOM | 620 | N | GLN | 100 | 81.249 | 90.336 | 93.813 | 1.00 | 21.74 |
| ATOM | 621 | CA | GLN | 100 | 81.495 | 89.437 | 92.698 | 1.00 | 22.80 |
| ATOM | 622 | CB | GLN | 100 | 80.488 | 89.671 | 91.581 | 1.00 | 22.40 |
| ATOM | 623 | CG | GLN | 100 | 80.388 | 88.486 | 90.646 | 1.00 | 22.81 |
| ATOM | 624 | CD | GLN | 100 | 79.585 | 88.781 | 89.417 | 1.00 | 21.83 |
| ATOM | 625 | OE1 | GLN | 100 | 79.391 | 89.941 | 89.051 | 1.00 | 25.98 |
| ATOM | 626 | NE2 | GLN | 100 | 79.120 | 87.739 | 88.758 | 1.00 | 19.59 |
| ATOM | 627 | C | GLN | 100 | 82.900 | 89.608 | 92.154 | 1.00 | 23.30 |
| ATOM | 628 | O | GLN | 100 | 83.625 | 88.626 | 91.951 | 1.00 | 23.42 |
| ATOM | 629 | N | ALA | 101 | 83.281 | 90.859 | 91.920 | 1.00 | 24.22 |
| ATOM | 630 | CA | ALA | 101 | 84.609 | 91.177 | 91.413 | 1.00 | 22.74 |
| ATOM | 631 | CB | ALA | 101 | 84.725 | 92.669 | 91.159 | 1.00 | 21.49 |
| ATOM | 632 | C | ALA | 101 | 85.689 | 90.706 | 92.395 | 1.00 | 22.04 |
| ATOM | 633 | O | ALA | 101 | 86.759 | 90.265 | 91.982 | 1.00 | 20.44 |
| ATOM | 634 | N | ASN | 102 | 85.399 | 90.769 | 93.691 | 1.00 | 22.30 |
| ATOM | 635 | CA | ASN | 102 | 86.366 | 90.324 | 94.687 | 1.00 | 23.36 |
| ATOM | 636 | CB | ASN | 102 | 85.939 | 90.714 | 96.101 | 1.00 | 24.55 |
| ATOM | 637 | CG | ASN | 102 | 86.996 | 90.378 | 97.142 | 1.00 | 27.11 |
| ATOM | 638 | OD1 | ASN | 102 | 88.152 | 90.789 | 97.028 | 1.00 | 29.62 |
| ATOM | 639 | ND2 | ASN | 102 | 86.602 | 89.629 | 98.165 | 1.00 | 27.00 |
| ATOM | 640 | C | ASN | 102 | 86.511 | 88.817 | 94.594 | 1.00 | 25.46 |
| ATOM | 641 | O | ASN | 102 | 87.604 | 88.277 | 94.797 | 1.00 | 28.34 |
| ATOM | 642 | N | GLU | 103 | 85.408 | 88.134 | 94.294 | 1.00 | 25.42 |
| ATOM | 643 | CA | GLU | 103 | 85.429 | 86.682 | 94.153 | 1.00 | 21.99 |
| ATOM | 644 | CB | GLU | 103 | 84.009 | 86.126 | 94.011 | 1.00 | 22.69 |
| ATOM | 645 | CG | GLU | 103 | 83.157 | 86.237 | 95.263 | 1.00 | 21.23 |
| ATOM | 646 | CD | GLU | 103 | 83.850 | 85.685 | 96.492 | 1.00 | 22.96 |

FIG. 1A-12

| ATOM | 647 | OE1 | GLU | 103 | 83.874 | 84.451 | 96.667 | 1.00 | 17.62 |
| --- | --- | --- | --- | --- | --- | --- | --- | --- | --- |
| ATOM | 648 | OE2 | GLU | 103 | 84.382 | 86.493 | 97.281 | 1.00 | 29.03 |
| ATOM | 649 | C | GLU | 103 | 86.278 | 86.304 | 92.940 | 1.00 | 20.97 |
| ATOM | 650 | O | GLU | 103 | 86.985 | 85.299 | 92.966 | 1.00 | 22.40 |
| ATOM | 651 | N | VAL | 104 | 86.217 | 87.116 | 91.887 | 1.00 | 18.20 |
| ATOM | 652 | CA | VAL | 104 | 87.017 | 86.873 | 90.683 | 1.00 | 18.88 |
| ATOM | 653 | CB | VAL | 104 | 86.620 | 87.824 | 89.521 | 1.00 | 17.86 |
| ATOM | 654 | CG1 | VAL | 104 | 87.427 | 87.506 | 88.255 | 1.00 | 16.68 |
| ATOM | 655 | CG2 | VAL | 104 | 85.138 | 87.722 | 89.245 | 1.00 | 17.68 |
| ATOM | 656 | C | VAL | 104 | 88.493 | 87.104 | 91.019 | 1.00 | 19.92 |
| ATOM | 657 | O | VAL | 104 | 89.355 | 86.302 | 90.666 | 1.00 | 21.70 |
| ATOM | 658 | N | ARG | 105 | 88.764 | 88.189 | 91.737 | 1.00 | 21.51 |
| ATOM | 659 | CA | ARG | 105 | 90.111 | 88.557 | 92.142 | 1.00 | 20.02 |
| ATOM | 660 | CB | ARG | 105 | 90.067 | 89.879 | 92.889 | 1.00 | 22.18 |
| ATOM | 661 | CG | ARG | 105 | 91.415 | 90.495 | 93.190 | 1.00 | 23.09 |
| ATOM | 662 | CD | ARG | 105 | 91.260 | 91.639 | 94.184 | 1.00 | 25.23 |
| ATOM | 663 | NE | ARG | 105 | 90.729 | 91.185 | 95.470 | 1.00 | 26.67 |
| ATOM | 664 | CZ | ARG | 105 | 91.421 | 90.471 | 96.356 | 1.00 | 25.55 |
| ATOM | 665 | NH1 | ARG | 105 | 92.678 | 90.128 | 96.101 | 1.00 | 23.83 |
| ATOM | 666 | NH2 | ARG | 105 | 90.854 | 90.091 | 97.494 | 1.00 | 24.03 |
| ATOM | 667 | C | ARG | 105 | 90.750 | 87.485 | 93.016 | 1.00 | 21.25 |
| ATOM | 668 | O | ARG | 105 | 91.927 | 87.173 | 92.846 | 1.00 | 23.00 |
| ATOM | 669 | N | LYS | 106 | 89.991 | 86.934 | 93.961 | 1.00 | 21.27 |
| ATOM | 670 | CA | LYS | 106 | 90.511 | 85.879 | 94.837 | 1.00 | 23.38 |
| ATOM | 671 | CB | LYS | 106 | 89.429 | 85.363 | 95.789 | 1.00 | 25.15 |
| ATOM | 672 | CG | LYS | 106 | 89.012 | 86.317 | 96.883 | 1.00 | 26.05 |
| ATOM | 673 | CD | LYS | 106 | 87.917 | 85.692 | 97.720 | 1.00 | 24.75 |
| ATOM | 674 | CE | LYS | 106 | 87.424 | 86.662 | 98.761 | 1.00 | 29.64 |
| ATOM | 675 | NZ | LYS | 106 | 86.273 | 86.122 | 99.528 | 1.00 | 31.16 |
| ATOM | 676 | C | LYS | 106 | 90.988 | 84.705 | 93.992 | 1.00 | 25.07 |
| ATOM | 677 | O | LYS | 106 | 92.099 | 84.199 | 94.174 | 1.00 | 25.83 |
| ATOM | 678 | N | VAL | 107 | 90.119 | 84.269 | 93.084 | 1.00 | 25.62 |
| ATOM | 679 | CA | VAL | 107 | 90.411 | 83.156 | 92.193 | 1.00 | 26.60 |
| ATOM | 680 | CB | VAL | 107 | 89.172 | 82.815 | 91.313 | 1.00 | 29.16 |
| ATOM | 681 | CG1 | VAL | 107 | 89.529 | 81.801 | 90.242 | 1.00 | 34.41 |
| ATOM | 682 | CG2 | VAL | 107 | 88.066 | 82.255 | 92.175 | 1.00 | 28.28 |
| ATOM | 683 | C | VAL | 107 | 91.622 | 83.488 | 91.323 | 1.00 | 26.84 |
| ATOM | 684 | O | VAL | 107 | 92.581 | 82.713 | 91.272 | 1.00 | 27.67 |
| ATOM | 685 | N | LYS | 108 | 91.602 | 84.662 | 90.694 | 1.00 | 25.49 |
| ATOM | 686 | CA | LYS | 108 | 92.704 | 85.083 | 89.838 | 1.00 | 24.82 |
| ATOM | 687 | CB | LYS | 108 | 92.386 | 86.418 | 89.155 | 1.00 | 22.18 |
| ATOM | 688 | CG | LYS | 108 | 91.232 | 86.364 | 88.163 | 1.00 | 17.36 |
| ATOM | 689 | CD | LYS | 108 | 91.391 | 85.228 | 87.161 | 1.00 | 13.78 |
| ATOM | 690 | CE | LYS | 108 | 92.605 | 85.400 | 86.276 | 1.00 | 12.98 |
| ATOM | 691 | NZ | LYS | 108 | 92.735 | 84.290 | 85.287 | 1.00 | 13.57 |
| ATOM | 692 | C | LYS | 108 | 94.057 | 85.164 | 90.558 | 1.00 | 24.98 |
| ATOM | 693 | O | LYS | 108 | 95.087 | 84.792 | 89.998 | 1.00 | 24.14 |
| ATOM | 694 | N | LYS | 109 | 94.053 | 85.621 | 91.804 | 1.00 | 27.11 |
| ATOM | 695 | CA | LYS | 109 | 95.284 | 85.746 | 92.579 | 1.00 | 28.48 |
| ATOM | 696 | CB | LYS | 109 | 95.200 | 86.933 | 93.541 | 1.00 | 29.75 |
| ATOM | 697 | CG | LYS | 109 | 95.849 | 88.195 | 93.020 | 1.00 | 31.35 |
| ATOM | 698 | CD | LYS | 109 | 95.139 | 88.710 | 91.789 | 1.00 | 35.15 |
| ATOM | 699 | CE | LYS | 109 | 95.870 | 89.897 | 91.196 | 1.00 | 40.43 |
| ATOM | 700 | NZ | LYS | 109 | 97.184 | 89.511 | 90.621 | 1.00 | 41.81 |
| ATOM | 701 | C | LYS | 109 | 95.651 | 84.503 | 93.369 | 1.00 | 29.07 |
| ATOM | 702 | O | LYS | 109 | 96.618 | 84.520 | 94.123 | 1.00 | 33.10 |
| ATOM | 703 | N | TYR | 110 | 94.891 | 83.430 | 93.219 | 1.00 | 29.29 |
| ATOM | 704 | CA | TYR | 110 | 95.195 | 82.212 | 93.956 | 1.00 | 29.26 |
| ATOM | 705 | CB | TYR | 110 | 94.086 | 81.186 | 93.770 | 1.00 | 23.08 |

FIG. 1A-13

| ATOM | 706 | CG | TYR | 110 | 94.334 | 79.910 | 94.521 | 1.00 | 18.23 |
|---|---|---|---|---|---|---|---|---|---|
| ATOM | 707 | CD1 | TYR | 110 | 94.840 | 78.788 | 93.873 | 1.00 | 16.87 |
| ATOM | 708 | CE1 | TYR | 110 | 95.064 | 77.606 | 94.563 | 1.00 | 20.13 |
| ATOM | 709 | CD2 | TYR | 110 | 94.058 | 79.822 | 95.884 | 1.00 | 16.67 |
| ATOM | 710 | CE2 | TYR | 110 | 94.278 | 78.647 | 96.586 | 1.00 | 15.96 |
| ATOM | 711 | CZ | TYR | 110 | 94.780 | 77.541 | 95.919 | 1.00 | 20.03 |
| ATOM | 712 | OH | TYR | 110 | 94.994 | 76.366 | 96.605 | 1.00 | 24.77 |
| ATOM | 713 | C | TYR | 110 | 96.541 | 81.605 | 93.551 | 1.00 | 31.47 |
| ATOM | 714 | O | TYR | 110 | 97.252 | 81.042 | 94.381 | 1.00 | 30.19 |
| ATOM | 715 | N | GLU | 111 | 96.865 | 81.693 | 92.268 | 1.00 | 33.91 |
| ATOM | 716 | CA | GLU | 111 | 98.120 | 81.158 | 91.757 | 1.00 | 36.77 |
| ATOM | 717 | CB | GLU | 111 | 97.881 | 79.801 | 91.087 | 1.00 | 39.21 |
| ATOM | 718 | CG | GLU | 111 | 99.153 | 79.035 | 90.772 | 1.00 | 40.47 |
| ATOM | 719 | CD | GLU | 111 | 98.894 | 77.697 | 90.115 | 1.00 | 40.03 |
| ATOM | 720 | OE1 | GLU | 111 | 97.978 | 76.970 | 90.552 | 1.00 | 36.17 |
| ATOM | 721 | OE2 | GLU | 111 | 99.623 | 77.367 | 89.160 | 1.00 | 47.17 |
| ATOM | 722 | C | GLU | 111 | 98.627 | 82.177 | 90.746 | 1.00 | 37.77 |
| ATOM | 723 | O | GLU | 111 | 97.867 | 82.622 | 89.886 | 1.00 | 36.85 |
| ATOM | 724 | N | GLN | 112 | 99.901 | 82.546 | 90.847 | 1.00 | 39.85 |
| ATOM | 725 | CA | GLN | 112 | 100.455 | 83.557 | 89.947 | 1.00 | 43.24 |
| ATOM | 726 | CB | GLN | 112 | 100.630 | 84.872 | 90.709 | 1.00 | 44.65 |
| ATOM | 727 | CG | GLN | 112 | 99.351 | 85.463 | 91.255 | 1.00 | 45.65 |
| ATOM | 728 | CD | GLN | 112 | 99.615 | 86.631 | 92.169 | 1.00 | 48.62 |
| ATOM | 729 | OE1 | GLN | 112 | 100.161 | 87.656 | 91.749 | 1.00 | 51.83 |
| ATOM | 730 | NE2 | GLN | 112 | 99.243 | 86.484 | 93.433 | 1.00 | 48.44 |
| ATOM | 731 | C | GLN | 112 | 101.768 | 83.239 | 89.236 | 1.00 | 43.51 |
| ATOM | 732 | O | GLN | 112 | 101.930 | 83.530 | 88.048 | 1.00 | 43.39 |
| ATOM | 733 | N | GLY | 113 | 102.727 | 82.694 | 89.972 | 1.00 | 43.98 |
| ATOM | 734 | CA | GLY | 113 | 104.016 | 82.417 | 89.370 | 1.00 | 46.07 |
| ATOM | 735 | C | GLY | 113 | 104.873 | 83.672 | 89.450 | 1.00 | 45.94 |
| ATOM | 736 | O | GLY | 113 | 105.211 | 84.114 | 90.551 | 1.00 | 44.69 |
| ATOM | 737 | N | PHE | 114 | 105.178 | 84.274 | 88.303 | 1.00 | 46.93 |
| ATOM | 738 | CA | PHE | 114 | 106.012 | 85.476 | 88.258 | 1.00 | 49.84 |
| ATOM | 739 | CB | PHE | 114 | 106.576 | 85.697 | 86.848 | 1.00 | 49.51 |
| ATOM | 740 | CG | PHE | 114 | 107.780 | 84.853 | 86.538 | 1.00 | 53.18 |
| ATOM | 741 | CD1 | PHE | 114 | 109.002 | 85.113 | 87.147 | 1.00 | 54.85 |
| ATOM | 742 | CD2 | PHE | 114 | 107.690 | 83.786 | 85.653 | 1.00 | 55.88 |
| ATOM | 743 | CE1 | PHE | 114 | 110.116 | 84.320 | 86.883 | 1.00 | 54.76 |
| ATOM | 744 | CE2 | PHE | 114 | 108.801 | 82.986 | 85.383 | 1.00 | 57.03 |
| ATOM | 745 | CZ | PHE | 114 | 110.017 | 83.256 | 86.002 | 1.00 | 56.60 |
| ATOM | 746 | C | PHE | 114 | 105.284 | 86.729 | 88.714 | 1.00 | 52.11 |
| ATOM | 747 | O | PHE | 114 | 104.750 | 87.471 | 87.889 | 1.00 | 54.09 |
| ATOM | 748 | N | ILE | 115 | 105.289 | 86.986 | 90.018 | 1.00 | 53.71 |
| ATOM | 749 | CA | ILE | 115 | 104.613 | 88.163 | 90.559 | 1.00 | 55.83 |
| ATOM | 750 | CB | ILE | 115 | 104.342 | 88.018 | 92.092 | 1.00 | 56.93 |
| ATOM | 751 | CG2 | ILE | 115 | 103.879 | 86.587 | 92.409 | 1.00 | 54.73 |
| ATOM | 752 | CG1 | ILE | 115 | 105.595 | 88.326 | 92.919 | 1.00 | 58.54 |
| ATOM | 753 | CD1 | ILE | 115 | 105.376 | 88.251 | 94.423 | 1.00 | 58.29 |
| ATOM | 754 | C | ILE | 115 | 105.429 | 89.418 | 90.237 | 1.00 | 56.92 |
| ATOM | 755 | O | ILE | 115 | 106.630 | 89.476 | 90.516 | 1.00 | 57.36 |
| ATOM | 756 | N | THR | 116 | 104.788 | 90.399 | 89.605 | 1.00 | 58.66 |
| ATOM | 757 | CA | THR | 116 | 105.474 | 91.633 | 89.222 | 1.00 | 61.25 |
| ATOM | 758 | CB | THR | 116 | 105.077 | 92.065 | 87.797 | 1.00 | 60.84 |
| ATOM | 759 | OG1 | THR | 116 | 105.221 | 90.952 | 86.908 | 1.00 | 59.09 |
| ATOM | 760 | CG2 | THR | 116 | 105.966 | 93.213 | 87.312 | 1.00 | 62.79 |
| ATOM | 761 | C | THR | 116 | 105.304 | 92.822 | 90.171 | 1.00 | 62.74 |
| ATOM | 762 | O | THR | 116 | 106.278 | 93.470 | 90.538 | 1.00 | 62.00 |
| ATOM | 763 | N | ASP | 117 | 104.067 | 93.118 | 90.553 | 1.00 | 65.44 |
| ATOM | 764 | CA | ASP | 117 | 103.803 | 94.241 | 91.448 | 1.00 | 68.28 |

FIG. 1A-14

| ATOM | 765 | CB  | ASP | 117 | 102.351 | 94.209  | 91.959  | 1.00 | 70.75  |
| ---- | --- | --- | --- | --- | ------- | ------- | ------- | ---- | ------ |
| ATOM | 766 | CG  | ASP | 117 | 101.990 | 92.899  | 92.650  | 1.00 | 73.11  |
| ATOM | 767 | OD1 | ASP | 117 | 102.166 | 92.805  | 93.884  | 1.00 | 74.55  |
| ATOM | 768 | OD2 | ASP | 117 | 101.512 | 91.970  | 91.961  | 1.00 | 74.48  |
| ATOM | 769 | C   | ASP | 117 | 104.789 | 94.296  | 92.614  | 1.00 | 68.68  |
| ATOM | 770 | O   | ASP | 117 | 105.478 | 95.303  | 92.819  | 1.00 | 69.52  |
| ATOM | 771 | N   | ALA | 118 | 104.909 | 93.187  | 93.333  | 1.00 | 68.01  |
| ATOM | 772 | CA  | ALA | 118 | 105.812 | 93.131  | 94.466  | 1.00 | 67.77  |
| ATOM | 773 | CB  | ALA | 118 | 105.317 | 92.112  | 95.483  | 1.00 | 65.37  |
| ATOM | 774 | C   | ALA | 118 | 107.224 | 92.790  | 94.003  | 1.00 | 68.47  |
| ATOM | 775 | O   | ALA | 118 | 107.904 | 91.980  | 94.640  | 1.00 | 70.14  |
| ATOM | 776 | N   | ALA | 119 | 107.681 | 93.441  | 92.933  | 1.00 | 67.63  |
| ATOM | 777 | CA  | ALA | 119 | 109.021 | 93.204  | 92.399  | 1.00 | 65.42  |
| ATOM | 778 | CB  | ALA | 119 | 109.170 | 91.741  | 92.014  | 1.00 | 66.53  |
| ATOM | 779 | C   | ALA | 119 | 109.392 | 94.098  | 91.210  | 1.00 | 64.47  |
| ATOM | 780 | O   | ALA | 119 | 109.417 | 93.639  | 90.065  | 1.00 | 64.14  |
| ATOM | 781 | N   | ALA | 120 | 109.706 | 95.360  | 91.489  | 1.00 | 63.47  |
| ATOM | 782 | CA  | ALA | 120 | 110.098 | 96.316  | 90.452  | 1.00 | 62.64  |
| ATOM | 783 | CB  | ALA | 120 | 109.071 | 96.341  | 89.320  | 1.00 | 62.95  |
| ATOM | 784 | C   | ALA | 120 | 110.260 | 97.714  | 91.040  | 1.00 | 62.70  |
| ATOM | 785 | O   | ALA | 120 | 111.374 | 98.267  | 90.938  | 1.00 | 61.41  |
| ATOM | 786 | CB  | ALA | 125 | 109.000 | 94.859  | 98.198  | 1.00 | 153.76 |
| ATOM | 787 | C   | ALA | 125 | 109.160 | 95.344  | 95.747  | 1.00 | 153.51 |
| ATOM | 788 | O   | ALA | 125 | 109.902 | 94.992  | 94.829  | 1.00 | 153.54 |
| ATOM | 789 | N   | ALA | 125 | 109.423 | 93.056  | 96.557  | 1.00 | 154.27 |
| ATOM | 790 | CA  | ALA | 125 | 108.704 | 94.339  | 96.796  | 1.00 | 153.73 |
| ATOM | 791 | N   | ALA | 126 | 108.691 | 96.581  | 95.860  | 1.00 | 153.23 |
| ATOM | 792 | CA  | ALA | 126 | 109.075 | 97.621  | 94.916  | 1.00 | 153.16 |
| ATOM | 793 | CB  | ALA | 126 | 108.212 | 98.860  | 95.121  | 1.00 | 153.36 |
| ATOM | 794 | C   | ALA | 126 | 110.549 | 97.962  | 95.120  | 1.00 | 153.01 |
| ATOM | 795 | O   | ALA | 126 | 111.079 | 97.803  | 96.222  | 1.00 | 153.16 |
| ATOM | 796 | N   | ALA | 127 | 111.212 | 98.384  | 94.048  | 1.00 | 152.83 |
| ATOM | 797 | CA  | ALA | 127 | 112.621 | 98.754  | 94.114  | 1.00 | 152.63 |
| ATOM | 798 | CB  | ALA | 127 | 113.447 | 97.885  | 93.169  | 1.00 | 152.13 |
| ATOM | 799 | C   | ALA | 127 | 112.758 | 100.234 | 93.758  | 1.00 | 152.39 |
| ATOM | 800 | O   | ALA | 127 | 112.812 | 101.083 | 94.650  | 1.00 | 152.11 |
| ATOM | 801 | N   | ALA | 128 | 112.772 | 100.532 | 92.459  | 1.00 | 152.16 |
| ATOM | 802 | CA  | ALA | 128 | 112.884 | 101.901 | 91.953  | 1.00 | 151.90 |
| ATOM | 803 | CB  | ALA | 128 | 111.505 | 102.561 | 91.919  | 1.00 | 151.79 |
| ATOM | 804 | C   | ALA | 128 | 113.871 | 102.776 | 92.727  | 1.00 | 151.56 |
| ATOM | 805 | O   | ALA | 128 | 115.058 | 102.392 | 92.783  | 1.00 | 151.27 |
| ATOM | 806 | CB  | ALA | 131 | 115.610 | 90.226  | 103.503 | 1.00 | 85.15  |
| ATOM | 807 | C   | ALA | 131 | 116.950 | 91.870  | 102.162 | 1.00 | 82.41  |
| ATOM | 808 | O   | ALA | 131 | 117.960 | 92.557  | 102.293 | 1.00 | 82.59  |
| ATOM | 809 | N   | ALA | 131 | 114.753 | 92.513  | 103.126 | 1.00 | 84.45  |
| ATOM | 810 | CA  | ALA | 131 | 115.979 | 91.696  | 103.329 | 1.00 | 83.91  |
| ATOM | 811 | N   | ALA | 132 | 116.601 | 91.294  | 101.015 | 1.00 | 81.04  |
| ATOM | 812 | CA  | ALA | 132 | 117.423 | 91.354  | 99.810  | 1.00 | 80.28  |
| ATOM | 813 | CB  | ALA | 132 | 116.642 | 90.807  | 98.627  | 1.00 | 80.36  |
| ATOM | 814 | C   | ALA | 132 | 117.962 | 92.740  | 99.476  | 1.00 | 80.39  |
| ATOM | 815 | O   | ALA | 132 | 117.357 | 93.757  | 99.820  | 1.00 | 80.20  |
| ATOM | 816 | N   | ALA | 133 | 119.116 | 92.771  | 98.819  | 1.00 | 80.93  |
| ATOM | 817 | CA  | ALA | 133 | 119.746 | 94.022  | 98.414  | 1.00 | 81.53  |
| ATOM | 818 | CB  | ALA | 133 | 121.079 | 94.193  | 99.123  | 1.00 | 80.70  |
| ATOM | 819 | C   | ALA | 133 | 119.942 | 94.038  | 96.902  | 1.00 | 82.58  |
| ATOM | 820 | O   | ALA | 133 | 121.026 | 94.358  | 96.414  | 1.00 | 82.75  |
| ATOM | 821 | N   | ALA | 134 | 118.887 | 93.681  | 96.173  | 1.00 | 83.81  |
| ATOM | 822 | CA  | ALA | 134 | 118.921 | 93.629  | 94.711  | 1.00 | 83.39  |
| ATOM | 823 | CB  | ALA | 134 | 117.965 | 92.545  | 94.198  | 1.00 | 82.19  |

FIG. 1A-15

| ATOM | 824 | C | ALA | 134 | 118.568 | 94.980 | 94.097 | 1.00 | 82.93 |
| --- | --- | --- | --- | --- | --- | --- | --- | --- | --- |
| ATOM | 825 | O | ALA | 134 | 119.388 | 95.912 | 94.241 | 1.00 | 82.67 |
| ATOM | 826 | CB | ALA | 150 | 120.001 | 97.614 | 89.743 | 1.00 | 101.69 |
| ATOM | 827 | C | ALA | 150 | 118.719 | 98.142 | 91.821 | 1.00 | 100.94 |
| ATOM | 828 | O | ALA | 150 | 117.883 | 97.395 | 92.335 | 1.00 | 100.35 |
| ATOM | 829 | N | ALA | 150 | 120.213 | 96.186 | 91.749 | 1.00 | 101.14 |
| ATOM | 830 | CA | ALA | 150 | 120.017 | 97.577 | 91.261 | 1.00 | 101.10 |
| ATOM | 831 | N | ALA | 151 | 118.540 | 99.452 | 91.659 | 1.00 | 101.13 |
| ATOM | 832 | CA | ALA | 151 | 117.370 | 100.181 | 92.157 | 1.00 | 100.24 |
| ATOM | 833 | CB | ALA | 151 | 116.061 | 99.469 | 91.761 | 1.00 | 100.01 |
| ATOM | 834 | C | ALA | 151 | 117.505 | 100.323 | 93.681 | 1.00 | 98.83 |
| ATOM | 835 | O | ALA | 151 | 118.409 | 101.018 | 94.154 | 1.00 | 99.01 |
| ATOM | 836 | N | ALA | 152 | 116.644 | 99.649 | 94.440 | 1.00 | 96.46 |
| ATOM | 837 | CA | ALA | 152 | 116.703 | 99.696 | 95.902 | 1.00 | 92.96 |
| ATOM | 838 | CB | ALA | 152 | 116.218 | 101.052 | 96.416 | 1.00 | 93.49 |
| ATOM | 839 | C | ALA | 152 | 115.857 | 98.567 | 96.484 | 1.00 | 90.09 |
| ATOM | 840 | O | ALA | 152 | 115.387 | 98.644 | 97.620 | 1.00 | 89.57 |
| ATOM | 841 | N | ALA | 153 | 115.715 | 97.496 | 95.710 | 1.00 | 87.27 |
| ATOM | 842 | CA | ALA | 153 | 114.922 | 96.345 | 96.118 | 1.00 | 85.11 |
| ATOM | 843 | CB | ALA | 153 | 115.035 | 95.242 | 95.089 | 1.00 | 87.03 |
| ATOM | 844 | C | ALA | 153 | 115.297 | 95.820 | 97.497 | 1.00 | 83.27 |
| ATOM | 845 | O | ALA | 153 | 116.343 | 95.190 | 97.687 | 1.00 | 82.09 |
| ATOM | 846 | N | ALA | 154 | 114.438 | 96.116 | 98.464 | 1.00 | 82.07 |
| ATOM | 847 | CA | ALA | 154 | 114.633 | 95.680 | 99.838 | 1.00 | 79.91 |
| ATOM | 848 | CB | ALA | 154 | 113.774 | 96.528 | 100.784 | 1.00 | 80.13 |
| ATOM | 849 | C | ALA | 154 | 114.308 | 94.188 | 100.000 | 1.00 | 77.83 |
| ATOM | 850 | O | ALA | 154 | 114.751 | 93.551 | 100.963 | 1.00 | 77.74 |
| ATOM | 851 | N | ALA | 155 | 113.533 | 93.640 | 99.066 | 1.00 | 74.67 |
| ATOM | 852 | CA | ALA | 155 | 113.145 | 92.231 | 99.083 | 1.00 | 71.48 |
| ATOM | 853 | CB | ALA | 155 | 112.173 | 91.958 | 100.221 | 1.00 | 70.07 |
| ATOM | 854 | C | ALA | 155 | 112.518 | 91.835 | 97.752 | 1.00 | 70.62 |
| ATOM | 855 | O | ALA | 155 | 112.036 | 92.752 | 97.053 | 1.00 | 68.84 |
| ATOM | 856 | CB | ALA | 178 | 117.058 | 95.505 | 102.209 | 1.00 | 58.93 |
| ATOM | 857 | C | ALA | 178 | 119.494 | 95.204 | 102.731 | 1.00 | 57.03 |
| ATOM | 858 | O | ALA | 178 | 120.605 | 95.013 | 102.255 | 1.00 | 55.07 |
| ATOM | 859 | N | ALA | 178 | 118.804 | 95.985 | 100.513 | 1.00 | 59.48 |
| ATOM | 860 | CA | ALA | 178 | 118.475 | 96.029 | 101.962 | 1.00 | 58.59 |
| ATOM | 861 | N | ALA | 179 | 119.102 | 94.724 | 103.907 | 1.00 | 57.92 |
| ATOM | 862 | CA | ALA | 179 | 119.967 | 93.936 | 104.773 | 1.00 | 60.34 |
| ATOM | 863 | CB | ALA | 179 | 119.171 | 93.363 | 105.938 | 1.00 | 61.38 |
| ATOM | 864 | C | ALA | 179 | 120.710 | 92.832 | 104.044 | 1.00 | 61.59 |
| ATOM | 865 | O | ALA | 179 | 121.839 | 93.038 | 103.606 | 1.00 | 61.85 |
| ATOM | 866 | N | THR | 180 | 120.087 | 91.663 | 103.923 | 1.00 | 63.95 |
| ATOM | 867 | CA | THR | 180 | 120.718 | 90.536 | 103.245 | 1.00 | 65.71 |
| ATOM | 868 | CB | THR | 180 | 119.769 | 89.327 | 103.154 | 1.00 | 66.48 |
| ATOM | 869 | OG1 | THR | 180 | 119.034 | 89.205 | 104.381 | 1.00 | 66.35 |
| ATOM | 870 | CG2 | THR | 180 | 120.569 | 88.047 | 102.927 | 1.00 | 66.06 |
| ATOM | 871 | C | THR | 180 | 121.139 | 90.989 | 101.851 | 1.00 | 66.16 |
| ATOM | 872 | O | THR | 180 | 120.313 | 91.168 | 100.950 | 1.00 | 67.87 |
| ATOM | 873 | N | LYS | 181 | 122.432 | 91.247 | 101.713 | 1.00 | 65.64 |
| ATOM | 874 | CA | LYS | 181 | 122.995 | 91.718 | 100.463 | 1.00 | 64.54 |
| ATOM | 875 | CB | LYS | 181 | 124.436 | 92.200 | 100.664 | 1.00 | 65.30 |
| ATOM | 876 | CG | LYS | 181 | 125.255 | 91.387 | 101.658 | 1.00 | 66.54 |
| ATOM | 877 | CD | LYS | 181 | 125.181 | 91.984 | 103.053 | 1.00 | 66.15 |
| ATOM | 878 | CE | LYS | 181 | 125.741 | 93.398 | 103.078 | 1.00 | 65.67 |
| ATOM | 879 | NZ | LYS | 181 | 125.692 | 93.970 | 104.451 | 1.00 | 68.13 |
| ATOM | 880 | C | LYS | 181 | 122.921 | 90.750 | 99.291 | 1.00 | 63.31 |
| ATOM | 881 | O | LYS | 181 | 122.910 | 89.522 | 99.456 | 1.00 | 63.71 |
| ATOM | 882 | N | ARG | 182 | 122.872 | 91.339 | 98.101 | 1.00 | 61.46 |

FIG. 1A-16

| ATOM | 883 | CA | ARG | 182 | 122.819 | 90.610 | 96.846 | 1.00 | 58.88 |
|------|-----|-----|------|-----|---------|--------|--------|------|-------|
| ATOM | 884 | CB | ARG | 182 | 122.421 | 91.564 | 95.716 | 1.00 | 54.15 |
| ATOM | 885 | CG | ARG | 182 | 121.792 | 90.907 | 94.497 | 1.00 | 48.60 |
| ATOM | 886 | CD | ARG | 182 | 122.610 | 89.741 | 94.004 | 1.00 | 43.01 |
| ATOM | 887 | NE | ARG | 182 | 122.512 | 89.563 | 92.565 | 1.00 | 39.07 |
| ATOM | 888 | CZ | ARG | 182 | 123.036 | 88.533 | 91.917 | 1.00 | 40.43 |
| ATOM | 889 | NH1 | ARG | 182 | 122.913 | 88.445 | 90.600 | 1.00 | 40.22 |
| ATOM | 890 | NH2 | ARG | 182 | 123.654 | 87.571 | 92.594 | 1.00 | 43.27 |
| ATOM | 891 | C | ARG | 182 | 124.217 | 90.054 | 96.573 | 1.00 | 59.57 |
| ATOM | 892 | O | ARG | 182 | 125.011 | 90.671 | 95.860 | 1.00 | 60.17 |
| ATOM | 893 | N | GLU | 183 | 124.519 | 88.916 | 97.187 | 1.00 | 59.09 |
| ATOM | 894 | CA | GLU | 183 | 125.801 | 88.231 | 97.025 | 1.00 | 59.57 |
| ATOM | 895 | CB | GLU | 183 | 126.975 | 89.090 | 97.517 | 1.00 | 58.15 |
| ATOM | 896 | CG | GLU | 183 | 126.849 | 89.602 | 98.937 | 1.00 | 57.54 |
| ATOM | 897 | CD | GLU | 183 | 127.979 | 90.536 | 99.327 | 1.00 | 57.01 |
| ATOM | 898 | OE1 | GLU | 183 | 128.763 | 90.171 | 100.233 | 1.00 | 55.91 |
| ATOM | 899 | OE2 | GLU | 183 | 128.075 | 91.637 | 98.738 | 1.00 | 53.83 |
| ATOM | 900 | C | GLU | 183 | 125.716 | 86.921 | 97.794 | 1.00 | 60.42 |
| ATOM | 901 | O | GLU | 183 | 126.235 | 85.891 | 97.356 | 1.00 | 60.81 |
| ATOM | 902 | N | ASP | 184 | 125.022 | 86.969 | 98.929 | 1.00 | 60.17 |
| ATOM | 903 | CA | ASP | 184 | 124.815 | 85.793 | 99.765 | 1.00 | 59.99 |
| ATOM | 904 | CB | ASP | 184 | 124.755 | 86.203 | 101.240 | 1.00 | 61.87 |
| ATOM | 905 | CG | ASP | 184 | 126.073 | 86.771 | 101.743 | 1.00 | 64.92 |
| ATOM | 906 | OD1 | ASP | 184 | 126.328 | 87.976 | 101.538 | 1.00 | 67.44 |
| ATOM | 907 | OD2 | ASP | 184 | 126.856 | 86.008 | 102.349 | 1.00 | 65.08 |
| ATOM | 908 | C | ASP | 184 | 123.499 | 85.119 | 99.348 | 1.00 | 59.20 |
| ATOM | 909 | O | ASP | 184 | 123.287 | 83.925 | 99.590 | 1.00 | 59.14 |
| ATOM | 910 | N | LEU | 185 | 122.649 | 85.897 | 98.677 | 1.00 | 57.41 |
| ATOM | 911 | CA | LEU | 185 | 121.339 | 85.451 | 98.208 | 1.00 | 54.68 |
| ATOM | 912 | CB | LEU | 185 | 120.368 | 86.630 | 98.202 | 1.00 | 59.34 |
| ATOM | 913 | CG | LEU | 185 | 119.442 | 86.732 | 99.410 | 1.00 | 65.19 |
| ATOM | 914 | CD1 | LEU | 185 | 118.532 | 87.934 | 99.228 | 1.00 | 68.24 |
| ATOM | 915 | CD2 | LEU | 185 | 118.621 | 85.444 | 99.556 | 1.00 | 67.95 |
| ATOM | 916 | C | LEU | 185 | 121.312 | 84.816 | 96.826 | 1.00 | 50.51 |
| ATOM | 917 | O | LEU | 185 | 121.970 | 85.296 | 95.903 | 1.00 | 51.04 |
| ATOM | 918 | N | VAL | 186 | 120.500 | 83.775 | 96.670 | 1.00 | 45.95 |
| ATOM | 919 | CA | VAL | 186 | 120.373 | 83.120 | 95.373 | 1.00 | 41.48 |
| ATOM | 920 | CB | VAL | 186 | 120.076 | 81.583 | 95.481 | 1.00 | 38.55 |
| ATOM | 921 | CG1 | VAL | 186 | 119.581 | 81.216 | 96.851 | 1.00 | 38.61 |
| ATOM | 922 | CG2 | VAL | 186 | 119.097 | 81.133 | 94.406 | 1.00 | 39.62 |
| ATOM | 923 | C | VAL | 186 | 119.351 | 83.878 | 94.523 | 1.00 | 38.45 |
| ATOM | 924 | O | VAL | 186 | 118.301 | 84.292 | 94.997 | 1.00 | 36.70 |
| ATOM | 925 | N | VAL | 187 | 119.710 | 84.081 | 93.268 | 1.00 | 37.17 |
| ATOM | 926 | CA | VAL | 187 | 118.910 | 84.821 | 92.316 | 1.00 | 35.95 |
| ATOM | 927 | CB | VAL | 187 | 119.653 | 86.153 | 92.008 | 1.00 | 34.84 |
| ATOM | 928 | CG1 | VAL | 187 | 119.220 | 86.767 | 90.701 | 1.00 | 36.63 |
| ATOM | 929 | CG2 | VAL | 187 | 119.444 | 87.125 | 93.149 | 1.00 | 34.16 |
| ATOM | 930 | C | VAL | 187 | 118.736 | 83.971 | 91.054 | 1.00 | 37.32 |
| ATOM | 931 | O | VAL | 187 | 119.364 | 82.919 | 90.922 | 1.00 | 37.20 |
| ATOM | 932 | N | ALA | 188 | 117.824 | 84.383 | 90.176 | 1.00 | 37.27 |
| ATOM | 933 | CA | ALA | 188 | 117.579 | 83.687 | 88.924 | 1.00 | 38.14 |
| ATOM | 934 | CB | ALA | 188 | 116.316 | 82.867 | 89.016 | 1.00 | 38.85 |
| ATOM | 935 | C | ALA | 188 | 117.462 | 84.720 | 87.812 | 1.00 | 39.78 |
| ATOM | 936 | O | ALA | 188 | 116.878 | 85.786 | 88.009 | 1.00 | 40.14 |
| ATOM | 937 | N | PRO | 189 | 118.041 | 84.430 | 86.637 | 1.00 | 42.72 |
| ATOM | 938 | CD | PRO | 189 | 118.817 | 83.213 | 86.349 | 1.00 | 42.66 |
| ATOM | 939 | CA | PRO | 189 | 118.024 | 85.317 | 85.463 | 1.00 | 44.91 |
| ATOM | 940 | CB | PRO | 189 | 118.901 | 84.563 | 84.454 | 1.00 | 42.51 |
| ATOM | 941 | CG | PRO | 189 | 119.766 | 83.699 | 85.305 | 1.00 | 41.78 |

FIG. 1A-17

| | | | | | | | | | |
|---|---|---|---|---|---|---|---|---|---|
| ATOM | 942 | C | PRO | 189 | 116.625 | 85.519 | 84.890 | 1.00 | 46.91 |
| ATOM | 943 | O | PRO | 189 | 115.741 | 84.675 | 85.063 | 1.00 | 47.16 |
| ATOM | 944 | N | ALA | 190 | 116.424 | 86.644 | 84.216 | 1.00 | 49.15 |
| ATOM | 945 | CA | ALA | 190 | 115.139 | 86.925 | 83.589 | 1.00 | 52.79 |
| ATOM | 946 | CB | ALA | 190 | 114.993 | 88.417 | 83.305 | 1.00 | 53.46 |
| ATOM | 947 | C | ALA | 190 | 115.121 | 86.130 | 82.291 | 1.00 | 54.43 |
| ATOM | 948 | O | ALA | 190 | 116.148 | 86.012 | 81.619 | 1.00 | 55.47 |
| ATOM | 949 | N | GLY | 191 | 113.966 | 85.577 | 81.941 | 1.00 | 55.80 |
| ATOM | 950 | CA | GLY | 191 | 113.873 | 84.792 | 80.727 | 1.00 | 57.80 |
| ATOM | 951 | C | GLY | 191 | 113.784 | 83.309 | 81.033 | 1.00 | 59.83 |
| ATOM | 952 | O | GLY | 191 | 113.512 | 82.502 | 80.142 | 1.00 | 61.79 |
| ATOM | 953 | N | ILE | 192 | 114.052 | 82.932 | 82.280 | 1.00 | 60.59 |
| ATOM | 954 | CA | ILE | 192 | 113.958 | 81.528 | 82.660 | 1.00 | 61.86 |
| ATOM | 955 | CB | ILE | 192 | 114.564 | 81.224 | 84.062 | 1.00 | 61.08 |
| ATOM | 956 | CG2 | ILE | 192 | 116.035 | 81.594 | 84.101 | 1.00 | 62.19 |
| ATOM | 957 | CG1 | ILE | 192 | 113.773 | 81.933 | 85.164 | 1.00 | 59.47 |
| ATOM | 958 | CD1 | ILE | 192 | 114.135 | 81.476 | 86.552 | 1.00 | 57.49 |
| ATOM | 959 | C | ILE | 192 | 112.481 | 81.175 | 82.692 | 1.00 | 63.40 |
| ATOM | 960 | O | ILE | 192 | 111.626 | 82.016 | 82.416 | 1.00 | 63.75 |
| ATOM | 961 | N | THR | 193 | 112.180 | 79.934 | 83.035 | 1.00 | 65.22 |
| ATOM | 962 | CA | THR | 193 | 110.800 | 79.504 | 83.110 | 1.00 | 68.24 |
| ATOM | 963 | CB | THR | 193 | 110.494 | 78.402 | 82.062 | 1.00 | 72.25 |
| ATOM | 964 | OG1 | THR | 193 | 109.082 | 78.122 | 82.046 | 1.00 | 75.84 |
| ATOM | 965 | CG2 | THR | 193 | 111.273 | 77.124 | 82.374 | 1.00 | 72.73 |
| ATOM | 966 | C | THR | 193 | 110.536 | 78.993 | 84.519 | 1.00 | 68.78 |
| ATOM | 967 | O | THR | 193 | 111.458 | 78.876 | 85.333 | 1.00 | 68.57 |
| ATOM | 968 | N | LEU | 194 | 109.274 | 78.680 | 84.790 | 1.00 | 69.53 |
| ATOM | 969 | CA | LEU | 194 | 108.848 | 78.179 | 86.089 | 1.00 | 70.58 |
| ATOM | 970 | CB | LEU | 194 | 107.334 | 77.982 | 86.095 | 1.00 | 67.74 |
| ATOM | 971 | CG | LEU | 194 | 106.529 | 79.277 | 86.033 | 1.00 | 62.43 |
| ATOM | 972 | CD1 | LEU | 194 | 105.081 | 78.958 | 85.786 | 1.00 | 62.21 |
| ATOM | 973 | CD2 | LEU | 194 | 106.697 | 80.049 | 87.328 | 1.00 | 60.58 |
| ATOM | 974 | C | LEU | 194 | 109.557 | 76.885 | 86.480 | 1.00 | 72.55 |
| ATOM | 975 | O | LEU | 194 | 109.900 | 76.687 | 87.651 | 1.00 | 72.45 |
| ATOM | 976 | N | LYS | 195 | 109.770 | 76.006 | 85.502 | 1.00 | 74.70 |
| ATOM | 977 | CA | LYS | 195 | 110.456 | 74.740 | 85.749 | 1.00 | 76.60 |
| ATOM | 978 | CB | LYS | 195 | 110.556 | 73.916 | 84.459 | 1.00 | 77.31 |
| ATOM | 979 | CG | LYS | 195 | 111.287 | 72.586 | 84.628 | 1.00 | 79.15 |
| ATOM | 980 | CD | LYS | 195 | 110.574 | 71.695 | 85.640 | 1.00 | 81.61 |
| ATOM | 981 | CE | LYS | 195 | 111.402 | 70.471 | 86.004 | 1.00 | 82.03 |
| ATOM | 982 | NZ | LYS | 195 | 111.733 | 69.639 | 84.814 | 1.00 | 83.87 |
| ATOM | 983 | C | LYS | 195 | 111.853 | 75.041 | 86.287 | 1.00 | 77.85 |
| ATOM | 984 | O | LYS | 195 | 112.252 | 74.519 | 87.330 | 1.00 | 77.77 |
| ATOM | 985 | N | GLU | 196 | 112.572 | 75.911 | 85.579 | 1.00 | 78.89 |
| ATOM | 986 | CA | GLU | 196 | 113.920 | 76.312 | 85.968 | 1.00 | 79.64 |
| ATOM | 987 | CB | GLU | 196 | 114.464 | 77.349 | 84.983 | 1.00 | 83.46 |
| ATOM | 988 | CG | GLU | 196 | 114.576 | 76.850 | 83.547 | 1.00 | 90.70 |
| ATOM | 989 | CD | GLU | 196 | 115.039 | 77.931 | 82.578 | 1.00 | 97.03 |
| ATOM | 990 | OE1 | GLU | 196 | 114.240 | 78.324 | 81.699 | 1.00 | 99.18 |
| ATOM | 991 | OE2 | GLU | 196 | 116.202 | 78.383 | 82.686 | 1.00 | 100.67 |
| ATOM | 992 | C | GLU | 196 | 113.859 | 76.918 | 87.362 | 1.00 | 78.68 |
| ATOM | 993 | O | GLU | 196 | 114.594 | 76.512 | 88.262 | 1.00 | 78.96 |
| ATOM | 994 | N | ALA | 197 | 112.928 | 77.850 | 87.533 | 1.00 | 77.97 |
| ATOM | 995 | CA | ALA | 197 | 112.707 | 78.556 | 88.789 | 1.00 | 77.86 |
| ATOM | 996 | CB | ALA | 197 | 111.471 | 79.418 | 88.666 | 1.00 | 76.91 |
| ATOM | 997 | C | ALA | 197 | 112.574 | 77.637 | 89.999 | 1.00 | 78.58 |
| ATOM | 998 | O | ALA | 197 | 113.120 | 77.920 | 91.067 | 1.00 | 77.61 |
| ATOM | 999 | N | ASN | 198 | 111.834 | 76.548 | 89.826 | 1.00 | 80.25 |
| ATOM | 1000 | CA | ASN | 198 | 111.604 | 75.581 | 90.897 | 1.00 | 82.34 |

FIG. 1A-18

| ATOM | 1001 | CB | ASN | 198 | 110.664 | 74.473 | 90.401 | 1.00 | 86.10 |
| --- | --- | --- | --- | --- | --- | --- | --- | --- | --- |
| ATOM | 1002 | CG | ASN | 198 | 110.268 | 73.502 | 91.502 | 1.00 | 89.51 |
| ATOM | 1003 | OD1 | ASN | 198 | 110.999 | 72.559 | 91.811 | 1.00 | 91.70 |
| ATOM | 1004 | ND2 | ASN | 198 | 109.095 | 73.718 | 92.085 | 1.00 | 90.35 |
| ATOM | 1005 | C | ASN | 198 | 112.898 | 74.968 | 91.429 | 1.00 | 81.89 |
| ATOM | 1006 | O | ASN | 198 | 113.207 | 75.067 | 92.620 | 1.00 | 81.46 |
| ATOM | 1007 | N | GLU | 199 | 113.666 | 74.360 | 90.533 | 1.00 | 81.93 |
| ATOM | 1008 | CA | GLU | 199 | 114.914 | 73.719 | 90.907 | 1.00 | 82.51 |
| ATOM | 1009 | CB | GLU | 199 | 115.504 | 72.990 | 89.701 | 1.00 | 84.93 |
| ATOM | 1010 | CG | GLU | 199 | 116.740 | 72.168 | 90.020 | 1.00 | 91.19 |
| ATOM | 1011 | CD | GLU | 199 | 117.236 | 71.365 | 88.829 | 1.00 | 95.27 |
| ATOM | 1012 | OE1 | GLU | 199 | 117.505 | 71.970 | 87.766 | 1.00 | 96.08 |
| ATOM | 1013 | OE2 | GLU | 199 | 117.356 | 70.126 | 88.962 | 1.00 | 97.16 |
| ATOM | 1014 | C | GLU | 199 | 115.924 | 74.712 | 91.472 | 1.00 | 82.16 |
| ATOM | 1015 | O | GLU | 199 | 116.461 | 74.496 | 92.562 | 1.00 | 82.41 |
| ATOM | 1016 | N | ILE | 200 | 116.127 | 75.816 | 90.751 | 1.00 | 81.63 |
| ATOM | 1017 | CA | ILE | 200 | 117.077 | 76.871 | 91.121 | 1.00 | 80.38 |
| ATOM | 1018 | CB | ILE | 200 | 116.824 | 78.167 | 90.306 | 1.00 | 76.64 |
| ATOM | 1019 | CG2 | ILE | 200 | 117.588 | 79.349 | 90.897 | 1.00 | 75.73 |
| ATOM | 1020 | CG1 | ILE | 200 | 117.232 | 77.948 | 88.846 | 1.00 | 74.46 |
| ATOM | 1021 | CD1 | ILE | 200 | 116.991 | 79.141 | 87.945 | 1.00 | 74.00 |
| ATOM | 1022 | C | ILE | 200 | 117.163 | 77.194 | 92.612 | 1.00 | 81.94 |
| ATOM | 1023 | O | ILE | 200 | 118.217 | 77.596 | 93.100 | 1.00 | 83.53 |
| ATOM | 1024 | N | LEU | 201 | 116.069 | 77.018 | 93.337 | 1.00 | 82.67 |
| ATOM | 1025 | CA | LEU | 201 | 116.081 | 77.281 | 94.766 | 1.00 | 84.58 |
| ATOM | 1026 | CB | LEU | 201 | 115.479 | 78.658 | 95.062 | 1.00 | 86.28 |
| ATOM | 1027 | CG | LEU | 201 | 115.486 | 79.153 | 96.510 | 1.00 | 87.58 |
| ATOM | 1028 | CD1 | LEU | 201 | 116.907 | 79.183 | 97.046 | 1.00 | 85.65 |
| ATOM | 1029 | CD2 | LEU | 201 | 114.851 | 80.534 | 96.583 | 1.00 | 89.05 |
| ATOM | 1030 | C | LEU | 201 | 115.289 | 76.180 | 95.443 | 1.00 | 85.36 |
| ATOM | 1031 | O | LEU | 201 | 114.254 | 76.425 | 96.056 | 1.00 | 84.76 |
| ATOM | 1032 | N | GLN | 202 | 115.785 | 74.956 | 95.332 | 1.00 | 87.32 |
| ATOM | 1033 | CA | GLN | 202 | 115.097 | 73.823 | 95.927 | 1.00 | 89.77 |
| ATOM | 1034 | CB | GLN | 202 | 115.698 | 72.501 | 95.445 | 1.00 | 92.70 |
| ATOM | 1035 | CG | GLN | 202 | 114.824 | 71.290 | 95.764 | 1.00 | 97.61 |
| ATOM | 1036 | CD | GLN | 202 | 113.358 | 71.499 | 95.387 | 1.00 | 101.05 |
| ATOM | 1037 | OE1 | GLN | 202 | 112.456 | 71.128 | 96.139 | 1.00 | 102.03 |
| ATOM | 1038 | NE2 | GLN | 202 | 113.120 | 72.105 | 94.229 | 1.00 | 102.67 |
| ATOM | 1039 | C | GLN | 202 | 115.054 | 73.883 | 97.451 | 1.00 | 89.76 |
| ATOM | 1040 | O | GLN | 202 | 115.836 | 73.222 | 98.142 | 1.00 | 90.00 |
| ATOM | 1041 | N | ARG | 203 | 114.144 | 74.709 | 97.955 | 1.00 | 89.49 |
| ATOM | 1042 | CA | ARG | 203 | 113.925 | 74.905 | 99.382 | 1.00 | 88.84 |
| ATOM | 1043 | CB | ARG | 203 | 115.140 | 75.579 | 100.049 | 1.00 | 88.34 |
| ATOM | 1044 | CG | ARG | 203 | 115.732 | 76.757 | 99.287 | 1.00 | 88.19 |
| ATOM | 1045 | CD | ARG | 203 | 117.240 | 76.607 | 99.126 | 1.00 | 88.80 |
| ATOM | 1046 | NE | ARG | 203 | 117.600 | 75.378 | 98.417 | 1.00 | 88.58 |
| ATOM | 1047 | CZ | ARG | 203 | 118.428 | 75.317 | 97.377 | 1.00 | 86.71 |
| ATOM | 1048 | NH1 | ARG | 203 | 118.998 | 76.418 | 96.908 | 1.00 | 86.45 |
| ATOM | 1049 | NH2 | ARG | 203 | 118.687 | 74.146 | 96.809 | 1.00 | 85.61 |
| ATOM | 1050 | C | ARG | 203 | 112.632 | 75.706 | 99.585 | 1.00 | 87.84 |
| ATOM | 1051 | O | ARG | 203 | 111.566 | 75.287 | 99.121 | 1.00 | 87.56 |
| ATOM | 1052 | N | ALA | 204 | 112.719 | 76.867 | 100.226 | 1.00 | 86.13 |
| ATOM | 1053 | CA | ALA | 204 | 111.531 | 77.671 | 100.471 | 1.00 | 83.50 |
| ATOM | 1054 | CB | ALA | 204 | 110.942 | 77.340 | 101.843 | 1.00 | 84.51 |
| ATOM | 1055 | C | ALA | 204 | 111.815 | 79.165 | 100.358 | 1.00 | 80.44 |
| ATOM | 1056 | O | ALA | 204 | 112.970 | 79.588 | 100.256 | 1.00 | 80.60 |
| ATOM | 1057 | N | GLY | 205 | 110.744 | 79.952 | 100.384 | 1.00 | 76.39 |
| ATOM | 1058 | CA | GLY | 205 | 110.859 | 81.392 | 100.283 | 1.00 | 69.88 |
| ATOM | 1059 | C | GLY | 205 | 110.338 | 81.872 | 98.946 | 1.00 | 64.80 |

FIG. 1A-19

| ATOM | 1060 | O   | GLY | 205 | 109.236 | 81.511 | 98.515 | 1.00 | 64.06 |
|------|------|-----|-----|-----|---------|--------|--------|------|-------|
| ATOM | 1061 | N   | ALA | 206 | 111.150 | 82.678 | 98.281 | 1.00 | 59.49 |
| ATOM | 1062 | CA  | ALA | 206 | 110.807 | 83.227 | 96.985 | 1.00 | 54.11 |
| ATOM | 1063 | CB  | ALA | 206 | 110.208 | 84.615 | 97.146 | 1.00 | 54.44 |
| ATOM | 1064 | C   | ALA | 206 | 112.108 | 83.310 | 96.226 | 1.00 | 49.90 |
| ATOM | 1065 | O   | ALA | 206 | 113.180 | 83.244 | 96.820 | 1.00 | 51.13 |
| ATOM | 1066 | N   | LEU | 209 | 112.026 | 83.413 | 94.912 | 1.00 | 45.11 |
| ATOM | 1067 | CA  | LEU | 209 | 113.225 | 83.517 | 94.111 | 1.00 | 40.05 |
| ATOM | 1068 | CB  | LEU | 209 | 113.239 | 82.427 | 93.048 | 1.00 | 36.41 |
| ATOM | 1069 | CG  | LEU | 209 | 114.558 | 81.773 | 92.645 | 1.00 | 34.85 |
| ATOM | 1070 | CD1 | LEU | 209 | 114.341 | 81.091 | 91.308 | 1.00 | 34.74 |
| ATOM | 1071 | CD2 | LEU | 209 | 115.691 | 82.771 | 92.546 | 1.00 | 29.56 |
| ATOM | 1072 | C   | LEU | 209 | 113.205 | 84.875 | 93.433 | 1.00 | 39.06 |
| ATOM | 1073 | O   | LEU | 209 | 112.312 | 85.153 | 92.634 | 1.00 | 39.13 |
| ATOM | 1074 | N   | PRO | 210 | 114.098 | 85.793 | 93.850 | 1.00 | 37.89 |
| ATOM | 1075 | CD  | PRO | 210 | 114.952 | 85.780 | 95.051 | 1.00 | 36.71 |
| ATOM | 1076 | CA  | PRO | 210 | 114.124 | 87.111 | 93.212 | 1.00 | 36.68 |
| ATOM | 1077 | CB  | PRO | 210 | 115.070 | 87.915 | 94.110 | 1.00 | 34.61 |
| ATOM | 1078 | CG  | PRO | 210 | 115.931 | 86.871 | 94.746 | 1.00 | 35.52 |
| ATOM | 1079 | C   | PRO | 210 | 114.656 | 86.987 | 91.786 | 1.00 | 36.86 |
| ATOM | 1080 | O   | PRO | 210 | 115.702 | 86.374 | 91.560 | 1.00 | 38.72 |
| ATOM | 1081 | N   | ILE | 211 | 113.889 | 87.477 | 90.818 | 1.00 | 35.16 |
| ATOM | 1082 | CA  | ILE | 211 | 114.316 | 87.415 | 89.432 | 1.00 | 33.61 |
| ATOM | 1083 | CB  | ILE | 211 | 113.131 | 87.224 | 88.473 | 1.00 | 31.67 |
| ATOM | 1084 | CG2 | ILE | 211 | 113.624 | 87.115 | 87.029 | 1.00 | 29.72 |
| ATOM | 1085 | CG1 | ILE | 211 | 112.373 | 85.953 | 88.852 | 1.00 | 26.60 |
| ATOM | 1086 | CD1 | ILE | 211 | 113.229 | 84.706 | 88.833 | 1.00 | 21.58 |
| ATOM | 1087 | C   | ILE | 211 | 115.036 | 88.709 | 89.147 | 1.00 | 34.69 |
| ATOM | 1088 | O   | ILE | 211 | 114.561 | 89.785 | 89.505 | 1.00 | 34.63 |
| ATOM | 1089 | N   | VAL | 212 | 116.189 | 88.597 | 88.506 | 1.00 | 37.32 |
| ATOM | 1090 | CA  | VAL | 212 | 117.016 | 89.750 | 88.209 | 1.00 | 41.26 |
| ATOM | 1091 | CB  | VAL | 212 | 118.393 | 89.593 | 88.910 | 1.00 | 39.76 |
| ATOM | 1092 | CG1 | VAL | 212 | 119.521 | 90.131 | 88.061 | 1.00 | 41.05 |
| ATOM | 1093 | CG2 | VAL | 212 | 118.357 | 90.286 | 90.264 | 1.00 | 36.94 |
| ATOM | 1094 | C   | VAL | 212 | 117.166 | 90.052 | 86.721 | 1.00 | 45.53 |
| ATOM | 1095 | O   | VAL | 212 | 117.324 | 89.149 | 85.898 | 1.00 | 46.04 |
| ATOM | 1096 | N   | ASN | 213 | 117.078 | 91.338 | 86.395 | 1.00 | 50.13 |
| ATOM | 1097 | CA  | ASN | 213 | 117.204 | 91.834 | 85.029 | 1.00 | 54.74 |
| ATOM | 1098 | CB  | ASN | 213 | 116.187 | 92.958 | 84.781 | 1.00 | 58.04 |
| ATOM | 1099 | CG  | ASN | 213 | 116.312 | 93.575 | 83.392 | 1.00 | 63.16 |
| ATOM | 1100 | OD1 | ASN | 213 | 117.392 | 94.001 | 82.976 | 1.00 | 63.63 |
| ATOM | 1101 | ND2 | ASN | 213 | 115.195 | 93.644 | 82.676 | 1.00 | 66.53 |
| ATOM | 1102 | C   | ASN | 213 | 118.611 | 92.385 | 84.886 | 1.00 | 56.69 |
| ATOM | 1103 | O   | ASN | 213 | 119.049 | 93.171 | 85.728 | 1.00 | 56.84 |
| ATOM | 1104 | N   | GLU | 214 | 119.293 | 91.970 | 83.820 | 1.00 | 58.00 |
| ATOM | 1105 | CA  | GLU | 214 | 120.662 | 92.379 | 83.487 | 1.00 | 59.26 |
| ATOM | 1106 | CB  | GLU | 214 | 120.708 | 93.007 | 82.095 | 1.00 | 63.79 |
| ATOM | 1107 | CG  | GLU | 214 | 122.122 | 93.176 | 81.565 | 1.00 | 70.73 |
| ATOM | 1108 | CD  | GLU | 214 | 122.888 | 91.861 | 81.539 | 1.00 | 76.36 |
| ATOM | 1109 | OE1 | GLU | 214 | 123.897 | 91.739 | 82.273 | 1.00 | 77.43 |
| ATOM | 1110 | OE2 | GLU | 214 | 122.470 | 90.947 | 80.791 | 1.00 | 78.72 |
| ATOM | 1111 | C   | GLU | 214 | 121.381 | 93.296 | 84.471 | 1.00 | 58.22 |
| ATOM | 1112 | O   | GLU | 214 | 122.362 | 92.900 | 85.088 | 1.00 | 59.28 |
| ATOM | 1113 | N   | ASN | 215 | 120.873 | 94.507 | 84.647 | 1.00 | 57.43 |
| ATOM | 1114 | CA  | ASN | 215 | 121.482 | 95.458 | 85.567 | 1.00 | 58.14 |
| ATOM | 1115 | CB  | ASN | 215 | 120.804 | 96.828 | 85.450 | 1.00 | 65.27 |
| ATOM | 1116 | CG  | ASN | 215 | 120.970 | 97.459 | 84.073 | 1.00 | 74.29 |
| ATOM | 1117 | OD1 | ASN | 215 | 121.139 | 96.766 | 83.065 | 1.00 | 78.55 |
| ATOM | 1118 | ND2 | ASN | 215 | 120.909 | 98.786 | 84.024 | 1.00 | 77.85 |

FIG. 1A-20

| | | | | | | | | |
|---|---|---|---|---|---|---|---|---|
| ATOM | 1119 | C | ASN | 215 | 121.395 | 94.976 | 87.014 | 1.00 | 55.81 |
| ATOM | 1120 | O | ASN | 215 | 121.650 | 95.747 | 87.945 | 1.00 | 56.29 |
| ATOM | 1121 | N | ASP | 216 | 121.026 | 93.711 | 87.202 | 1.00 | 52.49 |
| ATOM | 1122 | CA | ASP | 216 | 120.889 | 93.115 | 88.516 | 1.00 | 50.19 |
| ATOM | 1123 | CB | ASP | 216 | 122.212 | 93.201 | 89.271 | 1.00 | 51.39 |
| ATOM | 1124 | CG | ASP | 216 | 122.369 | 92.102 | 90.285 | 1.00 | 54.10 |
| ATOM | 1125 | OD1 | ASP | 216 | 121.951 | 92.299 | 91.445 | 1.00 | 57.69 |
| ATOM | 1126 | OD2 | ASP | 216 | 122.907 | 91.039 | 89.916 | 1.00 | 53.63 |
| ATOM | 1127 | C | ASP | 216 | 119.769 | 93.852 | 89.247 | 1.00 | 49.43 |
| ATOM | 1128 | O | ASP | 216 | 119.816 | 94.077 | 90.460 | 1.00 | 48.51 |
| ATOM | 1129 | N | GLU | 217 | 118.757 | 94.234 | 88.478 | 1.00 | 50.39 |
| ATOM | 1130 | CA | GLU | 217 | 117.600 | 94.959 | 88.994 | 1.00 | 51.67 |
| ATOM | 1131 | CB | GLU | 217 | 117.268 | 96.126 | 88.054 | 1.00 | 56.48 |
| ATOM | 1132 | CG | GLU | 217 | 117.200 | 95.734 | 86.571 | 1.00 | 62.18 |
| ATOM | 1133 | CD | GLU | 217 | 117.162 | 96.933 | 85.631 | 1.00 | 67.67 |
| ATOM | 1134 | OE1 | GLU | 217 | 116.508 | 97.948 | 85.966 | 1.00 | 71.20 |
| ATOM | 1135 | OE2 | GLU | 217 | 117.785 | 96.858 | 84.550 | 1.00 | 67.88 |
| ATOM | 1136 | C | GLU | 217 | 116.400 | 94.027 | 89.139 | 1.00 | 49.37 |
| ATOM | 1137 | O | GLU | 217 | 116.063 | 93.296 | 88.203 | 1.00 | 50.54 |
| ATOM | 1138 | N | LEU | 218 | 115.767 | 94.053 | 90.310 | 1.00 | 46.00 |
| ATOM | 1139 | CA | LEU | 218 | 114.611 | 93.209 | 90.595 | 1.00 | 42.82 |
| ATOM | 1140 | CB | LEU | 218 | 114.056 | 93.530 | 91.980 | 1.00 | 40.76 |
| ATOM | 1141 | CG | LEU | 218 | 113.035 | 92.537 | 92.525 | 1.00 | 43.30 |
| ATOM | 1142 | CD1 | LEU | 218 | 113.587 | 91.125 | 92.443 | 1.00 | 45.66 |
| ATOM | 1143 | CD2 | LEU | 218 | 112.684 | 92.888 | 93.961 | 1.00 | 44.41 |
| ATOM | 1144 | C | LEU | 218 | 113.530 | 93.392 | 89.539 | 1.00 | 41.76 |
| ATOM | 1145 | O | LEU | 218 | 112.841 | 94.411 | 89.512 | 1.00 | 42.68 |
| ATOM | 1146 | N | VAL | 219 | 113.395 | 92.399 | 88.665 | 1.00 | 40.13 |
| ATOM | 1147 | CA | VAL | 219 | 112.414 | 92.447 | 87.582 | 1.00 | 35.68 |
| ATOM | 1148 | CB | VAL | 219 | 113.056 | 91.969 | 86.234 | 1.00 | 32.66 |
| ATOM | 1149 | CG1 | VAL | 219 | 113.267 | 90.483 | 86.224 | 1.00 | 31.43 |
| ATOM | 1150 | CG2 | VAL | 219 | 112.223 | 92.386 | 85.057 | 1.00 | 34.92 |
| ATOM | 1151 | C | VAL | 219 | 111.150 | 91.649 | 87.927 | 1.00 | 33.78 |
| ATOM | 1152 | O | VAL | 219 | 110.092 | 91.864 | 87.337 | 1.00 | 34.95 |
| ATOM | 1153 | N | ALA | 220 | 111.258 | 90.741 | 88.892 | 1.00 | 31.81 |
| ATOM | 1154 | CA | ALA | 220 | 110.123 | 89.930 | 89.317 | 1.00 | 30.78 |
| ATOM | 1155 | CB | ALA | 220 | 109.624 | 89.053 | 88.167 | 1.00 | 31.87 |
| ATOM | 1156 | C | ALA | 220 | 110.538 | 89.062 | 90.486 | 1.00 | 29.91 |
| ATOM | 1157 | O | ALA | 220 | 111.678 | 89.127 | 90.939 | 1.00 | 29.19 |
| ATOM | 1158 | N | ILE | 221 | 109.588 | 88.290 | 90.996 | 1.00 | 30.38 |
| ATOM | 1159 | CA | ILE | 221 | 109.810 | 87.361 | 92.098 | 1.00 | 30.65 |
| ATOM | 1160 | CB | ILE | 221 | 109.456 | 87.998 | 93.475 | 1.00 | 33.29 |
| ATOM | 1161 | CG2 | ILE | 221 | 109.558 | 86.974 | 94.587 | 1.00 | 35.92 |
| ATOM | 1162 | CG1 | ILE | 221 | 110.430 | 89.126 | 93.814 | 1.00 | 36.90 |
| ATOM | 1163 | CD1 | ILE | 221 | 110.282 | 89.662 | 95.232 | 1.00 | 39.70 |
| ATOM | 1164 | C | ILE | 221 | 108.891 | 86.166 | 91.830 | 1.00 | 30.07 |
| ATOM | 1165 | O | ILE | 221 | 108.010 | 86.242 | 90.976 | 1.00 | 29.66 |
| ATOM | 1166 | N | ILE | 222 | 109.158 | 85.043 | 92.486 | 1.00 | 30.43 |
| ATOM | 1167 | CA | ILE | 222 | 108.339 | 83.843 | 92.352 | 1.00 | 32.62 |
| ATOM | 1168 | CB | ILE | 222 | 108.885 | 82.873 | 91.281 | 1.00 | 35.84 |
| ATOM | 1169 | CG2 | ILE | 222 | 108.282 | 83.173 | 89.929 | 1.00 | 38.08 |
| ATOM | 1170 | CG1 | ILE | 222 | 110.403 | 82.948 | 91.225 | 1.00 | 40.71 |
| ATOM | 1171 | CD1 | ILE | 222 | 110.979 | 82.332 | 89.992 | 1.00 | 48.17 |
| ATOM | 1172 | C | ILE | 222 | 108.307 | 83.143 | 93.699 | 1.00 | 32.70 |
| ATOM | 1173 | O | ILE | 222 | 109.336 | 82.696 | 94.202 | 1.00 | 32.91 |
| ATOM | 1174 | N | ALA | 223 | 107.131 | 83.096 | 94.304 | 1.00 | 34.15 |
| ATOM | 1175 | CA | ALA | 223 | 106.971 | 82.469 | 95.606 | 1.00 | 36.37 |
| ATOM | 1176 | CB | ALA | 223 | 105.677 | 82.936 | 96.253 | 1.00 | 40.47 |
| ATOM | 1177 | C | ALA | 223 | 106.981 | 80.962 | 95.481 | 1.00 | 36.88 |

FIG. 1A-21

| ATOM | 1178 | O | ALA | 223 | 106.339 | 80.408 | 94.592 | 1.00 | 38.29 |
|---|---|---|---|---|---|---|---|---|---|
| ATOM | 1179 | N | ARG | 224 | 107.683 | 80.300 | 96.393 | 1.00 | 37.92 |
| ATOM | 1180 | CA | ARG | 224 | 107.778 | 78.842 | 96.378 | 1.00 | 39.64 |
| ATOM | 1181 | CB | ARG | 224 | 108.533 | 78.336 | 97.623 | 1.00 | 40.36 |
| ATOM | 1182 | CG | ARG | 224 | 109.850 | 77.565 | 97.349 | 1.00 | 43.06 |
| ATOM | 1183 | CD | ARG | 224 | 111.088 | 78.471 | 97.101 | 1.00 | 43.23 |
| ATOM | 1184 | NE | ARG | 224 | 111.056 | 79.161 | 95.809 | 1.00 | 41.83 |
| ATOM | 1185 | CZ | ARG | 224 | 111.816 | 78.842 | 94.765 | 1.00 | 37.49 |
| ATOM | 1186 | NH1 | ARG | 224 | 112.680 | 77.847 | 94.848 | 1.00 | 33.15 |
| ATOM | 1187 | NH2 | ARG | 224 | 111.678 | 79.492 | 93.619 | 1.00 | 38.85 |
| ATOM | 1188 | C | ARG | 224 | 106.386 | 78.210 | 96.316 | 1.00 | 40.65 |
| ATOM | 1189 | O | ARG | 224 | 106.154 | 77.288 | 95.535 | 1.00 | 41.59 |
| ATOM | 1190 | N | THR | 225 | 105.446 | 78.768 | 97.076 | 1.00 | 42.15 |
| ATOM | 1191 | CA | THR | 225 | 104.072 | 78.264 | 97.136 | 1.00 | 42.10 |
| ATOM | 1192 | CB | THR | 225 | 103.201 | 79.140 | 98.056 | 1.00 | 41.51 |
| ATOM | 1193 | OG1 | THR | 225 | 103.319 | 80.515 | 97.667 | 1.00 | 42.81 |
| ATOM | 1194 | CG2 | THR | 225 | 103.651 | 78.995 | 99.501 | 1.00 | 40.52 |
| ATOM | 1195 | C | THR | 225 | 103.391 | 78.119 | 95.772 | 1.00 | 43.03 |
| ATOM | 1196 | O | THR | 225 | 102.639 | 77.170 | 95.545 | 1.00 | 43.47 |
| ATOM | 1197 | N | ASP | 226 | 103.658 | 79.051 | 94.866 | 1.00 | 43.78 |
| ATOM | 1198 | CA | ASP | 226 | 103.075 | 78.991 | 93.535 | 1.00 | 44.84 |
| ATOM | 1199 | CB | ASP | 226 | 103.324 | 80.296 | 92.775 | 1.00 | 48.02 |
| ATOM | 1200 | CG | ASP | 226 | 102.595 | 81.473 | 93.383 | 1.00 | 52.98 |
| ATOM | 1201 | OD1 | ASP | 226 | 101.569 | 81.264 | 94.073 | 1.00 | 55.78 |
| ATOM | 1202 | OD2 | ASP | 226 | 103.051 | 82.616 | 93.166 | 1.00 | 58.70 |
| ATOM | 1203 | C | ASP | 226 | 103.647 | 77.811 | 92.760 | 1.00 | 44.39 |
| ATOM | 1204 | O | ASP | 226 | 102.919 | 77.102 | 92.064 | 1.00 | 46.30 |
| ATOM | 1205 | N | LEU | 227 | 104.951 | 77.594 | 92.895 | 1.00 | 42.85 |
| ATOM | 1206 | CA | LEU | 227 | 105.617 | 76.488 | 92.211 | 1.00 | 41.91 |
| ATOM | 1207 | CB | LEU | 227 | 107.127 | 76.573 | 92.418 | 1.00 | 41.83 |
| ATOM | 1208 | CG | LEU | 227 | 107.875 | 77.618 | 91.581 | 1.00 | 43.67 |
| ATOM | 1209 | CD1 | LEU | 227 | 107.080 | 78.906 | 91.413 | 1.00 | 44.20 |
| ATOM | 1210 | CD2 | LEU | 227 | 109.207 | 77.911 | 92.234 | 1.00 | 45.65 |
| ATOM | 1211 | C | LEU | 227 | 105.060 | 75.161 | 92.727 | 1.00 | 41.23 |
| ATOM | 1212 | O | LEU | 227 | 105.052 | 74.159 | 92.008 | 1.00 | 40.43 |
| ATOM | 1213 | N | LYS | 228 | 104.581 | 75.173 | 93.969 | 1.00 | 41.25 |
| ATOM | 1214 | CA | LYS | 228 | 103.976 | 74.002 | 94.598 | 1.00 | 41.51 |
| ATOM | 1215 | CB | LYS | 228 | 103.801 | 74.242 | 96.103 | 1.00 | 42.68 |
| ATOM | 1216 | CG | LYS | 228 | 103.048 | 73.147 | 96.844 | 1.00 | 47.59 |
| ATOM | 1217 | CD | LYS | 228 | 102.737 | 73.585 | 98.272 | 1.00 | 53.52 |
| ATOM | 1218 | CE | LYS | 228 | 101.781 | 72.623 | 98.978 | 1.00 | 56.97 |
| ATOM | 1219 | NZ | LYS | 228 | 102.353 | 71.257 | 99.167 | 1.00 | 59.90 |
| ATOM | 1220 | C | LYS | 228 | 102.615 | 73.737 | 93.948 | 1.00 | 40.91 |
| ATOM | 1221 | O | LYS | 228 | 102.390 | 72.664 | 93.386 | 1.00 | 41.81 |
| ATOM | 1222 | N | LYS | 229 | 101.735 | 74.738 | 93.985 | 1.00 | 38.16 |
| ATOM | 1223 | CA | LYS | 229 | 100.392 | 74.627 | 93.412 | 1.00 | 36.08 |
| ATOM | 1224 | CB | LYS | 229 | 99.648 | 75.958 | 93.524 | 1.00 | 34.26 |
| ATOM | 1225 | CG | LYS | 229 | 99.472 | 76.460 | 94.936 | 1.00 | 32.34 |
| ATOM | 1226 | CD | LYS | 229 | 98.862 | 77.842 | 94.945 | 1.00 | 33.74 |
| ATOM | 1227 | CE | LYS | 229 | 98.789 | 78.398 | 96.358 | 1.00 | 36.97 |
| ATOM | 1228 | NZ | LYS | 229 | 98.186 | 79.757 | 96.400 | 1.00 | 37.99 |
| ATOM | 1229 | C | LYS | 229 | 100.475 | 74.236 | 91.946 | 1.00 | 36.73 |
| ATOM | 1230 | O | LYS | 229 | 99.659 | 73.457 | 91.446 | 1.00 | 36.54 |
| ATOM | 1231 | N | ASN | 230 | 101.459 | 74.790 | 91.254 | 1.00 | 36.88 |
| ATOM | 1232 | CA | ASN | 230 | 101.637 | 74.483 | 89.852 | 1.00 | 38.77 |
| ATOM | 1233 | CB | ASN | 230 | 102.698 | 75.386 | 89.229 | 1.00 | 40.52 |
| ATOM | 1234 | CG | ASN | 230 | 102.822 | 75.191 | 87.721 | 1.00 | 47.50 |
| ATOM | 1235 | OD1 | ASN | 230 | 103.865 | 75.473 | 87.135 | 1.00 | 49.21 |
| ATOM | 1236 | ND2 | ASN | 230 | 101.754 | 74.710 | 87.086 | 1.00 | 52.48 |

FIG. 1A-22

| ATOM | 1237 | C | ASN | 230 | 102.019 | 73.025 | 89.652 | 1.00 | 40.23 |
| --- | --- | --- | --- | --- | --- | --- | --- | --- | --- |
| ATOM | 1238 | O | ASN | 230 | 101.474 | 72.360 | 88.773 | 1.00 | 42.09 |
| ATOM | 1239 | N | ARG | 231 | 102.923 | 72.522 | 90.488 | 1.00 | 40.83 |
| ATOM | 1240 | CA | ARG | 231 | 103.389 | 71.141 | 90.377 | 1.00 | 41.51 |
| ATOM | 1241 | CB | ARG | 231 | 104.734 | 70.975 | 91.106 | 1.00 | 47.17 |
| ATOM | 1242 | CG | ARG | 231 | 105.495 | 69.686 | 90.773 | 1.00 | 54.46 |
| ATOM | 1243 | CD | ARG | 231 | 106.892 | 69.674 | 91.405 | 1.00 | 66.37 |
| ATOM | 1244 | NE | ARG | 231 | 107.667 | 68.482 | 91.043 | 1.00 | 76.11 |
| ATOM | 1245 | CZ | ARG | 231 | 108.942 | 68.267 | 91.378 | 1.00 | 78.92 |
| ATOM | 1246 | NH1 | ARG | 231 | 109.544 | 67.149 | 90.992 | 1.00 | 79.85 |
| ATOM | 1247 | NH2 | ARG | 231 | 109.621 | 69.156 | 92.100 | 1.00 | 78.17 |
| ATOM | 1248 | C | ARG | 231 | 102.366 | 70.126 | 90.892 | 1.00 | 38.99 |
| ATOM | 1249 | O | ARG | 231 | 102.328 | 68.976 | 90.442 | 1.00 | 37.79 |
| ATOM | 1250 | N | ASP | 232 | 101.525 | 70.565 | 91.820 | 1.00 | 36.95 |
| ATOM | 1251 | CA | ASP | 232 | 100.509 | 69.700 | 92.405 | 1.00 | 35.45 |
| ATOM | 1252 | CB | ASP | 232 | 100.007 | 70.287 | 93.730 | 1.00 | 40.00 |
| ATOM | 1253 | CG | ASP | 232 | 101.014 | 70.149 | 94.860 | 1.00 | 46.07 |
| ATOM | 1254 | OD1 | ASP | 232 | 102.209 | 69.902 | 94.588 | 1.00 | 48.49 |
| ATOM | 1255 | OD2 | ASP | 232 | 100.600 | 70.293 | 96.033 | 1.00 | 50.50 |
| ATOM | 1256 | C | ASP | 232 | 99.312 | 69.463 | 91.486 | 1.00 | 32.77 |
| ATOM | 1257 | O | ASP | 232 | 98.687 | 68.405 | 91.541 | 1.00 | 32.41 |
| ATOM | 1258 | N | TYR | 233 | 98.986 | 70.447 | 90.655 | 1.00 | 29.25 |
| ATOM | 1259 | CA | TYR | 233 | 97.840 | 70.334 | 89.769 | 1.00 | 24.64 |
| ATOM | 1260 | CB | TYR | 233 | 96.805 | 71.380 | 90.159 | 1.00 | 24.64 |
| ATOM | 1261 | CG | TYR | 233 | 96.403 | 71.287 | 91.606 | 1.00 | 20.42 |
| ATOM | 1262 | CD1 | TYR | 233 | 95.511 | 70.312 | 92.036 | 1.00 | 16.93 |
| ATOM | 1263 | CE1 | TYR | 233 | 95.139 | 70.222 | 93.369 | 1.00 | 20.69 |
| ATOM | 1264 | CD2 | TYR | 233 | 96.922 | 72.170 | 92.546 | 1.00 | 20.67 |
| ATOM | 1265 | CE2 | TYR | 233 | 96.557 | 72.090 | 93.883 | 1.00 | 22.46 |
| ATOM | 1266 | CZ | TYR | 233 | 95.666 | 71.114 | 94.289 | 1.00 | 22.03 |
| ATOM | 1267 | OH | TYR | 233 | 95.295 | 71.040 | 95.613 | 1.00 | 25.90 |
| ATOM | 1268 | C | TYR | 233 | 98.167 | 70.449 | 88.291 | 1.00 | 22.35 |
| ATOM | 1269 | O | TYR | 233 | 97.996 | 71.513 | 87.688 | 1.00 | 22.95 |
| ATOM | 1270 | N | PRO | 234 | 98.560 | 69.327 | 87.668 | 1.00 | 19.57 |
| ATOM | 1271 | CD | PRO | 234 | 98.710 | 68.020 | 88.321 | 1.00 | 15.74 |
| ATOM | 1272 | CA | PRO | 234 | 98.922 | 69.225 | 86.252 | 1.00 | 19.92 |
| ATOM | 1273 | CB | PRO | 234 | 99.379 | 67.778 | 86.122 | 1.00 | 15.39 |
| ATOM | 1274 | CG | PRO | 234 | 98.606 | 67.085 | 87.162 | 1.00 | 14.18 |
| ATOM | 1275 | C | PRO | 234 | 97.812 | 69.535 | 85.266 | 1.00 | 21.74 |
| ATOM | 1276 | O | PRO | 234 | 98.083 | 69.768 | 84.091 | 1.00 | 23.45 |
| ATOM | 1277 | N | LEU | 235 | 96.568 | 69.527 | 85.734 | 1.00 | 23.76 |
| ATOM | 1278 | CA | LEU | 235 | 95.436 | 69.806 | 84.856 | 1.00 | 24.11 |
| ATOM | 1279 | CB | LEU | 235 | 94.316 | 68.800 | 85.100 | 1.00 | 22.93 |
| ATOM | 1280 | CG | LEU | 235 | 94.640 | 67.346 | 84.788 | 1.00 | 17.74 |
| ATOM | 1281 | CD1 | LEU | 235 | 93.410 | 66.496 | 85.050 | 1.00 | 19.65 |
| ATOM | 1282 | CD2 | LEU | 235 | 95.074 | 67.241 | 83.346 | 1.00 | 15.28 |
| ATOM | 1283 | C | LEU | 235 | 94.885 | 71.210 | 85.019 | 1.00 | 24.65 |
| ATOM | 1284 | O | LEU | 235 | 93.947 | 71.597 | 84.315 | 1.00 | 26.71 |
| ATOM | 1285 | N | ALA | 236 | 95.476 | 71.967 | 85.939 | 1.00 | 24.68 |
| ATOM | 1286 | CA | ALA | 236 | 95.048 | 73.335 | 86.237 | 1.00 | 24.91 |
| ATOM | 1287 | CB | ALA | 236 | 96.086 | 74.025 | 87.114 | 1.00 | 26.10 |
| ATOM | 1288 | C | ALA | 236 | 94.718 | 74.215 | 85.031 | 1.00 | 24.07 |
| ATOM | 1289 | O | ALA | 236 | 95.522 | 74.358 | 84.107 | 1.00 | 24.73 |
| ATOM | 1290 | N | SER | 237 | 93.517 | 74.783 | 85.041 | 1.00 | 24.63 |
| ATOM | 1291 | CA | SER | 237 | 93.070 | 75.678 | 83.981 | 1.00 | 25.43 |
| ATOM | 1292 | CB | SER | 237 | 91.541 | 75.717 | 83.941 | 1.00 | 25.49 |
| ATOM | 1293 | OG | SER | 237 | 91.009 | 74.422 | 83.729 | 1.00 | 26.13 |
| ATOM | 1294 | C | SER | 237 | 93.625 | 77.068 | 84.292 | 1.00 | 25.26 |
| ATOM | 1295 | O | SER | 237 | 93.017 | 77.826 | 85.050 | 1.00 | 24.30 |

FIG. 1A-23

| ATOM | 1296 | N | LYS | 238 | 94.814 | 77.357 | 83.755 | 1.00 | 27.02 |
|------|------|-----|-----|-----|--------|--------|--------|------|-------|
| ATOM | 1297 | CA | LYS | 238 | 95.514 | 78.632 | 83.956 | 1.00 | 26.84 |
| ATOM | 1298 | CB | LYS | 238 | 96.955 | 78.373 | 84.417 | 1.00 | 25.90 |
| ATOM | 1299 | CG | LYS | 238 | 97.069 | 77.574 | 85.713 | 1.00 | 30.34 |
| ATOM | 1300 | CD | LYS | 238 | 98.498 | 77.545 | 86.261 | 1.00 | 36.02 |
| ATOM | 1301 | CE | LYS | 238 | 99.468 | 76.751 | 85.383 | 1.00 | 40.96 |
| ATOM | 1302 | NZ | LYS | 238 | 99.312 | 75.265 | 85.478 | 1.00 | 43.36 |
| ATOM | 1303 | C | LYS | 238 | 95.549 | 79.487 | 82.688 | 1.00 | 27.11 |
| ATOM | 1304 | O | LYS | 238 | 95.469 | 78.960 | 81.588 | 1.00 | 28.11 |
| ATOM | 1305 | N | ASP | 239 | 95.647 | 80.805 | 82.839 | 1.00 | 27.73 |
| ATOM | 1306 | CA | ASP | 239 | 95.712 | 81.703 | 81.684 | 1.00 | 28.78 |
| ATOM | 1307 | CB | ASP | 239 | 95.005 | 83.044 | 81.968 | 1.00 | 26.56 |
| ATOM | 1308 | CG | ASP | 239 | 95.633 | 83.832 | 83.116 | 1.00 | 24.59 |
| ATOM | 1309 | OD1 | ASP | 239 | 96.564 | 83.334 | 83.766 | 1.00 | 26.84 |
| ATOM | 1310 | OD2 | ASP | 239 | 95.189 | 84.968 | 83.374 | 1.00 | 24.38 |
| ATOM | 1311 | C | ASP | 239 | 97.169 | 81.927 | 81.268 | 1.00 | 30.60 |
| ATOM | 1312 | O | ASP | 239 | 98.087 | 81.343 | 81.855 | 1.00 | 32.51 |
| ATOM | 1313 | N | ALA | 240 | 97.389 | 82.805 | 80.296 | 1.00 | 30.28 |
| ATOM | 1314 | CA | ALA | 240 | 98.737 | 83.082 | 79.811 | 1.00 | 31.43 |
| ATOM | 1315 | CB | ALA | 240 | 98.686 | 84.111 | 78.705 | 1.00 | 32.61 |
| ATOM | 1316 | C | ALA | 240 | 99.701 | 83.536 | 80.905 | 1.00 | 33.16 |
| ATOM | 1317 | O | ALA | 240 | 100.915 | 83.424 | 80.756 | 1.00 | 34.13 |
| ATOM | 1318 | N | LYS | 241 | 99.158 | 84.024 | 82.013 | 1.00 | 34.52 |
| ATOM | 1319 | CA | LYS | 241 | 99.985 | 84.507 | 83.114 | 1.00 | 34.81 |
| ATOM | 1320 | CB | LYS | 241 | 99.422 | 85.834 | 83.639 | 1.00 | 37.50 |
| ATOM | 1321 | CG | LYS | 241 | 98.935 | 86.783 | 82.540 | 1.00 | 43.35 |
| ATOM | 1322 | CD | LYS | 241 | 100.062 | 87.283 | 81.631 | 1.00 | 46.22 |
| ATOM | 1323 | CE | LYS | 241 | 100.841 | 88.420 | 82.278 | 1.00 | 48.19 |
| ATOM | 1324 | NZ | LYS | 241 | 99.952 | 89.571 | 82.619 | 1.00 | 51.12 |
| ATOM | 1325 | C | LYS | 241 | 100.105 | 83.498 | 84.257 | 1.00 | 33.59 |
| ATOM | 1326 | O | LYS | 241 | 100.425 | 83.872 | 85.382 | 1.00 | 35.65 |
| ATOM | 1327 | N | LYS | 242 | 99.834 | 82.229 | 83.967 | 1.00 | 31.55 |
| ATOM | 1328 | CA | LYS | 242 | 99.909 | 81.160 | 84.963 | 1.00 | 30.28 |
| ATOM | 1329 | CB | LYS | 242 | 101.349 | 80.959 | 85.434 | 1.00 | 32.09 |
| ATOM | 1330 | CG | LYS | 242 | 102.261 | 80.473 | 84.336 | 1.00 | 39.25 |
| ATOM | 1331 | CD | LYS | 242 | 101.699 | 79.221 | 83.672 | 1.00 | 46.14 |
| ATOM | 1332 | CE | LYS | 242 | 102.685 | 78.627 | 82.676 | 1.00 | 51.26 |
| ATOM | 1333 | NZ | LYS | 242 | 103.060 | 79.601 | 81.608 | 1.00 | 54.72 |
| ATOM | 1334 | C | LYS | 242 | 98.972 | 81.316 | 86.160 | 1.00 | 28.29 |
| ATOM | 1335 | O | LYS | 242 | 99.236 | 80.787 | 87.249 | 1.00 | 26.69 |
| ATOM | 1336 | N | GLN | 243 | 97.856 | 82.000 | 85.926 | 1.00 | 26.16 |
| ATOM | 1337 | CA | GLN | 243 | 96.833 | 82.229 | 86.941 | 1.00 | 24.73 |
| ATOM | 1338 | CB | GLN | 243 | 96.364 | 83.679 | 86.905 | 1.00 | 25.73 |
| ATOM | 1339 | CG | GLN | 243 | 97.449 | 84.714 | 87.041 | 1.00 | 28.69 |
| ATOM | 1340 | CD | GLN | 243 | 96.883 | 86.108 | 86.960 | 1.00 | 31.37 |
| ATOM | 1341 | OE1 | GLN | 243 | 97.213 | 86.874 | 86.062 | 1.00 | 35.38 |
| ATOM | 1342 | NE2 | GLN | 243 | 95.986 | 86.431 | 87.877 | 1.00 | 35.92 |
| ATOM | 1343 | C | GLN | 243 | 95.625 | 81.346 | 86.646 | 1.00 | 23.19 |
| ATOM | 1344 | O | GLN | 243 | 95.335 | 81.062 | 85.488 | 1.00 | 22.08 |
| ATOM | 1345 | N | LEU | 244 | 94.907 | 80.934 | 87.684 | 1.00 | 22.67 |
| ATOM | 1346 | CA | LEU | 244 | 93.723 | 80.111 | 87.484 | 1.00 | 23.46 |
| ATOM | 1347 | CB | LEU | 244 | 93.144 | 79.655 | 88.824 | 1.00 | 22.03 |
| ATOM | 1348 | CG | LEU | 244 | 93.986 | 78.729 | 89.695 | 1.00 | 18.65 |
| ATOM | 1349 | CD1 | LEU | 244 | 93.196 | 78.359 | 90.934 | 1.00 | 13.02 |
| ATOM | 1350 | CD2 | LEU | 244 | 94.361 | 77.478 | 88.913 | 1.00 | 18.74 |
| ATOM | 1351 | C | LEU | 244 | 92.690 | 80.959 | 86.757 | 1.00 | 23.82 |
| ATOM | 1352 | O | LEU | 244 | 92.302 | 82.018 | 87.245 | 1.00 | 25.78 |
| ATOM | 1353 | N | LEU | 245 | 92.279 | 80.531 | 85.569 | 1.00 | 24.26 |
| ATOM | 1354 | CA | LEU | 245 | 91.286 | 81.298 | 84.836 | 1.00 | 22.59 |

FIG. 1A-24

| ATOM | 1355 | CB | LEU | 245 | 91.181 | 80.843 | 83.372 | 1.00 | 24.90 |
| --- | --- | --- | --- | --- | --- | --- | --- | --- | --- |
| ATOM | 1356 | CG | LEU | 245 | 91.196 | 79.370 | 82.962 | 1.00 | 25.75 |
| ATOM | 1357 | CD1 | LEU | 245 | 90.061 | 78.644 | 83.632 | 1.00 | 27.83 |
| ATOM | 1358 | CD2 | LEU | 245 | 91.086 | 79.250 | 81.443 | 1.00 | 21.78 |
| ATOM | 1359 | C | LEU | 245 | 89.949 | 81.241 | 85.564 | 1.00 | 21.43 |
| ATOM | 1360 | O | LEU | 245 | 89.665 | 80.286 | 86.286 | 1.00 | 22.49 |
| ATOM | 1361 | N | CYS | 246 | 89.151 | 82.288 | 85.401 | 1.00 | 20.00 |
| ATOM | 1362 | CA | CYS | 246 | 87.858 | 82.388 | 86.057 | 1.00 | 18.86 |
| ATOM | 1363 | CB | CYS | 246 | 88.004 | 83.243 | 87.321 | 1.00 | 17.47 |
| ATOM | 1364 | SG | CYS | 246 | 86.569 | 83.374 | 88.399 | 1.00 | 17.81 |
| ATOM | 1365 | C | CYS | 246 | 86.852 | 83.027 | 85.106 | 1.00 | 20.06 |
| ATOM | 1366 | O | CYS | 246 | 87.217 | 83.804 | 84.216 | 1.00 | 18.69 |
| ATOM | 1367 | N | GLY | 247 | 85.592 | 82.646 | 85.265 | 1.00 | 19.49 |
| ATOM | 1368 | CA | GLY | 247 | 84.532 | 83.197 | 84.449 | 1.00 | 17.64 |
| ATOM | 1369 | C | GLY | 247 | 83.474 | 83.715 | 85.398 | 1.00 | 16.99 |
| ATOM | 1370 | O | GLY | 247 | 83.420 | 83.287 | 86.553 | 1.00 | 18.25 |
| ATOM | 1371 | N | ALA | 248 | 82.630 | 84.626 | 84.935 | 1.00 | 16.02 |
| ATOM | 1372 | CA | ALA | 248 | 81.595 | 85.189 | 85.792 | 1.00 | 15.37 |
| ATOM | 1373 | CB | ALA | 248 | 82.055 | 86.520 | 86.362 | 1.00 | 10.50 |
| ATOM | 1374 | C | ALA | 248 | 80.299 | 85.360 | 85.016 | 1.00 | 15.60 |
| ATOM | 1375 | O | ALA | 248 | 80.319 | 85.477 | 83.788 | 1.00 | 15.68 |
| ATOM | 1376 | N | ALA | 249 | 79.174 | 85.357 | 85.724 | 1.00 | 15.70 |
| ATOM | 1377 | CA | ALA | 249 | 77.874 | 85.512 | 85.077 | 1.00 | 15.74 |
| ATOM | 1378 | CB | ALA | 249 | 76.918 | 84.445 | 85.574 | 1.00 | 12.70 |
| ATOM | 1379 | C | ALA | 249 | 77.282 | 86.891 | 85.327 | 1.00 | 14.03 |
| ATOM | 1380 | O | ALA | 249 | 77.329 | 87.381 | 86.452 | 1.00 | 14.73 |
| ATOM | 1381 | N | ILE | 250 | 76.759 | 87.531 | 84.286 | 1.00 | 12.46 |
| ATOM | 1382 | CA | ILE | 250 | 76.123 | 88.835 | 84.445 | 1.00 | 14.51 |
| ATOM | 1383 | CB | ILE | 250 | 76.965 | 90.018 | 83.895 | 1.00 | 11.80 |
| ATOM | 1384 | CG2 | ILE | 250 | 78.249 | 90.162 | 84.659 | 1.00 | 9.96 |
| ATOM | 1385 | CG1 | ILE | 250 | 77.207 | 89.866 | 82.395 | 1.00 | 15.67 |
| ATOM | 1386 | CD1 | ILE | 250 | 77.623 | 91.154 | 81.705 | 1.00 | 17.25 |
| ATOM | 1387 | C | ILE | 250 | 74.772 | 88.844 | 83.739 | 1.00 | 17.19 |
| ATOM | 1388 | O | ILE | 250 | 74.460 | 87.948 | 82.959 | 1.00 | 18.56 |
| ATOM | 1389 | N | GLY | 251 | 73.950 | 89.828 | 84.074 | 1.00 | 18.09 |
| ATOM | 1390 | CA | GLY | 251 | 72.655 | 89.954 | 83.447 | 1.00 | 18.30 |
| ATOM | 1391 | C | GLY | 251 | 72.821 | 90.758 | 82.176 | 1.00 | 20.39 |
| ATOM | 1392 | O | GLY | 251 | 73.944 | 90.968 | 81.721 | 1.00 | 20.47 |
| ATOM | 1393 | N | THR | 252 | 71.715 | 91.265 | 81.642 | 1.00 | 23.81 |
| ATOM | 1394 | CA | THR | 252 | 71.740 | 92.036 | 80.405 | 1.00 | 26.27 |
| ATOM | 1395 | CB | THR | 252 | 70.961 | 91.309 | 79.288 | 1.00 | 24.89 |
| ATOM | 1396 | OG1 | THR | 252 | 69.704 | 90.844 | 79.803 | 1.00 | 27.82 |
| ATOM | 1397 | CG2 | THR | 252 | 71.764 | 90.127 | 78.757 | 1.00 | 21.50 |
| ATOM | 1398 | C | THR | 252 | 71.216 | 93.467 | 80.537 | 1.00 | 28.88 |
| ATOM | 1399 | O | THR | 252 | 71.085 | 94.182 | 79.540 | 1.00 | 30.63 |
| ATOM | 1400 | N | HIS | 253 | 70.875 | 93.877 | 81.753 | 1.00 | 29.72 |
| ATOM | 1401 | CA | HIS | 253 | 70.393 | 95.235 | 81.970 | 1.00 | 32.38 |
| ATOM | 1402 | CB | HIS | 253 | 69.719 | 95.350 | 83.335 | 1.00 | 35.13 |
| ATOM | 1403 | CG | HIS | 253 | 68.545 | 94.438 | 83.516 | 1.00 | 38.59 |
| ATOM | 1404 | CD2 | HIS | 253 | 67.485 | 94.186 | 82.710 | 1.00 | 40.91 |
| ATOM | 1405 | ND1 | HIS | 253 | 68.367 | 93.659 | 84.636 | 1.00 | 41.86 |
| ATOM | 1406 | CE1 | HIS | 253 | 67.251 | 92.968 | 84.521 | 1.00 | 42.51 |
| ATOM | 1407 | NE2 | HIS | 253 | 66.691 | 93.269 | 83.360 | 1.00 | 43.09 |
| ATOM | 1408 | C | HIS | 253 | 71.596 | 96.171 | 81.905 | 1.00 | 34.27 |
| ATOM | 1409 | O | HIS | 253 | 72.735 | 95.728 | 82.055 | 1.00 | 34.56 |
| ATOM | 1410 | N | GLU | 254 | 71.347 | 97.461 | 81.696 | 1.00 | 36.70 |
| ATOM | 1411 | CA | GLU | 254 | 72.415 | 98.467 | 81.621 | 1.00 | 38.22 |
| ATOM | 1412 | CB | GLU | 254 | 71.811 | 99.877 | 81.566 | 1.00 | 39.91 |
| ATOM | 1413 | CG | GLU | 254 | 70.970 | 100.167 | 80.331 | 1.00 | 44.25 |

FIG. 1A-25

| | | | | | | | | | |
|---|---|---|---|---|---|---|---|---|---|
| ATOM | 1414 | CD | GLU | 254 | 71.797 | 100.264 | 79.060 | 1.00 | 47.81 |
| ATOM | 1415 | OE1 | GLU | 254 | 72.924 | 100.809 | 79.126 | 1.00 | 49.46 |
| ATOM | 1416 | OE2 | GLU | 254 | 71.316 | 99.808 | 77.995 | 1.00 | 46.89 |
| ATOM | 1417 | C | GLU | 254 | 73.363 | 98.376 | 82.821 | 1.00 | 38.45 |
| ATOM | 1418 | O | GLU | 254 | 74.576 | 98.556 | 82.690 | 1.00 | 37.95 |
| ATOM | 1419 | N | ASP | 255 | 72.791 | 98.085 | 83.986 | 1.00 | 39.23 |
| ATOM | 1420 | CA | ASP | 255 | 73.537 | 97.960 | 85.238 | 1.00 | 40.62 |
| ATOM | 1421 | CB | ASP | 255 | 72.618 | 97.427 | 86.346 | 1.00 | 48.75 |
| ATOM | 1422 | CG | ASP | 255 | 71.337 | 98.236 | 86.500 | 1.00 | 59.02 |
| ATOM | 1423 | OD1 | ASP | 255 | 71.359 | 99.251 | 87.238 | 1.00 | 63.37 |
| ATOM | 1424 | OD2 | ASP | 255 | 70.306 | 97.841 | 85.898 | 1.00 | 63.08 |
| ATOM | 1425 | C | ASP | 255 | 74.698 | 96.985 | 85.080 | 1.00 | 38.56 |
| ATOM | 1426 | O | ASP | 255 | 75.763 | 97.140 | 85.687 | 1.00 | 37.91 |
| ATOM | 1427 | N | ASP | 256 | 74.472 | 95.972 | 84.255 | 1.00 | 36.23 |
| ATOM | 1428 | CA | ASP | 256 | 75.467 | 94.943 | 84.028 | 1.00 | 32.80 |
| ATOM | 1429 | CB | ASP | 256 | 74.831 | 93.752 | 83.324 | 1.00 | 31.43 |
| ATOM | 1430 | CG | ASP | 256 | 73.752 | 93.113 | 84.164 | 1.00 | 31.85 |
| ATOM | 1431 | OD1 | ASP | 256 | 74.088 | 92.491 | 85.193 | 1.00 | 32.92 |
| ATOM | 1432 | OD2 | ASP | 256 | 72.566 | 93.253 | 83.817 | 1.00 | 33.76 |
| ATOM | 1433 | C | ASP | 256 | 76.702 | 95.433 | 83.311 | 1.00 | 30.28 |
| ATOM | 1434 | O | ASP | 256 | 77.730 | 94.760 | 83.307 | 1.00 | 30.73 |
| ATOM | 1435 | N | LYS | 257 | 76.623 | 96.620 | 82.732 | 1.00 | 27.82 |
| ATOM | 1436 | CA | LYS | 257 | 77.778 | 97.172 | 82.054 | 1.00 | 26.56 |
| ATOM | 1437 | CB | LYS | 257 | 77.360 | 98.332 | 81.163 | 1.00 | 27.33 |
| ATOM | 1438 | CG | LYS | 257 | 76.374 | 97.918 | 80.089 | 1.00 | 27.87 |
| ATOM | 1439 | CD | LYS | 257 | 76.064 | 99.065 | 79.168 | 1.00 | 29.75 |
| ATOM | 1440 | CE | LYS | 257 | 75.247 | 98.598 | 77.987 | 1.00 | 31.51 |
| ATOM | 1441 | NZ | LYS | 257 | 75.030 | 99.713 | 77.033 | 1.00 | 33.96 |
| ATOM | 1442 | C | LYS | 257 | 78.806 | 97.605 | 83.104 | 1.00 | 25.35 |
| ATOM | 1443 | O | LYS | 257 | 80.003 | 97.327 | 82.962 | 1.00 | 26.37 |
| ATOM | 1444 | N | TYR | 258 | 78.321 | 98.211 | 84.189 | 1.00 | 23.85 |
| ATOM | 1445 | CA | TYR | 258 | 79.171 | 98.661 | 85.294 | 1.00 | 22.66 |
| ATOM | 1446 | CB | TYR | 258 | 78.346 | 99.474 | 86.308 | 1.00 | 18.97 |
| ATOM | 1447 | CG | TYR | 258 | 78.981 | 99.660 | 87.677 | 1.00 | 18.12 |
| ATOM | 1448 | CD1 | TYR | 258 | 80.182 | 100.357 | 87.832 | 1.00 | 19.37 |
| ATOM | 1449 | CE1 | TYR | 258 | 80.765 | 100.518 | 89.096 | 1.00 | 19.31 |
| ATOM | 1450 | CD2 | TYR | 258 | 78.380 | 99.129 | 88.820 | 1.00 | 17.20 |
| ATOM | 1451 | CE2 | TYR | 258 | 78.955 | 99.284 | 90.081 | 1.00 | 17.71 |
| ATOM | 1452 | CZ | TYR | 258 | 80.144 | 99.978 | 90.213 | 1.00 | 18.86 |
| ATOM | 1453 | OH | TYR | 258 | 80.711 | 100.126 | 91.460 | 1.00 | 23.15 |
| ATOM | 1454 | C | TYR | 258 | 79.803 | 97.440 | 85.960 | 1.00 | 23.75 |
| ATOM | 1455 | O | TYR | 258 | 81.028 | 97.365 | 86.127 | 1.00 | 26.26 |
| ATOM | 1456 | N | ARG | 259 | 78.959 | 96.487 | 86.335 | 1.00 | 22.76 |
| ATOM | 1457 | CA | ARG | 259 | 79.415 | 95.251 | 86.955 | 1.00 | 21.36 |
| ATOM | 1458 | CB | ARG | 259 | 78.231 | 94.307 | 87.120 | 1.00 | 21.72 |
| ATOM | 1459 | CG | ARG | 259 | 78.579 | 92.912 | 87.567 | 1.00 | 20.25 |
| ATOM | 1460 | CD | ARG | 259 | 77.328 | 92.068 | 87.586 | 1.00 | 16.94 |
| ATOM | 1461 | NE | ARG | 259 | 76.371 | 92.538 | 88.583 | 1.00 | 9.97 |
| ATOM | 1462 | CZ | ARG | 259 | 76.422 | 92.204 | 89.866 | 1.00 | 11.33 |
| ATOM | 1463 | NH1 | ARG | 259 | 77.381 | 91.403 | 90.305 | 1.00 | 15.57 |
| ATOM | 1464 | NH2 | ARG | 259 | 75.511 | 92.658 | 90.710 | 1.00 | 9.18 |
| ATOM | 1465 | C | ARG | 259 | 80.479 | 94.607 | 86.070 | 1.00 | 20.76 |
| ATOM | 1466 | O | ARG | 259 | 81.534 | 94.217 | 86.555 | 1.00 | 23.26 |
| ATOM | 1467 | N | LEU | 260 | 80.217 | 94.557 | 84.766 | 1.00 | 19.61 |
| ATOM | 1468 | CA | LEU | 260 | 81.149 | 93.986 | 83.800 | 1.00 | 19.57 |
| ATOM | 1469 | CB | LEU | 260 | 80.614 | 94.141 | 82.372 | 1.00 | 15.34 |
| ATOM | 1470 | CG | LEU | 260 | 81.576 | 93.695 | 81.270 | 1.00 | 12.31 |
| ATOM | 1471 | CD1 | LEU | 260 | 81.799 | 92.187 | 81.352 | 1.00 | 13.03 |
| ATOM | 1472 | CD2 | LEU | 260 | 81.035 | 94.079 | 79.914 | 1.00 | 11.42 |

FIG. 1A-26

| ATOM | 1473 | C | LEU | 260 | 82.496 | 94.684 | 83.898 | 1.00 | 22.22 |
|---|---|---|---|---|---|---|---|---|---|
| ATOM | 1474 | O | LEU | 260 | 83.549 | 94.038 | 83.867 | 1.00 | 22.00 |
| ATOM | 1475 | N | ASP | 261 | 82.462 | 96.008 | 83.997 | 1.00 | 24.36 |
| ATOM | 1476 | CA | ASP | 261 | 83.688 | 96.785 | 84.090 | 1.00 | 23.45 |
| ATOM | 1477 | CB | ASP | 261 | 83.389 | 98.284 | 84.092 | 1.00 | 24.33 |
| ATOM | 1478 | CG | ASP | 261 | 82.896 | 98.788 | 82.739 | 1.00 | 26.27 |
| ATOM | 1479 | OD1 | ASP | 261 | 83.111 | 98.103 | 81.719 | 1.00 | 19.29 |
| ATOM | 1480 | OD2 | ASP | 261 | 82.295 | 99.881 | 82.693 | 1.00 | 32.41 |
| ATOM | 1481 | C | ASP | 261 | 84.480 | 96.378 | 85.315 | 1.00 | 22.43 |
| ATOM | 1482 | O | ASP | 261 | 85.689 | 96.169 | 85.219 | 1.00 | 25.11 |
| ATOM | 1483 | N | LEU | 262 | 83.801 | 96.197 | 86.445 | 1.00 | 19.65 |
| ATOM | 1484 | CA | LEU | 262 | 84.482 | 95.782 | 87.670 | 1.00 | 18.60 |
| ATOM | 1485 | CB | LEU | 262 | 83.547 | 95.857 | 88.877 | 1.00 | 16.65 |
| ATOM | 1486 | CG | LEU | 262 | 82.947 | 97.231 | 89.194 | 1.00 | 18.61 |
| ATOM | 1487 | CD1 | LEU | 262 | 82.651 | 97.321 | 90.682 | 1.00 | 14.11 |
| ATOM | 1488 | CD2 | LEU | 262 | 83.910 | 98.341 | 88.782 | 1.00 | 16.63 |
| ATOM | 1489 | C | LEU | 262 | 85.030 | 94.368 | 87.522 | 1.00 | 19.71 |
| ATOM | 1490 | O | LEU | 262 | 86.100 | 94.044 | 88.050 | 1.00 | 20.31 |
| ATOM | 1491 | N | LEU | 263 | 84.306 | 93.533 | 86.782 | 1.00 | 19.72 |
| ATOM | 1492 | CA | LEU | 263 | 84.728 | 92.158 | 86.546 | 1.00 | 18.62 |
| ATOM | 1493 | CB | LEU | 263 | 83.581 | 91.321 | 85.970 | 1.00 | 15.30 |
| ATOM | 1494 | CG | LEU | 263 | 82.386 | 91.120 | 86.909 | 1.00 | 13.44 |
| ATOM | 1495 | CD1 | LEU | 263 | 81.319 | 90.307 | 86.215 | 1.00 | 12.65 |
| ATOM | 1496 | CD2 | LEU | 263 | 82.828 | 90.450 | 88.194 | 1.00 | 8.53 |
| ATOM | 1497 | C | LEU | 263 | 85.925 | 92.145 | 85.608 | 1.00 | 19.87 |
| ATOM | 1498 | O | LEU | 263 | 86.802 | 91.288 | 85.730 | 1.00 | 19.89 |
| ATOM | 1499 | N | ALA | 264 | 85.966 | 93.104 | 84.685 | 1.00 | 20.77 |
| ATOM | 1500 | CA | ALA | 264 | 87.079 | 93.220 | 83.741 | 1.00 | 21.02 |
| ATOM | 1501 | CB | ALA | 264 | 86.809 | 94.324 | 82.728 | 1.00 | 19.62 |
| ATOM | 1502 | C | ALA | 264 | 88.331 | 93.540 | 84.553 | 1.00 | 20.05 |
| ATOM | 1503 | O | ALA | 264 | 89.330 | 92.824 | 84.484 | 1.00 | 19.96 |
| ATOM | 1504 | N | LEU | 265 | 88.235 | 94.582 | 85.374 | 1.00 | 19.65 |
| ATOM | 1505 | CA | LEU | 265 | 89.326 | 95.002 | 86.240 | 1.00 | 17.63 |
| ATOM | 1506 | CB | LEU | 265 | 88.875 | 96.165 | 87.118 | 1.00 | 14.88 |
| ATOM | 1507 | CG | LEU | 265 | 88.827 | 97.558 | 86.487 | 1.00 | 16.17 |
| ATOM | 1508 | CD1 | LEU | 265 | 88.122 | 98.539 | 87.420 | 1.00 | 14.22 |
| ATOM | 1509 | CD2 | LEU | 265 | 90.236 | 98.024 | 86.198 | 1.00 | 9.91 |
| ATOM | 1510 | C | LEU | 265 | 89.781 | 93.856 | 87.136 | 1.00 | 19.52 |
| ATOM | 1511 | O | LEU | 265 | 90.945 | 93.792 | 87.517 | 1.00 | 23.94 |
| ATOM | 1512 | N | ALA | 266 | 88.851 | 92.975 | 87.495 | 1.00 | 17.94 |
| ATOM | 1513 | CA | ALA | 266 | 89.144 | 91.827 | 88.349 | 1.00 | 14.70 |
| ATOM | 1514 | CB | ALA | 266 | 87.852 | 91.215 | 88.859 | 1.00 | 14.20 |
| ATOM | 1515 | C | ALA | 266 | 89.956 | 90.776 | 87.605 | 1.00 | 14.73 |
| ATOM | 1516 | O | ALA | 266 | 90.602 | 89.925 | 88.219 | 1.00 | 14.46 |
| ATOM | 1517 | N | GLY | 267 | 89.901 | 90.825 | 86.280 | 1.00 | 14.47 |
| ATOM | 1518 | CA | GLY | 267 | 90.638 | 89.869 | 85.480 | 1.00 | 15.93 |
| ATOM | 1519 | C | GLY | 267 | 89.848 | 88.638 | 85.089 | 1.00 | 19.86 |
| ATOM | 1520 | O | GLY | 267 | 90.427 | 87.567 | 84.889 | 1.00 | 23.99 |
| ATOM | 1521 | N | VAL | 268 | 88.528 | 88.774 | 84.996 | 1.00 | 21.02 |
| ATOM | 1522 | CA | VAL | 268 | 87.660 | 87.670 | 84.607 | 1.00 | 19.03 |
| ATOM | 1523 | CB | VAL | 268 | 86.178 | 88.107 | 84.620 | 1.00 | 16.96 |
| ATOM | 1524 | CG1 | VAL | 268 | 85.891 | 89.056 | 83.477 | 1.00 | 13.08 |
| ATOM | 1525 | CG2 | VAL | 268 | 85.266 | 86.907 | 84.565 | 1.00 | 18.26 |
| ATOM | 1526 | C | VAL | 268 | 88.076 | 87.274 | 83.188 | 1.00 | 19.74 |
| ATOM | 1527 | O | VAL | 268 | 88.452 | 88.136 | 82.393 | 1.00 | 21.80 |
| ATOM | 1528 | N | ASP | 269 | 88.035 | 85.980 | 82.886 | 1.00 | 18.77 |
| ATOM | 1529 | CA | ASP | 269 | 88.428 | 85.481 | 81.571 | 1.00 | 15.89 |
| ATOM | 1530 | CB | ASP | 269 | 89.229 | 84.193 | 81.728 | 1.00 | 15.41 |
| ATOM | 1531 | CG | ASP | 269 | 90.448 | 84.371 | 82.604 | 1.00 | 19.66 |

FIG. 1A-27

| | | | | | | | | | |
|---|---|---|---|---|---|---|---|---|---|
| ATOM | 1532 | OD1 | ASP | 269 | 91.555 | 84.564 | 82.070 | 1.00 | 22.69 |
| ATOM | 1533 | OD2 | ASP | 269 | 90.303 | 84.319 | 83.835 | 1.00 | 22.25 |
| ATOM | 1534 | C | ASP | 269 | 87.273 | 85.245 | 80.597 | 1.00 | 16.00 |
| ATOM | 1535 | O | ASP | 269 | 87.419 | 85.442 | 79.386 | 1.00 | 17.09 |
| ATOM | 1536 | N | VAL | 270 | 86.146 | 84.770 | 81.115 | 1.00 | 16.22 |
| ATOM | 1537 | CA | VAL | 270 | 84.978 | 84.491 | 80.289 | 1.00 | 16.09 |
| ATOM | 1538 | CB | VAL | 270 | 84.782 | 82.974 | 80.021 | 1.00 | 15.10 |
| ATOM | 1539 | CG1 | VAL | 270 | 85.722 | 82.506 | 78.967 | 1.00 | 20.52 |
| ATOM | 1540 | CG2 | VAL | 270 | 85.024 | 82.174 | 81.275 | 1.00 | 15.72 |
| ATOM | 1541 | C | VAL | 270 | 83.759 | 84.976 | 81.024 | 1.00 | 16.90 |
| ATOM | 1542 | O | VAL | 270 | 83.689 | 84.857 | 82.248 | 1.00 | 18.88 |
| ATOM | 1543 | N | VAL | 271 | 82.797 | 85.512 | 80.284 | 1.00 | 15.33 |
| ATOM | 1544 | CA | VAL | 271 | 81.574 | 86.005 | 80.885 | 1.00 | 13.74 |
| ATOM | 1545 | CB | VAL | 271 | 81.528 | 87.542 | 80.857 | 1.00 | 11.48 |
| ATOM | 1546 | CG1 | VAL | 271 | 80.130 | 88.035 | 81.173 | 1.00 | 11.74 |
| ATOM | 1547 | CG2 | VAL | 271 | 82.497 | 88.096 | 81.881 | 1.00 | 11.95 |
| ATOM | 1548 | C | VAL | 271 | 80.333 | 85.420 | 80.215 | 1.00 | 14.45 |
| ATOM | 1549 | O | VAL | 271 | 80.222 | 85.401 | 78.986 | 1.00 | 15.35 |
| ATOM | 1550 | N | VAL | 272 | 79.421 | 84.904 | 81.028 | 1.00 | 13.08 |
| ATOM | 1551 | CA | VAL | 272 | 78.193 | 84.341 | 80.511 | 1.00 | 12.88 |
| ATOM | 1552 | CB | VAL | 272 | 77.924 | 82.906 | 81.050 | 1.00 | 11.78 |
| ATOM | 1553 | CG1 | VAL | 272 | 77.855 | 82.893 | 82.547 | 1.00 | 13.59 |
| ATOM | 1554 | CG2 | VAL | 272 | 76.630 | 82.371 | 80.485 | 1.00 | 11.58 |
| ATOM | 1555 | C | VAL | 272 | 77.020 | 85.255 | 80.843 | 1.00 | 14.54 |
| ATOM | 1556 | O | VAL | 272 | 76.896 | 85.751 | 81.971 | 1.00 | 14.50 |
| ATOM | 1557 | N | LEU | 273 | 76.215 | 85.535 | 79.823 | 1.00 | 14.49 |
| ATOM | 1558 | CA | LEU | 273 | 75.031 | 86.362 | 79.969 | 1.00 | 13.78 |
| ATOM | 1559 | CB | LEU | 273 | 74.703 | 87.005 | 78.628 | 1.00 | 10.64 |
| ATOM | 1560 | CG | LEU | 273 | 75.900 | 87.845 | 78.168 | 1.00 | 8.78 |
| ATOM | 1561 | CD1 | LEU | 273 | 75.649 | 88.474 | 76.836 | 1.00 | 10.66 |
| ATOM | 1562 | CD2 | LEU | 273 | 76.186 | 88.927 | 79.188 | 1.00 | 9.83 |
| ATOM | 1563 | C | LEU | 273 | 73.916 | 85.434 | 80.469 | 1.00 | 16.26 |
| ATOM | 1564 | O | LEU | 273 | 73.510 | 84.478 | 79.781 | 1.00 | 15.19 |
| ATOM | 1565 | N | ASP | 274 | 73.499 | 85.689 | 81.708 | 1.00 | 15.97 |
| ATOM | 1566 | CA | ASP | 274 | 72.492 | 84.910 | 82.430 | 1.00 | 14.76 |
| ATOM | 1567 | CB | ASP | 274 | 72.706 | 85.144 | 83.932 | 1.00 | 14.18 |
| ATOM | 1568 | CG | ASP | 274 | 72.150 | 84.036 | 84.789 | 1.00 | 18.31 |
| ATOM | 1569 | OD1 | ASP | 274 | 72.007 | 82.901 | 84.291 | 1.00 | 23.20 |
| ATOM | 1570 | OD2 | ASP | 274 | 71.882 | 84.294 | 85.985 | 1.00 | 21.30 |
| ATOM | 1571 | C | ASP | 274 | 71.028 | 85.177 | 82.066 | 1.00 | 13.69 |
| ATOM | 1572 | O | ASP | 274 | 70.494 | 86.253 | 82.339 | 1.00 | 16.74 |
| ATOM | 1573 | N | SER | 275 | 70.367 | 84.174 | 81.501 | 1.00 | 11.17 |
| ATOM | 1574 | CA | SER | 275 | 68.963 | 84.287 | 81.122 | 1.00 | 10.14 |
| ATOM | 1575 | CB | SER | 275 | 68.784 | 85.240 | 79.934 | 1.00 | 8.75 |
| ATOM | 1576 | OG | SER | 275 | 69.604 | 84.882 | 78.828 | 1.00 | 18.88 |
| ATOM | 1577 | C | SER | 275 | 68.344 | 82.937 | 80.802 | 1.00 | 10.53 |
| ATOM | 1578 | O | SER | 275 | 69.030 | 82.021 | 80.351 | 1.00 | 10.72 |
| ATOM | 1579 | N | SER | 276 | 67.054 | 82.810 | 81.092 | 1.00 | 12.08 |
| ATOM | 1580 | CA | SER | 276 | 66.311 | 81.589 | 80.835 | 1.00 | 11.23 |
| ATOM | 1581 | CB | SER | 276 | 65.058 | 81.558 | 81.702 | 1.00 | 7.13 |
| ATOM | 1582 | OG | SER | 276 | 64.208 | 82.626 | 81.348 | 1.00 | 7.88 |
| ATOM | 1583 | C | SER | 276 | 65.921 | 81.513 | 79.359 | 1.00 | 13.13 |
| ATOM | 1584 | O | SER | 276 | 65.594 | 80.439 | 78.845 | 1.00 | 17.69 |
| ATOM | 1585 | N | GLN | 277 | 65.930 | 82.657 | 78.687 | 1.00 | 12.48 |
| ATOM | 1586 | CA | GLN | 277 | 65.583 | 82.720 | 77.275 | 1.00 | 14.28 |
| ATOM | 1587 | CB | GLN | 277 | 64.093 | 83.058 | 77.115 | 1.00 | 13.50 |
| ATOM | 1588 | CG | GLN | 277 | 63.387 | 82.326 | 75.968 | 1.00 | 10.64 |
| ATOM | 1589 | CD | GLN | 277 | 63.715 | 82.880 | 74.584 | 1.00 | 13.67 |
| ATOM | 1590 | OE1 | GLN | 277 | 62.891 | 83.547 | 73.959 | 1.00 | 13.62 |

FIG. 1A-28

| | | | | | | | | |
|---|---|---|---|---|---|---|---|---|
| ATOM | 1591 | NE2 | GLN | 277 | 64.906 | 82.574 | 74.088 | 1.00 | 14.26 |
| ATOM | 1592 | C | GLN | 277 | 66.463 | 83.823 | 76.702 | 1.00 | 15.33 |
| ATOM | 1593 | O | GLN | 277 | 66.047 | 84.981 | 76.612 | 1.00 | 17.75 |
| ATOM | 1594 | N | GLY | 278 | 67.685 | 83.453 | 76.329 | 1.00 | 13.77 |
| ATOM | 1595 | CA | GLY | 278 | 68.637 | 84.413 | 75.809 | 1.00 | 11.38 |
| ATOM | 1596 | C | GLY | 278 | 68.472 | 84.918 | 74.396 | 1.00 | 11.86 |
| ATOM | 1597 | O | GLY | 278 | 69.294 | 85.703 | 73.956 | 1.00 | 14.42 |
| ATOM | 1598 | N | ASN | 279 | 67.460 | 84.474 | 73.664 | 1.00 | 11.99 |
| ATOM | 1599 | CA | ASN | 279 | 67.282 | 84.959 | 72.299 | 1.00 | 13.64 |
| ATOM | 1600 | CB | ASN | 279 | 66.599 | 83.900 | 71.438 | 1.00 | 13.49 |
| ATOM | 1601 | CG | ASN | 279 | 66.410 | 84.345 | 70.001 | 1.00 | 12.47 |
| ATOM | 1602 | OD1 | ASN | 279 | 67.116 | 85.214 | 69.509 | 1.00 | 12.30 |
| ATOM | 1603 | ND2 | ASN | 279 | 65.435 | 83.757 | 69.331 | 1.00 | 14.37 |
| ATOM | 1604 | C | ASN | 279 | 66.452 | 86.240 | 72.335 | 1.00 | 15.97 |
| ATOM | 1605 | O | ASN | 279 | 65.286 | 86.256 | 71.941 | 1.00 | 18.11 |
| ATOM | 1606 | N | SER | 280 | 67.058 | 87.317 | 72.819 | 1.00 | 16.92 |
| ATOM | 1607 | CA | SER | 280 | 66.355 | 88.585 | 72.940 | 1.00 | 14.96 |
| ATOM | 1608 | CB | SER | 280 | 66.005 | 88.845 | 74.408 | 1.00 | 14.71 |
| ATOM | 1609 | OG | SER | 280 | 67.161 | 89.029 | 75.220 | 1.00 | 13.79 |
| ATOM | 1610 | C | SER | 280 | 67.165 | 89.747 | 72.419 | 1.00 | 15.56 |
| ATOM | 1611 | O | SER | 280 | 68.396 | 89.694 | 72.378 | 1.00 | 17.53 |
| ATOM | 1612 | N | ILE | 281 | 66.474 | 90.825 | 72.077 | 1.00 | 15.66 |
| ATOM | 1613 | CA | ILE | 281 | 67.135 | 92.022 | 71.584 | 1.00 | 14.41 |
| ATOM | 1614 | CB | ILE | 281 | 66.097 | 93.080 | 71.109 | 1.00 | 14.31 |
| ATOM | 1615 | CG2 | ILE | 281 | 65.235 | 93.547 | 72.266 | 1.00 | 11.29 |
| ATOM | 1616 | CG1 | ILE | 281 | 66.807 | 94.239 | 70.417 | 1.00 | 14.68 |
| ATOM | 1617 | CD1 | ILE | 281 | 67.730 | 93.792 | 69.281 | 1.00 | 14.99 |
| ATOM | 1618 | C | ILE | 281 | 68.042 | 92.588 | 72.683 | 1.00 | 13.74 |
| ATOM | 1619 | O | ILE | 281 | 69.099 | 93.153 | 72.404 | 1.00 | 12.52 |
| ATOM | 1620 | N | PHE | 282 | 67.659 | 92.368 | 73.937 | 1.00 | 15.03 |
| ATOM | 1621 | CA | PHE | 282 | 68.435 | 92.855 | 75.077 | 1.00 | 14.86 |
| ATOM | 1622 | CB | PHE | 282 | 67.707 | 92.591 | 76.399 | 1.00 | 14.56 |
| ATOM | 1623 | CG | PHE | 282 | 66.256 | 92.942 | 76.364 | 1.00 | 19.88 |
| ATOM | 1624 | CD1 | PHE | 282 | 65.835 | 94.187 | 75.904 | 1.00 | 25.20 |
| ATOM | 1625 | CD2 | PHE | 282 | 65.304 | 92.026 | 76.787 | 1.00 | 22.64 |
| ATOM | 1626 | CE1 | PHE | 282 | 64.485 | 94.509 | 75.845 | 1.00 | 27.06 |
| ATOM | 1627 | CE2 | PHE | 282 | 63.951 | 92.332 | 76.735 | 1.00 | 26.16 |
| ATOM | 1628 | CZ | PHE | 282 | 63.540 | 93.579 | 76.269 | 1.00 | 29.37 |
| ATOM | 1629 | C | PHE | 282 | 69.796 | 92.188 | 75.122 | 1.00 | 14.34 |
| ATOM | 1630 | O | PHE | 282 | 70.811 | 92.866 | 75.263 | 1.00 | 14.62 |
| ATOM | 1631 | N | GLN | 283 | 69.820 | 90.864 | 75.001 | 1.00 | 15.01 |
| ATOM | 1632 | CA | GLN | 283 | 71.087 | 90.148 | 75.052 | 1.00 | 17.13 |
| ATOM | 1633 | CB | GLN | 283 | 70.889 | 88.660 | 75.311 | 1.00 | 17.99 |
| ATOM | 1634 | CG | GLN | 283 | 72.196 | 87.972 | 75.692 | 1.00 | 18.78 |
| ATOM | 1635 | CD | GLN | 283 | 72.051 | 86.486 | 75.904 | 1.00 | 16.42 |
| ATOM | 1636 | OE1 | GLN | 283 | 72.606 | 85.697 | 75.154 | 1.00 | 16.50 |
| ATOM | 1637 | NE2 | GLN | 283 | 71.322 | 86.098 | 76.944 | 1.00 | 17.31 |
| ATOM | 1638 | C | GLN | 283 | 71.915 | 90.331 | 73.792 | 1.00 | 17.41 |
| ATOM | 1639 | O | GLN | 283 | 73.138 | 90.426 | 73.856 | 1.00 | 17.81 |
| ATOM | 1640 | N | ILE | 284 | 71.249 | 90.358 | 72.647 | 1.00 | 18.52 |
| ATOM | 1641 | CA | ILE | 284 | 71.935 | 90.546 | 71.373 | 1.00 | 19.90 |
| ATOM | 1642 | CB | ILE | 284 | 70.915 | 90.586 | 70.194 | 1.00 | 19.91 |
| ATOM | 1643 | CG2 | ILE | 284 | 71.604 | 91.001 | 68.900 | 1.00 | 20.36 |
| ATOM | 1644 | CG1 | ILE | 284 | 70.239 | 89.215 | 70.052 | 1.00 | 18.80 |
| ATOM | 1645 | CD1 | ILE | 284 | 69.221 | 89.133 | 68.948 | 1.00 | 20.66 |
| ATOM | 1646 | C | ILE | 284 | 72.749 | 91.841 | 71.426 | 1.00 | 19.77 |
| ATOM | 1647 | O | ILE | 284 | 73.962 | 91.831 | 71.201 | 1.00 | 21.96 |
| ATOM | 1648 | N | ASN | 285 | 72.097 | 92.934 | 71.811 | 1.00 | 18.02 |
| ATOM | 1649 | CA | ASN | 285 | 72.767 | 94.219 | 71.901 | 1.00 | 16.86 |

FIG. 1A-29

| ATOM | 1650 | CB | ASN | 285 | 71.758 | 95.335 | 72.136 | 1.00 | 9.23 |
| --- | --- | --- | --- | --- | --- | --- | --- | --- | --- |
| ATOM | 1651 | CG | ASN | 285 | 70.839 | 95.538 | 70.963 | 1.00 | 10.63 |
| ATOM | 1652 | OD1 | ASN | 285 | 71.251 | 95.416 | 69.805 | 1.00 | 14.11 |
| ATOM | 1653 | ND2 | ASN | 285 | 69.577 | 95.842 | 71.246 | 1.00 | 12.07 |
| ATOM | 1654 | C | ASN | 285 | 73.842 | 94.223 | 72.980 | 1.00 | 19.52 |
| ATOM | 1655 | O | ASN | 285 | 74.877 | 94.881 | 72.838 | 1.00 | 21.75 |
| ATOM | 1656 | N | MET | 286 | 73.610 | 93.474 | 74.051 | 1.00 | 20.87 |
| ATOM | 1657 | CA | MET | 286 | 74.582 | 93.388 | 75.132 | 1.00 | 24.40 |
| ATOM | 1658 | CB | MET | 286 | 73.979 | 92.662 | 76.335 | 1.00 | 25.20 |
| ATOM | 1659 | CG | MET | 286 | 74.934 | 92.449 | 77.501 | 1.00 | 29.91 |
| ATOM | 1660 | SD | MET | 286 | 75.778 | 93.921 | 78.086 | 1.00 | 26.75 |
| ATOM | 1661 | CE | MET | 286 | 74.626 | 94.506 | 79.322 | 1.00 | 30.56 |
| ATOM | 1662 | C | MET | 286 | 75.831 | 92.666 | 74.621 | 1.00 | 27.07 |
| ATOM | 1663 | O | MET | 286 | 76.958 | 93.069 | 74.930 | 1.00 | 27.63 |
| ATOM | 1664 | N | ILE | 287 | 75.621 | 91.634 | 73.803 | 1.00 | 28.55 |
| ATOM | 1665 | CA | ILE | 287 | 76.712 | 90.856 | 73.215 | 1.00 | 28.03 |
| ATOM | 1666 | CB | ILE | 287 | 76.175 | 89.730 | 72.294 | 1.00 | 26.14 |
| ATOM | 1667 | CG2 | ILE | 287 | 77.310 | 89.112 | 71.487 | 1.00 | 23.50 |
| ATOM | 1668 | CG1 | ILE | 287 | 75.472 | 88.648 | 73.114 | 1.00 | 26.20 |
| ATOM | 1669 | CD1 | ILE | 287 | 76.414 | 87.729 | 73.835 | 1.00 | 24.06 |
| ATOM | 1670 | C | ILE | 287 | 77.556 | 91.794 | 72.362 | 1.00 | 29.78 |
| ATOM | 1671 | O | ILE | 287 | 78.770 | 91.906 | 72.559 | 1.00 | 30.63 |
| ATOM | 1672 | N | LYS | 288 | 76.892 | 92.483 | 71.437 | 1.00 | 31.89 |
| ATOM | 1673 | CA | LYS | 288 | 77.549 | 93.417 | 70.523 | 1.00 | 34.53 |
| ATOM | 1674 | CB | LYS | 288 | 76.521 | 94.076 | 69.603 | 1.00 | 33.65 |
| ATOM | 1675 | CG | LYS | 288 | 75.860 | 93.124 | 68.623 | 1.00 | 33.76 |
| ATOM | 1676 | CD | LYS | 288 | 74.914 | 93.876 | 67.713 | 1.00 | 38.36 |
| ATOM | 1677 | CE | LYS | 288 | 74.279 | 92.962 | 66.684 | 1.00 | 43.07 |
| ATOM | 1678 | NZ | LYS | 288 | 73.338 | 93.710 | 65.798 | 1.00 | 47.95 |
| ATOM | 1679 | C | LYS | 288 | 78.343 | 94.485 | 71.265 | 1.00 | 37.00 |
| ATOM | 1680 | O | LYS | 288 | 79.420 | 94.897 | 70.819 | 1.00 | 39.41 |
| ATOM | 1681 | N | TYR | 289 | 77.790 | 94.945 | 72.383 | 1.00 | 36.27 |
| ATOM | 1682 | CA | TYR | 289 | 78.436 | 95.944 | 73.219 | 1.00 | 34.85 |
| ATOM | 1683 | CB | TYR | 289 | 77.514 | 96.292 | 74.390 | 1.00 | 32.73 |
| ATOM | 1684 | CG | TYR | 289 | 78.159 | 97.114 | 75.482 | 1.00 | 30.62 |
| ATOM | 1685 | CD1 | TYR | 289 | 78.359 | 98.484 | 75.327 | 1.00 | 31.85 |
| ATOM | 1686 | CE1 | TYR | 289 | 78.943 | 99.243 | 76.325 | 1.00 | 28.71 |
| ATOM | 1687 | CD2 | TYR | 289 | 78.574 | 96.522 | 76.668 | 1.00 | 31.04 |
| ATOM | 1688 | CE2 | TYR | 289 | 79.162 | 97.273 | 77.675 | 1.00 | 31.98 |
| ATOM | 1689 | CZ | TYR | 289 | 79.348 | 98.630 | 77.494 | 1.00 | 30.03 |
| ATOM | 1690 | OH | TYR | 289 | 79.931 | 99.374 | 78.485 | 1.00 | 32.92 |
| ATOM | 1691 | C | TYR | 289 | 79.770 | 95.401 | 73.744 | 1.00 | 35.05 |
| ATOM | 1692 | O | TYR | 289 | 80.833 | 95.979 | 73.507 | 1.00 | 34.75 |
| ATOM | 1693 | N | MET | 290 | 79.697 | 94.261 | 74.421 | 1.00 | 35.07 |
| ATOM | 1694 | CA | MET | 290 | 80.858 | 93.611 | 75.011 | 1.00 | 34.69 |
| ATOM | 1695 | CB | MET | 290 | 80.422 | 92.339 | 75.727 | 1.00 | 33.03 |
| ATOM | 1696 | CG | MET | 290 | 79.436 | 92.601 | 76.840 | 1.00 | 31.76 |
| ATOM | 1697 | SD | MET | 290 | 78.883 | 91.099 | 77.601 | 1.00 | 31.65 |
| ATOM | 1698 | CE | MET | 290 | 80.424 | 90.507 | 78.341 | 1.00 | 30.46 |
| ATOM | 1699 | C | MET | 290 | 81.958 | 93.295 | 74.012 | 1.00 | 36.51 |
| ATOM | 1700 | O | MET | 290 | 83.141 | 93.486 | 74.308 | 1.00 | 37.23 |
| ATOM | 1701 | N | LYS | 291 | 81.577 | 92.788 | 72.843 | 1.00 | 36.05 |
| ATOM | 1702 | CA | LYS | 291 | 82.550 | 92.458 | 71.803 | 1.00 | 34.69 |
| ATOM | 1703 | CB | LYS | 291 | 81.856 | 91.770 | 70.626 | 1.00 | 35.82 |
| ATOM | 1704 | CG | LYS | 291 | 82.396 | 90.391 | 70.284 | 1.00 | 36.35 |
| ATOM | 1705 | CD | LYS | 291 | 82.164 | 89.404 | 71.417 | 1.00 | 38.70 |
| ATOM | 1706 | CE | LYS | 291 | 83.442 | 89.107 | 72.198 | 1.00 | 38.01 |
| ATOM | 1707 | NZ | LYS | 291 | 84.404 | 88.262 | 71.437 | 1.00 | 33.80 |
| ATOM | 1708 | C | LYS | 291 | 83.243 | 93.733 | 71.328 | 1.00 | 34.40 |

FIG. 1A-30

| ATOM | 1709 | O | LYS | 291 | 84.393 | 93.699 | 70.897 | 1.00 | 33.76 |
| ATOM | 1710 | N | GLU | 292 | 82.528 | 94.853 | 71.401 | 1.00 | 34.73 |
| ATOM | 1711 | CA | GLU | 292 | 83.063 | 96.145 | 70.998 | 1.00 | 35.38 |
| ATOM | 1712 | CB | GLU | 292 | 81.933 | 97.156 | 70.798 | 1.00 | 41.72 |
| ATOM | 1713 | CG | GLU | 292 | 82.425 | 98.589 | 70.606 | 1.00 | 53.68 |
| ATOM | 1714 | CD | GLU | 292 | 81.320 | 99.627 | 70.724 | 1.00 | 64.47 |
| ATOM | 1715 | OE1 | GLU | 292 | 81.251 | 100.519 | 69.847 | 1.00 | 68.28 |
| ATOM | 1716 | OE2 | GLU | 292 | 80.533 | 99.564 | 71.698 | 1.00 | 69.72 |
| ATOM | 1717 | C | GLU | 292 | 84.021 | 96.681 | 72.051 | 1.00 | 33.49 |
| ATOM | 1718 | O | GLU | 292 | 85.194 | 96.928 | 71.773 | 1.00 | 32.22 |
| ATOM | 1719 | N | LYS | 293 | 83.503 | 96.868 | 73.259 | 1.00 | 32.85 |
| ATOM | 1720 | CA | LYS | 293 | 84.286 | 97.395 | 74.372 | 1.00 | 32.45 |
| ATOM | 1721 | CB | LYS | 293 | 83.386 | 97.603 | 75.592 | 1.00 | 30.22 |
| ATOM | 1722 | CG | LYS | 293 | 83.986 | 98.489 | 76.659 | 1.00 | 29.87 |
| ATOM | 1723 | CD | LYS | 293 | 83.036 | 98.648 | 77.822 | 1.00 | 32.75 |
| ATOM | 1724 | CE | LYS | 293 | 83.579 | 99.596 | 78.874 | 1.00 | 34.50 |
| ATOM | 1725 | NZ | LYS | 293 | 83.695 | 100.990 | 78.367 | 1.00 | 40.11 |
| ATOM | 1726 | C | LYS | 293 | 85.458 | 96.493 | 74.745 | 1.00 | 32.68 |
| ATOM | 1727 | O | LYS | 293 | 86.563 | 96.971 | 74.990 | 1.00 | 33.81 |
| ATOM | 1728 | N | TYR | 294 | 85.212 | 95.190 | 74.781 | 1.00 | 32.79 |
| ATOM | 1729 | CA | TYR | 294 | 86.233 | 94.216 | 75.135 | 1.00 | 33.40 |
| ATOM | 1730 | CB | TYR | 294 | 85.822 | 93.506 | 76.428 | 1.00 | 30.64 |
| ATOM | 1731 | CG | TYR | 294 | 85.685 | 94.421 | 77.628 | 1.00 | 27.56 |
| ATOM | 1732 | CD1 | TYR | 294 | 86.817 | 94.950 | 78.251 | 1.00 | 27.07 |
| ATOM | 1733 | CE1 | TYR | 294 | 86.713 | 95.786 | 79.358 | 1.00 | 25.34 |
| ATOM | 1734 | CD2 | TYR | 294 | 84.432 | 94.754 | 78.146 | 1.00 | 26.35 |
| ATOM | 1735 | CE2 | TYR | 294 | 84.314 | 95.591 | 79.259 | 1.00 | 25.10 |
| ATOM | 1736 | CZ | TYR | 294 | 85.463 | 96.102 | 79.856 | 1.00 | 27.67 |
| ATOM | 1737 | OH | TYR | 294 | 85.378 | 96.923 | 80.955 | 1.00 | 29.72 |
| ATOM | 1738 | C | TYR | 294 | 86.385 | 93.202 | 74.005 | 1.00 | 35.70 |
| ATOM | 1739 | O | TYR | 294 | 86.004 | 92.048 | 74.153 | 1.00 | 36.93 |
| ATOM | 1740 | N | PRO | 295 | 87.047 | 93.594 | 72.904 | 1.00 | 37.78 |
| ATOM | 1741 | CD | PRO | 295 | 87.797 | 94.854 | 72.787 | 1.00 | 38.64 |
| ATOM | 1742 | CA | PRO | 295 | 87.276 | 92.755 | 71.720 | 1.00 | 38.05 |
| ATOM | 1743 | CB | PRO | 295 | 88.340 | 93.532 | 70.952 | 1.00 | 38.38 |
| ATOM | 1744 | CG | PRO | 295 | 88.039 | 94.939 | 71.301 | 1.00 | 41.28 |
| ATOM | 1745 | C | PRO | 295 | 87.749 | 91.334 | 71.982 | 1.00 | 39.01 |
| ATOM | 1746 | O | PRO | 295 | 87.333 | 90.401 | 71.295 | 1.00 | 41.67 |
| ATOM | 1747 | N | ASN | 296 | 88.625 | 91.172 | 72.965 | 1.00 | 37.89 |
| ATOM | 1748 | CA | ASN | 296 | 89.174 | 89.859 | 73.274 | 1.00 | 38.39 |
| ATOM | 1749 | CB | ASN | 296 | 90.623 | 89.999 | 73.747 | 1.00 | 45.75 |
| ATOM | 1750 | CG | ASN | 296 | 91.562 | 90.469 | 72.645 | 1.00 | 53.22 |
| ATOM | 1751 | OD1 | ASN | 296 | 91.127 | 91.015 | 71.627 | 1.00 | 58.39 |
| ATOM | 1752 | ND2 | ASN | 296 | 92.860 | 90.266 | 72.850 | 1.00 | 54.67 |
| ATOM | 1753 | C | ASN | 296 | 88.393 | 89.020 | 74.280 | 1.00 | 37.03 |
| ATOM | 1754 | O | ASN | 296 | 88.561 | 87.796 | 74.329 | 1.00 | 39.51 |
| ATOM | 1755 | N | LEU | 297 | 87.531 | 89.664 | 75.066 | 1.00 | 33.27 |
| ATOM | 1756 | CA | LEU | 297 | 86.754 | 88.965 | 76.086 | 1.00 | 27.99 |
| ATOM | 1757 | CB | LEU | 297 | 85.902 | 89.945 | 76.898 | 1.00 | 23.39 |
| ATOM | 1758 | CG | LEU | 297 | 85.183 | 89.404 | 78.137 | 1.00 | 19.80 |
| ATOM | 1759 | CD1 | LEU | 297 | 86.188 | 88.783 | 79.104 | 1.00 | 12.69 |
| ATOM | 1760 | CD2 | LEU | 297 | 84.389 | 90.524 | 78.805 | 1.00 | 14.38 |
| ATOM | 1761 | C | LEU | 297 | 85.872 | 87.884 | 75.492 | 1.00 | 27.28 |
| ATOM | 1762 | O | LEU | 297 | 85.189 | 88.096 | 74.491 | 1.00 | 28.13 |
| ATOM | 1763 | N | GLN | 298 | 85.906 | 86.715 | 76.116 | 1.00 | 26.76 |
| ATOM | 1764 | CA | GLN | 298 | 85.122 | 85.577 | 75.670 | 1.00 | 23.04 |
| ATOM | 1765 | CB | GLN | 298 | 85.814 | 84.292 | 76.090 | 1.00 | 22.03 |
| ATOM | 1766 | CG | GLN | 298 | 87.125 | 84.068 | 75.373 | 1.00 | 20.61 |
| ATOM | 1767 | CD | GLN | 298 | 86.930 | 83.836 | 73.887 | 1.00 | 23.42 |

FIG. 1A-31

| ATOM | 1768 | OE1 | GLN | 298 | 86.604 | 82.728 | 73.459 | 1.00 | 22.37 |
|---|---|---|---|---|---|---|---|---|---|
| ATOM | 1769 | NE2 | GLN | 298 | 87.125 | 84.877 | 73.092 | 1.00 | 23.24 |
| ATOM | 1770 | C | GLN | 298 | 83.719 | 85.643 | 76.249 | 1.00 | 22.42 |
| ATOM | 1771 | O | GLN | 298 | 83.544 | 85.639 | 77.468 | 1.00 | 22.91 |
| ATOM | 1772 | N | VAL | 299 | 82.728 | 85.712 | 75.365 | 1.00 | 20.33 |
| ATOM | 1773 | CA | VAL | 299 | 81.333 | 85.797 | 75.767 | 1.00 | 17.94 |
| ATOM | 1774 | CB | VAL | 299 | 80.690 | 87.048 | 75.161 | 1.00 | 18.36 |
| ATOM | 1775 | CG1 | VAL | 299 | 79.317 | 87.271 | 75.737 | 1.00 | 16.17 |
| ATOM | 1776 | CG2 | VAL | 299 | 81.578 | 88.257 | 75.410 | 1.00 | 20.86 |
| ATOM | 1777 | C | VAL | 299 | 80.523 | 84.549 | 75.379 | 1.00 | 17.77 |
| ATOM | 1778 | O | VAL | 299 | 80.683 | 83.997 | 74.287 | 1.00 | 17.61 |
| ATOM | 1779 | N | ILE | 300 | 79.655 | 84.121 | 76.291 | 1.00 | 15.64 |
| ATOM | 1780 | CA | ILE | 300 | 78.803 | 82.955 | 76.113 | 1.00 | 11.70 |
| ATOM | 1781 | CB | ILE | 300 | 79.026 | 81.983 | 77.276 | 1.00 | 5.27 |
| ATOM | 1782 | CG2 | ILE | 300 | 78.130 | 80.794 | 77.157 | 1.00 | 9.90 |
| ATOM | 1783 | CG1 | ILE | 300 | 80.485 | 81.544 | 77.289 | 1.00 | 3.10 |
| ATOM | 1784 | CD1 | ILE | 300 | 80.845 | 80.697 | 78.471 | 1.00 | 6.58 |
| ATOM | 1785 | C | ILE | 300 | 77.340 | 83.423 | 76.059 | 1.00 | 13.85 |
| ATOM | 1786 | O | ILE | 300 | 76.928 | 84.238 | 76.876 | 1.00 | 13.73 |
| ATOM | 1787 | N | GLY | 301 | 76.569 | 82.902 | 75.105 | 1.00 | 16.05 |
| ATOM | 1788 | CA | GLY | 301 | 75.184 | 83.312 | 74.929 | 1.00 | 18.06 |
| ATOM | 1789 | C | GLY | 301 | 74.134 | 82.665 | 75.804 | 1.00 | 20.81 |
| ATOM | 1790 | O | GLY | 301 | 74.131 | 81.445 | 75.958 | 1.00 | 21.22 |
| ATOM | 1791 | N | GLY | 302 | 73.240 | 83.512 | 76.330 | 1.00 | 23.53 |
| ATOM | 1792 | CA | GLY | 302 | 72.133 | 83.145 | 77.218 | 1.00 | 22.62 |
| ATOM | 1793 | C | GLY | 302 | 71.470 | 81.838 | 76.874 | 1.00 | 23.12 |
| ATOM | 1794 | O | GLY | 302 | 71.613 | 81.391 | 75.733 | 1.00 | 26.43 |
| ATOM | 1795 | N | ASN | 303 | 70.684 | 81.263 | 77.791 | 1.00 | 18.57 |
| ATOM | 1796 | CA | ASN | 303 | 70.089 | 79.951 | 77.516 | 1.00 | 14.15 |
| ATOM | 1797 | CB | ASN | 303 | 69.434 | 79.345 | 78.750 | 1.00 | 10.27 |
| ATOM | 1798 | CG | ASN | 303 | 70.445 | 78.700 | 79.679 | 1.00 | 13.65 |
| ATOM | 1799 | OD1 | ASN | 303 | 70.297 | 77.553 | 80.098 | 1.00 | 14.49 |
| ATOM | 1800 | ND2 | ASN | 303 | 71.503 | 79.438 | 79.989 | 1.00 | 12.02 |
| ATOM | 1801 | C | ASN | 303 | 69.212 | 79.796 | 76.301 | 1.00 | 12.10 |
| ATOM | 1802 | O | ASN | 303 | 68.194 | 80.475 | 76.161 | 1.00 | 13.68 |
| ATOM | 1803 | N | VAL | 304 | 69.668 | 78.936 | 75.390 | 1.00 | 9.70 |
| ATOM | 1804 | CA | VAL | 304 | 68.963 | 78.635 | 74.149 | 1.00 | 9.71 |
| ATOM | 1805 | CB | VAL | 304 | 69.712 | 79.185 | 72.881 | 1.00 | 9.64 |
| ATOM | 1806 | CG1 | VAL | 304 | 69.948 | 80.697 | 72.987 | 1.00 | 5.85 |
| ATOM | 1807 | CG2 | VAL | 304 | 71.030 | 78.454 | 72.654 | 1.00 | 4.29 |
| ATOM | 1808 | C | VAL | 304 | 68.774 | 77.123 | 73.999 | 1.00 | 10.42 |
| ATOM | 1809 | O | VAL | 304 | 69.493 | 76.325 | 74.619 | 1.00 | 8.79 |
| ATOM | 1810 | N | VAL | 305 | 67.785 | 76.731 | 73.200 | 1.00 | 10.37 |
| ATOM | 1811 | CA | VAL | 305 | 67.510 | 75.313 | 72.963 | 1.00 | 9.42 |
| ATOM | 1812 | CB | VAL | 305 | 66.380 | 74.769 | 73.899 | 1.00 | 9.04 |
| ATOM | 1813 | CG1 | VAL | 305 | 66.785 | 74.892 | 75.349 | 1.00 | 6.04 |
| ATOM | 1814 | CG2 | VAL | 305 | 65.069 | 75.492 | 73.652 | 1.00 | 9.90 |
| ATOM | 1815 | C | VAL | 305 | 67.187 | 74.978 | 71.498 | 1.00 | 9.35 |
| ATOM | 1816 | O | VAL | 305 | 66.936 | 73.823 | 71.172 | 1.00 | 9.44 |
| ATOM | 1817 | N | THR | 306 | 67.212 | 75.977 | 70.617 | 1.00 | 9.59 |
| ATOM | 1818 | CA | THR | 306 | 66.929 | 75.762 | 69.197 | 1.00 | 11.26 |
| ATOM | 1819 | CB | THR | 306 | 65.522 | 76.277 | 68.796 | 1.00 | 15.29 |
| ATOM | 1820 | OG1 | THR | 306 | 65.485 | 77.702 | 68.918 | 1.00 | 24.72 |
| ATOM | 1821 | CG2 | THR | 306 | 64.427 | 75.679 | 69.673 | 1.00 | 13.39 |
| ATOM | 1822 | C | THR | 306 | 67.960 | 76.493 | 68.331 | 1.00 | 12.58 |
| ATOM | 1823 | O | THR | 306 | 68.531 | 77.502 | 68.748 | 1.00 | 11.97 |
| ATOM | 1824 | N | ALA | 307 | 68.164 | 76.001 | 67.112 | 1.00 | 13.41 |
| ATOM | 1825 | CA | ALA | 307 | 69.118 | 76.593 | 66.181 | 1.00 | 12.33 |
| ATOM | 1826 | CB | ALA | 307 | 69.226 | 75.725 | 64.947 | 1.00 | 10.43 |

FIG. 1A-32

| ATOM | 1827 | C | ALA | 307 | 68.764 | 78.035 | 65.794 | 1.00 | 14.20 |
| --- | --- | --- | --- | --- | --- | --- | --- | --- | --- |
| ATOM | 1828 | O | ALA | 307 | 69.645 | 78.870 | 65.605 | 1.00 | 17.80 |
| ATOM | 1829 | N | ALA | 308 | 67.477 | 78.328 | 65.670 | 1.00 | 14.93 |
| ATOM | 1830 | CA | ALA | 308 | 67.031 | 79.671 | 65.324 | 1.00 | 14.54 |
| ATOM | 1831 | CB | ALA | 308 | 65.529 | 79.700 | 65.176 | 1.00 | 11.96 |
| ATOM | 1832 | C | ALA | 308 | 67.488 | 80.675 | 66.390 | 1.00 | 17.15 |
| ATOM | 1833 | O | ALA | 308 | 67.893 | 81.790 | 66.060 | 1.00 | 18.96 |
| ATOM | 1834 | N | GLN | 309 | 67.412 | 80.281 | 67.663 | 1.00 | 17.15 |
| ATOM | 1835 | CA | GLN | 309 | 67.844 | 81.146 | 68.762 | 1.00 | 17.48 |
| ATOM | 1836 | CB | GLN | 309 | 67.486 | 80.545 | 70.117 | 1.00 | 15.04 |
| ATOM | 1837 | CG | GLN | 309 | 66.015 | 80.443 | 70.439 | 1.00 | 11.07 |
| ATOM | 1838 | CD | GLN | 309 | 65.813 | 79.776 | 71.777 | 1.00 | 11.92 |
| ATOM | 1839 | OE1 | GLN | 309 | 65.754 | 80.431 | 72.816 | 1.00 | 15.82 |
| ATOM | 1840 | NE2 | GLN | 309 | 65.783 | 78.461 | 71.769 | 1.00 | 11.54 |
| ATOM | 1841 | C | GLN | 309 | 69.361 | 81.291 | 68.704 | 1.00 | 19.46 |
| ATOM | 1842 | O | GLN | 309 | 69.899 | 82.400 | 68.800 | 1.00 | 22.14 |
| ATOM | 1843 | N | ALA | 310 | 70.048 | 80.162 | 68.577 | 1.00 | 18.81 |
| ATOM | 1844 | CA | ALA | 310 | 71.502 | 80.158 | 68.510 | 1.00 | 19.07 |
| ATOM | 1845 | CB | ALA | 310 | 72.027 | 78.744 | 68.259 | 1.00 | 16.86 |
| ATOM | 1846 | C | ALA | 310 | 71.997 | 81.107 | 67.429 | 1.00 | 20.18 |
| ATOM | 1847 | O | ALA | 310 | 72.896 | 81.907 | 67.685 | 1.00 | 21.07 |
| ATOM | 1848 | N | LYS | 311 | 71.368 | 81.071 | 66.253 | 1.00 | 19.18 |
| ATOM | 1849 | CA | LYS | 311 | 71.776 | 81.935 | 65.150 | 1.00 | 18.89 |
| ATOM | 1850 | CB | LYS | 311 | 70.870 | 81.777 | 63.934 | 1.00 | 19.89 |
| ATOM | 1851 | CG | LYS | 311 | 71.413 | 82.571 | 62.752 | 1.00 | 22.42 |
| ATOM | 1852 | CD | LYS | 311 | 70.399 | 82.826 | 61.664 | 1.00 | 23.48 |
| ATOM | 1853 | CE | LYS | 311 | 71.067 | 83.538 | 60.499 | 1.00 | 26.29 |
| ATOM | 1854 | NZ | LYS | 311 | 72.227 | 82.755 | 59.948 | 1.00 | 28.08 |
| ATOM | 1855 | C | LYS | 311 | 71.838 | 83.414 | 65.508 | 1.00 | 18.94 |
| ATOM | 1856 | O | LYS | 311 | 72.763 | 84.113 | 65.096 | 1.00 | 20.88 |
| ATOM | 1857 | N | ASN | 312 | 70.843 | 83.912 | 66.235 | 1.00 | 17.97 |
| ATOM | 1858 | CA | ASN | 312 | 70.849 | 85.319 | 66.611 | 1.00 | 19.27 |
| ATOM | 1859 | CB | ASN | 312 | 69.543 | 85.713 | 67.295 | 1.00 | 21.83 |
| ATOM | 1860 | CG | ASN | 312 | 68.409 | 85.916 | 66.311 | 1.00 | 28.87 |
| ATOM | 1861 | OD1 | ASN | 312 | 67.238 | 85.717 | 66.642 | 1.00 | 31.90 |
| ATOM | 1862 | ND2 | ASN | 312 | 68.747 | 86.338 | 65.094 | 1.00 | 29.09 |
| ATOM | 1863 | C | ASN | 312 | 72.037 | 85.665 | 67.497 | 1.00 | 20.98 |
| ATOM | 1864 | O | ASN | 312 | 72.734 | 86.661 | 67.258 | 1.00 | 22.46 |
| ATOM | 1865 | N | LEU | 313 | 72.292 | 84.821 | 68.494 | 1.00 | 21.52 |
| ATOM | 1866 | CA | LEU | 313 | 73.399 | 85.032 | 69.420 | 1.00 | 20.77 |
| ATOM | 1867 | CB | LEU | 313 | 73.259 | 84.117 | 70.639 | 1.00 | 17.46 |
| ATOM | 1868 | CG | LEU | 313 | 71.923 | 84.136 | 71.385 | 1.00 | 6.88 |
| ATOM | 1869 | CD1 | LEU | 313 | 72.126 | 83.569 | 72.760 | 1.00 | 9.49 |
| ATOM | 1870 | CD2 | LEU | 313 | 71.395 | 85.532 | 71.497 | 1.00 | 3.00 |
| ATOM | 1871 | C | LEU | 313 | 74.745 | 84.807 | 68.723 | 1.00 | 22.50 |
| ATOM | 1872 | O | LEU | 313 | 75.739 | 85.481 | 69.022 | 1.00 | 24.58 |
| ATOM | 1873 | N | ILE | 314 | 74.781 | 83.856 | 67.798 | 1.00 | 21.23 |
| ATOM | 1874 | CA | ILE | 314 | 75.993 | 83.579 | 67.049 | 1.00 | 20.90 |
| ATOM | 1875 | CB | ILE | 314 | 75.846 | 82.316 | 66.175 | 1.00 | 21.15 |
| ATOM | 1876 | CG2 | ILE | 314 | 76.962 | 82.257 | 65.143 | 1.00 | 23.20 |
| ATOM | 1877 | CG1 | ILE | 314 | 75.842 | 81.062 | 67.062 | 1.00 | 20.42 |
| ATOM | 1878 | CD1 | ILE | 314 | 75.839 | 79.736 | 66.299 | 1.00 | 14.79 |
| ATOM | 1879 | C | ILE | 314 | 76.281 | 84.806 | 66.181 | 1.00 | 22.74 |
| ATOM | 1880 | O | ILE | 314 | 77.417 | 85.285 | 66.129 | 1.00 | 23.40 |
| ATOM | 1881 | N | ASP | 315 | 75.241 | 85.338 | 65.540 | 1.00 | 22.48 |
| ATOM | 1882 | CA | ASP | 315 | 75.378 | 86.528 | 64.700 | 1.00 | 22.51 |
| ATOM | 1883 | CB | ASP | 315 | 74.060 | 86.854 | 63.997 | 1.00 | 21.37 |
| ATOM | 1884 | CG | ASP | 315 | 73.766 | 85.937 | 62.828 | 1.00 | 20.01 |
| ATOM | 1885 | OD1 | ASP | 315 | 74.687 | 85.252 | 62.339 | 1.00 | 20.88 |

FIG. 1A-33

| ATOM | 1886 | OD2 | ASP | 315 | 72.605 | 85.925 | 62.377 | 1.00 | 17.86 |
|---|---|---|---|---|---|---|---|---|---|
| ATOM | 1887 | C | ASP | 315 | 75.790 | 87.723 | 65.555 | 1.00 | 23.82 |
| ATOM | 1888 | O | ASP | 315 | 76.536 | 88.585 | 65.104 | 1.00 | 24.06 |
| ATOM | 1889 | N | ALA | 316 | 75.270 | 87.787 | 66.779 | 1.00 | 23.31 |
| ATOM | 1890 | CA | ALA | 316 | 75.602 | 88.868 | 67.691 | 1.00 | 21.76 |
| ATOM | 1891 | CB | ALA | 316 | 74.737 | 88.798 | 68.928 | 1.00 | 23.15 |
| ATOM | 1892 | C | ALA | 316 | 77.074 | 88.770 | 68.063 | 1.00 | 22.92 |
| ATOM | 1893 | O | ALA | 316 | 77.651 | 89.726 | 68.558 | 1.00 | 24.54 |
| ATOM | 1894 | N | GLY | 317 | 77.658 | 87.587 | 67.881 | 1.00 | 24.30 |
| ATOM | 1895 | CA | GLY | 317 | 79.073 | 87.395 | 68.160 | 1.00 | 24.83 |
| ATOM | 1896 | C | GLY | 317 | 79.476 | 86.539 | 69.350 | 1.00 | 24.46 |
| ATOM | 1897 | O | GLY | 317 | 80.532 | 86.763 | 69.931 | 1.00 | 25.80 |
| ATOM | 1898 | N | VAL | 318 | 78.672 | 85.545 | 69.710 | 1.00 | 22.39 |
| ATOM | 1899 | CA | VAL | 318 | 79.015 | 84.702 | 70.850 | 1.00 | 18.88 |
| ATOM | 1900 | CB | VAL | 318 | 77.820 | 83.880 | 71.330 | 1.00 | 16.89 |
| ATOM | 1901 | CG1 | VAL | 318 | 76.731 | 84.793 | 71.846 | 1.00 | 15.19 |
| ATOM | 1902 | CG2 | VAL | 318 | 77.301 | 83.005 | 70.206 | 1.00 | 17.48 |
| ATOM | 1903 | C | VAL | 318 | 80.185 | 83.760 | 70.586 | 1.00 | 18.75 |
| ATOM | 1904 | O | VAL | 318 | 80.346 | 83.231 | 69.483 | 1.00 | 18.57 |
| ATOM | 1905 | N | ASP | 319 | 80.996 | 83.551 | 71.617 | 1.00 | 17.81 |
| ATOM | 1906 | CA | ASP | 319 | 82.148 | 82.665 | 71.529 | 1.00 | 16.90 |
| ATOM | 1907 | CB | ASP | 319 | 83.286 | 83.188 | 72.406 | 1.00 | 20.18 |
| ATOM | 1908 | CG | ASP | 319 | 83.865 | 84.483 | 71.895 | 1.00 | 21.11 |
| ATOM | 1909 | OD1 | ASP | 319 | 84.463 | 84.475 | 70.797 | 1.00 | 24.71 |
| ATOM | 1910 | OD2 | ASP | 319 | 83.727 | 85.508 | 72.594 | 1.00 | 21.10 |
| ATOM | 1911 | C | ASP | 319 | 81.802 | 81.242 | 71.951 | 1.00 | 14.69 |
| ATOM | 1912 | O | ASP | 319 | 82.640 | 80.353 | 71.870 | 1.00 | 16.26 |
| ATOM | 1913 | N | ALA | 320 | 80.593 | 81.055 | 72.464 | 1.00 | 11.91 |
| ATOM | 1914 | CA | ALA | 320 | 80.102 | 79.758 | 72.914 | 1.00 | 7.79 |
| ATOM | 1915 | CB | ALA | 320 | 80.830 | 79.315 | 74.163 | 1.00 | 3.09 |
| ATOM | 1916 | C | ALA | 320 | 78.632 | 79.953 | 73.218 | 1.00 | 8.10 |
| ATOM | 1917 | O | ALA | 320 | 78.165 | 81.092 | 73.284 | 1.00 | 9.40 |
| ATOM | 1918 | N | LEU | 321 | 77.900 | 78.856 | 73.404 | 1.00 | 8.90 |
| ATOM | 1919 | CA | LEU | 321 | 76.467 | 78.917 | 73.713 | 1.00 | 6.89 |
| ATOM | 1920 | CB | LEU | 321 | 75.645 | 78.427 | 72.529 | 1.00 | 2.00 |
| ATOM | 1921 | CG | LEU | 321 | 75.538 | 79.283 | 71.268 | 1.00 | 2.00 |
| ATOM | 1922 | CD1 | LEU | 321 | 75.062 | 78.394 | 70.158 | 1.00 | 4.37 |
| ATOM | 1923 | CD2 | LEU | 321 | 74.589 | 80.461 | 71.444 | 1.00 | 2.00 |
| ATOM | 1924 | C | LEU | 321 | 76.121 | 78.088 | 74.947 | 1.00 | 8.16 |
| ATOM | 1925 | O | LEU | 321 | 76.665 | 77.008 | 75.144 | 1.00 | 10.39 |
| ATOM | 1926 | N | ARG | 322 | 75.258 | 78.618 | 75.804 | 1.00 | 7.97 |
| ATOM | 1927 | CA | ARG | 322 | 74.836 | 77.907 | 77.001 | 1.00 | 7.47 |
| ATOM | 1928 | CB | ARG | 322 | 74.697 | 78.883 | 78.168 | 1.00 | 9.30 |
| ATOM | 1929 | CG | ARG | 322 | 74.550 | 78.234 | 79.535 | 1.00 | 15.10 |
| ATOM | 1930 | CD | ARG | 322 | 74.657 | 79.288 | 80.642 | 1.00 | 18.83 |
| ATOM | 1931 | NE | ARG | 322 | 74.309 | 78.765 | 81.965 | 1.00 | 18.29 |
| ATOM | 1932 | CZ | ARG | 322 | 73.750 | 79.488 | 82.932 | 1.00 | 17.03 |
| ATOM | 1933 | NH1 | ARG | 322 | 73.483 | 80.771 | 82.740 | 1.00 | 18.79 |
| ATOM | 1934 | NH2 | ARG | 322 | 73.411 | 78.921 | 84.078 | 1.00 | 16.70 |
| ATOM | 1935 | C | ARG | 322 | 73.486 | 77.329 | 76.602 | 1.00 | 8.75 |
| ATOM | 1936 | O | ARG | 322 | 72.535 | 78.071 | 76.373 | 1.00 | 10.16 |
| ATOM | 1937 | N | VAL | 323 | 73.424 | 76.012 | 76.455 | 1.00 | 8.83 |
| ATOM | 1938 | CA | VAL | 323 | 72.209 | 75.346 | 76.023 | 1.00 | 10.03 |
| ATOM | 1939 | CB | VAL | 323 | 72.523 | 74.365 | 74.871 | 1.00 | 9.77 |
| ATOM | 1940 | CG1 | VAL | 323 | 71.306 | 73.549 | 74.507 | 1.00 | 16.85 |
| ATOM | 1941 | CG2 | VAL | 323 | 72.993 | 75.137 | 73.653 | 1.00 | 7.40 |
| ATOM | 1942 | C | VAL | 323 | 71.473 | 74.633 | 77.153 | 1.00 | 13.18 |
| ATOM | 1943 | O | VAL | 323 | 72.053 | 73.803 | 77.853 | 1.00 | 15.89 |
| ATOM | 1944 | N | GLY | 324 | 70.196 | 74.969 | 77.327 | 1.00 | 12.40 |

FIG. 1A-34

| ATOM | 1945 | CA  | GLY | 324   | 69.392 | 74.347 | 78.362 | 1.00 | 13.80 |
|------|------|-----|-----|-------|--------|--------|--------|------|-------|
| ATOM | 1946 | C   | GLY | 324   | 68.211 | 75.201 | 78.791 | 1.00 | 14.53 |
| ATOM | 1947 | O   | GLY | 324   | 68.367 | 76.397 | 78.997 | 1.00 | 17.39 |
| ATOM | 1948 | N   | MET | 325   | 67.026 | 74.613 | 78.901 | 1.00 | 11.83 |
| ATOM | 1949 | CA  | MET | 325   | 65.868 | 75.368 | 79.341 | 1.00 | 13.08 |
| ATOM | 1950 | CB  | MET | 325   | 65.201 | 76.124 | 78.186 | 1.00 | 12.41 |
| ATOM | 1951 | CG  | MET | 325   | 64.150 | 77.118 | 78.678 | 1.00 | 10.52 |
| ATOM | 1952 | SD  | MET | 325   | 63.227 | 78.025 | 77.440 | 1.00 | 13.36 |
| ATOM | 1953 | CE  | MET | 325   | 62.495 | 79.307 | 78.488 | 1.00 | 7.16  |
| ATOM | 1954 | C   | MET | 325   | 64.829 | 74.561 | 80.130 | 1.00 | 15.26 |
| ATOM | 1955 | O   | MET | 325   | 64.051 | 73.781 | 79.563 | 1.00 | 15.50 |
| ATOM | 1956 | N   | GLY | 326   | 64.848 | 74.751 | 81.447 | 1.00 | 15.85 |
| ATOM | 1957 | CA  | GLY | 326   | 63.899 | 74.093 | 82.323 | 1.00 | 17.08 |
| ATOM | 1958 | C   | GLY | 326   | 64.165 | 72.651 | 82.677 | 1.00 | 18.22 |
| ATOM | 1959 | O   | GLY | 326   | 63.270 | 71.957 | 83.148 | 1.00 | 18.82 |
| ATOM | 1960 | N   | CYS | 327   | 65.401 | 72.206 | 82.515 | 1.00 | 20.56 |
| ATOM | 1961 | CA  | CYS | 327   | 65.746 | 70.823 | 82.821 | 1.00 | 22.33 |
| ATOM | 1962 | CB  | CYS | 327   | 66.443 | 70.194 | 81.622 | 1.00 | 20.50 |
| ATOM | 1963 | SG  | CYS | 327   | 67.878 | 71.121 | 81.089 | 1.00 | 21.45 |
| ATOM | 1964 | C   | CYS | 327   | 66.633 | 70.710 | 84.061 | 1.00 | 24.86 |
| ATOM | 1965 | O   | CYS | 327   | 66.992 | 69.597 | 84.487 | 1.00 | 26.55 |
| ATOM | 1966 | N   | GLY | 328   | 67.007 | 71.859 | 84.619 | 1.00 | 23.64 |
| ATOM | 1967 | CA  | GLY | 328   | 67.846 | 71.867 | 85.802 | 1.00 | 23.90 |
| ATOM | 1968 | C   | GLY | 328   | 67.066 | 71.347 | 86.988 | 1.00 | 23.07 |
| ATOM | 1969 | O   | GLY | 328   | 65.913 | 71.735 | 87.168 | 1.00 | 23.22 |
| ATOM | 1970 | N   | SER | 329   | 67.706 | 70.528 | 87.822 | 1.00 | 23.68 |
| ATOM | 1971 | CA  | SER | 329   | 67.077 | 69.925 | 89.000 | 1.00 | 22.19 |
| ATOM | 1972 | CB  | SER | 329   | 68.150 | 69.406 | 89.964 | 1.00 | 19.55 |
| ATOM | 1973 | OG  | SER | 329   | 69.028 | 70.440 | 90.356 | 1.00 | 23.14 |
| ATOM | 1974 | C   | SER | 329   | 66.077 | 70.812 | 89.747 | 1.00 | 23.28 |
| ATOM | 1975 | O   | SER | 329   | 64.978 | 70.362 | 90.065 | 1.00 | 25.72 |
| ATOM | 1976 | N   | ILE | 330   | 66.444 | 72.070 | 89.992 | 1.00 | 22.81 |
| ATOM | 1977 | CA  | ILE | 330   | 65.584 | 73.024 | 90.700 | 1.00 | 19.85 |
| ATOM | 1978 | CB  | ILE | 330   | 66.410 | 74.017 | 91.589 | 1.00 | 15.67 |
| ATOM | 1979 | CG2 | ILE | 330   | 66.509 | 73.500 | 93.001 | 1.00 | 18.25 |
| ATOM | 1980 | CG1 | ILE | 330   | 67.795 | 74.289 | 90.994 | 1.00 | 7.11  |
| ATOM | 1981 | CD1 | ILE | 330   | 67.776 | 74.921 | 89.639 | 1.00 | 5.46  |
| ATOM | 1982 | C   | ILE | 330   | 64.703 | 73.869 | 89.786 | 1.00 | 20.60 |
| ATOM | 1983 | O   | ILE | 330   | 64.225 | 74.923 | 90.201 | 1.00 | 23.53 |
| ATOM | 1984 | N   | CYS | 331   | 64.425 | 73.400 | 88.579 | 1.00 | 19.32 |
| ATOM | 1985 | CA  | CYS | 331   | 63.641 | 74.206 | 87.649 | 1.00 | 20.33 |
| ATOM | 1986 | C   | CYS | 331   | 62.148 | 73.909 | 87.498 | 1.00 | 21.39 |
| ATOM | 1987 | O   | CYS | 331   | 61.737 | 72.757 | 87.342 | 1.00 | 22.62 |
| ATOM | 1988 | CB  | CYS | 331   | 64.310 | 74.200 | 86.277 | 1.00 | 19.26 |
| ATOM | 1989 | SG  | CYS | 331   | 64.038 | 75.775 | 85.516 | 1.00 | 16.83 |
| ATOM | 1990 | P   | IMP | A1331 | 71.205 | 71.206 | 87.339 | 1.00 | 24.40 |
| ATOM | 1991 | O1P | IMP | A1331 | 70.381 | 70.028 | 86.885 | 1.00 | 22.40 |
| ATOM | 1992 | O2P | IMP | A1331 | 72.615 | 71.144 | 86.864 | 1.00 | 18.66 |
| ATOM | 1993 | O3P | IMP | A1331 | 71.172 | 71.333 | 88.803 | 1.00 | 19.75 |
| ATOM | 1994 | O5* | IMP | A1331 | 70.688 | 72.534 | 86.798 | 1.00 | 22.96 |
| ATOM | 1995 | C5* | IMP | A1331 | 71.500 | 73.726 | 87.024 | 1.00 | 14.95 |
| ATOM | 1996 | C4* | IMP | A1331 | 71.156 | 74.601 | 85.831 | 1.00 | 11.32 |
| ATOM | 1997 | O4* | IMP | A1331 | 69.758 | 74.898 | 85.861 | 1.00 | 12.20 |
| ATOM | 1998 | C3* | IMP | A1331 | 71.865 | 75.962 | 85.934 | 1.00 | 12.62 |
| ATOM | 1999 | O3* | IMP | A1331 | 73.078 | 76.011 | 85.208 | 1.00 | 10.24 |
| ATOM | 2000 | C2* | IMP | A1331 | 70.883 | 76.903 | 85.210 | 1.00 | 13.74 |
| ATOM | 2001 | O2* | IMP | A1331 | 70.752 | 76.706 | 83.816 | 1.00 | 11.66 |
| ATOM | 2002 | C1* | IMP | A1331 | 69.602 | 76.308 | 85.761 | 1.00 | 14.52 |
| ATOM | 2003 | N9  | IMP | A1331 | 68.832 | 77.205 | 86.612 | 1.00 | 18.13 |

FIG. 1A-35

| ATOM | 2004 | C8 | IMP | A1331 | 69.321 | 78.030 | 87.599 | 1.00 | 18.02 |
|---|---|---|---|---|---|---|---|---|---|
| ATOM | 2005 | N7 | IMP | A1331 | 68.331 | 78.568 | 88.322 | 1.00 | 16.06 |
| ATOM | 2006 | C5 | IMP | A1331 | 67.170 | 78.093 | 87.806 | 1.00 | 19.77 |
| ATOM | 2007 | C6 | IMP | A1331 | 65.799 | 78.289 | 88.156 | 1.00 | 22.26 |
| ATOM | 2008 | O6 | IMP | A1331 | 65.412 | 78.995 | 89.085 | 1.00 | 17.37 |
| ATOM | 2009 | N1 | IMP | A1331 | 64.941 | 77.579 | 87.374 | 1.00 | 25.96 |
| ATOM | 2010 | C2 | IMP | A1331 | 65.296 | 76.706 | 86.299 | 1.00 | 23.29 |
| ATOM | 2011 | N3 | IMP | A1331 | 66.567 | 76.524 | 85.957 | 1.00 | 24.20 |
| ATOM | 2012 | C4 | IMP | A1331 | 67.498 | 77.200 | 86.693 | 1.00 | 21.15 |
| ATOM | 2013 | N | ILE | 332 | 61.333 | 74.959 | 87.564 | 1.00 | 19.04 |
| ATOM | 2014 | CA | ILE | 332 | 59.899 | 74.811 | 87.391 | 1.00 | 18.02 |
| ATOM | 2015 | CB | ILE | 332 | 59.071 | 75.097 | 88.696 | 1.00 | 16.99 |
| ATOM | 2016 | CG2 | ILE | 332 | 59.423 | 74.093 | 89.793 | 1.00 | 12.90 |
| ATOM | 2017 | CG1 | ILE | 332 | 59.283 | 76.525 | 89.191 | 1.00 | 14.79 |
| ATOM | 2018 | CD1 | ILE | 332 | 58.212 | 77.005 | 90.159 | 1.00 | 8.04 |
| ATOM | 2019 | C | ILE | 332 | 59.401 | 75.675 | 86.226 | 1.00 | 20.21 |
| ATOM | 2020 | O | ILE | 332 | 58.195 | 75.848 | 86.050 | 1.00 | 21.52 |
| ATOM | 2021 | N | THR | 333 | 60.330 | 76.195 | 85.420 | 1.00 | 20.15 |
| ATOM | 2022 | CA | THR | 333 | 59.993 | 77.020 | 84.251 | 1.00 | 19.79 |
| ATOM | 2023 | CB | THR | 333 | 61.287 | 77.491 | 83.467 | 1.00 | 20.47 |
| ATOM | 2024 | OG1 | THR | 333 | 61.948 | 78.537 | 84.191 | 1.00 | 18.21 |
| ATOM | 2025 | CG2 | THR | 333 | 60.949 | 77.996 | 82.058 | 1.00 | 16.88 |
| ATOM | 2026 | C | THR | 333 | 59.060 | 76.275 | 83.281 | 1.00 | 18.99 |
| ATOM | 2027 | O | THR | 333 | 58.124 | 76.861 | 82.737 | 1.00 | 19.34 |
| ATOM | 2028 | N | GLN | 334 | 59.308 | 74.988 | 83.063 | 1.00 | 16.88 |
| ATOM | 2029 | CA | GLN | 334 | 58.469 | 74.229 | 82.150 | 1.00 | 16.64 |
| ATOM | 2030 | CB | GLN | 334 | 59.077 | 72.850 | 81.863 | 1.00 | 15.49 |
| ATOM | 2031 | CG | GLN | 334 | 60.004 | 72.864 | 80.658 | 1.00 | 16.53 |
| ATOM | 2032 | CD | GLN | 334 | 60.874 | 71.628 | 80.536 | 1.00 | 18.34 |
| ATOM | 2033 | OE1 | GLN | 334 | 62.091 | 71.729 | 80.344 | 1.00 | 16.42 |
| ATOM | 2034 | NE2 | GLN | 334 | 60.257 | 70.461 | 80.604 | 1.00 | 20.90 |
| ATOM | 2035 | C | GLN | 334 | 57.046 | 74.122 | 82.667 | 1.00 | 16.88 |
| ATOM | 2036 | O | GLN | 334 | 56.091 | 74.293 | 81.916 | 1.00 | 15.78 |
| ATOM | 2037 | N | GLU | 335 | 56.910 | 73.919 | 83.971 | 1.00 | 19.92 |
| ATOM | 2038 | CA | GLU | 335 | 55.596 | 73.795 | 84.583 | 1.00 | 21.69 |
| ATOM | 2039 | CB | GLU | 335 | 55.699 | 73.203 | 85.987 | 1.00 | 25.79 |
| ATOM | 2040 | CG | GLU | 335 | 56.398 | 71.865 | 86.047 | 1.00 | 32.28 |
| ATOM | 2041 | CD | GLU | 335 | 57.745 | 71.971 | 86.700 | 1.00 | 37.56 |
| ATOM | 2042 | OE1 | GLU | 335 | 58.715 | 72.312 | 85.988 | 1.00 | 35.47 |
| ATOM | 2043 | OE2 | GLU | 335 | 57.826 | 71.736 | 87.930 | 1.00 | 40.35 |
| ATOM | 2044 | C | GLU | 335 | 54.878 | 75.123 | 84.675 | 1.00 | 20.91 |
| ATOM | 2045 | O | GLU | 335 | 53.680 | 75.192 | 84.440 | 1.00 | 23.86 |
| ATOM | 2046 | N | VAL | 336 | 55.608 | 76.176 | 85.022 | 1.00 | 20.29 |
| ATOM | 2047 | CA | VAL | 336 | 55.003 | 77.488 | 85.167 | 1.00 | 18.99 |
| ATOM | 2048 | CB | VAL | 336 | 55.776 | 78.368 | 86.175 | 1.00 | 19.44 |
| ATOM | 2049 | CG1 | VAL | 336 | 55.043 | 79.675 | 86.381 | 1.00 | 23.03 |
| ATOM | 2050 | CG2 | VAL | 336 | 55.922 | 77.651 | 87.510 | 1.00 | 16.34 |
| ATOM | 2051 | C | VAL | 336 | 54.822 | 78.232 | 83.851 | 1.00 | 16.99 |
| ATOM | 2052 | O | VAL | 336 | 53.752 | 78.764 | 83.595 | 1.00 | 17.91 |
| ATOM | 2053 | N | LEU | 337 | 55.837 | 78.239 | 82.997 | 1.00 | 14.89 |
| ATOM | 2054 | CA | LEU | 337 | 55.720 | 78.960 | 81.732 | 1.00 | 15.59 |
| ATOM | 2055 | CB | LEU | 337 | 56.918 | 79.902 | 81.534 | 1.00 | 14.85 |
| ATOM | 2056 | CG | LEU | 337 | 57.263 | 80.856 | 82.688 | 1.00 | 13.73 |
| ATOM | 2057 | CD1 | LEU | 337 | 58.394 | 81.763 | 82.271 | 1.00 | 14.07 |
| ATOM | 2058 | CD2 | LEU | 337 | 56.062 | 81.687 | 83.108 | 1.00 | 13.59 |
| ATOM | 2059 | C | LEU | 337 | 55.468 | 78.133 | 80.467 | 1.00 | 14.97 |
| ATOM | 2060 | O | LEU | 337 | 55.399 | 78.690 | 79.371 | 1.00 | 16.68 |
| ATOM | 2061 | N | ALA | 338 | 55.386 | 76.812 | 80.599 | 1.00 | 12.41 |
| ATOM | 2062 | CA | ALA | 338 | 55.109 | 75.933 | 79.456 | 1.00 | 12.62 |

FIG. 1A-36

| ATOM | 2063 | CB | ALA | 338 | 53.732 | 76.248 | 78.887 | 1.00 | 13.39 |
| --- | --- | --- | --- | --- | --- | --- | --- | --- | --- |
| ATOM | 2064 | C | ALA | 338 | 56.151 | 75.975 | 78.341 | 1.00 | 12.44 |
| ATOM | 2065 | O | ALA | 338 | 55.996 | 75.339 | 77.289 | 1.00 | 9.63 |
| ATOM | 2066 | N | CYS | 339 | 57.258 | 76.644 | 78.613 | 1.00 | 13.50 |
| ATOM | 2067 | CA | CYS | 339 | 58.298 | 76.791 | 77.622 | 1.00 | 15.19 |
| ATOM | 2068 | CB | CYS | 339 | 58.576 | 78.271 | 77.418 | 1.00 | 15.68 |
| ATOM | 2069 | SG | CYS | 339 | 59.263 | 78.657 | 75.830 | 1.00 | 27.20 |
| ATOM | 2070 | C | CYS | 339 | 59.558 | 76.077 | 78.057 | 1.00 | 16.02 |
| ATOM | 2071 | O | CYS | 339 | 59.891 | 76.073 | 79.247 | 1.00 | 17.04 |
| ATOM | 2072 | N | GLY | 340 | 60.249 | 75.480 | 77.086 | 1.00 | 14.98 |
| ATOM | 2073 | CA | GLY | 340 | 61.480 | 74.759 | 77.355 | 1.00 | 11.03 |
| ATOM | 2074 | C | GLY | 340 | 61.656 | 73.698 | 76.292 | 1.00 | 10.00 |
| ATOM | 2075 | O | GLY | 340 | 60.972 | 73.741 | 75.267 | 1.00 | 9.29 |
| ATOM | 2076 | N | ARG | 341 | 62.555 | 72.746 | 76.530 | 1.00 | 8.77 |
| ATOM | 2077 | CA | ARG | 341 | 62.802 | 71.656 | 75.581 | 1.00 | 8.44 |
| ATOM | 2078 | CB | ARG | 341 | 63.596 | 72.172 | 74.375 | 1.00 | 10.17 |
| ATOM | 2079 | CG | ARG | 341 | 63.945 | 71.097 | 73.365 | 1.00 | 7.40 |
| ATOM | 2080 | CD | ARG | 341 | 64.551 | 71.665 | 72.100 | 1.00 | 6.94 |
| ATOM | 2081 | NE | ARG | 341 | 64.227 | 70.798 | 70.969 | 1.00 | 5.84 |
| ATOM | 2082 | CZ | ARG | 341 | 64.577 | 71.034 | 69.712 | 1.00 | 2.98 |
| ATOM | 2083 | NH1 | ARG | 341 | 65.284 | 72.104 | 69.402 | 1.00 | 5.13 |
| ATOM | 2084 | NH2 | ARG | 341 | 64.143 | 70.240 | 68.750 | 1.00 | 5.18 |
| ATOM | 2085 | C | ARG | 341 | 63.572 | 70.514 | 76.250 | 1.00 | 9.48 |
| ATOM | 2086 | O | ARG | 341 | 64.384 | 70.756 | 77.140 | 1.00 | 10.70 |
| ATOM | 2087 | N | PRO | 342 | 63.259 | 69.246 | 75.900 | 1.00 | 8.96 |
| ATOM | 2088 | CD | PRO | 342 | 62.112 | 68.810 | 75.086 | 1.00 | 6.87 |
| ATOM | 2089 | CA | PRO | 342 | 63.951 | 68.085 | 76.480 | 1.00 | 6.48 |
| ATOM | 2090 | CB | PRO | 342 | 63.284 | 66.923 | 75.775 | 1.00 | 10.15 |
| ATOM | 2091 | CG | PRO | 342 | 61.877 | 67.426 | 75.596 | 1.00 | 7.34 |
| ATOM | 2092 | C | PRO | 342 | 65.446 | 68.168 | 76.164 | 1.00 | 8.19 |
| ATOM | 2093 | O | PRO | 342 | 65.847 | 68.263 | 75.002 | 1.00 | 9.62 |
| ATOM | 2094 | N | GLN | 343 | 66.267 | 68.096 | 77.206 | 1.00 | 9.33 |
| ATOM | 2095 | CA | GLN | 343 | 67.706 | 68.262 | 77.080 | 1.00 | 10.57 |
| ATOM | 2096 | CB | GLN | 343 | 68.385 | 68.138 | 78.440 | 1.00 | 11.05 |
| ATOM | 2097 | CG | GLN | 343 | 69.766 | 68.799 | 78.495 | 1.00 | 10.72 |
| ATOM | 2098 | CD | GLN | 343 | 69.749 | 70.264 | 78.090 | 1.00 | 16.93 |
| ATOM | 2099 | OE1 | GLN | 343 | 70.788 | 70.855 | 77.816 | 1.00 | 20.72 |
| ATOM | 2100 | NE2 | GLN | 343 | 68.571 | 70.865 | 78.082 | 1.00 | 20.86 |
| ATOM | 2101 | C | GLN | 343 | 68.502 | 67.524 | 76.021 | 1.00 | 13.27 |
| ATOM | 2102 | O | GLN | 343 | 69.166 | 68.160 | 75.202 | 1.00 | 15.52 |
| ATOM | 2103 | N | ALA | 344 | 68.473 | 66.198 | 76.033 | 1.00 | 14.40 |
| ATOM | 2104 | CA | ALA | 344 | 69.240 | 65.440 | 75.051 | 1.00 | 14.17 |
| ATOM | 2105 | CB | ALA | 344 | 68.883 | 63.966 | 75.124 | 1.00 | 15.46 |
| ATOM | 2106 | C | ALA | 344 | 69.011 | 65.983 | 73.643 | 1.00 | 14.10 |
| ATOM | 2107 | O | ALA | 344 | 69.960 | 66.198 | 72.891 | 1.00 | 14.21 |
| ATOM | 2108 | N | THR | 345 | 67.756 | 66.286 | 73.325 | 1.00 | 14.96 |
| ATOM | 2109 | CA | THR | 345 | 67.413 | 66.801 | 72.008 | 1.00 | 13.41 |
| ATOM | 2110 | CB | THR | 345 | 65.905 | 66.759 | 71.748 | 1.00 | 13.07 |
| ATOM | 2111 | OG1 | THR | 345 | 65.427 | 65.419 | 71.914 | 1.00 | 18.26 |
| ATOM | 2112 | CG2 | THR | 345 | 65.608 | 67.217 | 70.336 | 1.00 | 15.37 |
| ATOM | 2113 | C | THR | 345 | 67.921 | 68.218 | 71.831 | 1.00 | 12.88 |
| ATOM | 2114 | O | THR | 345 | 68.411 | 68.565 | 70.754 | 1.00 | 14.21 |
| ATOM | 2115 | N | ALA | 346 | 67.811 | 69.033 | 72.880 | 1.00 | 11.75 |
| ATOM | 2116 | CA | ALA | 346 | 68.286 | 70.418 | 72.817 | 1.00 | 9.99 |
| ATOM | 2117 | CB | ALA | 346 | 68.032 | 71.126 | 74.126 | 1.00 | 6.11 |
| ATOM | 2118 | C | ALA | 346 | 69.776 | 70.435 | 72.495 | 1.00 | 9.20 |
| ATOM | 2119 | O | ALA | 346 | 70.218 | 71.139 | 71.600 | 1.00 | 11.48 |
| ATOM | 2120 | N | VAL | 347 | 70.533 | 69.590 | 73.178 | 1.00 | 9.88 |
| ATOM | 2121 | CA | VAL | 347 | 71.969 | 69.515 | 72.975 | 1.00 | 11.35 |

FIG. 1A-37

| ATOM | 2122 | CB  | VAL | 347 | 72.623 | 68.574 | 73.997 | 1.00 | 12.64 |
| ATOM | 2123 | CG1 | VAL | 347 | 74.106 | 68.431 | 73.701 | 1.00 | 12.61 |
| ATOM | 2124 | CG2 | VAL | 347 | 72.405 | 69.110 | 75.406 | 1.00 | 12.53 |
| ATOM | 2125 | C   | VAL | 347 | 72.372 | 69.091 | 71.571 | 1.00 | 12.67 |
| ATOM | 2126 | O   | VAL | 347 | 73.259 | 69.716 | 70.974 | 1.00 | 13.58 |
| ATOM | 2127 | N   | TYR | 348 | 71.738 | 68.044 | 71.042 | 1.00 | 11.86 |
| ATOM | 2128 | CA  | TYR | 348 | 72.071 | 67.559 | 69.707 | 1.00 | 9.76  |
| ATOM | 2129 | CB  | TYR | 348 | 71.371 | 66.235 | 69.408 | 1.00 | 9.26  |
| ATOM | 2130 | CG  | TYR | 348 | 71.466 | 65.839 | 67.953 | 1.00 | 10.84 |
| ATOM | 2131 | CD1 | TYR | 348 | 72.667 | 65.377 | 67.408 | 1.00 | 13.49 |
| ATOM | 2132 | CE1 | TYR | 348 | 72.776 | 65.071 | 66.042 | 1.00 | 14.55 |
| ATOM | 2133 | CD2 | TYR | 348 | 70.374 | 65.981 | 67.105 | 1.00 | 10.80 |
| ATOM | 2134 | CE2 | TYR | 348 | 70.469 | 65.682 | 65.748 | 1.00 | 12.01 |
| ATOM | 2135 | CZ  | TYR | 348 | 71.669 | 65.229 | 65.220 | 1.00 | 14.93 |
| ATOM | 2136 | OH  | TYR | 348 | 71.751 | 64.947 | 63.872 | 1.00 | 15.11 |
| ATOM | 2137 | C   | TYR | 348 | 71.735 | 68.567 | 68.620 | 1.00 | 12.81 |
| ATOM | 2138 | O   | TYR | 348 | 72.572 | 68.878 | 67.777 | 1.00 | 14.63 |
| ATOM | 2139 | N   | LYS | 349 | 70.508 | 69.076 | 68.630 | 1.00 | 13.27 |
| ATOM | 2140 | CA  | LYS | 349 | 70.081 | 70.043 | 67.622 | 1.00 | 14.33 |
| ATOM | 2141 | CB  | LYS | 349 | 68.596 | 70.349 | 67.792 | 1.00 | 16.10 |
| ATOM | 2142 | CG  | LYS | 349 | 67.689 | 69.177 | 67.466 | 1.00 | 19.74 |
| ATOM | 2143 | CD  | LYS | 349 | 67.707 | 68.886 | 65.974 | 1.00 | 25.23 |
| ATOM | 2144 | CE  | LYS | 349 | 66.783 | 67.735 | 65.626 | 1.00 | 32.56 |
| ATOM | 2145 | NZ  | LYS | 349 | 65.343 | 68.000 | 65.941 | 1.00 | 40.46 |
| ATOM | 2146 | C   | LYS | 349 | 70.877 | 71.352 | 67.537 | 1.00 | 15.33 |
| ATOM | 2147 | O   | LYS | 349 | 71.183 | 71.821 | 66.440 | 1.00 | 17.10 |
| ATOM | 2148 | N   | VAL | 350 | 71.206 | 71.953 | 68.676 | 1.00 | 15.15 |
| ATOM | 2149 | CA  | VAL | 350 | 71.937 | 73.214 | 68.662 | 1.00 | 14.07 |
| ATOM | 2150 | CB  | VAL | 350 | 71.794 | 73.992 | 69.989 | 1.00 | 14.19 |
| ATOM | 2151 | CG1 | VAL | 350 | 72.362 | 75.386 | 69.838 | 1.00 | 11.97 |
| ATOM | 2152 | CG2 | VAL | 350 | 70.337 | 74.078 | 70.392 | 1.00 | 17.18 |
| ATOM | 2153 | C   | VAL | 350 | 73.406 | 73.019 | 68.349 | 1.00 | 16.29 |
| ATOM | 2154 | O   | VAL | 350 | 73.995 | 73.838 | 67.645 | 1.00 | 18.00 |
| ATOM | 2155 | N   | SER | 351 | 74.006 | 71.958 | 68.886 | 1.00 | 16.00 |
| ATOM | 2156 | CA  | SER | 351 | 75.418 | 71.663 | 68.637 | 1.00 | 12.71 |
| ATOM | 2157 | CB  | SER | 351 | 75.882 | 70.505 | 69.517 | 1.00 | 11.95 |
| ATOM | 2158 | OG  | SER | 351 | 75.765 | 70.816 | 70.894 | 1.00 | 11.62 |
| ATOM | 2159 | C   | SER | 351 | 75.636 | 71.308 | 67.168 | 1.00 | 12.57 |
| ATOM | 2160 | O   | SER | 351 | 76.627 | 71.708 | 66.558 | 1.00 | 12.81 |
| ATOM | 2161 | N   | GLU | 352 | 74.698 | 70.556 | 66.606 | 1.00 | 13.06 |
| ATOM | 2162 | CA  | GLU | 352 | 74.770 | 70.152 | 65.219 | 1.00 | 12.95 |
| ATOM | 2163 | CB  | GLU | 352 | 73.565 | 69.292 | 64.887 | 1.00 | 14.63 |
| ATOM | 2164 | CG  | GLU | 352 | 73.753 | 68.340 | 63.728 | 1.00 | 24.19 |
| ATOM | 2165 | CD  | GLU | 352 | 73.820 | 69.039 | 62.393 | 1.00 | 31.22 |
| ATOM | 2166 | OE1 | GLU | 352 | 73.003 | 69.956 | 62.165 | 1.00 | 41.17 |
| ATOM | 2167 | OE2 | GLU | 352 | 74.688 | 68.677 | 61.569 | 1.00 | 31.62 |
| ATOM | 2168 | C   | GLU | 352 | 74.805 | 71.404 | 64.349 | 1.00 | 15.08 |
| ATOM | 2169 | O   | GLU | 352 | 75.499 | 71.434 | 63.339 | 1.00 | 19.18 |
| ATOM | 2170 | N   | TYR | 353 | 74.089 | 72.446 | 64.770 | 1.00 | 15.73 |
| ATOM | 2171 | CA  | TYR | 353 | 74.032 | 73.725 | 64.046 | 1.00 | 16.16 |
| ATOM | 2172 | CB  | TYR | 353 | 72.735 | 74.473 | 64.395 | 1.00 | 16.64 |
| ATOM | 2173 | CG  | TYR | 353 | 72.674 | 75.902 | 63.885 | 1.00 | 17.24 |
| ATOM | 2174 | CD1 | TYR | 353 | 72.487 | 76.171 | 62.535 | 1.00 | 17.57 |
| ATOM | 2175 | CE1 | TYR | 353 | 72.440 | 77.477 | 62.060 | 1.00 | 19.38 |
| ATOM | 2176 | CD2 | TYR | 353 | 72.810 | 76.986 | 64.756 | 1.00 | 20.21 |
| ATOM | 2177 | CE2 | TYR | 353 | 72.769 | 78.298 | 64.290 | 1.00 | 18.45 |
| ATOM | 2178 | CZ  | TYR | 353 | 72.580 | 78.534 | 62.941 | 1.00 | 21.67 |
| ATOM | 2179 | OH  | TYR | 353 | 72.534 | 79.821 | 62.458 | 1.00 | 26.08 |
| ATOM | 2180 | C   | TYR | 353 | 75.228 | 74.638 | 64.346 | 1.00 | 17.36 |

FIG. 1A-38

| ATOM | 2181 | O | TYR | 353 | 75.930 | 75.099 | 63.438 | 1.00 | 16.84 |
|---|---|---|---|---|---|---|---|---|---|
| ATOM | 2182 | N | ALA | 354 | 75.436 | 74.904 | 65.631 | 1.00 | 16.45 |
| ATOM | 2183 | CA | ALA | 354 | 76.503 | 75.771 | 66.107 | 1.00 | 14.66 |
| ATOM | 2184 | CB | ALA | 354 | 76.450 | 75.861 | 67.626 | 1.00 | 12.08 |
| ATOM | 2185 | C | ALA | 354 | 77.881 | 75.327 | 65.649 | 1.00 | 15.93 |
| ATOM | 2186 | O | ALA | 354 | 78.791 | 76.150 | 65.502 | 1.00 | 17.40 |
| ATOM | 2187 | N | ARG | 355 | 78.044 | 74.029 | 65.412 | 1.00 | 16.56 |
| ATOM | 2188 | CA | ARG | 355 | 79.331 | 73.503 | 64.974 | 1.00 | 15.93 |
| ATOM | 2189 | CB | ARG | 355 | 79.327 | 71.972 | 64.970 | 1.00 | 12.81 |
| ATOM | 2190 | CG | ARG | 355 | 78.353 | 71.355 | 64.005 | 1.00 | 13.40 |
| ATOM | 2191 | CD | ARG | 355 | 78.750 | 69.953 | 63.679 | 1.00 | 10.78 |
| ATOM | 2192 | NE | ARG | 355 | 77.902 | 69.377 | 62.648 | 1.00 | 11.50 |
| ATOM | 2193 | CZ | ARG | 355 | 78.284 | 68.384 | 61.853 | 1.00 | 15.77 |
| ATOM | 2194 | NH1 | ARG | 355 | 79.500 | 67.863 | 61.977 | 1.00 | 20.37 |
| ATOM | 2195 | NH2 | ARG | 355 | 77.459 | 67.906 | 60.933 | 1.00 | 13.86 |
| ATOM | 2196 | C | ARG | 355 | 79.719 | 74.024 | 63.594 | 1.00 | 16.63 |
| ATOM | 2197 | O | ARG | 355 | 80.897 | 74.184 | 63.304 | 1.00 | 18.62 |
| ATOM | 2198 | N | ARG | 356 | 78.727 | 74.340 | 62.768 | 1.00 | 17.13 |
| ATOM | 2199 | CA | ARG | 356 | 78.980 | 74.844 | 61.424 | 1.00 | 18.61 |
| ATOM | 2200 | CB | ARG | 356 | 77.694 | 74.786 | 60.591 | 1.00 | 20.45 |
| ATOM | 2201 | CG | ARG | 356 | 76.842 | 73.548 | 60.869 | 1.00 | 26.84 |
| ATOM | 2202 | CD | ARG | 356 | 75.749 | 73.356 | 59.835 | 1.00 | 35.30 |
| ATOM | 2203 | NE | ARG | 356 | 76.289 | 72.781 | 58.600 | 1.00 | 45.31 |
| ATOM | 2204 | CZ | ARG | 356 | 76.031 | 71.549 | 58.155 | 1.00 | 44.56 |
| ATOM | 2205 | NH1 | ARG | 356 | 75.228 | 70.736 | 58.839 | 1.00 | 41.95 |
| ATOM | 2206 | NH2 | ARG | 356 | 76.575 | 71.131 | 57.015 | 1.00 | 42.41 |
| ATOM | 2207 | C | ARG | 356 | 79.518 | 76.277 | 61.478 | 1.00 | 20.86 |
| ATOM | 2208 | O | ARG | 356 | 79.804 | 76.885 | 60.446 | 1.00 | 22.43 |
| ATOM | 2209 | N | PHE | 357 | 79.651 | 76.816 | 62.687 | 1.00 | 21.28 |
| ATOM | 2210 | CA | PHE | 357 | 80.157 | 78.170 | 62.885 | 1.00 | 19.44 |
| ATOM | 2211 | CB | PHE | 357 | 79.031 | 79.081 | 63.369 | 1.00 | 17.23 |
| ATOM | 2212 | CG | PHE | 357 | 77.830 | 79.068 | 62.481 | 1.00 | 17.05 |
| ATOM | 2213 | CD1 | PHE | 357 | 76.836 | 78.119 | 62.654 | 1.00 | 19.73 |
| ATOM | 2214 | CD2 | PHE | 357 | 77.712 | 79.977 | 61.439 | 1.00 | 18.18 |
| ATOM | 2215 | CE1 | PHE | 357 | 75.744 | 78.073 | 61.805 | 1.00 | 21.80 |
| ATOM | 2216 | CE2 | PHE | 357 | 76.619 | 79.940 | 60.583 | 1.00 | 19.81 |
| ATOM | 2217 | CZ | PHE | 357 | 75.635 | 78.986 | 60.764 | 1.00 | 20.74 |
| ATOM | 2218 | C | PHE | 357 | 81.270 | 78.145 | 63.917 | 1.00 | 20.90 |
| ATOM | 2219 | O | PHE | 357 | 81.695 | 79.188 | 64.413 | 1.00 | 23.81 |
| ATOM | 2220 | N | GLY | 358 | 81.725 | 76.944 | 64.250 | 1.00 | 20.23 |
| ATOM | 2221 | CA | GLY | 358 | 82.782 | 76.794 | 65.230 | 1.00 | 21.34 |
| ATOM | 2222 | C | GLY | 358 | 82.440 | 77.326 | 66.609 | 1.00 | 22.66 |
| ATOM | 2223 | O | GLY | 358 | 83.319 | 77.829 | 67.308 | 1.00 | 25.20 |
| ATOM | 2224 | N | VAL | 359 | 81.172 | 77.235 | 67.009 | 1.00 | 23.04 |
| ATOM | 2225 | CA | VAL | 359 | 80.771 | 77.720 | 68.324 | 1.00 | 19.49 |
| ATOM | 2226 | CB | VAL | 359 | 79.551 | 78.656 | 68.252 | 1.00 | 18.13 |
| ATOM | 2227 | CG1 | VAL | 359 | 79.241 | 79.201 | 69.620 | 1.00 | 17.64 |
| ATOM | 2228 | CG2 | VAL | 359 | 79.821 | 79.803 | 67.306 | 1.00 | 20.63 |
| ATOM | 2229 | C | VAL | 359 | 80.472 | 76.555 | 69.262 | 1.00 | 17.44 |
| ATOM | 2230 | O | VAL | 359 | 79.623 | 75.710 | 68.982 | 1.00 | 18.55 |
| ATOM | 2231 | N | PRO | 360 | 81.251 | 76.441 | 70.341 | 1.00 | 15.36 |
| ATOM | 2232 | CD | PRO | 360 | 82.498 | 77.197 | 70.545 | 1.00 | 11.72 |
| ATOM | 2233 | CA | PRO | 360 | 81.108 | 75.392 | 71.353 | 1.00 | 14.20 |
| ATOM | 2234 | CB | PRO | 360 | 82.273 | 75.679 | 72.298 | 1.00 | 11.22 |
| ATOM | 2235 | CG | PRO | 360 | 83.302 | 76.259 | 71.388 | 1.00 | 11.79 |
| ATOM | 2236 | C | PRO | 360 | 79.774 | 75.498 | 72.096 | 1.00 | 14.81 |
| ATOM | 2237 | O | PRO | 360 | 79.312 | 76.602 | 72.393 | 1.00 | 16.13 |
| ATOM | 2238 | N | VAL | 361 | 79.153 | 74.355 | 72.372 | 1.00 | 13.23 |
| ATOM | 2239 | CA | VAL | 361 | 77.892 | 74.313 | 73.099 | 1.00 | 9.02 |

FIG. 1A-39

| ATOM | 2240 | CB | VAL | 361 | 76.849 | 73.453 | 72.362 | 1.00 | 6.35 |
|---|---|---|---|---|---|---|---|---|---|
| ATOM | 2241 | CG1 | VAL | 361 | 75.793 | 72.907 | 73.331 | 1.00 | 4.83 |
| ATOM | 2242 | CG2 | VAL | 361 | 76.175 | 74.289 | 71.286 | 1.00 | 9.33 |
| ATOM | 2243 | C | VAL | 361 | 78.154 | 73.739 | 74.483 | 1.00 | 11.18 |
| ATOM | 2244 | O | VAL | 361 | 78.917 | 72.775 | 74.623 | 1.00 | 12.24 |
| ATOM | 2245 | N | ILE | 362 | 77.545 | 74.359 | 75.495 | 1.00 | 10.96 |
| ATOM | 2246 | CA | ILE | 362 | 77.659 | 73.950 | 76.895 | 1.00 | 9.15 |
| ATOM | 2247 | CB | ILE | 362 | 77.836 | 75.184 | 77.831 | 1.00 | 9.87 |
| ATOM | 2248 | CG2 | ILE | 362 | 77.850 | 74.769 | 79.294 | 1.00 | 5.57 |
| ATOM | 2249 | CG1 | ILE | 362 | 79.130 | 75.931 | 77.504 | 1.00 | 14.42 |
| ATOM | 2250 | CD1 | ILE | 362 | 79.377 | 77.131 | 78.394 | 1.00 | 14.31 |
| ATOM | 2251 | C | ILE | 362 | 76.345 | 73.283 | 77.263 | 1.00 | 9.83 |
| ATOM | 2252 | O | ILE | 362 | 75.318 | 73.949 | 77.305 | 1.00 | 12.05 |
| ATOM | 2253 | N | ALA | 363 | 76.357 | 71.972 | 77.485 | 1.00 | 11.91 |
| ATOM | 2254 | CA | ALA | 363 | 75.136 | 71.256 | 77.868 | 1.00 | 11.28 |
| ATOM | 2255 | CB | ALA | 363 | 75.319 | 69.763 | 77.724 | 1.00 | 13.29 |
| ATOM | 2256 | C | ALA | 363 | 74.880 | 71.623 | 79.314 | 1.00 | 12.59 |
| ATOM | 2257 | O | ALA | 363 | 75.519 | 71.100 | 80.231 | 1.00 | 14.94 |
| ATOM | 2258 | N | ASP | 364 | 73.943 | 72.538 | 79.505 | 1.00 | 13.34 |
| ATOM | 2259 | CA | ASP | 364 | 73.617 | 73.056 | 80.816 | 1.00 | 12.33 |
| ATOM | 2260 | CB | ASP | 364 | 73.737 | 74.577 | 80.750 | 1.00 | 11.24 |
| ATOM | 2261 | CG | ASP | 364 | 73.210 | 75.255 | 81.966 | 1.00 | 15.61 |
| ATOM | 2262 | OD1 | ASP | 364 | 73.322 | 74.677 | 83.061 | 1.00 | 18.33 |
| ATOM | 2263 | OD2 | ASP | 364 | 72.680 | 76.372 | 81.820 | 1.00 | 22.45 |
| ATOM | 2264 | C | ASP | 364 | 72.257 | 72.630 | 81.371 | 1.00 | 14.11 |
| ATOM | 2265 | O | ASP | 364 | 71.207 | 73.094 | 80.915 | 1.00 | 12.91 |
| ATOM | 2266 | N | GLY | 365 | 72.294 | 71.795 | 82.409 | 1.00 | 15.80 |
| ATOM | 2267 | CA | GLY | 365 | 71.068 | 71.324 | 83.036 | 1.00 | 17.03 |
| ATOM | 2268 | C | GLY | 365 | 70.702 | 69.854 | 82.863 | 1.00 | 17.21 |
| ATOM | 2269 | O | GLY | 365 | 70.933 | 69.257 | 81.807 | 1.00 | 16.26 |
| ATOM | 2270 | N | GLY | 366 | 70.137 | 69.269 | 83.919 | 1.00 | 19.08 |
| ATOM | 2271 | CA | GLY | 366 | 69.711 | 67.883 | 83.875 | 1.00 | 20.17 |
| ATOM | 2272 | C | GLY | 366 | 70.777 | 66.832 | 84.104 | 1.00 | 21.83 |
| ATOM | 2273 | O | GLY | 366 | 70.487 | 65.635 | 84.002 | 1.00 | 22.67 |
| ATOM | 2274 | N | ILE | 367 | 72.009 | 67.253 | 84.384 | 1.00 | 22.88 |
| ATOM | 2275 | CA | ILE | 367 | 73.098 | 66.311 | 84.634 | 1.00 | 22.10 |
| ATOM | 2276 | CB | ILE | 367 | 74.484 | 66.959 | 84.444 | 1.00 | 20.00 |
| ATOM | 2277 | CG2 | ILE | 367 | 75.596 | 65.980 | 84.841 | 1.00 | 18.29 |
| ATOM | 2278 | CG1 | ILE | 367 | 74.643 | 67.462 | 83.002 | 1.00 | 18.25 |
| ATOM | 2279 | CD1 | ILE | 367 | 74.511 | 66.400 | 81.937 | 1.00 | 17.72 |
| ATOM | 2280 | C | ILE | 367 | 72.975 | 65.803 | 86.063 | 1.00 | 24.54 |
| ATOM | 2281 | O | ILE | 367 | 73.240 | 66.534 | 87.018 | 1.00 | 25.34 |
| ATOM | 2282 | N | GLN | 368 | 72.533 | 64.559 | 86.198 | 1.00 | 25.47 |
| ATOM | 2283 | CA | GLN | 368 | 72.352 | 63.929 | 87.500 | 1.00 | 26.05 |
| ATOM | 2284 | CB | GLN | 368 | 71.010 | 63.193 | 87.546 | 1.00 | 33.00 |
| ATOM | 2285 | CG | GLN | 368 | 69.808 | 63.960 | 87.016 | 1.00 | 41.39 |
| ATOM | 2286 | CD | GLN | 368 | 68.650 | 63.034 | 86.645 | 1.00 | 47.49 |
| ATOM | 2287 | OE1 | GLN | 368 | 68.857 | 61.864 | 86.306 | 1.00 | 50.05 |
| ATOM | 2288 | NE2 | GLN | 368 | 67.435 | 63.566 | 86.664 | 1.00 | 49.52 |
| ATOM | 2289 | C | GLN | 368 | 73.462 | 62.923 | 87.807 | 1.00 | 23.20 |
| ATOM | 2290 | O | GLN | 368 | 73.581 | 62.460 | 88.939 | 1.00 | 24.66 |
| ATOM | 2291 | N | ASN | 369 | 74.249 | 62.558 | 86.797 | 1.00 | 20.24 |
| ATOM | 2292 | CA | ASN | 369 | 75.322 | 61.586 | 86.979 | 1.00 | 17.49 |
| ATOM | 2293 | CB | ASN | 369 | 74.721 | 60.205 | 87.203 | 1.00 | 18.55 |
| ATOM | 2294 | CG | ASN | 369 | 73.906 | 59.736 | 86.025 | 1.00 | 19.68 |
| ATOM | 2295 | OD1 | ASN | 369 | 73.929 | 60.334 | 84.947 | 1.00 | 20.92 |
| ATOM | 2296 | ND2 | ASN | 369 | 73.182 | 58.654 | 86.217 | 1.00 | 27.57 |
| ATOM | 2297 | C | ASN | 369 | 76.269 | 61.537 | 85.781 | 1.00 | 16.13 |
| ATOM | 2298 | O | ASN | 369 | 76.062 | 62.238 | 84.790 | 1.00 | 16.39 |

FIG. 1A-40

| ATOM | 2299 | N | VAL | 370 | 77.274 | 60.670 | 85.859 | 1.00 | 15.11 |
|---|---|---|---|---|---|---|---|---|---|
| ATOM | 2300 | CA | VAL | 370 | 78.261 | 60.533 | 84.793 | 1.00 | 14.39 |
| ATOM | 2301 | CB | VAL | 370 | 79.396 | 59.566 | 85.179 | 1.00 | 10.30 |
| ATOM | 2302 | CG1 | VAL | 370 | 80.297 | 59.311 | 83.984 | 1.00 | 14.21 |
| ATOM | 2303 | CG2 | VAL | 370 | 80.216 | 60.150 | 86.300 | 1.00 | 7.21 |
| ATOM | 2304 | C | VAL | 370 | 77.693 | 60.122 | 83.438 | 1.00 | 16.18 |
| ATOM | 2305 | O | VAL | 370 | 78.148 | 60.616 | 82.406 | 1.00 | 20.19 |
| ATOM | 2306 | N | GLY | 371 | 76.702 | 59.238 | 83.429 | 1.00 | 15.14 |
| ATOM | 2307 | CA | GLY | 371 | 76.125 | 58.802 | 82.170 | 1.00 | 12.93 |
| ATOM | 2308 | C | GLY | 371 | 75.635 | 59.981 | 81.357 | 1.00 | 14.21 |
| ATOM | 2309 | O | GLY | 371 | 75.845 | 60.052 | 80.144 | 1.00 | 16.14 |
| ATOM | 2310 | N | HIS | 372 | 74.994 | 60.921 | 82.041 | 1.00 | 14.52 |
| ATOM | 2311 | CA | HIS | 372 | 74.467 | 62.121 | 81.411 | 1.00 | 12.09 |
| ATOM | 2312 | CB | HIS | 372 | 73.717 | 62.965 | 82.442 | 1.00 | 13.52 |
| ATOM | 2313 | CG | HIS | 372 | 72.452 | 62.338 | 82.941 | 1.00 | 11.76 |
| ATOM | 2314 | CD2 | HIS | 372 | 71.675 | 62.637 | 84.006 | 1.00 | 9.64 |
| ATOM | 2315 | ND1 | HIS | 372 | 71.836 | 61.283 | 82.301 | 1.00 | 11.22 |
| ATOM | 2316 | CE1 | HIS | 372 | 70.730 | 60.964 | 82.950 | 1.00 | 11.70 |
| ATOM | 2317 | NE2 | HIS | 372 | 70.609 | 61.769 | 83.989 | 1.00 | 13.93 |
| ATOM | 2318 | C | HIS | 372 | 75.584 | 62.936 | 80.783 | 1.00 | 11.92 |
| ATOM | 2319 | O | HIS | 372 | 75.477 | 63.351 | 79.633 | 1.00 | 13.70 |
| ATOM | 2320 | N | ILE | 373 | 76.664 | 63.150 | 81.529 | 1.00 | 11.48 |
| ATOM | 2321 | CA | ILE | 373 | 77.802 | 63.912 | 81.023 | 1.00 | 10.28 |
| ATOM | 2322 | CB | ILE | 373 | 78.970 | 63.936 | 82.020 | 1.00 | 9.11 |
| ATOM | 2323 | CG2 | ILE | 373 | 80.052 | 64.869 | 81.511 | 1.00 | 9.72 |
| ATOM | 2324 | CG1 | ILE | 373 | 78.500 | 64.430 | 83.390 | 1.00 | 12.51 |
| ATOM | 2325 | CD1 | ILE | 373 | 79.615 | 64.553 | 84.422 | 1.00 | 7.16 |
| ATOM | 2326 | C | ILE | 373 | 78.305 | 63.320 | 79.705 | 1.00 | 11.05 |
| ATOM | 2327 | O | ILE | 373 | 78.401 | 64.023 | 78.696 | 1.00 | 13.77 |
| ATOM | 2328 | N | ALA | 374 | 78.578 | 62.019 | 79.709 | 1.00 | 10.10 |
| ATOM | 2329 | CA | ALA | 374 | 79.059 | 61.323 | 78.521 | 1.00 | 7.10 |
| ATOM | 2330 | CB | ALA | 374 | 79.338 | 59.858 | 78.849 | 1.00 | 6.65 |
| ATOM | 2331 | C | ALA | 374 | 78.077 | 61.436 | 77.354 | 1.00 | 7.00 |
| ATOM | 2332 | O | ALA | 374 | 78.494 | 61.582 | 76.200 | 1.00 | 7.81 |
| ATOM | 2333 | N | LYS | 375 | 76.779 | 61.375 | 77.649 | 1.00 | 6.65 |
| ATOM | 2334 | CA | LYS | 375 | 75.747 | 61.485 | 76.618 | 1.00 | 7.92 |
| ATOM | 2335 | CB | LYS | 375 | 74.372 | 61.114 | 77.168 | 1.00 | 10.47 |
| ATOM | 2336 | CG | LYS | 375 | 74.227 | 59.656 | 77.562 | 1.00 | 12.38 |
| ATOM | 2337 | CD | LYS | 375 | 72.820 | 59.354 | 78.030 | 1.00 | 9.26 |
| ATOM | 2338 | CE | LYS | 375 | 72.730 | 57.927 | 78.518 | 1.00 | 7.92 |
| ATOM | 2339 | NZ | LYS | 375 | 71.353 | 57.566 | 78.921 | 1.00 | 7.20 |
| ATOM | 2340 | C | LYS | 375 | 75.680 | 62.885 | 76.021 | 1.00 | 9.52 |
| ATOM | 2341 | O | LYS | 375 | 75.457 | 63.036 | 74.825 | 1.00 | 12.41 |
| ATOM | 2342 | N | ALA | 376 | 75.847 | 63.911 | 76.850 | 1.00 | 8.56 |
| ATOM | 2343 | CA | ALA | 376 | 75.819 | 65.286 | 76.359 | 1.00 | 8.01 |
| ATOM | 2344 | CB | ALA | 376 | 75.989 | 66.258 | 77.505 | 1.00 | 6.06 |
| ATOM | 2345 | C | ALA | 376 | 76.951 | 65.466 | 75.362 | 1.00 | 7.56 |
| ATOM | 2346 | O | ALA | 376 | 76.755 | 65.969 | 74.261 | 1.00 | 6.99 |
| ATOM | 2347 | N | LEU | 377 | 78.137 | 65.031 | 75.766 | 1.00 | 9.38 |
| ATOM | 2348 | CA | LEU | 377 | 79.331 | 65.132 | 74.940 | 1.00 | 11.38 |
| ATOM | 2349 | CB | LEU | 377 | 80.550 | 64.633 | 75.725 | 1.00 | 10.28 |
| ATOM | 2350 | CG | LEU | 377 | 80.816 | 65.413 | 77.016 | 1.00 | 8.99 |
| ATOM | 2351 | CD1 | LEU | 377 | 81.864 | 64.704 | 77.875 | 1.00 | 8.49 |
| ATOM | 2352 | CD2 | LEU | 377 | 81.221 | 66.847 | 76.678 | 1.00 | 2.00 |
| ATOM | 2353 | C | LEU | 377 | 79.168 | 64.354 | 73.644 | 1.00 | 12.35 |
| ATOM | 2354 | O | LEU | 377 | 79.457 | 64.862 | 72.566 | 1.00 | 12.88 |
| ATOM | 2355 | N | ALA | 378 | 78.660 | 63.132 | 73.755 | 1.00 | 15.20 |
| ATOM | 2356 | CA | ALA | 378 | 78.436 | 62.270 | 72.598 | 1.00 | 14.02 |
| ATOM | 2357 | CB | ALA | 378 | 77.927 | 60.907 | 73.057 | 1.00 | 12.75 |

FIG. 1A-41

| ATOM | 2358 | C | ALA | 378 | 77.453 | 62.891 | 71.609 | 1.00 | 13.17 |
|---|---|---|---|---|---|---|---|---|---|
| ATOM | 2359 | O | ALA | 378 | 77.501 | 62.601 | 70.419 | 1.00 | 16.35 |
| ATOM | 2360 | N | LEU | 379 | 76.562 | 63.749 | 72.097 | 1.00 | 13.73 |
| ATOM | 2361 | CA | LEU | 379 | 75.567 | 64.376 | 71.236 | 1.00 | 12.58 |
| ATOM | 2362 | CB | LEU | 379 | 74.234 | 64.517 | 71.968 | 1.00 | 11.76 |
| ATOM | 2363 | CG | LEU | 379 | 73.485 | 63.201 | 72.194 | 1.00 | 12.16 |
| ATOM | 2364 | CD1 | LEU | 379 | 72.225 | 63.447 | 72.983 | 1.00 | 11.41 |
| ATOM | 2365 | CD2 | LEU | 379 | 73.171 | 62.563 | 70.863 | 1.00 | 10.14 |
| ATOM | 2366 | C | LEU | 379 | 75.980 | 65.706 | 70.621 | 1.00 | 14.62 |
| ATOM | 2367 | O | LEU | 379 | 75.220 | 66.294 | 69.848 | 1.00 | 16.75 |
| ATOM | 2368 | N | GLY | 380 | 77.175 | 66.183 | 70.950 | 1.00 | 14.81 |
| ATOM | 2369 | CA | GLY | 380 | 77.636 | 67.427 | 70.371 | 1.00 | 12.86 |
| ATOM | 2370 | C | GLY | 380 | 78.128 | 68.502 | 71.325 | 1.00 | 15.25 |
| ATOM | 2371 | O | GLY | 380 | 78.734 | 69.476 | 70.869 | 1.00 | 17.13 |
| ATOM | 2372 | N | ALA | 381 | 77.899 | 68.356 | 72.626 | 1.00 | 12.90 |
| ATOM | 2373 | CA | ALA | 381 | 78.348 | 69.390 | 73.547 | 1.00 | 12.21 |
| ATOM | 2374 | CB | ALA | 381 | 77.635 | 69.269 | 74.873 | 1.00 | 5.91 |
| ATOM | 2375 | C | ALA | 381 | 79.862 | 69.368 | 73.744 | 1.00 | 16.09 |
| ATOM | 2376 | O | ALA | 381 | 80.487 | 68.294 | 73.764 | 1.00 | 16.75 |
| ATOM | 2377 | N | SER | 382 | 80.461 | 70.553 | 73.833 | 1.00 | 16.25 |
| ATOM | 2378 | CA | SER | 382 | 81.898 | 70.647 | 74.050 | 1.00 | 14.46 |
| ATOM | 2379 | CB | SER | 382 | 82.464 | 71.911 | 73.394 | 1.00 | 15.52 |
| ATOM | 2380 | OG | SER | 382 | 82.399 | 71.835 | 71.978 | 1.00 | 12.28 |
| ATOM | 2381 | C | SER | 382 | 82.223 | 70.612 | 75.545 | 1.00 | 12.47 |
| ATOM | 2382 | O | SER | 382 | 83.293 | 70.160 | 75.946 | 1.00 | 12.89 |
| ATOM | 2383 | N | THR | 383 | 81.299 | 71.093 | 76.363 | 1.00 | 9.47 |
| ATOM | 2384 | CA | THR | 383 | 81.479 | 71.102 | 77.805 | 1.00 | 9.10 |
| ATOM | 2385 | CB | THR | 383 | 82.060 | 72.464 | 78.312 | 1.00 | 9.34 |
| ATOM | 2386 | OG1 | THR | 383 | 81.386 | 73.555 | 77.677 | 1.00 | 7.51 |
| ATOM | 2387 | CG2 | THR | 383 | 83.552 | 72.573 | 78.009 | 1.00 | 9.52 |
| ATOM | 2388 | C | THR | 383 | 80.122 | 70.814 | 78.452 | 1.00 | 9.96 |
| ATOM | 2389 | O | THR | 383 | 79.100 | 70.808 | 77.768 | 1.00 | 11.79 |
| ATOM | 2390 | N | VAL | 384 | 80.112 | 70.554 | 79.755 | 1.00 | 11.42 |
| ATOM | 2391 | CA | VAL | 384 | 78.884 | 70.254 | 80.489 | 1.00 | 12.61 |
| ATOM | 2392 | CB | VAL | 384 | 78.806 | 68.743 | 80.858 | 1.00 | 12.85 |
| ATOM | 2393 | CG1 | VAL | 384 | 77.655 | 68.485 | 81.816 | 1.00 | 9.44 |
| ATOM | 2394 | CG2 | VAL | 384 | 78.617 | 67.906 | 79.597 | 1.00 | 8.74 |
| ATOM | 2395 | C | VAL | 384 | 78.867 | 71.083 | 81.766 | 1.00 | 13.72 |
| ATOM | 2396 | O | VAL | 384 | 79.855 | 71.121 | 82.488 | 1.00 | 16.90 |
| ATOM | 2397 | N | MET | 385 | 77.743 | 71.737 | 82.042 | 1.00 | 12.85 |
| ATOM | 2398 | CA | MET | 385 | 77.603 | 72.568 | 83.235 | 1.00 | 11.55 |
| ATOM | 2399 | CB | MET | 385 | 77.037 | 73.941 | 82.849 | 1.00 | 9.59 |
| ATOM | 2400 | CG | MET | 385 | 76.925 | 74.933 | 83.997 | 1.00 | 8.37 |
| ATOM | 2401 | SD | MET | 385 | 76.483 | 76.589 | 83.443 | 1.00 | 15.71 |
| ATOM | 2402 | CE | MET | 385 | 78.077 | 77.210 | 82.918 | 1.00 | 11.94 |
| ATOM | 2403 | C | MET | 385 | 76.682 | 71.874 | 84.232 | 1.00 | 13.51 |
| ATOM | 2404 | O | MET | 385 | 75.617 | 71.391 | 83.855 | 1.00 | 16.34 |
| ATOM | 2405 | N | MET | 386 | 77.092 | 71.818 | 85.494 | 1.00 | 13.54 |
| ATOM | 2406 | CA | MET | 386 | 76.302 | 71.175 | 86.536 | 1.00 | 12.69 |
| ATOM | 2407 | CB | MET | 386 | 77.046 | 69.970 | 87.093 | 1.00 | 11.47 |
| ATOM | 2408 | CG | MET | 386 | 77.370 | 68.902 | 86.095 | 1.00 | 15.31 |
| ATOM | 2409 | SD | MET | 386 | 79.102 | 68.453 | 86.167 | 1.00 | 23.72 |
| ATOM | 2410 | CE | MET | 386 | 79.227 | 67.858 | 87.814 | 1.00 | 23.52 |
| ATOM | 2411 | C | MET | 386 | 75.996 | 72.107 | 87.700 | 1.00 | 14.87 |
| ATOM | 2412 | O | MET | 386 | 76.761 | 73.028 | 88.006 | 1.00 | 14.78 |
| ATOM | 2413 | N | GLY | 387 | 74.881 | 71.836 | 88.366 | 1.00 | 16.33 |
| ATOM | 2414 | CA | GLY | 387 | 74.471 | 72.615 | 89.517 | 1.00 | 16.37 |
| ATOM | 2415 | C | GLY | 387 | 74.350 | 71.680 | 90.700 | 1.00 | 17.64 |
| ATOM | 2416 | O | GLY | 387 | 75.172 | 71.725 | 91.611 | 1.00 | 18.53 |

FIG. 1A-42

| ATOM | 2417 | N | SER | 388 | 73.389 | 70.762 | 90.650 | 1.00 | 18.70 |
|---|---|---|---|---|---|---|---|---|---|
| ATOM | 2418 | CA | SER | 388 | 73.197 | 69.827 | 91.750 | 1.00 | 20.06 |
| ATOM | 2419 | CB | SER | 388 | 71.854 | 69.094 | 91.646 | 1.00 | 19.62 |
| ATOM | 2420 | OG | SER | 388 | 71.786 | 68.278 | 90.492 | 1.00 | 23.96 |
| ATOM | 2421 | C | SER | 388 | 74.324 | 68.822 | 91.904 | 1.00 | 21.02 |
| ATOM | 2422 | O | SER | 388 | 74.641 | 68.418 | 93.024 | 1.00 | 23.46 |
| ATOM | 2423 | N | LEU | 389 | 74.967 | 68.452 | 90.804 | 1.00 | 20.62 |
| ATOM | 2424 | CA | LEU | 389 | 76.048 | 67.475 | 90.873 | 1.00 | 19.98 |
| ATOM | 2425 | CB | LEU | 389 | 76.388 | 66.931 | 89.479 | 1.00 | 16.24 |
| ATOM | 2426 | CG | LEU | 389 | 76.903 | 65.485 | 89.459 | 1.00 | 12.91 |
| ATOM | 2427 | CD1 | LEU | 389 | 75.862 | 64.596 | 90.088 | 1.00 | 9.27 |
| ATOM | 2428 | CD2 | LEU | 389 | 77.207 | 65.012 | 88.053 | 1.00 | 7.57 |
| ATOM | 2429 | C | LEU | 389 | 77.294 | 68.028 | 91.555 | 1.00 | 22.25 |
| ATOM | 2430 | O | LEU | 389 | 78.297 | 67.335 | 91.656 | 1.00 | 24.36 |
| ATOM | 2431 | N | LEU | 390 | 77.224 | 69.269 | 92.033 | 1.00 | 23.31 |
| ATOM | 2432 | CA | LEU | 390 | 78.350 | 69.906 | 92.712 | 1.00 | 21.02 |
| ATOM | 2433 | CB | LEU | 390 | 79.049 | 70.892 | 91.769 | 1.00 | 17.40 |
| ATOM | 2434 | CG | LEU | 390 | 79.563 | 70.361 | 90.424 | 1.00 | 13.45 |
| ATOM | 2435 | CD1 | LEU | 390 | 80.108 | 71.494 | 89.584 | 1.00 | 11.98 |
| ATOM | 2436 | CD2 | LEU | 390 | 80.643 | 69.326 | 90.656 | 1.00 | 14.99 |
| ATOM | 2437 | C | LEU | 390 | 77.886 | 70.651 | 93.963 | 1.00 | 22.78 |
| ATOM | 2438 | O | LEU | 390 | 78.640 | 70.796 | 94.922 | 1.00 | 23.75 |
| ATOM | 2439 | N | ALA | 391 | 76.624 | 71.066 | 93.965 | 1.00 | 25.01 |
| ATOM | 2440 | CA | ALA | 391 | 76.020 | 71.827 | 95.061 | 1.00 | 27.66 |
| ATOM | 2441 | CB | ALA | 391 | 74.513 | 71.970 | 94.832 | 1.00 | 24.32 |
| ATOM | 2442 | C | ALA | 391 | 76.282 | 71.409 | 96.511 | 1.00 | 30.02 |
| ATOM | 2443 | O | ALA | 391 | 76.112 | 72.227 | 97.422 | 1.00 | 33.60 |
| ATOM | 2444 | N | ALA | 392 | 76.660 | 70.160 | 96.755 | 1.00 | 28.04 |
| ATOM | 2445 | CA | ALA | 392 | 76.897 | 69.748 | 98.136 | 1.00 | 27.13 |
| ATOM | 2446 | CB | ALA | 392 | 76.046 | 68.559 | 98.478 | 1.00 | 30.74 |
| ATOM | 2447 | C | ALA | 392 | 78.348 | 69.453 | 98.461 | 1.00 | 25.59 |
| ATOM | 2448 | O | ALA | 392 | 78.643 | 68.723 | 99.410 | 1.00 | 23.24 |
| ATOM | 2449 | N | THR | 393 | 79.256 | 69.969 | 97.649 | 1.00 | 24.15 |
| ATOM | 2450 | CA | THR | 393 | 80.663 | 69.734 | 97.895 | 1.00 | 22.30 |
| ATOM | 2451 | CB | THR | 393 | 81.502 | 69.799 | 96.599 | 1.00 | 18.89 |
| ATOM | 2452 | OG1 | THR | 393 | 81.294 | 71.053 | 95.952 | 1.00 | 21.65 |
| ATOM | 2453 | CG2 | THR | 393 | 81.121 | 68.666 | 95.651 | 1.00 | 15.42 |
| ATOM | 2454 | C | THR | 393 | 81.162 | 70.760 | 98.894 | 1.00 | 23.37 |
| ATOM | 2455 | O | THR | 393 | 80.514 | 71.781 | 99.133 | 1.00 | 23.21 |
| ATOM | 2456 | N | THR | 394 | 82.316 | 70.475 | 99.481 | 1.00 | 23.31 |
| ATOM | 2457 | CA | THR | 394 | 82.927 | 71.349 | 100.471 | 1.00 | 22.67 |
| ATOM | 2458 | CB | THR | 394 | 84.257 | 70.731 | 100.977 | 1.00 | 25.02 |
| ATOM | 2459 | OG1 | THR | 394 | 84.042 | 69.352 | 101.309 | 1.00 | 27.81 |
| ATOM | 2460 | CG2 | THR | 394 | 84.761 | 71.462 | 102.215 | 1.00 | 25.38 |
| ATOM | 2461 | C | THR | 394 | 83.206 | 72.756 | 99.933 | 1.00 | 20.08 |
| ATOM | 2462 | O | THR | 394 | 83.028 | 73.743 | 100.636 | 1.00 | 21.25 |
| ATOM | 2463 | N | GLU | 395 | 83.589 | 72.843 | 98.667 | 1.00 | 17.87 |
| ATOM | 2464 | CA | GLU | 395 | 83.935 | 74.115 | 98.066 | 1.00 | 15.59 |
| ATOM | 2465 | CB | GLU | 395 | 84.879 | 73.906 | 96.887 | 1.00 | 18.03 |
| ATOM | 2466 | CG | GLU | 395 | 86.264 | 73.351 | 97.255 | 1.00 | 21.45 |
| ATOM | 2467 | CD | GLU | 395 | 86.273 | 71.851 | 97.497 | 1.00 | 25.08 |
| ATOM | 2468 | OE1 | GLU | 395 | 87.250 | 71.342 | 98.094 | 1.00 | 23.12 |
| ATOM | 2469 | OE2 | GLU | 395 | 85.305 | 71.180 | 97.087 | 1.00 | 25.76 |
| ATOM | 2470 | C | GLU | 395 | 82.772 | 74.976 | 97.629 | 1.00 | 16.80 |
| ATOM | 2471 | O | GLU | 395 | 82.978 | 76.092 | 97.155 | 1.00 | 17.72 |
| ATOM | 2472 | N | ALA | 396 | 81.556 | 74.463 | 97.751 | 1.00 | 18.63 |
| ATOM | 2473 | CA | ALA | 396 | 80.373 | 75.226 | 97.353 | 1.00 | 20.65 |
| ATOM | 2474 | CB | ALA | 396 | 79.251 | 74.281 | 96.956 | 1.00 | 19.79 |
| ATOM | 2475 | C | ALA | 396 | 79.926 | 76.131 | 98.496 | 1.00 | 22.38 |

FIG. 1A-43

| ATOM | 2476 | O   | ALA | 396 | 80.183 | 75.834 | 99.665  | 1.00 | 23.05 |
| ---- | ---- | --- | --- | --- | ------ | ------ | ------- | ---- | ----- |
| ATOM | 2477 | N   | PRO | 397 | 79.301 | 77.279 | 98.171  | 1.00 | 23.70 |
| ATOM | 2478 | CD  | PRO | 397 | 79.085 | 77.782 | 96.806  | 1.00 | 24.23 |
| ATOM | 2479 | CA  | PRO | 397 | 78.809 | 78.250 | 99.152  | 1.00 | 25.59 |
| ATOM | 2480 | CB  | PRO | 397 | 78.129 | 79.296 | 98.275  | 1.00 | 23.05 |
| ATOM | 2481 | CG  | PRO | 397 | 78.922 | 79.255 | 97.029  | 1.00 | 22.14 |
| ATOM | 2482 | C   | PRO | 397 | 77.811 | 77.637 | 100.133 | 1.00 | 28.01 |
| ATOM | 2483 | O   | PRO | 397 | 77.055 | 76.741 | 99.780  | 1.00 | 28.32 |
| ATOM | 2484 | N   | GLY | 398 | 77.822 | 78.119 | 101.368 | 1.00 | 30.41 |
| ATOM | 2485 | CA  | GLY | 398 | 76.901 | 77.610 | 102.362 | 1.00 | 32.35 |
| ATOM | 2486 | C   | GLY | 398 | 77.536 | 76.719 | 103.406 | 1.00 | 35.07 |
| ATOM | 2487 | O   | GLY | 398 | 78.644 | 76.208 | 103.233 | 1.00 | 34.69 |
| ATOM | 2488 | N   | GLU | 399 | 76.820 | 76.556 | 104.512 | 1.00 | 37.44 |
| ATOM | 2489 | CA  | GLU | 399 | 77.259 | 75.728 | 105.628 | 1.00 | 38.51 |
| ATOM | 2490 | CB  | GLU | 399 | 77.005 | 76.480 | 106.944 | 1.00 | 44.33 |
| ATOM | 2491 | CG  | GLU | 399 | 77.219 | 75.665 | 108.222 | 1.00 | 55.44 |
| ATOM | 2492 | CD  | GLU | 399 | 75.930 | 75.413 | 109.025 | 1.00 | 65.22 |
| ATOM | 2493 | OE1 | GLU | 399 | 76.015 | 74.743 | 110.082 | 1.00 | 67.57 |
| ATOM | 2494 | OE2 | GLU | 399 | 74.837 | 75.871 | 108.610 | 1.00 | 69.24 |
| ATOM | 2495 | C   | GLU | 399 | 76.488 | 74.407 | 105.603 | 1.00 | 36.40 |
| ATOM | 2496 | O   | GLU | 399 | 75.347 | 74.359 | 105.136 | 1.00 | 36.14 |
| ATOM | 2497 | N   | TYR | 400 | 77.128 | 73.334 | 106.055 | 1.00 | 33.94 |
| ATOM | 2498 | CA  | TYR | 400 | 76.491 | 72.025 | 106.101 | 1.00 | 32.40 |
| ATOM | 2499 | CB  | TYR | 400 | 77.538 | 70.920 | 106.223 | 1.00 | 30.68 |
| ATOM | 2500 | CG  | TYR | 400 | 78.226 | 70.564 | 104.938 | 1.00 | 29.71 |
| ATOM | 2501 | CD1 | TYR | 400 | 77.633 | 69.688 | 104.026 | 1.00 | 28.20 |
| ATOM | 2502 | CE1 | TYR | 400 | 78.274 | 69.344 | 102.845 | 1.00 | 26.95 |
| ATOM | 2503 | CD2 | TYR | 400 | 79.477 | 71.089 | 104.632 | 1.00 | 28.87 |
| ATOM | 2504 | CE2 | TYR | 400 | 80.128 | 70.749 | 103.453 | 1.00 | 27.69 |
| ATOM | 2505 | CZ  | TYR | 400 | 79.523 | 69.882 | 102.565 | 1.00 | 25.06 |
| ATOM | 2506 | OH  | TYR | 400 | 80.169 | 69.554 | 101.403 | 1.00 | 21.76 |
| ATOM | 2507 | C   | TYR | 400 | 75.604 | 71.938 | 107.322 | 1.00 | 32.61 |
| ATOM | 2508 | O   | TYR | 400 | 75.895 | 72.543 | 108.347 | 1.00 | 35.88 |
| ATOM | 2509 | N   | PHE | 401 | 74.542 | 71.160 | 107.235 | 1.00 | 30.97 |
| ATOM | 2510 | CA  | PHE | 401 | 73.670 | 70.985 | 108.376 | 1.00 | 31.87 |
| ATOM | 2511 | CB  | PHE | 401 | 72.514 | 71.999 | 108.356 | 1.00 | 31.10 |
| ATOM | 2512 | CG  | PHE | 401 | 71.644 | 71.914 | 107.133 | 1.00 | 29.98 |
| ATOM | 2513 | CD1 | PHE | 401 | 72.023 | 72.543 | 105.950 | 1.00 | 27.03 |
| ATOM | 2514 | CD2 | PHE | 401 | 70.457 | 71.178 | 107.154 | 1.00 | 25.56 |
| ATOM | 2515 | CE1 | PHE | 401 | 71.238 | 72.438 | 104.806 | 1.00 | 25.34 |
| ATOM | 2516 | CE2 | PHE | 401 | 69.666 | 71.066 | 106.015 | 1.00 | 23.68 |
| ATOM | 2517 | CZ  | PHE | 401 | 70.057 | 71.697 | 104.838 | 1.00 | 25.95 |
| ATOM | 2518 | C   | PHE | 401 | 73.180 | 69.549 | 108.327 | 1.00 | 33.08 |
| ATOM | 2519 | O   | PHE | 401 | 73.597 | 68.779 | 107.465 | 1.00 | 32.13 |
| ATOM | 2520 | N   | PHE | 402 | 72.318 | 69.171 | 109.258 | 1.00 | 35.69 |
| ATOM | 2521 | CA  | PHE | 402 | 71.811 | 67.810 | 109.279 | 1.00 | 37.42 |
| ATOM | 2522 | CB  | PHE | 402 | 72.456 | 67.030 | 110.429 | 1.00 | 35.41 |
| ATOM | 2523 | CG  | PHE | 402 | 73.949 | 66.901 | 110.322 | 1.00 | 32.99 |
| ATOM | 2524 | CD1 | PHE | 402 | 74.525 | 65.726 | 109.847 | 1.00 | 33.35 |
| ATOM | 2525 | CD2 | PHE | 402 | 74.781 | 67.954 | 110.689 | 1.00 | 33.30 |
| ATOM | 2526 | CE1 | PHE | 402 | 75.916 | 65.603 | 109.737 | 1.00 | 31.57 |
| ATOM | 2527 | CE2 | PHE | 402 | 76.167 | 67.844 | 110.584 | 1.00 | 31.22 |
| ATOM | 2528 | CZ  | PHE | 402 | 76.734 | 66.665 | 110.106 | 1.00 | 32.49 |
| ATOM | 2529 | C   | PHE | 402 | 70.291 | 67.770 | 109.418 | 1.00 | 40.49 |
| ATOM | 2530 | O   | PHE | 402 | 69.680 | 68.689 | 109.973 | 1.00 | 41.28 |
| ATOM | 2531 | N   | SER | 403 | 69.689 | 66.726 | 108.862 | 1.00 | 43.51 |
| ATOM | 2532 | CA  | SER | 403 | 68.252 | 66.525 | 108.949 | 1.00 | 47.93 |
| ATOM | 2533 | CB  | SER | 403 | 67.617 | 66.581 | 107.560 | 1.00 | 49.52 |
| ATOM | 2534 | OG  | SER | 403 | 68.245 | 65.660 | 106.683 | 1.00 | 54.86 |

FIG. 1A-44

| ATOM | 2535 | C | SER | 403 | 68.053 | 65.154 | 109.607 | 1.00 | 51.47 |
|---|---|---|---|---|---|---|---|---|---|
| ATOM | 2536 | O | SER | 403 | 68.366 | 64.987 | 110.789 | 1.00 | 53.15 |
| ATOM | 2537 | N | ASP | 404 | 67.597 | 64.162 | 108.847 | 1.00 | 52.88 |
| ATOM | 2538 | CA | ASP | 404 | 67.393 | 62.821 | 109.395 | 1.00 | 54.43 |
| ATOM | 2539 | CB | ASP | 404 | 66.354 | 62.034 | 108.570 | 1.00 | 59.65 |
| ATOM | 2540 | CG | ASP | 404 | 66.498 | 62.238 | 107.056 | 1.00 | 64.80 |
| ATOM | 2541 | OD1 | ASP | 404 | 65.472 | 62.112 | 106.348 | 1.00 | 66.65 |
| ATOM | 2542 | OD2 | ASP | 404 | 67.617 | 62.520 | 106.569 | 1.00 | 67.01 |
| ATOM | 2543 | C | ASP | 404 | 68.727 | 62.080 | 109.468 | 1.00 | 53.52 |
| ATOM | 2544 | O | ASP | 404 | 68.899 | 61.003 | 108.893 | 1.00 | 54.08 |
| ATOM | 2545 | N | GLY | 405 | 69.673 | 62.674 | 110.186 | 1.00 | 52.57 |
| ATOM | 2546 | CA | GLY | 405 | 70.989 | 62.080 | 110.314 | 1.00 | 51.71 |
| ATOM | 2547 | C | GLY | 405 | 71.745 | 62.165 | 109.004 | 1.00 | 50.71 |
| ATOM | 2548 | O | GLY | 405 | 72.761 | 61.494 | 108.817 | 1.00 | 51.94 |
| ATOM | 2549 | N | ILE | 406 | 71.254 | 63.006 | 108.101 | 1.00 | 49.32 |
| ATOM | 2550 | CA | ILE | 406 | 71.873 | 63.185 | 106.797 | 1.00 | 46.50 |
| ATOM | 2551 | CB | ILE | 406 | 70.868 | 62.860 | 105.670 | 1.00 | 45.63 |
| ATOM | 2552 | CG2 | ILE | 406 | 71.409 | 63.303 | 104.321 | 1.00 | 45.90 |
| ATOM | 2553 | CG1 | ILE | 406 | 70.585 | 61.353 | 105.677 | 1.00 | 47.65 |
| ATOM | 2554 | CD1 | ILE | 406 | 69.620 | 60.887 | 104.620 | 1.00 | 51.01 |
| ATOM | 2555 | C | ILE | 406 | 72.443 | 64.592 | 106.648 | 1.00 | 44.89 |
| ATOM | 2556 | O | ILE | 406 | 71.744 | 65.588 | 106.886 | 1.00 | 45.23 |
| ATOM | 2557 | N | ARG | 407 | 73.727 | 64.662 | 106.306 | 1.00 | 42.16 |
| ATOM | 2558 | CA | ARG | 407 | 74.403 | 65.939 | 106.137 | 1.00 | 39.23 |
| ATOM | 2559 | CB | ARG | 407 | 75.918 | 65.756 | 106.126 | 1.00 | 38.21 |
| ATOM | 2560 | CG | ARG | 407 | 76.668 | 67.017 | 106.504 | 1.00 | 36.68 |
| ATOM | 2561 | CD | ARG | 407 | 78.142 | 66.747 | 106.691 | 1.00 | 38.88 |
| ATOM | 2562 | NE | ARG | 407 | 78.743 | 67.742 | 107.571 | 1.00 | 41.10 |
| ATOM | 2563 | CZ | ARG | 407 | 79.902 | 68.347 | 107.343 | 1.00 | 40.51 |
| ATOM | 2564 | NH1 | ARG | 407 | 80.604 | 68.063 | 106.255 | 1.00 | 36.09 |
| ATOM | 2565 | NH2 | ARG | 407 | 80.346 | 69.258 | 108.198 | 1.00 | 40.72 |
| ATOM | 2566 | C | ARG | 407 | 73.944 | 66.546 | 104.831 | 1.00 | 37.51 |
| ATOM | 2567 | O | ARG | 407 | 73.902 | 65.867 | 103.805 | 1.00 | 39.48 |
| ATOM | 2568 | N | LEU | 408 | 73.601 | 67.824 | 104.868 | 1.00 | 34.38 |
| ATOM | 2569 | CA | LEU | 408 | 73.115 | 68.504 | 103.683 | 1.00 | 31.16 |
| ATOM | 2570 | CB | LEU | 408 | 71.588 | 68.562 | 103.724 | 1.00 | 24.97 |
| ATOM | 2571 | CG | LEU | 408 | 70.844 | 67.249 | 103.927 | 1.00 | 20.15 |
| ATOM | 2572 | CD1 | LEU | 408 | 69.476 | 67.526 | 104.499 | 1.00 | 19.69 |
| ATOM | 2573 | CD2 | LEU | 408 | 70.784 | 66.473 | 102.631 | 1.00 | 14.81 |
| ATOM | 2574 | C | LEU | 408 | 73.656 | 69.921 | 103.581 | 1.00 | 31.84 |
| ATOM | 2575 | O | LEU | 408 | 74.160 | 70.493 | 104.551 | 1.00 | 33.47 |
| ATOM | 2576 | N | LYS | 409 | 73.548 | 70.470 | 102.381 | 1.00 | 30.46 |
| ATOM | 2577 | CA | LYS | 409 | 73.967 | 71.827 | 102.091 | 1.00 | 27.79 |
| ATOM | 2578 | CB | LYS | 409 | 75.332 | 71.834 | 101.402 | 1.00 | 27.10 |
| ATOM | 2579 | CG | LYS | 409 | 75.988 | 73.200 | 101.349 | 1.00 | 26.08 |
| ATOM | 2580 | CD | LYS | 409 | 77.168 | 73.220 | 100.398 | 1.00 | 26.04 |
| ATOM | 2581 | CE | LYS | 409 | 78.425 | 72.632 | 100.998 | 1.00 | 25.41 |
| ATOM | 2582 | NZ | LYS | 409 | 79.076 | 73.542 | 101.965 | 1.00 | 24.68 |
| ATOM | 2583 | C | LYS | 409 | 72.878 | 72.320 | 101.142 | 1.00 | 26.84 |
| ATOM | 2584 | O | LYS | 409 | 72.376 | 71.562 | 100.311 | 1.00 | 26.63 |
| ATOM | 2585 | N | LYS | 410 | 72.495 | 73.577 | 101.285 | 1.00 | 26.58 |
| ATOM | 2586 | CA | LYS | 410 | 71.452 | 74.169 | 100.468 | 1.00 | 27.15 |
| ATOM | 2587 | CB | LYS | 410 | 71.132 | 75.568 | 100.993 | 1.00 | 31.97 |
| ATOM | 2588 | CG | LYS | 410 | 70.054 | 75.605 | 102.062 | 1.00 | 40.07 |
| ATOM | 2589 | CD | LYS | 410 | 68.680 | 75.378 | 101.442 | 1.00 | 46.67 |
| ATOM | 2590 | CE | LYS | 410 | 68.389 | 76.403 | 100.339 | 1.00 | 47.01 |
| ATOM | 2591 | NZ | LYS | 410 | 67.072 | 76.159 | 99.700 | 1.00 | 43.19 |
| ATOM | 2592 | C | LYS | 410 | 71.758 | 74.260 | 98.980 | 1.00 | 25.29 |
| ATOM | 2593 | O | LYS | 410 | 72.895 | 74.479 | 98.576 | 1.00 | 25.69 |

FIG. 1A-45

| | | | | | | | | | |
|---|---|---|---|---|---|---|---|---|---|
| ATOM | 2594 | N | TYR | 411 | 70.725 | 74.071 | 98.174 | 1.00 | 22.53 |
| ATOM | 2595 | CA | TYR | 411 | 70.830 | 74.192 | 96.735 | 1.00 | 19.58 |
| ATOM | 2596 | CB | TYR | 411 | 71.035 | 72.840 | 96.051 | 1.00 | 16.64 |
| ATOM | 2597 | CG | TYR | 411 | 71.132 | 72.979 | 94.546 | 1.00 | 18.10 |
| ATOM | 2598 | CD1 | TYR | 411 | 71.895 | 74.000 | 93.974 | 1.00 | 18.77 |
| ATOM | 2599 | CE1 | TYR | 411 | 71.929 | 74.196 | 92.605 | 1.00 | 19.48 |
| ATOM | 2600 | CD2 | TYR | 411 | 70.409 | 72.145 | 93.693 | 1.00 | 17.87 |
| ATOM | 2601 | CE2 | TYR | 411 | 70.439 | 72.334 | 92.310 | 1.00 | 17.72 |
| ATOM | 2602 | CZ | TYR | 411 | 71.199 | 73.367 | 91.774 | 1.00 | 19.31 |
| ATOM | 2603 | OH | TYR | 411 | 71.210 | 73.599 | 90.412 | 1.00 | 22.34 |
| ATOM | 2604 | C | TYR | 411 | 69.510 | 74.820 | 96.295 | 1.00 | 20.78 |
| ATOM | 2605 | O | TYR | 411 | 68.432 | 74.278 | 96.570 | 1.00 | 20.50 |
| ATOM | 2606 | N | ARG | 412 | 69.582 | 75.968 | 95.631 | 1.00 | 19.85 |
| ATOM | 2607 | CA | ARG | 412 | 68.368 | 76.641 | 95.199 | 1.00 | 18.82 |
| ATOM | 2608 | CB | ARG | 412 | 67.992 | 77.750 | 96.187 | 1.00 | 16.10 |
| ATOM | 2609 | CG | ARG | 412 | 68.919 | 78.944 | 96.139 | 1.00 | 13.54 |
| ATOM | 2610 | CD | ARG | 412 | 68.454 | 80.049 | 97.034 | 1.00 | 10.34 |
| ATOM | 2611 | NE | ARG | 412 | 69.325 | 81.207 | 96.904 | 1.00 | 17.42 |
| ATOM | 2612 | CZ | ARG | 412 | 69.384 | 82.205 | 97.782 | 1.00 | 21.02 |
| ATOM | 2613 | NH1 | ARG | 412 | 68.621 | 82.193 | 98.864 | 1.00 | 22.12 |
| ATOM | 2614 | NH2 | ARG | 412 | 70.217 | 83.217 | 97.586 | 1.00 | 23.60 |
| ATOM | 2615 | C | ARG | 412 | 68.464 | 77.235 | 93.808 | 1.00 | 20.49 |
| ATOM | 2616 | O | ARG | 412 | 69.510 | 77.762 | 93.401 | 1.00 | 19.42 |
| ATOM | 2617 | N | GLY | 413 | 67.348 | 77.168 | 93.092 | 1.00 | 22.45 |
| ATOM | 2618 | CA | GLY | 413 | 67.295 | 77.725 | 91.759 | 1.00 | 22.08 |
| ATOM | 2619 | C | GLY | 413 | 67.358 | 79.233 | 91.846 | 1.00 | 20.93 |
| ATOM | 2620 | O | GLY | 413 | 66.791 | 79.831 | 92.761 | 1.00 | 19.19 |
| ATOM | 2621 | N | MET | 414 | 68.049 | 79.845 | 90.893 | 1.00 | 21.29 |
| ATOM | 2622 | CA | MET | 414 | 68.197 | 81.292 | 90.847 | 1.00 | 21.49 |
| ATOM | 2623 | CB | MET | 414 | 69.265 | 81.681 | 89.824 | 1.00 | 23.96 |
| ATOM | 2624 | CG | MET | 414 | 70.672 | 81.250 | 90.224 | 1.00 | 21.70 |
| ATOM | 2625 | SD | MET | 414 | 71.103 | 81.734 | 91.919 | 1.00 | 18.54 |
| ATOM | 2626 | CE | MET | 414 | 71.695 | 83.398 | 91.646 | 1.00 | 23.85 |
| ATOM | 2627 | C | MET | 414 | 66.888 | 82.025 | 90.567 | 1.00 | 20.64 |
| ATOM | 2628 | O | MET | 414 | 66.822 | 83.254 | 90.648 | 1.00 | 20.74 |
| ATOM | 2629 | N | GLY | 415 | 65.854 | 81.267 | 90.233 | 1.00 | 20.53 |
| ATOM | 2630 | CA | GLY | 415 | 64.558 | 81.851 | 89.972 | 1.00 | 19.68 |
| ATOM | 2631 | C | GLY | 415 | 63.640 | 81.592 | 91.147 | 1.00 | 21.08 |
| ATOM | 2632 | O | GLY | 415 | 62.425 | 81.726 | 91.021 | 1.00 | 23.65 |
| ATOM | 2633 | N | SER | 416 | 64.197 | 81.142 | 92.266 | 1.00 | 20.91 |
| ATOM | 2634 | CA | SER | 416 | 63.393 | 80.886 | 93.455 | 1.00 | 22.71 |
| ATOM | 2635 | CB | SER | 416 | 64.144 | 79.996 | 94.451 | 1.00 | 22.91 |
| ATOM | 2636 | OG | SER | 416 | 65.344 | 80.599 | 94.910 | 1.00 | 20.96 |
| ATOM | 2637 | C | SER | 416 | 63.105 | 82.236 | 94.087 | 1.00 | 24.99 |
| ATOM | 2638 | O | SER | 416 | 63.870 | 83.181 | 93.890 | 1.00 | 27.08 |
| ATOM | 2639 | N | LEU | 417 | 62.019 | 82.337 | 94.846 | 1.00 | 26.49 |
| ATOM | 2640 | CA | LEU | 417 | 61.679 | 83.601 | 95.485 | 1.00 | 29.42 |
| ATOM | 2641 | CB | LEU | 417 | 60.362 | 83.497 | 96.255 | 1.00 | 31.14 |
| ATOM | 2642 | CG | LEU | 417 | 59.054 | 83.276 | 95.486 | 1.00 | 30.31 |
| ATOM | 2643 | CD1 | LEU | 417 | 57.907 | 83.354 | 96.474 | 1.00 | 30.36 |
| ATOM | 2644 | CD2 | LEU | 417 | 58.862 | 84.302 | 94.378 | 1.00 | 25.63 |
| ATOM | 2645 | C | LEU | 417 | 62.795 | 84.055 | 96.420 | 1.00 | 32.03 |
| ATOM | 2646 | O | LEU | 417 | 63.061 | 85.249 | 96.532 | 1.00 | 33.75 |
| ATOM | 2647 | N | ASP | 418 | 63.445 | 83.095 | 97.081 | 1.00 | 35.21 |
| ATOM | 2648 | CA | ASP | 418 | 64.550 | 83.378 | 98.005 | 1.00 | 35.94 |
| ATOM | 2649 | CB | ASP | 418 | 64.942 | 82.121 | 98.797 | 1.00 | 35.59 |
| ATOM | 2650 | CG | ASP | 418 | 63.988 | 81.821 | 99.942 | 1.00 | 39.46 |
| ATOM | 2651 | OD1 | ASP | 418 | 63.295 | 82.749 | 100.423 | 1.00 | 40.20 |
| ATOM | 2652 | OD2 | ASP | 418 | 63.941 | 80.651 | 100.374 | 1.00 | 41.70 |

FIG. 1A-46

| ATOM | 2653 | C | ASP | 418 | 65.777 | 83.902 | 97.275 | 1.00 | 36.50 |
|---|---|---|---|---|---|---|---|---|---|
| ATOM | 2654 | O | ASP | 418 | 66.407 | 84.860 | 97.716 | 1.00 | 37.43 |
| ATOM | 2655 | N | ALA | 419 | 66.147 | 83.233 | 96.189 | 1.00 | 36.59 |
| ATOM | 2656 | CA | ALA | 419 | 67.301 | 83.646 | 95.411 | 1.00 | 37.48 |
| ATOM | 2657 | CB | ALA | 419 | 67.567 | 82.660 | 94.300 | 1.00 | 36.03 |
| ATOM | 2658 | C | ALA | 419 | 67.021 | 85.024 | 94.841 | 1.00 | 39.11 |
| ATOM | 2659 | O | ALA | 419 | 67.914 | 85.869 | 94.774 | 1.00 | 40.78 |
| ATOM | 2660 | N | MET | 420 | 65.770 | 85.245 | 94.446 | 1.00 | 39.62 |
| ATOM | 2661 | CA | MET | 420 | 65.348 | 86.521 | 93.884 | 1.00 | 40.26 |
| ATOM | 2662 | CB | MET | 420 | 64.039 | 86.368 | 93.096 | 1.00 | 40.92 |
| ATOM | 2663 | CG | MET | 420 | 64.124 | 85.453 | 91.879 | 1.00 | 38.85 |
| ATOM | 2664 | SD | MET | 420 | 62.752 | 85.698 | 90.733 | 1.00 | 35.95 |
| ATOM | 2665 | CE | MET | 420 | 61.390 | 84.999 | 91.678 | 1.00 | 32.77 |
| ATOM | 2666 | C | MET | 420 | 65.163 | 87.549 | 94.991 | 1.00 | 40.67 |
| ATOM | 2667 | O | MET | 420 | 65.352 | 88.741 | 94.681 | 1.00 | 41.51 |
| ATOM | 2668 | CB | ILE | 437 | 53.259 | 89.508 | 90.596 | 1.00 | 46.60 |
| ATOM | 2669 | CG2 | ILE | 437 | 53.123 | 88.263 | 91.473 | 1.00 | 42.38 |
| ATOM | 2670 | CG1 | ILE | 437 | 52.015 | 90.393 | 90.752 | 1.00 | 48.50 |
| ATOM | 2671 | CD1 | ILE | 437 | 51.671 | 91.225 | 89.513 | 1.00 | 48.60 |
| ATOM | 2672 | C | ILE | 437 | 55.751 | 89.463 | 90.476 | 1.00 | 46.43 |
| ATOM | 2673 | O | ILE | 437 | 56.179 | 89.615 | 89.324 | 1.00 | 47.38 |
| ATOM | 2674 | N | ILE | 437 | 54.637 | 91.629 | 90.302 | 1.00 | 47.00 |
| ATOM | 2675 | CA | ILE | 437 | 54.566 | 90.290 | 90.965 | 1.00 | 47.20 |
| ATOM | 2676 | N | LYS | 438 | 56.291 | 88.622 | 91.355 | 1.00 | 43.78 |
| ATOM | 2677 | CA | LYS | 438 | 57.413 | 87.764 | 91.001 | 1.00 | 40.48 |
| ATOM | 2678 | CB | LYS | 438 | 58.472 | 87.761 | 92.100 | 1.00 | 43.36 |
| ATOM | 2679 | CG | LYS | 438 | 59.340 | 89.005 | 92.099 | 1.00 | 52.37 |
| ATOM | 2680 | CD | LYS | 438 | 60.428 | 88.957 | 93.164 | 1.00 | 57.07 |
| ATOM | 2681 | CE | LYS | 438 | 61.260 | 90.234 | 93.136 | 1.00 | 57.16 |
| ATOM | 2682 | NZ | LYS | 438 | 62.246 | 90.282 | 94.245 | 1.00 | 58.75 |
| ATOM | 2683 | C | LYS | 438 | 56.919 | 86.350 | 90.749 | 1.00 | 37.61 |
| ATOM | 2684 | O | LYS | 438 | 56.197 | 85.778 | 91.564 | 1.00 | 37.45 |
| ATOM | 2685 | N | VAL | 439 | 57.249 | 85.835 | 89.572 | 1.00 | 34.22 |
| ATOM | 2686 | CA | VAL | 439 | 56.871 | 84.489 | 89.175 | 1.00 | 29.77 |
| ATOM | 2687 | CB | VAL | 439 | 56.519 | 84.430 | 87.670 | 1.00 | 25.38 |
| ATOM | 2688 | CG1 | VAL | 439 | 56.312 | 82.994 | 87.224 | 1.00 | 24.88 |
| ATOM | 2689 | CG2 | VAL | 439 | 55.279 | 85.246 | 87.396 | 1.00 | 22.94 |
| ATOM | 2690 | C | VAL | 439 | 58.098 | 83.637 | 89.436 | 1.00 | 29.52 |
| ATOM | 2691 | O | VAL | 439 | 59.152 | 83.867 | 88.836 | 1.00 | 30.63 |
| ATOM | 2692 | N | ALA | 440 | 57.991 | 82.723 | 90.392 | 1.00 | 28.23 |
| ATOM | 2693 | CA | ALA | 440 | 59.104 | 81.843 | 90.720 | 1.00 | 26.56 |
| ATOM | 2694 | CB | ALA | 440 | 58.859 | 81.151 | 92.037 | 1.00 | 23.10 |
| ATOM | 2695 | C | ALA | 440 | 59.277 | 80.818 | 89.606 | 1.00 | 26.95 |
| ATOM | 2696 | O | ALA | 440 | 58.298 | 80.297 | 89.072 | 1.00 | 28.49 |
| ATOM | 2697 | N | GLN | 441 | 60.524 | 80.584 | 89.212 | 1.00 | 26.65 |
| ATOM | 2698 | CA | GLN | 441 | 60.841 | 79.625 | 88.163 | 1.00 | 23.30 |
| ATOM | 2699 | CB | GLN | 441 | 61.463 | 80.328 | 86.967 | 1.00 | 22.34 |
| ATOM | 2700 | CG | GLN | 441 | 60.483 | 81.223 | 86.245 | 1.00 | 26.34 |
| ATOM | 2701 | CD | GLN | 441 | 61.126 | 81.994 | 85.126 | 1.00 | 30.83 |
| ATOM | 2702 | OE1 | GLN | 441 | 61.199 | 83.226 | 85.164 | 1.00 | 32.45 |
| ATOM | 2703 | NE2 | GLN | 441 | 61.608 | 81.277 | 84.119 | 1.00 | 32.37 |
| ATOM | 2704 | C | GLN | 441 | 61.787 | 78.582 | 88.700 | 1.00 | 22.70 |
| ATOM | 2705 | O | GLN | 441 | 62.100 | 77.609 | 88.017 | 1.00 | 24.78 |
| ATOM | 2706 | N | GLY | 442 | 62.192 | 78.763 | 89.949 | 1.00 | 21.19 |
| ATOM | 2707 | CA | GLY | 442 | 63.092 | 77.828 | 90.584 | 1.00 | 21.43 |
| ATOM | 2708 | C | GLY | 442 | 62.534 | 77.485 | 91.945 | 1.00 | 21.81 |
| ATOM | 2709 | O | GLY | 442 | 61.635 | 78.168 | 92.436 | 1.00 | 22.56 |
| ATOM | 2710 | N | VAL | 443 | 63.117 | 76.471 | 92.574 | 1.00 | 21.86 |
| ATOM | 2711 | CA | VAL | 443 | 62.699 | 75.985 | 93.886 | 1.00 | 20.15 |

FIG. 1A-47

| ATOM | 2712 | CB | VAL | 443 | 62.124 | 74.542 | 93.720 | 1.00 | 19.51 |
| --- | --- | --- | --- | --- | --- | --- | --- | --- | --- |
| ATOM | 2713 | CG1 | VAL | 443 | 62.997 | 73.490 | 94.406 | 1.00 | 18.43 |
| ATOM | 2714 | CG2 | VAL | 443 | 60.692 | 74.487 | 94.176 | 1.00 | 20.94 |
| ATOM | 2715 | C | VAL | 443 | 63.908 | 76.010 | 94.839 | 1.00 | 20.65 |
| ATOM | 2716 | O | VAL | 443 | 65.054 | 76.084 | 94.381 | 1.00 | 20.98 |
| ATOM | 2717 | N | SER | 444 | 63.657 | 75.985 | 96.149 | 1.00 | 21.18 |
| ATOM | 2718 | CA | SER | 444 | 64.733 | 75.988 | 97.149 | 1.00 | 21.80 |
| ATOM | 2719 | CB | SER | 444 | 64.582 | 77.171 | 98.108 | 1.00 | 24.85 |
| ATOM | 2720 | OG | SER | 444 | 64.906 | 78.399 | 97.480 | 1.00 | 33.77 |
| ATOM | 2721 | C | SER | 444 | 64.827 | 74.688 | 97.960 | 1.00 | 22.20 |
| ATOM | 2722 | O | SER | 444 | 63.955 | 74.394 | 98.791 | 1.00 | 23.12 |
| ATOM | 2723 | N | GLY | 445 | 65.917 | 73.948 | 97.777 | 1.00 | 21.40 |
| ATOM | 2724 | CA | GLY | 445 | 66.068 | 72.700 | 98.495 | 1.00 | 22.02 |
| ATOM | 2725 | C | GLY | 445 | 67.439 | 72.436 | 99.076 | 1.00 | 23.53 |
| ATOM | 2726 | O | GLY | 445 | 68.217 | 73.362 | 99.316 | 1.00 | 25.01 |
| ATOM | 2727 | N | ALA | 446 | 67.729 | 71.164 | 99.319 | 1.00 | 22.46 |
| ATOM | 2728 | CA | ALA | 446 | 69.004 | 70.768 | 99.890 | 1.00 | 21.42 |
| ATOM | 2729 | CB | ALA | 446 | 68.890 | 70.614 | 101.396 | 1.00 | 19.79 |
| ATOM | 2730 | C | ALA | 446 | 69.422 | 69.459 | 99.277 | 1.00 | 22.96 |
| ATOM | 2731 | O | ALA | 446 | 68.576 | 68.627 | 98.946 | 1.00 | 24.40 |
| ATOM | 2732 | N | VAL | 447 | 70.731 | 69.287 | 99.129 | 1.00 | 24.30 |
| ATOM | 2733 | CA | VAL | 447 | 71.326 | 68.080 | 98.572 | 1.00 | 23.81 |
| ATOM | 2734 | CB | VAL | 447 | 72.068 | 68.389 | 97.260 | 1.00 | 22.59 |
| ATOM | 2735 | CG1 | VAL | 447 | 71.078 | 68.801 | 96.195 | 1.00 | 23.88 |
| ATOM | 2736 | CG2 | VAL | 447 | 73.048 | 69.515 | 97.467 | 1.00 | 28.09 |
| ATOM | 2737 | C | VAL | 447 | 72.284 | 67.467 | 99.607 | 1.00 | 25.54 |
| ATOM | 2738 | O | VAL | 447 | 72.765 | 68.155 | 100.510 | 1.00 | 26.03 |
| ATOM | 2739 | N | GLN | 448 | 72.530 | 66.168 | 99.491 | 1.00 | 26.62 |
| ATOM | 2740 | CA | GLN | 448 | 73.401 | 65.460 | 100.420 | 1.00 | 27.39 |
| ATOM | 2741 | CB | GLN | 448 | 73.033 | 63.973 | 100.424 | 1.00 | 30.61 |
| ATOM | 2742 | CG | GLN | 448 | 73.722 | 63.113 | 101.477 | 1.00 | 33.45 |
| ATOM | 2743 | CD | GLN | 448 | 73.330 | 61.636 | 101.390 | 1.00 | 36.95 |
| ATOM | 2744 | OE1 | GLN | 448 | 73.820 | 60.811 | 102.160 | 1.00 | 40.13 |
| ATOM | 2745 | NE2 | GLN | 448 | 72.443 | 61.300 | 100.454 | 1.00 | 37.67 |
| ATOM | 2746 | C | GLN | 448 | 74.877 | 65.654 | 100.068 | 1.00 | 28.24 |
| ATOM | 2747 | O | GLN | 448 | 75.249 | 65.660 | 98.896 | 1.00 | 30.00 |
| ATOM | 2748 | N | ASP | 449 | 75.694 | 65.816 | 101.106 | 1.00 | 29.14 |
| ATOM | 2749 | CA | ASP | 449 | 77.142 | 66.029 | 101.025 | 1.00 | 26.21 |
| ATOM | 2750 | CB | ASP | 449 | 77.724 | 65.825 | 102.434 | 1.00 | 28.70 |
| ATOM | 2751 | CG | ASP | 449 | 79.212 | 66.116 | 102.524 | 1.00 | 33.19 |
| ATOM | 2752 | OD1 | ASP | 449 | 79.789 | 66.694 | 101.582 | 1.00 | 35.84 |
| ATOM | 2753 | OD2 | ASP | 449 | 79.811 | 65.771 | 103.566 | 1.00 | 34.41 |
| ATOM | 2754 | C | ASP | 449 | 77.842 | 65.112 | 100.022 | 1.00 | 23.36 |
| ATOM | 2755 | O | ASP | 449 | 77.731 | 63.895 | 100.114 | 1.00 | 23.48 |
| ATOM | 2756 | N | LYS | 450 | 78.582 | 65.708 | 99.087 | 1.00 | 23.13 |
| ATOM | 2757 | CA | LYS | 450 | 79.319 | 64.962 | 98.056 | 1.00 | 23.09 |
| ATOM | 2758 | CB | LYS | 450 | 79.048 | 65.539 | 96.665 | 1.00 | 24.74 |
| ATOM | 2759 | CG | LYS | 450 | 77.600 | 65.522 | 96.251 | 1.00 | 30.34 |
| ATOM | 2760 | CD | LYS | 450 | 77.445 | 65.993 | 94.816 | 1.00 | 34.49 |
| ATOM | 2761 | CE | LYS | 450 | 75.982 | 66.200 | 94.487 | 1.00 | 38.17 |
| ATOM | 2762 | NZ | LYS | 450 | 75.383 | 67.270 | 95.338 | 1.00 | 42.96 |
| ATOM | 2763 | C | LYS | 450 | 80.833 | 64.953 | 98.281 | 1.00 | 23.02 |
| ATOM | 2764 | O | LYS | 450 | 81.582 | 64.347 | 97.507 | 1.00 | 21.57 |
| ATOM | 2765 | N | GLY | 451 | 81.283 | 65.643 | 99.321 | 1.00 | 22.90 |
| ATOM | 2766 | CA | GLY | 451 | 82.701 | 65.694 | 99.611 | 1.00 | 23.16 |
| ATOM | 2767 | C | GLY | 451 | 83.381 | 66.831 | 98.874 | 1.00 | 23.95 |
| ATOM | 2768 | O | GLY | 451 | 82.729 | 67.801 | 98.485 | 1.00 | 24.66 |
| ATOM | 2769 | N | SER | 452 | 84.689 | 66.704 | 98.663 | 1.00 | 22.79 |
| ATOM | 2770 | CA | SER | 452 | 85.464 | 67.735 | 97.990 | 1.00 | 19.59 |

FIG. 1A-48

| ATOM | 2771 | CB | SER | 452 | 86.909 | 67.718 | 98.502 | 1.00 | 19.37 |
| ATOM | 2772 | OG | SER | 452 | 87.726 | 68.650 | 97.808 | 1.00 | 19.18 |
| ATOM | 2773 | C | SER | 452 | 85.463 | 67.616 | 96.482 | 1.00 | 17.85 |
| ATOM | 2774 | O | SER | 452 | 85.449 | 66.514 | 95.936 | 1.00 | 19.84 |
| ATOM | 2775 | N | ILE | 453 | 85.547 | 68.766 | 95.820 | 1.00 | 16.24 |
| ATOM | 2776 | CA | ILE | 453 | 85.604 | 68.843 | 94.369 | 1.00 | 14.58 |
| ATOM | 2777 | CB | ILE | 453 | 85.722 | 70.307 | 93.884 | 1.00 | 12.83 |
| ATOM | 2778 | CG2 | ILE | 453 | 86.387 | 70.376 | 92.525 | 1.00 | 10.62 |
| ATOM | 2779 | CG1 | ILE | 453 | 84.349 | 70.958 | 93.807 | 1.00 | 14.75 |
| ATOM | 2780 | CD1 | ILE | 453 | 83.437 | 70.321 | 92.791 | 1.00 | 14.86 |
| ATOM | 2781 | C | ILE | 453 | 86.880 | 68.118 | 93.990 | 1.00 | 16.06 |
| ATOM | 2782 | O | ILE | 453 | 86.919 | 67.393 | 93.005 | 1.00 | 17.00 |
| ATOM | 2783 | N | HIS | 454 | 87.900 | 68.257 | 94.831 | 1.00 | 17.66 |
| ATOM | 2784 | CA | HIS | 454 | 89.191 | 67.626 | 94.575 | 1.00 | 20.84 |
| ATOM | 2785 | CB | HIS | 454 | 90.263 | 68.161 | 95.534 | 1.00 | 21.96 |
| ATOM | 2786 | CG | HIS | 454 | 90.627 | 69.594 | 95.290 | 1.00 | 25.98 |
| ATOM | 2787 | CD2 | HIS | 454 | 90.299 | 70.725 | 95.961 | 1.00 | 27.87 |
| ATOM | 2788 | ND1 | HIS | 454 | 91.410 | 69.996 | 94.228 | 1.00 | 28.38 |
| ATOM | 2789 | CE1 | HIS | 454 | 91.551 | 71.312 | 94.254 | 1.00 | 27.52 |
| ATOM | 2790 | NE2 | HIS | 454 | 90.885 | 71.777 | 95.297 | 1.00 | 28.90 |
| ATOM | 2791 | C | HIS | 454 | 89.160 | 66.096 | 94.564 | 1.00 | 20.36 |
| ATOM | 2792 | O | HIS | 454 | 90.147 | 65.449 | 94.206 | 1.00 | 19.89 |
| ATOM | 2793 | N | LYS | 455 | 88.032 | 65.516 | 94.950 | 1.00 | 19.40 |
| ATOM | 2794 | CA | LYS | 455 | 87.909 | 64.070 | 94.926 | 1.00 | 21.55 |
| ATOM | 2795 | CB | LYS | 455 | 87.551 | 63.520 | 96.308 | 1.00 | 23.22 |
| ATOM | 2796 | CG | LYS | 455 | 88.653 | 63.668 | 97.367 | 1.00 | 29.03 |
| ATOM | 2797 | CD | LYS | 455 | 89.945 | 62.933 | 96.994 | 1.00 | 37.13 |
| ATOM | 2798 | CE | LYS | 455 | 89.757 | 61.421 | 96.873 | 1.00 | 45.38 |
| ATOM | 2799 | NZ | LYS | 455 | 89.383 | 60.783 | 98.171 | 1.00 | 51.78 |
| ATOM | 2800 | C | LYS | 455 | 86.819 | 63.728 | 93.920 | 1.00 | 22.09 |
| ATOM | 2801 | O | LYS | 455 | 86.992 | 62.862 | 93.051 | 1.00 | 21.63 |
| ATOM | 2802 | N | PHE | 456 | 85.733 | 64.489 | 93.980 | 1.00 | 21.70 |
| ATOM | 2803 | CA | PHE | 456 | 84.599 | 64.272 | 93.101 | 1.00 | 20.89 |
| ATOM | 2804 | CB | PHE | 456 | 83.416 | 65.142 | 93.523 | 1.00 | 18.96 |
| ATOM | 2805 | CG | PHE | 456 | 82.130 | 64.771 | 92.858 | 1.00 | 16.22 |
| ATOM | 2806 | CD1 | PHE | 456 | 81.401 | 63.671 | 93.296 | 1.00 | 18.25 |
| ATOM | 2807 | CD2 | PHE | 456 | 81.641 | 65.521 | 91.796 | 1.00 | 15.63 |
| ATOM | 2808 | CE1 | PHE | 456 | 80.197 | 63.319 | 92.684 | 1.00 | 19.07 |
| ATOM | 2809 | CE2 | PHE | 456 | 80.446 | 65.184 | 91.177 | 1.00 | 17.34 |
| ATOM | 2810 | CZ | PHE | 456 | 79.719 | 64.078 | 91.622 | 1.00 | 20.36 |
| ATOM | 2811 | C | PHE | 456 | 84.918 | 64.487 | 91.632 | 1.00 | 19.73 |
| ATOM | 2812 | O | PHE | 456 | 84.580 | 63.636 | 90.805 | 1.00 | 22.69 |
| ATOM | 2813 | N | VAL | 457 | 85.563 | 65.601 | 91.296 | 1.00 | 17.27 |
| ATOM | 2814 | CA | VAL | 457 | 85.891 | 65.868 | 89.899 | 1.00 | 17.66 |
| ATOM | 2815 | CB | VAL | 457 | 86.424 | 67.307 | 89.664 | 1.00 | 18.94 |
| ATOM | 2816 | CG1 | VAL | 457 | 86.985 | 67.457 | 88.240 | 1.00 | 16.68 |
| ATOM | 2817 | CG2 | VAL | 457 | 85.281 | 68.295 | 89.853 | 1.00 | 16.75 |
| ATOM | 2818 | C | VAL | 457 | 86.799 | 64.800 | 89.298 | 1.00 | 16.95 |
| ATOM | 2819 | O | VAL | 457 | 86.588 | 64.383 | 88.158 | 1.00 | 18.92 |
| ATOM | 2820 | N | PRO | 458 | 87.833 | 64.358 | 90.035 | 1.00 | 16.13 |
| ATOM | 2821 | CD | PRO | 458 | 88.457 | 64.985 | 91.214 | 1.00 | 15.29 |
| ATOM | 2822 | CA | PRO | 458 | 88.710 | 63.313 | 89.489 | 1.00 | 15.15 |
| ATOM | 2823 | CB | PRO | 458 | 89.669 | 63.058 | 90.638 | 1.00 | 12.23 |
| ATOM | 2824 | CG | PRO | 458 | 89.866 | 64.440 | 91.171 | 1.00 | 13.07 |
| ATOM | 2825 | C | PRO | 458 | 87.881 | 62.074 | 89.176 | 1.00 | 15.35 |
| ATOM | 2826 | O | PRO | 458 | 88.106 | 61.392 | 88.168 | 1.00 | 15.34 |
| ATOM | 2827 | N | TYR | 459 | 86.901 | 61.809 | 90.034 | 1.00 | 17.57 |
| ATOM | 2828 | CA | TYR | 459 | 86.008 | 60.675 | 89.856 | 1.00 | 18.14 |
| ATOM | 2829 | CB | TYR | 459 | 85.077 | 60.521 | 91.059 | 1.00 | 17.11 |

FIG. 1A-49

| ATOM | 2830 | CG | TYR | 459 | 83.808 | 59.775 | 90.725 | 1.00 | 21.11 |
|------|------|-----|-----|-----|--------|--------|--------|------|-------|
| ATOM | 2831 | CD1 | TYR | 459 | 83.826 | 58.407 | 90.420 | 1.00 | 18.93 |
| ATOM | 2832 | CE1 | TYR | 459 | 82.671 | 57.751 | 90.004 | 1.00 | 14.76 |
| ATOM | 2833 | CD2 | TYR | 459 | 82.597 | 60.457 | 90.625 | 1.00 | 20.85 |
| ATOM | 2834 | CE2 | TYR | 459 | 81.446 | 59.815 | 90.213 | 1.00 | 15.55 |
| ATOM | 2835 | CZ | TYR | 459 | 81.488 | 58.470 | 89.903 | 1.00 | 13.80 |
| ATOM | 2836 | OH | TYR | 459 | 80.340 | 57.885 | 89.442 | 1.00 | 13.75 |
| ATOM | 2837 | C | TYR | 459 | 85.203 | 60.830 | 88.559 | 1.00 | 20.12 |
| ATOM | 2838 | O | TYR | 459 | 85.135 | 59.896 | 87.758 | 1.00 | 22.54 |
| ATOM | 2839 | N | LEU | 460 | 84.590 | 61.996 | 88.351 | 1.00 | 18.20 |
| ATOM | 2840 | CA | LEU | 460 | 83.824 | 62.232 | 87.126 | 1.00 | 15.92 |
| ATOM | 2841 | CB | LEU | 460 | 83.214 | 63.638 | 87.115 | 1.00 | 15.26 |
| ATOM | 2842 | CG | LEU | 460 | 82.226 | 63.958 | 88.233 | 1.00 | 14.02 |
| ATOM | 2843 | CD1 | LEU | 460 | 81.818 | 65.404 | 88.150 | 1.00 | 12.72 |
| ATOM | 2844 | CD2 | LEU | 460 | 81.020 | 63.058 | 88.143 | 1.00 | 12.27 |
| ATOM | 2845 | C | LEU | 460 | 84.735 | 62.052 | 85.916 | 1.00 | 15.36 |
| ATOM | 2846 | O | LEU | 460 | 84.326 | 61.488 | 84.902 | 1.00 | 15.87 |
| ATOM | 2847 | N | ILE | 461 | 85.970 | 62.542 | 86.027 | 1.00 | 16.13 |
| ATOM | 2848 | CA | ILE | 461 | 86.968 | 62.428 | 84.952 | 1.00 | 15.25 |
| ATOM | 2849 | CB | ILE | 461 | 88.288 | 63.144 | 85.336 | 1.00 | 14.67 |
| ATOM | 2850 | CG2 | ILE | 461 | 89.444 | 62.676 | 84.463 | 1.00 | 9.67 |
| ATOM | 2851 | CG1 | ILE | 461 | 88.103 | 64.667 | 85.247 | 1.00 | 17.36 |
| ATOM | 2852 | CD1 | ILE | 461 | 89.216 | 65.455 | 85.902 | 1.00 | 16.02 |
| ATOM | 2853 | C | ILE | 461 | 87.233 | 60.951 | 84.640 | 1.00 | 15.38 |
| ATOM | 2854 | O | ILE | 461 | 87.260 | 60.551 | 83.476 | 1.00 | 14.40 |
| ATOM | 2855 | N | ALA | 462 | 87.395 | 60.143 | 85.683 | 1.00 | 14.36 |
| ATOM | 2856 | CA | ALA | 462 | 87.622 | 58.722 | 85.500 | 1.00 | 15.50 |
| ATOM | 2857 | CB | ALA | 462 | 87.932 | 58.070 | 86.830 | 1.00 | 14.39 |
| ATOM | 2858 | C | ALA | 462 | 86.379 | 58.093 | 84.871 | 1.00 | 17.54 |
| ATOM | 2859 | O | ALA | 462 | 86.473 | 57.338 | 83.902 | 1.00 | 19.03 |
| ATOM | 2860 | N | GLY | 463 | 85.211 | 58.440 | 85.399 | 1.00 | 18.74 |
| ATOM | 2861 | CA | GLY | 463 | 83.968 | 57.899 | 84.884 | 1.00 | 18.66 |
| ATOM | 2862 | C | GLY | 463 | 83.795 | 58.158 | 83.403 | 1.00 | 19.50 |
| ATOM | 2863 | O | GLY | 463 | 83.533 | 57.224 | 82.638 | 1.00 | 20.45 |
| ATOM | 2864 | N | ILE | 464 | 83.992 | 59.410 | 82.992 | 1.00 | 18.46 |
| ATOM | 2865 | CA | ILE | 464 | 83.845 | 59.797 | 81.594 | 1.00 | 18.81 |
| ATOM | 2866 | CB | ILE | 464 | 84.106 | 61.298 | 81.371 | 1.00 | 16.10 |
| ATOM | 2867 | CG2 | ILE | 464 | 83.833 | 61.663 | 79.915 | 1.00 | 13.53 |
| ATOM | 2868 | CG1 | ILE | 464 | 83.196 | 62.129 | 82.270 | 1.00 | 12.34 |
| ATOM | 2869 | CD1 | ILE | 464 | 83.384 | 63.605 | 82.091 | 1.00 | 13.25 |
| ATOM | 2870 | C | ILE | 464 | 84.791 | 59.007 | 80.703 | 1.00 | 21.38 |
| ATOM | 2871 | O | ILE | 464 | 84.399 | 58.551 | 79.622 | 1.00 | 22.86 |
| ATOM | 2872 | N | GLN | 465 | 86.024 | 58.826 | 81.177 | 1.00 | 20.93 |
| ATOM | 2873 | CA | GLN | 465 | 87.050 | 58.085 | 80.443 | 1.00 | 19.17 |
| ATOM | 2874 | CB | GLN | 465 | 88.360 | 58.086 | 81.216 | 1.00 | 16.09 |
| ATOM | 2875 | CG | GLN | 465 | 89.063 | 59.411 | 81.190 | 1.00 | 13.01 |
| ATOM | 2876 | CD | GLN | 465 | 90.394 | 59.341 | 81.867 | 1.00 | 12.51 |
| ATOM | 2877 | OE1 | GLN | 465 | 90.513 | 58.832 | 82.983 | 1.00 | 14.37 |
| ATOM | 2878 | NE2 | GLN | 465 | 91.418 | 59.829 | 81.193 | 1.00 | 16.53 |
| ATOM | 2879 | C | GLN | 465 | 86.659 | 56.650 | 80.132 | 1.00 | 20.16 |
| ATOM | 2880 | O | GLN | 465 | 86.902 | 56.159 | 79.027 | 1.00 | 22.29 |
| ATOM | 2881 | N | HIS | 466 | 86.084 | 55.964 | 81.113 | 1.00 | 20.52 |
| ATOM | 2882 | CA | HIS | 466 | 85.658 | 54.586 | 80.911 | 1.00 | 21.13 |
| ATOM | 2883 | CB | HIS | 466 | 85.157 | 53.979 | 82.218 | 1.00 | 24.96 |
| ATOM | 2884 | CG | HIS | 466 | 86.235 | 53.772 | 83.235 | 1.00 | 31.10 |
| ATOM | 2885 | CD2 | HIS | 466 | 86.820 | 54.632 | 84.100 | 1.00 | 30.04 |
| ATOM | 2886 | ND1 | HIS | 466 | 86.847 | 52.554 | 83.432 | 1.00 | 36.54 |
| ATOM | 2887 | CE1 | HIS | 466 | 87.763 | 52.673 | 84.374 | 1.00 | 37.26 |
| ATOM | 2888 | NE2 | HIS | 466 | 87.768 | 53.924 | 84.795 | 1.00 | 34.17 |

FIG. 1A-50

| ATOM | 2889 | C | HIS | 466 | 84.565 | 54.536 | 79.846 | 1.00 | 21.83 |
| --- | --- | --- | --- | --- | --- | --- | --- | --- | --- |
| ATOM | 2890 | O | HIS | 466 | 84.597 | 53.688 | 78.955 | 1.00 | 22.78 |
| ATOM | 2891 | N | SER | 467 | 83.623 | 55.475 | 79.913 | 1.00 | 21.38 |
| ATOM | 2892 | CA | SER | 467 | 82.541 | 55.528 | 78.939 | 1.00 | 18.96 |
| ATOM | 2893 | CB | SER | 467 | 81.607 | 56.692 | 79.242 | 1.00 | 19.31 |
| ATOM | 2894 | OG | SER | 467 | 80.530 | 56.712 | 78.336 | 1.00 | 19.95 |
| ATOM | 2895 | C | SER | 467 | 83.124 | 55.653 | 77.539 | 1.00 | 17.24 |
| ATOM | 2896 | O | SER | 467 | 82.725 | 54.928 | 76.639 | 1.00 | 20.25 |
| ATOM | 2897 | N | CYS | 468 | 84.087 | 56.553 | 77.361 | 1.00 | 17.11 |
| ATOM | 2898 | CA | CYS | 468 | 84.738 | 56.727 | 76.067 | 1.00 | 15.35 |
| ATOM | 2899 | CB | CYS | 468 | 85.823 | 57.810 | 76.120 | 1.00 | 15.72 |
| ATOM | 2900 | SG | CYS | 468 | 85.235 | 59.525 | 75.957 | 1.00 | 15.92 |
| ATOM | 2901 | C | CYS | 468 | 85.366 | 55.413 | 75.649 | 1.00 | 15.52 |
| ATOM | 2902 | O | CYS | 468 | 85.356 | 55.077 | 74.471 | 1.00 | 16.61 |
| ATOM | 2903 | N | GLN | 469 | 85.894 | 54.656 | 76.609 | 1.00 | 14.54 |
| ATOM | 2904 | CA | GLN | 469 | 86.505 | 53.376 | 76.285 | 1.00 | 14.20 |
| ATOM | 2905 | CB | GLN | 469 | 87.231 | 52.779 | 77.480 | 1.00 | 12.53 |
| ATOM | 2906 | CG | GLN | 469 | 87.852 | 51.442 | 77.130 | 1.00 | 10.20 |
| ATOM | 2907 | CD | GLN | 469 | 88.499 | 50.763 | 78.303 | 1.00 | 10.73 |
| ATOM | 2908 | OE1 | GLN | 469 | 87.958 | 50.756 | 79.409 | 1.00 | 11.90 |
| ATOM | 2909 | NE2 | GLN | 469 | 89.665 | 50.171 | 78.071 | 1.00 | 11.04 |
| ATOM | 2910 | C | GLN | 469 | 85.492 | 52.364 | 75.766 | 1.00 | 15.39 |
| ATOM | 2911 | O | GLN | 469 | 85.708 | 51.734 | 74.736 | 1.00 | 17.75 |
| ATOM | 2912 | N | ASP | 470 | 84.402 | 52.180 | 76.496 | 1.00 | 14.75 |
| ATOM | 2913 | CA | ASP | 470 | 83.384 | 51.240 | 76.078 | 1.00 | 14.71 |
| ATOM | 2914 | CB | ASP | 470 | 82.213 | 51.243 | 77.059 | 1.00 | 14.31 |
| ATOM | 2915 | CG | ASP | 470 | 82.524 | 50.507 | 78.352 | 1.00 | 16.63 |
| ATOM | 2916 | OD1 | ASP | 470 | 83.543 | 49.784 | 78.426 | 1.00 | 13.27 |
| ATOM | 2917 | OD2 | ASP | 470 | 81.720 | 50.650 | 79.299 | 1.00 | 17.13 |
| ATOM | 2918 | C | ASP | 470 | 82.890 | 51.580 | 74.679 | 1.00 | 15.71 |
| ATOM | 2919 | O | ASP | 470 | 82.766 | 50.701 | 73.826 | 1.00 | 15.68 |
| ATOM | 2920 | N | ILE | 471 | 82.656 | 52.864 | 74.427 | 1.00 | 15.09 |
| ATOM | 2921 | CA | ILE | 471 | 82.164 | 53.276 | 73.121 | 1.00 | 17.16 |
| ATOM | 2922 | CB | ILE | 471 | 81.410 | 54.644 | 73.178 | 1.00 | 15.42 |
| ATOM | 2923 | CG2 | ILE | 471 | 80.441 | 54.662 | 74.361 | 1.00 | 12.68 |
| ATOM | 2924 | CG1 | ILE | 471 | 82.379 | 55.815 | 73.305 | 1.00 | 16.88 |
| ATOM | 2925 | CD1 | ILE | 471 | 81.675 | 57.153 | 73.500 | 1.00 | 19.09 |
| ATOM | 2926 | C | ILE | 471 | 83.245 | 53.261 | 72.033 | 1.00 | 18.70 |
| ATOM | 2927 | O | ILE | 471 | 82.945 | 53.462 | 70.855 | 1.00 | 21.58 |
| ATOM | 2928 | N | GLY | 472 | 84.488 | 52.986 | 72.429 | 1.00 | 18.31 |
| ATOM | 2929 | CA | GLY | 472 | 85.594 | 52.915 | 71.484 | 1.00 | 17.02 |
| ATOM | 2930 | C | GLY | 472 | 86.170 | 54.225 | 70.983 | 1.00 | 17.61 |
| ATOM | 2931 | O | GLY | 472 | 86.616 | 54.308 | 69.838 | 1.00 | 19.06 |
| ATOM | 2932 | N | ALA | 473 | 86.203 | 55.236 | 71.846 | 1.00 | 18.13 |
| ATOM | 2933 | CA | ALA | 473 | 86.735 | 56.552 | 71.490 | 1.00 | 16.93 |
| ATOM | 2934 | CB | ALA | 473 | 85.629 | 57.580 | 71.524 | 1.00 | 15.29 |
| ATOM | 2935 | C | ALA | 473 | 87.870 | 56.968 | 72.428 | 1.00 | 17.85 |
| ATOM | 2936 | O | ALA | 473 | 87.718 | 56.945 | 73.651 | 1.00 | 19.09 |
| ATOM | 2937 | N | LYS | 474 | 89.010 | 57.325 | 71.847 | 1.00 | 16.96 |
| ATOM | 2938 | CA | LYS | 474 | 90.182 | 57.748 | 72.611 | 1.00 | 17.79 |
| ATOM | 2939 | CB | LYS | 474 | 91.462 | 57.563 | 71.789 | 1.00 | 21.65 |
| ATOM | 2940 | CG | LYS | 474 | 91.817 | 56.137 | 71.397 | 1.00 | 31.55 |
| ATOM | 2941 | CD | LYS | 474 | 93.090 | 56.130 | 70.525 | 1.00 | 40.40 |
| ATOM | 2942 | CE | LYS | 474 | 93.447 | 54.741 | 69.987 | 1.00 | 44.48 |
| ATOM | 2943 | NZ | LYS | 474 | 93.906 | 53.804 | 71.052 | 1.00 | 47.47 |
| ATOM | 2944 | C | LYS | 474 | 90.121 | 59.202 | 73.065 | 1.00 | 15.79 |
| ATOM | 2945 | O | LYS | 474 | 90.995 | 59.643 | 73.801 | 1.00 | 15.96 |
| ATOM | 2946 | N | SER | 475 | 89.118 | 59.952 | 72.614 | 1.00 | 14.00 |
| ATOM | 2947 | CA | SER | 475 | 88.987 | 61.356 | 72.991 | 1.00 | 13.63 |

FIG. 1A-51

| ATOM | 2948 | CB | SER | 475 | 89.987 | 62.207 | 72.213 | 1.00 | 12.89 |
|---|---|---|---|---|---|---|---|---|---|
| ATOM | 2949 | OG | SER | 475 | 89.804 | 62.056 | 70.815 | 1.00 | 11.85 |
| ATOM | 2950 | C | SER | 475 | 87.590 | 61.892 | 72.727 | 1.00 | 14.26 |
| ATOM | 2951 | O | SER | 475 | 86.876 | 61.379 | 71.867 | 1.00 | 15.62 |
| ATOM | 2952 | N | LEU | 476 | 87.222 | 62.960 | 73.429 | 1.00 | 15.53 |
| ATOM | 2953 | CA | LEU | 476 | 85.903 | 63.572 | 73.258 | 1.00 | 16.54 |
| ATOM | 2954 | CB | LEU | 476 | 85.707 | 64.745 | 74.226 | 1.00 | 12.36 |
| ATOM | 2955 | CG | LEU | 476 | 85.603 | 64.398 | 75.718 | 1.00 | 11.06 |
| ATOM | 2956 | CD1 | LEU | 476 | 85.238 | 65.641 | 76.512 | 1.00 | 6.39 |
| ATOM | 2957 | CD2 | LEU | 476 | 84.557 | 63.318 | 75.932 | 1.00 | 9.52 |
| ATOM | 2958 | C | LEU | 476 | 85.736 | 64.036 | 71.823 | 1.00 | 17.37 |
| ATOM | 2959 | O | LEU | 476 | 84.658 | 63.935 | 71.238 | 1.00 | 19.71 |
| ATOM | 2960 | N | THR | 477 | 86.828 | 64.512 | 71.244 | 1.00 | 19.45 |
| ATOM | 2961 | CA | THR | 477 | 86.835 | 64.971 | 69.867 | 1.00 | 20.10 |
| ATOM | 2962 | CB | THR | 477 | 88.227 | 65.479 | 69.481 | 1.00 | 20.18 |
| ATOM | 2963 | OG1 | THR | 477 | 88.655 | 66.456 | 70.438 | 1.00 | 20.52 |
| ATOM | 2964 | CG2 | THR | 477 | 88.202 | 66.085 | 68.088 | 1.00 | 21.34 |
| ATOM | 2965 | C | THR | 477 | 86.473 | 63.801 | 68.956 | 1.00 | 20.32 |
| ATOM | 2966 | O | THR | 477 | 85.716 | 63.962 | 68.004 | 1.00 | 20.43 |
| ATOM | 2967 | N | GLN | 478 | 87.002 | 62.623 | 69.276 | 1.00 | 19.47 |
| ATOM | 2968 | CA | GLN | 478 | 86.735 | 61.430 | 68.485 | 1.00 | 19.30 |
| ATOM | 2969 | CB | GLN | 478 | 87.649 | 60.278 | 68.902 | 1.00 | 20.23 |
| ATOM | 2970 | CG | GLN | 478 | 87.681 | 59.135 | 67.896 | 1.00 | 21.67 |
| ATOM | 2971 | CD | GLN | 478 | 88.536 | 57.970 | 68.345 | 1.00 | 22.44 |
| ATOM | 2972 | OE1 | GLN | 478 | 89.243 | 58.049 | 69.343 | 1.00 | 22.21 |
| ATOM | 2973 | NE2 | GLN | 478 | 88.457 | 56.871 | 67.619 | 1.00 | 25.65 |
| ATOM | 2974 | C | GLN | 478 | 85.284 | 61.005 | 68.635 | 1.00 | 18.53 |
| ATOM | 2975 | O | GLN | 478 | 84.634 | 60.653 | 67.646 | 1.00 | 20.45 |
| ATOM | 2976 | N | VAL | 479 | 84.774 | 61.057 | 69.862 | 1.00 | 16.40 |
| ATOM | 2977 | CA | VAL | 479 | 83.390 | 60.676 | 70.122 | 1.00 | 15.90 |
| ATOM | 2978 | CB | VAL | 479 | 82.986 | 60.898 | 71.597 | 1.00 | 15.74 |
| ATOM | 2979 | CG1 | VAL | 479 | 81.591 | 60.352 | 71.849 | 1.00 | 13.93 |
| ATOM | 2980 | CG2 | VAL | 479 | 83.965 | 60.205 | 72.515 | 1.00 | 17.75 |
| ATOM | 2981 | C | VAL | 479 | 82.436 | 61.439 | 69.207 | 1.00 | 14.57 |
| ATOM | 2982 | O | VAL | 479 | 81.536 | 60.843 | 68.613 | 1.00 | 14.93 |
| ATOM | 2983 | N | ARG | 480 | 82.649 | 62.743 | 69.059 | 1.00 | 14.86 |
| ATOM | 2984 | CA | ARG | 480 | 81.788 | 63.537 | 68.180 | 1.00 | 14.83 |
| ATOM | 2985 | CB | ARG | 480 | 82.017 | 65.021 | 68.390 | 1.00 | 13.38 |
| ATOM | 2986 | CG | ARG | 480 | 81.403 | 65.513 | 69.661 | 1.00 | 13.20 |
| ATOM | 2987 | CD | ARG | 480 | 81.994 | 66.825 | 70.054 | 1.00 | 17.86 |
| ATOM | 2988 | NE | ARG | 480 | 82.330 | 66.787 | 71.468 | 1.00 | 27.35 |
| ATOM | 2989 | CZ | ARG | 480 | 83.501 | 67.159 | 71.967 | 1.00 | 31.62 |
| ATOM | 2990 | NH1 | ARG | 480 | 84.459 | 67.606 | 71.162 | 1.00 | 30.46 |
| ATOM | 2991 | NH2 | ARG | 480 | 83.718 | 67.065 | 73.273 | 1.00 | 35.55 |
| ATOM | 2992 | C | ARG | 480 | 81.925 | 63.179 | 66.706 | 1.00 | 13.45 |
| ATOM | 2993 | O | ARG | 480 | 80.930 | 63.121 | 65.986 | 1.00 | 13.13 |
| ATOM | 2994 | N | ALA | 481 | 83.145 | 62.909 | 66.260 | 1.00 | 13.31 |
| ATOM | 2995 | CA | ALA | 481 | 83.369 | 62.534 | 64.869 | 1.00 | 15.17 |
| ATOM | 2996 | CB | ALA | 481 | 84.844 | 62.311 | 64.610 | 1.00 | 16.26 |
| ATOM | 2997 | C | ALA | 481 | 82.590 | 61.256 | 64.590 | 1.00 | 16.54 |
| ATOM | 2998 | O | ALA | 481 | 81.852 | 61.177 | 63.605 | 1.00 | 18.67 |
| ATOM | 2999 | N | MET | 482 | 82.752 | 60.265 | 65.465 | 1.00 | 15.36 |
| ATOM | 3000 | CA | MET | 482 | 82.057 | 58.985 | 65.350 | 1.00 | 15.54 |
| ATOM | 3001 | CB | MET | 482 | 82.430 | 58.061 | 66.512 | 1.00 | 14.12 |
| ATOM | 3002 | CG | MET | 482 | 83.821 | 57.466 | 66.432 | 1.00 | 14.38 |
| ATOM | 3003 | SD | MET | 482 | 84.228 | 56.501 | 67.895 | 1.00 | 19.57 |
| ATOM | 3004 | CE | MET | 482 | 83.309 | 55.013 | 67.579 | 1.00 | 5.26 |
| ATOM | 3005 | C | MET | 482 | 80.544 | 59.175 | 65.333 | 1.00 | 17.70 |
| ATOM | 3006 | O | MET | 482 | 79.835 | 58.490 | 64.597 | 1.00 | 21.04 |

FIG. 1A-52

| ATOM | 3007 | N   | MET | 483 | 80.045 | 60.101 | 66.142 | 1.00 | 17.24 |
|------|------|-----|-----|-----|--------|--------|--------|------|-------|
| ATOM | 3008 | CA  | MET | 483 | 78.617 | 60.350 | 66.190 | 1.00 | 17.79 |
| ATOM | 3009 | CB  | MET | 483 | 78.254 | 61.118 | 67.467 | 1.00 | 20.77 |
| ATOM | 3010 | CG  | MET | 483 | 78.076 | 62.603 | 67.310 | 1.00 | 25.75 |
| ATOM | 3011 | SD  | MET | 483 | 76.433 | 62.978 | 66.748 | 1.00 | 27.11 |
| ATOM | 3012 | CE  | MET | 483 | 76.244 | 64.529 | 67.464 | 1.00 | 28.07 |
| ATOM | 3013 | C   | MET | 483 | 78.141 | 61.057 | 64.921 | 1.00 | 17.84 |
| ATOM | 3014 | O   | MET | 483 | 77.122 | 60.677 | 64.347 | 1.00 | 18.55 |
| ATOM | 3015 | N   | TYR | 484 | 78.907 | 62.034 | 64.442 | 1.00 | 18.23 |
| ATOM | 3016 | CA  | TYR | 484 | 78.553 | 62.769 | 63.221 | 1.00 | 18.32 |
| ATOM | 3017 | CB  | TYR | 484 | 79.324 | 64.084 | 63.136 | 1.00 | 13.90 |
| ATOM | 3018 | CG  | TYR | 484 | 78.821 | 65.154 | 64.062 | 1.00 | 12.61 |
| ATOM | 3019 | CD1 | TYR | 484 | 77.504 | 65.594 | 64.000 | 1.00 | 10.69 |
| ATOM | 3020 | CE1 | TYR | 484 | 77.044 | 66.605 | 64.854 | 1.00 | 11.90 |
| ATOM | 3021 | CD2 | TYR | 484 | 79.670 | 65.740 | 64.999 | 1.00 | 13.80 |
| ATOM | 3022 | CE2 | TYR | 484 | 79.228 | 66.741 | 65.851 | 1.00 | 10.55 |
| ATOM | 3023 | CZ  | TYR | 484 | 77.916 | 67.169 | 65.772 | 1.00 | 8.99  |
| ATOM | 3024 | OH  | TYR | 484 | 77.503 | 68.179 | 66.596 | 1.00 | 7.99  |
| ATOM | 3025 | C   | TYR | 484 | 78.767 | 61.985 | 61.923 | 1.00 | 19.94 |
| ATOM | 3026 | O   | TYR | 484 | 78.141 | 62.282 | 60.902 | 1.00 | 22.03 |
| ATOM | 3027 | N   | SER | 485 | 79.671 | 61.012 | 61.951 | 1.00 | 18.19 |
| ATOM | 3028 | CA  | SER | 485 | 79.947 | 60.192 | 60.775 | 1.00 | 18.62 |
| ATOM | 3029 | CB  | SER | 485 | 81.329 | 59.558 | 60.882 | 1.00 | 21.82 |
| ATOM | 3030 | OG  | SER | 485 | 81.401 | 58.715 | 62.023 | 1.00 | 27.56 |
| ATOM | 3031 | C   | SER | 485 | 78.927 | 59.074 | 60.659 | 1.00 | 18.30 |
| ATOM | 3032 | O   | SER | 485 | 78.865 | 58.388 | 59.639 | 1.00 | 19.04 |
| ATOM | 3033 | N   | GLY | 486 | 78.200 | 58.840 | 61.747 | 1.00 | 17.81 |
| ATOM | 3034 | CA  | GLY | 486 | 77.204 | 57.789 | 61.774 | 1.00 | 14.51 |
| ATOM | 3035 | C   | GLY | 486 | 77.740 | 56.579 | 62.510 | 1.00 | 13.19 |
| ATOM | 3036 | O   | GLY | 486 | 76.973 | 55.791 | 63.042 | 1.00 | 15.77 |
| ATOM | 3037 | N   | GLU | 487 | 79.061 | 56.462 | 62.589 | 1.00 | 11.32 |
| ATOM | 3038 | CA  | GLU | 487 | 79.705 | 55.335 | 63.251 | 1.00 | 10.96 |
| ATOM | 3039 | CB  | GLU | 487 | 81.213 | 55.561 | 63.311 | 1.00 | 12.35 |
| ATOM | 3040 | CG  | GLU | 487 | 81.980 | 54.438 | 63.999 | 1.00 | 11.26 |
| ATOM | 3041 | CD  | GLU | 487 | 83.483 | 54.632 | 63.984 | 1.00 | 12.67 |
| ATOM | 3042 | OE1 | GLU | 487 | 83.978 | 55.618 | 63.383 | 1.00 | 14.49 |
| ATOM | 3043 | OE2 | GLU | 487 | 84.177 | 53.785 | 64.574 | 1.00 | 15.10 |
| ATOM | 3044 | C   | GLU | 487 | 79.196 | 54.984 | 64.650 | 1.00 | 11.80 |
| ATOM | 3045 | O   | GLU | 487 | 79.117 | 53.806 | 65.002 | 1.00 | 10.47 |
| ATOM | 3046 | N   | LEU | 488 | 78.915 | 55.999 | 65.464 | 1.00 | 11.14 |
| ATOM | 3047 | CA  | LEU | 488 | 78.433 | 55.769 | 66.819 | 1.00 | 9.95  |
| ATOM | 3048 | CB  | LEU | 488 | 78.671 | 57.006 | 67.691 | 1.00 | 9.92  |
| ATOM | 3049 | CG  | LEU | 488 | 78.505 | 56.890 | 69.213 | 1.00 | 10.98 |
| ATOM | 3050 | CD1 | LEU | 488 | 79.352 | 55.770 | 69.767 | 1.00 | 13.79 |
| ATOM | 3051 | CD2 | LEU | 488 | 78.912 | 58.186 | 69.869 | 1.00 | 10.11 |
| ATOM | 3052 | C   | LEU | 488 | 76.951 | 55.448 | 66.731 | 1.00 | 12.30 |
| ATOM | 3053 | O   | LEU | 488 | 76.206 | 56.132 | 66.034 | 1.00 | 13.80 |
| ATOM | 3054 | N   | LYS | 489 | 76.529 | 54.385 | 67.407 | 1.00 | 12.49 |
| ATOM | 3055 | CA  | LYS | 489 | 75.133 | 53.983 | 67.385 | 1.00 | 9.72  |
| ATOM | 3056 | CB  | LYS | 489 | 75.013 | 52.534 | 66.927 | 1.00 | 7.65  |
| ATOM | 3057 | CG  | LYS | 489 | 75.553 | 52.273 | 65.542 | 1.00 | 6.90  |
| ATOM | 3058 | CD  | LYS | 489 | 74.793 | 53.048 | 64.486 | 1.00 | 8.74  |
| ATOM | 3059 | CE  | LYS | 489 | 75.343 | 52.755 | 63.105 | 1.00 | 8.65  |
| ATOM | 3060 | NZ  | LYS | 489 | 74.236 | 52.827 | 62.110 | 1.00 | 21.71 |
| ATOM | 3061 | C   | LYS | 489 | 74.480 | 54.143 | 68.744 | 1.00 | 10.66 |
| ATOM | 3062 | O   | LYS | 489 | 75.137 | 54.063 | 69.777 | 1.00 | 10.17 |
| ATOM | 3063 | N   | PHE | 490 | 73.169 | 54.332 | 68.730 | 1.00 | 11.10 |
| ATOM | 3064 | CA  | PHE | 490 | 72.391 | 54.500 | 69.941 | 1.00 | 10.52 |
| ATOM | 3065 | CB  | PHE | 490 | 71.884 | 55.947 | 70.063 | 1.00 | 10.19 |

FIG. 1A-53

| ATOM | 3066 | CG | PHE | 490 | 72.968 | 56.987 | 69.999 | 1.00 | 11.62 |
|---|---|---|---|---|---|---|---|---|---|
| ATOM | 3067 | CD1 | PHE | 490 | 73.510 | 57.375 | 68.784 | 1.00 | 10.59 |
| ATOM | 3068 | CD2 | PHE | 490 | 73.450 | 57.576 | 71.161 | 1.00 | 14.71 |
| ATOM | 3069 | CE1 | PHE | 490 | 74.513 | 58.332 | 68.728 | 1.00 | 10.01 |
| ATOM | 3070 | CE2 | PHE | 490 | 74.456 | 58.537 | 71.113 | 1.00 | 11.23 |
| ATOM | 3071 | CZ | PHE | 490 | 74.987 | 58.911 | 69.899 | 1.00 | 8.86 |
| ATOM | 3072 | C | PHE | 490 | 71.186 | 53.585 | 69.808 | 1.00 | 12.95 |
| ATOM | 3073 | O | PHE | 490 | 70.974 | 52.955 | 68.754 | 1.00 | 12.71 |
| ATOM | 3074 | N | GLU | 491 | 70.404 | 53.523 | 70.883 | 1.00 | 13.66 |
| ATOM | 3075 | CA | GLU | 491 | 69.174 | 52.742 | 70.943 | 1.00 | 14.24 |
| ATOM | 3076 | CB | GLU | 491 | 69.480 | 51.260 | 71.171 | 1.00 | 14.20 |
| ATOM | 3077 | CG | GLU | 491 | 68.245 | 50.402 | 71.226 | 1.00 | 11.29 |
| ATOM | 3078 | CD | GLU | 491 | 68.526 | 48.976 | 70.870 | 1.00 | 12.52 |
| ATOM | 3079 | OE1 | GLU | 491 | 68.577 | 48.667 | 69.662 | 1.00 | 14.42 |
| ATOM | 3080 | OE2 | GLU | 491 | 68.704 | 48.168 | 71.796 | 1.00 | 12.45 |
| ATOM | 3081 | C | GLU | 491 | 68.252 | 53.288 | 72.050 | 1.00 | 15.42 |
| ATOM | 3082 | O | GLU | 491 | 68.698 | 53.544 | 73.177 | 1.00 | 15.37 |
| ATOM | 3083 | N | LYS | 492 | 66.989 | 53.521 | 71.704 | 1.00 | 15.56 |
| ATOM | 3084 | CA | LYS | 492 | 66.013 | 54.038 | 72.658 | 1.00 | 16.28 |
| ATOM | 3085 | CB | LYS | 492 | 64.674 | 54.295 | 71.970 | 1.00 | 16.97 |
| ATOM | 3086 | CG | LYS | 492 | 64.727 | 55.368 | 70.906 | 1.00 | 22.04 |
| ATOM | 3087 | CD | LYS | 492 | 63.471 | 55.376 | 70.050 | 1.00 | 30.69 |
| ATOM | 3088 | CE | LYS | 492 | 62.229 | 55.692 | 70.876 | 1.00 | 40.54 |
| ATOM | 3089 | NZ | LYS | 492 | 60.981 | 55.643 | 70.060 | 1.00 | 44.71 |
| ATOM | 3090 | C | LYS | 492 | 65.797 | 53.034 | 73.772 | 1.00 | 16.62 |
| ATOM | 3091 | O | LYS | 492 | 65.940 | 51.834 | 73.562 | 1.00 | 18.55 |
| ATOM | 3092 | N | ARG | 493 | 65.445 | 53.534 | 74.950 | 1.00 | 17.23 |
| ATOM | 3093 | CA | ARG | 493 | 65.184 | 52.698 | 76.114 | 1.00 | 15.40 |
| ATOM | 3094 | CB | ARG | 493 | 66.068 | 53.110 | 77.292 | 1.00 | 12.64 |
| ATOM | 3095 | CG | ARG | 493 | 67.464 | 52.564 | 77.237 | 1.00 | 16.13 |
| ATOM | 3096 | CD | ARG | 493 | 68.060 | 52.481 | 78.616 | 1.00 | 14.05 |
| ATOM | 3097 | NE | ARG | 493 | 68.213 | 53.788 | 79.232 | 1.00 | 15.84 |
| ATOM | 3098 | CZ | ARG | 493 | 68.714 | 53.978 | 80.450 | 1.00 | 19.92 |
| ATOM | 3099 | NH1 | ARG | 493 | 69.108 | 52.940 | 81.179 | 1.00 | 17.89 |
| ATOM | 3100 | NH2 | ARG | 493 | 68.816 | 55.206 | 80.947 | 1.00 | 20.74 |
| ATOM | 3101 | C | ARG | 493 | 63.741 | 52.822 | 76.559 | 1.00 | 16.72 |
| ATOM | 3102 | O | ARG | 493 | 63.316 | 53.891 | 76.991 | 1.00 | 17.93 |
| ATOM | 3103 | N | THR | 494 | 62.972 | 51.747 | 76.444 | 1.00 | 17.78 |
| ATOM | 3104 | CA | THR | 494 | 61.593 | 51.785 | 76.911 | 1.00 | 18.02 |
| ATOM | 3105 | CB | THR | 494 | 60.873 | 50.472 | 76.627 | 1.00 | 16.97 |
| ATOM | 3106 | OG1 | THR | 494 | 61.699 | 49.381 | 77.047 | 1.00 | 19.57 |
| ATOM | 3107 | CG2 | THR | 494 | 60.573 | 50.333 | 75.155 | 1.00 | 17.62 |
| ATOM | 3108 | C | THR | 494 | 61.700 | 51.959 | 78.425 | 1.00 | 19.69 |
| ATOM | 3109 | O | THR | 494 | 62.782 | 51.780 | 78.998 | 1.00 | 22.59 |
| ATOM | 3110 | N | SER | 495 | 60.602 | 52.311 | 79.079 | 1.00 | 19.02 |
| ATOM | 3111 | CA | SER | 495 | 60.608 | 52.496 | 80.523 | 1.00 | 18.50 |
| ATOM | 3112 | CB | SER | 495 | 59.226 | 52.910 | 80.981 | 1.00 | 24.80 |
| ATOM | 3113 | OG | SER | 495 | 58.776 | 53.997 | 80.183 | 1.00 | 39.46 |
| ATOM | 3114 | C | SER | 495 | 61.072 | 51.239 | 81.254 | 1.00 | 18.35 |
| ATOM | 3115 | O | SER | 495 | 61.835 | 51.326 | 82.214 | 1.00 | 17.67 |
| ATOM | 3116 | N | SER | 496 | 60.631 | 50.071 | 80.784 | 1.00 | 17.30 |
| ATOM | 3117 | CA | SER | 496 | 61.042 | 48.802 | 81.378 | 1.00 | 16.26 |
| ATOM | 3118 | CB | SER | 496 | 60.331 | 47.633 | 80.697 | 1.00 | 15.19 |
| ATOM | 3119 | OG | SER | 496 | 58.931 | 47.811 | 80.695 | 1.00 | 20.72 |
| ATOM | 3120 | C | SER | 496 | 62.545 | 48.665 | 81.156 | 1.00 | 17.45 |
| ATOM | 3121 | O | SER | 496 | 63.272 | 48.164 | 82.023 | 1.00 | 17.49 |
| ATOM | 3122 | N | ALA | 497 | 62.998 | 49.116 | 79.987 | 1.00 | 16.53 |
| ATOM | 3123 | CA | ALA | 497 | 64.403 | 49.069 | 79.625 | 1.00 | 16.21 |
| ATOM | 3124 | CB | ALA | 497 | 64.582 | 49.440 | 78.172 | 1.00 | 15.16 |

FIG. 1A-54

| ATOM | 3125 | C | ALA | 497 | 65.211 | 50.000 | 80.522 | 1.00 | 17.84 |
| --- | --- | --- | --- | --- | --- | --- | --- | --- | --- |
| ATOM | 3126 | O | ALA | 497 | 66.365 | 49.712 | 80.842 | 1.00 | 19.41 |
| ATOM | 3127 | N | GLN | 498 | 64.603 | 51.109 | 80.938 | 1.00 | 18.51 |
| ATOM | 3128 | CA | GLN | 498 | 65.268 | 52.067 | 81.829 | 1.00 | 18.22 |
| ATOM | 3129 | CB | GLN | 498 | 64.520 | 53.391 | 81.838 | 1.00 | 14.72 |
| ATOM | 3130 | CG | GLN | 498 | 64.614 | 54.155 | 80.542 | 1.00 | 16.17 |
| ATOM | 3131 | CD | GLN | 498 | 63.737 | 55.389 | 80.552 | 1.00 | 21.61 |
| ATOM | 3132 | OE1 | GLN | 498 | 63.701 | 56.134 | 81.530 | 1.00 | 23.31 |
| ATOM | 3133 | NE2 | GLN | 498 | 63.000 | 55.597 | 79.471 | 1.00 | 25.52 |
| ATOM | 3134 | C | GLN | 498 | 65.319 | 51.510 | 83.248 | 1.00 | 19.49 |
| ATOM | 3135 | O | GLN | 498 | 66.288 | 51.728 | 83.973 | 1.00 | 21.42 |
| ATOM | 3136 | N | VAL | 499 | 64.258 | 50.802 | 83.633 | 1.00 | 19.64 |
| ATOM | 3137 | CA | VAL | 499 | 64.137 | 50.166 | 84.945 | 1.00 | 20.58 |
| ATOM | 3138 | CB | VAL | 499 | 62.712 | 49.567 | 85.124 | 1.00 | 24.21 |
| ATOM | 3139 | CG1 | VAL | 499 | 62.670 | 48.559 | 86.284 | 1.00 | 26.96 |
| ATOM | 3140 | CG2 | VAL | 499 | 61.714 | 50.682 | 85.364 | 1.00 | 23.58 |
| ATOM | 3141 | C | VAL | 499 | 65.166 | 49.042 | 85.060 | 1.00 | 20.51 |
| ATOM | 3142 | O | VAL | 499 | 65.775 | 48.828 | 86.117 | 1.00 | 17.74 |
| ATOM | 3143 | N | GLU | 500 | 65.318 | 48.310 | 83.960 | 1.00 | 22.30 |
| ATOM | 3144 | CA | GLU | 500 | 66.255 | 47.202 | 83.871 | 1.00 | 22.71 |
| ATOM | 3145 | CB | GLU | 500 | 66.028 | 46.436 | 82.574 | 1.00 | 17.71 |
| ATOM | 3146 | CG | GLU | 500 | 67.069 | 45.379 | 82.317 | 1.00 | 17.26 |
| ATOM | 3147 | CD | GLU | 500 | 66.915 | 44.749 | 80.966 | 1.00 | 21.30 |
| ATOM | 3148 | OE1 | GLU | 500 | 66.357 | 43.633 | 80.903 | 1.00 | 24.96 |
| ATOM | 3149 | OE2 | GLU | 500 | 67.346 | 45.365 | 79.965 | 1.00 | 21.01 |
| ATOM | 3150 | C | GLU | 500 | 67.692 | 47.709 | 83.913 | 1.00 | 25.21 |
| ATOM | 3151 | O | GLU | 500 | 68.579 | 47.027 | 84.432 | 1.00 | 27.22 |
| ATOM | 3152 | N | GLY | 501 | 67.912 | 48.879 | 83.316 | 1.00 | 24.95 |
| ATOM | 3153 | CA | GLY | 501 | 69.230 | 49.484 | 83.285 | 1.00 | 23.31 |
| ATOM | 3154 | C | GLY | 501 | 69.723 | 49.914 | 84.653 | 1.00 | 23.43 |
| ATOM | 3155 | O | GLY | 501 | 70.931 | 49.967 | 84.885 | 1.00 | 24.54 |
| ATOM | 3156 | N | GLY | 502 | 68.801 | 50.268 | 85.544 | 1.00 | 22.98 |
| ATOM | 3157 | CA | GLY | 502 | 69.185 | 50.676 | 86.886 | 1.00 | 21.16 |
| ATOM | 3158 | C | GLY | 502 | 69.157 | 49.489 | 87.833 | 1.00 | 20.14 |
| ATOM | 3159 | O | GLY | 502 | 68.977 | 48.347 | 87.404 | 1.00 | 19.33 |
| ATOM | 3160 | N | VAL | 503 | 69.330 | 49.747 | 89.123 | 1.00 | 18.98 |
| ATOM | 3161 | CA | VAL | 503 | 69.304 | 48.679 | 90.113 | 1.00 | 19.85 |
| ATOM | 3162 | CB | VAL | 503 | 69.848 | 49.145 | 91.468 | 1.00 | 15.03 |
| ATOM | 3163 | CG1 | VAL | 503 | 69.691 | 48.039 | 92.503 | 1.00 | 15.02 |
| ATOM | 3164 | CG2 | VAL | 503 | 71.291 | 49.559 | 91.329 | 1.00 | 12.67 |
| ATOM | 3165 | C | VAL | 503 | 67.876 | 48.185 | 90.316 | 1.00 | 24.02 |
| ATOM | 3166 | O | VAL | 503 | 66.956 | 48.976 | 90.545 | 1.00 | 25.36 |
| ATOM | 3167 | N | HIS | 504 | 67.697 | 46.870 | 90.252 | 1.00 | 26.21 |
| ATOM | 3168 | CA | HIS | 504 | 66.383 | 46.270 | 90.443 | 1.00 | 27.57 |
| ATOM | 3169 | CB | HIS | 504 | 65.643 | 46.117 | 89.102 | 1.00 | 23.86 |
| ATOM | 3170 | CG | HIS | 504 | 66.377 | 45.298 | 88.078 | 1.00 | 21.19 |
| ATOM | 3171 | CD2 | HIS | 504 | 67.136 | 45.667 | 87.021 | 1.00 | 19.48 |
| ATOM | 3172 | ND1 | HIS | 504 | 66.340 | 43.919 | 88.056 | 1.00 | 16.78 |
| ATOM | 3173 | CE1 | HIS | 504 | 67.044 | 43.478 | 87.029 | 1.00 | 11.24 |
| ATOM | 3174 | NE2 | HIS | 504 | 67.539 | 44.517 | 86.387 | 1.00 | 12.99 |
| ATOM | 3175 | C | HIS | 504 | 66.492 | 44.922 | 91.135 | 1.00 | 29.67 |
| ATOM | 3176 | O | HIS | 504 | 67.588 | 44.401 | 91.334 | 1.00 | 29.30 |
| ATOM | 3177 | N | SER | 505 | 65.347 | 44.407 | 91.567 | 1.00 | 31.87 |
| ATOM | 3178 | CA | SER | 505 | 65.255 | 43.100 | 92.201 | 1.00 | 34.64 |
| ATOM | 3179 | CB | SER | 505 | 65.572 | 42.008 | 91.169 | 1.00 | 36.20 |
| ATOM | 3180 | OG | SER | 505 | 64.746 | 42.151 | 90.016 | 1.00 | 38.33 |
| ATOM | 3181 | C | SER | 505 | 66.070 | 42.882 | 93.476 | 1.00 | 36.15 |
| ATOM | 3182 | O | SER | 505 | 66.369 | 41.735 | 93.837 | 1.00 | 38.12 |
| ATOM | 3183 | N | LEU | 506 | 66.411 | 43.960 | 94.172 | 1.00 | 35.02 |

FIG. 1A-55

| ATOM | 3184 | CA | LEU | 506 | 67.161 | 43.825 | 95.415 | 1.00 | 35.93 |
|---|---|---|---|---|---|---|---|---|---|
| ATOM | 3185 | CB | LEU | 506 | 68.354 | 44.779 | 95.454 | 1.00 | 33.98 |
| ATOM | 3186 | CG | LEU | 506 | 69.443 | 44.537 | 94.419 | 1.00 | 32.60 |
| ATOM | 3187 | CD1 | LEU | 506 | 70.627 | 45.416 | 94.745 | 1.00 | 31.60 |
| ATOM | 3188 | CD2 | LEU | 506 | 69.842 | 43.068 | 94.416 | 1.00 | 30.24 |
| ATOM | 3189 | C | LEU | 506 | 66.245 | 44.112 | 96.591 | 1.00 | 37.40 |
| ATOM | 3190 | O | LEU | 506 | 65.313 | 44.911 | 96.478 | 1.00 | 39.36 |
| ATOM | 3191 | N | HIS | 507 | 66.475 | 43.433 | 97.707 | 1.00 | 37.50 |
| ATOM | 3192 | CA | HIS | 507 | 65.666 | 43.667 | 98.888 | 1.00 | 36.26 |
| ATOM | 3193 | CB | HIS | 507 | 65.771 | 42.502 | 99.863 | 1.00 | 36.36 |
| ATOM | 3194 | CG | HIS | 507 | 64.968 | 42.689 | 101.107 | 1.00 | 39.58 |
| ATOM | 3195 | CD2 | HIS | 507 | 63.726 | 42.268 | 101.439 | 1.00 | 40.11 |
| ATOM | 3196 | ND1 | HIS | 507 | 65.426 | 43.420 | 102.184 | 1.00 | 41.90 |
| ATOM | 3197 | CE1 | HIS | 507 | 64.501 | 43.442 | 103.127 | 1.00 | 42.56 |
| ATOM | 3198 | NE2 | HIS | 507 | 63.458 | 42.753 | 102.700 | 1.00 | 44.44 |
| ATOM | 3199 | C | HIS | 507 | 66.169 | 44.951 | 99.535 | 1.00 | 36.56 |
| ATOM | 3200 | O | HIS | 507 | 65.407 | 45.670 | 100.173 | 1.00 | 38.46 |
| ATOM | 3201 | N | SER | 508 | 67.458 | 45.227 | 99.372 | 1.00 | 36.54 |
| ATOM | 3202 | CA | SER | 508 | 68.083 | 46.427 | 99.917 | 1.00 | 36.63 |
| ATOM | 3203 | CB | SER | 508 | 68.229 | 46.328 | 101.438 | 1.00 | 37.89 |
| ATOM | 3204 | OG | SER | 508 | 69.053 | 45.232 | 101.811 | 1.00 | 39.59 |
| ATOM | 3205 | C | SER | 508 | 69.458 | 46.530 | 99.296 | 1.00 | 36.63 |
| ATOM | 3206 | O | SER | 508 | 69.994 | 45.527 | 98.824 | 1.00 | 36.76 |
| ATOM | 3207 | N | TYR | 509 | 70.012 | 47.738 | 99.274 | 1.00 | 37.19 |
| ATOM | 3208 | CA | TYR | 509 | 71.346 | 47.968 | 98.727 | 1.00 | 39.23 |
| ATOM | 3209 | CB | TYR | 509 | 71.360 | 47.768 | 97.208 | 1.00 | 33.64 |
| ATOM | 3210 | CG | TYR | 509 | 70.764 | 48.911 | 96.415 | 1.00 | 29.36 |
| ATOM | 3211 | CD1 | TYR | 509 | 71.578 | 49.902 | 95.870 | 1.00 | 27.11 |
| ATOM | 3212 | CE1 | TYR | 509 | 71.046 | 50.942 | 95.118 | 1.00 | 22.91 |
| ATOM | 3213 | CD2 | TYR | 509 | 69.392 | 48.990 | 96.189 | 1.00 | 26.29 |
| ATOM | 3214 | CE2 | TYR | 509 | 68.849 | 50.027 | 95.437 | 1.00 | 25.07 |
| ATOM | 3215 | CZ | TYR | 509 | 69.683 | 50.999 | 94.902 | 1.00 | 23.09 |
| ATOM | 3216 | OH | TYR | 509 | 69.155 | 52.024 | 94.146 | 1.00 | 24.38 |
| ATOM | 3217 | C | TYR | 509 | 71.835 | 49.374 | 99.048 | 1.00 | 42.36 |
| ATOM | 3218 | O | TYR | 509 | 71.051 | 50.252 | 99.404 | 1.00 | 43.20 |
| ATOM | 3219 | N | GLU | 510 | 73.138 | 49.574 | 98.930 | 1.00 | 46.38 |
| ATOM | 3220 | CA | GLU | 510 | 73.746 | 50.873 | 99.159 | 1.00 | 50.81 |
| ATOM | 3221 | CB | GLU | 510 | 74.723 | 50.813 | 100.334 | 1.00 | 53.83 |
| ATOM | 3222 | CG | GLU | 510 | 75.845 | 49.801 | 100.161 | 1.00 | 63.78 |
| ATOM | 3223 | CD | GLU | 510 | 76.718 | 49.675 | 101.394 | 1.00 | 71.79 |
| ATOM | 3224 | OE1 | GLU | 510 | 76.330 | 48.919 | 102.314 | 1.00 | 75.41 |
| ATOM | 3225 | OE2 | GLU | 510 | 77.788 | 50.325 | 101.441 | 1.00 | 73.41 |
| ATOM | 3226 | C | GLU | 510 | 74.482 | 51.166 | 97.857 | 1.00 | 52.99 |
| ATOM | 3227 | O | GLU | 510 | 74.884 | 50.238 | 97.148 | 1.00 | 53.50 |
| ATOM | 3228 | N | LYS | 511 | 74.621 | 52.439 | 97.509 | 1.00 | 54.97 |
| ATOM | 3229 | CA | LYS | 511 | 75.312 | 52.795 | 96.280 | 1.00 | 55.10 |
| ATOM | 3230 | CB | LYS | 511 | 74.354 | 53.494 | 95.312 | 1.00 | 56.27 |
| ATOM | 3231 | CG | LYS | 511 | 74.918 | 53.698 | 93.908 | 1.00 | 57.13 |
| ATOM | 3232 | CD | LYS | 511 | 73.909 | 54.392 | 92.994 | 1.00 | 58.18 |
| ATOM | 3233 | CE | LYS | 511 | 72.631 | 53.576 | 92.849 | 1.00 | 59.33 |
| ATOM | 3234 | NZ | LYS | 511 | 71.639 | 54.229 | 91.955 | 1.00 | 58.37 |
| ATOM | 3235 | C | LYS | 511 | 76.507 | 53.688 | 96.571 | 1.00 | 54.99 |
| ATOM | 3236 | O | LYS | 511 | 76.424 | 54.609 | 97.382 | 1.00 | 54.53 |
| ATOM | 3237 | N | ARG | 512 | 77.628 | 53.362 | 95.942 | 1.00 | 56.46 |
| ATOM | 3238 | CA | ARG | 512 | 78.868 | 54.115 | 96.081 | 1.00 | 57.97 |
| ATOM | 3239 | CB | ARG | 512 | 79.803 | 53.447 | 97.085 | 1.00 | 58.04 |
| ATOM | 3240 | CG | ARG | 512 | 79.468 | 53.766 | 98.529 | 1.00 | 62.49 |
| ATOM | 3241 | CD | ARG | 512 | 80.493 | 53.185 | 99.482 | 1.00 | 64.62 |
| ATOM | 3242 | NE | ARG | 512 | 80.419 | 51.727 | 99.537 | 1.00 | 63.61 |

FIG. 1A-56

| ATOM | 3243 | CZ | ARG | 512 | 81.447 | 50.933 | 99.823 | 1.00 | 61.12 |
|------|------|-----|-----|-----|--------|--------|--------|------|-------|
| ATOM | 3244 | NH1 | ARG | 512 | 82.644 | 51.445 | 100.083 | 1.00 | 56.55 |
| ATOM | 3245 | NH2 | ARG | 512 | 81.269 | 49.621 | 99.853 | 1.00 | 61.94 |
| ATOM | 3246 | C | ARG | 512 | 79.500 | 54.115 | 94.702 | 1.00 | 58.54 |
| ATOM | 3247 | O | ARG | 512 | 79.178 | 53.252 | 93.884 | 1.00 | 59.96 |
| ATOM | 3248 | N | LEU | 513 | 80.391 | 55.065 | 94.434 | 1.00 | 57.83 |
| ATOM | 3249 | CA | LEU | 513 | 81.016 | 55.124 | 93.123 | 1.00 | 57.56 |
| ATOM | 3250 | CB | LEU | 513 | 80.303 | 56.148 | 92.257 | 1.00 | 61.92 |
| ATOM | 3251 | CG | LEU | 513 | 79.439 | 55.464 | 91.197 | 1.00 | 68.38 |
| ATOM | 3252 | CD1 | LEU | 513 | 78.247 | 56.348 | 90.818 | 1.00 | 71.78 |
| ATOM | 3253 | CD2 | LEU | 513 | 80.308 | 55.085 | 89.991 | 1.00 | 65.83 |
| ATOM | 3254 | C | LEU | 513 | 82.510 | 55.358 | 93.107 | 1.00 | 55.65 |
| ATOM | 3255 | O | LEU | 513 | 83.188 | 54.979 | 92.152 | 1.00 | 55.17 |
| ATOM | 3256 | N | PHE | 514 | 83.012 | 55.993 | 94.157 | 1.00 | 54.01 |
| ATOM | 3257 | CA | PHE | 514 | 84.434 | 56.272 | 94.282 | 1.00 | 52.79 |
| ATOM | 3258 | CB | PHE | 514 | 84.809 | 57.567 | 93.540 | 1.00 | 51.46 |
| ATOM | 3259 | CG | PHE | 514 | 84.134 | 58.813 | 94.071 | 1.00 | 47.21 |
| ATOM | 3260 | CD1 | PHE | 514 | 82.819 | 59.113 | 93.731 | 1.00 | 45.39 |
| ATOM | 3261 | CD2 | PHE | 514 | 84.833 | 59.707 | 94.873 | 1.00 | 42.42 |
| ATOM | 3262 | CE1 | PHE | 514 | 82.217 | 60.281 | 94.180 | 1.00 | 44.25 |
| ATOM | 3263 | CE2 | PHE | 514 | 84.238 | 60.874 | 95.325 | 1.00 | 41.86 |
| ATOM | 3264 | CZ | PHE | 514 | 82.930 | 61.163 | 94.978 | 1.00 | 43.49 |
| ATOM | 3265 | C | PHE | 514 | 84.837 | 56.352 | 95.752 | 1.00 | 52.80 |
| ATOM | 3266 | O | PHE | 514 | 83.988 | 55.991 | 96.597 | 1.00 | 52.32 |
| ATOM | 3267 | CB | SER | 1011 | 57.929 | 87.366 | 59.237 | 1.00 | 58.03 |
| ATOM | 3268 | OG | SER | 1011 | 58.006 | 88.780 | 59.293 | 1.00 | 63.01 |
| ATOM | 3269 | C | SER | 1011 | 59.129 | 85.247 | 59.802 | 1.00 | 54.25 |
| ATOM | 3270 | O | SER | 1011 | 60.185 | 84.781 | 59.351 | 1.00 | 53.59 |
| ATOM | 3271 | N | SER | 1011 | 60.325 | 87.376 | 59.863 | 1.00 | 55.40 |
| ATOM | 3272 | CA | SER | 1011 | 59.010 | 86.732 | 60.117 | 1.00 | 55.46 |
| ATOM | 3273 | N | TYR | 1012 | 58.046 | 84.513 | 60.043 | 1.00 | 51.61 |
| ATOM | 3274 | CA | TYR | 1012 | 58.026 | 83.086 | 59.791 | 1.00 | 48.08 |
| ATOM | 3275 | CB | TYR | 1012 | 56.873 | 82.419 | 60.545 | 1.00 | 41.27 |
| ATOM | 3276 | CG | TYR | 1012 | 56.809 | 80.925 | 60.332 | 1.00 | 34.35 |
| ATOM | 3277 | CD1 | TYR | 1012 | 57.930 | 80.127 | 60.548 | 1.00 | 28.76 |
| ATOM | 3278 | CE1 | TYR | 1012 | 57.899 | 78.760 | 60.325 | 1.00 | 29.64 |
| ATOM | 3279 | CD2 | TYR | 1012 | 55.641 | 80.312 | 59.888 | 1.00 | 34.30 |
| ATOM | 3280 | CE2 | TYR | 1012 | 55.597 | 78.934 | 59.663 | 1.00 | 36.50 |
| ATOM | 3281 | CZ | TYR | 1012 | 56.734 | 78.163 | 59.885 | 1.00 | 34.98 |
| ATOM | 3282 | OH | TYR | 1012 | 56.704 | 76.797 | 59.672 | 1.00 | 36.25 |
| ATOM | 3283 | C | TYR | 1012 | 57.892 | 82.790 | 58.309 | 1.00 | 48.56 |
| ATOM | 3284 | O | TYR | 1012 | 57.098 | 83.422 | 57.604 | 1.00 | 49.57 |
| ATOM | 3285 | N | VAL | 1013 | 58.707 | 81.859 | 57.833 | 1.00 | 48.25 |
| ATOM | 3286 | CA | VAL | 1013 | 58.651 | 81.436 | 56.446 | 1.00 | 47.55 |
| ATOM | 3287 | CB | VAL | 1013 | 59.816 | 81.975 | 55.598 | 1.00 | 48.39 |
| ATOM | 3288 | CG1 | VAL | 1013 | 59.361 | 82.123 | 54.154 | 1.00 | 47.70 |
| ATOM | 3289 | CG2 | VAL | 1013 | 60.348 | 83.289 | 56.162 | 1.00 | 49.99 |
| ATOM | 3290 | C | VAL | 1013 | 58.732 | 79.916 | 56.490 | 1.00 | 47.43 |
| ATOM | 3291 | O | VAL | 1013 | 59.714 | 79.348 | 56.978 | 1.00 | 47.21 |
| ATOM | 3292 | N | PRO | 1014 | 57.640 | 79.243 | 56.114 | 1.00 | 47.63 |
| ATOM | 3293 | CD | PRO | 1014 | 56.292 | 79.787 | 55.872 | 1.00 | 47.66 |
| ATOM | 3294 | CA | PRO | 1014 | 57.622 | 77.781 | 56.122 | 1.00 | 48.55 |
| ATOM | 3295 | CB | PRO | 1014 | 56.148 | 77.452 | 55.855 | 1.00 | 49.13 |
| ATOM | 3296 | CG | PRO | 1014 | 55.629 | 78.665 | 55.137 | 1.00 | 49.10 |
| ATOM | 3297 | C | PRO | 1014 | 58.568 | 77.153 | 55.097 | 1.00 | 48.71 |
| ATOM | 3298 | O | PRO | 1014 | 58.646 | 77.595 | 53.944 | 1.00 | 49.40 |
| ATOM | 3299 | N | ASP | 1015 | 59.323 | 76.153 | 55.549 | 1.00 | 48.60 |
| ATOM | 3300 | CA | ASP | 1015 | 60.273 | 75.454 | 54.687 | 1.00 | 48.10 |
| ATOM | 3301 | CB | ASP | 1015 | 61.138 | 74.468 | 55.501 | 1.00 | 53.10 |

FIG. 1A-57

| | | | | | | | | | |
|---|---|---|---|---|---|---|---|---|---|
| ATOM | 3302 | CG  | ASP | 1015 | 60.310 | 73.484 | 56.334 | 1.00 | 60.22 |
| ATOM | 3303 | OD1 | ASP | 1015 | 59.891 | 73.846 | 57.460 | 1.00 | 63.12 |
| ATOM | 3304 | OD2 | ASP | 1015 | 60.104 | 72.338 | 55.873 | 1.00 | 64.06 |
| ATOM | 3305 | C   | ASP | 1015 | 59.552 | 74.750 | 53.538 | 1.00 | 44.68 |
| ATOM | 3306 | O   | ASP | 1015 | 58.389 | 74.360 | 53.659 | 1.00 | 44.03 |
| ATOM | 3307 | N   | ASP | 1016 | 60.250 | 74.583 | 52.425 | 1.00 | 40.80 |
| ATOM | 3308 | CA  | ASP | 1016 | 59.657 | 73.952 | 51.264 | 1.00 | 38.03 |
| ATOM | 3309 | CB  | ASP | 1016 | 59.204 | 75.037 | 50.278 | 1.00 | 39.43 |
| ATOM | 3310 | CG  | ASP | 1016 | 57.769 | 74.858 | 49.822 | 1.00 | 38.43 |
| ATOM | 3311 | OD1 | ASP | 1016 | 57.008 | 75.848 | 49.852 | 1.00 | 34.54 |
| ATOM | 3312 | OD2 | ASP | 1016 | 57.405 | 73.730 | 49.430 | 1.00 | 41.54 |
| ATOM | 3313 | C   | ASP | 1016 | 60.665 | 73.024 | 50.594 | 1.00 | 35.83 |
| ATOM | 3314 | O   | ASP | 1016 | 61.813 | 73.399 | 50.366 | 1.00 | 37.51 |
| ATOM | 3315 | N   | GLY | 1017 | 60.230 | 71.811 | 50.285 | 1.00 | 32.24 |
| ATOM | 3316 | CA  | GLY | 1017 | 61.101 | 70.858 | 49.630 | 1.00 | 27.23 |
| ATOM | 3317 | C   | GLY | 1017 | 61.868 | 69.973 | 50.589 | 1.00 | 25.42 |
| ATOM | 3318 | O   | GLY | 1017 | 61.837 | 70.165 | 51.804 | 1.00 | 27.96 |
| ATOM | 3319 | N   | LEU | 1018 | 62.552 | 68.985 | 50.029 | 1.00 | 22.02 |
| ATOM | 3320 | CA  | LEU | 1018 | 63.340 | 68.043 | 50.798 | 1.00 | 18.75 |
| ATOM | 3321 | CB  | LEU | 1018 | 63.108 | 66.632 | 50.268 | 1.00 | 17.25 |
| ATOM | 3322 | CG  | LEU | 1018 | 61.713 | 66.062 | 50.485 | 1.00 | 16.23 |
| ATOM | 3323 | CD1 | LEU | 1018 | 61.601 | 64.734 | 49.768 | 1.00 | 16.81 |
| ATOM | 3324 | CD2 | LEU | 1018 | 61.452 | 65.896 | 51.978 | 1.00 | 13.24 |
| ATOM | 3325 | C   | LEU | 1018 | 64.814 | 68.361 | 50.687 | 1.00 | 15.88 |
| ATOM | 3326 | O   | LEU | 1018 | 65.252 | 68.972 | 49.724 | 1.00 | 17.36 |
| ATOM | 3327 | N   | THR | 1019 | 65.580 | 67.966 | 51.687 | 1.00 | 13.27 |
| ATOM | 3328 | CA  | THR | 1019 | 67.007 | 68.179 | 51.634 | 1.00 | 14.14 |
| ATOM | 3329 | CB  | THR | 1019 | 67.611 | 68.222 | 53.031 | 1.00 | 12.51 |
| ATOM | 3330 | OG1 | THR | 1019 | 67.263 | 67.029 | 53.737 | 1.00 | 17.30 |
| ATOM | 3331 | CG2 | THR | 1019 | 67.076 | 69.419 | 53.799 | 1.00 | 8.68 |
| ATOM | 3332 | C   | THR | 1019 | 67.505 | 66.954 | 50.878 | 1.00 | 16.62 |
| ATOM | 3333 | O   | THR | 1019 | 66.768 | 65.967 | 50.761 | 1.00 | 17.81 |
| ATOM | 3334 | N   | ALA | 1020 | 68.723 | 67.007 | 50.341 | 1.00 | 16.80 |
| ATOM | 3335 | CA  | ALA | 1020 | 69.253 | 65.872 | 49.598 | 1.00 | 16.84 |
| ATOM | 3336 | CB  | ALA | 1020 | 70.620 | 66.183 | 49.042 | 1.00 | 17.48 |
| ATOM | 3337 | C   | ALA | 1020 | 69.282 | 64.630 | 50.485 | 1.00 | 17.70 |
| ATOM | 3338 | O   | ALA | 1020 | 69.021 | 63.514 | 50.020 | 1.00 | 19.09 |
| ATOM | 3339 | N   | GLN | 1021 | 69.548 | 64.825 | 51.771 | 1.00 | 16.33 |
| ATOM | 3340 | CA  | GLN | 1021 | 69.568 | 63.704 | 52.693 | 1.00 | 17.71 |
| ATOM | 3341 | CB  | GLN | 1021 | 70.003 | 64.152 | 54.088 | 1.00 | 21.58 |
| ATOM | 3342 | CG  | GLN | 1021 | 69.993 | 63.035 | 55.126 | 1.00 | 33.97 |
| ATOM | 3343 | CD  | GLN | 1021 | 71.118 | 63.171 | 56.141 | 1.00 | 44.79 |
| ATOM | 3344 | OE1 | GLN | 1021 | 71.121 | 64.087 | 56.972 | 1.00 | 47.71 |
| ATOM | 3345 | NE2 | GLN | 1021 | 72.092 | 62.267 | 56.068 | 1.00 | 49.18 |
| ATOM | 3346 | C   | GLN | 1021 | 68.202 | 63.012 | 52.754 | 1.00 | 17.20 |
| ATOM | 3347 | O   | GLN | 1021 | 68.118 | 61.805 | 52.578 | 1.00 | 17.20 |
| ATOM | 3348 | N   | GLN | 1022 | 67.131 | 63.778 | 52.944 | 1.00 | 16.52 |
| ATOM | 3349 | CA  | GLN | 1022 | 65.790 | 63.202 | 53.028 | 1.00 | 15.89 |
| ATOM | 3350 | CB  | GLN | 1022 | 64.758 | 64.276 | 53.323 | 1.00 | 15.47 |
| ATOM | 3351 | CG  | GLN | 1022 | 65.023 | 65.126 | 54.536 | 1.00 | 17.25 |
| ATOM | 3352 | CD  | GLN | 1022 | 63.960 | 66.191 | 54.684 | 1.00 | 23.78 |
| ATOM | 3353 | OE1 | GLN | 1022 | 62.816 | 65.890 | 55.009 | 1.00 | 31.89 |
| ATOM | 3354 | NE2 | GLN | 1022 | 64.318 | 67.436 | 54.403 | 1.00 | 26.89 |
| ATOM | 3355 | C   | GLN | 1022 | 65.381 | 62.524 | 51.733 | 1.00 | 17.02 |
| ATOM | 3356 | O   | GLN | 1022 | 64.887 | 61.402 | 51.731 | 1.00 | 19.29 |
| ATOM | 3357 | N   | LEU | 1023 | 65.579 | 63.237 | 50.635 | 1.00 | 17.87 |
| ATOM | 3358 | CA  | LEU | 1023 | 65.228 | 62.773 | 49.307 | 1.00 | 17.81 |
| ATOM | 3359 | CB  | LEU | 1023 | 65.552 | 63.877 | 48.291 | 1.00 | 18.45 |
| ATOM | 3360 | CG  | LEU | 1023 | 65.210 | 63.689 | 46.812 | 1.00 | 19.08 |

FIG. 1A-58

| ATOM | 3361 | CD1 | LEU | 1023 | 63.703 | 63.664 | 46.612 | 1.00 | 18.39 |
| ATOM | 3362 | CD2 | LEU | 1023 | 65.827 | 64.815 | 46.014 | 1.00 | 16.88 |
| ATOM | 3363 | C | LEU | 1023 | 65.927 | 61.479 | 48.909 | 1.00 | 20.42 |
| ATOM | 3364 | O | LEU | 1023 | 65.280 | 60.543 | 48.436 | 1.00 | 19.06 |
| ATOM | 3365 | N | PHE | 1024 | 67.244 | 61.425 | 49.093 | 1.00 | 23.89 |
| ATOM | 3366 | CA | PHE | 1024 | 68.023 | 60.249 | 48.704 | 1.00 | 25.50 |
| ATOM | 3367 | CB | PHE | 1024 | 69.421 | 60.657 | 48.257 | 1.00 | 19.33 |
| ATOM | 3368 | CG | PHE | 1024 | 69.405 | 61.431 | 46.990 | 1.00 | 17.62 |
| ATOM | 3369 | CD1 | PHE | 1024 | 69.404 | 60.778 | 45.770 | 1.00 | 16.25 |
| ATOM | 3370 | CD2 | PHE | 1024 | 69.241 | 62.810 | 47.013 | 1.00 | 23.98 |
| ATOM | 3371 | CE1 | PHE | 1024 | 69.226 | 61.477 | 44.590 | 1.00 | 21.25 |
| ATOM | 3372 | CE2 | PHE | 1024 | 69.062 | 63.525 | 45.841 | 1.00 | 25.54 |
| ATOM | 3373 | CZ | PHE | 1024 | 69.052 | 62.856 | 44.625 | 1.00 | 27.04 |
| ATOM | 3374 | C | PHE | 1024 | 68.064 | 59.117 | 49.693 | 1.00 | 28.39 |
| ATOM | 3375 | O | PHE | 1024 | 68.248 | 57.961 | 49.321 | 1.00 | 30.05 |
| ATOM | 3376 | N | ASN | 1025 | 67.867 | 59.444 | 50.957 | 1.00 | 31.89 |
| ATOM | 3377 | CA | ASN | 1025 | 67.846 | 58.427 | 51.987 | 1.00 | 36.32 |
| ATOM | 3378 | CB | ASN | 1025 | 68.597 | 58.917 | 53.232 | 1.00 | 41.18 |
| ATOM | 3379 | CG | ASN | 1025 | 70.085 | 59.192 | 52.944 | 1.00 | 41.83 |
| ATOM | 3380 | OD1 | ASN | 1025 | 70.957 | 58.409 | 53.319 | 1.00 | 47.33 |
| ATOM | 3381 | ND2 | ASN | 1025 | 70.369 | 60.292 | 52.263 | 1.00 | 38.75 |
| ATOM | 3382 | C | ASN | 1025 | 66.357 | 58.169 | 52.207 | 1.00 | 36.28 |
| ATOM | 3383 | O | ASN | 1025 | 65.818 | 58.279 | 53.313 | 1.00 | 36.13 |
| ATOM | 3384 | N | CYS | 1026 | 65.724 | 57.839 | 51.080 | 1.00 | 36.85 |
| ATOM | 3385 | CA | CYS | 1026 | 64.298 | 57.551 | 50.945 | 1.00 | 34.82 |
| ATOM | 3386 | CB | CYS | 1026 | 63.662 | 58.629 | 50.061 | 1.00 | 37.24 |
| ATOM | 3387 | SG | CYS | 1026 | 62.051 | 59.254 | 50.560 | 1.00 | 47.39 |
| ATOM | 3388 | C | CYS | 1026 | 64.120 | 56.177 | 50.266 | 1.00 | 33.53 |
| ATOM | 3389 | O | CYS | 1026 | 63.007 | 55.667 | 50.174 | 1.00 | 32.71 |
| ATOM | 3390 | N | GLY | 1027 | 65.204 | 55.624 | 49.723 | 1.00 | 32.56 |
| ATOM | 3391 | CA | GLY | 1027 | 65.154 | 54.316 | 49.082 | 1.00 | 31.56 |
| ATOM | 3392 | C | GLY | 1027 | 64.429 | 54.193 | 47.749 | 1.00 | 31.84 |
| ATOM | 3393 | O | GLY | 1027 | 64.181 | 53.084 | 47.270 | 1.00 | 30.93 |
| ATOM | 3394 | N | ASP | 1028 | 64.141 | 55.323 | 47.119 | 1.00 | 31.14 |
| ATOM | 3395 | CA | ASP | 1028 | 63.421 | 55.326 | 45.853 | 1.00 | 30.56 |
| ATOM | 3396 | CB | ASP | 1028 | 62.755 | 56.691 | 45.623 | 1.00 | 36.90 |
| ATOM | 3397 | CG | ASP | 1028 | 61.541 | 56.924 | 46.530 | 1.00 | 43.07 |
| ATOM | 3398 | OD1 | ASP | 1028 | 60.926 | 55.938 | 47.010 | 1.00 | 45.77 |
| ATOM | 3399 | OD2 | ASP | 1028 | 61.193 | 58.108 | 46.742 | 1.00 | 46.97 |
| ATOM | 3400 | C | ASP | 1028 | 64.230 | 54.935 | 44.622 | 1.00 | 28.09 |
| ATOM | 3401 | O | ASP | 1028 | 63.652 | 54.695 | 43.563 | 1.00 | 28.66 |
| ATOM | 3402 | N | GLY | 1029 | 65.553 | 54.898 | 44.744 | 1.00 | 24.86 |
| ATOM | 3403 | CA | GLY | 1029 | 66.378 | 54.534 | 43.606 | 1.00 | 21.35 |
| ATOM | 3404 | C | GLY | 1029 | 66.189 | 55.526 | 42.471 | 1.00 | 21.27 |
| ATOM | 3405 | O | GLY | 1029 | 65.868 | 55.145 | 41.332 | 1.00 | 21.10 |
| ATOM | 3406 | N | LEU | 1030 | 66.397 | 56.806 | 42.774 | 1.00 | 20.08 |
| ATOM | 3407 | CA | LEU | 1030 | 66.225 | 57.848 | 41.772 | 1.00 | 18.05 |
| ATOM | 3408 | CB | LEU | 1030 | 65.340 | 58.992 | 42.303 | 1.00 | 17.70 |
| ATOM | 3409 | CG | LEU | 1030 | 65.138 | 59.328 | 43.782 | 1.00 | 14.68 |
| ATOM | 3410 | CD1 | LEU | 1030 | 66.426 | 59.721 | 44.418 | 1.00 | 21.75 |
| ATOM | 3411 | CD2 | LEU | 1030 | 64.175 | 60.474 | 43.905 | 1.00 | 13.20 |
| ATOM | 3412 | C | LEU | 1030 | 67.490 | 58.408 | 41.126 | 1.00 | 18.04 |
| ATOM | 3413 | O | LEU | 1030 | 68.601 | 58.272 | 41.651 | 1.00 | 15.80 |
| ATOM | 3414 | N | THR | 1031 | 67.303 | 58.964 | 39.932 | 1.00 | 18.36 |
| ATOM | 3415 | CA | THR | 1031 | 68.371 | 59.591 | 39.167 | 1.00 | 17.66 |
| ATOM | 3416 | CB | THR | 1031 | 68.653 | 58.880 | 37.850 | 1.00 | 17.35 |
| ATOM | 3417 | OG1 | THR | 1031 | 67.489 | 58.168 | 37.410 | 1.00 | 20.68 |
| ATOM | 3418 | CG2 | THR | 1031 | 69.798 | 57.957 | 38.023 | 1.00 | 19.52 |
| ATOM | 3419 | C | THR | 1031 | 68.014 | 61.024 | 38.850 | 1.00 | 17.30 |

FIG. 1A-59

| ATOM | 3420 | O   | THR | 1031 | 66.990 | 61.528 | 39.295 | 1.00 | 18.68 |
| --- | --- | --- | --- | --- | --- | --- | --- | --- | --- |
| ATOM | 3421 | N   | TYR | 1032 | 68.834 | 61.641 | 38.012 | 1.00 | 16.44 |
| ATOM | 3422 | CA  | TYR | 1032 | 68.674 | 63.031 | 37.617 | 1.00 | 16.87 |
| ATOM | 3423 | CB  | TYR | 1032 | 69.631 | 63.343 | 36.463 | 1.00 | 14.97 |
| ATOM | 3424 | CG  | TYR | 1032 | 71.073 | 63.021 | 36.756 | 1.00 | 8.96 |
| ATOM | 3425 | CD1 | TYR | 1032 | 71.641 | 63.357 | 37.975 | 1.00 | 11.80 |
| ATOM | 3426 | CE1 | TYR | 1032 | 72.972 | 63.071 | 38.250 | 1.00 | 14.63 |
| ATOM | 3427 | CD2 | TYR | 1032 | 71.870 | 62.390 | 35.809 | 1.00 | 5.18 |
| ATOM | 3428 | CE2 | TYR | 1032 | 73.194 | 62.102 | 36.068 | 1.00 | 7.16 |
| ATOM | 3429 | CZ  | TYR | 1032 | 73.746 | 62.447 | 37.291 | 1.00 | 12.40 |
| ATOM | 3430 | OH  | TYR | 1032 | 75.074 | 62.186 | 37.557 | 1.00 | 13.92 |
| ATOM | 3431 | C   | TYR | 1032 | 67.266 | 63.513 | 37.249 | 1.00 | 18.29 |
| ATOM | 3432 | O   | TYR | 1032 | 66.758 | 64.472 | 37.834 | 1.00 | 16.95 |
| ATOM | 3433 | N   | ASN | 1033 | 66.623 | 62.840 | 36.301 | 1.00 | 19.44 |
| ATOM | 3434 | CA  | ASN | 1033 | 65.304 | 63.277 | 35.860 | 1.00 | 19.44 |
| ATOM | 3435 | CB  | ASN | 1033 | 64.954 | 62.644 | 34.519 | 1.00 | 17.54 |
| ATOM | 3436 | CG  | ASN | 1033 | 65.762 | 63.226 | 33.386 | 1.00 | 24.27 |
| ATOM | 3437 | OD1 | ASN | 1033 | 66.375 | 64.288 | 33.528 | 1.00 | 27.27 |
| ATOM | 3438 | ND2 | ASN | 1033 | 65.795 | 62.530 | 32.261 | 1.00 | 24.84 |
| ATOM | 3439 | C   | ASN | 1033 | 64.154 | 63.126 | 36.833 | 1.00 | 19.96 |
| ATOM | 3440 | O   | ASN | 1033 | 63.058 | 63.613 | 36.570 | 1.00 | 21.81 |
| ATOM | 3441 | N   | ASP | 1034 | 64.413 | 62.507 | 37.977 | 1.00 | 18.51 |
| ATOM | 3442 | CA  | ASP | 1034 | 63.369 | 62.288 | 38.966 | 1.00 | 16.08 |
| ATOM | 3443 | CB  | ASP | 1034 | 63.602 | 60.964 | 39.695 | 1.00 | 13.85 |
| ATOM | 3444 | CG  | ASP | 1034 | 63.376 | 59.770 | 38.806 | 1.00 | 17.69 |
| ATOM | 3445 | OD1 | ASP | 1034 | 62.332 | 59.729 | 38.121 | 1.00 | 22.84 |
| ATOM | 3446 | OD2 | ASP | 1034 | 64.242 | 58.877 | 38.783 | 1.00 | 17.41 |
| ATOM | 3447 | C   | ASP | 1034 | 63.212 | 63.402 | 39.979 | 1.00 | 15.01 |
| ATOM | 3448 | O   | ASP | 1034 | 62.325 | 63.326 | 40.835 | 1.00 | 17.19 |
| ATOM | 3449 | N   | PHE | 1035 | 64.053 | 64.426 | 39.910 | 1.00 | 11.94 |
| ATOM | 3450 | CA  | PHE | 1035 | 63.942 | 65.504 | 40.881 | 1.00 | 12.57 |
| ATOM | 3451 | CB  | PHE | 1035 | 64.743 | 65.178 | 42.149 | 1.00 | 10.75 |
| ATOM | 3452 | CG  | PHE | 1035 | 66.224 | 65.195 | 41.946 | 1.00 | 10.13 |
| ATOM | 3453 | CD1 | PHE | 1035 | 66.943 | 66.375 | 42.108 | 1.00 | 12.40 |
| ATOM | 3454 | CD2 | PHE | 1035 | 66.897 | 64.044 | 41.572 | 1.00 | 13.01 |
| ATOM | 3455 | CE1 | PHE | 1035 | 68.315 | 66.405 | 41.901 | 1.00 | 14.59 |
| ATOM | 3456 | CE2 | PHE | 1035 | 68.275 | 64.059 | 41.361 | 1.00 | 17.26 |
| ATOM | 3457 | CZ  | PHE | 1035 | 68.986 | 65.241 | 41.524 | 1.00 | 16.88 |
| ATOM | 3458 | C   | PHE | 1035 | 64.344 | 66.866 | 40.345 | 1.00 | 12.04 |
| ATOM | 3459 | O   | PHE | 1035 | 64.903 | 66.984 | 39.257 | 1.00 | 11.35 |
| ATOM | 3460 | N   | LEU | 1036 | 64.061 | 67.889 | 41.138 | 1.00 | 12.75 |
| ATOM | 3461 | CA  | LEU | 1036 | 64.372 | 69.261 | 40.774 | 1.00 | 16.81 |
| ATOM | 3462 | CB  | LEU | 1036 | 63.098 | 69.993 | 40.359 | 1.00 | 17.81 |
| ATOM | 3463 | CG  | LEU | 1036 | 62.568 | 69.755 | 38.955 | 1.00 | 18.45 |
| ATOM | 3464 | CD1 | LEU | 1036 | 61.203 | 70.408 | 38.829 | 1.00 | 15.39 |
| ATOM | 3465 | CD2 | LEU | 1036 | 63.555 | 70.308 | 37.936 | 1.00 | 18.87 |
| ATOM | 3466 | C   | LEU | 1036 | 64.992 | 70.009 | 41.941 | 1.00 | 17.35 |
| ATOM | 3467 | O   | LEU | 1036 | 64.808 | 69.633 | 43.100 | 1.00 | 20.23 |
| ATOM | 3468 | N   | ILE | 1037 | 65.745 | 71.056 | 41.626 | 1.00 | 15.55 |
| ATOM | 3469 | CA  | ILE | 1037 | 66.354 | 71.878 | 42.648 | 1.00 | 12.98 |
| ATOM | 3470 | CB  | ILE | 1037 | 67.771 | 72.312 | 42.254 | 1.00 | 13.94 |
| ATOM | 3471 | CG2 | ILE | 1037 | 68.491 | 72.873 | 43.470 | 1.00 | 13.02 |
| ATOM | 3472 | CG1 | ILE | 1037 | 68.555 | 71.115 | 41.698 | 1.00 | 16.53 |
| ATOM | 3473 | CD1 | ILE | 1037 | 69.945 | 71.454 | 41.180 | 1.00 | 13.78 |
| ATOM | 3474 | C   | ILE | 1037 | 65.445 | 73.095 | 42.706 | 1.00 | 13.09 |
| ATOM | 3475 | O   | ILE | 1037 | 65.202 | 73.744 | 41.680 | 1.00 | 13.21 |
| ATOM | 3476 | N   | LEU | 1038 | 64.861 | 73.344 | 43.869 | 1.00 | 10.11 |
| ATOM | 3477 | CA  | LEU | 1038 | 63.980 | 74.486 | 44.014 | 1.00 | 10.59 |
| ATOM | 3478 | CB  | LEU | 1038 | 63.183 | 74.398 | 45.322 | 1.00 | 10.09 |

FIG. 1A-60

| ATOM | 3479 | CG | LEU | 1038 | 62.147 | 73.275 | 45.416 | 1.00 | 3.81 |
|---|---|---|---|---|---|---|---|---|---|
| ATOM | 3480 | CD1 | LEU | 1038 | 61.367 | 73.428 | 46.684 | 1.00 | 3.17 |
| ATOM | 3481 | CD2 | LEU | 1038 | 61.213 | 73.318 | 44.237 | 1.00 | 2.82 |
| ATOM | 3482 | C | LEU | 1038 | 64.849 | 75.738 | 43.976 | 1.00 | 12.67 |
| ATOM | 3483 | O | LEU | 1038 | 65.959 | 75.735 | 44.514 | 1.00 | 14.13 |
| ATOM | 3484 | N | PRO | 1039 | 64.375 | 76.811 | 43.311 | 1.00 | 12.96 |
| ATOM | 3485 | CD | PRO | 1039 | 63.052 | 76.923 | 42.671 | 1.00 | 13.41 |
| ATOM | 3486 | CA | PRO | 1039 | 65.115 | 78.075 | 43.194 | 1.00 | 11.42 |
| ATOM | 3487 | CB | PRO | 1039 | 64.226 | 78.890 | 42.262 | 1.00 | 12.86 |
| ATOM | 3488 | CG | PRO | 1039 | 62.853 | 78.408 | 42.613 | 1.00 | 11.92 |
| ATOM | 3489 | C | PRO | 1039 | 65.328 | 78.779 | 44.522 | 1.00 | 11.00 |
| ATOM | 3490 | O | PRO | 1039 | 64.657 | 78.473 | 45.505 | 1.00 | 12.52 |
| ATOM | 3491 | N | GLY | 1040 | 66.239 | 79.745 | 44.536 | 1.00 | 12.23 |
| ATOM | 3492 | CA | GLY | 1040 | 66.525 | 80.482 | 45.754 | 1.00 | 12.18 |
| ATOM | 3493 | C | GLY | 1040 | 66.517 | 81.987 | 45.570 | 1.00 | 12.14 |
| ATOM | 3494 | O | GLY | 1040 | 65.700 | 82.516 | 44.821 | 1.00 | 13.21 |
| ATOM | 3495 | N | TYR | 1041 | 67.434 | 82.671 | 46.248 | 1.00 | 13.56 |
| ATOM | 3496 | CA | TYR | 1041 | 67.542 | 84.127 | 46.182 | 1.00 | 13.97 |
| ATOM | 3497 | CB | TYR | 1041 | 67.703 | 84.702 | 47.593 | 1.00 | 14.19 |
| ATOM | 3498 | CG | TYR | 1041 | 67.872 | 86.207 | 47.636 | 1.00 | 17.57 |
| ATOM | 3499 | CD1 | TYR | 1041 | 66.893 | 87.057 | 47.115 | 1.00 | 18.66 |
| ATOM | 3500 | CE1 | TYR | 1041 | 67.054 | 88.441 | 47.137 | 1.00 | 18.65 |
| ATOM | 3501 | CD2 | TYR | 1041 | 69.017 | 86.782 | 48.185 | 1.00 | 15.46 |
| ATOM | 3502 | CE2 | TYR | 1041 | 69.183 | 88.163 | 48.213 | 1.00 | 18.22 |
| ATOM | 3503 | CZ | TYR | 1041 | 68.200 | 88.989 | 47.687 | 1.00 | 18.97 |
| ATOM | 3504 | OH | TYR | 1041 | 68.374 | 90.361 | 47.714 | 1.00 | 19.15 |
| ATOM | 3505 | C | TYR | 1041 | 68.720 | 84.550 | 45.313 | 1.00 | 14.59 |
| ATOM | 3506 | O | TYR | 1041 | 69.868 | 84.240 | 45.631 | 1.00 | 16.29 |
| ATOM | 3507 | N | ILE | 1042 | 68.434 | 85.272 | 44.231 | 1.00 | 15.26 |
| ATOM | 3508 | CA | ILE | 1042 | 69.469 | 85.742 | 43.306 | 1.00 | 14.94 |
| ATOM | 3509 | CB | ILE | 1042 | 68.926 | 85.844 | 41.871 | 1.00 | 11.71 |
| ATOM | 3510 | CG2 | ILE | 1042 | 70.016 | 86.310 | 40.926 | 1.00 | 7.14 |
| ATOM | 3511 | CG1 | ILE | 1042 | 68.367 | 84.483 | 41.444 | 1.00 | 8.36 |
| ATOM | 3512 | CD1 | ILE | 1042 | 67.843 | 84.452 | 40.058 | 1.00 | 5.40 |
| ATOM | 3513 | C | ILE | 1042 | 70.068 | 87.074 | 43.744 | 1.00 | 17.59 |
| ATOM | 3514 | O | ILE | 1042 | 69.428 | 88.127 | 43.688 | 1.00 | 18.42 |
| ATOM | 3515 | N | ASP | 1043 | 71.331 | 87.011 | 44.130 | 1.00 | 21.17 |
| ATOM | 3516 | CA | ASP | 1043 | 72.060 | 88.163 | 44.629 | 1.00 | 24.79 |
| ATOM | 3517 | CB | ASP | 1043 | 72.676 | 87.773 | 45.978 | 1.00 | 25.19 |
| ATOM | 3518 | CG | ASP | 1043 | 72.641 | 88.897 | 46.981 | 1.00 | 33.67 |
| ATOM | 3519 | OD1 | ASP | 1043 | 71.841 | 89.846 | 46.812 | 1.00 | 39.64 |
| ATOM | 3520 | OD2 | ASP | 1043 | 73.410 | 88.823 | 47.961 | 1.00 | 37.45 |
| ATOM | 3521 | C | ASP | 1043 | 73.176 | 88.612 | 43.688 | 1.00 | 26.69 |
| ATOM | 3522 | O | ASP | 1043 | 73.903 | 89.564 | 43.990 | 1.00 | 28.10 |
| ATOM | 3523 | N | PHE | 1044 | 73.272 | 87.976 | 42.526 | 1.00 | 25.31 |
| ATOM | 3524 | CA | PHE | 1044 | 74.343 | 88.271 | 41.587 | 1.00 | 22.89 |
| ATOM | 3525 | CB | PHE | 1044 | 75.567 | 87.446 | 41.975 | 1.00 | 21.97 |
| ATOM | 3526 | CG | PHE | 1044 | 75.286 | 85.977 | 42.022 | 1.00 | 25.11 |
| ATOM | 3527 | CD1 | PHE | 1044 | 74.503 | 85.440 | 43.048 | 1.00 | 24.61 |
| ATOM | 3528 | CD2 | PHE | 1044 | 75.696 | 85.145 | 40.991 | 1.00 | 25.66 |
| ATOM | 3529 | CE1 | PHE | 1044 | 74.127 | 84.108 | 43.034 | 1.00 | 22.42 |
| ATOM | 3530 | CE2 | PHE | 1044 | 75.321 | 83.806 | 40.972 | 1.00 | 24.74 |
| ATOM | 3531 | CZ | PHE | 1044 | 74.535 | 83.291 | 41.994 | 1.00 | 23.97 |
| ATOM | 3532 | C | PHE | 1044 | 73.946 | 87.861 | 40.186 | 1.00 | 23.67 |
| ATOM | 3533 | O | PHE | 1044 | 72.930 | 87.193 | 39.974 | 1.00 | 24.13 |
| ATOM | 3534 | N | THR | 1045 | 74.810 | 88.195 | 39.240 | 1.00 | 24.33 |
| ATOM | 3535 | CA | THR | 1045 | 74.589 | 87.866 | 37.847 | 1.00 | 23.97 |
| ATOM | 3536 | CB | THR | 1045 | 75.099 | 88.999 | 36.918 | 1.00 | 21.89 |
| ATOM | 3537 | OG1 | THR | 1045 | 76.524 | 89.071 | 36.965 | 1.00 | 22.39 |

FIG. 1A-61

| ATOM | 3538 | CG2 | THR | 1045 | 74.551 | 90.335 | 37.382 | 1.00 | 17.41 |
|------|------|-----|-----|------|--------|--------|--------|------|-------|
| ATOM | 3539 | C | THR | 1045 | 75.307 | 86.552 | 37.558 | 1.00 | 24.74 |
| ATOM | 3540 | O | THR | 1045 | 76.320 | 86.234 | 38.189 | 1.00 | 23.80 |
| ATOM | 3541 | N | ALA | 1046 | 74.761 | 85.786 | 36.618 | 1.00 | 26.52 |
| ATOM | 3542 | CA | ALA | 1046 | 75.305 | 84.487 | 36.229 | 1.00 | 26.11 |
| ATOM | 3543 | CB | ALA | 1046 | 74.539 | 83.935 | 35.036 | 1.00 | 24.43 |
| ATOM | 3544 | C | ALA | 1046 | 76.792 | 84.490 | 35.929 | 1.00 | 26.72 |
| ATOM | 3545 | O | ALA | 1046 | 77.516 | 83.597 | 36.350 | 1.00 | 27.98 |
| ATOM | 3546 | N | ASP | 1047 | 77.255 | 85.504 | 35.212 | 1.00 | 29.16 |
| ATOM | 3547 | CA | ASP | 1047 | 78.666 | 85.586 | 34.851 | 1.00 | 31.33 |
| ATOM | 3548 | CB | ASP | 1047 | 78.923 | 86.779 | 33.923 | 1.00 | 38.14 |
| ATOM | 3549 | CG | ASP | 1047 | 78.465 | 88.107 | 34.519 | 1.00 | 46.25 |
| ATOM | 3550 | OD1 | ASP | 1047 | 79.291 | 88.799 | 35.165 | 1.00 | 48.68 |
| ATOM | 3551 | OD2 | ASP | 1047 | 77.279 | 88.467 | 34.319 | 1.00 | 50.20 |
| ATOM | 3552 | C | ASP | 1047 | 79.604 | 85.638 | 36.046 | 1.00 | 28.88 |
| ATOM | 3553 | O | ASP | 1047 | 80.810 | 85.557 | 35.890 | 1.00 | 31.35 |
| ATOM | 3554 | N | GLN | 1048 | 79.049 | 85.740 | 37.241 | 1.00 | 27.79 |
| ATOM | 3555 | CA | GLN | 1048 | 79.862 | 85.810 | 38.437 | 1.00 | 27.71 |
| ATOM | 3556 | CB | GLN | 1048 | 79.237 | 86.797 | 39.411 | 1.00 | 31.21 |
| ATOM | 3557 | CG | GLN | 1048 | 78.900 | 88.121 | 38.785 | 1.00 | 38.83 |
| ATOM | 3558 | CD | GLN | 1048 | 78.268 | 89.067 | 39.771 | 1.00 | 47.10 |
| ATOM | 3559 | OE1 | GLN | 1048 | 77.175 | 89.582 | 39.547 | 1.00 | 49.42 |
| ATOM | 3560 | NE2 | GLN | 1048 | 78.953 | 89.305 | 40.879 | 1.00 | 52.51 |
| ATOM | 3561 | C | GLN | 1048 | 80.025 | 84.471 | 39.133 | 1.00 | 26.49 |
| ATOM | 3562 | O | GLN | 1048 | 80.688 | 84.393 | 40.165 | 1.00 | 29.30 |
| ATOM | 3563 | N | VAL | 1049 | 79.406 | 83.427 | 38.598 | 1.00 | 23.74 |
| ATOM | 3564 | CA | VAL | 1049 | 79.486 | 82.120 | 39.220 | 1.00 | 19.66 |
| ATOM | 3565 | CB | VAL | 1049 | 78.365 | 81.196 | 38.736 | 1.00 | 19.77 |
| ATOM | 3566 | CG1 | VAL | 1049 | 78.453 | 79.838 | 39.437 | 1.00 | 14.56 |
| ATOM | 3567 | CG2 | VAL | 1049 | 77.014 | 81.850 | 39.003 | 1.00 | 21.34 |
| ATOM | 3568 | C | VAL | 1049 | 80.820 | 81.478 | 38.945 | 1.00 | 19.62 |
| ATOM | 3569 | O | VAL | 1049 | 81.276 | 81.442 | 37.810 | 1.00 | 22.57 |
| ATOM | 3570 | N | ASP | 1050 | 81.437 | 80.964 | 39.998 | 1.00 | 18.17 |
| ATOM | 3571 | CA | ASP | 1050 | 82.732 | 80.314 | 39.908 | 1.00 | 17.07 |
| ATOM | 3572 | CB | ASP | 1050 | 83.546 | 80.635 | 41.163 | 1.00 | 16.95 |
| ATOM | 3573 | CG | ASP | 1050 | 84.989 | 80.170 | 41.078 | 1.00 | 22.48 |
| ATOM | 3574 | OD1 | ASP | 1050 | 85.453 | 79.784 | 39.982 | 1.00 | 26.67 |
| ATOM | 3575 | OD2 | ASP | 1050 | 85.674 | 80.196 | 42.119 | 1.00 | 26.60 |
| ATOM | 3576 | C | ASP | 1050 | 82.540 | 78.807 | 39.784 | 1.00 | 18.43 |
| ATOM | 3577 | O | ASP | 1050 | 81.944 | 78.173 | 40.662 | 1.00 | 20.72 |
| ATOM | 3578 | N | LEU | 1051 | 83.053 | 78.231 | 38.700 | 1.00 | 17.50 |
| ATOM | 3579 | CA | LEU | 1051 | 82.944 | 76.792 | 38.483 | 1.00 | 14.50 |
| ATOM | 3580 | CB | LEU | 1051 | 82.500 | 76.493 | 37.052 | 1.00 | 7.44 |
| ATOM | 3581 | CG | LEU | 1051 | 81.227 | 77.157 | 36.539 | 1.00 | 5.31 |
| ATOM | 3582 | CD1 | LEU | 1051 | 80.887 | 76.556 | 35.188 | 1.00 | 4.75 |
| ATOM | 3583 | CD2 | LEU | 1051 | 80.076 | 76.967 | 37.519 | 1.00 | 3.50 |
| ATOM | 3584 | C | LEU | 1051 | 84.244 | 76.035 | 38.768 | 1.00 | 15.17 |
| ATOM | 3585 | O | LEU | 1051 | 84.392 | 74.894 | 38.344 | 1.00 | 14.20 |
| ATOM | 3586 | N | THR | 1052 | 85.194 | 76.669 | 39.452 | 1.00 | 18.28 |
| ATOM | 3587 | CA | THR | 1052 | 86.468 | 76.017 | 39.772 | 1.00 | 20.55 |
| ATOM | 3588 | CB | THR | 1052 | 87.351 | 76.892 | 40.686 | 1.00 | 22.00 |
| ATOM | 3589 | OG1 | THR | 1052 | 87.488 | 78.202 | 40.115 | 1.00 | 16.85 |
| ATOM | 3590 | CG2 | THR | 1052 | 88.731 | 76.270 | 40.827 | 1.00 | 19.87 |
| ATOM | 3591 | C | THR | 1052 | 86.172 | 74.698 | 40.470 | 1.00 | 20.87 |
| ATOM | 3592 | O | THR | 1052 | 85.483 | 74.677 | 41.489 | 1.00 | 20.43 |
| ATOM | 3593 | N | SER | 1053 | 86.701 | 73.608 | 39.922 | 1.00 | 23.45 |
| ATOM | 3594 | CA | SER | 1053 | 86.453 | 72.273 | 40.460 | 1.00 | 24.39 |
| ATOM | 3595 | CB | SER | 1053 | 85.559 | 71.492 | 39.496 | 1.00 | 25.65 |
| ATOM | 3596 | OG | SER | 1053 | 84.344 | 72.178 | 39.258 | 1.00 | 28.54 |

FIG. 1A-62

| ATOM | 3597 | C | SER | 1053 | 87.705 | 71.455 | 40.726 | 1.00 | 25.65 |
|---|---|---|---|---|---|---|---|---|---|
| ATOM | 3598 | O | SER | 1053 | 88.673 | 71.514 | 39.965 | 1.00 | 26.93 |
| ATOM | 3599 | N | ALA | 1054 | 87.663 | 70.664 | 41.796 | 1.00 | 24.99 |
| ATOM | 3600 | CA | ALA | 1054 | 88.775 | 69.799 | 42.170 | 1.00 | 22.41 |
| ATOM | 3601 | CB | ALA | 1054 | 88.768 | 69.564 | 43.664 | 1.00 | 21.17 |
| ATOM | 3602 | C | ALA | 1054 | 88.636 | 68.472 | 41.438 | 1.00 | 22.07 |
| ATOM | 3603 | O | ALA | 1054 | 87.684 | 67.729 | 41.678 | 1.00 | 24.02 |
| ATOM | 3604 | N | LEU | 1055 | 89.562 | 68.192 | 40.527 | 1.00 | 21.30 |
| ATOM | 3605 | CA | LEU | 1055 | 89.544 | 66.943 | 39.764 | 1.00 | 20.33 |
| ATOM | 3606 | CB | LEU | 1055 | 90.431 | 67.057 | 38.514 | 1.00 | 17.85 |
| ATOM | 3607 | CG | LEU | 1055 | 90.570 | 65.821 | 37.621 | 1.00 | 14.28 |
| ATOM | 3608 | CD1 | LEU | 1055 | 89.285 | 65.584 | 36.870 | 1.00 | 14.74 |
| ATOM | 3609 | CD2 | LEU | 1055 | 91.691 | 66.013 | 36.637 | 1.00 | 15.53 |
| ATOM | 3610 | C | LEU | 1055 | 90.037 | 65.793 | 40.641 | 1.00 | 20.19 |
| ATOM | 3611 | O | LEU | 1055 | 89.503 | 64.680 | 40.590 | 1.00 | 18.90 |
| ATOM | 3612 | N | THR | 1056 | 91.072 | 66.069 | 41.427 | 1.00 | 20.07 |
| ATOM | 3613 | CA | THR | 1056 | 91.663 | 65.082 | 42.316 | 1.00 | 19.85 |
| ATOM | 3614 | CB | THR | 1056 | 92.894 | 64.409 | 41.683 | 1.00 | 18.25 |
| ATOM | 3615 | OG1 | THR | 1056 | 93.885 | 65.401 | 41.397 | 1.00 | 19.25 |
| ATOM | 3616 | CG2 | THR | 1056 | 92.531 | 63.690 | 40.403 | 1.00 | 14.77 |
| ATOM | 3617 | C | THR | 1056 | 92.131 | 65.838 | 43.540 | 1.00 | 20.51 |
| ATOM | 3618 | O | THR | 1056 | 91.976 | 67.058 | 43.604 | 1.00 | 21.19 |
| ATOM | 3619 | N | LYS | 1057 | 92.722 | 65.128 | 44.497 | 1.00 | 21.94 |
| ATOM | 3620 | CA | LYS | 1057 | 93.220 | 65.761 | 45.714 | 1.00 | 23.37 |
| ATOM | 3621 | CB | LYS | 1057 | 93.972 | 64.764 | 46.588 | 1.00 | 21.65 |
| ATOM | 3622 | CG | LYS | 1057 | 93.112 | 63.737 | 47.272 | 1.00 | 19.15 |
| ATOM | 3623 | CD | LYS | 1057 | 93.705 | 63.415 | 48.622 | 1.00 | 17.97 |
| ATOM | 3624 | CE | LYS | 1057 | 93.180 | 62.105 | 49.138 | 1.00 | 27.69 |
| ATOM | 3625 | NZ | LYS | 1057 | 93.665 | 60.994 | 48.278 | 1.00 | 36.74 |
| ATOM | 3626 | C | LYS | 1057 | 94.142 | 66.935 | 45.423 | 1.00 | 26.24 |
| ATOM | 3627 | O | LYS | 1057 | 94.125 | 67.929 | 46.146 | 1.00 | 27.88 |
| ATOM | 3628 | N | LYS | 1058 | 94.956 | 66.818 | 44.375 | 1.00 | 28.24 |
| ATOM | 3629 | CA | LYS | 1058 | 95.876 | 67.890 | 44.021 | 1.00 | 28.47 |
| ATOM | 3630 | CB | LYS | 1058 | 97.334 | 67.441 | 44.196 | 1.00 | 31.38 |
| ATOM | 3631 | CG | LYS | 1058 | 97.711 | 67.172 | 45.662 | 1.00 | 35.79 |
| ATOM | 3632 | CD | LYS | 1058 | 99.219 | 67.048 | 45.876 | 1.00 | 41.70 |
| ATOM | 3633 | CE | LYS | 1058 | 99.818 | 65.871 | 45.107 | 1.00 | 45.88 |
| ATOM | 3634 | NZ | LYS | 1058 | 101.284 | 65.717 | 45.357 | 1.00 | 48.09 |
| ATOM | 3635 | C | LYS | 1058 | 95.647 | 68.564 | 42.663 | 1.00 | 27.92 |
| ATOM | 3636 | O | LYS | 1058 | 96.298 | 69.560 | 42.352 | 1.00 | 29.57 |
| ATOM | 3637 | N | ILE | 1059 | 94.732 | 68.040 | 41.852 | 1.00 | 26.71 |
| ATOM | 3638 | CA | ILE | 1059 | 94.434 | 68.674 | 40.570 | 1.00 | 24.61 |
| ATOM | 3639 | CB | ILE | 1059 | 94.403 | 67.678 | 39.404 | 1.00 | 20.79 |
| ATOM | 3640 | CG2 | ILE | 1059 | 93.915 | 68.372 | 38.142 | 1.00 | 22.24 |
| ATOM | 3641 | CG1 | ILE | 1059 | 95.800 | 67.113 | 39.159 | 1.00 | 21.03 |
| ATOM | 3642 | CD1 | ILE | 1059 | 95.930 | 66.308 | 37.874 | 1.00 | 19.39 |
| ATOM | 3643 | C | ILE | 1059 | 93.095 | 69.415 | 40.656 | 1.00 | 25.03 |
| ATOM | 3644 | O | ILE | 1059 | 92.101 | 68.866 | 41.137 | 1.00 | 24.20 |
| ATOM | 3645 | N | THR | 1060 | 93.092 | 70.656 | 40.171 | 1.00 | 24.97 |
| ATOM | 3646 | CA | THR | 1060 | 91.924 | 71.540 | 40.174 | 1.00 | 24.93 |
| ATOM | 3647 | CB | THR | 1060 | 92.113 | 72.671 | 41.220 | 1.00 | 22.96 |
| ATOM | 3648 | OG1 | THR | 1060 | 92.137 | 72.118 | 42.541 | 1.00 | 26.30 |
| ATOM | 3649 | CG2 | THR | 1060 | 91.001 | 73.692 | 41.134 | 1.00 | 21.60 |
| ATOM | 3650 | C | THR | 1060 | 91.789 | 72.193 | 38.795 | 1.00 | 25.85 |
| ATOM | 3651 | O | THR | 1060 | 92.780 | 72.660 | 38.235 | 1.00 | 29.42 |
| ATOM | 3652 | N | LEU | 1061 | 90.578 | 72.230 | 38.251 | 1.00 | 23.74 |
| ATOM | 3653 | CA | LEU | 1061 | 90.341 | 72.831 | 36.945 | 1.00 | 21.19 |
| ATOM | 3654 | CB | LEU | 1061 | 89.598 | 71.847 | 36.052 | 1.00 | 20.39 |
| ATOM | 3655 | CG | LEU | 1061 | 90.136 | 70.423 | 35.971 | 1.00 | 20.17 |

FIG. 1A-63

| ATOM | 3656 | CD1 | LEU | 1061 | 89.053 | 69.484 | 35.447 | 1.00 | 15.54 |
| --- | --- | --- | --- | --- | --- | --- | --- | --- | --- |
| ATOM | 3657 | CD2 | LEU | 1061 | 91.367 | 70.405 | 35.085 | 1.00 | 20.41 |
| ATOM | 3658 | C | LEU | 1061 | 89.480 | 74.067 | 37.115 | 1.00 | 22.35 |
| ATOM | 3659 | O | LEU | 1061 | 88.876 | 74.279 | 38.171 | 1.00 | 22.51 |
| ATOM | 3660 | N | LYS | 1062 | 89.391 | 74.867 | 36.061 | 1.00 | 24.07 |
| ATOM | 3661 | CA | LYS | 1062 | 88.578 | 76.078 | 36.093 | 1.00 | 25.75 |
| ATOM | 3662 | CB | LYS | 1062 | 89.028 | 77.063 | 35.008 | 1.00 | 30.52 |
| ATOM | 3663 | CG | LYS | 1062 | 90.476 | 77.540 | 35.142 | 1.00 | 34.98 |
| ATOM | 3664 | CD | LYS | 1062 | 90.667 | 78.567 | 36.249 | 1.00 | 35.68 |
| ATOM | 3665 | CE | LYS | 1062 | 92.160 | 78.787 | 36.548 | 1.00 | 40.74 |
| ATOM | 3666 | NZ | LYS | 1062 | 92.979 | 79.256 | 35.378 | 1.00 | 40.68 |
| ATOM | 3667 | C | LYS | 1062 | 87.115 | 75.714 | 35.884 | 1.00 | 25.76 |
| ATOM | 3668 | O | LYS | 1062 | 86.234 | 76.534 | 36.111 | 1.00 | 28.56 |
| ATOM | 3669 | N | THR | 1063 | 86.866 | 74.503 | 35.386 | 1.00 | 26.18 |
| ATOM | 3670 | CA | THR | 1063 | 85.509 | 74.007 | 35.154 | 1.00 | 24.51 |
| ATOM | 3671 | CB | THR | 1063 | 85.121 | 74.068 | 33.657 | 1.00 | 22.57 |
| ATOM | 3672 | OG1 | THR | 1063 | 85.783 | 73.022 | 32.945 | 1.00 | 24.96 |
| ATOM | 3673 | CG2 | THR | 1063 | 85.509 | 75.409 | 33.054 | 1.00 | 19.73 |
| ATOM | 3674 | C | THR | 1063 | 85.419 | 72.547 | 35.628 | 1.00 | 23.22 |
| ATOM | 3675 | O | THR | 1063 | 86.438 | 71.909 | 35.888 | 1.00 | 24.35 |
| ATOM | 3676 | N | PRO | 1064 | 84.204 | 72.011 | 35.781 | 1.00 | 20.91 |
| ATOM | 3677 | CD | PRO | 1064 | 82.906 | 72.709 | 35.907 | 1.00 | 19.27 |
| ATOM | 3678 | CA | PRO | 1064 | 84.095 | 70.623 | 36.234 | 1.00 | 18.80 |
| ATOM | 3679 | CB | PRO | 1064 | 82.838 | 70.658 | 37.087 | 1.00 | 16.86 |
| ATOM | 3680 | CG | PRO | 1064 | 81.969 | 71.608 | 36.332 | 1.00 | 17.27 |
| ATOM | 3681 | C | PRO | 1064 | 83.949 | 69.618 | 35.086 | 1.00 | 18.82 |
| ATOM | 3682 | O | PRO | 1064 | 83.593 | 68.464 | 35.310 | 1.00 | 21.11 |
| ATOM | 3683 | N | LEU | 1065 | 84.272 | 70.034 | 33.870 | 1.00 | 17.47 |
| ATOM | 3684 | CA | LEU | 1065 | 84.101 | 69.176 | 32.711 | 1.00 | 13.63 |
| ATOM | 3685 | CB | LEU | 1065 | 83.717 | 70.038 | 31.507 | 1.00 | 16.00 |
| ATOM | 3686 | CG | LEU | 1065 | 82.675 | 71.127 | 31.834 | 1.00 | 15.86 |
| ATOM | 3687 | CD1 | LEU | 1065 | 82.457 | 72.076 | 30.657 | 1.00 | 13.35 |
| ATOM | 3688 | CD2 | LEU | 1065 | 81.370 | 70.476 | 32.267 | 1.00 | 12.21 |
| ATOM | 3689 | C | LEU | 1065 | 85.308 | 68.303 | 32.410 | 1.00 | 15.32 |
| ATOM | 3690 | O | LEU | 1065 | 86.440 | 68.778 | 32.304 | 1.00 | 15.30 |
| ATOM | 3691 | N | VAL | 1066 | 85.036 | 67.018 | 32.233 | 1.00 | 17.58 |
| ATOM | 3692 | CA | VAL | 1066 | 86.052 | 66.003 | 31.962 | 1.00 | 17.87 |
| ATOM | 3693 | CB | VAL | 1066 | 86.165 | 65.019 | 33.179 | 1.00 | 18.83 |
| ATOM | 3694 | CG1 | VAL | 1066 | 87.154 | 63.908 | 32.889 | 1.00 | 18.72 |
| ATOM | 3695 | CG2 | VAL | 1066 | 86.556 | 65.763 | 34.447 | 1.00 | 19.44 |
| ATOM | 3696 | C | VAL | 1066 | 85.579 | 65.177 | 30.767 | 1.00 | 18.45 |
| ATOM | 3697 | O | VAL | 1066 | 84.395 | 64.849 | 30.686 | 1.00 | 20.05 |
| ATOM | 3698 | N | SER | 1067 | 86.470 | 64.856 | 29.834 | 1.00 | 18.12 |
| ATOM | 3699 | CA | SER | 1067 | 86.059 | 64.027 | 28.709 | 1.00 | 19.04 |
| ATOM | 3700 | CB | SER | 1067 | 86.741 | 64.447 | 27.401 | 1.00 | 17.98 |
| ATOM | 3701 | OG | SER | 1067 | 88.120 | 64.138 | 27.393 | 1.00 | 24.06 |
| ATOM | 3702 | C | SER | 1067 | 86.343 | 62.564 | 29.060 | 1.00 | 19.98 |
| ATOM | 3703 | O | SER | 1067 | 87.329 | 62.249 | 29.739 | 1.00 | 19.91 |
| ATOM | 3704 | N | SER | 1068 | 85.432 | 61.688 | 28.651 | 1.00 | 20.10 |
| ATOM | 3705 | CA | SER | 1068 | 85.535 | 60.264 | 28.925 | 1.00 | 20.27 |
| ATOM | 3706 | CB | SER | 1068 | 84.174 | 59.597 | 28.708 | 1.00 | 24.52 |
| ATOM | 3707 | OG | SER | 1068 | 84.224 | 58.192 | 28.931 | 1.00 | 26.68 |
| ATOM | 3708 | C | SER | 1068 | 86.569 | 59.557 | 28.081 | 1.00 | 20.17 |
| ATOM | 3709 | O | SER | 1068 | 86.617 | 59.743 | 26.865 | 1.00 | 21.59 |
| ATOM | 3710 | N | PRO | 1069 | 87.392 | 58.706 | 28.710 | 1.00 | 19.67 |
| ATOM | 3711 | CD | PRO | 1069 | 87.490 | 58.496 | 30.167 | 1.00 | 18.49 |
| ATOM | 3712 | CA | PRO | 1069 | 88.430 | 57.953 | 28.009 | 1.00 | 18.30 |
| ATOM | 3713 | CB | PRO | 1069 | 89.249 | 57.373 | 29.158 | 1.00 | 17.03 |
| ATOM | 3714 | CG | PRO | 1069 | 88.245 | 57.203 | 30.248 | 1.00 | 15.39 |

FIG. 1A-64

| ATOM | 3715 | C | PRO | 1069 | 87.805 | 56.852 | 27.153 | 1.00 | 20.15 |
| --- | --- | --- | --- | --- | --- | --- | --- | --- | --- |
| ATOM | 3716 | O | PRO | 1069 | 87.676 | 55.707 | 27.588 | 1.00 | 22.07 |
| ATOM | 3717 | N | MET | 1070 | 87.384 | 57.209 | 25.948 | 1.00 | 20.29 |
| ATOM | 3718 | CA | MET | 1070 | 86.770 | 56.254 | 25.035 | 1.00 | 20.57 |
| ATOM | 3719 | CB | MET | 1070 | 85.254 | 56.423 | 25.053 | 1.00 | 20.27 |
| ATOM | 3720 | CG | MET | 1070 | 84.621 | 56.059 | 26.379 | 1.00 | 21.67 |
| ATOM | 3721 | SD | MET | 1070 | 82.879 | 56.473 | 26.451 | 1.00 | 21.01 |
| ATOM | 3722 | CE | MET | 1070 | 82.210 | 55.085 | 25.547 | 1.00 | 20.49 |
| ATOM | 3723 | C | MET | 1070 | 87.331 | 56.501 | 23.641 | 1.00 | 22.45 |
| ATOM | 3724 | O | MET | 1070 | 87.575 | 57.650 | 23.261 | 1.00 | 20.92 |
| ATOM | 3725 | N | ASP | 1071 | 87.515 | 55.432 | 22.867 | 1.00 | 24.82 |
| ATOM | 3726 | CA | ASP | 1071 | 88.092 | 55.573 | 21.533 | 1.00 | 25.66 |
| ATOM | 3727 | CB | ASP | 1071 | 88.454 | 54.216 | 20.894 | 1.00 | 27.27 |
| ATOM | 3728 | CG | ASP | 1071 | 87.308 | 53.226 | 20.881 | 1.00 | 31.83 |
| ATOM | 3729 | OD1 | ASP | 1071 | 86.158 | 53.615 | 20.588 | 1.00 | 37.06 |
| ATOM | 3730 | OD2 | ASP | 1071 | 87.574 | 52.035 | 21.143 | 1.00 | 33.11 |
| ATOM | 3731 | C | ASP | 1071 | 87.367 | 56.478 | 20.549 | 1.00 | 24.21 |
| ATOM | 3732 | O | ASP | 1071 | 87.972 | 56.939 | 19.587 | 1.00 | 25.35 |
| ATOM | 3733 | N | THR | 1072 | 86.092 | 56.752 | 20.797 | 1.00 | 24.00 |
| ATOM | 3734 | CA | THR | 1072 | 85.327 | 57.638 | 19.924 | 1.00 | 22.90 |
| ATOM | 3735 | CB | THR | 1072 | 84.036 | 56.961 | 19.415 | 1.00 | 19.61 |
| ATOM | 3736 | OG1 | THR | 1072 | 83.200 | 56.592 | 20.524 | 1.00 | 16.40 |
| ATOM | 3737 | CG2 | THR | 1072 | 84.378 | 55.728 | 18.621 | 1.00 | 18.17 |
| ATOM | 3738 | C | THR | 1072 | 84.980 | 58.947 | 20.641 | 1.00 | 23.02 |
| ATOM | 3739 | O | THR | 1072 | 84.010 | 59.624 | 20.289 | 1.00 | 24.03 |
| ATOM | 3740 | N | VAL | 1073 | 85.766 | 59.292 | 21.658 | 1.00 | 22.41 |
| ATOM | 3741 | CA | VAL | 1073 | 85.529 | 60.510 | 22.420 | 1.00 | 21.20 |
| ATOM | 3742 | CB | VAL | 1073 | 84.752 | 60.229 | 23.741 | 1.00 | 19.24 |
| ATOM | 3743 | CG1 | VAL | 1073 | 84.571 | 61.504 | 24.535 | 1.00 | 17.63 |
| ATOM | 3744 | CG2 | VAL | 1073 | 83.394 | 59.641 | 23.452 | 1.00 | 16.74 |
| ATOM | 3745 | C | VAL | 1073 | 86.823 | 61.232 | 22.764 | 1.00 | 22.61 |
| ATOM | 3746 | O | VAL | 1073 | 86.969 | 62.417 | 22.477 | 1.00 | 22.14 |
| ATOM | 3747 | N | THR | 1074 | 87.793 | 60.516 | 23.318 | 1.00 | 24.79 |
| ATOM | 3748 | CA | THR | 1074 | 89.025 | 61.187 | 23.708 | 1.00 | 26.86 |
| ATOM | 3749 | CB | THR | 1074 | 89.104 | 61.359 | 25.247 | 1.00 | 29.38 |
| ATOM | 3750 | OG1 | THR | 1074 | 87.865 | 61.893 | 25.735 | 1.00 | 32.73 |
| ATOM | 3751 | CG2 | THR | 1074 | 90.217 | 62.324 | 25.622 | 1.00 | 30.82 |
| ATOM | 3752 | C | THR | 1074 | 90.370 | 60.686 | 23.199 | 1.00 | 26.15 |
| ATOM | 3753 | O | THR | 1074 | 90.750 | 59.529 | 23.380 | 1.00 | 25.91 |
| ATOM | 3754 | N | GLU | 1075 | 91.091 | 61.622 | 22.595 | 1.00 | 28.59 |
| ATOM | 3755 | CA | GLU | 1075 | 92.431 | 61.443 | 22.059 | 1.00 | 31.08 |
| ATOM | 3756 | CB | GLU | 1075 | 92.402 | 60.912 | 20.627 | 1.00 | 30.41 |
| ATOM | 3757 | CG | GLU | 1075 | 92.244 | 59.400 | 20.558 | 1.00 | 29.53 |
| ATOM | 3758 | CD | GLU | 1075 | 92.481 | 58.825 | 19.178 | 1.00 | 30.14 |
| ATOM | 3759 | OE1 | GLU | 1075 | 92.098 | 57.659 | 18.958 | 1.00 | 32.49 |
| ATOM | 3760 | OE2 | GLU | 1075 | 93.059 | 59.519 | 18.314 | 1.00 | 33.89 |
| ATOM | 3761 | C | GLU | 1075 | 93.065 | 62.833 | 22.121 | 1.00 | 34.13 |
| ATOM | 3762 | O | GLU | 1075 | 92.462 | 63.751 | 22.683 | 1.00 | 36.70 |
| ATOM | 3763 | N | ALA | 1076 | 94.251 | 63.002 | 21.538 | 1.00 | 35.59 |
| ATOM | 3764 | CA | ALA | 1076 | 94.956 | 64.292 | 21.570 | 1.00 | 35.10 |
| ATOM | 3765 | CB | ALA | 1076 | 96.151 | 64.275 | 20.620 | 1.00 | 35.89 |
| ATOM | 3766 | C | ALA | 1076 | 94.100 | 65.532 | 21.319 | 1.00 | 34.42 |
| ATOM | 3767 | O | ALA | 1076 | 93.986 | 66.389 | 22.194 | 1.00 | 34.97 |
| ATOM | 3768 | N | GLY | 1077 | 93.480 | 65.613 | 20.144 | 1.00 | 34.10 |
| ATOM | 3769 | CA | GLY | 1077 | 92.655 | 66.763 | 19.810 | 1.00 | 34.49 |
| ATOM | 3770 | C | GLY | 1077 | 91.655 | 67.146 | 20.886 | 1.00 | 35.44 |
| ATOM | 3771 | O | GLY | 1077 | 91.574 | 68.314 | 21.278 | 1.00 | 35.30 |
| ATOM | 3772 | N | MET | 1078 | 90.895 | 66.159 | 21.356 | 1.00 | 35.00 |
| ATOM | 3773 | CA | MET | 1078 | 89.892 | 66.361 | 22.400 | 1.00 | 32.60 |

FIG. 1A-65

| ATOM | 3774 | CB  | MET | 1078 | 89.122 | 65.060 | 22.650 | 1.00 | 30.21 |
|------|------|-----|-----|------|--------|--------|--------|------|-------|
| ATOM | 3775 | CG  | MET | 1078 | 88.115 | 65.119 | 23.787 | 1.00 | 23.97 |
| ATOM | 3776 | SD  | MET | 1078 | 86.729 | 66.180 | 23.420 | 1.00 | 22.65 |
| ATOM | 3777 | CE  | MET | 1078 | 85.882 | 65.186 | 22.153 | 1.00 | 13.83 |
| ATOM | 3778 | C   | MET | 1078 | 90.562 | 66.806 | 23.691 | 1.00 | 32.54 |
| ATOM | 3779 | O   | MET | 1078 | 90.281 | 67.890 | 24.205 | 1.00 | 33.25 |
| ATOM | 3780 | N   | ALA | 1079 | 91.473 | 65.975 | 24.191 | 1.00 | 29.80 |
| ATOM | 3781 | CA  | ALA | 1079 | 92.185 | 66.264 | 25.426 | 1.00 | 26.90 |
| ATOM | 3782 | CB  | ALA | 1079 | 93.312 | 65.272 | 25.625 | 1.00 | 25.36 |
| ATOM | 3783 | C   | ALA | 1079 | 92.719 | 67.686 | 25.411 | 1.00 | 26.03 |
| ATOM | 3784 | O   | ALA | 1079 | 92.675 | 68.385 | 26.426 | 1.00 | 25.26 |
| ATOM | 3785 | N   | ILE | 1080 | 93.163 | 68.132 | 24.238 | 1.00 | 26.03 |
| ATOM | 3786 | CA  | ILE | 1080 | 93.696 | 69.481 | 24.082 | 1.00 | 25.73 |
| ATOM | 3787 | CB  | ILE | 1080 | 94.486 | 69.632 | 22.761 | 1.00 | 23.56 |
| ATOM | 3788 | CG2 | ILE | 1080 | 94.898 | 71.086 | 22.540 | 1.00 | 22.24 |
| ATOM | 3789 | CG1 | ILE | 1080 | 95.740 | 68.763 | 22.810 | 1.00 | 21.45 |
| ATOM | 3790 | CD1 | ILE | 1080 | 96.565 | 68.809 | 21.554 | 1.00 | 22.68 |
| ATOM | 3791 | C   | ILE | 1080 | 92.587 | 70.530 | 24.154 | 1.00 | 26.48 |
| ATOM | 3792 | O   | ILE | 1080 | 92.645 | 71.444 | 24.979 | 1.00 | 25.96 |
| ATOM | 3793 | N   | ALA | 1081 | 91.559 | 70.369 | 23.323 | 1.00 | 27.21 |
| ATOM | 3794 | CA  | ALA | 1081 | 90.438 | 71.305 | 23.285 | 1.00 | 25.13 |
| ATOM | 3795 | CB  | ALA | 1081 | 89.422 | 70.866 | 22.240 | 1.00 | 23.36 |
| ATOM | 3796 | C   | ALA | 1081 | 89.778 | 71.410 | 24.652 | 1.00 | 25.14 |
| ATOM | 3797 | O   | ALA | 1081 | 89.335 | 72.484 | 25.064 | 1.00 | 26.40 |
| ATOM | 3798 | N   | MET | 1082 | 89.762 | 70.295 | 25.369 | 1.00 | 25.59 |
| ATOM | 3799 | CA  | MET | 1082 | 89.162 | 70.232 | 26.691 | 1.00 | 26.26 |
| ATOM | 3800 | CB  | MET | 1082 | 89.051 | 68.771 | 27.146 | 1.00 | 27.01 |
| ATOM | 3801 | CG  | MET | 1082 | 87.856 | 68.464 | 28.048 | 1.00 | 28.65 |
| ATOM | 3802 | SD  | MET | 1082 | 86.249 | 68.526 | 27.203 | 1.00 | 26.79 |
| ATOM | 3803 | CE  | MET | 1082 | 85.315 | 69.478 | 28.353 | 1.00 | 23.90 |
| ATOM | 3804 | C   | MET | 1082 | 89.992 | 71.056 | 27.675 | 1.00 | 25.81 |
| ATOM | 3805 | O   | MET | 1082 | 89.442 | 71.851 | 28.434 | 1.00 | 26.89 |
| ATOM | 3806 | N   | ALA | 1083 | 91.314 | 70.913 | 27.624 | 1.00 | 25.36 |
| ATOM | 3807 | CA  | ALA | 1083 | 92.195 | 71.663 | 28.519 | 1.00 | 23.07 |
| ATOM | 3808 | CB  | ALA | 1083 | 93.594 | 71.105 | 28.472 | 1.00 | 19.47 |
| ATOM | 3809 | C   | ALA | 1083 | 92.217 | 73.158 | 28.205 | 1.00 | 24.00 |
| ATOM | 3810 | O   | ALA | 1083 | 92.330 | 73.990 | 29.107 | 1.00 | 23.89 |
| ATOM | 3811 | N   | LEU | 1084 | 92.117 | 73.508 | 26.927 | 1.00 | 24.04 |
| ATOM | 3812 | CA  | LEU | 1084 | 92.133 | 74.913 | 26.550 | 1.00 | 21.88 |
| ATOM | 3813 | CB  | LEU | 1084 | 92.278 | 75.092 | 25.031 | 1.00 | 20.51 |
| ATOM | 3814 | CG  | LEU | 1084 | 93.621 | 74.803 | 24.333 | 1.00 | 17.98 |
| ATOM | 3815 | CD1 | LEU | 1084 | 93.489 | 75.021 | 22.834 | 1.00 | 10.91 |
| ATOM | 3816 | CD2 | LEU | 1084 | 94.728 | 75.687 | 24.892 | 1.00 | 16.24 |
| ATOM | 3817 | C   | LEU | 1084 | 90.872 | 75.603 | 27.038 | 1.00 | 23.28 |
| ATOM | 3818 | O   | LEU | 1084 | 90.939 | 76.749 | 27.472 | 1.00 | 24.38 |
| ATOM | 3819 | N   | THR | 1085 | 89.738 | 74.897 | 27.009 | 1.00 | 23.36 |
| ATOM | 3820 | CA  | THR | 1085 | 88.458 | 75.477 | 27.433 | 1.00 | 22.95 |
| ATOM | 3821 | CB  | THR | 1085 | 87.267 | 74.937 | 26.604 | 1.00 | 20.99 |
| ATOM | 3822 | OG1 | THR | 1085 | 87.256 | 73.508 | 26.631 | 1.00 | 25.05 |
| ATOM | 3823 | CG2 | THR | 1085 | 87.370 | 75.410 | 25.176 | 1.00 | 16.76 |
| ATOM | 3824 | C   | THR | 1085 | 88.117 | 75.425 | 28.921 | 1.00 | 23.92 |
| ATOM | 3825 | O   | THR | 1085 | 87.077 | 75.954 | 29.342 | 1.00 | 25.16 |
| ATOM | 3826 | N   | GLY | 1086 | 88.973 | 74.791 | 29.716 | 1.00 | 24.85 |
| ATOM | 3827 | CA  | GLY | 1086 | 88.731 | 74.748 | 31.150 | 1.00 | 26.30 |
| ATOM | 3828 | C   | GLY | 1086 | 88.614 | 73.400 | 31.835 | 1.00 | 25.84 |
| ATOM | 3829 | O   | GLY | 1086 | 88.517 | 73.336 | 33.063 | 1.00 | 26.47 |
| ATOM | 3830 | N   | GLY | 1087 | 88.570 | 72.332 | 31.057 | 1.00 | 25.34 |
| ATOM | 3831 | CA  | GLY | 1087 | 88.464 | 71.013 | 31.641 | 1.00 | 24.99 |
| ATOM | 3832 | C   | GLY | 1087 | 89.723 | 70.212 | 31.406 | 1.00 | 24.03 |

FIG. 1A-66

| ATOM | 3833 | O | GLY | 1087 | 90.823 | 70.761 | 31.358 | 1.00 | 23.72 |
|---|---|---|---|---|---|---|---|---|---|
| ATOM | 3834 | N | ILE | 1088 | 89.555 | 68.908 | 31.244 | 1.00 | 23.71 |
| ATOM | 3835 | CA | ILE | 1088 | 90.673 | 68.007 | 31.006 | 1.00 | 23.17 |
| ATOM | 3836 | CB | ILE | 1088 | 91.360 | 67.582 | 32.352 | 1.00 | 20.71 |
| ATOM | 3837 | CG2 | ILE | 1088 | 90.444 | 66.669 | 33.153 | 1.00 | 20.78 |
| ATOM | 3838 | CG1 | ILE | 1088 | 92.706 | 66.886 | 32.090 | 1.00 | 17.22 |
| ATOM | 3839 | CD1 | ILE | 1088 | 93.545 | 66.593 | 33.353 | 1.00 | 5.96 |
| ATOM | 3840 | C | ILE | 1088 | 90.083 | 66.799 | 30.283 | 1.00 | 22.59 |
| ATOM | 3841 | O | ILE | 1088 | 88.862 | 66.605 | 30.281 | 1.00 | 22.13 |
| ATOM | 3842 | N | GLY | 1089 | 90.939 | 66.023 | 29.630 | 1.00 | 22.64 |
| ATOM | 3843 | CA | GLY | 1089 | 90.476 | 64.853 | 28.912 | 1.00 | 21.60 |
| ATOM | 3844 | C | GLY | 1089 | 91.292 | 63.622 | 29.250 | 1.00 | 22.41 |
| ATOM | 3845 | O | GLY | 1089 | 92.433 | 63.728 | 29.697 | 1.00 | 22.07 |
| ATOM | 3846 | N | PHE | 1090 | 90.702 | 62.449 | 29.068 | 1.00 | 22.64 |
| ATOM | 3847 | CA | PHE | 1090 | 91.403 | 61.215 | 29.350 | 1.00 | 22.39 |
| ATOM | 3848 | CB | PHE | 1090 | 90.668 | 60.425 | 30.423 | 1.00 | 24.55 |
| ATOM | 3849 | CG | PHE | 1090 | 90.775 | 61.026 | 31.782 | 1.00 | 27.69 |
| ATOM | 3850 | CD1 | PHE | 1090 | 89.903 | 62.032 | 32.181 | 1.00 | 28.68 |
| ATOM | 3851 | CD2 | PHE | 1090 | 91.775 | 60.616 | 32.658 | 1.00 | 26.87 |
| ATOM | 3852 | CE1 | PHE | 1090 | 90.034 | 62.628 | 33.439 | 1.00 | 29.16 |
| ATOM | 3853 | CE2 | PHE | 1090 | 91.912 | 61.207 | 33.917 | 1.00 | 26.20 |
| ATOM | 3854 | CZ | PHE | 1090 | 91.041 | 62.214 | 34.304 | 1.00 | 28.03 |
| ATOM | 3855 | C | PHE | 1090 | 91.568 | 60.380 | 28.096 | 1.00 | 22.82 |
| ATOM | 3856 | O | PHE | 1090 | 90.579 | 59.940 | 27.511 | 1.00 | 23.69 |
| ATOM | 3857 | N | ILE | 1091 | 92.816 | 60.191 | 27.668 | 1.00 | 21.96 |
| ATOM | 3858 | CA | ILE | 1091 | 93.114 | 59.394 | 26.480 | 1.00 | 20.77 |
| ATOM | 3859 | CB | ILE | 1091 | 94.633 | 59.423 | 26.128 | 1.00 | 19.10 |
| ATOM | 3860 | CG2 | ILE | 1091 | 94.892 | 58.635 | 24.846 | 1.00 | 15.49 |
| ATOM | 3861 | CG1 | ILE | 1091 | 95.147 | 60.867 | 25.999 | 1.00 | 13.00 |
| ATOM | 3862 | CD1 | ILE | 1091 | 94.662 | 61.607 | 24.779 | 1.00 | 9.34 |
| ATOM | 3863 | C | ILE | 1091 | 92.722 | 57.950 | 26.795 | 1.00 | 20.88 |
| ATOM | 3864 | O | ILE | 1091 | 92.958 | 57.464 | 27.907 | 1.00 | 21.15 |
| ATOM | 3865 | N | HIS | 1092 | 92.101 | 57.276 | 25.832 | 1.00 | 21.96 |
| ATOM | 3866 | CA | HIS | 1092 | 91.686 | 55.882 | 26.019 | 1.00 | 23.97 |
| ATOM | 3867 | CB | HIS | 1092 | 90.613 | 55.492 | 24.994 | 1.00 | 23.05 |
| ATOM | 3868 | CG | HIS | 1092 | 91.114 | 55.427 | 23.584 | 1.00 | 18.52 |
| ATOM | 3869 | CD2 | HIS | 1092 | 91.563 | 54.381 | 22.849 | 1.00 | 13.17 |
| ATOM | 3870 | ND1 | HIS | 1092 | 91.196 | 56.534 | 22.768 | 1.00 | 15.63 |
| ATOM | 3871 | CE1 | HIS | 1092 | 91.672 | 56.173 | 21.592 | 1.00 | 14.27 |
| ATOM | 3872 | NE2 | HIS | 1092 | 91.908 | 54.873 | 21.614 | 1.00 | 12.20 |
| ATOM | 3873 | C | HIS | 1092 | 92.887 | 54.946 | 25.895 | 1.00 | 25.60 |
| ATOM | 3874 | O | HIS | 1092 | 93.957 | 55.369 | 25.467 | 1.00 | 28.13 |
| ATOM | 3875 | N | HIS | 1093 | 92.708 | 53.675 | 26.242 | 1.00 | 26.03 |
| ATOM | 3876 | CA | HIS | 1093 | 93.805 | 52.715 | 26.139 | 1.00 | 27.95 |
| ATOM | 3877 | CB | HIS | 1093 | 94.247 | 52.205 | 27.515 | 1.00 | 29.78 |
| ATOM | 3878 | CG | HIS | 1093 | 93.231 | 51.358 | 28.218 | 1.00 | 33.05 |
| ATOM | 3879 | CD2 | HIS | 1093 | 93.243 | 50.043 | 28.548 | 1.00 | 34.27 |
| ATOM | 3880 | ND1 | HIS | 1093 | 92.056 | 51.867 | 28.728 | 1.00 | 33.28 |
| ATOM | 3881 | CE1 | HIS | 1093 | 91.388 | 50.906 | 29.338 | 1.00 | 32.87 |
| ATOM | 3882 | NE2 | HIS | 1093 | 92.088 | 49.790 | 29.245 | 1.00 | 34.75 |
| ATOM | 3883 | C | HIS | 1093 | 93.518 | 51.557 | 25.193 | 1.00 | 28.37 |
| ATOM | 3884 | O | HIS | 1093 | 94.052 | 50.467 | 25.351 | 1.00 | 26.48 |
| ATOM | 3885 | N | ASN | 1094 | 92.596 | 51.785 | 24.265 | 1.00 | 30.84 |
| ATOM | 3886 | CA | ASN | 1094 | 92.241 | 50.807 | 23.237 | 1.00 | 32.45 |
| ATOM | 3887 | CB | ASN | 1094 | 90.769 | 50.963 | 22.842 | 1.00 | 35.56 |
| ATOM | 3888 | CG | ASN | 1094 | 90.371 | 50.081 | 21.671 | 1.00 | 39.33 |
| ATOM | 3889 | OD1 | ASN | 1094 | 89.850 | 50.568 | 20.668 | 1.00 | 43.29 |
| ATOM | 3890 | ND2 | ASN | 1094 | 90.594 | 48.780 | 21.800 | 1.00 | 38.01 |
| ATOM | 3891 | C | ASN | 1094 | 93.158 | 51.228 | 22.090 | 1.00 | 33.74 |

FIG. 1A-67

| ATOM | 3892 | O | ASN | 1094 | 92.722 | 51.794 | 21.079 | 1.00 | 34.48 |
|---|---|---|---|---|---|---|---|---|---|
| ATOM | 3893 | N | CYS | 1095 | 94.451 | 51.061 | 22.345 | 1.00 | 33.96 |
| ATOM | 3894 | CA | CYS | 1095 | 95.517 | 51.431 | 21.427 | 1.00 | 32.91 |
| ATOM | 3895 | CB | CYS | 1095 | 95.534 | 52.950 | 21.271 | 1.00 | 31.80 |
| ATOM | 3896 | SG | CYS | 1095 | 95.537 | 53.866 | 22.840 | 1.00 | 33.34 |
| ATOM | 3897 | C | CYS | 1095 | 96.829 | 50.961 | 22.057 | 1.00 | 33.35 |
| ATOM | 3898 | O | CYS | 1095 | 96.876 | 50.692 | 23.257 | 1.00 | 34.13 |
| ATOM | 3899 | N | THR | 1096 | 97.889 | 50.860 | 21.257 | 1.00 | 32.75 |
| ATOM | 3900 | CA | THR | 1096 | 99.185 | 50.411 | 21.762 | 1.00 | 30.51 |
| ATOM | 3901 | CB | THR | 1096 | 100.229 | 50.384 | 20.647 | 1.00 | 31.43 |
| ATOM | 3902 | OG1 | THR | 1096 | 100.530 | 51.722 | 20.243 | 1.00 | 34.77 |
| ATOM | 3903 | CG2 | THR | 1096 | 99.706 | 49.629 | 19.445 | 1.00 | 34.07 |
| ATOM | 3904 | C | THR | 1096 | 99.659 | 51.379 | 22.835 | 1.00 | 28.94 |
| ATOM | 3905 | O | THR | 1096 | 99.314 | 52.558 | 22.793 | 1.00 | 30.80 |
| ATOM | 3906 | N | PRO | 1097 | 100.461 | 50.902 | 23.807 | 1.00 | 28.40 |
| ATOM | 3907 | CD | PRO | 1097 | 100.925 | 49.519 | 24.021 | 1.00 | 28.11 |
| ATOM | 3908 | CA | PRO | 1097 | 100.958 | 51.781 | 24.869 | 1.00 | 27.84 |
| ATOM | 3909 | CB | PRO | 1097 | 101.916 | 50.878 | 25.632 | 1.00 | 26.37 |
| ATOM | 3910 | CG | PRO | 1097 | 101.293 | 49.531 | 25.481 | 1.00 | 25.06 |
| ATOM | 3911 | C | PRO | 1097 | 101.689 | 52.956 | 24.258 | 1.00 | 29.88 |
| ATOM | 3912 | O | PRO | 1097 | 101.583 | 54.084 | 24.739 | 1.00 | 30.91 |
| ATOM | 3913 | N | GLU | 1098 | 102.384 | 52.683 | 23.156 | 1.00 | 32.60 |
| ATOM | 3914 | CA | GLU | 1098 | 103.153 | 53.686 | 22.420 | 1.00 | 35.02 |
| ATOM | 3915 | CB | GLU | 1098 | 103.974 | 53.017 | 21.310 | 1.00 | 37.79 |
| ATOM | 3916 | CG | GLU | 1098 | 105.119 | 52.122 | 21.796 | 1.00 | 44.17 |
| ATOM | 3917 | CD | GLU | 1098 | 104.669 | 50.740 | 22.271 | 1.00 | 48.86 |
| ATOM | 3918 | OE1 | GLU | 1098 | 103.779 | 50.132 | 21.628 | 1.00 | 49.58 |
| ATOM | 3919 | OE2 | GLU | 1098 | 105.229 | 50.256 | 23.281 | 1.00 | 49.09 |
| ATOM | 3920 | C | GLU | 1098 | 102.269 | 54.787 | 21.814 | 1.00 | 35.22 |
| ATOM | 3921 | O | GLU | 1098 | 102.590 | 55.975 | 21.907 | 1.00 | 35.11 |
| ATOM | 3922 | N | PHE | 1099 | 101.170 | 54.378 | 21.182 | 1.00 | 34.71 |
| ATOM | 3923 | CA | PHE | 1099 | 100.217 | 55.295 | 20.550 | 1.00 | 31.99 |
| ATOM | 3924 | CB | PHE | 1099 | 99.114 | 54.487 | 19.854 | 1.00 | 30.86 |
| ATOM | 3925 | CG | PHE | 1099 | 97.961 | 55.316 | 19.356 | 1.00 | 30.84 |
| ATOM | 3926 | CD1 | PHE | 1099 | 97.896 | 55.708 | 18.027 | 1.00 | 30.84 |
| ATOM | 3927 | CD2 | PHE | 1099 | 96.906 | 55.654 | 20.203 | 1.00 | 30.22 |
| ATOM | 3928 | CE1 | PHE | 1099 | 96.795 | 56.418 | 17.543 | 1.00 | 32.30 |
| ATOM | 3929 | CE2 | PHE | 1099 | 95.807 | 56.360 | 19.730 | 1.00 | 29.93 |
| ATOM | 3930 | CZ | PHE | 1099 | 95.750 | 56.742 | 18.395 | 1.00 | 30.84 |
| ATOM | 3931 | C | PHE | 1099 | 99.591 | 56.202 | 21.591 | 1.00 | 30.63 |
| ATOM | 3932 | O | PHE | 1099 | 99.468 | 57.412 | 21.385 | 1.00 | 29.46 |
| ATOM | 3933 | N | GLN | 1100 | 99.169 | 55.592 | 22.694 | 1.00 | 31.39 |
| ATOM | 3934 | CA | GLN | 1100 | 98.535 | 56.312 | 23.782 | 1.00 | 33.54 |
| ATOM | 3935 | CB | GLN | 1100 | 98.087 | 55.341 | 24.873 | 1.00 | 33.46 |
| ATOM | 3936 | CG | GLN | 1100 | 97.206 | 56.000 | 25.918 | 1.00 | 33.43 |
| ATOM | 3937 | CD | GLN | 1100 | 96.860 | 55.082 | 27.061 | 1.00 | 31.11 |
| ATOM | 3938 | OE1 | GLN | 1100 | 97.552 | 54.111 | 27.321 | 1.00 | 30.24 |
| ATOM | 3939 | NE2 | GLN | 1100 | 95.784 | 55.397 | 27.765 | 1.00 | 34.07 |
| ATOM | 3940 | C | GLN | 1100 | 99.497 | 57.342 | 24.354 | 1.00 | 35.00 |
| ATOM | 3941 | O | GLN | 1100 | 99.145 | 58.518 | 24.499 | 1.00 | 35.07 |
| ATOM | 3942 | N | ALA | 1101 | 100.714 | 56.895 | 24.665 | 1.00 | 35.47 |
| ATOM | 3943 | CA | ALA | 1101 | 101.752 | 57.772 | 25.206 | 1.00 | 34.10 |
| ATOM | 3944 | CB | ALA | 1101 | 103.010 | 56.973 | 25.524 | 1.00 | 34.60 |
| ATOM | 3945 | C | ALA | 1101 | 102.062 | 58.868 | 24.192 | 1.00 | 33.13 |
| ATOM | 3946 | O | ALA | 1101 | 102.335 | 60.008 | 24.564 | 1.00 | 33.43 |
| ATOM | 3947 | N | ASN | 1102 | 102.004 | 58.515 | 22.911 | 1.00 | 31.74 |
| ATOM | 3948 | CA | ASN | 1102 | 102.251 | 59.464 | 21.831 | 1.00 | 31.93 |
| ATOM | 3949 | CB | ASN | 1102 | 102.220 | 58.754 | 20.478 | 1.00 | 35.75 |
| ATOM | 3950 | CG | ASN | 1102 | 102.222 | 59.722 | 19.314 | 1.00 | 38.97 |

FIG. 1A-68

| ATOM | 3951 | OD1 | ASN | 1102 | 103.115 | 60.562 | 19.188 | 1.00 | 35.68 |
|---|---|---|---|---|---|---|---|---|---|
| ATOM | 3952 | ND2 | ASN | 1102 | 101.207 | 59.617 | 18.460 | 1.00 | 44.14 |
| ATOM | 3953 | C | ASN | 1102 | 101.174 | 60.535 | 21.878 | 1.00 | 30.58 |
| ATOM | 3954 | O | ASN | 1102 | 101.465 | 61.734 | 21.820 | 1.00 | 28.72 |
| ATOM | 3955 | N | GLU | 1103 | 99.926 | 60.092 | 21.994 | 1.00 | 30.88 |
| ATOM | 3956 | CA | GLU | 1103 | 98.797 | 61.008 | 22.081 | 1.00 | 31.29 |
| ATOM | 3957 | CB | GLU | 1103 | 97.496 | 60.236 | 22.305 | 1.00 | 29.94 |
| ATOM | 3958 | CG | GLU | 1103 | 97.107 | 59.345 | 21.143 | 1.00 | 26.07 |
| ATOM | 3959 | CD | GLU | 1103 | 97.147 | 60.077 | 19.817 | 1.00 | 26.39 |
| ATOM | 3960 | OE1 | GLU | 1103 | 96.367 | 61.041 | 19.642 | 1.00 | 23.03 |
| ATOM | 3961 | OE2 | GLU | 1103 | 97.972 | 59.695 | 18.957 | 1.00 | 27.36 |
| ATOM | 3962 | C | GLU | 1103 | 99.033 | 61.971 | 23.236 | 1.00 | 31.53 |
| ATOM | 3963 | O | GLU | 1103 | 98.880 | 63.183 | 23.077 | 1.00 | 32.08 |
| ATOM | 3964 | N | VAL | 1104 | 99.448 | 61.421 | 24.378 | 1.00 | 32.16 |
| ATOM | 3965 | CA | VAL | 1104 | 99.731 | 62.201 | 25.585 | 1.00 | 33.27 |
| ATOM | 3966 | CB | VAL | 1104 | 100.191 | 61.286 | 26.744 | 1.00 | 30.58 |
| ATOM | 3967 | CG1 | VAL | 1104 | 100.569 | 62.110 | 27.962 | 1.00 | 28.79 |
| ATOM | 3968 | CG2 | VAL | 1104 | 99.093 | 60.304 | 27.096 | 1.00 | 32.06 |
| ATOM | 3969 | C | VAL | 1104 | 100.823 | 63.225 | 25.306 | 1.00 | 34.57 |
| ATOM | 3970 | O | VAL | 1104 | 100.695 | 64.404 | 25.649 | 1.00 | 34.06 |
| ATOM | 3971 | N | ARG | 1105 | 101.876 | 62.762 | 24.642 | 1.00 | 36.12 |
| ATOM | 3972 | CA | ARG | 1105 | 103.020 | 63.591 | 24.291 | 1.00 | 37.17 |
| ATOM | 3973 | CB | ARG | 1105 | 103.981 | 62.780 | 23.422 | 1.00 | 41.18 |
| ATOM | 3974 | CG | ARG | 1105 | 105.100 | 63.589 | 22.822 | 1.00 | 48.61 |
| ATOM | 3975 | CD | ARG | 1105 | 105.767 | 62.842 | 21.689 | 1.00 | 54.64 |
| ATOM | 3976 | NE | ARG | 1105 | 106.570 | 63.746 | 20.872 | 1.00 | 59.97 |
| ATOM | 3977 | CZ | ARG | 1105 | 106.096 | 64.448 | 19.845 | 1.00 | 63.88 |
| ATOM | 3978 | NH1 | ARG | 1105 | 104.816 | 64.349 | 19.494 | 1.00 | 63.25 |
| ATOM | 3979 | NH2 | ARG | 1105 | 106.899 | 65.269 | 19.180 | 1.00 | 67.43 |
| ATOM | 3980 | C | ARG | 1105 | 102.572 | 64.848 | 23.552 | 1.00 | 35.76 |
| ATOM | 3981 | O | ARG | 1105 | 102.880 | 65.968 | 23.966 | 1.00 | 34.77 |
| ATOM | 3982 | N | LYS | 1106 | 101.805 | 64.649 | 22.485 | 1.00 | 34.78 |
| ATOM | 3983 | CA | LYS | 1106 | 101.301 | 65.747 | 21.669 | 1.00 | 34.00 |
| ATOM | 3984 | CB | LYS | 1106 | 100.467 | 65.198 | 20.514 | 1.00 | 32.67 |
| ATOM | 3985 | CG | LYS | 1106 | 101.212 | 64.189 | 19.670 | 1.00 | 31.83 |
| ATOM | 3986 | CD | LYS | 1106 | 100.416 | 63.780 | 18.457 | 1.00 | 34.20 |
| ATOM | 3987 | CE | LYS | 1106 | 99.090 | 63.176 | 18.846 | 1.00 | 39.46 |
| ATOM | 3988 | NZ | LYS | 1106 | 98.374 | 62.649 | 17.655 | 1.00 | 43.75 |
| ATOM | 3989 | C | LYS | 1106 | 100.485 | 66.760 | 22.465 | 1.00 | 34.26 |
| ATOM | 3990 | O | LYS | 1106 | 100.459 | 67.946 | 22.128 | 1.00 | 35.05 |
| ATOM | 3991 | N | VAL | 1107 | 99.808 | 66.293 | 23.510 | 1.00 | 33.42 |
| ATOM | 3992 | CA | VAL | 1107 | 99.002 | 67.178 | 24.338 | 1.00 | 33.04 |
| ATOM | 3993 | CB | VAL | 1107 | 97.977 | 66.394 | 25.195 | 1.00 | 29.85 |
| ATOM | 3994 | CG1 | VAL | 1107 | 97.189 | 67.340 | 26.089 | 1.00 | 24.12 |
| ATOM | 3995 | CG2 | VAL | 1107 | 97.031 | 65.624 | 24.302 | 1.00 | 30.73 |
| ATOM | 3996 | C | VAL | 1107 | 99.920 | 67.967 | 25.258 | 1.00 | 35.29 |
| ATOM | 3997 | O | VAL | 1107 | 99.868 | 69.196 | 25.300 | 1.00 | 36.49 |
| ATOM | 3998 | N | LYS | 1108 | 100.793 | 67.258 | 25.959 | 1.00 | 36.76 |
| ATOM | 3999 | CA | LYS | 1108 | 101.710 | 67.892 | 26.888 | 1.00 | 38.65 |
| ATOM | 4000 | CB | LYS | 1108 | 102.483 | 66.838 | 27.673 | 1.00 | 37.67 |
| ATOM | 4001 | CG | LYS | 1108 | 101.612 | 66.008 | 28.598 | 1.00 | 36.98 |
| ATOM | 4002 | CD | LYS | 1108 | 100.862 | 66.881 | 29.597 | 1.00 | 36.47 |
| ATOM | 4003 | CE | LYS | 1108 | 101.809 | 67.684 | 30.471 | 1.00 | 36.82 |
| ATOM | 4004 | NZ | LYS | 1108 | 101.090 | 68.507 | 31.484 | 1.00 | 38.27 |
| ATOM | 4005 | C | LYS | 1108 | 102.663 | 68.859 | 26.208 | 1.00 | 41.58 |
| ATOM | 4006 | O | LYS | 1108 | 103.097 | 69.835 | 26.821 | 1.00 | 41.70 |
| ATOM | 4007 | N | LYS | 1109 | 102.970 | 68.598 | 24.939 | 1.00 | 44.26 |
| ATOM | 4008 | CA | LYS | 1109 | 103.866 | 69.457 | 24.172 | 1.00 | 46.63 |
| ATOM | 4009 | CB | LYS | 1109 | 104.735 | 68.625 | 23.227 | 1.00 | 48.92 |

FIG. 1A-69

| ATOM | 4010 | CG | LYS | 1109 | 105.765 | 67.752 | 23.925 | 1.00 | 55.10 |
|---|---|---|---|---|---|---|---|---|---|
| ATOM | 4011 | CD | LYS | 1109 | 106.649 | 67.038 | 22.917 | 1.00 | 57.86 |
| ATOM | 4012 | CE | LYS | 1109 | 107.698 | 66.190 | 23.607 | 1.00 | 60.67 |
| ATOM | 4013 | NZ | LYS | 1109 | 108.539 | 65.453 | 22.624 | 1.00 | 64.20 |
| ATOM | 4014 | C | LYS | 1109 | 103.116 | 70.503 | 23.361 | 1.00 | 48.09 |
| ATOM | 4015 | O | LYS | 1109 | 103.704 | 71.143 | 22.494 | 1.00 | 50.31 |
| ATOM | 4016 | N | TYR | 1110 | 101.823 | 70.671 | 23.622 | 1.00 | 49.80 |
| ATOM | 4017 | CA | TYR | 1110 | 101.032 | 71.647 | 22.883 | 1.00 | 50.56 |
| ATOM | 4018 | CB | TYR | 1110 | 99.526 | 71.410 | 23.054 | 1.00 | 49.06 |
| ATOM | 4019 | CG | TYR | 1110 | 98.671 | 72.376 | 22.240 | 1.00 | 45.63 |
| ATOM | 4020 | CD1 | TYR | 1110 | 98.377 | 72.117 | 20.902 | 1.00 | 42.22 |
| ATOM | 4021 | CE1 | TYR | 1110 | 97.615 | 73.001 | 20.145 | 1.00 | 39.41 |
| ATOM | 4022 | CD2 | TYR | 1110 | 98.172 | 73.556 | 22.805 | 1.00 | 41.44 |
| ATOM | 4023 | CE2 | TYR | 1110 | 97.410 | 74.449 | 22.053 | 1.00 | 38.41 |
| ATOM | 4024 | CZ | TYR | 1110 | 97.135 | 74.162 | 20.723 | 1.00 | 39.73 |
| ATOM | 4025 | OH | TYR | 1110 | 96.377 | 75.028 | 19.969 | 1.00 | 42.38 |
| ATOM | 4026 | C | TYR | 1110 | 101.338 | 73.080 | 23.262 | 1.00 | 52.16 |
| ATOM | 4027 | O | TYR | 1110 | 101.405 | 73.433 | 24.436 | 1.00 | 50.66 |
| ATOM | 4028 | N | GLU | 1111 | 101.470 | 73.909 | 22.238 | 1.00 | 56.35 |
| ATOM | 4029 | CA | GLU | 1111 | 101.726 | 75.326 | 22.407 | 1.00 | 62.85 |
| ATOM | 4030 | CB | GLU | 1111 | 103.170 | 75.580 | 22.846 | 1.00 | 68.99 |
| ATOM | 4031 | CG | GLU | 1111 | 103.473 | 77.039 | 23.221 | 1.00 | 78.92 |
| ATOM | 4032 | CD | GLU | 1111 | 102.841 | 77.479 | 24.544 | 1.00 | 86.72 |
| ATOM | 4033 | OE1 | GLU | 1111 | 103.602 | 77.833 | 25.476 | 1.00 | 88.71 |
| ATOM | 4034 | OE2 | GLU | 1111 | 101.591 | 77.492 | 24.650 | 1.00 | 89.94 |
| ATOM | 4035 | C | GLU | 1111 | 101.456 | 75.977 | 21.063 | 1.00 | 64.72 |
| ATOM | 4036 | O | GLU | 1111 | 102.047 | 75.595 | 20.049 | 1.00 | 64.03 |
| ATOM | 4037 | N | GLN | 1112 | 100.489 | 76.890 | 21.049 | 1.00 | 67.72 |
| ATOM | 4038 | CA | GLN | 1112 | 100.103 | 77.616 | 19.842 | 1.00 | 71.20 |
| ATOM | 4039 | CB | GLN | 1112 | 99.391 | 76.686 | 18.850 | 1.00 | 74.46 |
| ATOM | 4040 | CG | GLN | 1112 | 99.112 | 77.314 | 17.482 | 1.00 | 77.35 |
| ATOM | 4041 | CD | GLN | 1112 | 98.260 | 76.426 | 16.589 | 1.00 | 78.90 |
| ATOM | 4042 | OE1 | GLN | 1112 | 97.039 | 76.566 | 16.542 | 1.00 | 79.16 |
| ATOM | 4043 | NE2 | GLN | 1112 | 98.901 | 75.505 | 15.876 | 1.00 | 79.35 |
| ATOM | 4044 | C | GLN | 1112 | 99.168 | 78.752 | 20.240 | 1.00 | 71.94 |
| ATOM | 4045 | O | GLN | 1112 | 98.417 | 78.542 | 21.217 | 1.00 | 72.65 |
| ATOM | 4046 | CB | TYR | 1233 | 92.594 | 79.434 | 26.175 | 1.00 | 39.31 |
| ATOM | 4047 | CG | TYR | 1233 | 92.140 | 78.944 | 24.817 | 1.00 | 39.59 |
| ATOM | 4048 | CD1 | TYR | 1233 | 90.810 | 78.606 | 24.585 | 1.00 | 39.63 |
| ATOM | 4049 | CE1 | TYR | 1233 | 90.390 | 78.142 | 23.339 | 1.00 | 42.81 |
| ATOM | 4050 | CD2 | TYR | 1233 | 93.045 | 78.808 | 23.766 | 1.00 | 42.38 |
| ATOM | 4051 | CE2 | TYR | 1233 | 92.637 | 78.345 | 22.511 | 1.00 | 42.93 |
| ATOM | 4052 | CZ | TYR | 1233 | 91.306 | 78.015 | 22.306 | 1.00 | 42.57 |
| ATOM | 4053 | OH | TYR | 1233 | 90.884 | 77.574 | 21.072 | 1.00 | 41.24 |
| ATOM | 4054 | C | TYR | 1233 | 92.326 | 81.012 | 28.108 | 1.00 | 34.30 |
| ATOM | 4055 | O | TYR | 1233 | 93.223 | 80.365 | 28.647 | 1.00 | 35.38 |
| ATOM | 4056 | N | TYR | 1233 | 92.175 | 81.859 | 25.767 | 1.00 | 37.90 |
| ATOM | 4057 | CA | TYR | 1233 | 91.886 | 80.707 | 26.674 | 1.00 | 36.86 |
| ATOM | 4058 | N | PRO | 1234 | 91.675 | 81.987 | 28.757 | 1.00 | 31.05 |
| ATOM | 4059 | CD | PRO | 1234 | 90.523 | 82.770 | 28.281 | 1.00 | 31.27 |
| ATOM | 4060 | CA | PRO | 1234 | 92.027 | 82.350 | 30.133 | 1.00 | 28.70 |
| ATOM | 4061 | CB | PRO | 1234 | 91.180 | 83.594 | 30.376 | 1.00 | 29.55 |
| ATOM | 4062 | CG | PRO | 1234 | 89.951 | 83.318 | 29.567 | 1.00 | 31.87 |
| ATOM | 4063 | C | PRO | 1234 | 91.729 | 81.267 | 31.164 | 1.00 | 27.05 |
| ATOM | 4064 | O | PRO | 1234 | 92.097 | 81.409 | 32.327 | 1.00 | 24.79 |
| ATOM | 4065 | N | LEU | 1235 | 91.013 | 80.224 | 30.740 | 1.00 | 28.44 |
| ATOM | 4066 | CA | LEU | 1235 | 90.639 | 79.101 | 31.607 | 1.00 | 27.99 |
| ATOM | 4067 | CB | LEU | 1235 | 89.174 | 78.715 | 31.406 | 1.00 | 27.25 |
| ATOM | 4068 | CG | LEU | 1235 | 88.100 | 79.751 | 31.680 | 1.00 | 25.62 |

FIG. 1A-70

| ATOM | 4069 | CD1 | LEU | 1235 | 86.739 | 79.084 | 31.530 | 1.00 | 24.42 |
|---|---|---|---|---|---|---|---|---|---|
| ATOM | 4070 | CD2 | LEU | 1235 | 88.292 | 80.323 | 33.078 | 1.00 | 26.15 |
| ATOM | 4071 | C | LEU | 1235 | 91.466 | 77.876 | 31.299 | 1.00 | 28.14 |
| ATOM | 4072 | O | LEU | 1235 | 91.308 | 76.835 | 31.944 | 1.00 | 25.67 |
| ATOM | 4073 | N | ALA | 1236 | 92.279 | 77.979 | 30.253 | 1.00 | 29.94 |
| ATOM | 4074 | CA | ALA | 1236 | 93.130 | 76.884 | 29.843 | 1.00 | 31.57 |
| ATOM | 4075 | CB | ALA | 1236 | 94.179 | 77.373 | 28.891 | 1.00 | 32.74 |
| ATOM | 4076 | C | ALA | 1236 | 93.765 | 76.314 | 31.094 | 1.00 | 33.80 |
| ATOM | 4077 | O | ALA | 1236 | 94.304 | 77.050 | 31.926 | 1.00 | 34.29 |
| ATOM | 4078 | N | SER | 1237 | 93.574 | 75.020 | 31.288 | 1.00 | 35.41 |
| ATOM | 4079 | CA | SER | 1237 | 94.118 | 74.352 | 32.445 | 1.00 | 39.00 |
| ATOM | 4080 | CB | SER | 1237 | 93.041 | 73.452 | 33.068 | 1.00 | 42.92 |
| ATOM | 4081 | OG | SER | 1237 | 91.989 | 74.237 | 33.636 | 1.00 | 43.86 |
| ATOM | 4082 | C | SER | 1237 | 95.401 | 73.599 | 32.085 | 1.00 | 39.38 |
| ATOM | 4083 | O | SER | 1237 | 95.403 | 72.668 | 31.270 | 1.00 | 39.77 |
| ATOM | 4084 | N | LYS | 1238 | 96.507 | 74.064 | 32.656 | 1.00 | 39.71 |
| ATOM | 4085 | CA | LYS | 1238 | 97.813 | 73.474 | 32.413 | 1.00 | 41.61 |
| ATOM | 4086 | CB | LYS | 1238 | 98.587 | 74.304 | 31.382 | 1.00 | 43.64 |
| ATOM | 4087 | CG | LYS | 1238 | 98.336 | 75.804 | 31.401 | 1.00 | 46.63 |
| ATOM | 4088 | CD | LYS | 1238 | 98.532 | 76.385 | 29.993 | 1.00 | 49.43 |
| ATOM | 4089 | CE | LYS | 1238 | 98.469 | 77.915 | 29.954 | 1.00 | 52.17 |
| ATOM | 4090 | NZ | LYS | 1238 | 97.166 | 78.480 | 30.418 | 1.00 | 53.93 |
| ATOM | 4091 | C | LYS | 1238 | 98.611 | 73.306 | 33.697 | 1.00 | 41.85 |
| ATOM | 4092 | O | LYS | 1238 | 98.215 | 73.815 | 34.745 | 1.00 | 42.33 |
| ATOM | 4093 | N | ASP | 1239 | 99.695 | 72.538 | 33.627 | 1.00 | 42.02 |
| ATOM | 4094 | CA | ASP | 1239 | 100.541 | 72.289 | 34.788 | 1.00 | 43.25 |
| ATOM | 4095 | CB | ASP | 1239 | 101.277 | 70.950 | 34.637 | 1.00 | 42.65 |
| ATOM | 4096 | CG | ASP | 1239 | 102.252 | 70.933 | 33.470 | 1.00 | 41.63 |
| ATOM | 4097 | OD1 | ASP | 1239 | 102.274 | 71.902 | 32.694 | 1.00 | 43.12 |
| ATOM | 4098 | OD2 | ASP | 1239 | 103.007 | 69.946 | 33.328 | 1.00 | 41.56 |
| ATOM | 4099 | C | ASP | 1239 | 101.534 | 73.416 | 35.085 | 1.00 | 45.87 |
| ATOM | 4100 | O | ASP | 1239 | 101.579 | 74.430 | 34.381 | 1.00 | 46.72 |
| ATOM | 4101 | N | ALA | 1240 | 102.364 | 73.196 | 36.104 | 1.00 | 46.78 |
| ATOM | 4102 | CA | ALA | 1240 | 103.370 | 74.162 | 36.548 | 1.00 | 46.30 |
| ATOM | 4103 | CB | ALA | 1240 | 104.203 | 73.562 | 37.676 | 1.00 | 46.81 |
| ATOM | 4104 | C | ALA | 1240 | 104.282 | 74.683 | 35.439 | 1.00 | 45.64 |
| ATOM | 4105 | O | ALA | 1240 | 104.675 | 75.851 | 35.446 | 1.00 | 46.51 |
| ATOM | 4106 | N | LYS | 1241 | 104.628 | 73.816 | 34.495 | 1.00 | 43.50 |
| ATOM | 4107 | CA | LYS | 1241 | 105.486 | 74.216 | 33.391 | 1.00 | 41.50 |
| ATOM | 4108 | CB | LYS | 1241 | 106.327 | 73.028 | 32.927 | 1.00 | 42.33 |
| ATOM | 4109 | CG | LYS | 1241 | 107.198 | 72.458 | 34.040 | 1.00 | 45.75 |
| ATOM | 4110 | CD | LYS | 1241 | 108.136 | 71.364 | 33.549 | 1.00 | 52.02 |
| ATOM | 4111 | CE | LYS | 1241 | 107.394 | 70.096 | 33.147 | 1.00 | 56.80 |
| ATOM | 4112 | NZ | LYS | 1241 | 108.330 | 69.053 | 32.625 | 1.00 | 59.79 |
| ATOM | 4113 | C | LYS | 1241 | 104.668 | 74.808 | 32.246 | 1.00 | 40.64 |
| ATOM | 4114 | O | LYS | 1241 | 105.119 | 74.850 | 31.102 | 1.00 | 39.48 |
| ATOM | 4115 | N | LYS | 1242 | 103.451 | 75.244 | 32.575 | 1.00 | 40.74 |
| ATOM | 4116 | CA | LYS | 1242 | 102.525 | 75.863 | 31.635 | 1.00 | 40.98 |
| ATOM | 4117 | CB | LYS | 1242 | 103.130 | 77.162 | 31.102 | 1.00 | 46.48 |
| ATOM | 4118 | CG | LYS | 1242 | 103.655 | 78.106 | 32.184 | 1.00 | 54.66 |
| ATOM | 4119 | CD | LYS | 1242 | 104.504 | 79.227 | 31.567 | 1.00 | 63.33 |
| ATOM | 4120 | CE | LYS | 1242 | 105.116 | 80.153 | 32.623 | 1.00 | 68.01 |
| ATOM | 4121 | NZ | LYS | 1242 | 106.121 | 79.459 | 33.488 | 1.00 | 71.11 |
| ATOM | 4122 | C | LYS | 1242 | 102.068 | 74.977 | 30.471 | 1.00 | 40.38 |
| ATOM | 4123 | O | LYS | 1242 | 101.545 | 75.471 | 29.472 | 1.00 | 40.63 |
| ATOM | 4124 | N | GLN | 1243 | 102.281 | 73.672 | 30.582 | 1.00 | 38.45 |
| ATOM | 4125 | CA | GLN | 1243 | 101.863 | 72.749 | 29.531 | 1.00 | 37.94 |
| ATOM | 4126 | CB | GLN | 1243 | 102.905 | 71.640 | 29.338 | 1.00 | 42.14 |
| ATOM | 4127 | CG | GLN | 1243 | 104.293 | 72.126 | 28.894 | 1.00 | 50.87 |

FIG. 1A-71

| ATOM | 4128 | CD  | GLN | 1243 | 104.296 | 72.805 | 27.516 | 1.00 | 58.97 |
| ---- | ---- | --- | --- | ---- | ------- | ------ | ------ | ---- | ----- |
| ATOM | 4129 | OE1 | GLN | 1243 | 104.790 | 72.248 | 26.533 | 1.00 | 61.73 |
| ATOM | 4130 | NE2 | GLN | 1243 | 103.777 | 74.026 | 27.454 | 1.00 | 61.92 |
| ATOM | 4131 | C   | GLN | 1243 | 100.502 | 72.162 | 29.907 | 1.00 | 35.65 |
| ATOM | 4132 | O   | GLN | 1243 | 100.286 | 71.781 | 31.059 | 1.00 | 34.91 |
| ATOM | 4133 | N   | LEU | 1244 | 99.577  | 72.130 | 28.949 | 1.00 | 33.29 |
| ATOM | 4134 | CA  | LEU | 1244 | 98.221  | 71.614 | 29.176 | 1.00 | 29.46 |
| ATOM | 4135 | CB  | LEU | 1244 | 97.495  | 71.389 | 27.848 | 1.00 | 27.97 |
| ATOM | 4136 | CG  | LEU | 1244 | 97.232  | 72.570 | 26.922 | 1.00 | 25.53 |
| ATOM | 4137 | CD1 | LEU | 1244 | 96.497  | 72.069 | 25.701 | 1.00 | 23.64 |
| ATOM | 4138 | CD2 | LEU | 1244 | 96.426  | 73.639 | 27.631 | 1.00 | 26.68 |
| ATOM | 4139 | C   | LEU | 1244 | 98.174  | 70.315 | 29.964 | 1.00 | 26.37 |
| ATOM | 4140 | O   | LEU | 1244 | 98.990  | 69.423 | 29.759 | 1.00 | 25.40 |
| ATOM | 4141 | N   | LEU | 1245 | 97.203  | 70.208 | 30.861 | 1.00 | 24.19 |
| ATOM | 4142 | CA  | LEU | 1245 | 97.043  | 69.000 | 31.654 | 1.00 | 21.24 |
| ATOM | 4143 | CB  | LEU | 1245 | 96.010  | 69.226 | 32.750 | 1.00 | 17.87 |
| ATOM | 4144 | CG  | LEU | 1245 | 96.388  | 70.166 | 33.886 | 1.00 | 13.30 |
| ATOM | 4145 | CD1 | LEU | 1245 | 95.278  | 70.190 | 34.957 | 1.00 | 8.28  |
| ATOM | 4146 | CD2 | LEU | 1245 | 97.692  | 69.691 | 34.476 | 1.00 | 12.89 |
| ATOM | 4147 | C   | LEU | 1245 | 96.577  | 67.851 | 30.760 | 1.00 | 22.73 |
| ATOM | 4148 | O   | LEU | 1245 | 95.875  | 68.067 | 29.772 | 1.00 | 22.07 |
| ATOM | 4149 | N   | CYS | 1246 | 96.970  | 66.631 | 31.097 | 1.00 | 23.09 |
| ATOM | 4150 | CA  | CYS | 1246 | 96.561  | 65.481 | 30.311 | 1.00 | 24.22 |
| ATOM | 4151 | CB  | CYS | 1246 | 97.564  | 65.167 | 29.213 | 1.00 | 23.07 |
| ATOM | 4152 | SG  | CYS | 1246 | 96.980  | 63.858 | 28.114 | 1.00 | 28.22 |
| ATOM | 4153 | C   | CYS | 1246 | 96.409  | 64.271 | 31.199 | 1.00 | 25.46 |
| ATOM | 4154 | O   | CYS | 1246 | 97.177  | 64.087 | 32.149 | 1.00 | 26.61 |
| ATOM | 4155 | N   | GLY | 1247 | 95.405  | 63.457 | 30.899 | 1.00 | 24.77 |
| ATOM | 4156 | CA  | GLY | 1247 | 95.159  | 62.257 | 31.669 | 1.00 | 23.54 |
| ATOM | 4157 | C   | GLY | 1247 | 95.056  | 61.081 | 30.724 | 1.00 | 22.83 |
| ATOM | 4158 | O   | GLY | 1247 | 94.823  | 61.260 | 29.525 | 1.00 | 22.59 |
| ATOM | 4159 | N   | ALA | 1248 | 95.230  | 59.878 | 31.252 | 1.00 | 20.75 |
| ATOM | 4160 | CA  | ALA | 1248 | 95.150  | 58.678 | 30.437 | 1.00 | 20.33 |
| ATOM | 4161 | CB  | ALA | 1248 | 96.536  | 58.256 | 29.990 | 1.00 | 21.90 |
| ATOM | 4162 | C   | ALA | 1248 | 94.485  | 57.561 | 31.222 | 1.00 | 20.51 |
| ATOM | 4163 | O   | ALA | 1248 | 94.619  | 57.473 | 32.447 | 1.00 | 18.34 |
| ATOM | 4164 | N   | ALA | 1249 | 93.740  | 56.727 | 30.514 | 1.00 | 20.76 |
| ATOM | 4165 | CA  | ALA | 1249 | 93.050  | 55.622 | 31.140 | 1.00 | 22.52 |
| ATOM | 4166 | CB  | ALA | 1249 | 91.670  | 55.477 | 30.543 | 1.00 | 22.47 |
| ATOM | 4167 | C   | ALA | 1249 | 93.825  | 54.342 | 30.928 | 1.00 | 24.15 |
| ATOM | 4168 | O   | ALA | 1249 | 94.183  | 54.019 | 29.790 | 1.00 | 25.00 |
| ATOM | 4169 | N   | ILE | 1250 | 94.105  | 53.616 | 32.005 | 1.00 | 23.49 |
| ATOM | 4170 | CA  | ILE | 1250 | 94.794  | 52.341 | 31.860 | 1.00 | 24.48 |
| ATOM | 4171 | CB  | ILE | 1250 | 96.254  | 52.330 | 32.417 | 1.00 | 22.98 |
| ATOM | 4172 | CG2 | ILE | 1250 | 97.088  | 53.412 | 31.760 | 1.00 | 24.80 |
| ATOM | 4173 | CG1 | ILE | 1250 | 96.276  | 52.433 | 33.939 | 1.00 | 20.21 |
| ATOM | 4174 | CD1 | ILE | 1250 | 97.629  | 52.107 | 34.530 | 1.00 | 18.03 |
| ATOM | 4175 | C   | ILE | 1250 | 93.999  | 51.227 | 32.520 | 1.00 | 25.11 |
| ATOM | 4176 | O   | ILE | 1250 | 93.044  | 51.476 | 33.253 | 1.00 | 21.56 |
| ATOM | 4177 | N   | GLY | 1251 | 94.337  | 49.998 | 32.156 | 1.00 | 29.40 |
| ATOM | 4178 | CA  | GLY | 1251 | 93.693  | 48.842 | 32.740 | 1.00 | 32.82 |
| ATOM | 4179 | C   | GLY | 1251 | 94.479  | 48.532 | 33.996 | 1.00 | 36.17 |
| ATOM | 4180 | O   | GLY | 1251 | 95.271  | 49.350 | 34.451 | 1.00 | 38.38 |
| ATOM | 4181 | N   | THR | 1252 | 94.345  | 47.326 | 34.513 | 1.00 | 39.63 |
| ATOM | 4182 | CA  | THR | 1252 | 95.060  | 46.990 | 35.725 | 1.00 | 43.76 |
| ATOM | 4183 | CB  | THR | 1252 | 94.057  | 46.575 | 36.818 | 1.00 | 41.72 |
| ATOM | 4184 | OG1 | THR | 1252 | 93.203  | 47.687 | 37.124 | 1.00 | 37.90 |
| ATOM | 4185 | CG2 | THR | 1252 | 94.771  | 46.155 | 38.066 | 1.00 | 47.51 |
| ATOM | 4186 | C   | THR | 1252 | 96.179  | 45.956 | 35.538 | 1.00 | 48.10 |

FIG. 1A-72

| | | | | | | | | |
|---|---|---|---|---|---|---|---|---|
| ATOM | 4187 | O | THR | 1252 | 97.349 | 46.256 | 35.772 | 1.00 | 48.88 |
| ATOM | 4188 | N | HIS | 1253 | 95.825 | 44.772 | 35.047 | 1.00 | 51.97 |
| ATOM | 4189 | CA | HIS | 1253 | 96.790 | 43.689 | 34.844 | 1.00 | 56.55 |
| ATOM | 4190 | CB | HIS | 1253 | 96.197 | 42.583 | 33.956 | 1.00 | 63.58 |
| ATOM | 4191 | CG | HIS | 1253 | 95.708 | 43.060 | 32.625 | 1.00 | 71.59 |
| ATOM | 4192 | CD2 | HIS | 1253 | 94.873 | 44.069 | 32.288 | 1.00 | 76.45 |
| ATOM | 4193 | ND1 | HIS | 1253 | 96.072 | 42.451 | 31.439 | 1.00 | 77.55 |
| ATOM | 4194 | CE1 | HIS | 1253 | 95.480 | 43.071 | 30.431 | 1.00 | 81.02 |
| ATOM | 4195 | NE2 | HIS | 1253 | 94.749 | 44.055 | 30.917 | 1.00 | 80.91 |
| ATOM | 4196 | C | HIS | 1253 | 98.173 | 44.083 | 34.334 | 1.00 | 56.12 |
| ATOM | 4197 | O | HIS | 1253 | 98.295 | 44.864 | 33.398 | 1.00 | 56.78 |
| ATOM | 4198 | N | GLU | 1254 | 99.191 | 43.495 | 34.963 | 1.00 | 56.64 |
| ATOM | 4199 | CA | GLU | 1254 | 100.617 | 43.690 | 34.672 | 1.00 | 56.02 |
| ATOM | 4200 | CB | GLU | 1254 | 101.309 | 42.329 | 34.570 | 1.00 | 57.76 |
| ATOM | 4201 | CG | GLU | 1254 | 101.379 | 41.554 | 35.879 | 1.00 | 61.36 |
| ATOM | 4202 | CD | GLU | 1254 | 102.378 | 42.136 | 36.867 | 1.00 | 64.92 |
| ATOM | 4203 | OE1 | GLU | 1254 | 103.524 | 42.443 | 36.458 | 1.00 | 64.68 |
| ATOM | 4204 | OE2 | GLU | 1254 | 102.016 | 42.270 | 38.058 | 1.00 | 66.93 |
| ATOM | 4205 | C | GLU | 1254 | 101.009 | 44.525 | 33.462 | 1.00 | 53.65 |
| ATOM | 4206 | O | GLU | 1254 | 101.767 | 45.480 | 33.582 | 1.00 | 53.34 |
| ATOM | 4207 | N | ASP | 1255 | 100.532 | 44.113 | 32.294 | 1.00 | 52.31 |
| ATOM | 4208 | CA | ASP | 1255 | 100.803 | 44.782 | 31.024 | 1.00 | 50.29 |
| ATOM | 4209 | CB | ASP | 1255 | 99.804 | 44.290 | 29.973 | 1.00 | 55.04 |
| ATOM | 4210 | CG | ASP | 1255 | 99.626 | 42.775 | 29.993 | 1.00 | 61.28 |
| ATOM | 4211 | OD1 | ASP | 1255 | 98.900 | 42.259 | 30.881 | 1.00 | 59.30 |
| ATOM | 4212 | OD2 | ASP | 1255 | 100.220 | 42.105 | 29.118 | 1.00 | 65.78 |
| ATOM | 4213 | C | ASP | 1255 | 100.695 | 46.301 | 31.129 | 1.00 | 47.04 |
| ATOM | 4214 | O | ASP | 1255 | 101.447 | 47.039 | 30.490 | 1.00 | 46.57 |
| ATOM | 4215 | N | ASP | 1256 | 99.768 | 46.752 | 31.967 | 1.00 | 44.52 |
| ATOM | 4216 | CA | ASP | 1256 | 99.501 | 48.173 | 32.171 | 1.00 | 41.04 |
| ATOM | 4217 | CB | ASP | 1256 | 98.142 | 48.352 | 32.847 | 1.00 | 39.06 |
| ATOM | 4218 | CG | ASP | 1256 | 97.012 | 47.813 | 32.003 | 1.00 | 36.49 |
| ATOM | 4219 | OD1 | ASP | 1256 | 96.720 | 48.422 | 30.955 | 1.00 | 32.75 |
| ATOM | 4220 | OD2 | ASP | 1256 | 96.432 | 46.769 | 32.368 | 1.00 | 37.91 |
| ATOM | 4221 | C | ASP | 1256 | 100.584 | 48.924 | 32.920 | 1.00 | 37.97 |
| ATOM | 4222 | O | ASP | 1256 | 100.585 | 50.153 | 32.945 | 1.00 | 35.60 |
| ATOM | 4223 | N | LYS | 1257 | 101.505 | 48.180 | 33.520 | 1.00 | 37.65 |
| ATOM | 4224 | CA | LYS | 1257 | 102.619 | 48.765 | 34.253 | 1.00 | 36.92 |
| ATOM | 4225 | CB | LYS | 1257 | 103.325 | 47.693 | 35.078 | 1.00 | 36.40 |
| ATOM | 4226 | CG | LYS | 1257 | 102.465 | 47.092 | 36.172 | 1.00 | 37.53 |
| ATOM | 4227 | CD | LYS | 1257 | 103.251 | 46.074 | 36.978 | 1.00 | 41.41 |
| ATOM | 4228 | CE | LYS | 1257 | 102.581 | 45.760 | 38.309 | 1.00 | 43.29 |
| ATOM | 4229 | NZ | LYS | 1257 | 101.232 | 45.166 | 38.132 | 1.00 | 47.58 |
| ATOM | 4230 | C | LYS | 1257 | 103.590 | 49.406 | 33.258 | 1.00 | 36.36 |
| ATOM | 4231 | O | LYS | 1257 | 104.009 | 50.554 | 33.431 | 1.00 | 34.55 |
| ATOM | 4232 | N | TYR | 1258 | 103.911 | 48.678 | 32.193 | 1.00 | 36.40 |
| ATOM | 4233 | CA | TYR | 1258 | 104.809 | 49.189 | 31.164 | 1.00 | 36.55 |
| ATOM | 4234 | CB | TYR | 1258 | 105.067 | 48.121 | 30.108 | 1.00 | 36.16 |
| ATOM | 4235 | CG | TYR | 1258 | 105.807 | 48.636 | 28.901 | 1.00 | 37.86 |
| ATOM | 4236 | CD1 | TYR | 1258 | 107.115 | 49.115 | 29.004 | 1.00 | 37.73 |
| ATOM | 4237 | CE1 | TYR | 1258 | 107.794 | 49.573 | 27.883 | 1.00 | 39.68 |
| ATOM | 4238 | CD2 | TYR | 1258 | 105.203 | 48.630 | 27.648 | 1.00 | 41.35 |
| ATOM | 4239 | CE2 | TYR | 1258 | 105.872 | 49.084 | 26.525 | 1.00 | 42.25 |
| ATOM | 4240 | CZ | TYR | 1258 | 107.162 | 49.548 | 26.644 | 1.00 | 42.30 |
| ATOM | 4241 | OH | TYR | 1258 | 107.808 | 49.978 | 25.510 | 1.00 | 46.56 |
| ATOM | 4242 | C | TYR | 1258 | 104.149 | 50.402 | 30.525 | 1.00 | 37.00 |
| ATOM | 4243 | O | TYR | 1258 | 104.794 | 51.427 | 30.276 | 1.00 | 39.78 |
| ATOM | 4244 | N | ARG | 1259 | 102.858 | 50.250 | 30.243 | 1.00 | 35.45 |
| ATOM | 4245 | CA | ARG | 1259 | 102.029 | 51.299 | 29.665 | 1.00 | 33.10 |

FIG. 1A-73

| ATOM | 4246 | CB | ARG | 1259 | 100.571 | 50.829 | 29.669 | 1.00 | 35.78 |
|---|---|---|---|---|---|---|---|---|---|
| ATOM | 4247 | CG | ARG | 1259 | 99.531 | 51.895 | 29.376 | 1.00 | 37.91 |
| ATOM | 4248 | CD | ARG | 1259 | 99.265 | 52.018 | 27.901 | 1.00 | 35.20 |
| ATOM | 4249 | NE | ARG | 1259 | 98.672 | 50.807 | 27.350 | 1.00 | 32.06 |
| ATOM | 4250 | CZ | ARG | 1259 | 97.749 | 50.790 | 26.396 | 1.00 | 26.80 |
| ATOM | 4251 | NH1 | ARG | 1259 | 97.295 | 51.923 | 25.883 | 1.00 | 25.25 |
| ATOM | 4252 | NH2 | ARG | 1259 | 97.331 | 49.634 | 25.907 | 1.00 | 23.32 |
| ATOM | 4253 | C | ARG | 1259 | 102.169 | 52.521 | 30.558 | 1.00 | 30.96 |
| ATOM | 4254 | O | ARG | 1259 | 102.497 | 53.609 | 30.098 | 1.00 | 31.64 |
| ATOM | 4255 | N | LEU | 1260 | 101.983 | 52.309 | 31.853 | 1.00 | 30.09 |
| ATOM | 4256 | CA | LEU | 1260 | 102.087 | 53.382 | 32.820 | 1.00 | 30.15 |
| ATOM | 4257 | CB | LEU | 1260 | 101.862 | 52.848 | 34.237 | 1.00 | 26.22 |
| ATOM | 4258 | CG | LEU | 1260 | 101.775 | 53.919 | 35.324 | 1.00 | 28.20 |
| ATOM | 4259 | CD1 | LEU | 1260 | 100.640 | 54.876 | 34.984 | 1.00 | 28.15 |
| ATOM | 4260 | CD2 | LEU | 1260 | 101.578 | 53.289 | 36.698 | 1.00 | 23.65 |
| ATOM | 4261 | C | LEU | 1260 | 103.453 | 54.058 | 32.704 | 1.00 | 31.69 |
| ATOM | 4262 | O | LEU | 1260 | 103.545 | 55.285 | 32.784 | 1.00 | 31.52 |
| ATOM | 4263 | N | ASP | 1261 | 104.503 | 53.267 | 32.481 | 1.00 | 32.30 |
| ATOM | 4264 | CA | ASP | 1261 | 105.855 | 53.811 | 32.347 | 1.00 | 32.19 |
| ATOM | 4265 | CB | ASP | 1261 | 106.879 | 52.703 | 32.075 | 1.00 | 35.55 |
| ATOM | 4266 | CG | ASP | 1261 | 107.187 | 51.867 | 33.304 | 1.00 | 40.79 |
| ATOM | 4267 | OD1 | ASP | 1261 | 107.086 | 52.388 | 34.434 | 1.00 | 40.34 |
| ATOM | 4268 | OD2 | ASP | 1261 | 107.547 | 50.680 | 33.136 | 1.00 | 45.81 |
| ATOM | 4269 | C | ASP | 1261 | 105.918 | 54.821 | 31.212 | 1.00 | 31.49 |
| ATOM | 4270 | O | ASP | 1261 | 106.286 | 55.983 | 31.421 | 1.00 | 30.59 |
| ATOM | 4271 | N | LEU | 1262 | 105.520 | 54.377 | 30.021 | 1.00 | 28.76 |
| ATOM | 4272 | CA | LEU | 1262 | 105.536 | 55.225 | 28.836 | 1.00 | 27.39 |
| ATOM | 4273 | CB | LEU | 1262 | 105.089 | 54.431 | 27.606 | 1.00 | 25.44 |
| ATOM | 4274 | CG | LEU | 1262 | 105.782 | 53.082 | 27.388 | 1.00 | 20.68 |
| ATOM | 4275 | CD1 | LEU | 1262 | 105.355 | 52.486 | 26.063 | 1.00 | 16.25 |
| ATOM | 4276 | CD2 | LEU | 1262 | 107.284 | 53.263 | 27.435 | 1.00 | 19.30 |
| ATOM | 4277 | C | LEU | 1262 | 104.683 | 56.484 | 29.010 | 1.00 | 27.65 |
| ATOM | 4278 | O | LEU | 1262 | 105.096 | 57.578 | 28.616 | 1.00 | 28.28 |
| ATOM | 4279 | N | LEU | 1263 | 103.502 | 56.336 | 29.603 | 1.00 | 26.91 |
| ATOM | 4280 | CA | LEU | 1263 | 102.615 | 57.476 | 29.837 | 1.00 | 25.75 |
| ATOM | 4281 | CB | LEU | 1263 | 101.267 | 57.021 | 30.393 | 1.00 | 24.46 |
| ATOM | 4282 | CG | LEU | 1263 | 100.379 | 56.129 | 29.534 | 1.00 | 21.80 |
| ATOM | 4283 | CD1 | LEU | 1263 | 99.135 | 55.764 | 30.338 | 1.00 | 14.76 |
| ATOM | 4284 | CD2 | LEU | 1263 | 100.030 | 56.831 | 28.216 | 1.00 | 18.42 |
| ATOM | 4285 | C | LEU | 1263 | 103.254 | 58.430 | 30.833 | 1.00 | 25.07 |
| ATOM | 4286 | O | LEU | 1263 | 103.218 | 59.642 | 30.650 | 1.00 | 24.45 |
| ATOM | 4287 | N | ALA | 1264 | 103.811 | 57.867 | 31.901 | 1.00 | 26.55 |
| ATOM | 4288 | CA | ALA | 1264 | 104.469 | 58.643 | 32.945 | 1.00 | 27.92 |
| ATOM | 4289 | CB | ALA | 1264 | 105.004 | 57.727 | 34.030 | 1.00 | 26.27 |
| ATOM | 4290 | C | ALA | 1264 | 105.609 | 59.400 | 32.301 | 1.00 | 29.62 |
| ATOM | 4291 | O | ALA | 1264 | 105.830 | 60.578 | 32.587 | 1.00 | 31.44 |
| ATOM | 4292 | N | LEU | 1265 | 106.282 | 58.718 | 31.379 | 1.00 | 30.37 |
| ATOM | 4293 | CA | LEU | 1265 | 107.419 | 59.262 | 30.646 | 1.00 | 29.10 |
| ATOM | 4294 | CB | LEU | 1265 | 108.104 | 58.150 | 29.859 | 1.00 | 28.95 |
| ATOM | 4295 | CG | LEU | 1265 | 109.498 | 58.414 | 29.306 | 1.00 | 31.50 |
| ATOM | 4296 | CD1 | LEU | 1265 | 110.532 | 58.266 | 30.422 | 1.00 | 30.76 |
| ATOM | 4297 | CD2 | LEU | 1265 | 109.784 | 57.415 | 28.187 | 1.00 | 33.34 |
| ATOM | 4298 | C | LEU | 1265 | 106.980 | 60.354 | 29.683 | 1.00 | 28.32 |
| ATOM | 4299 | O | LEU | 1265 | 107.746 | 61.272 | 29.399 | 1.00 | 30.26 |
| ATOM | 4300 | N | ALA | 1266 | 105.766 | 60.221 | 29.151 | 1.00 | 27.20 |
| ATOM | 4301 | CA | ALA | 1266 | 105.212 | 61.196 | 28.209 | 1.00 | 24.22 |
| ATOM | 4302 | CB | ALA | 1266 | 104.134 | 60.554 | 27.352 | 1.00 | 23.15 |
| ATOM | 4303 | C | ALA | 1266 | 104.659 | 62.432 | 28.919 | 1.00 | 22.49 |
| ATOM | 4304 | O | ALA | 1266 | 104.268 | 63.399 | 28.267 | 1.00 | 21.03 |

FIG. 1A-74

| ATOM | 4305 | N | GLY | 1267 | 104.611 | 62.387 | 30.249 | 1.00 | 21.17 |
| --- | --- | --- | --- | --- | --- | --- | --- | --- | --- |
| ATOM | 4306 | CA | GLY | 1267 | 104.127 | 63.523 | 31.014 | 1.00 | 22.19 |
| ATOM | 4307 | C | GLY | 1267 | 102.648 | 63.543 | 31.355 | 1.00 | 22.76 |
| ATOM | 4308 | O | GLY | 1267 | 102.041 | 64.613 | 31.431 | 1.00 | 21.01 |
| ATOM | 4309 | N | VAL | 1268 | 102.065 | 62.372 | 31.591 | 1.00 | 23.69 |
| ATOM | 4310 | CA | VAL | 1268 | 100.653 | 62.307 | 31.941 | 1.00 | 23.87 |
| ATOM | 4311 | CB | VAL | 1268 | 100.080 | 60.893 | 31.731 | 1.00 | 20.71 |
| ATOM | 4312 | CG1 | VAL | 1268 | 100.520 | 59.964 | 32.826 | 1.00 | 17.95 |
| ATOM | 4313 | CG2 | VAL | 1268 | 98.578 | 60.950 | 31.626 | 1.00 | 20.64 |
| ATOM | 4314 | C | VAL | 1268 | 100.452 | 62.771 | 33.384 | 1.00 | 25.49 |
| ATOM | 4315 | O | VAL | 1268 | 101.144 | 62.322 | 34.303 | 1.00 | 26.11 |
| ATOM | 4316 | N | ASP | 1269 | 99.518 | 63.697 | 33.566 | 1.00 | 25.93 |
| ATOM | 4317 | CA | ASP | 1269 | 99.222 | 64.259 | 34.879 | 1.00 | 26.16 |
| ATOM | 4318 | CB | ASP | 1269 | 98.559 | 65.635 | 34.722 | 1.00 | 28.20 |
| ATOM | 4319 | CG | ASP | 1269 | 99.417 | 66.619 | 33.933 | 1.00 | 31.21 |
| ATOM | 4320 | OD1 | ASP | 1269 | 99.365 | 66.591 | 32.686 | 1.00 | 31.29 |
| ATOM | 4321 | OD2 | ASP | 1269 | 100.138 | 67.425 | 34.558 | 1.00 | 33.35 |
| ATOM | 4322 | C | ASP | 1269 | 98.347 | 63.358 | 35.750 | 1.00 | 25.89 |
| ATOM | 4323 | O | ASP | 1269 | 98.545 | 63.282 | 36.961 | 1.00 | 28.47 |
| ATOM | 4324 | N | VAL | 1270 | 97.355 | 62.709 | 35.145 | 1.00 | 24.11 |
| ATOM | 4325 | CA | VAL | 1270 | 96.455 | 61.833 | 35.889 | 1.00 | 21.61 |
| ATOM | 4326 | CB | VAL | 1270 | 95.073 | 62.465 | 36.165 | 1.00 | 21.00 |
| ATOM | 4327 | CG1 | VAL | 1270 | 94.877 | 62.637 | 37.649 | 1.00 | 23.22 |
| ATOM | 4328 | CG2 | VAL | 1270 | 94.880 | 63.776 | 35.396 | 1.00 | 19.40 |
| ATOM | 4329 | C | VAL | 1270 | 96.165 | 60.554 | 35.148 | 1.00 | 21.02 |
| ATOM | 4330 | O | VAL | 1270 | 95.971 | 60.559 | 33.932 | 1.00 | 19.61 |
| ATOM | 4331 | N | VAL | 1271 | 96.102 | 59.460 | 35.889 | 1.00 | 20.75 |
| ATOM | 4332 | CA | VAL | 1271 | 95.790 | 58.183 | 35.290 | 1.00 | 22.08 |
| ATOM | 4333 | CB | VAL | 1271 | 96.978 | 57.212 | 35.333 | 1.00 | 24.24 |
| ATOM | 4334 | CG1 | VAL | 1271 | 96.520 | 55.814 | 34.937 | 1.00 | 20.83 |
| ATOM | 4335 | CG2 | VAL | 1271 | 98.078 | 57.697 | 34.380 | 1.00 | 25.92 |
| ATOM | 4336 | C | VAL | 1271 | 94.590 | 57.598 | 36.014 | 1.00 | 23.47 |
| ATOM | 4337 | O | VAL | 1271 | 94.499 | 57.643 | 37.246 | 1.00 | 22.00 |
| ATOM | 4338 | N | VAL | 1272 | 93.641 | 57.111 | 35.227 | 1.00 | 23.18 |
| ATOM | 4339 | CA | VAL | 1272 | 92.437 | 56.526 | 35.761 | 1.00 | 21.99 |
| ATOM | 4340 | CB | VAL | 1272 | 91.168 | 57.241 | 35.221 | 1.00 | 25.19 |
| ATOM | 4341 | CG1 | VAL | 1272 | 91.239 | 57.393 | 33.715 | 1.00 | 25.64 |
| ATOM | 4342 | CG2 | VAL | 1272 | 89.900 | 56.475 | 35.637 | 1.00 | 26.87 |
| ATOM | 4343 | C | VAL | 1272 | 92.393 | 55.052 | 35.421 | 1.00 | 22.23 |
| ATOM | 4344 | O | VAL | 1272 | 92.586 | 54.654 | 34.266 | 1.00 | 21.79 |
| ATOM | 4345 | N | LEU | 1273 | 92.195 | 54.241 | 36.448 | 1.00 | 21.58 |
| ATOM | 4346 | CA | LEU | 1273 | 92.103 | 52.812 | 36.265 | 1.00 | 21.13 |
| ATOM | 4347 | CB | LEU | 1273 | 92.339 | 52.122 | 37.605 | 1.00 | 24.63 |
| ATOM | 4348 | CG | LEU | 1273 | 93.680 | 52.535 | 38.230 | 1.00 | 24.94 |
| ATOM | 4349 | CD1 | LEU | 1273 | 93.830 | 51.939 | 39.598 | 1.00 | 27.27 |
| ATOM | 4350 | CD2 | LEU | 1273 | 94.823 | 52.085 | 37.343 | 1.00 | 26.50 |
| ATOM | 4351 | C | LEU | 1273 | 90.704 | 52.537 | 35.706 | 1.00 | 20.20 |
| ATOM | 4352 | O | LEU | 1273 | 89.702 | 52.722 | 36.389 | 1.00 | 18.03 |
| ATOM | 4353 | N | ASP | 1274 | 90.656 | 52.158 | 34.435 | 1.00 | 20.86 |
| ATOM | 4354 | CA | ASP | 1274 | 89.408 | 51.891 | 33.719 | 1.00 | 21.60 |
| ATOM | 4355 | CB | ASP | 1274 | 89.674 | 52.044 | 32.224 | 1.00 | 25.04 |
| ATOM | 4356 | CG | ASP | 1274 | 88.417 | 52.154 | 31.422 | 1.00 | 27.01 |
| ATOM | 4357 | OD1 | ASP | 1274 | 87.498 | 52.859 | 31.877 | 1.00 | 34.85 |
| ATOM | 4358 | OD2 | ASP | 1274 | 88.352 | 51.553 | 30.328 | 1.00 | 29.20 |
| ATOM | 4359 | C | ASP | 1274 | 88.768 | 50.524 | 34.001 | 1.00 | 21.35 |
| ATOM | 4360 | O | ASP | 1274 | 89.274 | 49.492 | 33.550 | 1.00 | 22.84 |
| ATOM | 4361 | N | SER | 1275 | 87.613 | 50.531 | 34.666 | 1.00 | 20.22 |
| ATOM | 4362 | CA | SER | 1275 | 86.906 | 49.302 | 35.025 | 1.00 | 18.99 |
| ATOM | 4363 | CB | SER | 1275 | 87.538 | 48.702 | 36.282 | 1.00 | 19.46 |

FIG. 1A-75

| ATOM | 4364 | OG | SER | 1275 | 86.699 | 47.720 | 36.863 | 1.00 | 23.41 |
| --- | --- | --- | --- | --- | --- | --- | --- | --- | --- |
| ATOM | 4365 | C | SER | 1275 | 85.418 | 49.542 | 35.274 | 1.00 | 18.85 |
| ATOM | 4366 | O | SER | 1275 | 85.021 | 50.632 | 35.680 | 1.00 | 18.12 |
| ATOM | 4367 | N | SER | 1276 | 84.603 | 48.517 | 35.033 | 1.00 | 17.36 |
| ATOM | 4368 | CA | SER | 1276 | 83.166 | 48.615 | 35.239 | 1.00 | 15.68 |
| ATOM | 4369 | CB | SER | 1276 | 82.433 | 47.646 | 34.334 | 1.00 | 13.74 |
| ATOM | 4370 | OG | SER | 1276 | 82.567 | 46.332 | 34.821 | 1.00 | 15.88 |
| ATOM | 4371 | C | SER | 1276 | 82.783 | 48.315 | 36.684 | 1.00 | 17.25 |
| ATOM | 4372 | O | SER | 1276 | 81.669 | 48.604 | 37.107 | 1.00 | 19.29 |
| ATOM | 4373 | N | GLN | 1277 | 83.683 | 47.672 | 37.414 | 1.00 | 16.78 |
| ATOM | 4374 | CA | GLN | 1277 | 83.451 | 47.330 | 38.813 | 1.00 | 15.86 |
| ATOM | 4375 | CB | GLN | 1277 | 82.899 | 45.897 | 38.924 | 1.00 | 13.83 |
| ATOM | 4376 | CG | GLN | 1277 | 81.879 | 45.659 | 40.038 | 1.00 | 10.35 |
| ATOM | 4377 | CD | GLN | 1277 | 82.484 | 45.685 | 41.435 | 1.00 | 15.01 |
| ATOM | 4378 | OE1 | GLN | 1277 | 83.130 | 46.656 | 41.831 | 1.00 | 21.16 |
| ATOM | 4379 | NE2 | GLN | 1277 | 82.261 | 44.626 | 42.195 | 1.00 | 12.93 |
| ATOM | 4380 | C | GLN | 1277 | 84.836 | 47.450 | 39.437 | 1.00 | 15.34 |
| ATOM | 4381 | O | GLN | 1277 | 85.623 | 46.510 | 39.435 | 1.00 | 15.76 |
| ATOM | 4382 | N | GLY | 1278 | 85.138 | 48.635 | 39.942 | 1.00 | 17.13 |
| ATOM | 4383 | CA | GLY | 1278 | 86.449 | 48.884 | 40.510 | 1.00 | 19.13 |
| ATOM | 4384 | C | GLY | 1278 | 86.805 | 48.355 | 41.884 | 1.00 | 20.39 |
| ATOM | 4385 | O | GLY | 1278 | 87.963 | 48.465 | 42.286 | 1.00 | 22.24 |
| ATOM | 4386 | N | ASN | 1279 | 85.855 | 47.796 | 42.622 | 1.00 | 19.95 |
| ATOM | 4387 | CA | ASN | 1279 | 86.184 | 47.296 | 43.946 | 1.00 | 18.23 |
| ATOM | 4388 | CB | ASN | 1279 | 84.968 | 47.357 | 44.861 | 1.00 | 17.99 |
| ATOM | 4389 | CG | ASN | 1279 | 85.299 | 46.994 | 46.291 | 1.00 | 20.23 |
| ATOM | 4390 | OD1 | ASN | 1279 | 84.431 | 46.559 | 47.047 | 1.00 | 22.30 |
| ATOM | 4391 | ND2 | ASN | 1279 | 86.550 | 47.187 | 46.677 | 1.00 | 18.73 |
| ATOM | 4392 | C | ASN | 1279 | 86.726 | 45.879 | 43.858 | 1.00 | 20.11 |
| ATOM | 4393 | O | ASN | 1279 | 86.015 | 44.912 | 44.132 | 1.00 | 22.26 |
| ATOM | 4394 | N | SER | 1280 | 87.990 | 45.754 | 43.469 | 1.00 | 18.39 |
| ATOM | 4395 | CA | SER | 1280 | 88.603 | 44.445 | 43.340 | 1.00 | 18.72 |
| ATOM | 4396 | CB | SER | 1280 | 88.592 | 43.985 | 41.884 | 1.00 | 17.06 |
| ATOM | 4397 | OG | SER | 1280 | 89.394 | 44.815 | 41.060 | 1.00 | 14.94 |
| ATOM | 4398 | C | SER | 1280 | 90.027 | 44.464 | 43.839 | 1.00 | 20.85 |
| ATOM | 4399 | O | SER | 1280 | 90.630 | 45.525 | 43.958 | 1.00 | 20.91 |
| ATOM | 4400 | N | ILE | 1281 | 90.560 | 43.279 | 44.122 | 1.00 | 22.22 |
| ATOM | 4401 | CA | ILE | 1281 | 91.928 | 43.134 | 44.599 | 1.00 | 18.70 |
| ATOM | 4402 | CB | ILE | 1281 | 92.204 | 41.707 | 45.097 | 1.00 | 17.63 |
| ATOM | 4403 | CG2 | ILE | 1281 | 92.096 | 40.712 | 43.959 | 1.00 | 16.82 |
| ATOM | 4404 | CG1 | ILE | 1281 | 93.589 | 41.636 | 45.733 | 1.00 | 23.52 |
| ATOM | 4405 | CD1 | ILE | 1281 | 93.744 | 42.497 | 46.970 | 1.00 | 27.11 |
| ATOM | 4406 | C | ILE | 1281 | 92.901 | 43.473 | 43.486 | 1.00 | 17.34 |
| ATOM | 4407 | O | ILE | 1281 | 93.942 | 44.057 | 43.733 | 1.00 | 17.63 |
| ATOM | 4408 | N | PHE | 1282 | 92.540 | 43.128 | 42.255 | 1.00 | 18.73 |
| ATOM | 4409 | CA | PHE | 1282 | 93.385 | 43.402 | 41.092 | 1.00 | 20.07 |
| ATOM | 4410 | CB | PHE | 1282 | 92.670 | 43.005 | 39.795 | 1.00 | 17.08 |
| ATOM | 4411 | CG | PHE | 1282 | 92.159 | 41.588 | 39.792 | 1.00 | 22.43 |
| ATOM | 4412 | CD1 | PHE | 1282 | 93.039 | 40.515 | 39.820 | 1.00 | 26.46 |
| ATOM | 4413 | CD2 | PHE | 1282 | 90.794 | 41.325 | 39.785 | 1.00 | 26.55 |
| ATOM | 4414 | CE1 | PHE | 1282 | 92.563 | 39.201 | 39.843 | 1.00 | 30.07 |
| ATOM | 4415 | CE2 | PHE | 1282 | 90.309 | 40.014 | 39.808 | 1.00 | 25.06 |
| ATOM | 4416 | CZ | PHE | 1282 | 91.192 | 38.956 | 39.838 | 1.00 | 27.50 |
| ATOM | 4417 | C | PHE | 1282 | 93.705 | 44.888 | 41.066 | 1.00 | 22.54 |
| ATOM | 4418 | O | PHE | 1282 | 94.874 | 45.287 | 41.056 | 1.00 | 25.62 |
| ATOM | 4419 | N | GLN | 1283 | 92.661 | 45.709 | 41.115 | 1.00 | 22.95 |
| ATOM | 4420 | CA | GLN | 1283 | 92.832 | 47.146 | 41.093 | 1.00 | 21.25 |
| ATOM | 4421 | CB | GLN | 1283 | 91.511 | 47.840 | 40.854 | 1.00 | 22.07 |
| ATOM | 4422 | CG | GLN | 1283 | 91.664 | 49.331 | 40.945 | 1.00 | 26.78 |

FIG. 1A-76

| ATOM | 4423 | CD | GLN | 1283 | 90.504 | 50.068 | 40.363 | 1.00 | 25.14 |
|---|---|---|---|---|---|---|---|---|---|
| ATOM | 4424 | OE1 | GLN | 1283 | 90.003 | 51.012 | 40.961 | 1.00 | 25.91 |
| ATOM | 4425 | NE2 | GLN | 1283 | 90.077 | 49.658 | 39.178 | 1.00 | 27.92 |
| ATOM | 4426 | C | GLN | 1283 | 93.462 | 47.689 | 42.360 | 1.00 | 21.70 |
| ATOM | 4427 | O | GLN | 1283 | 94.318 | 48.564 | 42.290 | 1.00 | 22.53 |
| ATOM | 4428 | N | ILE | 1284 | 93.002 | 47.207 | 43.512 | 1.00 | 22.32 |
| ATOM | 4429 | CA | ILE | 1284 | 93.535 | 47.628 | 44.813 | 1.00 | 22.57 |
| ATOM | 4430 | CB | ILE | 1284 | 92.981 | 46.745 | 45.976 | 1.00 | 22.24 |
| ATOM | 4431 | CG2 | ILE | 1284 | 93.803 | 46.933 | 47.237 | 1.00 | 24.28 |
| ATOM | 4432 | CG1 | ILE | 1284 | 91.519 | 47.079 | 46.267 | 1.00 | 19.88 |
| ATOM | 4433 | CD1 | ILE | 1284 | 90.888 | 46.144 | 47.282 | 1.00 | 18.19 |
| ATOM | 4434 | C | ILE | 1284 | 95.053 | 47.490 | 44.800 | 1.00 | 23.74 |
| ATOM | 4435 | O | ILE | 1284 | 95.775 | 48.376 | 45.271 | 1.00 | 26.46 |
| ATOM | 4436 | N | ASN | 1285 | 95.532 | 46.372 | 44.267 | 1.00 | 22.44 |
| ATOM | 4437 | CA | ASN | 1285 | 96.961 | 46.124 | 44.198 | 1.00 | 23.17 |
| ATOM | 4438 | CB | ASN | 1285 | 97.253 | 44.684 | 43.759 | 1.00 | 20.77 |
| ATOM | 4439 | CG | ASN | 1285 | 97.072 | 43.669 | 44.887 | 1.00 | 20.36 |
| ATOM | 4440 | OD1 | ASN | 1285 | 96.805 | 42.490 | 44.631 | 1.00 | 24.13 |
| ATOM | 4441 | ND2 | ASN | 1285 | 97.246 | 44.108 | 46.128 | 1.00 | 14.74 |
| ATOM | 4442 | C | ASN | 1285 | 97.617 | 47.117 | 43.246 | 1.00 | 25.34 |
| ATOM | 4443 | O | ASN | 1285 | 98.677 | 47.666 | 43.546 | 1.00 | 28.24 |
| ATOM | 4444 | N | MET | 1286 | 96.963 | 47.387 | 42.124 | 1.00 | 25.91 |
| ATOM | 4445 | CA | MET | 1286 | 97.505 | 48.323 | 41.152 | 1.00 | 28.16 |
| ATOM | 4446 | CB | MET | 1286 | 96.630 | 48.363 | 39.902 | 1.00 | 28.67 |
| ATOM | 4447 | CG | MET | 1286 | 97.171 | 49.264 | 38.799 | 1.00 | 36.28 |
| ATOM | 4448 | SD | MET | 1286 | 98.715 | 48.689 | 38.035 | 1.00 | 38.55 |
| ATOM | 4449 | CE | MET | 1286 | 98.426 | 49.121 | 36.310 | 1.00 | 33.76 |
| ATOM | 4450 | C | MET | 1286 | 97.648 | 49.731 | 41.738 | 1.00 | 29.19 |
| ATOM | 4451 | O | MET | 1286 | 98.662 | 50.393 | 41.527 | 1.00 | 30.56 |
| ATOM | 4452 | N | ILE | 1287 | 96.652 | 50.174 | 42.501 | 1.00 | 27.85 |
| ATOM | 4453 | CA | ILE | 1287 | 96.688 | 51.502 | 43.092 | 1.00 | 25.81 |
| ATOM | 4454 | CB | ILE | 1287 | 95.405 | 51.813 | 43.873 | 1.00 | 24.59 |
| ATOM | 4455 | CG2 | ILE | 1287 | 95.458 | 53.237 | 44.415 | 1.00 | 25.47 |
| ATOM | 4456 | CG1 | ILE | 1287 | 94.193 | 51.660 | 42.953 | 1.00 | 22.46 |
| ATOM | 4457 | CD1 | ILE | 1287 | 92.874 | 51.620 | 43.673 | 1.00 | 23.78 |
| ATOM | 4458 | C | ILE | 1287 | 97.891 | 51.643 | 44.005 | 1.00 | 26.84 |
| ATOM | 4459 | O | ILE | 1287 | 98.594 | 52.654 | 43.950 | 1.00 | 28.07 |
| ATOM | 4460 | N | LYS | 1288 | 98.143 | 50.623 | 44.820 | 1.00 | 27.20 |
| ATOM | 4461 | CA | LYS | 1288 | 99.284 | 50.640 | 45.736 | 1.00 | 27.46 |
| ATOM | 4462 | CB | LYS | 1288 | 99.252 | 49.417 | 46.650 | 1.00 | 30.05 |
| ATOM | 4463 | CG | LYS | 1288 | 98.036 | 49.335 | 47.562 | 1.00 | 30.55 |
| ATOM | 4464 | CD | LYS | 1288 | 98.070 | 48.045 | 48.367 | 1.00 | 32.83 |
| ATOM | 4465 | CE | LYS | 1288 | 96.838 | 47.890 | 49.229 | 1.00 | 39.32 |
| ATOM | 4466 | NZ | LYS | 1288 | 96.699 | 49.020 | 50.186 | 1.00 | 47.11 |
| ATOM | 4467 | C | LYS | 1288 | 100.596 | 50.673 | 44.951 | 1.00 | 27.26 |
| ATOM | 4468 | O | LYS | 1288 | 101.502 | 51.438 | 45.273 | 1.00 | 27.28 |
| ATOM | 4469 | N | TYR | 1289 | 100.684 | 49.846 | 43.914 | 1.00 | 27.29 |
| ATOM | 4470 | CA | TYR | 1289 | 101.865 | 49.791 | 43.056 | 1.00 | 28.47 |
| ATOM | 4471 | CB | TYR | 1289 | 101.625 | 48.799 | 41.903 | 1.00 | 28.60 |
| ATOM | 4472 | CG | TYR | 1289 | 102.557 | 48.960 | 40.722 | 1.00 | 28.87 |
| ATOM | 4473 | CD1 | TYR | 1289 | 102.192 | 49.728 | 39.614 | 1.00 | 29.46 |
| ATOM | 4474 | CE1 | TYR | 1289 | 103.069 | 49.914 | 38.547 | 1.00 | 31.03 |
| ATOM | 4475 | CD2 | TYR | 1289 | 103.820 | 48.375 | 40.728 | 1.00 | 31.59 |
| ATOM | 4476 | CE2 | TYR | 1289 | 104.708 | 48.553 | 39.664 | 1.00 | 29.02 |
| ATOM | 4477 | CZ | TYR | 1289 | 104.327 | 49.321 | 38.581 | 1.00 | 31.10 |
| ATOM | 4478 | OH | TYR | 1289 | 105.207 | 49.484 | 37.536 | 1.00 | 30.82 |
| ATOM | 4479 | C | TYR | 1289 | 102.193 | 51.180 | 42.493 | 1.00 | 28.78 |
| ATOM | 4480 | O | TYR | 1289 | 103.305 | 51.669 | 42.641 | 1.00 | 29.48 |
| ATOM | 4481 | N | MET | 1290 | 101.201 | 51.816 | 41.883 | 1.00 | 29.89 |

FIG. 1A-77

| ATOM | 4482 | CA | MET | 1290 | 101.348 | 53.133 | 41.276 | 1.00 | 30.44 |
| --- | --- | --- | --- | --- | --- | --- | --- | --- | --- |
| ATOM | 4483 | CB | MET | 1290 | 100.028 | 53.561 | 40.643 | 1.00 | 31.57 |
| ATOM | 4484 | CG | MET | 1290 | 99.579 | 52.680 | 39.497 | 1.00 | 33.84 |
| ATOM | 4485 | SD | MET | 1290 | 98.003 | 53.207 | 38.816 | 1.00 | 34.81 |
| ATOM | 4486 | CE | MET | 1290 | 98.487 | 54.694 | 37.920 | 1.00 | 30.99 |
| ATOM | 4487 | C | MET | 1290 | 101.822 | 54.226 | 42.225 | 1.00 | 32.79 |
| ATOM | 4488 | O | MET | 1290 | 102.509 | 55.159 | 41.804 | 1.00 | 31.48 |
| ATOM | 4489 | N | LYS | 1291 | 101.417 | 54.139 | 43.489 | 1.00 | 35.25 |
| ATOM | 4490 | CA | LYS | 1291 | 101.810 | 55.132 | 44.487 | 1.00 | 37.17 |
| ATOM | 4491 | CB | LYS | 1291 | 100.763 | 55.209 | 45.602 | 1.00 | 38.08 |
| ATOM | 4492 | CG | LYS | 1291 | 99.336 | 55.394 | 45.099 | 1.00 | 36.81 |
| ATOM | 4493 | CD | LYS | 1291 | 99.172 | 56.661 | 44.268 | 1.00 | 38.58 |
| ATOM | 4494 | CE | LYS | 1291 | 99.288 | 57.907 | 45.130 | 1.00 | 38.10 |
| ATOM | 4495 | NZ | LYS | 1291 | 99.087 | 59.155 | 44.349 | 1.00 | 34.25 |
| ATOM | 4496 | C | LYS | 1291 | 103.196 | 54.824 | 45.053 | 1.00 | 38.96 |
| ATOM | 4497 | O | LYS | 1291 | 103.878 | 55.711 | 45.563 | 1.00 | 39.01 |
| ATOM | 4498 | N | GLU | 1292 | 103.592 | 53.556 | 44.994 | 1.00 | 41.96 |
| ATOM | 4499 | CA | GLU | 1292 | 104.916 | 53.144 | 45.456 | 1.00 | 45.55 |
| ATOM | 4500 | CB | GLU | 1292 | 105.037 | 51.608 | 45.509 | 1.00 | 51.52 |
| ATOM | 4501 | CG | GLU | 1292 | 104.263 | 50.910 | 46.636 | 1.00 | 62.57 |
| ATOM | 4502 | CD | GLU | 1292 | 104.341 | 49.374 | 46.570 | 1.00 | 68.88 |
| ATOM | 4503 | OE1 | GLU | 1292 | 103.372 | 48.706 | 47.005 | 1.00 | 67.53 |
| ATOM | 4504 | OE2 | GLU | 1292 | 105.366 | 48.833 | 46.090 | 1.00 | 72.18 |
| ATOM | 4505 | C | GLU | 1292 | 105.907 | 53.672 | 44.417 | 1.00 | 44.62 |
| ATOM | 4506 | O | GLU | 1292 | 106.841 | 54.406 | 44.740 | 1.00 | 46.70 |
| ATOM | 4507 | N | LYS | 1293 | 105.642 | 53.333 | 43.159 | 1.00 | 42.18 |
| ATOM | 4508 | CA | LYS | 1293 | 106.485 | 53.724 | 42.041 | 1.00 | 39.72 |
| ATOM | 4509 | CB | LYS | 1293 | 106.106 | 52.921 | 40.799 | 1.00 | 36.18 |
| ATOM | 4510 | CG | LYS | 1293 | 107.107 | 53.036 | 39.677 | 1.00 | 34.73 |
| ATOM | 4511 | CD | LYS | 1293 | 106.759 | 52.096 | 38.554 | 1.00 | 34.72 |
| ATOM | 4512 | CE | LYS | 1293 | 107.897 | 51.979 | 37.575 | 1.00 | 34.77 |
| ATOM | 4513 | NZ | LYS | 1293 | 109.072 | 51.348 | 38.214 | 1.00 | 35.52 |
| ATOM | 4514 | C | LYS | 1293 | 106.464 | 55.214 | 41.719 | 1.00 | 39.53 |
| ATOM | 4515 | O | LYS | 1293 | 107.513 | 55.821 | 41.526 | 1.00 | 40.47 |
| ATOM | 4516 | N | TYR | 1294 | 105.278 | 55.800 | 41.650 | 1.00 | 39.92 |
| ATOM | 4517 | CA | TYR | 1294 | 105.139 | 57.217 | 41.333 | 1.00 | 41.35 |
| ATOM | 4518 | CB | TYR | 1294 | 104.370 | 57.373 | 40.019 | 1.00 | 39.56 |
| ATOM | 4519 | CG | TYR | 1294 | 105.002 | 56.664 | 38.846 | 1.00 | 37.42 |
| ATOM | 4520 | CD1 | TYR | 1294 | 106.057 | 57.248 | 38.146 | 1.00 | 34.52 |
| ATOM | 4521 | CE1 | TYR | 1294 | 106.647 | 56.609 | 37.074 | 1.00 | 30.70 |
| ATOM | 4522 | CD2 | TYR | 1294 | 104.546 | 55.414 | 38.430 | 1.00 | 36.48 |
| ATOM | 4523 | CE2 | TYR | 1294 | 105.134 | 54.765 | 37.354 | 1.00 | 34.69 |
| ATOM | 4524 | CZ | TYR | 1294 | 106.184 | 55.373 | 36.681 | 1.00 | 33.54 |
| ATOM | 4525 | OH | TYR | 1294 | 106.785 | 54.740 | 35.622 | 1.00 | 34.85 |
| ATOM | 4526 | C | TYR | 1294 | 104.396 | 57.940 | 42.455 | 1.00 | 43.75 |
| ATOM | 4527 | O | TYR | 1294 | 103.263 | 58.389 | 42.269 | 1.00 | 45.43 |
| ATOM | 4528 | N | PRO | 1295 | 105.062 | 58.156 | 43.599 | 1.00 | 44.48 |
| ATOM | 4529 | CD | PRO | 1295 | 106.490 | 57.864 | 43.816 | 1.00 | 44.93 |
| ATOM | 4530 | CA | PRO | 1295 | 104.496 | 58.825 | 44.778 | 1.00 | 45.66 |
| ATOM | 4531 | CB | PRO | 1295 | 105.734 | 59.120 | 45.618 | 1.00 | 46.12 |
| ATOM | 4532 | CG | PRO | 1295 | 106.608 | 57.952 | 45.318 | 1.00 | 46.75 |
| ATOM | 4533 | C | PRO | 1295 | 103.672 | 60.095 | 44.541 | 1.00 | 46.24 |
| ATOM | 4534 | O | PRO | 1295 | 102.885 | 60.495 | 45.403 | 1.00 | 47.08 |
| ATOM | 4535 | N | ASN | 1296 | 103.824 | 60.717 | 43.378 | 1.00 | 45.80 |
| ATOM | 4536 | CA | ASN | 1296 | 103.090 | 61.945 | 43.114 | 1.00 | 45.31 |
| ATOM | 4537 | CB | ASN | 1296 | 104.068 | 63.107 | 42.963 | 1.00 | 46.95 |
| ATOM | 4538 | CG | ASN | 1296 | 104.850 | 63.368 | 44.235 | 1.00 | 50.05 |
| ATOM | 4539 | OD1 | ASN | 1296 | 106.078 | 63.384 | 44.226 | 1.00 | 54.17 |
| ATOM | 4540 | ND2 | ASN | 1296 | 104.143 | 63.555 | 45.343 | 1.00 | 49.91 |

FIG. 1A-78

| | | | | | | | | |
|---|---|---|---|---|---|---|---|---|
| ATOM | 4541 | C | ASN | 1296 | 102.076 | 61.935 | 41.972 | 1.00 | 44.03 |
| ATOM | 4542 | O | ASN | 1296 | 101.339 | 62.911 | 41.799 | 1.00 | 46.11 |
| ATOM | 4543 | N | LEU | 1297 | 102.014 | 60.845 | 41.207 | 1.00 | 39.68 |
| ATOM | 4544 | CA | LEU | 1297 | 101.058 | 60.752 | 40.106 | 1.00 | 34.77 |
| ATOM | 4545 | CB | LEU | 1297 | 101.385 | 59.569 | 39.188 | 1.00 | 32.40 |
| ATOM | 4546 | CG | LEU | 1297 | 100.414 | 59.204 | 38.056 | 1.00 | 26.62 |
| ATOM | 4547 | CD1 | LEU | 1297 | 100.234 | 60.363 | 37.092 | 1.00 | 20.76 |
| ATOM | 4548 | CD2 | LEU | 1297 | 100.934 | 57.977 | 37.324 | 1.00 | 27.04 |
| ATOM | 4549 | C | LEU | 1297 | 99.661 | 60.579 | 40.688 | 1.00 | 32.96 |
| ATOM | 4550 | O | LEU | 1297 | 99.408 | 59.653 | 41.465 | 1.00 | 33.13 |
| ATOM | 4551 | N | GLN | 1298 | 98.767 | 61.492 | 40.331 | 1.00 | 30.12 |
| ATOM | 4552 | CA | GLN | 1298 | 97.398 | 61.445 | 40.812 | 1.00 | 28.27 |
| ATOM | 4553 | CB | GLN | 1298 | 96.683 | 62.753 | 40.474 | 1.00 | 26.70 |
| ATOM | 4554 | CG | GLN | 1298 | 97.320 | 63.998 | 41.072 | 1.00 | 26.80 |
| ATOM | 4555 | CD | GLN | 1298 | 97.048 | 64.155 | 42.553 | 1.00 | 25.70 |
| ATOM | 4556 | OE1 | GLN | 1298 | 95.959 | 64.565 | 42.952 | 1.00 | 25.44 |
| ATOM | 4557 | NE2 | GLN | 1298 | 98.037 | 63.844 | 43.376 | 1.00 | 26.28 |
| ATOM | 4558 | C | GLN | 1298 | 96.683 | 60.268 | 40.148 | 1.00 | 27.95 |
| ATOM | 4559 | O | GLN | 1298 | 96.686 | 60.146 | 38.914 | 1.00 | 28.23 |
| ATOM | 4560 | N | VAL | 1299 | 96.099 | 59.394 | 40.968 | 1.00 | 25.50 |
| ATOM | 4561 | CA | VAL | 1299 | 95.381 | 58.227 | 40.470 | 1.00 | 23.49 |
| ATOM | 4562 | CB | VAL | 1299 | 96.023 | 56.927 | 40.980 | 1.00 | 25.33 |
| ATOM | 4563 | CG1 | VAL | 1299 | 95.354 | 55.721 | 40.333 | 1.00 | 26.24 |
| ATOM | 4564 | CG2 | VAL | 1299 | 97.527 | 56.929 | 40.686 | 1.00 | 25.54 |
| ATOM | 4565 | C | VAL | 1299 | 93.899 | 58.241 | 40.846 | 1.00 | 21.79 |
| ATOM | 4566 | O | VAL | 1299 | 93.522 | 58.728 | 41.914 | 1.00 | 18.96 |
| ATOM | 4567 | N | ILE | 1300 | 93.072 | 57.711 | 39.945 | 1.00 | 23.20 |
| ATOM | 4568 | CA | ILE | 1300 | 91.619 | 57.613 | 40.106 | 1.00 | 20.97 |
| ATOM | 4569 | CB | ILE | 1300 | 90.902 | 58.402 | 38.992 | 1.00 | 18.02 |
| ATOM | 4570 | CG2 | ILE | 1300 | 89.407 | 58.388 | 39.200 | 1.00 | 23.79 |
| ATOM | 4571 | CG1 | ILE | 1300 | 91.387 | 59.851 | 38.986 | 1.00 | 15.75 |
| ATOM | 4572 | CD1 | ILE | 1300 | 90.869 | 60.662 | 37.831 | 1.00 | 11.52 |
| ATOM | 4573 | C | ILE | 1300 | 91.259 | 56.116 | 40.021 | 1.00 | 23.56 |
| ATOM | 4574 | O | ILE | 1300 | 91.835 | 55.376 | 39.203 | 1.00 | 23.77 |
| ATOM | 4575 | N | GLY | 1301 | 90.281 | 55.680 | 40.817 | 1.00 | 24.52 |
| ATOM | 4576 | CA | GLY | 1301 | 89.931 | 54.267 | 40.842 | 1.00 | 25.42 |
| ATOM | 4577 | C | GLY | 1301 | 88.656 | 53.667 | 40.264 | 1.00 | 26.79 |
| ATOM | 4578 | O | GLY | 1301 | 87.544 | 54.127 | 40.527 | 1.00 | 23.49 |
| ATOM | 4579 | N | GLY | 1302 | 88.872 | 52.560 | 39.545 | 1.00 | 30.40 |
| ATOM | 4580 | CA | GLY | 1302 | 87.841 | 51.757 | 38.899 | 1.00 | 27.86 |
| ATOM | 4581 | C | GLY | 1302 | 86.635 | 52.519 | 38.468 | 1.00 | 29.36 |
| ATOM | 4582 | O | GLY | 1302 | 86.703 | 53.334 | 37.558 | 1.00 | 34.73 |
| ATOM | 4583 | N | ASN | 1303 | 85.521 | 52.201 | 39.105 | 1.00 | 26.96 |
| ATOM | 4584 | CA | ASN | 1303 | 84.243 | 52.853 | 38.878 | 1.00 | 22.20 |
| ATOM | 4585 | CB | ASN | 1303 | 83.665 | 52.538 | 37.502 | 1.00 | 19.58 |
| ATOM | 4586 | CG | ASN | 1303 | 83.615 | 53.764 | 36.600 | 1.00 | 21.65 |
| ATOM | 4587 | OD1 | ASN | 1303 | 84.623 | 54.160 | 36.019 | 1.00 | 23.46 |
| ATOM | 4588 | ND2 | ASN | 1303 | 82.441 | 54.373 | 36.483 | 1.00 | 19.93 |
| ATOM | 4589 | C | ASN | 1303 | 83.405 | 52.256 | 39.975 | 1.00 | 21.48 |
| ATOM | 4590 | O | ASN | 1303 | 83.237 | 51.031 | 40.036 | 1.00 | 23.60 |
| ATOM | 4591 | N | VAL | 1304 | 83.008 | 53.104 | 40.917 | 1.00 | 19.16 |
| ATOM | 4592 | CA | VAL | 1304 | 82.219 | 52.680 | 42.064 | 1.00 | 15.46 |
| ATOM | 4593 | CB | VAL | 1304 | 82.972 | 52.975 | 43.389 | 1.00 | 12.26 |
| ATOM | 4594 | CG1 | VAL | 1304 | 84.255 | 52.158 | 43.465 | 1.00 | 11.22 |
| ATOM | 4595 | CG2 | VAL | 1304 | 83.279 | 54.464 | 43.512 | 1.00 | 6.37 |
| ATOM | 4596 | C | VAL | 1304 | 80.851 | 53.346 | 42.131 | 1.00 | 15.07 |
| ATOM | 4597 | O | VAL | 1304 | 80.628 | 54.392 | 41.527 | 1.00 | 14.88 |
| ATOM | 4598 | N | VAL | 1305 | 79.921 | 52.707 | 42.833 | 1.00 | 15.51 |
| ATOM | 4599 | CA | VAL | 1305 | 78.583 | 53.256 | 43.023 | 1.00 | 16.66 |

FIG. 1A-79

| ATOM | 4600 | CB | VAL | 1305 | 77.522 | 52.568 | 42.135 | 1.00 | 11.85 |
|---|---|---|---|---|---|---|---|---|---|
| ATOM | 4601 | CG1 | VAL | 1305 | 77.863 | 52.742 | 40.686 | 1.00 | 16.33 |
| ATOM | 4602 | CG2 | VAL | 1305 | 77.387 | 51.113 | 42.484 | 1.00 | 9.15 |
| ATOM | 4603 | C | VAL | 1305 | 78.162 | 53.113 | 44.484 | 1.00 | 19.22 |
| ATOM | 4604 | O | VAL | 1305 | 77.079 | 53.565 | 44.871 | 1.00 | 21.20 |
| ATOM | 4605 | N | THR | 1306 | 79.049 | 52.550 | 45.302 | 1.00 | 19.23 |
| ATOM | 4606 | CA | THR | 1306 | 78.757 | 52.328 | 46.715 | 1.00 | 19.71 |
| ATOM | 4607 | CB | THR | 1306 | 78.495 | 50.838 | 46.959 | 1.00 | 18.95 |
| ATOM | 4608 | OG1 | THR | 1306 | 77.323 | 50.444 | 46.239 | 1.00 | 19.72 |
| ATOM | 4609 | CG2 | THR | 1306 | 78.309 | 50.546 | 48.425 | 1.00 | 23.97 |
| ATOM | 4610 | C | THR | 1306 | 79.843 | 52.805 | 47.683 | 1.00 | 19.97 |
| ATOM | 4611 | O | THR | 1306 | 81.036 | 52.772 | 47.374 | 1.00 | 19.43 |
| ATOM | 4612 | N | ALA | 1307 | 79.411 | 53.232 | 48.866 | 1.00 | 20.52 |
| ATOM | 4613 | CA | ALA | 1307 | 80.310 | 53.703 | 49.908 | 1.00 | 20.85 |
| ATOM | 4614 | CB | ALA | 1307 | 79.502 | 54.112 | 51.123 | 1.00 | 20.42 |
| ATOM | 4615 | C | ALA | 1307 | 81.341 | 52.624 | 50.282 | 1.00 | 22.03 |
| ATOM | 4616 | O | ALA | 1307 | 82.516 | 52.922 | 50.508 | 1.00 | 23.72 |
| ATOM | 4617 | N | ALA | 1308 | 80.897 | 51.372 | 50.323 | 1.00 | 20.40 |
| ATOM | 4618 | CA | ALA | 1308 | 81.761 | 50.245 | 50.653 | 1.00 | 18.53 |
| ATOM | 4619 | CB | ALA | 1308 | 80.937 | 48.987 | 50.770 | 1.00 | 21.04 |
| ATOM | 4620 | C | ALA | 1308 | 82.870 | 50.059 | 49.623 | 1.00 | 18.54 |
| ATOM | 4621 | O | ALA | 1308 | 84.023 | 49.828 | 49.983 | 1.00 | 22.02 |
| ATOM | 4622 | N | GLN | 1309 | 82.517 | 50.135 | 48.344 | 1.00 | 16.74 |
| ATOM | 4623 | CA | GLN | 1309 | 83.498 | 50.009 | 47.276 | 1.00 | 18.03 |
| ATOM | 4624 | CB | GLN | 1309 | 82.828 | 50.091 | 45.913 | 1.00 | 20.48 |
| ATOM | 4625 | CG | GLN | 1309 | 81.908 | 48.962 | 45.530 | 1.00 | 16.20 |
| ATOM | 4626 | CD | GLN | 1309 | 81.190 | 49.286 | 44.240 | 1.00 | 16.50 |
| ATOM | 4627 | OE1 | GLN | 1309 | 80.346 | 50.187 | 44.202 | 1.00 | 18.85 |
| ATOM | 4628 | NE2 | GLN | 1309 | 81.552 | 48.599 | 43.164 | 1.00 | 12.20 |
| ATOM | 4629 | C | GLN | 1309 | 84.468 | 51.179 | 47.376 | 1.00 | 19.43 |
| ATOM | 4630 | O | GLN | 1309 | 85.679 | 51.011 | 47.245 | 1.00 | 21.03 |
| ATOM | 4631 | N | ALA | 1310 | 83.916 | 52.373 | 47.569 | 1.00 | 20.11 |
| ATOM | 4632 | CA | ALA | 1310 | 84.718 | 53.586 | 47.686 | 1.00 | 21.85 |
| ATOM | 4633 | CB | ALA | 1310 | 83.817 | 54.794 | 47.940 | 1.00 | 20.77 |
| ATOM | 4634 | C | ALA | 1310 | 85.771 | 53.463 | 48.791 | 1.00 | 22.24 |
| ATOM | 4635 | O | ALA | 1310 | 86.928 | 53.834 | 48.593 | 1.00 | 22.99 |
| ATOM | 4636 | N | LYS | 1311 | 85.384 | 52.886 | 49.924 | 1.00 | 21.35 |
| ATOM | 4637 | CA | LYS | 1311 | 86.295 | 52.719 | 51.050 | 1.00 | 22.31 |
| ATOM | 4638 | CB | LYS | 1311 | 85.611 | 51.979 | 52.197 | 1.00 | 22.74 |
| ATOM | 4639 | CG | LYS | 1311 | 86.520 | 51.778 | 53.397 | 1.00 | 24.78 |
| ATOM | 4640 | CD | LYS | 1311 | 86.100 | 50.572 | 54.208 | 1.00 | 32.40 |
| ATOM | 4641 | CE | LYS | 1311 | 87.095 | 50.274 | 55.319 | 1.00 | 37.18 |
| ATOM | 4642 | NZ | LYS | 1311 | 87.287 | 51.440 | 56.238 | 1.00 | 41.69 |
| ATOM | 4643 | C | LYS | 1311 | 87.588 | 51.990 | 50.696 | 1.00 | 22.69 |
| ATOM | 4644 | O | LYS | 1311 | 88.672 | 52.397 | 51.117 | 1.00 | 22.36 |
| ATOM | 4645 | N | ASN | 1312 | 87.483 | 50.899 | 49.946 | 1.00 | 23.27 |
| ATOM | 4646 | CA | ASN | 1312 | 88.672 | 50.136 | 49.578 | 1.00 | 22.53 |
| ATOM | 4647 | CB | ASN | 1312 | 88.304 | 48.830 | 48.861 | 1.00 | 23.31 |
| ATOM | 4648 | CG | ASN | 1312 | 87.556 | 47.850 | 49.754 | 1.00 | 24.55 |
| ATOM | 4649 | OD1 | ASN | 1312 | 86.738 | 47.074 | 49.269 | 1.00 | 25.84 |
| ATOM | 4650 | ND2 | ASN | 1312 | 87.846 | 47.863 | 51.053 | 1.00 | 23.39 |
| ATOM | 4651 | C | ASN | 1312 | 89.630 | 50.943 | 48.718 | 1.00 | 22.69 |
| ATOM | 4652 | O | ASN | 1312 | 90.836 | 50.943 | 48.974 | 1.00 | 24.35 |
| ATOM | 4653 | N | LEU | 1313 | 89.101 | 51.646 | 47.718 | 1.00 | 20.91 |
| ATOM | 4654 | CA | LEU | 1313 | 89.941 | 52.441 | 46.827 | 1.00 | 18.39 |
| ATOM | 4655 | CB | LEU | 1313 | 89.133 | 52.934 | 45.622 | 1.00 | 16.38 |
| ATOM | 4656 | CG | LEU | 1313 | 88.328 | 51.881 | 44.846 | 1.00 | 11.74 |
| ATOM | 4657 | CD1 | LEU | 1313 | 87.723 | 52.500 | 43.610 | 1.00 | 10.15 |
| ATOM | 4658 | CD2 | LEU | 1313 | 89.213 | 50.719 | 44.453 | 1.00 | 12.09 |

FIG. 1A-80

| ATOM | 4659 | C | LEU | 1313 | 90.557 | 53.613 | 47.599 | 1.00 | 18.99 |
| --- | --- | --- | --- | --- | --- | --- | --- | --- | --- |
| ATOM | 4660 | O | LEU | 1313 | 91.721 | 53.981 | 47.386 | 1.00 | 19.65 |
| ATOM | 4661 | N | ILE | 1314 | 89.775 | 54.193 | 48.499 | 1.00 | 17.22 |
| ATOM | 4662 | CA | ILE | 1314 | 90.255 | 55.290 | 49.315 | 1.00 | 18.32 |
| ATOM | 4663 | CB | ILE | 1314 | 89.112 | 55.909 | 50.147 | 1.00 | 19.59 |
| ATOM | 4664 | CG2 | ILE | 1314 | 89.665 | 56.822 | 51.214 | 1.00 | 19.87 |
| ATOM | 4665 | CG1 | ILE | 1314 | 88.178 | 56.697 | 49.226 | 1.00 | 19.36 |
| ATOM | 4666 | CD1 | ILE | 1314 | 86.994 | 57.311 | 49.932 | 1.00 | 23.63 |
| ATOM | 4667 | C | ILE | 1314 | 91.368 | 54.756 | 50.207 | 1.00 | 18.18 |
| ATOM | 4668 | O | ILE | 1314 | 92.424 | 55.366 | 50.331 | 1.00 | 17.86 |
| ATOM | 4669 | N | ASP | 1315 | 91.146 | 53.582 | 50.786 | 1.00 | 21.02 |
| ATOM | 4670 | CA | ASP | 1315 | 92.144 | 52.943 | 51.644 | 1.00 | 21.47 |
| ATOM | 4671 | CB | ASP | 1315 | 91.606 | 51.630 | 52.210 | 1.00 | 20.30 |
| ATOM | 4672 | CG | ASP | 1315 | 90.642 | 51.835 | 53.358 | 1.00 | 21.08 |
| ATOM | 4673 | OD1 | ASP | 1315 | 90.549 | 52.963 | 53.888 | 1.00 | 23.31 |
| ATOM | 4674 | OD2 | ASP | 1315 | 89.986 | 50.849 | 53.742 | 1.00 | 23.73 |
| ATOM | 4675 | C | ASP | 1315 | 93.402 | 52.656 | 50.846 | 1.00 | 21.19 |
| ATOM | 4676 | O | ASP | 1315 | 94.505 | 52.809 | 51.351 | 1.00 | 22.38 |
| ATOM | 4677 | N | ALA | 1316 | 93.217 | 52.230 | 49.600 | 1.00 | 22.07 |
| ATOM | 4678 | CA | ALA | 1316 | 94.316 | 51.917 | 48.703 | 1.00 | 21.27 |
| ATOM | 4679 | CB | ALA | 1316 | 93.792 | 51.254 | 47.440 | 1.00 | 18.78 |
| ATOM | 4680 | C | ALA | 1316 | 95.091 | 53.185 | 48.361 | 1.00 | 23.36 |
| ATOM | 4681 | O | ALA | 1316 | 96.242 | 53.113 | 47.931 | 1.00 | 25.93 |
| ATOM | 4682 | N | GLY | 1317 | 94.456 | 54.343 | 48.522 | 1.00 | 23.56 |
| ATOM | 4683 | CA | GLY | 1317 | 95.140 | 55.593 | 48.248 | 1.00 | 22.93 |
| ATOM | 4684 | C | GLY | 1317 | 94.764 | 56.334 | 46.981 | 1.00 | 25.16 |
| ATOM | 4685 | O | GLY | 1317 | 95.605 | 57.027 | 46.405 | 1.00 | 26.81 |
| ATOM | 4686 | N | VAL | 1318 | 93.526 | 56.191 | 46.518 | 1.00 | 24.52 |
| ATOM | 4687 | CA | VAL | 1318 | 93.112 | 56.915 | 45.321 | 1.00 | 22.03 |
| ATOM | 4688 | CB | VAL | 1318 | 91.762 | 56.416 | 44.781 | 1.00 | 19.33 |
| ATOM | 4689 | CG1 | VAL | 1318 | 91.851 | 54.939 | 44.419 | 1.00 | 17.47 |
| ATOM | 4690 | CG2 | VAL | 1318 | 90.658 | 56.681 | 45.793 | 1.00 | 14.65 |
| ATOM | 4691 | C | VAL | 1318 | 92.992 | 58.407 | 45.644 | 1.00 | 23.29 |
| ATOM | 4692 | O | VAL | 1318 | 92.686 | 58.784 | 46.779 | 1.00 | 21.11 |
| ATOM | 4693 | N | ASP | 1319 | 93.237 | 59.247 | 44.642 | 1.00 | 24.55 |
| ATOM | 4694 | CA | ASP | 1319 | 93.156 | 60.702 | 44.792 | 1.00 | 24.09 |
| ATOM | 4695 | CB | ASP | 1319 | 94.255 | 61.374 | 43.966 | 1.00 | 24.39 |
| ATOM | 4696 | CG | ASP | 1319 | 95.637 | 60.944 | 44.391 | 1.00 | 27.24 |
| ATOM | 4697 | OD1 | ASP | 1319 | 96.101 | 61.403 | 45.454 | 1.00 | 29.40 |
| ATOM | 4698 | OD2 | ASP | 1319 | 96.252 | 60.129 | 43.678 | 1.00 | 29.66 |
| ATOM | 4699 | C | ASP | 1319 | 91.793 | 61.284 | 44.397 | 1.00 | 23.19 |
| ATOM | 4700 | O | ASP | 1319 | 91.499 | 62.450 | 44.692 | 1.00 | 22.82 |
| ATOM | 4701 | N | ALA | 1320 | 90.985 | 60.469 | 43.717 | 1.00 | 21.37 |
| ATOM | 4702 | CA | ALA | 1320 | 89.648 | 60.837 | 43.248 | 1.00 | 18.83 |
| ATOM | 4703 | CB | ALA | 1320 | 89.734 | 61.685 | 41.991 | 1.00 | 17.58 |
| ATOM | 4704 | C | ALA | 1320 | 88.921 | 59.544 | 42.934 | 1.00 | 19.14 |
| ATOM | 4705 | O | ALA | 1320 | 89.555 | 58.500 | 42.779 | 1.00 | 21.36 |
| ATOM | 4706 | N | LEU | 1321 | 87.600 | 59.606 | 42.817 | 1.00 | 18.91 |
| ATOM | 4707 | CA | LEU | 1321 | 86.806 | 58.417 | 42.512 | 1.00 | 18.35 |
| ATOM | 4708 | CB | LEU | 1321 | 85.902 | 58.065 | 43.697 | 1.00 | 19.13 |
| ATOM | 4709 | CG | LEU | 1321 | 86.535 | 57.340 | 44.889 | 1.00 | 18.32 |
| ATOM | 4710 | CD1 | LEU | 1321 | 85.605 | 57.384 | 46.085 | 1.00 | 18.96 |
| ATOM | 4711 | CD2 | LEU | 1321 | 86.850 | 55.905 | 44.510 | 1.00 | 16.25 |
| ATOM | 4712 | C | LEU | 1321 | 85.959 | 58.608 | 41.259 | 1.00 | 17.08 |
| ATOM | 4713 | O | LEU | 1321 | 85.424 | 59.689 | 41.027 | 1.00 | 16.83 |
| ATOM | 4714 | N | ARG | 1322 | 85.887 | 57.581 | 40.421 | 1.00 | 14.82 |
| ATOM | 4715 | CA | ARG | 1322 | 85.071 | 57.654 | 39.216 | 1.00 | 14.44 |
| ATOM | 4716 | CB | ARG | 1322 | 85.820 | 57.032 | 38.043 | 1.00 | 11.02 |
| ATOM | 4717 | CG | ARG | 1322 | 85.147 | 57.239 | 36.713 | 1.00 | 13.22 |

FIG. 1A-81

| ATOM | 4718 | CD | ARG | 1322 | 86.089 | 56.862 | 35.596 | 1.00 | 14.14 |
|---|---|---|---|---|---|---|---|---|---|
| ATOM | 4719 | NE | ARG | 1322 | 85.437 | 56.859 | 34.295 | 1.00 | 16.06 |
| ATOM | 4720 | CZ | ARG | 1322 | 85.739 | 56.013 | 33.312 | 1.00 | 18.68 |
| ATOM | 4721 | NH1 | ARG | 1322 | 86.688 | 55.103 | 33.480 | 1.00 | 12.90 |
| ATOM | 4722 | NH2 | ARG | 1322 | 85.089 | 56.065 | 32.160 | 1.00 | 22.89 |
| ATOM | 4723 | C | ARG | 1322 | 83.788 | 56.877 | 39.565 | 1.00 | 15.81 |
| ATOM | 4724 | O | ARG | 1322 | 83.828 | 55.671 | 39.806 | 1.00 | 15.90 |
| ATOM | 4725 | N | VAL | 1323 | 82.666 | 57.583 | 39.648 | 1.00 | 15.81 |
| ATOM | 4726 | CA | VAL | 1323 | 81.407 | 56.972 | 40.047 | 1.00 | 16.05 |
| ATOM | 4727 | CB | VAL | 1323 | 80.766 | 57.791 | 41.177 | 1.00 | 15.65 |
| ATOM | 4728 | CG1 | VAL | 1323 | 79.392 | 57.253 | 41.525 | 1.00 | 19.48 |
| ATOM | 4729 | CG2 | VAL | 1323 | 81.676 | 57.789 | 42.396 | 1.00 | 16.93 |
| ATOM | 4730 | C | VAL | 1323 | 80.368 | 56.743 | 38.961 | 1.00 | 18.35 |
| ATOM | 4731 | O | VAL | 1323 | 79.986 | 57.670 | 38.238 | 1.00 | 19.74 |
| ATOM | 4732 | N | GLY | 1324 | 79.864 | 55.514 | 38.903 | 1.00 | 17.75 |
| ATOM | 4733 | CA | GLY | 1324 | 78.850 | 55.170 | 37.927 | 1.00 | 15.53 |
| ATOM | 4734 | C | GLY | 1324 | 78.957 | 53.738 | 37.447 | 1.00 | 15.75 |
| ATOM | 4735 | O | GLY | 1324 | 80.061 | 53.250 | 37.213 | 1.00 | 16.50 |
| ATOM | 4736 | N | MET | 1325 | 77.828 | 53.032 | 37.409 | 1.00 | 15.15 |
| ATOM | 4737 | CA | MET | 1325 | 77.793 | 51.668 | 36.902 | 1.00 | 14.24 |
| ATOM | 4738 | CB | MET | 1325 | 77.998 | 50.635 | 37.999 | 1.00 | 13.83 |
| ATOM | 4739 | CG | MET | 1325 | 78.194 | 49.236 | 37.432 | 1.00 | 18.02 |
| ATOM | 4740 | SD | MET | 1325 | 78.376 | 47.970 | 38.682 | 1.00 | 25.48 |
| ATOM | 4741 | CE | MET | 1325 | 79.669 | 48.707 | 39.673 | 1.00 | 29.99 |
| ATOM | 4742 | C | MET | 1325 | 76.496 | 51.387 | 36.140 | 1.00 | 13.62 |
| ATOM | 4743 | O | MET | 1325 | 75.433 | 51.229 | 36.732 | 1.00 | 14.65 |
| ATOM | 4744 | N | GLY | 1326 | 76.592 | 51.401 | 34.816 | 1.00 | 15.59 |
| ATOM | 4745 | CA | GLY | 1326 | 75.449 | 51.129 | 33.968 | 1.00 | 18.92 |
| ATOM | 4746 | C | GLY | 1326 | 74.629 | 52.296 | 33.448 | 1.00 | 21.59 |
| ATOM | 4747 | O | GLY | 1326 | 73.781 | 52.111 | 32.576 | 1.00 | 23.28 |
| ATOM | 4748 | N | CYS | 1327 | 74.872 | 53.496 | 33.954 | 1.00 | 23.19 |
| ATOM | 4749 | CA | CYS | 1327 | 74.110 | 54.665 | 33.521 | 1.00 | 23.22 |
| ATOM | 4750 | CB | CYS | 1327 | 74.136 | 55.729 | 34.613 | 1.00 | 18.50 |
| ATOM | 4751 | SG | CYS | 1327 | 75.784 | 56.191 | 35.112 | 1.00 | 18.84 |
| ATOM | 4752 | C | CYS | 1327 | 74.565 | 55.266 | 32.189 | 1.00 | 24.78 |
| ATOM | 4753 | O | CYS | 1327 | 73.901 | 56.161 | 31.646 | 1.00 | 26.13 |
| ATOM | 4754 | N | GLY | 1328 | 75.684 | 54.778 | 31.664 | 1.00 | 24.46 |
| ATOM | 4755 | CA | GLY | 1328 | 76.203 | 55.293 | 30.410 | 1.00 | 23.45 |
| ATOM | 4756 | C | GLY | 1328 | 75.240 | 55.065 | 29.268 | 1.00 | 23.29 |
| ATOM | 4757 | O | GLY | 1328 | 74.710 | 53.966 | 29.132 | 1.00 | 22.34 |
| ATOM | 4758 | N | SER | 1329 | 75.065 | 56.075 | 28.418 | 1.00 | 23.67 |
| ATOM | 4759 | CA | SER | 1329 | 74.153 | 56.010 | 27.275 | 1.00 | 21.72 |
| ATOM | 4760 | CB | SER | 1329 | 74.309 | 57.264 | 26.411 | 1.00 | 18.83 |
| ATOM | 4761 | OG | SER | 1329 | 75.661 | 57.486 | 26.073 | 1.00 | 19.92 |
| ATOM | 4762 | C | SER | 1329 | 74.294 | 54.757 | 26.417 | 1.00 | 21.22 |
| ATOM | 4763 | O | SER | 1329 | 73.307 | 54.248 | 25.880 | 1.00 | 21.26 |
| ATOM | 4764 | N | ILE | 1330 | 75.516 | 54.254 | 26.312 | 1.00 | 21.88 |
| ATOM | 4765 | CA | ILE | 1330 | 75.806 | 53.052 | 25.519 | 1.00 | 24.67 |
| ATOM | 4766 | CB | ILE | 1330 | 77.068 | 53.257 | 24.611 | 1.00 | 21.54 |
| ATOM | 4767 | CG2 | ILE | 1330 | 76.852 | 54.403 | 23.637 | 1.00 | 16.03 |
| ATOM | 4768 | CG1 | ILE | 1330 | 78.350 | 53.410 | 25.459 | 1.00 | 21.35 |
| ATOM | 4769 | CD1 | ILE | 1330 | 78.372 | 54.506 | 26.530 | 1.00 | 20.54 |
| ATOM | 4770 | C | ILE | 1330 | 76.012 | 51.780 | 26.370 | 1.00 | 26.47 |
| ATOM | 4771 | O | ILE | 1330 | 76.448 | 50.742 | 25.863 | 1.00 | 25.65 |
| ATOM | 4772 | N | XMP | 1331 | 75.664 | 51.857 | 27.651 | 1.00 | 28.61 |
| ATOM | 4773 | CA | XMP | 1331 | 75.844 | 50.741 | 28.572 | 1.00 | 28.95 |
| ATOM | 4774 | C | XMP | 1331 | 74.656 | 49.800 | 28.600 | 1.00 | 29.12 |
| ATOM | 4775 | O | XMP | 1331 | 73.505 | 50.234 | 28.475 | 1.00 | 28.98 |
| ATOM | 4776 | CB | XMP | 1331 | 76.081 | 51.261 | 29.992 | 1.00 | 27.68 |

FIG. 1A-82

| ATOM | 4777 | P | XMP | 1331 | 77.704 | 58.672 | 28.766 | 1.00 | 29.98 |
|---|---|---|---|---|---|---|---|---|---|
| ATOM | 4778 | O1P | XMP | 1331 | 76.256 | 58.670 | 29.170 | 1.00 | 33.22 |
| ATOM | 4779 | O2P | XMP | 1331 | 78.417 | 59.884 | 29.259 | 1.00 | 29.73 |
| ATOM | 4780 | O3P | XMP | 1331 | 77.839 | 58.575 | 27.286 | 1.00 | 26.90 |
| ATOM | 4781 | O5* | XMP | 1331 | 78.406 | 57.457 | 29.329 | 1.00 | 29.08 |
| ATOM | 4782 | C5* | XMP | 1331 | 79.849 | 57.458 | 29.143 | 1.00 | 27.18 |
| ATOM | 4783 | C4* | XMP | 1331 | 80.422 | 56.661 | 30.308 | 1.00 | 25.84 |
| ATOM | 4784 | O4* | XMP | 1331 | 79.820 | 55.352 | 30.328 | 1.00 | 25.54 |
| ATOM | 4785 | C3* | XMP | 1331 | 81.939 | 56.485 | 30.136 | 1.00 | 24.54 |
| ATOM | 4786 | O3* | XMP | 1331 | 82.715 | 57.371 | 30.927 | 1.00 | 21.39 |
| ATOM | 4787 | C2* | XMP | 1331 | 82.130 | 55.094 | 30.761 | 1.00 | 27.13 |
| ATOM | 4788 | O2* | XMP | 1331 | 82.153 | 55.101 | 32.198 | 1.00 | 27.86 |
| ATOM | 4789 | C1* | XMP | 1331 | 80.839 | 54.378 | 30.373 | 1.00 | 24.51 |
| ATOM | 4790 | N9 | XMP | 1331 | 80.999 | 53.219 | 29.508 | 1.00 | 24.31 |
| ATOM | 4791 | C8 | XMP | 1331 | 81.856 | 53.197 | 28.430 | 1.00 | 22.51 |
| ATOM | 4792 | N7 | XMP | 1331 | 81.706 | 52.077 | 27.686 | 1.00 | 24.73 |
| ATOM | 4793 | C5 | XMP | 1331 | 80.739 | 51.343 | 28.276 | 1.00 | 25.50 |
| ATOM | 4794 | C6 | XMP | 1331 | 80.170 | 50.097 | 27.929 | 1.00 | 27.15 |
| ATOM | 4795 | O6 | XMP | 1331 | 80.485 | 49.462 | 26.923 | 1.00 | 26.74 |
| ATOM | 4796 | N1 | XMP | 1331 | 79.200 | 49.689 | 28.807 | 1.00 | 29.27 |
| ATOM | 4797 | C2 | XMP | 1331 | 78.744 | 50.365 | 29.951 | 1.00 | 27.87 |
| ATOM | 4798 | N3 | XMP | 1331 | 79.265 | 51.550 | 30.288 | 1.00 | 29.76 |
| ATOM | 4799 | C4 | XMP | 1331 | 80.257 | 52.067 | 29.478 | 1.00 | 27.38 |
| ATOM | 4800 | N | ILE | 1332 | 74.948 | 48.507 | 28.729 | 1.00 | 29.28 |
| ATOM | 4801 | CA | ILE | 1332 | 73.921 | 47.470 | 28.833 | 1.00 | 27.71 |
| ATOM | 4802 | CB | ILE | 1332 | 73.681 | 46.671 | 27.490 | 1.00 | 24.78 |
| ATOM | 4803 | CG2 | ILE | 1332 | 73.064 | 47.559 | 26.417 | 1.00 | 18.53 |
| ATOM | 4804 | CG1 | ILE | 1332 | 74.970 | 46.053 | 26.968 | 1.00 | 25.48 |
| ATOM | 4805 | CD1 | ILE | 1332 | 74.778 | 45.288 | 25.687 | 1.00 | 24.77 |
| ATOM | 4806 | C | ILE | 1332 | 74.313 | 46.524 | 29.982 | 1.00 | 28.17 |
| ATOM | 4807 | O | ILE | 1332 | 73.772 | 45.430 | 30.121 | 1.00 | 28.90 |
| ATOM | 4808 | N | THR | 1333 | 75.253 | 46.970 | 30.814 | 1.00 | 26.35 |
| ATOM | 4809 | CA | THR | 1333 | 75.716 | 46.195 | 31.960 | 1.00 | 24.76 |
| ATOM | 4810 | CB | THR | 1333 | 76.791 | 46.995 | 32.754 | 1.00 | 24.26 |
| ATOM | 4811 | OG1 | THR | 1333 | 77.978 | 47.124 | 31.966 | 1.00 | 24.79 |
| ATOM | 4812 | CG2 | THR | 1333 | 77.137 | 46.321 | 34.068 | 1.00 | 25.12 |
| ATOM | 4813 | C | THR | 1333 | 74.529 | 45.859 | 32.881 | 1.00 | 24.51 |
| ATOM | 4814 | O | THR | 1333 | 74.308 | 44.697 | 33.222 | 1.00 | 25.59 |
| ATOM | 4815 | N | GLN | 1334 | 73.750 | 46.872 | 33.253 | 1.00 | 21.99 |
| ATOM | 4816 | CA | GLN | 1334 | 72.611 | 46.669 | 34.142 | 1.00 | 20.76 |
| ATOM | 4817 | CB | GLN | 1334 | 71.885 | 47.986 | 34.423 | 1.00 | 13.81 |
| ATOM | 4818 | CG | GLN | 1334 | 72.640 | 48.912 | 35.332 | 1.00 | 13.57 |
| ATOM | 4819 | CD | GLN | 1334 | 71.931 | 50.230 | 35.559 | 1.00 | 14.57 |
| ATOM | 4820 | OE1 | GLN | 1334 | 70.738 | 50.367 | 35.303 | 1.00 | 15.41 |
| ATOM | 4821 | NE2 | GLN | 1334 | 72.666 | 51.209 | 36.043 | 1.00 | 17.86 |
| ATOM | 4822 | C | GLN | 1334 | 71.632 | 45.669 | 33.570 | 1.00 | 22.28 |
| ATOM | 4823 | O | GLN | 1334 | 71.001 | 44.915 | 34.300 | 1.00 | 23.73 |
| ATOM | 4824 | N | GLU | 1335 | 71.508 | 45.663 | 32.254 | 1.00 | 23.82 |
| ATOM | 4825 | CA | GLU | 1335 | 70.594 | 44.756 | 31.580 | 1.00 | 25.32 |
| ATOM | 4826 | CB | GLU | 1335 | 70.360 | 45.267 | 30.171 | 1.00 | 25.53 |
| ATOM | 4827 | CG | GLU | 1335 | 69.381 | 44.477 | 29.366 | 1.00 | 29.41 |
| ATOM | 4828 | CD | GLU | 1335 | 69.322 | 44.957 | 27.934 | 1.00 | 38.03 |
| ATOM | 4829 | OE1 | GLU | 1335 | 69.186 | 44.090 | 27.043 | 1.00 | 42.46 |
| ATOM | 4830 | OE2 | GLU | 1335 | 69.424 | 46.192 | 27.699 | 1.00 | 36.41 |
| ATOM | 4831 | C | GLU | 1335 | 71.178 | 43.353 | 31.513 | 1.00 | 25.11 |
| ATOM | 4832 | O | GLU | 1335 | 70.540 | 42.371 | 31.899 | 1.00 | 26.60 |
| ATOM | 4833 | N | VAL | 1336 | 72.414 | 43.284 | 31.046 | 1.00 | 23.82 |
| ATOM | 4834 | CA | VAL | 1336 | 73.109 | 42.031 | 30.881 | 1.00 | 21.29 |
| ATOM | 4835 | CB | VAL | 1336 | 74.304 | 42.203 | 29.918 | 1.00 | 21.41 |

FIG. 1A-83

| ATOM | 4836 | CG1 | VAL | 1336 | 75.046 | 40.888 | 29.741 | 1.00 | 21.41 |
| --- | --- | --- | --- | --- | --- | --- | --- | --- | --- |
| ATOM | 4837 | CG2 | VAL | 1336 | 73.801 | 42.698 | 28.565 | 1.00 | 21.02 |
| ATOM | 4838 | C | VAL | 1336 | 73.550 | 41.416 | 32.199 | 1.00 | 20.70 |
| ATOM | 4839 | O | VAL | 1336 | 73.153 | 40.306 | 32.520 | 1.00 | 22.89 |
| ATOM | 4840 | N | LEU | 1337 | 74.327 | 42.140 | 32.989 | 1.00 | 19.08 |
| ATOM | 4841 | CA | LEU | 1337 | 74.808 | 41.580 | 34.246 | 1.00 | 17.04 |
| ATOM | 4842 | CB | LEU | 1337 | 76.270 | 41.989 | 34.471 | 1.00 | 12.90 |
| ATOM | 4843 | CG | LEU | 1337 | 77.161 | 41.754 | 33.233 | 1.00 | 8.37 |
| ATOM | 4844 | CD1 | LEU | 1337 | 78.560 | 42.206 | 33.495 | 1.00 | 11.26 |
| ATOM | 4845 | CD2 | LEU | 1337 | 77.158 | 40.305 | 32.807 | 1.00 | 6.79 |
| ATOM | 4846 | C | LEU | 1337 | 73.925 | 41.823 | 35.480 | 1.00 | 17.70 |
| ATOM | 4847 | O | LEU | 1337 | 74.249 | 41.372 | 36.587 | 1.00 | 16.95 |
| ATOM | 4848 | N | ALA | 1338 | 72.804 | 42.518 | 35.280 | 1.00 | 17.48 |
| ATOM | 4849 | CA | ALA | 1338 | 71.831 | 42.798 | 36.346 | 1.00 | 16.50 |
| ATOM | 4850 | CB | ALA | 1338 | 71.220 | 41.501 | 36.841 | 1.00 | 14.26 |
| ATOM | 4851 | C | ALA | 1338 | 72.385 | 43.597 | 37.522 | 1.00 | 16.49 |
| ATOM | 4852 | O | ALA | 1338 | 71.763 | 43.684 | 38.586 | 1.00 | 15.31 |
| ATOM | 4853 | N | CYS | 1339 | 73.511 | 44.252 | 37.287 | 1.00 | 16.65 |
| ATOM | 4854 | CA | CYS | 1339 | 74.177 | 45.015 | 38.317 | 1.00 | 15.82 |
| ATOM | 4855 | CB | CYS | 1339 | 75.476 | 44.302 | 38.685 | 1.00 | 15.47 |
| ATOM | 4856 | SG | CYS | 1339 | 76.455 | 45.090 | 39.958 | 1.00 | 28.64 |
| ATOM | 4857 | C | CYS | 1339 | 74.450 | 46.448 | 37.874 | 1.00 | 14.06 |
| ATOM | 4858 | O | CYS | 1339 | 74.604 | 46.729 | 36.680 | 1.00 | 15.04 |
| ATOM | 4859 | N | GLY | 1340 | 74.481 | 47.352 | 38.843 | 1.00 | 11.34 |
| ATOM | 4860 | CA | GLY | 1340 | 74.737 | 48.749 | 38.558 | 1.00 | 10.79 |
| ATOM | 4861 | C | GLY | 1340 | 74.000 | 49.565 | 39.591 | 1.00 | 11.07 |
| ATOM | 4862 | O | GLY | 1340 | 73.620 | 49.021 | 40.632 | 1.00 | 10.32 |
| ATOM | 4863 | N | ARG | 1341 | 73.787 | 50.852 | 39.322 | 1.00 | 10.55 |
| ATOM | 4864 | CA | ARG | 1341 | 73.054 | 51.690 | 40.261 | 1.00 | 9.89 |
| ATOM | 4865 | CB | ARG | 1341 | 73.904 | 51.970 | 41.499 | 1.00 | 9.18 |
| ATOM | 4866 | CG | ARG | 1341 | 73.133 | 52.654 | 42.605 | 1.00 | 10.84 |
| ATOM | 4867 | CD | ARG | 1341 | 73.922 | 52.777 | 43.883 | 1.00 | 12.53 |
| ATOM | 4868 | NE | ARG | 1341 | 73.047 | 53.124 | 44.997 | 1.00 | 9.59 |
| ATOM | 4869 | CZ | ARG | 1341 | 73.471 | 53.550 | 46.177 | 1.00 | 6.38 |
| ATOM | 4870 | NH1 | ARG | 1341 | 74.766 | 53.690 | 46.412 | 1.00 | 3.80 |
| ATOM | 4871 | NH2 | ARG | 1341 | 72.593 | 53.820 | 47.128 | 1.00 | 3.16 |
| ATOM | 4872 | C | ARG | 1341 | 72.579 | 53.009 | 39.660 | 1.00 | 10.77 |
| ATOM | 4873 | O | ARG | 1341 | 73.217 | 53.550 | 38.753 | 1.00 | 11.78 |
| ATOM | 4874 | N | PRO | 1342 | 71.383 | 53.481 | 40.069 | 1.00 | 10.84 |
| ATOM | 4875 | CD | PRO | 1342 | 70.343 | 52.728 | 40.802 | 1.00 | 9.90 |
| ATOM | 4876 | CA | PRO | 1342 | 70.840 | 54.746 | 39.568 | 1.00 | 10.04 |
| ATOM | 4877 | CB | PRO | 1342 | 69.528 | 54.864 | 40.334 | 1.00 | 11.35 |
| ATOM | 4878 | CG | PRO | 1342 | 69.078 | 53.444 | 40.408 | 1.00 | 8.27 |
| ATOM | 4879 | C | PRO | 1342 | 71.822 | 55.876 | 39.908 | 1.00 | 12.01 |
| ATOM | 4880 | O | PRO | 1342 | 72.144 | 56.118 | 41.080 | 1.00 | 14.18 |
| ATOM | 4881 | N | GLN | 1343 | 72.267 | 56.583 | 38.877 | 1.00 | 12.98 |
| ATOM | 4882 | CA | GLN | 1343 | 73.258 | 57.645 | 39.005 | 1.00 | 13.22 |
| ATOM | 4883 | CB | GLN | 1343 | 73.562 | 58.248 | 37.630 | 1.00 | 11.87 |
| ATOM | 4884 | CG | GLN | 1343 | 74.898 | 58.969 | 37.559 | 1.00 | 15.91 |
| ATOM | 4885 | CD | GLN | 1343 | 76.076 | 58.115 | 38.015 | 1.00 | 20.74 |
| ATOM | 4886 | OE1 | GLN | 1343 | 75.935 | 56.919 | 38.293 | 1.00 | 23.33 |
| ATOM | 4887 | NE2 | GLN | 1343 | 77.247 | 58.730 | 38.090 | 1.00 | 21.84 |
| ATOM | 4888 | C | GLN | 1343 | 73.132 | 58.742 | 40.060 | 1.00 | 14.18 |
| ATOM | 4889 | O | GLN | 1343 | 74.038 | 58.911 | 40.867 | 1.00 | 16.74 |
| ATOM | 4890 | N | ALA | 1344 | 72.052 | 59.512 | 40.064 | 1.00 | 14.34 |
| ATOM | 4891 | CA | ALA | 1344 | 71.940 | 60.572 | 41.062 | 1.00 | 14.79 |
| ATOM | 4892 | CB | ALA | 1344 | 70.638 | 61.304 | 40.927 | 1.00 | 14.45 |
| ATOM | 4893 | C | ALA | 1344 | 72.086 | 60.012 | 42.466 | 1.00 | 15.98 |
| ATOM | 4894 | O | ALA | 1344 | 72.612 | 60.685 | 43.351 | 1.00 | 18.86 |

FIG. 1A-84

| ATOM | 4895 | N | THR | 1345 | 71.632 | 58.775 | 42.664 | 1.00 | 17.15 |
| --- | --- | --- | --- | --- | --- | --- | --- | --- | --- |
| ATOM | 4896 | CA | THR | 1345 | 71.724 | 58.118 | 43.965 | 1.00 | 17.05 |
| ATOM | 4897 | CB | THR | 1345 | 70.834 | 56.859 | 44.039 | 1.00 | 15.53 |
| ATOM | 4898 | OG1 | THR | 1345 | 69.452 | 57.234 | 43.996 | 1.00 | 13.75 |
| ATOM | 4899 | CG2 | THR | 1345 | 71.101 | 56.095 | 45.329 | 1.00 | 12.86 |
| ATOM | 4900 | C | THR | 1345 | 73.168 | 57.734 | 44.284 | 1.00 | 17.66 |
| ATOM | 4901 | O | THR | 1345 | 73.638 | 57.958 | 45.402 | 1.00 | 18.39 |
| ATOM | 4902 | N | ALA | 1346 | 73.861 | 57.151 | 43.304 | 1.00 | 16.69 |
| ATOM | 4903 | CA | ALA | 1346 | 75.257 | 56.738 | 43.478 | 1.00 | 14.38 |
| ATOM | 4904 | CB | ALA | 1346 | 75.737 | 55.973 | 42.253 | 1.00 | 11.74 |
| ATOM | 4905 | C | ALA | 1346 | 76.139 | 57.959 | 43.716 | 1.00 | 13.89 |
| ATOM | 4906 | O | ALA | 1346 | 77.034 | 57.947 | 44.562 | 1.00 | 15.03 |
| ATOM | 4907 | N | VAL | 1347 | 75.858 | 59.022 | 42.977 | 1.00 | 13.19 |
| ATOM | 4908 | CA | VAL | 1347 | 76.610 | 60.255 | 43.098 | 1.00 | 13.37 |
| ATOM | 4909 | CB | VAL | 1347 | 76.216 | 61.260 | 41.994 | 1.00 | 10.97 |
| ATOM | 4910 | CG1 | VAL | 1347 | 76.915 | 62.601 | 42.199 | 1.00 | 7.46 |
| ATOM | 4911 | CG2 | VAL | 1347 | 76.578 | 60.679 | 40.638 | 1.00 | 7.82 |
| ATOM | 4912 | C | VAL | 1347 | 76.419 | 60.852 | 44.488 | 1.00 | 15.39 |
| ATOM | 4913 | O | VAL | 1347 | 77.404 | 61.225 | 45.133 | 1.00 | 18.76 |
| ATOM | 4914 | N | TYR | 1348 | 75.179 | 60.893 | 44.979 | 1.00 | 15.23 |
| ATOM | 4915 | CA | TYR | 1348 | 74.927 | 61.441 | 46.311 | 1.00 | 15.80 |
| ATOM | 4916 | CB | TYR | 1348 | 73.428 | 61.571 | 46.601 | 1.00 | 11.70 |
| ATOM | 4917 | CG | TYR | 1348 | 73.169 | 62.031 | 48.018 | 1.00 | 11.19 |
| ATOM | 4918 | CD1 | TYR | 1348 | 73.374 | 63.354 | 48.383 | 1.00 | 13.82 |
| ATOM | 4919 | CE1 | TYR | 1348 | 73.219 | 63.775 | 49.704 | 1.00 | 12.58 |
| ATOM | 4920 | CD2 | TYR | 1348 | 72.792 | 61.132 | 49.014 | 1.00 | 13.36 |
| ATOM | 4921 | CE2 | TYR | 1348 | 72.633 | 61.545 | 50.341 | 1.00 | 11.68 |
| ATOM | 4922 | CZ | TYR | 1348 | 72.850 | 62.872 | 50.672 | 1.00 | 12.94 |
| ATOM | 4923 | OH | TYR | 1348 | 72.686 | 63.308 | 51.965 | 1.00 | 18.66 |
| ATOM | 4924 | C | TYR | 1348 | 75.580 | 60.593 | 47.409 | 1.00 | 17.42 |
| ATOM | 4925 | O | TYR | 1348 | 76.324 | 61.106 | 48.259 | 1.00 | 16.32 |
| ATOM | 4926 | N | LYS | 1349 | 75.312 | 59.291 | 47.369 | 1.00 | 18.79 |
| ATOM | 4927 | CA | LYS | 1349 | 75.838 | 58.352 | 48.357 | 1.00 | 20.46 |
| ATOM | 4928 | CB | LYS | 1349 | 75.219 | 56.968 | 48.145 | 1.00 | 19.89 |
| ATOM | 4929 | CG | LYS | 1349 | 73.738 | 56.904 | 48.472 | 1.00 | 23.35 |
| ATOM | 4930 | CD | LYS | 1349 | 73.490 | 57.148 | 49.949 | 1.00 | 28.79 |
| ATOM | 4931 | CE | LYS | 1349 | 72.043 | 56.872 | 50.314 | 1.00 | 36.89 |
| ATOM | 4932 | NZ | LYS | 1349 | 71.678 | 55.439 | 50.063 | 1.00 | 44.76 |
| ATOM | 4933 | C | LYS | 1349 | 77.367 | 58.247 | 48.435 | 1.00 | 20.13 |
| ATOM | 4934 | O | LYS | 1349 | 77.944 | 58.367 | 49.517 | 1.00 | 18.39 |
| ATOM | 4935 | N | VAL | 1350 | 78.024 | 58.022 | 47.302 | 1.00 | 20.35 |
| ATOM | 4936 | CA | VAL | 1350 | 79.473 | 57.903 | 47.312 | 1.00 | 22.48 |
| ATOM | 4937 | CB | VAL | 1350 | 80.027 | 57.357 | 45.980 | 1.00 | 20.88 |
| ATOM | 4938 | CG1 | VAL | 1350 | 81.521 | 57.142 | 46.088 | 1.00 | 21.08 |
| ATOM | 4939 | CG2 | VAL | 1350 | 79.369 | 56.049 | 45.642 | 1.00 | 19.89 |
| ATOM | 4940 | C | VAL | 1350 | 80.168 | 59.215 | 47.682 | 1.00 | 24.15 |
| ATOM | 4941 | O | VAL | 1350 | 81.035 | 59.227 | 48.561 | 1.00 | 24.28 |
| ATOM | 4942 | N | SER | 1351 | 79.766 | 60.323 | 47.062 | 1.00 | 25.26 |
| ATOM | 4943 | CA | SER | 1351 | 80.395 | 61.608 | 47.360 | 1.00 | 23.83 |
| ATOM | 4944 | CB | SER | 1351 | 79.819 | 62.711 | 46.468 | 1.00 | 21.66 |
| ATOM | 4945 | OG | SER | 1351 | 78.474 | 62.989 | 46.807 | 1.00 | 28.89 |
| ATOM | 4946 | C | SER | 1351 | 80.285 | 61.967 | 48.851 | 1.00 | 24.46 |
| ATOM | 4947 | O | SER | 1351 | 81.282 | 62.319 | 49.483 | 1.00 | 25.39 |
| ATOM | 4948 | N | GLU | 1352 | 79.094 | 61.807 | 49.422 | 1.00 | 24.65 |
| ATOM | 4949 | CA | GLU | 1352 | 78.857 | 62.093 | 50.836 | 1.00 | 23.20 |
| ATOM | 4950 | CB | GLU | 1352 | 77.455 | 61.619 | 51.209 | 1.00 | 25.97 |
| ATOM | 4951 | CG | GLU | 1352 | 76.866 | 62.256 | 52.452 | 1.00 | 34.13 |
| ATOM | 4952 | CD | GLU | 1352 | 77.649 | 61.943 | 53.704 | 1.00 | 42.02 |
| ATOM | 4953 | OE1 | GLU | 1352 | 77.762 | 60.747 | 54.050 | 1.00 | 48.38 |

FIG. 1A-85

| ATOM | 4954 | OE2 | GLU | 1352 | 78.171 | 62.892 | 54.332 | 1.00 | 44.72 |
|---|---|---|---|---|---|---|---|---|---|
| ATOM | 4955 | C | GLU | 1352 | 79.899 | 61.407 | 51.731 | 1.00 | 22.30 |
| ATOM | 4956 | O | GLU | 1352 | 80.380 | 61.989 | 52.704 | 1.00 | 20.98 |
| ATOM | 4957 | N | TYR | 1353 | 80.249 | 60.173 | 51.387 | 1.00 | 22.48 |
| ATOM | 4958 | CA | TYR | 1353 | 81.228 | 59.396 | 52.145 | 1.00 | 24.18 |
| ATOM | 4959 | CB | TYR | 1353 | 81.048 | 57.902 | 51.846 | 1.00 | 22.91 |
| ATOM | 4960 | CG | TYR | 1353 | 82.042 | 56.985 | 52.531 | 1.00 | 24.38 |
| ATOM | 4961 | CD1 | TYR | 1353 | 81.967 | 56.739 | 53.904 | 1.00 | 24.43 |
| ATOM | 4962 | CE1 | TYR | 1353 | 82.863 | 55.872 | 54.537 | 1.00 | 20.67 |
| ATOM | 4963 | CD2 | TYR | 1353 | 83.043 | 56.342 | 51.805 | 1.00 | 25.32 |
| ATOM | 4964 | CE2 | TYR | 1353 | 83.945 | 55.475 | 52.432 | 1.00 | 24.34 |
| ATOM | 4965 | CZ | TYR | 1353 | 83.848 | 55.245 | 53.795 | 1.00 | 22.43 |
| ATOM | 4966 | OH | TYR | 1353 | 84.732 | 54.388 | 54.416 | 1.00 | 27.27 |
| ATOM | 4967 | C | TYR | 1353 | 82.666 | 59.806 | 51.821 | 1.00 | 26.03 |
| ATOM | 4968 | O | TYR | 1353 | 83.472 | 60.082 | 52.714 | 1.00 | 27.29 |
| ATOM | 4969 | N | ALA | 1354 | 82.979 | 59.822 | 50.531 | 1.00 | 26.11 |
| ATOM | 4970 | CA | ALA | 1354 | 84.309 | 60.156 | 50.046 | 1.00 | 22.63 |
| ATOM | 4971 | CB | ALA | 1354 | 84.326 | 60.152 | 48.524 | 1.00 | 19.88 |
| ATOM | 4972 | C | ALA | 1354 | 84.797 | 61.486 | 50.564 | 1.00 | 21.85 |
| ATOM | 4973 | O | ALA | 1354 | 85.963 | 61.622 | 50.921 | 1.00 | 22.98 |
| ATOM | 4974 | N | ARG | 1355 | 83.903 | 62.463 | 50.632 | 1.00 | 22.11 |
| ATOM | 4975 | CA | ARG | 1355 | 84.282 | 63.791 | 51.091 | 1.00 | 22.54 |
| ATOM | 4976 | CB | ARG | 1355 | 83.086 | 64.747 | 51.088 | 1.00 | 22.76 |
| ATOM | 4977 | CG | ARG | 1355 | 82.002 | 64.399 | 52.084 | 1.00 | 26.76 |
| ATOM | 4978 | CD | ARG | 1355 | 80.976 | 65.498 | 52.193 | 1.00 | 26.94 |
| ATOM | 4979 | NE | ARG | 1355 | 79.997 | 65.202 | 53.231 | 1.00 | 29.46 |
| ATOM | 4980 | CZ | ARG | 1355 | 79.579 | 66.082 | 54.135 | 1.00 | 29.32 |
| ATOM | 4981 | NH1 | ARG | 1355 | 80.057 | 67.325 | 54.130 | 1.00 | 29.47 |
| ATOM | 4982 | NH2 | ARG | 1355 | 78.692 | 65.716 | 55.050 | 1.00 | 25.26 |
| ATOM | 4983 | C | ARG | 1355 | 84.900 | 63.726 | 52.473 | 1.00 | 23.92 |
| ATOM | 4984 | O | ARG | 1355 | 85.777 | 64.520 | 52.799 | 1.00 | 25.40 |
| ATOM | 4985 | N | ARG | 1356 | 84.488 | 62.741 | 53.262 | 1.00 | 24.35 |
| ATOM | 4986 | CA | ARG | 1356 | 85.020 | 62.575 | 54.610 | 1.00 | 25.43 |
| ATOM | 4987 | CB | ARG | 1356 | 84.189 | 61.540 | 55.386 | 1.00 | 26.45 |
| ATOM | 4988 | CG | ARG | 1356 | 82.714 | 61.888 | 55.487 | 1.00 | 33.21 |
| ATOM | 4989 | CD | ARG | 1356 | 81.948 | 60.892 | 56.336 | 1.00 | 37.91 |
| ATOM | 4990 | NE | ARG | 1356 | 80.540 | 61.270 | 56.459 | 1.00 | 44.13 |
| ATOM | 4991 | CZ | ARG | 1356 | 80.064 | 62.180 | 57.311 | 1.00 | 50.10 |
| ATOM | 4992 | NH1 | ARG | 1356 | 80.876 | 62.829 | 58.142 | 1.00 | 50.72 |
| ATOM | 4993 | NH2 | ARG | 1356 | 78.765 | 62.456 | 57.327 | 1.00 | 51.78 |
| ATOM | 4994 | C | ARG | 1356 | 86.505 | 62.167 | 54.580 | 1.00 | 24.79 |
| ATOM | 4995 | O | ARG | 1356 | 87.144 | 62.017 | 55.626 | 1.00 | 28.39 |
| ATOM | 4996 | N | PHE | 1357 | 87.053 | 62.006 | 53.380 | 1.00 | 20.35 |
| ATOM | 4997 | CA | PHE | 1357 | 88.440 | 61.617 | 53.214 | 1.00 | 19.19 |
| ATOM | 4998 | CB | PHE | 1357 | 88.495 | 60.141 | 52.842 | 1.00 | 18.36 |
| ATOM | 4999 | CG | PHE | 1357 | 87.699 | 59.288 | 53.765 | 1.00 | 19.85 |
| ATOM | 5000 | CD1 | PHE | 1357 | 88.239 | 58.871 | 54.978 | 1.00 | 21.81 |
| ATOM | 5001 | CD2 | PHE | 1357 | 86.367 | 59.018 | 53.499 | 1.00 | 19.20 |
| ATOM | 5002 | CE1 | PHE | 1357 | 87.456 | 58.211 | 55.919 | 1.00 | 18.86 |
| ATOM | 5003 | CE2 | PHE | 1357 | 85.583 | 58.362 | 54.432 | 1.00 | 20.85 |
| ATOM | 5004 | CZ | PHE | 1357 | 86.129 | 57.960 | 55.646 | 1.00 | 18.81 |
| ATOM | 5005 | C | PHE | 1357 | 89.113 | 62.473 | 52.158 | 1.00 | 20.97 |
| ATOM | 5006 | O | PHE | 1357 | 90.140 | 62.092 | 51.590 | 1.00 | 22.54 |
| ATOM | 5007 | N | GLY | 1358 | 88.509 | 63.626 | 51.884 | 1.00 | 20.40 |
| ATOM | 5008 | CA | GLY | 1358 | 89.043 | 64.549 | 50.899 | 1.00 | 17.74 |
| ATOM | 5009 | C | GLY | 1358 | 89.167 | 63.989 | 49.498 | 1.00 | 17.67 |
| ATOM | 5010 | O | GLY | 1358 | 89.860 | 64.575 | 48.660 | 1.00 | 19.43 |
| ATOM | 5011 | N | VAL | 1359 | 88.485 | 62.883 | 49.221 | 1.00 | 15.95 |
| ATOM | 5012 | CA | VAL | 1359 | 88.562 | 62.270 | 47.902 | 1.00 | 15.11 |

FIG. 1A-86

| ATOM | 5013 | CB | VAL | 1359 | 88.490 | 60.742 | 47.991 | 1.00 | 11.79 |
|---|---|---|---|---|---|---|---|---|---|
| ATOM | 5014 | CG1 | VAL | 1359 | 88.597 | 60.139 | 46.612 | 1.00 | 12.33 |
| ATOM | 5015 | CG2 | VAL | 1359 | 89.604 | 60.219 | 48.871 | 1.00 | 13.37 |
| ATOM | 5016 | C | VAL | 1359 | 87.455 | 62.766 | 46.976 | 1.00 | 15.32 |
| ATOM | 5017 | O | VAL | 1359 | 86.276 | 62.506 | 47.213 | 1.00 | 16.23 |
| ATOM | 5018 | N | PRO | 1360 | 87.823 | 63.527 | 45.933 | 1.00 | 15.11 |
| ATOM | 5019 | CD | PRO | 1360 | 89.158 | 64.109 | 45.719 | 1.00 | 14.19 |
| ATOM | 5020 | CA | PRO | 1360 | 86.871 | 64.067 | 44.960 | 1.00 | 15.11 |
| ATOM | 5021 | CB | PRO | 1360 | 87.766 | 64.902 | 44.047 | 1.00 | 15.19 |
| ATOM | 5022 | CG | PRO | 1360 | 88.832 | 65.371 | 44.977 | 1.00 | 12.72 |
| ATOM | 5023 | C | PRO | 1360 | 86.138 | 62.962 | 44.195 | 1.00 | 14.73 |
| ATOM | 5024 | O | PRO | 1360 | 86.675 | 61.875 | 43.995 | 1.00 | 15.41 |
| ATOM | 5025 | N | VAL | 1361 | 84.919 | 63.262 | 43.756 | 1.00 | 14.39 |
| ATOM | 5026 | CA | VAL | 1361 | 84.074 | 62.311 | 43.048 | 1.00 | 13.41 |
| ATOM | 5027 | CB | VAL | 1361 | 82.783 | 62.027 | 43.881 | 1.00 | 12.70 |
| ATOM | 5028 | CG1 | VAL | 1361 | 81.633 | 61.550 | 43.000 | 1.00 | 11.96 |
| ATOM | 5029 | CG2 | VAL | 1361 | 83.084 | 60.991 | 44.951 | 1.00 | 11.77 |
| ATOM | 5030 | C | VAL | 1361 | 83.703 | 62.786 | 41.647 | 1.00 | 13.98 |
| ATOM | 5031 | O | VAL | 1361 | 83.104 | 63.845 | 41.483 | 1.00 | 14.14 |
| ATOM | 5032 | N | ILE | 1362 | 84.069 | 61.991 | 40.647 | 1.00 | 15.72 |
| ATOM | 5033 | CA | ILE | 1362 | 83.770 | 62.280 | 39.244 | 1.00 | 17.31 |
| ATOM | 5034 | CB | ILE | 1362 | 84.853 | 61.691 | 38.273 | 1.00 | 15.17 |
| ATOM | 5035 | CG2 | ILE | 1362 | 84.462 | 61.952 | 36.822 | 1.00 | 7.15 |
| ATOM | 5036 | CG1 | ILE | 1362 | 86.246 | 62.259 | 38.587 | 1.00 | 15.08 |
| ATOM | 5037 | CD1 | ILE | 1362 | 87.343 | 61.761 | 37.659 | 1.00 | 5.33 |
| ATOM | 5038 | C | ILE | 1362 | 82.452 | 61.584 | 38.917 | 1.00 | 19.48 |
| ATOM | 5039 | O | ILE | 1362 | 82.396 | 60.348 | 38.906 | 1.00 | 20.54 |
| ATOM | 5040 | N | ALA | 1363 | 81.393 | 62.363 | 38.685 | 1.00 | 19.94 |
| ATOM | 5041 | CA | ALA | 1363 | 80.082 | 61.807 | 38.337 | 1.00 | 18.31 |
| ATOM | 5042 | CB | ALA | 1363 | 78.996 | 62.841 | 38.555 | 1.00 | 17.29 |
| ATOM | 5043 | C | ALA | 1363 | 80.158 | 61.387 | 36.869 | 1.00 | 18.95 |
| ATOM | 5044 | O | ALA | 1363 | 80.061 | 62.218 | 35.961 | 1.00 | 17.38 |
| ATOM | 5045 | N | ASP | 1364 | 80.309 | 60.083 | 36.656 | 1.00 | 21.34 |
| ATOM | 5046 | CA | ASP | 1364 | 80.484 | 59.502 | 35.327 | 1.00 | 22.87 |
| ATOM | 5047 | CB | ASP | 1364 | 81.804 | 58.715 | 35.345 | 1.00 | 22.78 |
| ATOM | 5048 | CG | ASP | 1364 | 82.068 | 57.973 | 34.065 | 1.00 | 19.89 |
| ATOM | 5049 | OD1 | ASP | 1364 | 81.786 | 58.524 | 32.990 | 1.00 | 18.84 |
| ATOM | 5050 | OD2 | ASP | 1364 | 82.571 | 56.838 | 34.139 | 1.00 | 22.02 |
| ATOM | 5051 | C | ASP | 1364 | 79.354 | 58.638 | 34.739 | 1.00 | 22.91 |
| ATOM | 5052 | O | ASP | 1364 | 79.172 | 57.479 | 35.123 | 1.00 | 22.90 |
| ATOM | 5053 | N | GLY | 1365 | 78.675 | 59.179 | 33.731 | 1.00 | 22.55 |
| ATOM | 5054 | CA | GLY | 1365 | 77.601 | 58.453 | 33.081 | 1.00 | 22.28 |
| ATOM | 5055 | C | GLY | 1365 | 76.211 | 59.013 | 33.325 | 1.00 | 22.48 |
| ATOM | 5056 | O | GLY | 1365 | 75.886 | 59.417 | 34.439 | 1.00 | 22.82 |
| ATOM | 5057 | N | GLY | 1366 | 75.398 | 59.047 | 32.272 | 1.00 | 23.81 |
| ATOM | 5058 | CA | GLY | 1366 | 74.037 | 59.540 | 32.383 | 1.00 | 25.79 |
| ATOM | 5059 | C | GLY | 1366 | 73.820 | 61.032 | 32.203 | 1.00 | 27.55 |
| ATOM | 5060 | O | GLY | 1366 | 72.827 | 61.578 | 32.678 | 1.00 | 30.08 |
| ATOM | 5061 | N | ILE | 1367 | 74.742 | 61.711 | 31.536 | 1.00 | 29.05 |
| ATOM | 5062 | CA | ILE | 1367 | 74.600 | 63.139 | 31.305 | 1.00 | 28.73 |
| ATOM | 5063 | CB | ILE | 1367 | 75.948 | 63.897 | 31.486 | 1.00 | 29.81 |
| ATOM | 5064 | CG2 | ILE | 1367 | 75.757 | 65.397 | 31.255 | 1.00 | 29.11 |
| ATOM | 5065 | CG1 | ILE | 1367 | 76.546 | 63.631 | 32.873 | 1.00 | 28.67 |
| ATOM | 5066 | CD1 | ILE | 1367 | 75.734 | 64.175 | 34.022 | 1.00 | 28.35 |
| ATOM | 5067 | C | ILE | 1367 | 74.138 | 63.310 | 29.862 | 1.00 | 30.48 |
| ATOM | 5068 | O | ILE | 1367 | 74.561 | 62.565 | 28.969 | 1.00 | 31.42 |
| ATOM | 5069 | N | GLN | 1368 | 73.237 | 64.261 | 29.645 | 1.00 | 31.28 |
| ATOM | 5070 | CA | GLN | 1368 | 72.734 | 64.561 | 28.308 | 1.00 | 33.21 |
| ATOM | 5071 | CB | GLN | 1368 | 71.673 | 63.558 | 27.850 | 1.00 | 38.74 |

FIG. 1A-87

| ATOM | 5072 | CG | GLN | 1368 | 72.188 | 62.559 | 26.791 | 1.00 | 47.07 |
| ATOM | 5073 | CD | GLN | 1368 | 72.526 | 63.203 | 25.434 | 1.00 | 49.78 |
| ATOM | 5074 | OE1 | GLN | 1368 | 71.694 | 63.239 | 24.523 | 1.00 | 51.57 |
| ATOM | 5075 | NE2 | GLN | 1368 | 73.759 | 63.666 | 25.287 | 1.00 | 49.82 |
| ATOM | 5076 | C | GLN | 1368 | 72.217 | 65.984 | 28.212 | 1.00 | 31.65 |
| ATOM | 5077 | O | GLN | 1368 | 71.541 | 66.347 | 27.258 | 1.00 | 33.54 |
| ATOM | 5078 | N | ASN | 1369 | 72.551 | 66.786 | 29.213 | 1.00 | 28.87 |
| ATOM | 5079 | CA | ASN | 1369 | 72.176 | 68.185 | 29.253 | 1.00 | 27.68 |
| ATOM | 5080 | CB | ASN | 1369 | 70.650 | 68.398 | 29.193 | 1.00 | 26.97 |
| ATOM | 5081 | CG | ASN | 1369 | 69.903 | 67.728 | 30.324 | 1.00 | 26.85 |
| ATOM | 5082 | OD1 | ASN | 1369 | 70.263 | 67.852 | 31.496 | 1.00 | 26.95 |
| ATOM | 5083 | ND2 | ASN | 1369 | 68.829 | 67.037 | 29.978 | 1.00 | 28.12 |
| ATOM | 5084 | C | ASN | 1369 | 72.782 | 68.803 | 30.494 | 1.00 | 27.65 |
| ATOM | 5085 | O | ASN | 1369 | 73.240 | 68.082 | 31.396 | 1.00 | 27.37 |
| ATOM | 5086 | N | VAL | 1370 | 72.844 | 70.133 | 30.497 | 1.00 | 26.63 |
| ATOM | 5087 | CA | VAL | 1370 | 73.404 | 70.901 | 31.601 | 1.00 | 23.97 |
| ATOM | 5088 | CB | VAL | 1370 | 73.319 | 72.421 | 31.311 | 1.00 | 25.11 |
| ATOM | 5089 | CG1 | VAL | 1370 | 73.858 | 73.222 | 32.487 | 1.00 | 25.59 |
| ATOM | 5090 | CG2 | VAL | 1370 | 74.089 | 72.758 | 30.038 | 1.00 | 18.81 |
| ATOM | 5091 | C | VAL | 1370 | 72.684 | 70.569 | 32.902 | 1.00 | 22.46 |
| ATOM | 5092 | O | VAL | 1370 | 73.298 | 70.540 | 33.967 | 1.00 | 21.96 |
| ATOM | 5093 | N | GLY | 1371 | 71.389 | 70.285 | 32.799 | 1.00 | 22.70 |
| ATOM | 5094 | CA | GLY | 1371 | 70.599 | 69.939 | 33.968 | 1.00 | 20.55 |
| ATOM | 5095 | C | GLY | 1371 | 71.251 | 68.798 | 34.714 | 1.00 | 19.42 |
| ATOM | 5096 | O | GLY | 1371 | 71.468 | 68.881 | 35.914 | 1.00 | 20.90 |
| ATOM | 5097 | N | HIS | 1372 | 71.613 | 67.746 | 33.993 | 1.00 | 18.46 |
| ATOM | 5098 | CA | HIS | 1372 | 72.260 | 66.596 | 34.600 | 1.00 | 17.54 |
| ATOM | 5099 | CB | HIS | 1372 | 72.555 | 65.532 | 33.538 | 1.00 | 19.84 |
| ATOM | 5100 | CG | HIS | 1372 | 71.327 | 64.935 | 32.917 | 1.00 | 19.86 |
| ATOM | 5101 | CD2 | HIS | 1372 | 71.148 | 64.297 | 31.733 | 1.00 | 16.94 |
| ATOM | 5102 | ND1 | HIS | 1372 | 70.099 | 64.914 | 33.540 | 1.00 | 20.56 |
| ATOM | 5103 | CE1 | HIS | 1372 | 69.222 | 64.291 | 32.779 | 1.00 | 18.07 |
| ATOM | 5104 | NE2 | HIS | 1372 | 69.841 | 63.907 | 31.674 | 1.00 | 18.04 |
| ATOM | 5105 | C | HIS | 1372 | 73.556 | 67.024 | 35.287 | 1.00 | 16.89 |
| ATOM | 5106 | O | HIS | 1372 | 73.819 | 66.642 | 36.425 | 1.00 | 16.89 |
| ATOM | 5107 | N | ILE | 1373 | 74.337 | 67.860 | 34.610 | 1.00 | 17.42 |
| ATOM | 5108 | CA | ILE | 1373 | 75.606 | 68.341 | 35.154 | 1.00 | 15.96 |
| ATOM | 5109 | CB | ILE | 1373 | 76.362 | 69.204 | 34.134 | 1.00 | 15.20 |
| ATOM | 5110 | CG2 | ILE | 1373 | 77.651 | 69.733 | 34.748 | 1.00 | 17.65 |
| ATOM | 5111 | CG1 | ILE | 1373 | 76.666 | 68.381 | 32.880 | 1.00 | 9.89 |
| ATOM | 5112 | CD1 | ILE | 1373 | 77.325 | 69.185 | 31.795 | 1.00 | 8.53 |
| ATOM | 5113 | C | ILE | 1373 | 75.433 | 69.121 | 36.456 | 1.00 | 15.25 |
| ATOM | 5114 | O | ILE | 1373 | 76.138 | 68.863 | 37.430 | 1.00 | 16.51 |
| ATOM | 5115 | N | ALA | 1374 | 74.498 | 70.065 | 36.477 | 1.00 | 14.86 |
| ATOM | 5116 | CA | ALA | 1374 | 74.235 | 70.854 | 37.679 | 1.00 | 14.25 |
| ATOM | 5117 | CB | ALA | 1374 | 73.204 | 71.923 | 37.394 | 1.00 | 11.74 |
| ATOM | 5118 | C | ALA | 1374 | 73.758 | 69.963 | 38.823 | 1.00 | 15.36 |
| ATOM | 5119 | O | ALA | 1374 | 74.166 | 70.146 | 39.967 | 1.00 | 16.74 |
| ATOM | 5120 | N | LYS | 1375 | 72.923 | 68.977 | 38.506 | 1.00 | 16.36 |
| ATOM | 5121 | CA | LYS | 1375 | 72.390 | 68.063 | 39.515 | 1.00 | 16.18 |
| ATOM | 5122 | CB | LYS | 1375 | 71.293 | 67.177 | 38.921 | 1.00 | 16.44 |
| ATOM | 5123 | CG | LYS | 1375 | 70.020 | 67.950 | 38.597 | 1.00 | 16.99 |
| ATOM | 5124 | CD | LYS | 1375 | 68.973 | 67.103 | 37.894 | 1.00 | 17.81 |
| ATOM | 5125 | CE | LYS | 1375 | 67.701 | 67.914 | 37.671 | 1.00 | 18.59 |
| ATOM | 5126 | NZ | LYS | 1375 | 66.576 | 67.092 | 37.162 | 1.00 | 16.68 |
| ATOM | 5127 | C | LYS | 1375 | 73.484 | 67.219 | 40.137 | 1.00 | 15.85 |
| ATOM | 5128 | O | LYS | 1375 | 73.546 | 67.080 | 41.359 | 1.00 | 16.57 |
| ATOM | 5129 | N | ALA | 1376 | 74.357 | 66.672 | 39.300 | 1.00 | 14.84 |
| ATOM | 5130 | CA | ALA | 1376 | 75.468 | 65.867 | 39.786 | 1.00 | 13.60 |

FIG. 1A-88

| ATOM | 5131 | CB | ALA | 1376 | 76.314 | 65.398 | 38.633 | 1.00 | 11.96 |
|---|---|---|---|---|---|---|---|---|---|
| ATOM | 5132 | C | ALA | 1376 | 76.309 | 66.714 | 40.732 | 1.00 | 14.60 |
| ATOM | 5133 | O | ALA | 1376 | 76.601 | 66.300 | 41.849 | 1.00 | 17.56 |
| ATOM | 5134 | N | LEU | 1377 | 76.661 | 67.918 | 40.295 | 1.00 | 13.87 |
| ATOM | 5135 | CA | LEU | 1377 | 77.466 | 68.829 | 41.100 | 1.00 | 14.63 |
| ATOM | 5136 | CB | LEU | 1377 | 77.741 | 70.126 | 40.322 | 1.00 | 14.18 |
| ATOM | 5137 | CG | LEU | 1377 | 78.412 | 70.033 | 38.945 | 1.00 | 11.92 |
| ATOM | 5138 | CD1 | LEU | 1377 | 78.385 | 71.376 | 38.281 | 1.00 | 11.93 |
| ATOM | 5139 | CD2 | LEU | 1377 | 79.831 | 69.521 | 39.049 | 1.00 | 10.66 |
| ATOM | 5140 | C | LEU | 1377 | 76.728 | 69.155 | 42.394 | 1.00 | 15.88 |
| ATOM | 5141 | O | LEU | 1377 | 77.289 | 69.070 | 43.482 | 1.00 | 16.02 |
| ATOM | 5142 | N | ALA | 1378 | 75.442 | 69.460 | 42.266 | 1.00 | 18.34 |
| ATOM | 5143 | CA | ALA | 1378 | 74.606 | 69.813 | 43.406 | 1.00 | 18.74 |
| ATOM | 5144 | CB | ALA | 1378 | 73.235 | 70.252 | 42.931 | 1.00 | 18.93 |
| ATOM | 5145 | C | ALA | 1378 | 74.474 | 68.688 | 44.414 | 1.00 | 20.05 |
| ATOM | 5146 | O | ALA | 1378 | 74.233 | 68.927 | 45.600 | 1.00 | 23.62 |
| ATOM | 5147 | N | LEU | 1379 | 74.631 | 67.456 | 43.957 | 1.00 | 19.27 |
| ATOM | 5148 | CA | LEU | 1379 | 74.514 | 66.330 | 44.862 | 1.00 | 17.31 |
| ATOM | 5149 | CB | LEU | 1379 | 73.839 | 65.160 | 44.158 | 1.00 | 14.86 |
| ATOM | 5150 | CG | LEU | 1379 | 72.367 | 65.373 | 43.794 | 1.00 | 11.16 |
| ATOM | 5151 | CD1 | LEU | 1379 | 71.828 | 64.139 | 43.131 | 1.00 | 13.25 |
| ATOM | 5152 | CD2 | LEU | 1379 | 71.563 | 65.666 | 45.038 | 1.00 | 12.87 |
| ATOM | 5153 | C | LEU | 1379 | 75.820 | 65.902 | 45.530 | 1.00 | 19.22 |
| ATOM | 5154 | O | LEU | 1379 | 75.799 | 65.039 | 46.406 | 1.00 | 22.97 |
| ATOM | 5155 | N | GLY | 1380 | 76.951 | 66.490 | 45.137 | 1.00 | 18.29 |
| ATOM | 5156 | CA | GLY | 1380 | 78.210 | 66.122 | 45.773 | 1.00 | 18.10 |
| ATOM | 5157 | C | GLY | 1380 | 79.440 | 65.888 | 44.907 | 1.00 | 17.70 |
| ATOM | 5158 | O | GLY | 1380 | 80.567 | 66.032 | 45.380 | 1.00 | 14.69 |
| ATOM | 5159 | N | ALA | 1381 | 79.240 | 65.501 | 43.653 | 1.00 | 18.38 |
| ATOM | 5160 | CA | ALA | 1381 | 80.359 | 65.247 | 42.753 | 1.00 | 18.79 |
| ATOM | 5161 | CB | ALA | 1381 | 79.849 | 64.746 | 41.422 | 1.00 | 17.88 |
| ATOM | 5162 | C | ALA | 1381 | 81.179 | 66.507 | 42.545 | 1.00 | 19.77 |
| ATOM | 5163 | O | ALA | 1381 | 80.628 | 67.601 | 42.532 | 1.00 | 22.90 |
| ATOM | 5164 | N | SER | 1382 | 82.492 | 66.358 | 42.400 | 1.00 | 20.02 |
| ATOM | 5165 | CA | SER | 1382 | 83.367 | 67.507 | 42.160 | 1.00 | 20.59 |
| ATOM | 5166 | CB | SER | 1382 | 84.749 | 67.266 | 42.768 | 1.00 | 18.13 |
| ATOM | 5167 | OG | SER | 1382 | 84.652 | 67.191 | 44.180 | 1.00 | 15.75 |
| ATOM | 5168 | C | SER | 1382 | 83.475 | 67.871 | 40.668 | 1.00 | 20.80 |
| ATOM | 5169 | O | SER | 1382 | 83.501 | 69.054 | 40.304 | 1.00 | 21.81 |
| ATOM | 5170 | N | THR | 1383 | 83.535 | 66.856 | 39.813 | 1.00 | 17.88 |
| ATOM | 5171 | CA | THR | 1383 | 83.621 | 67.065 | 38.377 | 1.00 | 17.53 |
| ATOM | 5172 | CB | THR | 1383 | 85.075 | 66.831 | 37.818 | 1.00 | 17.61 |
| ATOM | 5173 | OG1 | THR | 1383 | 85.611 | 65.603 | 38.328 | 1.00 | 20.84 |
| ATOM | 5174 | CG2 | THR | 1383 | 86.013 | 67.982 | 38.180 | 1.00 | 8.94 |
| ATOM | 5175 | C | THR | 1383 | 82.639 | 66.100 | 37.719 | 1.00 | 17.87 |
| ATOM | 5176 | O | THR | 1383 | 82.062 | 65.243 | 38.388 | 1.00 | 18.28 |
| ATOM | 5177 | N | VAL | 1384 | 82.457 | 66.225 | 36.411 | 1.00 | 17.76 |
| ATOM | 5178 | CA | VAL | 1384 | 81.531 | 65.370 | 35.689 | 1.00 | 18.85 |
| ATOM | 5179 | CB | VAL | 1384 | 80.239 | 66.138 | 35.325 | 1.00 | 20.09 |
| ATOM | 5180 | CG1 | VAL | 1384 | 79.243 | 65.206 | 34.650 | 1.00 | 22.58 |
| ATOM | 5181 | CG2 | VAL | 1384 | 79.618 | 66.748 | 36.576 | 1.00 | 19.94 |
| ATOM | 5182 | C | VAL | 1384 | 82.211 | 64.888 | 34.417 | 1.00 | 19.13 |
| ATOM | 5183 | O | VAL | 1384 | 82.887 | 65.665 | 33.747 | 1.00 | 19.52 |
| ATOM | 5184 | N | MET | 1385 | 82.044 | 63.606 | 34.104 | 1.00 | 19.13 |
| ATOM | 5185 | CA | MET | 1385 | 82.645 | 62.997 | 32.915 | 1.00 | 18.23 |
| ATOM | 5186 | CB | MET | 1385 | 83.345 | 61.688 | 33.284 | 1.00 | 17.04 |
| ATOM | 5187 | CG | MET | 1385 | 84.081 | 61.051 | 32.136 | 1.00 | 13.46 |
| ATOM | 5188 | SD | MET | 1385 | 84.923 | 59.571 | 32.655 | 1.00 | 19.09 |
| ATOM | 5189 | CE | MET | 1385 | 86.456 | 60.251 | 33.317 | 1.00 | 21.08 |

FIG. 1A-89

| ATOM | 5190 | C | MET | 1385 | 81.578 | 62.719 | 31.868 | 1.00 | 17.99 |
| --- | --- | --- | --- | --- | --- | --- | --- | --- | --- |
| ATOM | 5191 | O | MET | 1385 | 80.519 | 62.179 | 32.182 | 1.00 | 19.60 |
| ATOM | 5192 | N | MET | 1386 | 81.875 | 63.037 | 30.615 | 1.00 | 18.35 |
| ATOM | 5193 | CA | MET | 1386 | 80.910 | 62.837 | 29.541 | 1.00 | 16.61 |
| ATOM | 5194 | CB | MET | 1386 | 80.431 | 64.190 | 29.027 | 1.00 | 14.36 |
| ATOM | 5195 | CG | MET | 1386 | 79.810 | 65.051 | 30.087 | 1.00 | 12.38 |
| ATOM | 5196 | SD | MET | 1386 | 79.667 | 66.733 | 29.547 | 1.00 | 18.87 |
| ATOM | 5197 | CE | MET | 1386 | 81.312 | 67.356 | 29.974 | 1.00 | 17.73 |
| ATOM | 5198 | C | MET | 1386 | 81.441 | 62.023 | 28.376 | 1.00 | 15.70 |
| ATOM | 5199 | O | MET | 1386 | 82.617 | 62.092 | 28.044 | 1.00 | 11.01 |
| ATOM | 5200 | N | GLY | 1387 | 80.561 | 61.212 | 27.806 | 1.00 | 19.29 |
| ATOM | 5201 | CA | GLY | 1387 | 80.901 | 60.398 | 26.659 | 1.00 | 23.41 |
| ATOM | 5202 | C | GLY | 1387 | 80.052 | 60.931 | 25.523 | 1.00 | 26.99 |
| ATOM | 5203 | O | GLY | 1387 | 80.526 | 61.715 | 24.698 | 1.00 | 29.23 |
| ATOM | 5204 | N | SER | 1388 | 78.761 | 60.624 | 25.566 | 1.00 | 28.65 |
| ATOM | 5205 | CA | SER | 1388 | 77.815 | 61.065 | 24.545 | 1.00 | 31.48 |
| ATOM | 5206 | CB | SER | 1388 | 76.399 | 60.589 | 24.898 | 1.00 | 35.04 |
| ATOM | 5207 | OG | SER | 1388 | 75.483 | 60.905 | 23.859 | 1.00 | 41.86 |
| ATOM | 5208 | C | SER | 1388 | 77.803 | 62.578 | 24.284 | 1.00 | 31.07 |
| ATOM | 5209 | O | SER | 1388 | 77.956 | 63.008 | 23.142 | 1.00 | 31.04 |
| ATOM | 5210 | N | LEU | 1389 | 77.646 | 63.379 | 25.336 | 1.00 | 30.90 |
| ATOM | 5211 | CA | LEU | 1389 | 77.599 | 64.835 | 25.204 | 1.00 | 29.63 |
| ATOM | 5212 | CB | LEU | 1389 | 77.516 | 65.514 | 26.574 | 1.00 | 27.98 |
| ATOM | 5213 | CG | LEU | 1389 | 76.164 | 66.067 | 27.033 | 1.00 | 28.79 |
| ATOM | 5214 | CD1 | LEU | 1389 | 76.373 | 67.062 | 28.167 | 1.00 | 26.81 |
| ATOM | 5215 | CD2 | LEU | 1389 | 75.460 | 66.758 | 25.889 | 1.00 | 28.61 |
| ATOM | 5216 | C | LEU | 1389 | 78.762 | 65.450 | 24.438 | 1.00 | 30.59 |
| ATOM | 5217 | O | LEU | 1389 | 78.662 | 66.588 | 23.989 | 1.00 | 33.45 |
| ATOM | 5218 | N | LEU | 1390 | 79.866 | 64.723 | 24.304 | 1.00 | 28.48 |
| ATOM | 5219 | CA | LEU | 1390 | 81.030 | 65.247 | 23.601 | 1.00 | 26.24 |
| ATOM | 5220 | CB | LEU | 1390 | 82.189 | 65.398 | 24.585 | 1.00 | 23.55 |
| ATOM | 5221 | CG | LEU | 1390 | 81.834 | 66.123 | 25.890 | 1.00 | 23.78 |
| ATOM | 5222 | CD1 | LEU | 1390 | 82.978 | 66.032 | 26.883 | 1.00 | 24.77 |
| ATOM | 5223 | CD2 | LEU | 1390 | 81.467 | 67.578 | 25.614 | 1.00 | 20.41 |
| ATOM | 5224 | C | LEU | 1390 | 81.427 | 64.325 | 22.456 | 1.00 | 27.34 |
| ATOM | 5225 | O | LEU | 1390 | 82.375 | 64.599 | 21.727 | 1.00 | 26.38 |
| ATOM | 5226 | N | ALA | 1391 | 80.642 | 63.270 | 22.265 | 1.00 | 29.15 |
| ATOM | 5227 | CA | ALA | 1391 | 80.890 | 62.267 | 21.235 | 1.00 | 31.26 |
| ATOM | 5228 | CB | ALA | 1391 | 79.927 | 61.100 | 21.404 | 1.00 | 31.73 |
| ATOM | 5229 | C | ALA | 1391 | 80.903 | 62.719 | 19.777 | 1.00 | 32.50 |
| ATOM | 5230 | O | ALA | 1391 | 81.734 | 62.250 | 18.998 | 1.00 | 35.88 |
| ATOM | 5231 | N | ALA | 1392 | 79.975 | 63.585 | 19.383 | 1.00 | 30.95 |
| ATOM | 5232 | CA | ALA | 1392 | 79.932 | 64.034 | 17.990 | 1.00 | 28.80 |
| ATOM | 5233 | CB | ALA | 1392 | 78.504 | 64.045 | 17.489 | 1.00 | 28.83 |
| ATOM | 5234 | C | ALA | 1392 | 80.576 | 65.393 | 17.754 | 1.00 | 27.78 |
| ATOM | 5235 | O | ALA | 1392 | 80.169 | 66.121 | 16.849 | 1.00 | 28.88 |
| ATOM | 5236 | N | THR | 1393 | 81.551 | 65.757 | 18.579 | 1.00 | 26.43 |
| ATOM | 5237 | CA | THR | 1393 | 82.217 | 67.042 | 18.418 | 1.00 | 23.76 |
| ATOM | 5238 | CB | THR | 1393 | 82.798 | 67.557 | 19.742 | 1.00 | 19.29 |
| ATOM | 5239 | OG1 | THR | 1393 | 83.646 | 66.563 | 20.316 | 1.00 | 20.30 |
| ATOM | 5240 | CG2 | THR | 1393 | 81.684 | 67.894 | 20.719 | 1.00 | 15.86 |
| ATOM | 5241 | C | THR | 1393 | 83.323 | 66.910 | 17.373 | 1.00 | 24.72 |
| ATOM | 5242 | O | THR | 1393 | 83.803 | 65.807 | 17.109 | 1.00 | 25.78 |
| ATOM | 5243 | N | THR | 1394 | 83.735 | 68.032 | 16.795 | 1.00 | 23.33 |
| ATOM | 5244 | CA | THR | 1394 | 84.761 | 68.036 | 15.767 | 1.00 | 22.70 |
| ATOM | 5245 | CB | THR | 1394 | 85.078 | 69.469 | 15.314 | 1.00 | 22.05 |
| ATOM | 5246 | OG1 | THR | 1394 | 83.898 | 70.271 | 15.392 | 1.00 | 23.20 |
| ATOM | 5247 | CG2 | THR | 1394 | 85.552 | 69.468 | 13.882 | 1.00 | 23.82 |
| ATOM | 5248 | C | THR | 1394 | 86.052 | 67.361 | 16.224 | 1.00 | 23.54 |

FIG. 1A-90

| ATOM | 5249 | O   | THR | 1394 | 86.690 | 66.643 | 15.448 | 1.00 | 24.72 |
| ---- | ---- | --- | --- | ---- | ------ | ------ | ------ | ---- | ----- |
| ATOM | 5250 | N   | GLU | 1395 | 86.409 | 67.566 | 17.490 | 1.00 | 22.73 |
| ATOM | 5251 | CA  | GLU | 1395 | 87.634 | 67.007 | 18.059 | 1.00 | 23.52 |
| ATOM | 5252 | CB  | GLU | 1395 | 88.078 | 67.819 | 19.283 | 1.00 | 25.10 |
| ATOM | 5253 | CG  | GLU | 1395 | 88.494 | 69.254 | 18.995 | 1.00 | 27.32 |
| ATOM | 5254 | CD  | GLU | 1395 | 87.322 | 70.185 | 18.752 | 1.00 | 31.55 |
| ATOM | 5255 | OE1 | GLU | 1395 | 86.177 | 69.833 | 19.102 | 1.00 | 34.70 |
| ATOM | 5256 | OE2 | GLU | 1395 | 87.547 | 71.287 | 18.216 | 1.00 | 35.64 |
| ATOM | 5257 | C   | GLU | 1395 | 87.560 | 65.536 | 18.460 | 1.00 | 23.45 |
| ATOM | 5258 | O   | GLU | 1395 | 88.578 | 64.936 | 18.817 | 1.00 | 26.40 |
| ATOM | 5259 | N   | ALA | 1396 | 86.367 | 64.966 | 18.462 | 1.00 | 22.70 |
| ATOM | 5260 | CA  | ALA | 1396 | 86.219 | 63.570 | 18.842 | 1.00 | 23.99 |
| ATOM | 5261 | CB  | ALA | 1396 | 84.743 | 63.219 | 18.969 | 1.00 | 23.65 |
| ATOM | 5262 | C   | ALA | 1396 | 86.880 | 62.703 | 17.779 | 1.00 | 25.22 |
| ATOM | 5263 | O   | ALA | 1396 | 86.920 | 63.081 | 16.611 | 1.00 | 26.43 |
| ATOM | 5264 | N   | PRO | 1397 | 87.487 | 61.570 | 18.184 | 1.00 | 25.84 |
| ATOM | 5265 | CD  | PRO | 1397 | 87.743 | 61.103 | 19.555 | 1.00 | 26.36 |
| ATOM | 5266 | CA  | PRO | 1397 | 88.134 | 60.685 | 17.218 | 1.00 | 26.48 |
| ATOM | 5267 | CB  | PRO | 1397 | 88.672 | 59.565 | 18.102 | 1.00 | 21.83 |
| ATOM | 5268 | CG  | PRO | 1397 | 88.969 | 60.251 | 19.370 | 1.00 | 22.65 |
| ATOM | 5269 | C   | PRO | 1397 | 87.080 | 60.149 | 16.261 | 1.00 | 31.18 |
| ATOM | 5270 | O   | PRO | 1397 | 85.947 | 59.901 | 16.667 | 1.00 | 31.61 |
| ATOM | 5271 | N   | GLY | 1398 | 87.435 | 60.013 | 14.988 | 1.00 | 34.68 |
| ATOM | 5272 | CA  | GLY | 1398 | 86.490 | 59.487 | 14.023 | 1.00 | 38.08 |
| ATOM | 5273 | C   | GLY | 1398 | 86.157 | 60.474 | 12.931 | 1.00 | 41.29 |
| ATOM | 5274 | O   | GLY | 1398 | 86.563 | 61.635 | 12.975 | 1.00 | 43.61 |
| ATOM | 5275 | N   | GLU | 1399 | 85.442 | 60.001 | 11.922 | 1.00 | 42.43 |
| ATOM | 5276 | CA  | GLU | 1399 | 85.060 | 60.853 | 10.811 | 1.00 | 44.81 |
| ATOM | 5277 | CB  | GLU | 1399 | 85.423 | 60.179 | 9.485  | 1.00 | 50.25 |
| ATOM | 5278 | CG  | GLU | 1399 | 86.908 | 59.863 | 9.328  | 1.00 | 57.39 |
| ATOM | 5279 | CD  | GLU | 1399 | 87.787 | 61.093 | 9.490  | 1.00 | 63.38 |
| ATOM | 5280 | OE1 | GLU | 1399 | 87.617 | 62.057 | 8.710  | 1.00 | 64.91 |
| ATOM | 5281 | OE2 | GLU | 1399 | 88.642 | 61.097 | 10.405 | 1.00 | 66.89 |
| ATOM | 5282 | C   | GLU | 1399 | 83.564 | 61.103 | 10.876 | 1.00 | 44.39 |
| ATOM | 5283 | O   | GLU | 1399 | 82.861 | 60.497 | 11.696 | 1.00 | 45.82 |
| ATOM | 5284 | N   | TYR | 1400 | 83.081 | 62.012 | 10.038 | 1.00 | 42.99 |
| ATOM | 5285 | CA  | TYR | 1400 | 81.658 | 62.318 | 9.993  | 1.00 | 42.22 |
| ATOM | 5286 | CB  | TYR | 1400 | 81.424 | 63.815 | 9.838  | 1.00 | 38.80 |
| ATOM | 5287 | CG  | TYR | 1400 | 81.485 | 64.579 | 11.134 | 1.00 | 38.42 |
| ATOM | 5288 | CD1 | TYR | 1400 | 80.406 | 64.577 | 12.019 | 1.00 | 34.56 |
| ATOM | 5289 | CE1 | TYR | 1400 | 80.451 | 65.302 | 13.202 | 1.00 | 34.48 |
| ATOM | 5290 | CD2 | TYR | 1400 | 82.611 | 65.326 | 11.467 | 1.00 | 39.18 |
| ATOM | 5291 | CE2 | TYR | 1400 | 82.667 | 66.057 | 12.643 | 1.00 | 37.95 |
| ATOM | 5292 | CZ  | TYR | 1400 | 81.584 | 66.046 | 13.507 | 1.00 | 37.33 |
| ATOM | 5293 | OH  | TYR | 1400 | 81.637 | 66.803 | 14.656 | 1.00 | 35.83 |
| ATOM | 5294 | C   | TYR | 1400 | 81.010 | 61.592 | 8.828  | 1.00 | 43.85 |
| ATOM | 5295 | O   | TYR | 1400 | 81.693 | 61.121 | 7.915  | 1.00 | 46.67 |
| ATOM | 5296 | N   | PHE | 1401 | 79.691 | 61.485 | 8.874  | 1.00 | 42.83 |
| ATOM | 5297 | CA  | PHE | 1401 | 78.946 | 60.838 | 7.815  | 1.00 | 43.05 |
| ATOM | 5298 | CB  | PHE | 1401 | 79.094 | 59.311 | 7.881  | 1.00 | 45.25 |
| ATOM | 5299 | CG  | PHE | 1401 | 78.640 | 58.695 | 9.177  | 1.00 | 45.71 |
| ATOM | 5300 | CD1 | PHE | 1401 | 77.292 | 58.411 | 9.395  | 1.00 | 47.44 |
| ATOM | 5301 | CD2 | PHE | 1401 | 79.562 | 58.361 | 10.162 | 1.00 | 44.15 |
| ATOM | 5302 | CE1 | PHE | 1401 | 76.873 | 57.804 | 10.573 | 1.00 | 47.10 |
| ATOM | 5303 | CE2 | PHE | 1401 | 79.155 | 57.754 | 11.345 | 1.00 | 44.90 |
| ATOM | 5304 | CZ  | PHE | 1401 | 77.809 | 57.475 | 11.551 | 1.00 | 47.14 |
| ATOM | 5305 | C   | PHE | 1401 | 77.496 | 61.250 | 7.920  | 1.00 | 43.47 |
| ATOM | 5306 | O   | PHE | 1401 | 77.089 | 61.848 | 8.907  | 1.00 | 42.96 |
| ATOM | 5307 | N   | PHE | 1402 | 76.719 | 60.952 | 6.891  | 1.00 | 43.97 |

FIG. 1A-91

| | | | | | | | | | |
|---|---|---|---|---|---|---|---|---|---|
| ATOM | 5308 | CA | PHE | 1402 | 75.322 | 61.318 | 6.899 | 1.00 | 44.22 |
| ATOM | 5309 | CB | PHE | 1402 | 75.016 | 62.274 | 5.745 | 1.00 | 42.02 |
| ATOM | 5310 | CG | PHE | 1402 | 75.651 | 63.622 | 5.890 | 1.00 | 38.81 |
| ATOM | 5311 | CD1 | PHE | 1402 | 77.011 | 63.797 | 5.644 | 1.00 | 39.76 |
| ATOM | 5312 | CD2 | PHE | 1402 | 74.897 | 64.716 | 6.296 | 1.00 | 35.67 |
| ATOM | 5313 | CE1 | PHE | 1402 | 77.614 | 65.049 | 5.806 | 1.00 | 38.11 |
| ATOM | 5314 | CE2 | PHE | 1402 | 75.485 | 65.969 | 6.460 | 1.00 | 35.15 |
| ATOM | 5315 | CZ | PHE | 1402 | 76.848 | 66.136 | 6.216 | 1.00 | 36.13 |
| ATOM | 5316 | C | PHE | 1402 | 74.438 | 60.097 | 6.789 | 1.00 | 46.31 |
| ATOM | 5317 | O | PHE | 1402 | 74.732 | 59.177 | 6.035 | 1.00 | 46.36 |
| ATOM | 5318 | N | SER | 1403 | 73.380 | 60.072 | 7.583 | 1.00 | 48.81 |
| ATOM | 5319 | CA | SER | 1403 | 72.422 | 58.986 | 7.540 | 1.00 | 52.64 |
| ATOM | 5320 | CB | SER | 1403 | 72.183 | 58.429 | 8.936 | 1.00 | 54.92 |
| ATOM | 5321 | OG | SER | 1403 | 73.384 | 57.885 | 9.455 | 1.00 | 59.46 |
| ATOM | 5322 | C | SER | 1403 | 71.170 | 59.648 | 6.997 | 1.00 | 55.38 |
| ATOM | 5323 | O | SER | 1403 | 70.155 | 59.769 | 7.684 | 1.00 | 56.51 |
| ATOM | 5324 | N | ASP | 1404 | 71.302 | 60.146 | 5.769 | 1.00 | 57.77 |
| ATOM | 5325 | CA | ASP | 1404 | 70.240 | 60.843 | 5.048 | 1.00 | 58.06 |
| ATOM | 5326 | CB | ASP | 1404 | 69.000 | 59.958 | 4.873 | 1.00 | 61.87 |
| ATOM | 5327 | CG | ASP | 1404 | 68.045 | 60.501 | 3.819 | 1.00 | 67.61 |
| ATOM | 5328 | OD1 | ASP | 1404 | 68.524 | 60.956 | 2.751 | 1.00 | 65.71 |
| ATOM | 5329 | OD2 | ASP | 1404 | 66.816 | 60.469 | 4.060 | 1.00 | 72.76 |
| ATOM | 5330 | C | ASP | 1404 | 69.877 | 62.150 | 5.735 | 1.00 | 56.48 |
| ATOM | 5331 | O | ASP | 1404 | 68.911 | 62.228 | 6.497 | 1.00 | 55.20 |
| ATOM | 5332 | N | GLY | 1405 | 70.685 | 63.171 | 5.470 | 1.00 | 55.34 |
| ATOM | 5333 | CA | GLY | 1405 | 70.449 | 64.477 | 6.054 | 1.00 | 54.46 |
| ATOM | 5334 | C | GLY | 1405 | 71.232 | 64.720 | 7.327 | 1.00 | 53.22 |
| ATOM | 5335 | O | GLY | 1405 | 71.901 | 65.747 | 7.461 | 1.00 | 54.73 |
| ATOM | 5336 | N | ILE | 1406 | 71.161 | 63.779 | 8.262 | 1.00 | 51.10 |
| ATOM | 5337 | CA | ILE | 1406 | 71.872 | 63.919 | 9.528 | 1.00 | 47.34 |
| ATOM | 5338 | CB | ILE | 1406 | 71.181 | 63.149 | 10.693 | 1.00 | 47.55 |
| ATOM | 5339 | CG2 | ILE | 1406 | 70.137 | 64.040 | 11.359 | 1.00 | 46.87 |
| ATOM | 5340 | CG1 | ILE | 1406 | 70.582 | 61.817 | 10.214 | 1.00 | 47.02 |
| ATOM | 5341 | CD1 | ILE | 1406 | 69.158 | 61.912 | 9.660 | 1.00 | 43.14 |
| ATOM | 5342 | C | ILE | 1406 | 73.356 | 63.562 | 9.465 | 1.00 | 44.59 |
| ATOM | 5343 | O | ILE | 1406 | 73.738 | 62.474 | 9.026 | 1.00 | 43.27 |
| ATOM | 5344 | N | ARG | 1407 | 74.179 | 64.521 | 9.878 | 1.00 | 42.11 |
| ATOM | 5345 | CA | ARG | 1407 | 75.628 | 64.377 | 9.910 | 1.00 | 40.01 |
| ATOM | 5346 | CB | ARG | 1407 | 76.280 | 65.759 | 9.797 | 1.00 | 38.99 |
| ATOM | 5347 | CG | ARG | 1407 | 77.774 | 65.750 | 9.540 | 1.00 | 34.88 |
| ATOM | 5348 | CD | ARG | 1407 | 78.321 | 67.167 | 9.600 | 1.00 | 33.23 |
| ATOM | 5349 | NE | ARG | 1407 | 79.698 | 67.250 | 9.123 | 1.00 | 34.81 |
| ATOM | 5350 | CZ | ARG | 1407 | 80.671 | 67.912 | 9.745 | 1.00 | 33.80 |
| ATOM | 5351 | NH1 | ARG | 1407 | 80.430 | 68.551 | 10.883 | 1.00 | 35.60 |
| ATOM | 5352 | NH2 | ARG | 1407 | 81.881 | 67.972 | 9.207 | 1.00 | 31.88 |
| ATOM | 5353 | C | ARG | 1407 | 75.957 | 63.749 | 11.259 | 1.00 | 39.81 |
| ATOM | 5354 | O | ARG | 1407 | 75.848 | 64.399 | 12.299 | 1.00 | 40.00 |
| ATOM | 5355 | N | LEU | 1408 | 76.299 | 62.469 | 11.240 | 1.00 | 39.11 |
| ATOM | 5356 | CA | LEU | 1408 | 76.610 | 61.734 | 12.451 | 1.00 | 38.94 |
| ATOM | 5357 | CB | LEU | 1408 | 75.765 | 60.464 | 12.489 | 1.00 | 35.80 |
| ATOM | 5358 | CG | LEU | 1408 | 74.271 | 60.639 | 12.265 | 1.00 | 33.00 |
| ATOM | 5359 | CD1 | LEU | 1408 | 73.658 | 59.302 | 12.000 | 1.00 | 35.13 |
| ATOM | 5360 | CD2 | LEU | 1408 | 73.637 | 61.293 | 13.466 | 1.00 | 33.45 |
| ATOM | 5361 | C | LEU | 1408 | 78.077 | 61.349 | 12.582 | 1.00 | 39.97 |
| ATOM | 5362 | O | LEU | 1408 | 78.846 | 61.421 | 11.621 | 1.00 | 41.20 |
| ATOM | 5363 | N | LYS | 1409 | 78.444 | 60.922 | 13.784 | 1.00 | 39.40 |
| ATOM | 5364 | CA | LYS | 1409 | 79.793 | 60.475 | 14.088 | 1.00 | 37.55 |
| ATOM | 5365 | CB | LYS | 1409 | 80.574 | 61.559 | 14.812 | 1.00 | 34.49 |
| ATOM | 5366 | CG | LYS | 1409 | 82.070 | 61.410 | 14.684 | 1.00 | 31.73 |

FIG. 1A-92

| | | | | | | | | |
|---|---|---|---|---|---|---|---|---|
| ATOM | 5367 | CD | LYS | 1409 | 82.748 | 62.681 | 15.122 | 1.00 | 31.14 |
| ATOM | 5368 | CE | LYS | 1409 | 84.117 | 62.821 | 14.504 | 1.00 | 30.59 |
| ATOM | 5369 | NZ | LYS | 1409 | 84.738 | 64.118 | 14.889 | 1.00 | 30.87 |
| ATOM | 5370 | C | LYS | 1409 | 79.616 | 59.261 | 14.990 | 1.00 | 38.36 |
| ATOM | 5371 | O | LYS | 1409 | 78.648 | 59.181 | 15.760 | 1.00 | 38.95 |
| ATOM | 5372 | N | LYS | 1410 | 80.538 | 58.314 | 14.878 | 1.00 | 37.52 |
| ATOM | 5373 | CA | LYS | 1410 | 80.481 | 57.083 | 15.654 | 1.00 | 37.57 |
| ATOM | 5374 | CB | LYS | 1410 | 81.473 | 56.045 | 15.106 | 1.00 | 39.72 |
| ATOM | 5375 | CG | LYS | 1410 | 81.424 | 55.848 | 13.586 | 1.00 | 47.39 |
| ATOM | 5376 | CD | LYS | 1410 | 82.257 | 56.898 | 12.828 | 1.00 | 54.46 |
| ATOM | 5377 | CE | LYS | 1410 | 83.704 | 56.437 | 12.552 | 1.00 | 57.97 |
| ATOM | 5378 | NZ | LYS | 1410 | 84.528 | 56.135 | 13.772 | 1.00 | 58.51 |
| ATOM | 5379 | C | LYS | 1410 | 80.737 | 57.292 | 17.144 | 1.00 | 36.58 |
| ATOM | 5380 | O | LYS | 1410 | 81.503 | 58.169 | 17.548 | 1.00 | 36.90 |
| ATOM | 5381 | N | TYR | 1411 | 80.045 | 56.504 | 17.956 | 1.00 | 33.81 |
| ATOM | 5382 | CA | TYR | 1411 | 80.196 | 56.538 | 19.398 | 1.00 | 29.59 |
| ATOM | 5383 | CB | TYR | 1411 | 79.308 | 57.606 | 20.036 | 1.00 | 28.89 |
| ATOM | 5384 | CG | TYR | 1411 | 79.468 | 57.638 | 21.536 | 1.00 | 29.67 |
| ATOM | 5385 | CD1 | TYR | 1411 | 80.735 | 57.684 | 22.113 | 1.00 | 27.56 |
| ATOM | 5386 | CE1 | TYR | 1411 | 80.900 | 57.654 | 23.484 | 1.00 | 32.21 |
| ATOM | 5387 | CD2 | TYR | 1411 | 78.363 | 57.575 | 22.380 | 1.00 | 32.44 |
| ATOM | 5388 | CE2 | TYR | 1411 | 78.515 | 57.547 | 23.767 | 1.00 | 35.34 |
| ATOM | 5389 | CZ | TYR | 1411 | 79.792 | 57.588 | 24.313 | 1.00 | 35.21 |
| ATOM | 5390 | OH | TYR | 1411 | 79.975 | 57.562 | 25.683 | 1.00 | 32.62 |
| ATOM | 5391 | C | TYR | 1411 | 79.794 | 55.156 | 19.890 | 1.00 | 28.28 |
| ATOM | 5392 | O | TYR | 1411 | 78.666 | 54.717 | 19.658 | 1.00 | 29.51 |
| ATOM | 5393 | N | ARG | 1412 | 80.705 | 54.482 | 20.583 | 1.00 | 25.07 |
| ATOM | 5394 | CA | ARG | 1412 | 80.442 | 53.131 | 21.067 | 1.00 | 22.53 |
| ATOM | 5395 | CB | ARG | 1412 | 81.072 | 52.122 | 20.104 | 1.00 | 22.14 |
| ATOM | 5396 | CG | ARG | 1412 | 82.573 | 52.254 | 20.020 | 1.00 | 22.85 |
| ATOM | 5397 | CD | ARG | 1412 | 83.202 | 51.252 | 19.099 | 1.00 | 21.78 |
| ATOM | 5398 | NE | ARG | 1412 | 84.655 | 51.364 | 19.163 | 1.00 | 24.40 |
| ATOM | 5399 | CZ | ARG | 1412 | 85.496 | 50.726 | 18.355 | 1.00 | 28.25 |
| ATOM | 5400 | NH1 | ARG | 1412 | 85.037 | 49.921 | 17.410 | 1.00 | 29.33 |
| ATOM | 5401 | NH2 | ARG | 1412 | 86.803 | 50.887 | 18.501 | 1.00 | 31.56 |
| ATOM | 5402 | C | ARG | 1412 | 80.980 | 52.865 | 22.469 | 1.00 | 20.00 |
| ATOM | 5403 | O | ARG | 1412 | 81.990 | 53.437 | 22.881 | 1.00 | 19.85 |
| ATOM | 5404 | N | GLY | 1413 | 80.316 | 51.966 | 23.183 | 1.00 | 18.06 |
| ATOM | 5405 | CA | GLY | 1413 | 80.765 | 51.618 | 24.512 | 1.00 | 18.17 |
| ATOM | 5406 | C | GLY | 1413 | 82.049 | 50.841 | 24.373 | 1.00 | 19.69 |
| ATOM | 5407 | O | GLY | 1413 | 82.237 | 50.126 | 23.384 | 1.00 | 19.71 |
| ATOM | 5408 | N | MET | 1414 | 82.944 | 50.988 | 25.342 | 1.00 | 20.34 |
| ATOM | 5409 | CA | MET | 1414 | 84.221 | 50.282 | 25.309 | 1.00 | 22.12 |
| ATOM | 5410 | CB | MET | 1414 | 85.180 | 50.857 | 26.356 | 1.00 | 22.03 |
| ATOM | 5411 | CG | MET | 1414 | 85.671 | 52.265 | 26.041 | 1.00 | 23.32 |
| ATOM | 5412 | SD | MET | 1414 | 86.555 | 52.417 | 24.466 | 1.00 | 26.75 |
| ATOM | 5413 | CE | MET | 1414 | 85.214 | 52.711 | 23.391 | 1.00 | 28.28 |
| ATOM | 5414 | C | MET | 1414 | 84.040 | 48.781 | 25.504 | 1.00 | 22.54 |
| ATOM | 5415 | O | MET | 1414 | 84.896 | 47.981 | 25.112 | 1.00 | 23.42 |
| ATOM | 5416 | N | GLY | 1415 | 82.907 | 48.405 | 26.086 | 1.00 | 22.77 |
| ATOM | 5417 | CA | GLY | 1415 | 82.626 | 47.006 | 26.313 | 1.00 | 22.65 |
| ATOM | 5418 | C | GLY | 1415 | 81.802 | 46.428 | 25.190 | 1.00 | 23.70 |
| ATOM | 5419 | O | GLY | 1415 | 81.146 | 45.412 | 25.378 | 1.00 | 24.44 |
| ATOM | 5420 | N | SER | 1416 | 81.783 | 47.091 | 24.039 | 1.00 | 25.46 |
| ATOM | 5421 | CA | SER | 1416 | 81.025 | 46.578 | 22.911 | 1.00 | 28.36 |
| ATOM | 5422 | CB | SER | 1416 | 80.623 | 47.703 | 21.945 | 1.00 | 26.46 |
| ATOM | 5423 | OG | SER | 1416 | 81.743 | 48.329 | 21.341 | 1.00 | 25.07 |
| ATOM | 5424 | C | SER | 1416 | 81.858 | 45.522 | 22.194 | 1.00 | 32.07 |
| ATOM | 5425 | O | SER | 1416 | 83.089 | 45.526 | 22.278 | 1.00 | 32.48 |

FIG. 1A-93

| ATOM | 5426 | N | LEU | 1417 | 81.175 | 44.625 | 21.490 | 1.00 | 35.05 |
|---|---|---|---|---|---|---|---|---|---|
| ATOM | 5427 | CA | LEU | 1417 | 81.815 | 43.551 | 20.746 | 1.00 | 37.86 |
| ATOM | 5428 | CB | LEU | 1417 | 80.744 | 42.758 | 19.989 | 1.00 | 37.24 |
| ATOM | 5429 | CG | LEU | 1417 | 80.467 | 41.322 | 20.443 | 1.00 | 36.80 |
| ATOM | 5430 | CD1 | LEU | 1417 | 81.602 | 40.422 | 19.990 | 1.00 | 41.48 |
| ATOM | 5431 | CD2 | LEU | 1417 | 80.305 | 41.258 | 21.948 | 1.00 | 32.76 |
| ATOM | 5432 | C | LEU | 1417 | 82.909 | 44.029 | 19.777 | 1.00 | 41.62 |
| ATOM | 5433 | O | LEU | 1417 | 83.996 | 43.447 | 19.726 | 1.00 | 42.91 |
| ATOM | 5434 | N | ASP | 1418 | 82.625 | 45.096 | 19.029 | 1.00 | 43.98 |
| ATOM | 5435 | CA | ASP | 1418 | 83.582 | 45.628 | 18.056 | 1.00 | 44.77 |
| ATOM | 5436 | CB | ASP | 1418 | 82.852 | 46.360 | 16.916 | 1.00 | 45.89 |
| ATOM | 5437 | CG | ASP | 1418 | 82.267 | 47.696 | 17.345 | 1.00 | 49.84 |
| ATOM | 5438 | OD1 | ASP | 1418 | 81.466 | 47.728 | 18.304 | 1.00 | 54.75 |
| ATOM | 5439 | OD2 | ASP | 1418 | 82.600 | 48.718 | 16.706 | 1.00 | 49.55 |
| ATOM | 5440 | C | ASP | 1418 | 84.658 | 46.521 | 18.672 | 1.00 | 44.00 |
| ATOM | 5441 | O | ASP | 1418 | 85.700 | 46.754 | 18.067 | 1.00 | 45.96 |
| ATOM | 5442 | N | ALA | 1419 | 84.383 | 47.068 | 19.848 | 1.00 | 42.92 |
| ATOM | 5443 | CA | ALA | 1419 | 85.363 | 47.908 | 20.511 | 1.00 | 41.90 |
| ATOM | 5444 | CB | ALA | 1419 | 84.712 | 48.728 | 21.612 | 1.00 | 39.79 |
| ATOM | 5445 | C | ALA | 1419 | 86.398 | 46.970 | 21.100 | 1.00 | 42.91 |
| ATOM | 5446 | O | ALA | 1419 | 87.598 | 47.217 | 20.994 | 1.00 | 43.77 |
| ATOM | 5447 | N | MET | 1420 | 85.919 | 45.878 | 21.692 | 1.00 | 44.17 |
| ATOM | 5448 | CA | MET | 1420 | 86.783 | 44.882 | 22.324 | 1.00 | 46.58 |
| ATOM | 5449 | CB | MET | 1420 | 85.960 | 43.956 | 23.228 | 1.00 | 44.85 |
| ATOM | 5450 | CG | MET | 1420 | 85.222 | 44.663 | 24.359 | 1.00 | 40.59 |
| ATOM | 5451 | SD | MET | 1420 | 84.557 | 43.506 | 25.583 | 1.00 | 37.46 |
| ATOM | 5452 | CE | MET | 1420 | 83.211 | 42.736 | 24.659 | 1.00 | 35.09 |
| ATOM | 5453 | C | MET | 1420 | 87.615 | 44.049 | 21.340 | 1.00 | 48.15 |
| ATOM | 5454 | O | MET | 1420 | 87.079 | 43.674 | 20.273 | 1.00 | 49.93 |
| ATOM | 5455 | CB | ILE | 1437 | 81.342 | 33.951 | 22.925 | 1.00 | 66.55 |
| ATOM | 5456 | CG2 | ILE | 1437 | 81.311 | 33.579 | 21.441 | 1.00 | 68.42 |
| ATOM | 5457 | CG1 | ILE | 1437 | 80.618 | 32.891 | 23.774 | 1.00 | 66.87 |
| ATOM | 5458 | CD1 | ILE | 1437 | 80.344 | 33.296 | 25.209 | 1.00 | 65.86 |
| ATOM | 5459 | C | ILE | 1437 | 82.900 | 35.253 | 24.433 | 1.00 | 60.65 |
| ATOM | 5460 | O | ILE | 1437 | 83.257 | 34.991 | 25.582 | 1.00 | 60.18 |
| ATOM | 5461 | N | ILE | 1437 | 83.398 | 32.887 | 23.943 | 1.00 | 64.00 |
| ATOM | 5462 | CA | ILE | 1437 | 82.815 | 34.144 | 23.394 | 1.00 | 63.11 |
| ATOM | 5463 | N | LYS | 1438 | 82.590 | 36.480 | 24.022 | 1.00 | 58.06 |
| ATOM | 5464 | CA | LYS | 1438 | 82.649 | 37.632 | 24.916 | 1.00 | 54.30 |
| ATOM | 5465 | CB | LYS | 1438 | 83.479 | 38.752 | 24.283 | 1.00 | 57.05 |
| ATOM | 5466 | CG | LYS | 1438 | 84.954 | 38.440 | 24.118 | 1.00 | 61.76 |
| ATOM | 5467 | CD | LYS | 1438 | 85.719 | 39.680 | 23.684 | 1.00 | 66.01 |
| ATOM | 5468 | CE | LYS | 1438 | 87.222 | 39.446 | 23.713 | 1.00 | 70.05 |
| ATOM | 5469 | NZ | LYS | 1438 | 87.994 | 40.707 | 23.490 | 1.00 | 72.96 |
| ATOM | 5470 | C | LYS | 1438 | 81.264 | 38.170 | 25.269 | 1.00 | 50.75 |
| ATOM | 5471 | O | LYS | 1438 | 80.359 | 38.186 | 24.437 | 1.00 | 51.21 |
| ATOM | 5472 | N | VAL | 1439 | 81.109 | 38.618 | 26.508 | 1.00 | 47.03 |
| ATOM | 5473 | CA | VAL | 1439 | 79.841 | 39.171 | 26.969 | 1.00 | 42.02 |
| ATOM | 5474 | CB | VAL | 1439 | 79.561 | 38.776 | 28.441 | 1.00 | 39.60 |
| ATOM | 5475 | CG1 | VAL | 1439 | 78.227 | 39.331 | 28.893 | 1.00 | 37.77 |
| ATOM | 5476 | CG2 | VAL | 1439 | 79.573 | 37.261 | 28.589 | 1.00 | 37.89 |
| ATOM | 5477 | C | VAL | 1439 | 79.903 | 40.694 | 26.830 | 1.00 | 39.68 |
| ATOM | 5478 | O | VAL | 1439 | 80.562 | 41.372 | 27.623 | 1.00 | 39.64 |
| ATOM | 5479 | N | ALA | 1440 | 79.266 | 41.214 | 25.782 | 1.00 | 36.52 |
| ATOM | 5480 | CA | ALA | 1440 | 79.244 | 42.651 | 25.514 | 1.00 | 33.16 |
| ATOM | 5481 | CB | ALA | 1440 | 78.640 | 42.931 | 24.151 | 1.00 | 33.07 |
| ATOM | 5482 | C | ALA | 1440 | 78.487 | 43.425 | 26.578 | 1.00 | 31.48 |
| ATOM | 5483 | O | ALA | 1440 | 77.377 | 43.055 | 26.964 | 1.00 | 31.26 |
| ATOM | 5484 | N | GLN | 1441 | 79.092 | 44.517 | 27.031 | 1.00 | 30.45 |

FIG. 1A-94

| ATOM | 5485 | CA | GLN | 1441 | 78.497 | 45.369 | 28.049 | 1.00 | 27.44 |
|------|------|-----|-----|------|--------|--------|--------|------|-------|
| ATOM | 5486 | CB | GLN | 1441 | 79.453 | 45.525 | 29.225 | 1.00 | 23.78 |
| ATOM | 5487 | CG | GLN | 1441 | 79.765 | 44.207 | 29.902 | 1.00 | 22.17 |
| ATOM | 5488 | CD | GLN | 1441 | 80.382 | 44.395 | 31.258 | 1.00 | 23.37 |
| ATOM | 5489 | OE1 | GLN | 1441 | 79.840 | 45.109 | 32.100 | 1.00 | 22.22 |
| ATOM | 5490 | NE2 | GLN | 1441 | 81.515 | 43.750 | 31.489 | 1.00 | 25.42 |
| ATOM | 5491 | C | GLN | 1441 | 78.086 | 46.733 | 27.501 | 1.00 | 28.00 |
| ATOM | 5492 | O | GLN | 1441 | 77.548 | 47.565 | 28.230 | 1.00 | 28.70 |
| ATOM | 5493 | N | GLY | 1442 | 78.273 | 46.929 | 26.200 | 1.00 | 28.38 |
| ATOM | 5494 | CA | GLY | 1442 | 77.905 | 48.184 | 25.576 | 1.00 | 27.33 |
| ATOM | 5495 | C | GLY | 1442 | 77.463 | 47.982 | 24.138 | 1.00 | 27.30 |
| ATOM | 5496 | O | GLY | 1442 | 77.656 | 46.902 | 23.564 | 1.00 | 27.61 |
| ATOM | 5497 | N | VAL | 1443 | 76.833 | 49.005 | 23.572 | 1.00 | 26.10 |
| ATOM | 5498 | CA | VAL | 1443 | 76.376 | 48.970 | 22.187 | 1.00 | 23.86 |
| ATOM | 5499 | CB | VAL | 1443 | 74.867 | 49.329 | 22.057 | 1.00 | 21.54 |
| ATOM | 5500 | CG1 | VAL | 1443 | 74.027 | 48.384 | 22.884 | 1.00 | 16.72 |
| ATOM | 5501 | CG2 | VAL | 1443 | 74.618 | 50.775 | 22.470 | 1.00 | 21.56 |
| ATOM | 5502 | C | VAL | 1443 | 77.202 | 49.988 | 21.406 | 1.00 | 23.54 |
| ATOM | 5503 | O | VAL | 1443 | 77.823 | 50.877 | 21.995 | 1.00 | 23.22 |
| ATOM | 5504 | N | SER | 1444 | 77.234 | 49.841 | 20.088 | 1.00 | 24.09 |
| ATOM | 5505 | CA | SER | 1444 | 77.980 | 50.765 | 19.248 | 1.00 | 23.73 |
| ATOM | 5506 | CB | SER | 1444 | 78.953 | 49.995 | 18.359 | 1.00 | 24.52 |
| ATOM | 5507 | OG | SER | 1444 | 79.897 | 50.872 | 17.774 | 1.00 | 30.92 |
| ATOM | 5508 | C | SER | 1444 | 76.972 | 51.502 | 18.392 | 1.00 | 24.25 |
| ATOM | 5509 | O | SER | 1444 | 76.180 | 50.874 | 17.689 | 1.00 | 25.44 |
| ATOM | 5510 | N | GLY | 1445 | 76.973 | 52.825 | 18.454 | 1.00 | 24.61 |
| ATOM | 5511 | CA | GLY | 1445 | 76.017 | 53.576 | 17.662 | 1.00 | 26.65 |
| ATOM | 5512 | C | GLY | 1445 | 76.569 | 54.849 | 17.063 | 1.00 | 28.09 |
| ATOM | 5513 | O | GLY | 1445 | 77.767 | 54.951 | 16.794 | 1.00 | 29.89 |
| ATOM | 5514 | N | ALA | 1446 | 75.695 | 55.822 | 16.841 | 1.00 | 27.70 |
| ATOM | 5515 | CA | ALA | 1446 | 76.112 | 57.090 | 16.272 | 1.00 | 28.08 |
| ATOM | 5516 | CB | ALA | 1446 | 75.848 | 57.105 | 14.782 | 1.00 | 25.75 |
| ATOM | 5517 | C | ALA | 1446 | 75.364 | 58.220 | 16.947 | 1.00 | 29.63 |
| ATOM | 5518 | O | ALA | 1446 | 74.307 | 58.004 | 17.543 | 1.00 | 29.07 |
| ATOM | 5519 | N | VAL | 1447 | 75.935 | 59.416 | 16.879 | 1.00 | 31.82 |
| ATOM | 5520 | CA | VAL | 1447 | 75.325 | 60.612 | 17.454 | 1.00 | 35.50 |
| ATOM | 5521 | CB | VAL | 1447 | 75.954 | 60.996 | 18.819 | 1.00 | 38.59 |
| ATOM | 5522 | CG1 | VAL | 1447 | 75.443 | 60.074 | 19.917 | 1.00 | 41.19 |
| ATOM | 5523 | CG2 | VAL | 1447 | 77.464 | 60.914 | 18.744 | 1.00 | 41.83 |
| ATOM | 5524 | C | VAL | 1447 | 75.471 | 61.767 | 16.460 | 1.00 | 36.50 |
| ATOM | 5525 | O | VAL | 1447 | 76.389 | 61.781 | 15.633 | 1.00 | 36.46 |
| ATOM | 5526 | N | GLN | 1448 | 74.543 | 62.715 | 16.527 | 1.00 | 37.04 |
| ATOM | 5527 | CA | GLN | 1448 | 74.538 | 63.863 | 15.632 | 1.00 | 37.13 |
| ATOM | 5528 | CB | GLN | 1448 | 73.145 | 64.492 | 15.624 | 1.00 | 40.18 |
| ATOM | 5529 | CG | GLN | 1448 | 72.945 | 65.593 | 14.589 | 1.00 | 42.82 |
| ATOM | 5530 | CD | GLN | 1448 | 71.498 | 66.047 | 14.492 | 1.00 | 42.85 |
| ATOM | 5531 | OE1 | GLN | 1448 | 70.612 | 65.492 | 15.146 | 1.00 | 41.67 |
| ATOM | 5532 | NE2 | GLN | 1448 | 71.251 | 67.054 | 13.666 | 1.00 | 43.75 |
| ATOM | 5533 | C | GLN | 1448 | 75.603 | 64.919 | 15.941 | 1.00 | 36.41 |
| ATOM | 5534 | O | GLN | 1448 | 75.812 | 65.298 | 17.096 | 1.00 | 37.30 |
| ATOM | 5535 | N | ASP | 1449 | 76.263 | 65.383 | 14.885 | 1.00 | 35.19 |
| ATOM | 5536 | CA | ASP | 1449 | 77.311 | 66.399 | 14.941 | 1.00 | 34.49 |
| ATOM | 5537 | CB | ASP | 1449 | 77.536 | 66.948 | 13.524 | 1.00 | 33.54 |
| ATOM | 5538 | CG | ASP | 1449 | 78.452 | 68.160 | 13.483 | 1.00 | 34.61 |
| ATOM | 5539 | OD1 | ASP | 1449 | 79.444 | 68.210 | 14.242 | 1.00 | 34.88 |
| ATOM | 5540 | OD2 | ASP | 1449 | 78.183 | 69.063 | 12.663 | 1.00 | 35.64 |
| ATOM | 5541 | C | ASP | 1449 | 76.961 | 67.537 | 15.896 | 1.00 | 33.86 |
| ATOM | 5542 | O | ASP | 1449 | 76.038 | 68.301 | 15.642 | 1.00 | 35.06 |
| ATOM | 5543 | N | LYS | 1450 | 77.714 | 67.647 | 16.986 | 1.00 | 33.79 |

FIG. 1A-95

| ATOM | 5544 | CA | LYS | 1450 | 77.487 | 68.696 | 17.977 | 1.00 | 34.79 |
| ATOM | 5545 | CB | LYS | 1450 | 77.726 | 68.163 | 19.393 | 1.00 | 38.05 |
| ATOM | 5546 | CG | LYS | 1450 | 76.750 | 67.084 | 19.820 | 1.00 | 47.10 |
| ATOM | 5547 | CD | LYS | 1450 | 77.088 | 66.552 | 21.200 | 1.00 | 52.04 |
| ATOM | 5548 | CE | LYS | 1450 | 76.150 | 65.422 | 21.602 | 1.00 | 57.04 |
| ATOM | 5549 | NZ | LYS | 1450 | 76.264 | 64.232 | 20.705 | 1.00 | 59.52 |
| ATOM | 5550 | C | LYS | 1450 | 78.356 | 69.931 | 17.754 | 1.00 | 33.28 |
| ATOM | 5551 | O | LYS | 1450 | 78.324 | 70.864 | 18.555 | 1.00 | 34.18 |
| ATOM | 5552 | N | GLY | 1451 | 79.148 | 69.934 | 16.687 | 1.00 | 32.00 |
| ATOM | 5553 | CA | GLY | 1451 | 80.005 | 71.074 | 16.413 | 1.00 | 29.42 |
| ATOM | 5554 | C | GLY | 1451 | 81.354 | 70.937 | 17.086 | 1.00 | 28.07 |
| ATOM | 5555 | O | GLY | 1451 | 81.808 | 69.818 | 17.335 | 1.00 | 26.57 |
| ATOM | 5556 | N | SER | 1452 | 81.971 | 72.066 | 17.426 | 1.00 | 27.12 |
| ATOM | 5557 | CA | SER | 1452 | 83.290 | 72.062 | 18.058 | 1.00 | 26.69 |
| ATOM | 5558 | CB | SER | 1452 | 84.206 | 73.084 | 17.364 | 1.00 | 30.79 |
| ATOM | 5559 | OG | SER | 1452 | 85.474 | 73.215 | 18.000 | 1.00 | 30.53 |
| ATOM | 5560 | C | SER | 1452 | 83.285 | 72.312 | 19.560 | 1.00 | 25.17 |
| ATOM | 5561 | O | SER | 1452 | 82.528 | 73.154 | 20.057 | 1.00 | 25.27 |
| ATOM | 5562 | N | ILE | 1453 | 84.186 | 71.615 | 20.259 | 1.00 | 23.64 |
| ATOM | 5563 | CA | ILE | 1453 | 84.360 | 71.724 | 21.712 | 1.00 | 21.74 |
| ATOM | 5564 | CB | ILE | 1453 | 85.588 | 70.911 | 22.193 | 1.00 | 18.90 |
| ATOM | 5565 | CG2 | ILE | 1453 | 86.084 | 71.414 | 23.541 | 1.00 | 15.69 |
| ATOM | 5566 | CG1 | ILE | 1453 | 85.247 | 69.420 | 22.276 | 1.00 | 18.69 |
| ATOM | 5567 | CD1 | ILE | 1453 | 84.246 | 69.068 | 23.344 | 1.00 | 16.28 |
| ATOM | 5568 | C | ILE | 1453 | 84.571 | 73.172 | 22.119 | 1.00 | 23.00 |
| ATOM | 5569 | O | ILE | 1453 | 84.144 | 73.598 | 23.192 | 1.00 | 23.69 |
| ATOM | 5570 | N | HIS | 1454 | 85.195 | 73.931 | 21.228 | 1.00 | 25.62 |
| ATOM | 5571 | CA | HIS | 1454 | 85.494 | 75.331 | 21.472 | 1.00 | 26.80 |
| ATOM | 5572 | CB | HIS | 1454 | 86.497 | 75.828 | 20.437 | 1.00 | 26.77 |
| ATOM | 5573 | CG | HIS | 1454 | 87.850 | 75.202 | 20.581 | 1.00 | 29.51 |
| ATOM | 5574 | CD2 | HIS | 1454 | 88.430 | 74.172 | 19.927 | 1.00 | 28.95 |
| ATOM | 5575 | ND1 | HIS | 1454 | 88.757 | 75.608 | 21.538 | 1.00 | 33.65 |
| ATOM | 5576 | CE1 | HIS | 1454 | 89.836 | 74.848 | 21.470 | 1.00 | 33.07 |
| ATOM | 5577 | NE2 | HIS | 1454 | 89.663 | 73.971 | 20.498 | 1.00 | 31.26 |
| ATOM | 5578 | C | HIS | 1454 | 84.281 | 76.251 | 21.580 | 1.00 | 27.40 |
| ATOM | 5579 | O | HIS | 1454 | 84.418 | 77.414 | 21.963 | 1.00 | 25.97 |
| ATOM | 5580 | N | LYS | 1455 | 83.103 | 75.725 | 21.259 | 1.00 | 27.47 |
| ATOM | 5581 | CA | LYS | 1455 | 81.864 | 76.488 | 21.360 | 1.00 | 30.12 |
| ATOM | 5582 | CB | LYS | 1455 | 81.153 | 76.575 | 20.012 | 1.00 | 35.92 |
| ATOM | 5583 | CG | LYS | 1455 | 81.922 | 77.286 | 18.917 | 1.00 | 45.61 |
| ATOM | 5584 | CD | LYS | 1455 | 81.370 | 76.898 | 17.543 | 1.00 | 57.31 |
| ATOM | 5585 | CE | LYS | 1455 | 81.386 | 75.368 | 17.347 | 1.00 | 61.81 |
| ATOM | 5586 | NZ | LYS | 1455 | 80.920 | 74.895 | 16.006 | 1.00 | 60.26 |
| ATOM | 5587 | C | LYS | 1455 | 80.950 | 75.771 | 22.344 | 1.00 | 28.06 |
| ATOM | 5588 | O | LYS | 1455 | 80.318 | 76.399 | 23.195 | 1.00 | 30.49 |
| ATOM | 5589 | N | PHE | 1456 | 80.915 | 74.446 | 22.242 | 1.00 | 24.81 |
| ATOM | 5590 | CA | PHE | 1456 | 80.071 | 73.625 | 23.096 | 1.00 | 20.59 |
| ATOM | 5591 | CB | PHE | 1456 | 80.105 | 72.165 | 22.636 | 1.00 | 21.85 |
| ATOM | 5592 | CG | PHE | 1456 | 79.036 | 71.314 | 23.258 | 1.00 | 23.75 |
| ATOM | 5593 | CD1 | PHE | 1456 | 77.723 | 71.383 | 22.797 | 1.00 | 20.86 |
| ATOM | 5594 | CD2 | PHE | 1456 | 79.328 | 70.479 | 24.335 | 1.00 | 22.64 |
| ATOM | 5595 | CE1 | PHE | 1456 | 76.714 | 70.636 | 23.404 | 1.00 | 21.49 |
| ATOM | 5596 | CE2 | PHE | 1456 | 78.325 | 69.729 | 24.945 | 1.00 | 22.84 |
| ATOM | 5597 | CZ | PHE | 1456 | 77.015 | 69.810 | 24.480 | 1.00 | 20.55 |
| ATOM | 5598 | C | PHE | 1456 | 80.411 | 73.729 | 24.579 | 1.00 | 17.53 |
| ATOM | 5599 | O | PHE | 1456 | 79.529 | 73.929 | 25.403 | 1.00 | 15.84 |
| ATOM | 5600 | N | VAL | 1457 | 81.682 | 73.586 | 24.928 | 1.00 | 17.91 |
| ATOM | 5601 | CA | VAL | 1457 | 82.073 | 73.685 | 26.329 | 1.00 | 19.08 |
| ATOM | 5602 | CB | VAL | 1457 | 83.571 | 73.399 | 26.536 | 1.00 | 15.14 |

FIG. 1A-96

| ATOM | 5603 | CG1 | VAL | 1457 | 83.994 | 73.760 | 27.953 | 1.00 | 13.44 |
| --- | --- | --- | --- | --- | --- | --- | --- | --- | --- |
| ATOM | 5604 | CG2 | VAL | 1457 | 83.833 | 71.932 | 26.304 | 1.00 | 16.34 |
| ATOM | 5605 | C | VAL | 1457 | 81.681 | 75.051 | 26.904 | 1.00 | 22.53 |
| ATOM | 5606 | O | VAL | 1457 | 81.080 | 75.131 | 27.983 | 1.00 | 22.20 |
| ATOM | 5607 | N | PRO | 1458 | 82.013 | 76.145 | 26.191 | 1.00 | 24.20 |
| ATOM | 5608 | CD | PRO | 1458 | 82.911 | 76.261 | 25.027 | 1.00 | 24.44 |
| ATOM | 5609 | CA | PRO | 1458 | 81.651 | 77.475 | 26.695 | 1.00 | 25.28 |
| ATOM | 5610 | CB | PRO | 1458 | 82.122 | 78.392 | 25.573 | 1.00 | 27.34 |
| ATOM | 5611 | CG | PRO | 1458 | 83.363 | 77.702 | 25.107 | 1.00 | 25.79 |
| ATOM | 5612 | C | PRO | 1458 | 80.147 | 77.576 | 26.939 | 1.00 | 24.20 |
| ATOM | 5613 | O | PRO | 1458 | 79.693 | 78.307 | 27.823 | 1.00 | 25.91 |
| ATOM | 5614 | N | TYR | 1459 | 79.373 | 76.849 | 26.147 | 1.00 | 22.70 |
| ATOM | 5615 | CA | TYR | 1459 | 77.934 | 76.832 | 26.337 | 1.00 | 22.83 |
| ATOM | 5616 | CB | TYR | 1459 | 77.255 | 76.104 | 25.177 | 1.00 | 21.77 |
| ATOM | 5617 | CG | TYR | 1459 | 75.901 | 75.539 | 25.531 | 1.00 | 26.38 |
| ATOM | 5618 | CD1 | TYR | 1459 | 74.833 | 76.374 | 25.869 | 1.00 | 29.53 |
| ATOM | 5619 | CE1 | TYR | 1459 | 73.595 | 75.845 | 26.230 | 1.00 | 30.45 |
| ATOM | 5620 | CD2 | TYR | 1459 | 75.693 | 74.160 | 25.559 | 1.00 | 28.56 |
| ATOM | 5621 | CE2 | TYR | 1459 | 74.462 | 73.619 | 25.917 | 1.00 | 26.79 |
| ATOM | 5622 | CZ | TYR | 1459 | 73.419 | 74.463 | 26.250 | 1.00 | 28.78 |
| ATOM | 5623 | OH | TYR | 1459 | 72.209 | 73.912 | 26.604 | 1.00 | 26.01 |
| ATOM | 5624 | C | TYR | 1459 | 77.635 | 76.123 | 27.669 | 1.00 | 22.79 |
| ATOM | 5625 | O | TYR | 1459 | 76.879 | 76.634 | 28.497 | 1.00 | 22.57 |
| ATOM | 5626 | N | LEU | 1460 | 78.261 | 74.966 | 27.883 | 1.00 | 22.45 |
| ATOM | 5627 | CA | LEU | 1460 | 78.062 | 74.188 | 29.105 | 1.00 | 20.94 |
| ATOM | 5628 | CB | LEU | 1460 | 78.909 | 72.908 | 29.091 | 1.00 | 18.74 |
| ATOM | 5629 | CG | LEU | 1460 | 78.564 | 71.821 | 28.062 | 1.00 | 15.82 |
| ATOM | 5630 | CD1 | LEU | 1460 | 79.566 | 70.675 | 28.136 | 1.00 | 11.15 |
| ATOM | 5631 | CD2 | LEU | 1460 | 77.157 | 71.307 | 28.295 | 1.00 | 12.28 |
| ATOM | 5632 | C | LEU | 1460 | 78.376 | 75.016 | 30.341 | 1.00 | 20.69 |
| ATOM | 5633 | O | LEU | 1460 | 77.619 | 75.015 | 31.309 | 1.00 | 22.07 |
| ATOM | 5634 | N | ILE | 1461 | 79.486 | 75.737 | 30.301 | 1.00 | 21.57 |
| ATOM | 5635 | CA | ILE | 1461 | 79.880 | 76.583 | 31.423 | 1.00 | 22.27 |
| ATOM | 5636 | CB | ILE | 1461 | 81.223 | 77.296 | 31.134 | 1.00 | 18.97 |
| ATOM | 5637 | CG2 | ILE | 1461 | 81.550 | 78.264 | 32.239 | 1.00 | 19.35 |
| ATOM | 5638 | CG1 | ILE | 1461 | 82.346 | 76.269 | 30.990 | 1.00 | 15.84 |
| ATOM | 5639 | CD1 | ILE | 1461 | 83.661 | 76.851 | 30.523 | 1.00 | 15.19 |
| ATOM | 5640 | C | ILE | 1461 | 78.785 | 77.623 | 31.683 | 1.00 | 22.73 |
| ATOM | 5641 | O | ILE | 1461 | 78.374 | 77.849 | 32.823 | 1.00 | 24.12 |
| ATOM | 5642 | N | ALA | 1462 | 78.286 | 78.233 | 30.618 | 1.00 | 22.40 |
| ATOM | 5643 | CA | ALA | 1462 | 77.240 | 79.227 | 30.767 | 1.00 | 23.17 |
| ATOM | 5644 | CB | ALA | 1462 | 76.969 | 79.901 | 29.446 | 1.00 | 24.38 |
| ATOM | 5645 | C | ALA | 1462 | 75.969 | 78.596 | 31.316 | 1.00 | 22.99 |
| ATOM | 5646 | O | ALA | 1462 | 75.247 | 79.227 | 32.085 | 1.00 | 23.60 |
| ATOM | 5647 | N | GLY | 1463 | 75.712 | 77.347 | 30.939 | 1.00 | 22.00 |
| ATOM | 5648 | CA | GLY | 1463 | 74.524 | 76.655 | 31.404 | 1.00 | 20.76 |
| ATOM | 5649 | C | GLY | 1463 | 74.563 | 76.411 | 32.893 | 1.00 | 21.18 |
| ATOM | 5650 | O | GLY | 1463 | 73.586 | 76.670 | 33.595 | 1.00 | 22.33 |
| ATOM | 5651 | N | ILE | 1464 | 75.707 | 75.935 | 33.376 | 1.00 | 21.45 |
| ATOM | 5652 | CA | ILE | 1464 | 75.907 | 75.650 | 34.795 | 1.00 | 21.45 |
| ATOM | 5653 | CB | ILE | 1464 | 77.279 | 74.972 | 35.048 | 1.00 | 17.77 |
| ATOM | 5654 | CG2 | ILE | 1464 | 77.472 | 74.652 | 36.525 | 1.00 | 16.84 |
| ATOM | 5655 | CG1 | ILE | 1464 | 77.375 | 73.672 | 34.263 | 1.00 | 12.39 |
| ATOM | 5656 | CD1 | ILE | 1464 | 78.696 | 72.995 | 34.442 | 1.00 | 21.13 |
| ATOM | 5657 | C | ILE | 1464 | 75.819 | 76.933 | 35.621 | 1.00 | 24.69 |
| ATOM | 5658 | O | ILE | 1464 | 75.201 | 76.948 | 36.693 | 1.00 | 27.98 |
| ATOM | 5659 | N | GLN | 1465 | 76.420 | 78.010 | 35.115 | 1.00 | 23.43 |
| ATOM | 5660 | CA | GLN | 1465 | 76.396 | 79.291 | 35.810 | 1.00 | 20.44 |
| ATOM | 5661 | CB | GLN | 1465 | 77.198 | 80.333 | 35.046 | 1.00 | 20.47 |

FIG. 1A-97

| ATOM | 5662 | CG | GLN | 1465 | 78.672 | 80.037 | 34.997 | 1.00 | 21.90 |
|---|---|---|---|---|---|---|---|---|---|
| ATOM | 5663 | CD | GLN | 1465 | 79.479 | 81.241 | 34.585 | 1.00 | 23.86 |
| ATOM | 5664 | OE1 | GLN | 1465 | 80.564 | 81.483 | 35.108 | 1.00 | 24.24 |
| ATOM | 5665 | NE2 | GLN | 1465 | 78.944 | 82.019 | 33.655 | 1.00 | 25.91 |
| ATOM | 5666 | C | GLN | 1465 | 74.977 | 79.790 | 36.029 | 1.00 | 19.83 |
| ATOM | 5667 | O | GLN | 1465 | 74.672 | 80.390 | 37.060 | 1.00 | 20.11 |
| ATOM | 5668 | N | HIS | 1466 | 74.106 | 79.557 | 35.058 | 1.00 | 20.26 |
| ATOM | 5669 | CA | HIS | 1466 | 72.725 | 79.977 | 35.208 | 1.00 | 22.99 |
| ATOM | 5670 | CB | HIS | 1466 | 71.998 | 79.979 | 33.873 | 1.00 | 24.47 |
| ATOM | 5671 | CG | HIS | 1466 | 72.288 | 81.191 | 33.047 | 1.00 | 30.20 |
| ATOM | 5672 | CD2 | HIS | 1466 | 71.599 | 82.347 | 32.892 | 1.00 | 33.03 |
| ATOM | 5673 | ND1 | HIS | 1466 | 73.426 | 81.319 | 32.283 | 1.00 | 31.81 |
| ATOM | 5674 | CE1 | HIS | 1466 | 73.429 | 82.501 | 31.692 | 1.00 | 34.48 |
| ATOM | 5675 | NE2 | HIS | 1466 | 72.331 | 83.145 | 32.047 | 1.00 | 35.24 |
| ATOM | 5676 | C | HIS | 1466 | 71.998 | 79.108 | 36.229 | 1.00 | 24.73 |
| ATOM | 5677 | O | HIS | 1466 | 71.124 | 79.608 | 36.940 | 1.00 | 27.97 |
| ATOM | 5678 | N | SER | 1467 | 72.363 | 77.826 | 36.328 | 1.00 | 22.87 |
| ATOM | 5679 | CA | SER | 1467 | 71.734 | 76.941 | 37.307 | 1.00 | 21.98 |
| ATOM | 5680 | CB | SER | 1467 | 72.240 | 75.510 | 37.173 | 1.00 | 19.47 |
| ATOM | 5681 | OG | SER | 1467 | 71.817 | 74.941 | 35.958 | 1.00 | 25.92 |
| ATOM | 5682 | C | SER | 1467 | 72.070 | 77.443 | 38.694 | 1.00 | 22.35 |
| ATOM | 5683 | O | SER | 1467 | 71.182 | 77.701 | 39.502 | 1.00 | 26.52 |
| ATOM | 5684 | N | CYS | 1468 | 73.361 | 77.616 | 38.950 | 1.00 | 21.86 |
| ATOM | 5685 | CA | CYS | 1468 | 73.833 | 78.089 | 40.241 | 1.00 | 21.15 |
| ATOM | 5686 | CB | CYS | 1468 | 75.349 | 78.280 | 40.219 | 1.00 | 19.89 |
| ATOM | 5687 | SG | CYS | 1468 | 76.268 | 76.742 | 40.093 | 1.00 | 17.63 |
| ATOM | 5688 | C | CYS | 1468 | 73.141 | 79.382 | 40.633 | 1.00 | 20.36 |
| ATOM | 5689 | O | CYS | 1468 | 72.698 | 79.535 | 41.771 | 1.00 | 20.45 |
| ATOM | 5690 | N | GLN | 1469 | 73.003 | 80.285 | 39.673 | 1.00 | 20.12 |
| ATOM | 5691 | CA | GLN | 1469 | 72.351 | 81.554 | 39.927 | 1.00 | 20.40 |
| ATOM | 5692 | CB | GLN | 1469 | 72.357 | 82.412 | 38.678 | 1.00 | 17.82 |
| ATOM | 5693 | CG | GLN | 1469 | 71.694 | 83.733 | 38.897 | 1.00 | 17.81 |
| ATOM | 5694 | CD | GLN | 1469 | 71.523 | 84.486 | 37.619 | 1.00 | 23.77 |
| ATOM | 5695 | OE1 | GLN | 1469 | 71.323 | 83.894 | 36.558 | 1.00 | 22.20 |
| ATOM | 5696 | NE2 | GLN | 1469 | 71.611 | 85.810 | 37.699 | 1.00 | 28.08 |
| ATOM | 5697 | C | GLN | 1469 | 70.919 | 81.356 | 40.393 | 1.00 | 21.30 |
| ATOM | 5698 | O | GLN | 1469 | 70.508 | 81.907 | 41.411 | 1.00 | 23.33 |
| ATOM | 5699 | N | ASP | 1470 | 70.153 | 80.578 | 39.641 | 1.00 | 21.99 |
| ATOM | 5700 | CA | ASP | 1470 | 68.771 | 80.323 | 40.004 | 1.00 | 22.24 |
| ATOM | 5701 | CB | ASP | 1470 | 68.112 | 79.398 | 38.983 | 1.00 | 22.86 |
| ATOM | 5702 | CG | ASP | 1470 | 67.573 | 80.146 | 37.766 | 1.00 | 25.39 |
| ATOM | 5703 | OD1 | ASP | 1470 | 67.784 | 81.375 | 37.639 | 1.00 | 21.98 |
| ATOM | 5704 | OD2 | ASP | 1470 | 66.913 | 79.488 | 36.937 | 1.00 | 24.95 |
| ATOM | 5705 | C | ASP | 1470 | 68.664 | 79.731 | 41.401 | 1.00 | 22.03 |
| ATOM | 5706 | O | ASP | 1470 | 67.805 | 80.139 | 42.187 | 1.00 | 22.26 |
| ATOM | 5707 | N | ILE | 1471 | 69.564 | 78.807 | 41.726 | 1.00 | 21.04 |
| ATOM | 5708 | CA | ILE | 1471 | 69.543 | 78.170 | 43.037 | 1.00 | 21.12 |
| ATOM | 5709 | CB | ILE | 1471 | 70.160 | 76.725 | 43.012 | 1.00 | 22.81 |
| ATOM | 5710 | CG2 | ILE | 1471 | 69.450 | 75.859 | 41.976 | 1.00 | 19.90 |
| ATOM | 5711 | CG1 | ILE | 1471 | 71.653 | 76.755 | 42.689 | 1.00 | 25.14 |
| ATOM | 5712 | CD1 | ILE | 1471 | 72.284 | 75.374 | 42.600 | 1.00 | 21.70 |
| ATOM | 5713 | C | ILE | 1471 | 70.160 | 79.040 | 44.139 | 1.00 | 20.42 |
| ATOM | 5714 | O | ILE | 1471 | 70.011 | 78.739 | 45.324 | 1.00 | 20.93 |
| ATOM | 5715 | N | GLY | 1472 | 70.808 | 80.137 | 43.751 | 1.00 | 19.66 |
| ATOM | 5716 | CA | GLY | 1472 | 71.403 | 81.047 | 44.722 | 1.00 | 19.79 |
| ATOM | 5717 | C | GLY | 1472 | 72.859 | 80.822 | 45.102 | 1.00 | 21.16 |
| ATOM | 5718 | O | GLY | 1472 | 73.376 | 81.445 | 46.042 | 1.00 | 21.66 |
| ATOM | 5719 | N | ALA | 1473 | 73.537 | 79.951 | 44.364 | 1.00 | 21.76 |
| ATOM | 5720 | CA | ALA | 1473 | 74.932 | 79.640 | 44.631 | 1.00 | 21.14 |

FIG. 1A-98

| ATOM | 5721 | CB | ALA | 1473 | 75.157 | 78.164 | 44.468 | 1.00 | 23.54 |
|---|---|---|---|---|---|---|---|---|---|
| ATOM | 5722 | C | ALA | 1473 | 75.862 | 80.413 | 43.708 | 1.00 | 21.24 |
| ATOM | 5723 | O | ALA | 1473 | 75.714 | 80.365 | 42.493 | 1.00 | 20.90 |
| ATOM | 5724 | N | LYS | 1474 | 76.821 | 81.124 | 44.290 | 1.00 | 22.52 |
| ATOM | 5725 | CA | LYS | 1474 | 77.783 | 81.903 | 43.516 | 1.00 | 23.89 |
| ATOM | 5726 | CB | LYS | 1474 | 78.276 | 83.110 | 44.326 | 1.00 | 28.89 |
| ATOM | 5727 | CG | LYS | 1474 | 77.167 | 84.009 | 44.856 | 1.00 | 38.03 |
| ATOM | 5728 | CD | LYS | 1474 | 77.720 | 85.285 | 45.496 | 1.00 | 44.94 |
| ATOM | 5729 | CE | LYS | 1474 | 76.605 | 86.167 | 46.073 | 1.00 | 47.23 |
| ATOM | 5730 | NZ | LYS | 1474 | 75.848 | 85.496 | 47.173 | 1.00 | 49.89 |
| ATOM | 5731 | C | LYS | 1474 | 78.983 | 81.057 | 43.110 | 1.00 | 22.37 |
| ATOM | 5732 | O | LYS | 1474 | 79.919 | 81.561 | 42.506 | 1.00 | 23.41 |
| ATOM | 5733 | N | SER | 1475 | 78.959 | 79.775 | 43.452 | 1.00 | 22.61 |
| ATOM | 5734 | CA | SER | 1475 | 80.056 | 78.871 | 43.128 | 1.00 | 22.50 |
| ATOM | 5735 | CB | SER | 1475 | 81.273 | 79.205 | 43.990 | 1.00 | 26.45 |
| ATOM | 5736 | OG | SER | 1475 | 80.945 | 79.161 | 45.376 | 1.00 | 32.98 |
| ATOM | 5737 | C | SER | 1475 | 79.645 | 77.430 | 43.393 | 1.00 | 21.22 |
| ATOM | 5738 | O | SER | 1475 | 78.702 | 77.177 | 44.152 | 1.00 | 20.30 |
| ATOM | 5739 | N | LEU | 1476 | 80.354 | 76.488 | 42.780 | 1.00 | 20.38 |
| ATOM | 5740 | CA | LEU | 1476 | 80.051 | 75.077 | 42.987 | 1.00 | 18.61 |
| ATOM | 5741 | CB | LEU | 1476 | 80.837 | 74.200 | 42.017 | 1.00 | 13.19 |
| ATOM | 5742 | CG | LEU | 1476 | 80.552 | 74.458 | 40.530 | 1.00 | 9.83 |
| ATOM | 5743 | CD1 | LEU | 1476 | 81.212 | 73.391 | 39.698 | 1.00 | 6.72 |
| ATOM | 5744 | CD2 | LEU | 1476 | 79.066 | 74.458 | 40.248 | 1.00 | 9.78 |
| ATOM | 5745 | C | LEU | 1476 | 80.297 | 74.670 | 44.443 | 1.00 | 18.33 |
| ATOM | 5746 | O | LEU | 1476 | 79.567 | 73.858 | 44.997 | 1.00 | 21.64 |
| ATOM | 5747 | N | THR | 1477 | 81.282 | 75.280 | 45.085 | 1.00 | 18.50 |
| ATOM | 5748 | CA | THR | 1477 | 81.564 | 74.985 | 46.484 | 1.00 | 20.62 |
| ATOM | 5749 | CB | THR | 1477 | 82.787 | 75.775 | 46.994 | 1.00 | 22.41 |
| ATOM | 5750 | OG1 | THR | 1477 | 83.954 | 75.394 | 46.249 | 1.00 | 24.52 |
| ATOM | 5751 | CG2 | THR | 1477 | 83.012 | 75.512 | 48.480 | 1.00 | 24.60 |
| ATOM | 5752 | C | THR | 1477 | 80.352 | 75.394 | 47.315 | 1.00 | 21.09 |
| ATOM | 5753 | O | THR | 1477 | 79.919 | 74.666 | 48.209 | 1.00 | 20.03 |
| ATOM | 5754 | N | GLN | 1478 | 79.801 | 76.560 | 46.988 | 1.00 | 23.03 |
| ATOM | 5755 | CA | GLN | 1478 | 78.633 | 77.097 | 47.682 | 1.00 | 21.72 |
| ATOM | 5756 | CB | GLN | 1478 | 78.298 | 78.499 | 47.157 | 1.00 | 20.38 |
| ATOM | 5757 | CG | GLN | 1478 | 77.346 | 79.323 | 48.022 | 1.00 | 22.66 |
| ATOM | 5758 | CD | GLN | 1478 | 77.277 | 80.785 | 47.584 | 1.00 | 27.92 |
| ATOM | 5759 | OE1 | GLN | 1478 | 78.058 | 81.230 | 46.746 | 1.00 | 30.51 |
| ATOM | 5760 | NE2 | GLN | 1478 | 76.339 | 81.533 | 48.147 | 1.00 | 30.65 |
| ATOM | 5761 | C | GLN | 1478 | 77.455 | 76.164 | 47.483 | 1.00 | 21.55 |
| ATOM | 5762 | O | GLN | 1478 | 76.688 | 75.939 | 48.415 | 1.00 | 23.57 |
| ATOM | 5763 | N | VAL | 1479 | 77.342 | 75.575 | 46.294 | 1.00 | 21.36 |
| ATOM | 5764 | CA | VAL | 1479 | 76.233 | 74.660 | 46.017 | 1.00 | 21.51 |
| ATOM | 5765 | CB | VAL | 1479 | 76.236 | 74.108 | 44.575 | 1.00 | 22.74 |
| ATOM | 5766 | CG1 | VAL | 1479 | 75.022 | 73.222 | 44.365 | 1.00 | 23.03 |
| ATOM | 5767 | CG2 | VAL | 1479 | 76.209 | 75.240 | 43.567 | 1.00 | 26.07 |
| ATOM | 5768 | C | VAL | 1479 | 76.258 | 73.484 | 46.974 | 1.00 | 19.18 |
| ATOM | 5769 | O | VAL | 1479 | 75.302 | 73.271 | 47.718 | 1.00 | 22.44 |
| ATOM | 5770 | N | ARG | 1480 | 77.364 | 72.748 | 46.988 | 1.00 | 16.57 |
| ATOM | 5771 | CA | ARG | 1480 | 77.491 | 71.593 | 47.872 | 1.00 | 15.29 |
| ATOM | 5772 | CB | ARG | 1480 | 78.815 | 70.881 | 47.628 | 1.00 | 10.45 |
| ATOM | 5773 | CG | ARG | 1480 | 78.930 | 70.342 | 46.217 | 1.00 | 9.69 |
| ATOM | 5774 | CD | ARG | 1480 | 80.084 | 69.386 | 46.086 | 1.00 | 16.38 |
| ATOM | 5775 | NE | ARG | 1480 | 81.362 | 70.000 | 46.434 | 1.00 | 21.07 |
| ATOM | 5776 | CZ | ARG | 1480 | 82.036 | 70.818 | 45.632 | 1.00 | 25.55 |
| ATOM | 5777 | NH1 | ARG | 1480 | 81.551 | 71.129 | 44.433 | 1.00 | 27.33 |
| ATOM | 5778 | NH2 | ARG | 1480 | 83.198 | 71.322 | 46.026 | 1.00 | 26.79 |
| ATOM | 5779 | C | ARG | 1480 | 77.343 | 71.961 | 49.345 | 1.00 | 16.36 |

FIG. 1A-99

| ATOM | 5780 | O | ARG | 1480 | 76.749 | 71.215 | 50.121 | 1.00 | 18.23 |
|---|---|---|---|---|---|---|---|---|---|
| ATOM | 5781 | N | ALA | 1481 | 77.855 | 73.126 | 49.724 | 1.00 | 17.05 |
| ATOM | 5782 | CA | ALA | 1481 | 77.767 | 73.594 | 51.103 | 1.00 | 15.72 |
| ATOM | 5783 | CB | ALA | 1481 | 78.547 | 74.874 | 51.265 | 1.00 | 14.94 |
| ATOM | 5784 | C | ALA | 1481 | 76.311 | 73.811 | 51.507 | 1.00 | 16.85 |
| ATOM | 5785 | O | ALA | 1481 | 75.902 | 73.446 | 52.612 | 1.00 | 16.33 |
| ATOM | 5786 | N | MET | 1482 | 75.541 | 74.409 | 50.604 | 1.00 | 16.63 |
| ATOM | 5787 | CA | MET | 1482 | 74.129 | 74.678 | 50.837 | 1.00 | 16.66 |
| ATOM | 5788 | CB | MET | 1482 | 73.578 | 75.588 | 49.745 | 1.00 | 16.75 |
| ATOM | 5789 | CG | MET | 1482 | 74.147 | 76.989 | 49.757 | 1.00 | 16.82 |
| ATOM | 5790 | SD | MET | 1482 | 73.715 | 77.910 | 48.286 | 1.00 | 20.66 |
| ATOM | 5791 | CE | MET | 1482 | 71.961 | 77.896 | 48.402 | 1.00 | 17.74 |
| ATOM | 5792 | C | MET | 1482 | 73.327 | 73.386 | 50.867 | 1.00 | 17.97 |
| ATOM | 5793 | O | MET | 1482 | 72.324 | 73.286 | 51.576 | 1.00 | 18.54 |
| ATOM | 5794 | N | MET | 1483 | 73.753 | 72.404 | 50.081 | 1.00 | 16.86 |
| ATOM | 5795 | CA | MET | 1483 | 73.061 | 71.126 | 50.046 | 1.00 | 18.50 |
| ATOM | 5796 | CB | MET | 1483 | 73.510 | 70.306 | 48.832 | 1.00 | 20.94 |
| ATOM | 5797 | CG | MET | 1483 | 72.920 | 68.905 | 48.753 | 1.00 | 21.75 |
| ATOM | 5798 | SD | MET | 1483 | 74.049 | 67.613 | 49.328 | 1.00 | 25.70 |
| ATOM | 5799 | CE | MET | 1483 | 73.300 | 67.145 | 50.866 | 1.00 | 28.55 |
| ATOM | 5800 | C | MET | 1483 | 73.301 | 70.366 | 51.347 | 1.00 | 18.59 |
| ATOM | 5801 | O | MET | 1483 | 72.349 | 70.004 | 52.041 | 1.00 | 19.17 |
| ATOM | 5802 | N | TYR | 1484 | 74.569 | 70.174 | 51.703 | 1.00 | 17.46 |
| ATOM | 5803 | CA | TYR | 1484 | 74.924 | 69.459 | 52.929 | 1.00 | 17.19 |
| ATOM | 5804 | CB | TYR | 1484 | 76.447 | 69.295 | 53.052 | 1.00 | 14.82 |
| ATOM | 5805 | CG | TYR | 1484 | 77.058 | 68.304 | 52.068 | 1.00 | 12.90 |
| ATOM | 5806 | CD1 | TYR | 1484 | 76.709 | 66.952 | 52.087 | 1.00 | 11.22 |
| ATOM | 5807 | CE1 | TYR | 1484 | 77.286 | 66.040 | 51.195 | 1.00 | 4.92 |
| ATOM | 5808 | CD2 | TYR | 1484 | 77.998 | 68.717 | 51.132 | 1.00 | 11.91 |
| ATOM | 5809 | CE2 | TYR | 1484 | 78.578 | 67.817 | 50.244 | 1.00 | 8.93 |
| ATOM | 5810 | CZ | TYR | 1484 | 78.220 | 66.486 | 50.283 | 1.00 | 9.49 |
| ATOM | 5811 | OH | TYR | 1484 | 78.824 | 65.617 | 49.411 | 1.00 | 16.42 |
| ATOM | 5812 | C | TYR | 1484 | 74.342 | 70.094 | 54.196 | 1.00 | 17.55 |
| ATOM | 5813 | O | TYR | 1484 | 73.985 | 69.386 | 55.137 | 1.00 | 20.47 |
| ATOM | 5814 | N | SER | 1485 | 74.255 | 71.419 | 54.223 | 1.00 | 16.85 |
| ATOM | 5815 | CA | SER | 1485 | 73.693 | 72.128 | 55.367 | 1.00 | 15.90 |
| ATOM | 5816 | CB | SER | 1485 | 73.993 | 73.619 | 55.260 | 1.00 | 16.94 |
| ATOM | 5817 | OG | SER | 1485 | 73.387 | 74.177 | 54.100 | 1.00 | 20.34 |
| ATOM | 5818 | C | SER | 1485 | 72.185 | 71.943 | 55.375 | 1.00 | 16.36 |
| ATOM | 5819 | O | SER | 1485 | 71.520 | 72.200 | 56.374 | 1.00 | 15.00 |
| ATOM | 5820 | N | GLY | 1486 | 71.645 | 71.562 | 54.223 | 1.00 | 18.94 |
| ATOM | 5821 | CA | GLY | 1486 | 70.213 | 71.363 | 54.101 | 1.00 | 19.06 |
| ATOM | 5822 | C | GLY | 1486 | 69.528 | 72.559 | 53.469 | 1.00 | 20.47 |
| ATOM | 5823 | O | GLY | 1486 | 68.349 | 72.482 | 53.105 | 1.00 | 21.02 |
| ATOM | 5824 | N | GLU | 1487 | 70.268 | 73.655 | 53.306 | 1.00 | 19.69 |
| ATOM | 5825 | CA | GLU | 1487 | 69.717 | 74.868 | 52.716 | 1.00 | 17.15 |
| ATOM | 5826 | CB | GLU | 1487 | 70.761 | 75.970 | 52.669 | 1.00 | 15.86 |
| ATOM | 5827 | CG | GLU | 1487 | 70.258 | 77.209 | 51.946 | 1.00 | 16.32 |
| ATOM | 5828 | CD | GLU | 1487 | 71.152 | 78.412 | 52.111 | 1.00 | 17.63 |
| ATOM | 5829 | OE1 | GLU | 1487 | 72.336 | 78.241 | 52.488 | 1.00 | 21.20 |
| ATOM | 5830 | OE2 | GLU | 1487 | 70.658 | 79.536 | 51.866 | 1.00 | 20.22 |
| ATOM | 5831 | C | GLU | 1487 | 69.131 | 74.669 | 51.325 | 1.00 | 17.26 |
| ATOM | 5832 | O | GLU | 1487 | 68.021 | 75.127 | 51.053 | 1.00 | 18.70 |
| ATOM | 5833 | N | LEU | 1488 | 69.901 | 74.056 | 50.431 | 1.00 | 15.56 |
| ATOM | 5834 | CA | LEU | 1488 | 69.429 | 73.808 | 49.076 | 1.00 | 13.65 |
| ATOM | 5835 | CB | LEU | 1488 | 70.553 | 73.244 | 48.207 | 1.00 | 10.67 |
| ATOM | 5836 | CG | LEU | 1488 | 70.361 | 73.271 | 46.691 | 1.00 | 9.52 |
| ATOM | 5837 | CD1 | LEU | 1488 | 70.425 | 74.691 | 46.200 | 1.00 | 9.10 |
| ATOM | 5838 | CD2 | LEU | 1488 | 71.446 | 72.456 | 46.021 | 1.00 | 9.59 |

FIG. 1A-100

| ATOM | 5839 | C | LEU | 1488 | 68.307 | 72.787 | 49.221 | 1.00 | 15.23 |
|------|------|---|-----|------|--------|--------|--------|------|-------|
| ATOM | 5840 | O | LEU | 1488 | 68.473 | 71.779 | 49.912 | 1.00 | 16.81 |
| ATOM | 5841 | N | LYS | 1489 | 67.158 | 73.074 | 48.617 | 1.00 | 13.29 |
| ATOM | 5842 | CA | LYS | 1489 | 66.008 | 72.186 | 48.695 | 1.00 | 12.48 |
| ATOM | 5843 | CB | LYS | 1489 | 64.798 | 72.959 | 49.209 | 1.00 | 11.34 |
| ATOM | 5844 | CG | LYS | 1489 | 64.876 | 73.337 | 50.681 | 1.00 | 11.57 |
| ATOM | 5845 | CD | LYS | 1489 | 64.740 | 72.104 | 51.568 | 1.00 | 16.04 |
| ATOM | 5846 | CE | LYS | 1489 | 64.503 | 72.469 | 53.025 | 1.00 | 15.13 |
| ATOM | 5847 | NZ | LYS | 1489 | 65.702 | 73.077 | 53.666 | 1.00 | 18.46 |
| ATOM | 5848 | C | LYS | 1489 | 65.694 | 71.562 | 47.344 | 1.00 | 13.92 |
| ATOM | 5849 | O | LYS | 1489 | 65.850 | 72.208 | 46.310 | 1.00 | 15.51 |
| ATOM | 5850 | N | PHE | 1490 | 65.249 | 70.307 | 47.366 | 1.00 | 14.08 |
| ATOM | 5851 | CA | PHE | 1490 | 64.903 | 69.550 | 46.163 | 1.00 | 13.44 |
| ATOM | 5852 | CB | PHE | 1490 | 65.772 | 68.304 | 46.044 | 1.00 | 13.69 |
| ATOM | 5853 | CG | PHE | 1490 | 67.229 | 68.579 | 45.960 | 1.00 | 13.40 |
| ATOM | 5854 | CD1 | PHE | 1490 | 67.936 | 68.979 | 47.082 | 1.00 | 13.78 |
| ATOM | 5855 | CD2 | PHE | 1490 | 67.908 | 68.394 | 44.762 | 1.00 | 14.98 |
| ATOM | 5856 | CE1 | PHE | 1490 | 69.303 | 69.193 | 47.016 | 1.00 | 14.99 |
| ATOM | 5857 | CE2 | PHE | 1490 | 69.283 | 68.604 | 44.683 | 1.00 | 15.84 |
| ATOM | 5858 | CZ | PHE | 1490 | 69.979 | 69.003 | 45.810 | 1.00 | 15.19 |
| ATOM | 5859 | C | PHE | 1490 | 63.464 | 69.061 | 46.240 | 1.00 | 14.19 |
| ATOM | 5860 | O | PHE | 1490 | 62.866 | 69.020 | 47.315 | 1.00 | 13.40 |
| ATOM | 5861 | N | GLU | 1491 | 62.937 | 68.611 | 45.109 | 1.00 | 14.95 |
| ATOM | 5862 | CA | GLU | 1491 | 61.585 | 68.072 | 45.062 | 1.00 | 16.53 |
| ATOM | 5863 | CB | GLU | 1491 | 60.559 | 69.180 | 44.844 | 1.00 | 15.55 |
| ATOM | 5864 | CG | GLU | 1491 | 59.148 | 68.662 | 44.957 | 1.00 | 15.94 |
| ATOM | 5865 | CD | GLU | 1491 | 58.131 | 69.757 | 45.021 | 1.00 | 17.10 |
| ATOM | 5866 | OE1 | GLU | 1491 | 57.873 | 70.392 | 43.986 | 1.00 | 22.71 |
| ATOM | 5867 | OE2 | GLU | 1491 | 57.585 | 69.984 | 46.110 | 1.00 | 17.64 |
| ATOM | 5868 | C | GLU | 1491 | 61.458 | 67.002 | 43.979 | 1.00 | 17.22 |
| ATOM | 5869 | O | GLU | 1491 | 61.933 | 67.183 | 42.858 | 1.00 | 18.10 |
| ATOM | 5870 | N | LYS | 1492 | 60.857 | 65.870 | 44.331 | 1.00 | 18.86 |
| ATOM | 5871 | CA | LYS | 1492 | 60.675 | 64.771 | 43.385 | 1.00 | 20.24 |
| ATOM | 5872 | CB | LYS | 1492 | 59.955 | 63.588 | 44.045 | 1.00 | 21.24 |
| ATOM | 5873 | CG | LYS | 1492 | 60.671 | 62.965 | 45.228 | 1.00 | 29.14 |
| ATOM | 5874 | CD | LYS | 1492 | 59.814 | 61.878 | 45.880 | 1.00 | 40.81 |
| ATOM | 5875 | CE | LYS | 1492 | 60.384 | 61.403 | 47.225 | 1.00 | 47.79 |
| ATOM | 5876 | NZ | LYS | 1492 | 59.540 | 60.341 | 47.876 | 1.00 | 51.47 |
| ATOM | 5877 | C | LYS | 1492 | 59.863 | 65.245 | 42.189 | 1.00 | 21.19 |
| ATOM | 5878 | O | LYS | 1492 | 59.241 | 66.304 | 42.225 | 1.00 | 22.42 |
| ATOM | 5879 | N | ARG | 1493 | 59.812 | 64.418 | 41.155 | 1.00 | 22.65 |
| ATOM | 5880 | CA | ARG | 1493 | 59.090 | 64.758 | 39.944 | 1.00 | 20.77 |
| ATOM | 5881 | CB | ARG | 1493 | 60.090 | 65.283 | 38.907 | 1.00 | 17.58 |
| ATOM | 5882 | CG | ARG | 1493 | 59.509 | 66.229 | 37.886 | 1.00 | 21.05 |
| ATOM | 5883 | CD | ARG | 1493 | 60.557 | 67.199 | 37.349 | 1.00 | 13.84 |
| ATOM | 5884 | NE | ARG | 1493 | 61.609 | 66.516 | 36.612 | 1.00 | 15.28 |
| ATOM | 5885 | CZ | ARG | 1493 | 62.023 | 66.864 | 35.395 | 1.00 | 19.75 |
| ATOM | 5886 | NH1 | ARG | 1493 | 61.478 | 67.901 | 34.762 | 1.00 | 12.43 |
| ATOM | 5887 | NH2 | ARG | 1493 | 62.995 | 66.170 | 34.806 | 1.00 | 22.01 |
| ATOM | 5888 | C | ARG | 1493 | 58.361 | 63.526 | 39.411 | 1.00 | 22.38 |
| ATOM | 5889 | O | ARG | 1493 | 58.986 | 62.534 | 39.036 | 1.00 | 24.72 |
| ATOM | 5890 | N | THR | 1494 | 57.035 | 63.554 | 39.460 | 1.00 | 21.33 |
| ATOM | 5891 | CA | THR | 1494 | 56.240 | 62.449 | 38.938 | 1.00 | 17.93 |
| ATOM | 5892 | CB | THR | 1494 | 54.767 | 62.647 | 39.278 | 1.00 | 13.07 |
| ATOM | 5893 | OG1 | THR | 1494 | 54.283 | 63.821 | 38.613 | 1.00 | 16.64 |
| ATOM | 5894 | CG2 | THR | 1494 | 54.590 | 62.840 | 40.758 | 1.00 | 9.17 |
| ATOM | 5895 | C | THR | 1494 | 56.397 | 62.517 | 37.418 | 1.00 | 19.78 |
| ATOM | 5896 | O | THR | 1494 | 56.855 | 63.534 | 36.893 | 1.00 | 21.83 |
| ATOM | 5897 | N | SER | 1495 | 55.998 | 61.470 | 36.701 | 1.00 | 21.91 |

FIG. 1A-101

| ATOM | 5898 | CA | SER | 1495 | 56.108 | 61.482 | 35.243 | 1.00 | 22.93 |
| --- | --- | --- | --- | --- | --- | --- | --- | --- | --- |
| ATOM | 5899 | CB | SER | 1495 | 55.591 | 60.187 | 34.637 | 1.00 | 22.00 |
| ATOM | 5900 | OG | SER | 1495 | 56.544 | 59.159 | 34.813 | 1.00 | 29.94 |
| ATOM | 5901 | C | SER | 1495 | 55.356 | 62.665 | 34.653 | 1.00 | 25.21 |
| ATOM | 5902 | O | SER | 1495 | 55.863 | 63.339 | 33.757 | 1.00 | 26.52 |
| ATOM | 5903 | N | SER | 1496 | 54.151 | 62.922 | 35.154 | 1.00 | 25.45 |
| ATOM | 5904 | CA | SER | 1496 | 53.376 | 64.056 | 34.681 | 1.00 | 24.09 |
| ATOM | 5905 | CB | SER | 1496 | 52.026 | 64.125 | 35.397 | 1.00 | 24.76 |
| ATOM | 5906 | OG | SER | 1496 | 51.146 | 63.121 | 34.928 | 1.00 | 24.43 |
| ATOM | 5907 | C | SER | 1496 | 54.201 | 65.317 | 34.946 | 1.00 | 23.62 |
| ATOM | 5908 | O | SER | 1496 | 54.329 | 66.172 | 34.071 | 1.00 | 26.31 |
| ATOM | 5909 | N | ALA | 1497 | 54.811 | 65.405 | 36.125 | 1.00 | 20.98 |
| ATOM | 5910 | CA | ALA | 1497 | 55.637 | 66.561 | 36.462 | 1.00 | 20.31 |
| ATOM | 5911 | CB | ALA | 1497 | 56.022 | 66.526 | 37.931 | 1.00 | 20.07 |
| ATOM | 5912 | C | ALA | 1497 | 56.885 | 66.612 | 35.564 | 1.00 | 19.59 |
| ATOM | 5913 | O | ALA | 1497 | 57.508 | 67.665 | 35.404 | 1.00 | 18.61 |
| ATOM | 5914 | N | GLN | 1498 | 57.244 | 65.469 | 34.985 | 1.00 | 18.72 |
| ATOM | 5915 | CA | GLN | 1498 | 58.388 | 65.390 | 34.078 | 1.00 | 20.53 |
| ATOM | 5916 | CB | GLN | 1498 | 58.963 | 63.965 | 34.035 | 1.00 | 22.06 |
| ATOM | 5917 | CG | GLN | 1498 | 59.614 | 63.495 | 35.334 | 1.00 | 22.10 |
| ATOM | 5918 | CD | GLN | 1498 | 60.314 | 62.146 | 35.192 | 1.00 | 24.33 |
| ATOM | 5919 | OE1 | GLN | 1498 | 60.366 | 61.348 | 36.136 | 1.00 | 28.22 |
| ATOM | 5920 | NE2 | GLN | 1498 | 60.864 | 61.890 | 34.018 | 1.00 | 25.10 |
| ATOM | 5921 | C | GLN | 1498 | 57.959 | 65.822 | 32.668 | 1.00 | 19.53 |
| ATOM | 5922 | O | GLN | 1498 | 58.644 | 66.610 | 32.011 | 1.00 | 17.18 |
| ATOM | 5923 | N | VAL | 1499 | 56.807 | 65.327 | 32.225 | 1.00 | 19.64 |
| ATOM | 5924 | CA | VAL | 1499 | 56.260 | 65.664 | 30.912 | 1.00 | 21.79 |
| ATOM | 5925 | CB | VAL | 1499 | 54.935 | 64.916 | 30.648 | 1.00 | 24.74 |
| ATOM | 5926 | CG1 | VAL | 1499 | 54.392 | 65.273 | 29.271 | 1.00 | 28.60 |
| ATOM | 5927 | CG2 | VAL | 1499 | 55.146 | 63.416 | 30.752 | 1.00 | 23.82 |
| ATOM | 5928 | C | VAL | 1499 | 55.989 | 67.165 | 30.866 | 1.00 | 21.34 |
| ATOM | 5929 | O | VAL | 1499 | 56.251 | 67.836 | 29.871 | 1.00 | 20.70 |
| ATOM | 5930 | N | GLU | 1500 | 55.469 | 67.679 | 31.970 | 1.00 | 23.11 |
| ATOM | 5931 | CA | GLU | 1500 | 55.168 | 69.089 | 32.100 | 1.00 | 24.20 |
| ATOM | 5932 | CB | GLU | 1500 | 54.407 | 69.337 | 33.397 | 1.00 | 21.44 |
| ATOM | 5933 | CG | GLU | 1500 | 54.165 | 70.797 | 33.682 | 1.00 | 20.79 |
| ATOM | 5934 | CD | GLU | 1500 | 53.539 | 71.018 | 35.029 | 1.00 | 22.34 |
| ATOM | 5935 | OE1 | GLU | 1500 | 54.295 | 71.197 | 36.010 | 1.00 | 19.52 |
| ATOM | 5936 | OE2 | GLU | 1500 | 52.289 | 71.013 | 35.109 | 1.00 | 25.92 |
| ATOM | 5937 | C | GLU | 1500 | 56.439 | 69.931 | 32.093 | 1.00 | 26.10 |
| ATOM | 5938 | O | GLU | 1500 | 56.414 | 71.097 | 31.692 | 1.00 | 29.46 |
| ATOM | 5939 | N | GLY | 1501 | 57.529 | 69.361 | 32.594 | 1.00 | 25.56 |
| ATOM | 5940 | CA | GLY | 1501 | 58.782 | 70.089 | 32.637 | 1.00 | 25.86 |
| ATOM | 5941 | C | GLY | 1501 | 59.460 | 70.189 | 31.284 | 1.00 | 26.27 |
| ATOM | 5942 | O | GLY | 1501 | 60.303 | 71.064 | 31.065 | 1.00 | 26.75 |
| ATOM | 5943 | N | GLY | 1502 | 59.127 | 69.270 | 30.386 | 1.00 | 25.70 |
| ATOM | 5944 | CA | GLY | 1502 | 59.720 | 69.302 | 29.066 | 1.00 | 24.56 |
| ATOM | 5945 | C | GLY | 1502 | 58.752 | 69.921 | 28.084 | 1.00 | 24.73 |
| ATOM | 5946 | O | GLY | 1502 | 57.611 | 70.224 | 28.444 | 1.00 | 24.99 |
| ATOM | 5947 | N | VAL | 1503 | 59.192 | 70.112 | 26.846 | 1.00 | 23.11 |
| ATOM | 5948 | CA | VAL | 1503 | 58.327 | 70.685 | 25.836 | 1.00 | 23.44 |
| ATOM | 5949 | CB | VAL | 1503 | 59.041 | 70.797 | 24.492 | 1.00 | 19.90 |
| ATOM | 5950 | CG1 | VAL | 1503 | 58.095 | 71.365 | 23.450 | 1.00 | 21.64 |
| ATOM | 5951 | CG2 | VAL | 1503 | 60.264 | 71.678 | 24.637 | 1.00 | 14.59 |
| ATOM | 5952 | C | VAL | 1503 | 57.092 | 69.798 | 25.697 | 1.00 | 27.31 |
| ATOM | 5953 | O | VAL | 1503 | 57.186 | 68.568 | 25.736 | 1.00 | 27.96 |
| ATOM | 5954 | N | HIS | 1504 | 55.932 | 70.429 | 25.558 | 1.00 | 28.89 |
| ATOM | 5955 | CA | HIS | 1504 | 54.682 | 69.702 | 25.431 | 1.00 | 30.28 |
| ATOM | 5956 | CB | HIS | 1504 | 54.257 | 69.149 | 26.799 | 1.00 | 26.93 |

FIG. 1A-102

| | | | | | | | | | |
|---|---|---|---|---|---|---|---|---|---|
| ATOM | 5957 | CG | HIS | 1504 | 54.047 | 70.203 | 27.850 | 1.00 | 24.05 |
| ATOM | 5958 | CD2 | HIS | 1504 | 54.848 | 70.636 | 28.851 | 1.00 | 23.41 |
| ATOM | 5959 | ND1 | HIS | 1504 | 52.870 | 70.913 | 27.970 | 1.00 | 21.05 |
| ATOM | 5960 | CE1 | HIS | 1504 | 52.957 | 71.734 | 29.002 | 1.00 | 19.17 |
| ATOM | 5961 | NE2 | HIS | 1504 | 54.146 | 71.585 | 29.555 | 1.00 | 17.87 |
| ATOM | 5962 | C | HIS | 1504 | 53.577 | 70.595 | 24.891 | 1.00 | 33.15 |
| ATOM | 5963 | O | HIS | 1504 | 53.683 | 71.817 | 24.937 | 1.00 | 33.63 |
| ATOM | 5964 | N | SER | 1505 | 52.527 | 69.971 | 24.363 | 1.00 | 36.01 |
| ATOM | 5965 | CA | SER | 1505 | 51.355 | 70.683 | 23.855 | 1.00 | 39.13 |
| ATOM | 5966 | CB | SER | 1505 | 50.766 | 71.540 | 24.978 | 1.00 | 41.06 |
| ATOM | 5967 | OG | SER | 1505 | 50.603 | 70.761 | 26.158 | 1.00 | 43.13 |
| ATOM | 5968 | C | SER | 1505 | 51.558 | 71.522 | 22.591 | 1.00 | 39.96 |
| ATOM | 5969 | O | SER | 1505 | 50.737 | 72.391 | 22.268 | 1.00 | 42.24 |
| ATOM | 5970 | N | LEU | 1506 | 52.625 | 71.228 | 21.858 | 1.00 | 38.97 |
| ATOM | 5971 | CA | LEU | 1506 | 52.928 | 71.943 | 20.629 | 1.00 | 37.89 |
| ATOM | 5972 | CB | LEU | 1506 | 54.389 | 72.400 | 20.626 | 1.00 | 34.20 |
| ATOM | 5973 | CG | LEU | 1506 | 54.817 | 73.321 | 21.768 | 1.00 | 33.10 |
| ATOM | 5974 | CD1 | LEU | 1506 | 56.290 | 73.647 | 21.623 | 1.00 | 32.84 |
| ATOM | 5975 | CD2 | LEU | 1506 | 53.974 | 74.597 | 21.772 | 1.00 | 33.22 |
| ATOM | 5976 | C | LEU | 1506 | 52.671 | 71.024 | 19.444 | 1.00 | 38.79 |
| ATOM | 5977 | O | LEU | 1506 | 52.590 | 69.807 | 19.600 | 1.00 | 40.77 |
| ATOM | 5978 | N | HIS | 1507 | 52.501 | 71.610 | 18.267 | 1.00 | 38.76 |
| ATOM | 5979 | CA | HIS | 1507 | 52.277 | 70.833 | 17.064 | 1.00 | 38.33 |
| ATOM | 5980 | CB | HIS | 1507 | 51.428 | 71.623 | 16.079 | 1.00 | 36.69 |
| ATOM | 5981 | CG | HIS | 1507 | 51.148 | 70.886 | 14.812 | 1.00 | 37.52 |
| ATOM | 5982 | CD2 | HIS | 1507 | 51.836 | 70.819 | 13.649 | 1.00 | 36.79 |
| ATOM | 5983 | ND1 | HIS | 1507 | 50.062 | 70.054 | 14.668 | 1.00 | 39.80 |
| ATOM | 5984 | CE1 | HIS | 1507 | 50.093 | 69.501 | 13.467 | 1.00 | 42.20 |
| ATOM | 5985 | NE2 | HIS | 1507 | 51.160 | 69.950 | 12.828 | 1.00 | 39.42 |
| ATOM | 5986 | C | HIS | 1507 | 53.628 | 70.488 | 16.436 | 1.00 | 40.28 |
| ATOM | 5987 | O | HIS | 1507 | 53.735 | 69.574 | 15.619 | 1.00 | 41.56 |
| ATOM | 5988 | N | SER | 1508 | 54.643 | 71.264 | 16.795 | 1.00 | 40.86 |
| ATOM | 5989 | CA | SER | 1508 | 56.006 | 71.085 | 16.311 | 1.00 | 40.77 |
| ATOM | 5990 | CB | SER | 1508 | 56.075 | 71.209 | 14.782 | 1.00 | 43.11 |
| ATOM | 5991 | OG | SER | 1508 | 55.586 | 72.461 | 14.328 | 1.00 | 46.02 |
| ATOM | 5992 | C | SER | 1508 | 56.818 | 72.186 | 16.963 | 1.00 | 40.37 |
| ATOM | 5993 | O | SER | 1508 | 56.250 | 73.152 | 17.472 | 1.00 | 39.76 |
| ATOM | 5994 | N | TYR | 1509 | 58.136 | 72.044 | 16.957 | 1.00 | 41.93 |
| ATOM | 5995 | CA | TYR | 1509 | 59.001 | 73.037 | 17.569 | 1.00 | 44.96 |
| ATOM | 5996 | CB | TYR | 1509 | 58.817 | 73.039 | 19.090 | 1.00 | 42.23 |
| ATOM | 5997 | CG | TYR | 1509 | 59.187 | 71.736 | 19.772 | 1.00 | 40.95 |
| ATOM | 5998 | CD1 | TYR | 1509 | 58.297 | 70.663 | 19.800 | 1.00 | 40.13 |
| ATOM | 5999 | CE1 | TYR | 1509 | 58.621 | 69.474 | 20.452 | 1.00 | 39.44 |
| ATOM | 6000 | CD2 | TYR | 1509 | 60.420 | 71.587 | 20.411 | 1.00 | 39.93 |
| ATOM | 6001 | CE2 | TYR | 1509 | 60.755 | 70.403 | 21.065 | 1.00 | 37.74 |
| ATOM | 6002 | CZ | TYR | 1509 | 59.852 | 69.350 | 21.084 | 1.00 | 37.07 |
| ATOM | 6003 | OH | TYR | 1509 | 60.173 | 68.183 | 21.744 | 1.00 | 34.33 |
| ATOM | 6004 | C | TYR | 1509 | 60.462 | 72.782 | 17.243 | 1.00 | 48.47 |
| ATOM | 6005 | O | TYR | 1509 | 60.834 | 71.688 | 16.810 | 1.00 | 49.70 |
| ATOM | 6006 | N | GLU | 1510 | 61.279 | 73.809 | 17.443 | 1.00 | 51.00 |
| ATOM | 6007 | CA | GLU | 1510 | 62.709 | 73.723 | 17.213 | 1.00 | 53.89 |
| ATOM | 6008 | CB | GLU | 1510 | 63.194 | 74.861 | 16.298 | 1.00 | 57.15 |
| ATOM | 6009 | CG | GLU | 1510 | 62.659 | 74.847 | 14.866 | 1.00 | 63.16 |
| ATOM | 6010 | CD | GLU | 1510 | 61.265 | 75.448 | 14.728 | 1.00 | 65.36 |
| ATOM | 6011 | OE1 | GLU | 1510 | 60.287 | 74.674 | 14.650 | 1.00 | 67.81 |
| ATOM | 6012 | OE2 | GLU | 1510 | 61.149 | 76.694 | 14.677 | 1.00 | 65.33 |
| ATOM | 6013 | C | GLU | 1510 | 63.361 | 73.881 | 18.579 | 1.00 | 54.90 |
| ATOM | 6014 | O | GLU | 1510 | 63.159 | 74.902 | 19.247 | 1.00 | 53.02 |
| ATOM | 6015 | N | LYS | 1511 | 64.059 | 72.848 | 19.037 | 1.00 | 57.49 |

FIG. 1A-103

| ATOM | 6016 | CA | LYS | 1511 | 64.748 | 72.939 | 20.316 | 1.00 | 61.49 |
|---|---|---|---|---|---|---|---|---|---|
| ATOM | 6017 | CB | LYS | 1511 | 64.687 | 71.622 | 21.097 | 1.00 | 60.99 |
| ATOM | 6018 | CG | LYS | 1511 | 65.450 | 71.678 | 22.425 | 1.00 | 61.77 |
| ATOM | 6019 | CD | LYS | 1511 | 64.736 | 70.941 | 23.554 | 1.00 | 62.61 |
| ATOM | 6020 | CE | LYS | 1511 | 64.610 | 69.451 | 23.290 | 1.00 | 62.49 |
| ATOM | 6021 | NZ | LYS | 1511 | 63.891 | 68.781 | 24.404 | 1.00 | 59.52 |
| ATOM | 6022 | C | LYS | 1511 | 66.184 | 73.322 | 19.989 | 1.00 | 64.39 |
| ATOM | 6023 | O | LYS | 1511 | 66.991 | 72.475 | 19.609 | 1.00 | 64.69 |
| ATOM | 6024 | N | ARG | 1512 | 66.462 | 74.621 | 20.073 | 1.00 | 67.99 |
| ATOM | 6025 | CA | ARG | 1512 | 67.778 | 75.174 | 19.769 | 1.00 | 71.02 |
| ATOM | 6026 | CB | ARG | 1512 | 67.660 | 76.148 | 18.587 | 1.00 | 72.88 |
| ATOM | 6027 | CG | ARG | 1512 | 68.917 | 76.940 | 18.264 | 1.00 | 76.14 |
| ATOM | 6028 | CD | ARG | 1512 | 68.686 | 77.854 | 17.070 | 1.00 | 77.65 |
| ATOM | 6029 | NE | ARG | 1512 | 69.670 | 78.931 | 17.012 | 1.00 | 78.89 |
| ATOM | 6030 | CZ | ARG | 1512 | 69.434 | 80.130 | 16.489 | 1.00 | 79.72 |
| ATOM | 6031 | NH1 | ARG | 1512 | 70.386 | 81.052 | 16.487 | 1.00 | 81.31 |
| ATOM | 6032 | NH2 | ARG | 1512 | 68.246 | 80.411 | 15.967 | 1.00 | 80.18 |
| ATOM | 6033 | C | ARG | 1512 | 68.351 | 75.882 | 20.994 | 1.00 | 72.40 |
| ATOM | 6034 | O | ARG | 1512 | 67.735 | 76.808 | 21.536 | 1.00 | 73.61 |
| ATOM | 6035 | N | LEU | 1513 | 69.526 | 75.431 | 21.425 | 1.00 | 72.64 |
| ATOM | 6036 | CA | LEU | 1513 | 70.202 | 75.995 | 22.589 | 1.00 | 72.96 |
| ATOM | 6037 | CB | LEU | 1513 | 70.450 | 74.903 | 23.633 | 1.00 | 74.17 |
| ATOM | 6038 | CG | LEU | 1513 | 69.907 | 75.114 | 25.046 | 1.00 | 75.57 |
| ATOM | 6039 | CD1 | LEU | 1513 | 70.459 | 76.390 | 25.644 | 1.00 | 74.67 |
| ATOM | 6040 | CD2 | LEU | 1513 | 68.403 | 75.154 | 25.002 | 1.00 | 76.98 |
| ATOM | 6041 | C | LEU | 1513 | 71.540 | 76.569 | 22.157 | 1.00 | 72.37 |
| ATOM | 6042 | O | LEU | 1513 | 72.330 | 75.870 | 21.524 | 1.00 | 74.72 |
| ATOM | 6043 | N | PHE | 1514 | 71.786 | 77.831 | 22.493 | 1.00 | 70.03 |
| ATOM | 6044 | CA | PHE | 1514 | 73.035 | 78.501 | 22.150 | 1.00 | 69.17 |
| ATOM | 6045 | CB | PHE | 1514 | 74.187 | 77.962 | 23.022 | 1.00 | 68.65 |
| ATOM | 6046 | CG | PHE | 1514 | 75.234 | 77.176 | 22.266 | 1.00 | 69.27 |
| ATOM | 6047 | CD1 | PHE | 1514 | 76.334 | 77.821 | 21.704 | 1.00 | 69.25 |
| ATOM | 6048 | CD2 | PHE | 1514 | 75.139 | 75.790 | 22.144 | 1.00 | 68.83 |
| ATOM | 6049 | CE1 | PHE | 1514 | 77.322 | 77.102 | 21.032 | 1.00 | 69.55 |
| ATOM | 6050 | CE2 | PHE | 1514 | 76.124 | 75.058 | 21.472 | 1.00 | 67.98 |
| ATOM | 6051 | CZ | PHE | 1514 | 77.217 | 75.716 | 20.917 | 1.00 | 68.62 |
| ATOM | 6052 | C | PHE | 1514 | 73.358 | 78.403 | 20.663 | 1.00 | 69.23 |
| ATOM | 6053 | O | PHE | 1514 | 72.555 | 78.935 | 19.871 | 1.00 | 69.84 |

MYCOPHENOLIC ACID COORDINATES

| ATOM | 6054 | C1 | MPA | 600 | 65.465 | 77.946 | 82.675 | 1.00 | 22.52 |
|---|---|---|---|---|---|---|---|---|---|
| ATOM | 6055 | C2 | MPA | 600 | 64.965 | 82.390 | 86.174 | 1.00 | 28.62 |
| ATOM | 6056 | C3 | MPA | 600 | 65.184 | 83.667 | 86.507 | 1.00 | 27.05 |
| ATOM | 6057 | C4 | MPA | 600 | 64.287 | 84.707 | 85.868 | 1.00 | 28.54 |
| ATOM | 6058 | C5 | MPA | 600 | 65.137 | 85.590 | 84.963 | 1.00 | 30.58 |
| ATOM | 6059 | C6 | MPA | 600 | 65.253 | 85.045 | 83.556 | 1.00 | 30.28 |
| ATOM | 6060 | C7 | MPA | 600 | 69.774 | 80.138 | 83.532 | 1.00 | 16.82 |
| ATOM | 6061 | C8 | MPA | 600 | 68.434 | 82.955 | 84.968 | 1.00 | 25.41 |
| ATOM | 6062 | C9 | MPA | 600 | 66.289 | 84.104 | 87.463 | 1.00 | 21.05 |
| ATOM | 6063 | C10 | MPA | 600 | 67.752 | 78.112 | 82.103 | 1.00 | 22.44 |
| ATOM | 6064 | C11 | MPA | 600 | 67.453 | 79.077 | 83.229 | 1.00 | 23.81 |
| ATOM | 6065 | C12 | MPA | 600 | 68.329 | 79.977 | 83.900 | 1.00 | 22.85 |
| ATOM | 6066 | C13 | MPA | 600 | 67.789 | 80.724 | 84.953 | 1.00 | 19.51 |
| ATOM | 6067 | C14 | MPA | 600 | 66.447 | 80.564 | 85.334 | 1.00 | 20.51 |
| ATOM | 6068 | C15 | MPA | 600 | 65.599 | 79.682 | 84.658 | 1.00 | 21.29 |
| ATOM | 6069 | C16 | MPA | 600 | 66.128 | 78.943 | 83.588 | 1.00 | 20.87 |
| ATOM | 6070 | C17 | MPA | 600 | 65.922 | 81.277 | 86.548 | 1.00 | 26.71 |

FIG. 1A-104

| ATOM | 6071 | O1 | MPA | 600 | 64.326 | 77.614 | 82.588 | 1.00 | 24.71 |
|------|------|-----|-----|------|--------|--------|--------|------|-------|
| ATOM | 6072 | O2 | MPA | 600 | 66.444 | 77.474 | 81.897 | 1.00 | 22.84 |
| ATOM | 6073 | O3 | MPA | 600 | 68.589 | 81.644 | 85.549 | 1.00 | 22.76 |
| ATOM | 6074 | O4 | MPA | 600 | 64.288 | 79.552 | 85.100 | 1.00 | 22.58 |
| ATOM | 6075 | O5 | MPA | 600 | 64.203 | 84.705 | 82.966 | 1.00 | 29.39 |
| ATOM | 6076 | O6 | MPA | 600 | 66.393 | 84.955 | 83.045 | 1.00 | 26.99 |
| ATOM | 6077 | C1 | MPA | 1600 | 79.693 | 50.178 | 33.345 | 1.00 | 26.44 |
| ATOM | 6078 | C2 | MPA | 1600 | 83.159 | 47.108 | 29.935 | 1.00 | 29.82 |
| ATOM | 6079 | C3 | MPA | 1600 | 84.293 | 46.491 | 29.575 | 1.00 | 34.15 |
| ATOM | 6080 | C4 | MPA | 1600 | 84.532 | 45.067 | 30.003 | 1.00 | 37.23 |
| ATOM | 6081 | C5 | MPA | 1600 | 85.484 | 45.043 | 31.192 | 1.00 | 40.84 |
| ATOM | 6082 | C6 | MPA | 1600 | 84.826 | 45.492 | 32.482 | 1.00 | 44.96 |
| ATOM | 6083 | C7 | MPA | 1600 | 84.075 | 52.238 | 32.906 | 1.00 | 17.32 |
| ATOM | 6084 | C8 | MPA | 1600 | 85.729 | 49.609 | 31.503 | 1.00 | 27.67 |
| ATOM | 6085 | C9 | MPA | 1600 | 85.387 | 47.148 | 28.760 | 1.00 | 35.11 |
| ATOM | 6086 | C10 | MPA | 1600 | 81.252 | 51.809 | 34.093 | 1.00 | 28.90 |
| ATOM | 6087 | C11 | MPA | 1600 | 81.874 | 51.061 | 32.928 | 1.00 | 26.34 |
| ATOM | 6088 | C12 | MPA | 1600 | 83.142 | 51.217 | 32.355 | 1.00 | 22.18 |
| ATOM | 6089 | C13 | MPA | 1600 | 83.489 | 50.344 | 31.304 | 1.00 | 24.79 |
| ATOM | 6090 | C14 | MPA | 1600 | 82.574 | 49.363 | 30.850 | 1.00 | 26.59 |
| ATOM | 6091 | C15 | MPA | 1600 | 81.294 | 49.201 | 31.461 | 1.00 | 29.67 |
| ATOM | 6092 | C16 | MPA | 1600 | 80.967 | 50.093 | 32.513 | 1.00 | 28.76 |
| ATOM | 6093 | C17 | MPA | 1600 | 82.921 | 48.553 | 29.618 | 1.00 | 25.16 |
| ATOM | 6094 | O1 | MPA | 1600 | 78.656 | 49.607 | 33.246 | 1.00 | 25.25 |
| ATOM | 6095 | O2 | MPA | 1600 | 79.927 | 51.146 | 34.238 | 1.00 | 27.50 |
| ATOM | 6096 | O3 | MPA | 1600 | 84.766 | 50.358 | 30.746 | 1.00 | 26.41 |
| ATOM | 6097 | O4 | MPA | 1600 | 80.486 | 48.095 | 31.123 | 1.00 | 27.52 |
| ATOM | 6098 | O5 | MPA | 1600 | 83.932 | 44.764 | 32.975 | 1.00 | 45.51 |
| ATOM | 6099 | O6 | MPA | 1600 | 85.195 | 46.576 | 33.001 | 1.00 | 44.94 |

POTASSIUM ION COORDINATES

| ATOM | 6100 | K | POT | 601 | 63.503 | 70.962 | 85.991 | 1.00 | 41.47 |
|------|------|---|-----|-----|--------|--------|--------|------|-------|
| ATOM | 6101 | K | POT | 602 | 72.494 | 52.620 | 29.752 | 1.00 | 37.46 |

WATER MOLECULE COORDINATES

| ATOM | 6102 | OH2 | TIP3 | 603 | 63.529 | 79.256 | 47.792 | 1.00 | 13.93 |
|------|------|-----|------|-----|--------|--------|--------|------|-------|
| ATOM | 6103 | OH2 | TIP3 | 604 | 91.351 | 74.319 | 96.225 | 1.00 | 20.69 |
| ATOM | 6104 | OH2 | TIP3 | 605 | 72.344 | 46.035 | 101.631 | 1.00 | 17.67 |
| ATOM | 6105 | OH2 | TIP3 | 606 | 85.033 | 54.784 | 29.616 | 1.00 | 20.16 |
| ATOM | 6106 | OH2 | TIP3 | 607 | 96.774 | 41.059 | 42.265 | 1.00 | 21.27 |
| ATOM | 6107 | OH2 | TIP3 | 608 | 64.807 | 62.160 | 83.369 | 1.00 | 22.21 |
| ATOM | 6108 | OH2 | TIP3 | 609 | 74.275 | 63.885 | 63.004 | 1.00 | 27.93 |
| ATOM | 6109 | OH2 | TIP3 | 610 | 87.085 | 56.492 | 64.953 | 1.00 | 59.52 |
| ATOM | 6110 | OH2 | TIP3 | 611 | 68.730 | 96.796 | 74.318 | 1.00 | 25.43 |
| ATOM | 6111 | OH2 | TIP3 | 612 | 91.223 | 66.176 | 88.226 | 1.00 | 23.25 |
| ATOM | 6112 | OH2 | TIP3 | 613 | 66.928 | 74.617 | 83.416 | 1.00 | 21.39 |
| ATOM | 6113 | OH2 | TIP3 | 614 | 71.384 | 87.659 | 97.919 | 1.00 | 52.73 |
| ATOM | 6114 | OH2 | TIP3 | 615 | 70.964 | 58.275 | 81.606 | 1.00 | 37.09 |
| ATOM | 6115 | OH2 | TIP3 | 616 | 66.840 | 52.566 | 68.535 | 1.00 | 30.80 |
| ATOM | 6116 | OH2 | TIP3 | 617 | 72.339 | 79.150 | 86.746 | 1.00 | 26.56 |
| ATOM | 6117 | OH2 | TIP3 | 618 | 77.701 | 57.856 | 53.021 | 1.00 | 59.36 |
| ATOM | 6118 | OH2 | TIP3 | 619 | 88.760 | 76.344 | 71.423 | 1.00 | 25.83 |
| ATOM | 6119 | OH2 | TIP3 | 620 | 85.731 | 78.904 | 27.766 | 1.00 | 53.37 |
| ATOM | 6120 | OH2 | TIP3 | 621 | 92.864 | 86.761 | 83.337 | 1.00 | 50.40 |
| ATOM | 6121 | OH2 | TIP3 | 622 | 52.798 | 60.668 | 36.659 | 1.00 | 44.29 |

FIG. 1A-105

| ATOM | 6122 | OH2 | TIP3 | 623 | 90.156 | 46.925 | 37.917 | 1.00 | 54.24 |
|------|------|-----|------|-----|--------|--------|--------|------|-------|
| ATOM | 6123 | OH2 | TIP3 | 624 | 66.346 | 64.284 | 84.367 | 1.00 | 41.00 |
| ATOM | 6124 | OH2 | TIP3 | 625 | 78.607 | 68.770 | 56.915 | 1.00 | 48.73 |
| ATOM | 6125 | OH2 | TIP3 | 626 | 85.421 | 51.000 | 81.149 | 1.00 | 29.22 |
| ATOM | 6126 | OH2 | TIP3 | 627 | 81.905 | 76.656 | 101.724 | 1.00 | 40.26 |
| ATOM | 6127 | OH2 | TIP3 | 628 | 69.287 | 88.078 | 78.412 | 1.00 | 41.23 |
| ATOM | 6128 | OH2 | TIP3 | 629 | 79.428 | 72.947 | 68.392 | 1.00 | 18.91 |
| ATOM | 6129 | OH2 | TIP3 | 630 | 68.417 | 98.204 | 82.153 | 1.00 | 40.95 |
| ATOM | 6130 | OH2 | TIP3 | 631 | 74.926 | 65.022 | 60.600 | 1.00 | 56.88 |
| ATOM | 6131 | OH2 | TIP3 | 632 | 97.224 | 50.021 | 75.346 | 1.00 | 35.64 |
| ATOM | 6132 | OH2 | TIP3 | 633 | 71.296 | 88.279 | 64.915 | 1.00 | 54.34 |
| ATOM | 6133 | OH2 | TIP3 | 634 | 80.899 | 65.865 | 59.607 | 1.00 | 32.10 |
| ATOM | 6134 | OH2 | TIP3 | 635 | 66.483 | 65.049 | 30.246 | 1.00 | 20.26 |
| ATOM | 6135 | OH2 | TIP3 | 636 | 93.787 | 75.011 | 36.209 | 1.00 | 40.10 |
| ATOM | 6136 | OH2 | TIP3 | 637 | 83.837 | 45.961 | 49.613 | 1.00 | 30.53 |
| ATOM | 6137 | OH2 | TIP3 | 638 | 110.170 | 56.656 | 42.696 | 1.00 | 41.92 |
| ATOM | 6138 | OH2 | TIP3 | 639 | 84.500 | 64.574 | 47.772 | 1.00 | 42.47 |
| ATOM | 6139 | OH2 | TIP3 | 640 | 84.650 | 68.995 | 68.569 | 1.00 | 22.92 |
| ATOM | 6140 | OH2 | TIP3 | 641 | 75.389 | 62.003 | 106.019 | 1.00 | 64.07 |
| ATOM | 6141 | OH2 | TIP3 | 642 | 65.093 | 83.895 | 66.370 | 1.00 | 35.20 |
| ATOM | 6142 | OH2 | TIP3 | 643 | 79.572 | 69.513 | 68.092 | 1.00 | 41.73 |
| ATOM | 6143 | OH2 | TIP3 | 644 | 81.705 | 69.807 | 13.345 | 1.00 | 75.61 |
| ATOM | 6144 | OH2 | TIP3 | 645 | 79.766 | 83.945 | 66.824 | 1.00 | 38.58 |
| ATOM | 6145 | OH2 | TIP3 | 646 | 76.630 | 91.036 | 98.006 | 1.00 | 30.86 |
| ATOM | 6146 | OH2 | TIP3 | 647 | 92.426 | 72.749 | 82.096 | 1.00 | 23.28 |
| ATOM | 6147 | OH2 | TIP3 | 648 | 92.577 | 69.692 | 44.133 | 1.00 | 36.85 |
| ATOM | 6148 | OH2 | TIP3 | 649 | 82.576 | 41.782 | 29.517 | 1.00 | 39.32 |
| ATOM | 6149 | OH2 | TIP3 | 650 | 65.551 | 66.516 | 32.182 | 1.00 | 34.30 |
| ATOM | 6150 | OH2 | TIP3 | 651 | 61.739 | 81.979 | 81.423 | 1.00 | 21.79 |
| ATOM | 6151 | OH2 | TIP3 | 652 | 74.532 | 61.047 | 62.982 | 1.00 | 23.13 |
| ATOM | 6152 | OH2 | TIP3 | 653 | 73.416 | 69.959 | 84.520 | 1.00 | 24.72 |
| ATOM | 6153 | OH2 | TIP3 | 654 | 87.526 | 78.696 | 87.501 | 1.00 | 28.42 |
| ATOM | 6154 | OH2 | TIP3 | 655 | 73.301 | 97.166 | 75.481 | 1.00 | 29.52 |
| ATOM | 6155 | OH2 | TIP3 | 656 | 80.797 | 97.236 | 80.169 | 1.00 | 36.44 |
| ATOM | 6156 | OH2 | TIP3 | 657 | 72.410 | 82.003 | 80.433 | 1.00 | 39.64 |
| ATOM | 6157 | OH2 | TIP3 | 658 | 70.797 | 81.205 | 86.943 | 1.00 | 26.15 |
| ATOM | 6158 | OH2 | TIP3 | 659 | 69.119 | 86.448 | 85.434 | 1.00 | 37.81 |
| ATOM | 6159 | OH2 | TIP3 | 660 | 65.869 | 78.967 | 75.344 | 1.00 | 39.42 |
| ATOM | 6160 | OH2 | TIP3 | 661 | 87.122 | 84.588 | 70.107 | 1.00 | 41.94 |
| ATOM | 6161 | OH2 | TIP3 | 662 | 66.313 | 71.983 | 78.252 | 1.00 | 15.40 |
| ATOM | 6162 | OH2 | TIP3 | 663 | 61.479 | 73.532 | 84.529 | 1.00 | 24.10 |
| ATOM | 6163 | OH2 | TIP3 | 664 | 73.933 | 69.027 | 88.128 | 1.00 | 25.97 |
| ATOM | 6164 | OH2 | TIP3 | 665 | 63.498 | 69.506 | 79.814 | 1.00 | 26.48 |
| ATOM | 6165 | OH2 | TIP3 | 666 | 61.100 | 68.368 | 79.010 | 1.00 | 45.05 |
| ATOM | 6166 | OH2 | TIP3 | 667 | 73.033 | 68.873 | 79.995 | 1.00 | 10.40 |
| ATOM | 6167 | OH2 | TIP3 | 668 | 75.053 | 67.738 | 67.556 | 1.00 | 25.98 |
| ATOM | 6168 | OH2 | TIP3 | 669 | 70.945 | 65.926 | 61.108 | 1.00 | 30.20 |
| ATOM | 6169 | OH2 | TIP3 | 670 | 79.966 | 71.965 | 70.861 | 1.00 | 14.26 |
| ATOM | 6170 | OH2 | TIP3 | 671 | 73.205 | 58.622 | 82.862 | 1.00 | 34.10 |
| ATOM | 6171 | OH2 | TIP3 | 672 | 77.591 | 58.927 | 88.294 | 1.00 | 31.75 |
| ATOM | 6172 | OH2 | TIP3 | 673 | 82.216 | 67.818 | 102.675 | 1.00 | 31.66 |
| ATOM | 6173 | OH2 | TIP3 | 674 | 82.356 | 78.417 | 96.074 | 1.00 | 45.06 |
| ATOM | 6174 | OH2 | TIP3 | 675 | 74.350 | 76.446 | 100.156 | 1.00 | 20.12 |
| ATOM | 6175 | OH2 | TIP3 | 676 | 73.281 | 74.984 | 103.568 | 1.00 | 37.74 |
| ATOM | 6176 | OH2 | TIP3 | 677 | 67.784 | 70.872 | 110.507 | 1.00 | 50.41 |
| ATOM | 6177 | OH2 | TIP3 | 678 | 78.658 | 70.113 | 110.447 | 1.00 | 37.54 |
| ATOM | 6178 | OH2 | TIP3 | 679 | 68.600 | 84.196 | 101.581 | 1.00 | 67.03 |
| ATOM | 6179 | OH2 | TIP3 | 680 | 68.093 | 85.770 | 90.932 | 1.00 | 32.35 |
| ATOM | 6180 | OH2 | TIP3 | 681 | 60.473 | 85.655 | 86.947 | 1.00 | 34.10 |

FIG. 1A-106

| | | | | | | | | | |
|---|---|---|---|---|---|---|---|---|---|
| ATOM | 6181 | OH2 | TIP3 | 682 | 84.197 | 63.598 | 97.245 | 1.00 | 34.52 |
| ATOM | 6182 | OH2 | TIP3 | 683 | 90.212 | 55.985 | 83.506 | 1.00 | 56.22 |
| ATOM | 6183 | OH2 | TIP3 | 684 | 88.466 | 52.166 | 69.315 | 1.00 | 46.13 |
| ATOM | 6184 | OH2 | TIP3 | 685 | 93.732 | 59.819 | 73.153 | 1.00 | 29.48 |
| ATOM | 6185 | OH2 | TIP3 | 686 | 74.318 | 60.741 | 59.818 | 1.00 | 33.51 |
| ATOM | 6186 | OH2 | TIP3 | 687 | 84.856 | 56.311 | 60.236 | 1.00 | 55.85 |
| ATOM | 6187 | OH2 | TIP3 | 688 | 75.504 | 58.569 | 65.142 | 1.00 | 24.35 |
| ATOM | 6188 | OH2 | TIP3 | 689 | 66.245 | 47.634 | 93.849 | 1.00 | 35.24 |
| ATOM | 6189 | OH2 | TIP3 | 690 | 88.810 | 54.683 | 17.033 | 1.00 | 68.14 |
| ATOM | 6190 | OH2 | TIP3 | 691 | 83.094 | 60.169 | 17.837 | 1.00 | 42.20 |
| ATOM | 6191 | OH2 | TIP3 | 692 | 92.231 | 70.264 | 19.371 | 1.00 | 22.36 |
| ATOM | 6192 | OH2 | TIP3 | 693 | 89.874 | 79.054 | 28.213 | 1.00 | 23.97 |
| ATOM | 6193 | OH2 | TIP3 | 694 | 93.455 | 67.246 | 28.718 | 1.00 | 19.81 |
| ATOM | 6194 | OH2 | TIP3 | 695 | 104.670 | 51.741 | 36.100 | 1.00 | 54.63 |
| ATOM | 6195 | OH2 | TIP3 | 696 | 80.782 | 44.301 | 34.548 | 1.00 | 31.71 |
| ATOM | 6196 | OH2 | TIP3 | 697 | 81.029 | 45.306 | 48.967 | 1.00 | 21.33 |
| ATOM | 6197 | OH2 | TIP3 | 698 | 97.717 | 63.697 | 46.528 | 1.00 | 47.29 |
| ATOM | 6198 | OH2 | TIP3 | 699 | 93.154 | 58.370 | 49.439 | 1.00 | 29.43 |
| ATOM | 6199 | OH2 | TIP3 | 700 | 73.721 | 49.371 | 31.619 | 1.00 | 28.64 |
| ATOM | 6200 | OH2 | TIP3 | 701 | 75.341 | 54.478 | 37.368 | 1.00 | 44.88 |
| ATOM | 6201 | OH2 | TIP3 | 702 | 71.483 | 53.761 | 36.481 | 1.00 | 43.75 |
| ATOM | 6202 | OH2 | TIP3 | 703 | 70.805 | 48.134 | 29.440 | 1.00 | 45.27 |
| ATOM | 6203 | OH2 | TIP3 | 704 | 67.240 | 57.027 | 45.672 | 1.00 | 23.68 |
| ATOM | 6204 | OH2 | TIP3 | 705 | 73.938 | 65.367 | 53.641 | 1.00 | 35.21 |
| ATOM | 6205 | OH2 | TIP3 | 706 | 76.765 | 63.952 | 48.838 | 1.00 | 39.11 |
| ATOM | 6206 | OH2 | TIP3 | 707 | 86.429 | 64.888 | 41.271 | 1.00 | 47.43 |
| ATOM | 6207 | OH2 | TIP3 | 708 | 79.337 | 55.169 | 33.298 | 1.00 | 25.21 |
| ATOM | 6208 | OH2 | TIP3 | 709 | 77.021 | 61.621 | 35.635 | 1.00 | 12.75 |
| ATOM | 6209 | OH2 | TIP3 | 710 | 77.475 | 62.445 | 28.068 | 1.00 | 17.76 |
| ATOM | 6210 | OH2 | TIP3 | 711 | 65.308 | 68.280 | 34.978 | 1.00 | 60.08 |
| ATOM | 6211 | OH2 | TIP3 | 712 | 81.233 | 66.515 | 47.960 | 1.00 | 16.11 |
| ATOM | 6212 | OH2 | TIP3 | 713 | 85.329 | 69.050 | 46.064 | 1.00 | 41.01 |
| ATOM | 6213 | OH2 | TIP3 | 714 | 78.087 | 61.162 | 31.841 | 1.00 | 33.88 |
| ATOM | 6214 | OH2 | TIP3 | 715 | 83.936 | 58.250 | 16.183 | 1.00 | 19.59 |
| ATOM | 6215 | OH2 | TIP3 | 716 | 84.076 | 55.186 | 22.421 | 1.00 | 52.59 |
| ATOM | 6216 | OH2 | TIP3 | 717 | 71.928 | 61.664 | 18.579 | 1.00 | 20.02 |
| ATOM | 6217 | OH2 | TIP3 | 718 | 71.233 | 71.762 | 28.181 | 1.00 | 52.28 |
| ATOM | 6218 | OH2 | TIP3 | 719 | 82.842 | 72.092 | 48.741 | 1.00 | 29.08 |
| ATOM | 6219 | OH2 | TIP3 | 720 | 66.512 | 75.646 | 47.219 | 1.00 | 30.30 |
| ATOM | 6220 | OH2 | TIP3 | 721 | 47.558 | 69.374 | 15.382 | 1.00 | 63.67 |
| ATOM | 6221 | OH2 | TIP3 | 722 | 57.528 | 74.361 | 14.349 | 1.00 | 17.13 |
| ATOM | 6222 | OH2 | TIP3 | 723 | 92.602 | 74.600 | 98.553 | 1.00 | 40.55 |
| ATOM | 6223 | OH2 | TIP3 | 724 | 95.012 | 73.669 | 97.163 | 1.00 | 52.61 |
| ATOM | 6224 | OH2 | TIP3 | 725 | 85.703 | 52.369 | 29.241 | 1.00 | 33.33 |
| ATOM | 6225 | OH2 | TIP3 | 726 | 87.263 | 53.317 | 35.120 | 1.00 | 33.57 |
| ATOM | 6226 | OH2 | TIP3 | 727 | 97.146 | 44.242 | 39.694 | 1.00 | 51.07 |
| ATOM | 6227 | OH2 | TIP3 | 728 | 66.879 | 61.968 | 81.685 | 1.00 | 21.70 |
| ATOM | 6228 | OH2 | TIP3 | 729 | 63.716 | 59.555 | 84.121 | 1.00 | 19.58 |
| ATOM | 6229 | OH2 | TIP3 | 730 | 68.397 | 64.441 | 82.651 | 1.00 | 40.07 |
| ATOM | 6230 | OH2 | TIP3 | 731 | 71.867 | 59.240 | 59.629 | 1.00 | 50.06 |
| ATOM | 6231 | OH2 | TIP3 | 732 | 89.666 | 54.437 | 68.351 | 1.00 | 47.64 |
| ATOM | 6232 | OH2 | TIP3 | 733 | 71.067 | 95.544 | 76.431 | 1.00 | 60.59 |
| ATOM | 6233 | OH2 | TIP3 | 734 | 65.904 | 98.120 | 73.267 | 1.00 | 71.60 |
| ATOM | 6234 | OH2 | TIP3 | 735 | 92.274 | 63.420 | 87.295 | 1.00 | 34.70 |
| ATOM | 6235 | OH2 | TIP3 | 736 | 91.884 | 59.474 | 86.045 | 1.00 | 39.11 |
| ATOM | 6236 | OH2 | TIP3 | 737 | 97.536 | 64.003 | 85.787 | 1.00 | 41.08 |
| ATOM | 6237 | OH2 | TIP3 | 738 | 69.252 | 74.894 | 82.126 | 1.00 | 22.96 |
| ATOM | 6238 | OH2 | TIP3 | 739 | 71.940 | 55.321 | 80.912 | 1.00 | 34.50 |
| ATOM | 6239 | OH2 | TIP3 | 740 | 70.550 | 55.962 | 83.229 | 1.00 | 38.09 |

FIG. 1A-107

| | | | | | | | | | |
|---|---|---|---|---|---|---|---|---|---|
| ATOM | 6240 | OH2 | TIP3 | 741 | 68.530 | 50.686 | 67.504 | 1.00 | 36.49 |
| ATOM | 6241 | OH2 | TIP3 | 742 | 67.078 | 49.872 | 64.964 | 1.00 | 43.81 |
| ATOM | 6242 | OH2 | TIP3 | 743 | 79.200 | 58.771 | 55.790 | 1.00 | 36.92 |
| ATOM | 6243 | OH2 | TIP3 | 744 | 87.067 | 77.893 | 23.397 | 1.00 | 43.96 |
| ATOM | 6244 | OH2 | TIP3 | 745 | 54.640 | 58.967 | 38.719 | 1.00 | 36.98 |
| ATOM | 6245 | OH2 | TIP3 | 746 | 51.786 | 59.284 | 33.944 | 1.00 | 44.76 |
| ATOM | 6246 | OH2 | TIP3 | 747 | 90.904 | 49.068 | 36.430 | 1.00 | 163.82 |
| ATOM | 6247 | OH2 | TIP3 | 748 | 82.871 | 63.204 | 61.483 | 1.00 | 41.80 |
| ATOM | 6248 | OH2 | TIP3 | 749 | 88.761 | 50.228 | 82.920 | 1.00 | 58.55 |
| ATOM | 6249 | OH2 | TIP3 | 750 | 81.750 | 74.065 | 103.304 | 1.00 | 39.00 |
| ATOM | 6250 | OH2 | TIP3 | 751 | 66.504 | 88.568 | 77.984 | 1.00 | 65.75 |
| ATOM | 6251 | OH2 | TIP3 | 752 | 69.412 | 89.769 | 82.897 | 1.00 | 56.13 |
| ATOM | 6252 | OH2 | TIP3 | 753 | 82.689 | 72.715 | 67.756 | 1.00 | 22.04 |
| ATOM | 6253 | OH2 | TIP3 | 754 | 93.644 | 47.147 | 67.273 | 1.00 | 54.18 |
| ATOM | 6254 | OH2 | TIP3 | 755 | 97.081 | 53.639 | 71.995 | 1.00 | 69.31 |
| ATOM | 6255 | OH2 | TIP3 | 756 | 70.064 | 87.291 | 62.433 | 1.00 | 102.37 |
| ATOM | 6256 | OH2 | TIP3 | 757 | 73.191 | 90.367 | 65.078 | 1.00 | 50.53 |
| ATOM | 6257 | OH2 | TIP3 | 758 | 67.919 | 65.829 | 34.994 | 1.00 | 46.46 |
| ATOM | 6258 | OH2 | TIP3 | 759 | 67.766 | 62.682 | 29.909 | 1.00 | 48.04 |
| ATOM | 6259 | OH2 | TIP3 | 760 | 67.898 | 67.872 | 33.364 | 1.00 | 55.10 |
| ATOM | 6260 | OH2 | TIP3 | 761 | 75.277 | 82.599 | 61.330 | 1.00 | 58.80 |
| ATOM | 6261 | OH2 | TIP3 | 762 | 74.827 | 82.595 | 58.575 | 1.00 | 49.19 |
| ATOM | 6262 | OH2 | TIP3 | 763 | 83.123 | 64.992 | 45.218 | 1.00 | 29.88 |
| ATOM | 6263 | OH2 | TIP3 | 764 | 84.728 | 65.820 | 66.470 | 1.00 | 45.69 |
| ATOM | 6264 | OH2 | TIP3 | 765 | 85.961 | 70.489 | 71.473 | 1.00 | 38.35 |
| ATOM | 6265 | OH2 | TIP3 | 766 | 87.324 | 68.224 | 72.271 | 1.00 | 28.55 |
| ATOM | 6266 | OH2 | TIP3 | 767 | 84.928 | 69.467 | 73.731 | 1.00 | 44.55 |
| ATOM | 6267 | OH2 | TIP3 | 768 | 76.765 | 62.520 | 103.736 | 1.00 | 58.67 |
| ATOM | 6268 | OH2 | TIP3 | 769 | 84.140 | 39.796 | 28.646 | 1.00 | 45.66 |
| ATOM | 6269 | OH2 | TIP3 | 770 | 83.628 | 41.922 | 32.632 | 1.00 | 43.68 |
| ATOM | 6270 | OH2 | TIP3 | 771 | 82.432 | 41.152 | 35.014 | 1.00 | 41.03 |
| ATOM | 6271 | OH2 | TIP3 | 772 | 85.785 | 40.516 | 31.870 | 1.00 | 77.32 |
| ATOM | 6272 | OH2 | TIP3 | 773 | 61.289 | 85.672 | 83.306 | 1.00 | 52.50 |
| ATOM | 6273 | OH2 | TIP3 | 774 | 80.035 | 101.956 | 82.899 | 1.00 | 37.06 |
| ATOM | 6274 | OH2 | TIP3 | 775 | 63.097 | 79.370 | 68.380 | 1.00 | 24.13 |
| ATOM | 6275 | OH2 | TIP3 | 776 | 88.040 | 87.256 | 70.554 | 1.00 | 40.73 |
| ATOM | 6276 | OH2 | TIP3 | 777 | 66.901 | 59.286 | 59.258 | 1.00 | 43.62 |
| ATOM | 6277 | OH2 | TIP3 | 778 | 81.864 | 74.462 | 75.134 | 1.00 | 36.80 |
| ATOM | 6278 | OH2 | TIP3 | 779 | 83.881 | 83.471 | 99.167 | 1.00 | 44.32 |
| ATOM | 6279 | OH2 | TIP3 | 780 | 83.457 | 80.677 | 98.481 | 1.00 | 44.09 |
| ATOM | 6280 | OH2 | TIP3 | 781 | 82.376 | 85.551 | 101.068 | 1.00 | 37.49 |
| ATOM | 6281 | OH2 | TIP3 | 782 | 75.550 | 74.768 | 98.408 | 1.00 | 52.97 |
| ATOM | 6282 | OH2 | TIP3 | 783 | 73.955 | 78.953 | 101.355 | 1.00 | 57.37 |
| ATOM | 6283 | OH2 | TIP3 | 784 | 80.713 | 64.405 | 109.404 | 1.00 | 44.25 |
| ATOM | 6284 | OH2 | TIP3 | 785 | 58.907 | 87.813 | 87.475 | 1.00 | 61.21 |
| ATOM | 6285 | OH2 | TIP3 | 786 | 80.267 | 61.506 | 96.956 | 1.00 | 36.10 |
| ATOM | 6286 | OH2 | TIP3 | 787 | 84.222 | 58.111 | 62.183 | 1.00 | 70.74 |
| ATOM | 6287 | OH2 | TIP3 | 788 | 83.160 | 57.267 | 58.302 | 1.00 | 52.72 |
| ATOM | 6288 | OH2 | TIP3 | 789 | 66.464 | 47.762 | 96.657 | 1.00 | 59.25 |
| ATOM | 6289 | OH2 | TIP3 | 790 | 69.394 | 52.614 | 90.763 | 1.00 | 48.67 |
| ATOM | 6290 | OH2 | TIP3 | 791 | 92.257 | 73.130 | 19.969 | 1.00 | 51.24 |
| ATOM | 6291 | OH2 | TIP3 | 792 | 99.638 | 61.766 | 45.543 | 1.00 | 54.79 |
| ATOM | 6292 | OH2 | TIP3 | 793 | 97.433 | 64.794 | 49.071 | 1.00 | 47.02 |
| ATOM | 6293 | OH2 | TIP3 | 794 | 77.710 | 52.845 | 32.368 | 1.00 | 35.15 |
| ATOM | 6294 | OH2 | TIP3 | 795 | 69.444 | 52.278 | 37.349 | 1.00 | 59.52 |
| ATOM | 6295 | OH2 | TIP3 | 796 | 68.211 | 49.099 | 26.477 | 1.00 | 47.09 |
| ATOM | 6296 | OH2 | TIP3 | 797 | 65.300 | 58.001 | 47.307 | 1.00 | 45.39 |
| ATOM | 6297 | OH2 | TIP3 | 798 | 67.739 | 54.960 | 47.317 | 1.00 | 52.04 |
| ATOM | 6298 | OH2 | TIP3 | 799 | 65.578 | 50.677 | 47.117 | 1.00 | 40.40 |

FIG. 1A-108

| ATOM | 6299 | OH2 | TIP3 | 800 | 70.910 | 67.580 | 52.751 | 1.00 | 35.66 |
| ATOM | 6300 | OH2 | TIP3 | 801 | 70.015 | 69.737 | 50.764 | 1.00 | 27.41 |
| ATOM | 6301 | OH2 | TIP3 | 802 | 80.334 | 70.409 | 42.183 | 1.00 | 97.77 |
| ATOM | 6302 | OH2 | TIP3 | 803 | 64.245 | 76.692 | 48.798 | 1.00 | 16.97 |
| ATOM | 6303 | OH2 | TIP3 | 804 | 65.457 | 76.921 | 51.491 | 1.00 | 31.17 |

CRYSTALS OF INOSINE MONOPHOSPHATE DEHYDROGENASE/OXIDIZED INOSINE MONOPHOSPHATE THIOMIDATE INTERMEDIATE/MYCOPHENOLIC ACID (IIMPDH/XMP*/MPA)

CROSS-REFERENCE TO RELATED APPLICATION

This application is a divisional application of U.S. application Ser. No. 09/678,016, filed Oct. 2, 2000, now U.S. Pat. No.7,216,041, which is a divisional application of U.S. application Ser. No. 08/640,164, filed Apr. 30, 1996, now U.S. Pat. No. 6,128,582.

TECHNICAL FIELD OF INVENTION

The present invention relates to a data storage medium encoded with the structural coordinates of crystallized molecules and molecular complexes which comprise the active site binding pockets of IMPDH. Such data storage material is capable of displaying such molecules and molecular complexes, or their structural homologues, as a graphical three-dimensional representation on a computer screen. This invention also relates to methods of using the structure coordinates to solve the structure of homologous proteins or protein complexes. In addition, this invention relates to methods of using the structure coordinates to screen and design compounds, including inhibitory compounds, that bind to IMPDH or homologues thereof. This invention also relates to molecules and molecular complexes which comprise the active site binding pockets of IMPDH or close structural homologues of the active site binding pockets. This invention also relates to compounds and pharmaceutical compositions which are inhibitors of IMPDH.

BACKGROUND OF THE INVENTION

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH; EC 1.1.1.205) is an enzyme involved in the de novo synthesis of guanosine nucleotides. IMPDH catalyzes the NAD-dependent oxidation of inosine-5'-monophosphate (IMP) to xanthosine-5'-monophosphate (XMP), which is the committed step in guanosine nucleotide synthesis. [R. C. Jackson et. al., Nature, 256, pp. 331-333 (1975)].

IMPDH is ubiquitous in eukaryotes, bacteria and protozoa [Y. Natsumeda and S. F. Carr, Ann. N.Y. Acad. Sci., 696, pp. 88-93 (1993). The prokaryotic forms share 30-40% sequence identity with the human enzyme. Regardless of species, the enzyme follows an ordered Bi-Bi reaction sequence, where IMP binding precedes that of NAD, and NADH is released prior to XMP [S. F. Carr et al., J. Biol. Chem. 268, pp. 27286-27290 (1993); E. W. Holmes; Biochim. Biophys. Acta 364, pp. 209-217 (1974)]. This mechanism differs from that of most other known NAD-dependent dehydrogenases, which have either a random order of substrate addition or require that NAD bind before substrate.

The de novo synthesis of guanosine nucleotides, and thus the activity of IMPDH, is particularly important in B- and T-lymphocytes. These cells depend on the de novo, rather than salvage pathway to generate sufficient levels of nucleotides necessary to initiate a proliferative response to mitogen or antigen [A. C. Allison et. al., Lancet II, 1179 (1975) and A. C. Allison et. al., Ciba Found. Symp., 48, 207 (1977)]. Thus, IMPDH is an attractive target for selectively inhibiting the immune system without also inhibiting the proliferation of other cells.

Immunosuppression has been achieved by inhibiting a variety of enzymes including for example, the phosphatase calcineurin (inhibited by cyclosporin A and FK-506); dihydroorotate dehydrogenase, an enzyme involved in the biosynthesis of pyrimidines (inhibited by leflunomide and brequinar); the kinase FRAP (inhibited by rapamycin); and the heat shock protein hsp70 (inhibited by deoxyspergualin). [See B. D. Kahan, Immunological Reviews, 136, pp. 29-49 (1993); R. E. Morris, The Journal of Heart and Lung Transplantation, 12(6), pp. S275-S286 (1993)].

Inhibitors of IMPDH are also known. U.S. Pat. Nos. 5,380,879 and 5,444,072 and PCT publications WO 94/01105 and WO 94/12184 describe mycophenolic acid (MPA) and some of its derivatives as potent, uncompetitive, reversible inhibitors of human IMPDH type I and type II. MPA has been demonstrated to block the response of B and T-cells to mitogen or antigen [A. C. Allison et. al., Ann. N. Y. Acad. Sci., 696, 63 (1993).

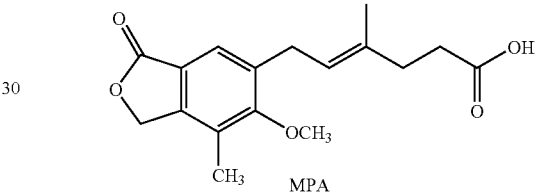

MPA

Immunosuppressants, such as MPA, are useful drugs in the treatment of transplant rejection and autoimmune diseases [R. E. Morris, Kidney Intel., 49, Suppl. 53, S-26 (1996)]. MPA, however, is characterized by undesirable pharmacological properties, such as gastrointestinal toxicity and poor bioavailability. [L. M. Shaw, et. al., Therapeutic Drug Monitoring, 17, pp. 690-699, (1995)].

Nucleoside analogs such as tiazofurin, ribavirin and mizoribine also inhibit IMPDH [L. Hedstrom et. al., Biochemistry, 29, pp. 849-854 (1990)]. These compounds, however, are not specific for IMPDH.

Mycophenolate mofetil, a prodrug which quickly liberates free MPA in vivo, was recently approved to prevent acute renal allograft rejection following kidney transplantation [L. M. Shaw et al., Therapeutic Drug Monitoring, 17, pp. 690-699 (1995); H. W. Sollinger, Transplantation, 60, pp. 225-232 (1995)]. However, because of gastrointestinal and other side-effects, the therapeutic potential of this drug appears limited [L. M. Shaw et al., Therapeutic Drug Monitoring, 17, pp. 690-699 (1995); A. C. Allison and E. M. Eugui Immunological Rev., 136, pp. 5-28 (1993)].

It is also known that IMPDH plays a role in other metabolic events. Increased IMPDH activity has been observed in rapidly proliferating human leukemic cell lines and other tumor cell lines, indicating IMPDH is a target for anti-cancer as well as immunosuppressive chemotherapy [M. Nagai et. al., Cancer Res., 51, pp. 3886-3890 (1991)].

IMPDH has also been shown to play a role in the proliferation of smooth muscle cells, indicating that inhibitors of IMPDH, such as MPA or rapamycin, may be useful in preventing restenosis or other hyperproliferative vascular diseases [C. R. Gregory et al., *Transplantation*, 59, pp. 655-61 (1995); PCT publication WO 94/12184; and PCT publication WO 94/01105].

Additionally, IMPDH has been shown to play a role in viral replication in some viral cell lines [S. F. Carr, *J. Biol. Chem.*, 268, pp. 27286-27290 (1993)]. Analogous to lymphocyte and tumor cell lines, the implication is that the de novo, rather than the salvage, pathway is critical in the viral replication process.

Thus, there remains a need for potent IMPDH inhibitors with improved pharmacological properties. Such inhibitors would have therapeutic potential as immunosuppressants, anti-cancer agents, anti-vascular hyperproliferative agents and anti-viral agents. Specifically, such compounds may be used in the treatment of transplant rejection and autoimmune diseases, such as rheumatoid arthritis, multiple sclerosis, juvenile diabetes, asthma, inflammatory bowel disease, as well as in the treatment of cancer and tumors, such as lymphomas and leukemia, vascular diseases, such as restenosis, and viral replication diseases, such as retroviral diseases and herpes.

Two isoforms of human IMPDH, designated type I and type II, have been identified [F. R. Collart and E. Huberman, *J. Biol. Chem.*, 263, pp. 15769-15772 (1988); Y. Natsumeda et. al., *J. Biol. Chem.*, 265, pp. 5292-5295 (1990)]. Each is 514 amino acids, and they share 84% sequence identity. Both IMPDH type I and type II form active tetramers in solution, with subunit molecular weights of 56 kDa [Y. Yamada et. al., *Biochemistry*, 27, pp. 2737-2745 (1988)].

Both human IMPDH isoforms have been characterized by their cDNA and amino acid sequences [Y. Natsumeda et. al., *J. Biol. Chem.*, 265, pp. 5222-5295 (1990)]. Chinese hamster IMPDH has been characterized by its cDNA and its amino acid sequence (F. R Collart and E. Hubermann, *J. Biol. Chem.*, 263, pp. 15769-15772 (1988). Knowledge of the primary structure, i.e., amino acid sequence, of IMPDH, however, does not allow prediction of its tertiary structure. Nor does it afford an understanding of the structural, conformational and chemical interactions of IMPDH with MPA, IMP, or other compounds or inhibitors.

The crystal structure of IMPDH has not been reported. Nor has the crystal structure of a IMPDH homologue or a IMPDH co-complex been reported. The need, therefore, exists for determining the crystal structure of IMPDH to provide a more accurate description of the structure of IMPDH to aid in the design of improved IMPDH inhibitors. The crystal structure of a complex comprising IMPDH, IMP and MPA would provide such a description.

SUMMARY OF THE INVENTION

Applicants have solved this problem by achieving, for the first time, the crystallization of Chinese hamster type II IMPDH in complex with XMP* and MPA and have solved the three-dimensional structure of that complex. This isoform of IMPDH differs by only 6 amino acids from the human type II enzyme while retaining similar enzymatic characteristics and the ability to be inhibited by MPA. Solving this crystal structure has allowed applicants to determine the key structural features of IMPDH, particularly the shape of its XMP* binding pocket and its MPA binding pocket.

Thus, the present invention provides molecules or molecular complexes that comprise all or parts of either one or two of these binding pockets, or homologues of these binding pockets that have similar three-dimensional shapes.

The invention also provides a machine readable storage medium which comprises the structure coordinates of IMPDH, including all or any parts of the XMP* and MPA binding pockets. Such storage medium encoded with these data are capable of displaying on a computer screen or similar viewing device, a three-dimensional graphical representation of a molecule or molecular complex which comprises such binding pockets or similarly shaped homologous binding pockets.

The invention also provides methods for designing, evaluating and identifying compounds which bind to all or parts of the aforementioned binding pockets. Such compounds are potential inhibitors of IMPDH or its homologues.

The invention also provides novel classes of compounds, and pharmaceutical compositions thereof, that are useful as inhibitors of IMPDH or its homologues.

The invention also provides a method for determining at least a portion of the three-dimensional structure of molecules or molecular complexes which contain at least some structurally similar features to IMPDH. This is achieved by using at least some of the structural coordinates obtained for the Chinese hamster type II IMPDH/XMP*/MPA complex.

The invention also provides a method for crystallizing a Chinese hamster type II IMPDH/XMP*/MPA complex and related complexes.

The invention also provides a crystalline form of a Chinese hamster type II IMPDH/XMP*/MPA complex and related complexes.

BRIEF DESCRIPTION OF THE FIGURES

FIG. 1 lists the atomic structure coordinates for Chinese hamster IMPDH type II (hereafter referred to as IMPDH) in complex with XMP* and MPA as derived by X-ray diffraction from a crystal of that complex. The following abbreviations are used in FIG. 1:

"Atom type" refers to the element whose coordinates are measured. The first letter in the column defines the element.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

Figure 2A:
Figure 2B:

FIG. 2 is a stereo ribbon diagram depicting the fold and conformation of IMPDH in three-dimensions as determined by X-ray crystallography.

Figure 3:
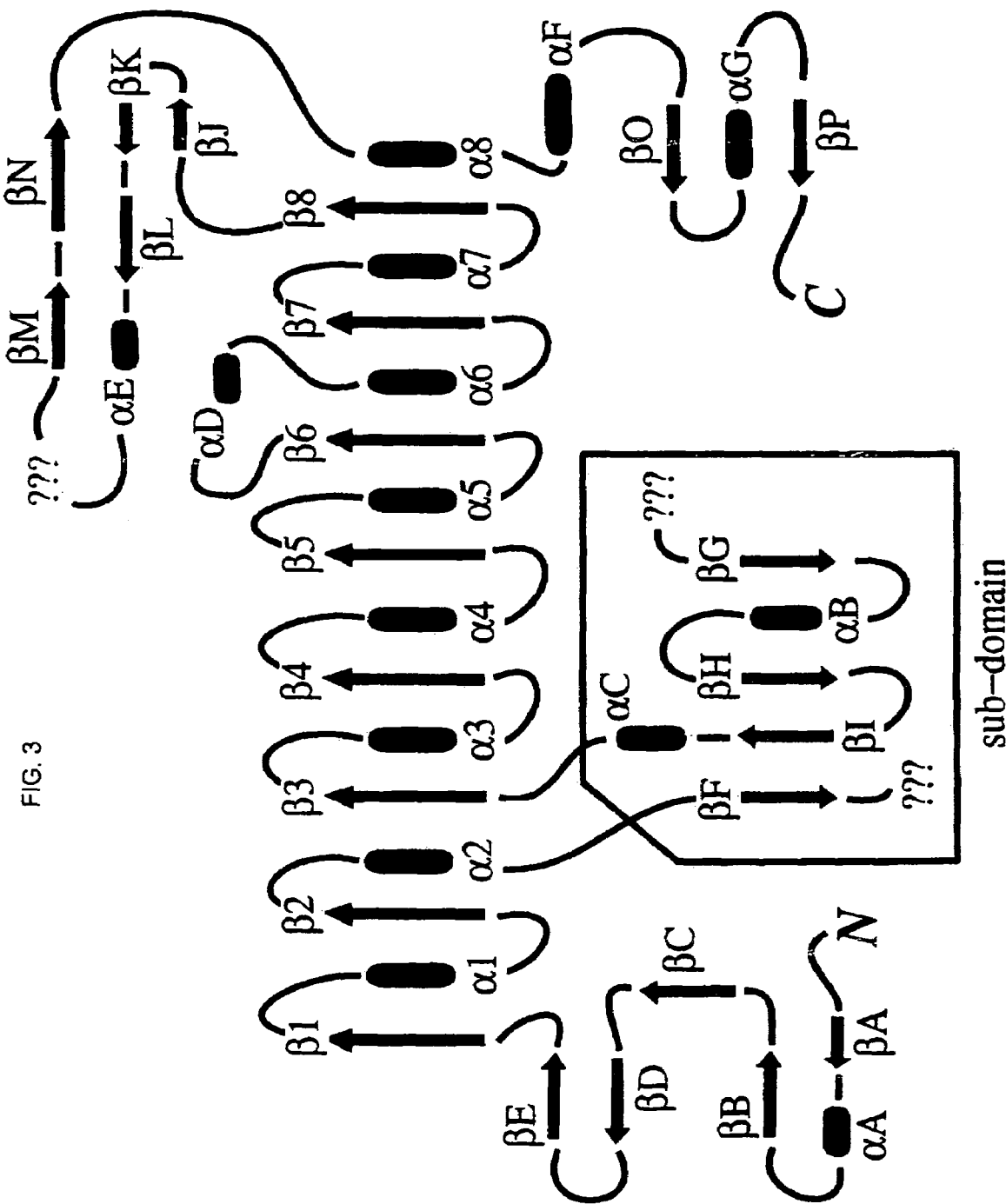

FIG. 3 is a topology diagram of the IMPDH fold.

Figure 4:
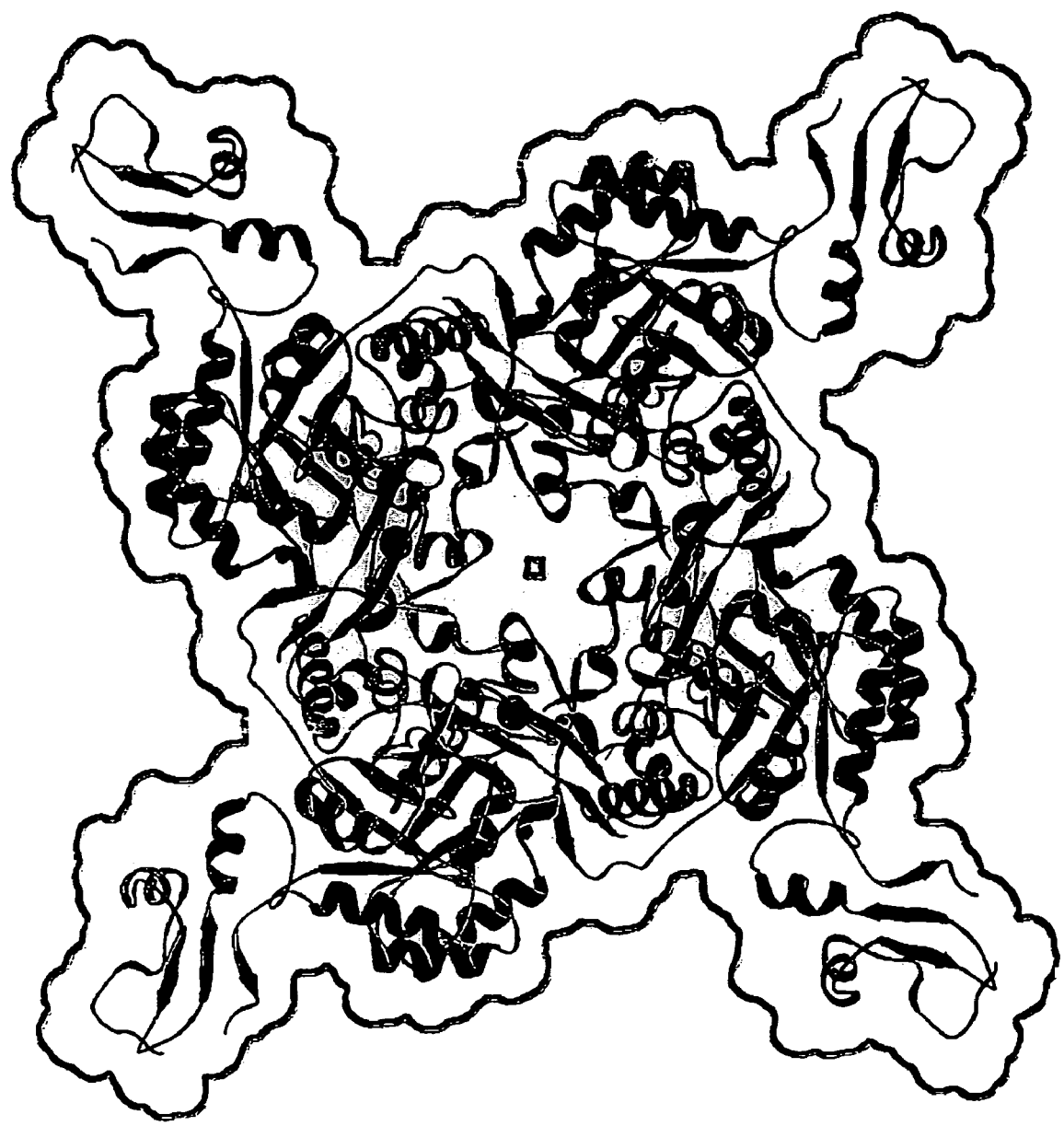

FIG. 4 is a ribbon drawing of the IMPDH tetramer.

Figure 5A:
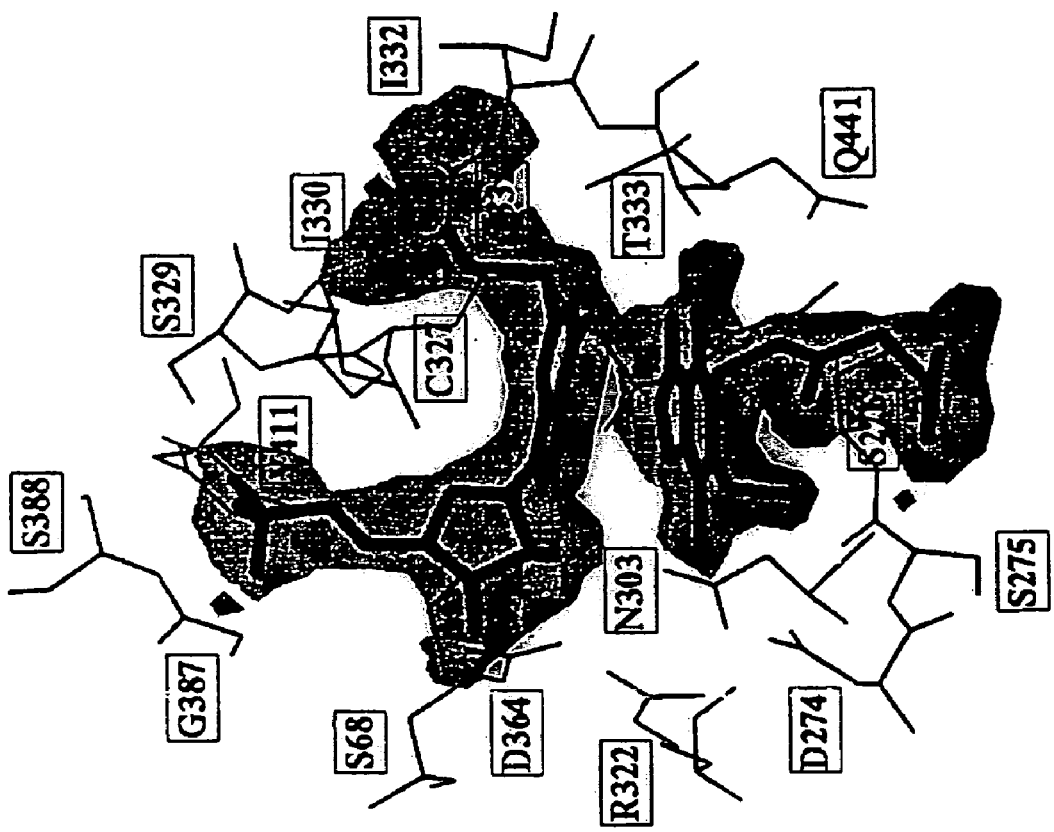
Figure 5B:
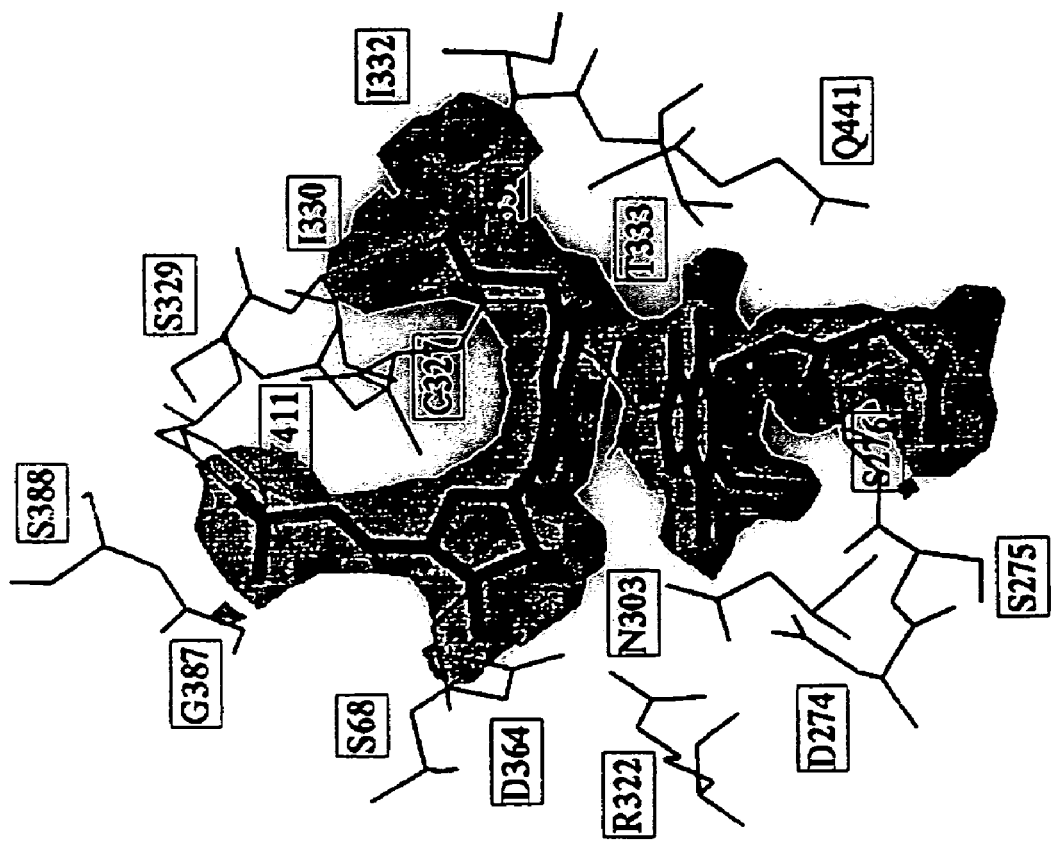

FIG. 5 depicts a stereo view of the conformation and electron densities of XMP* and MPA and some of the IMPDH active site amino acid residues surrounding these ligands.

Figure 6:
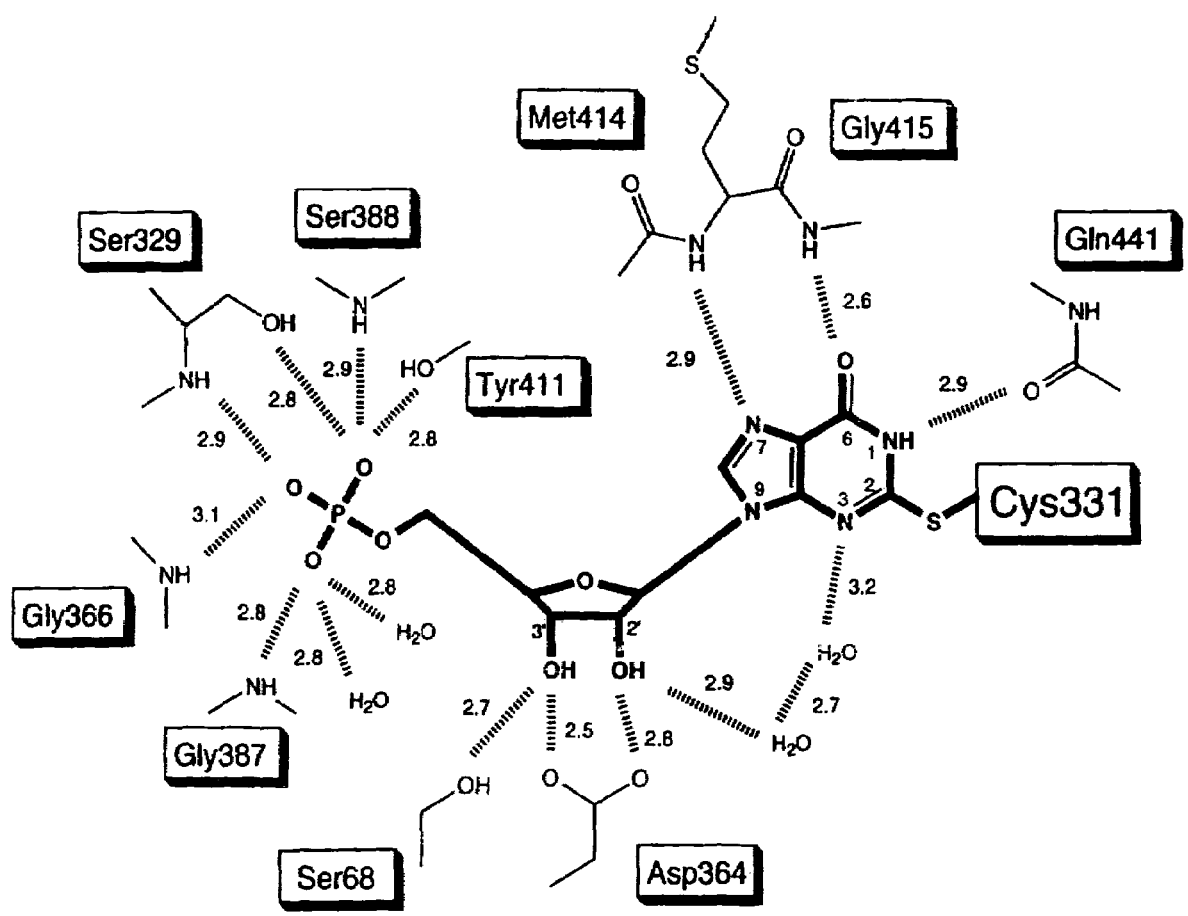

FIG. 6 schematically depicts the XMP*-IMPDH interactions.

Figure 7:
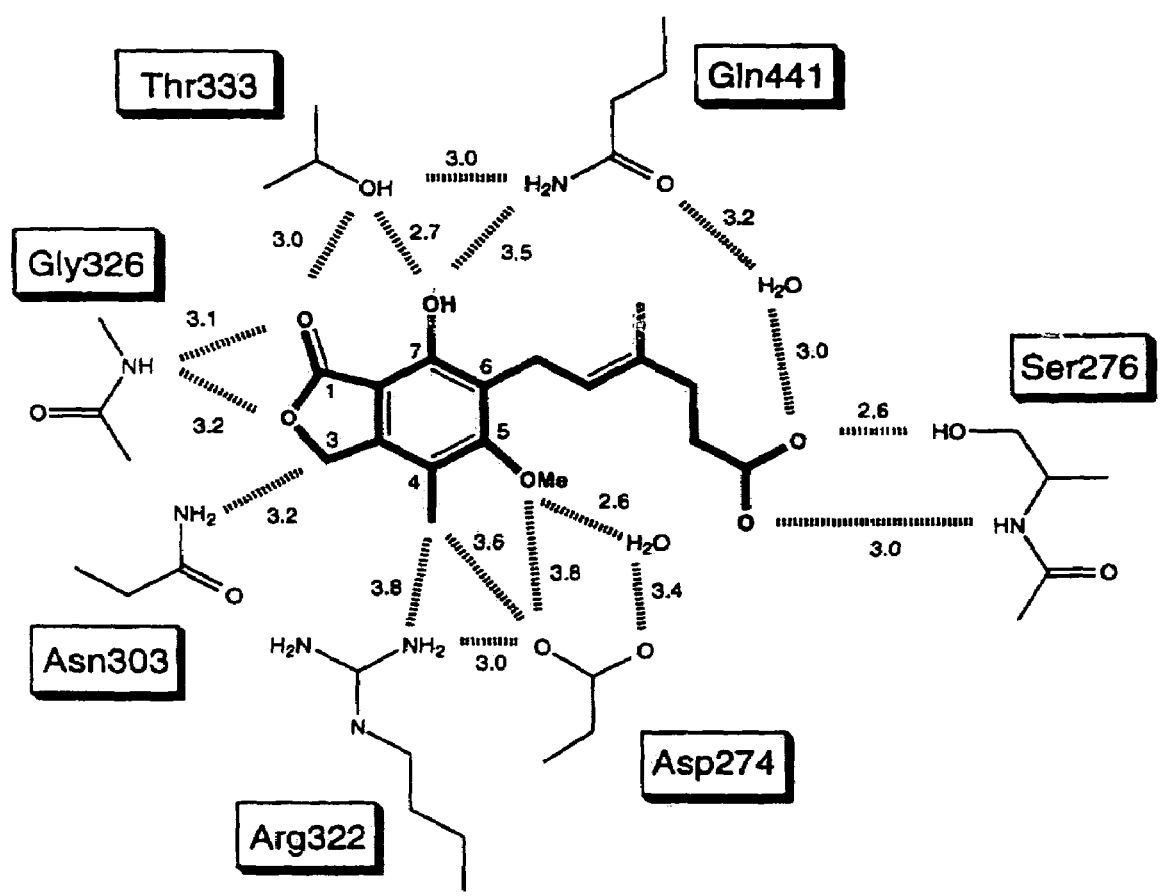

FIG. 7 schematically depicts the MPA-IMPDH interactions.

Figure 8:
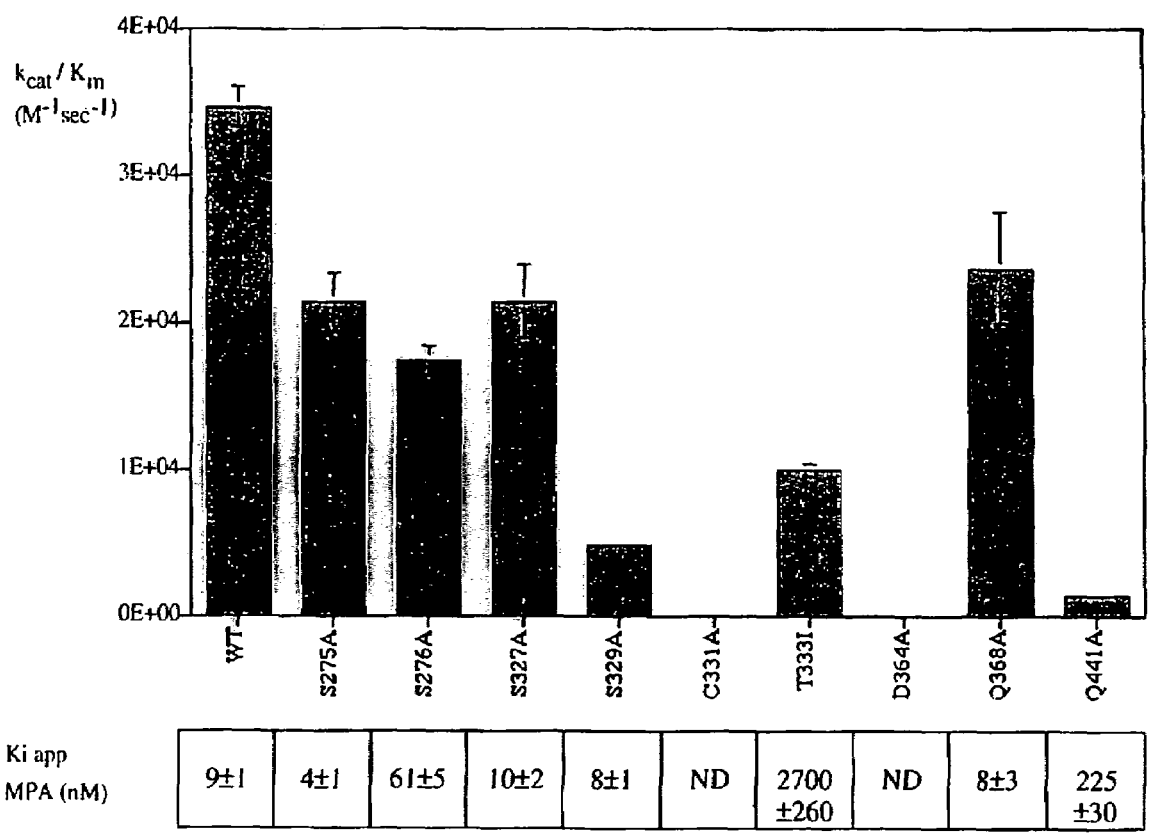

FIG. 8 shows the specific activity of IMPDH mutants for IMP substrates and the inhibition of the mutants by MPA.

Figure 9:
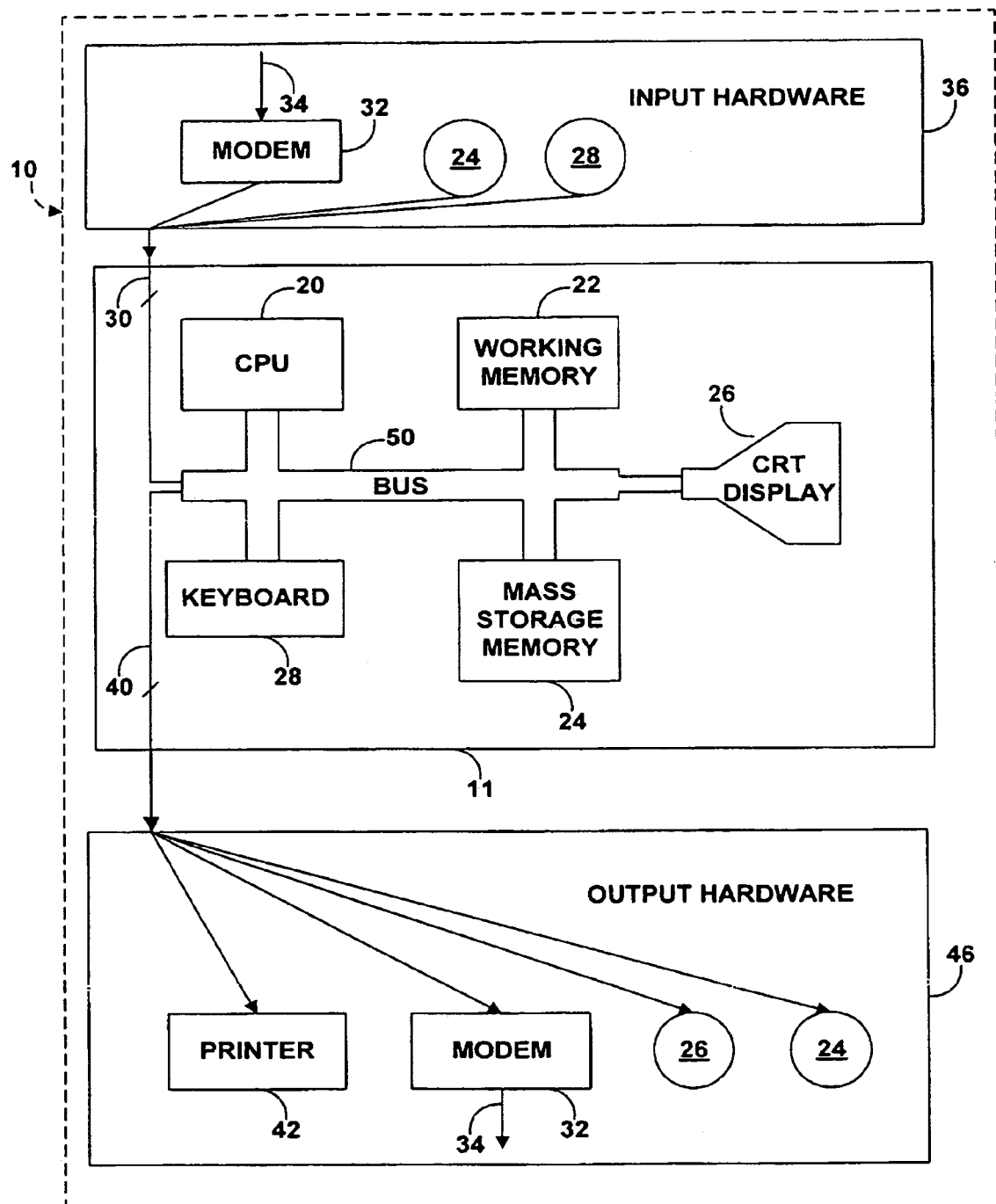
Figure 10:
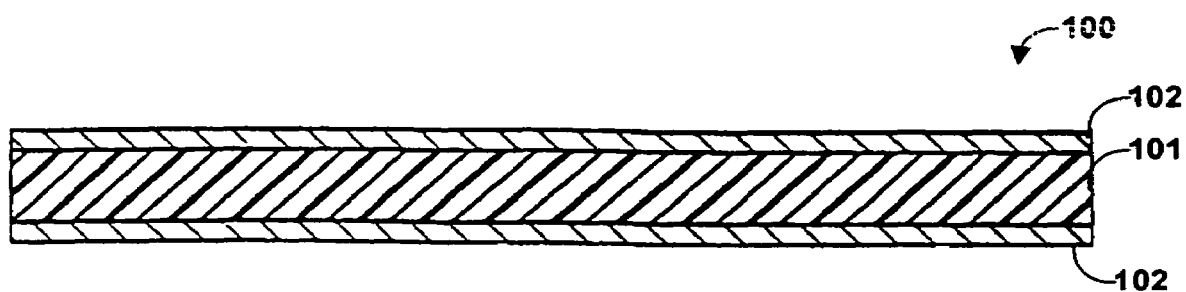
Figure 11:
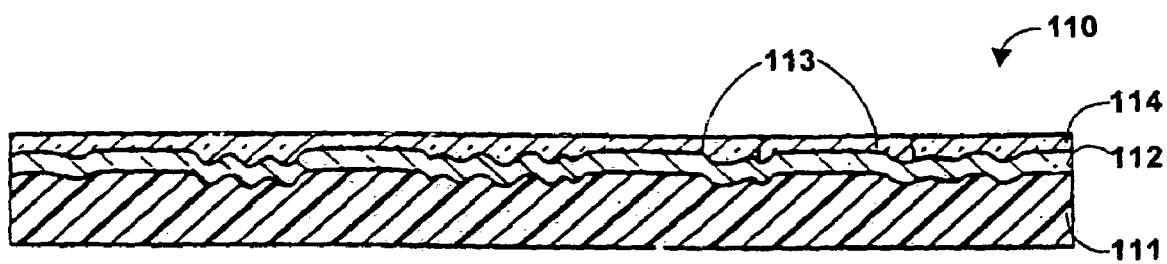

FIG. 9 shows a diagram of a system used to carry out the instructions encoded by the storage medium of FIGS. 10 and 11.

FIG. 10 shows a cross section of a magnetic storage medium.

FIG. 11 shows a cross section of a optically-readable data storage medium.

DETAILED DESCRIPTION OF THE INVENTION

The following abbreviations are used throughout the application:

A = Ala = Alanine
V = Val = Valine
L = Leu = Leucine
I = Ile = Isoleucine
P = Pro = Proline
F = Phe = Phenylalanine
W = Trp = Tryptophan
M = Met = Methionine
G = Gly = Glycine
S = Ser = Serine
T = Thr = Threonine
C = Cys = Cysteine
Y = Tyr = Tyrosine
N = Asn = Asparagine
Q = Gln = Glutamine
D = Asp = Aspartic Acid
E = Glu = Glutamic Acid
K = Lys = Lysine
R = Arg = Arginine
H = His = Histidine IMPDH=Chinese hamster type II inosine monophosphate dehydrogenase
IMP=inosine monophosphate
MPA=mycophenolic acid
NAD=nicotinamide adenine dinucleotide
KCl=potassium chloride
BME=2-mercaptoethanol
EDTA=ethylenediaminetetracetic acid
Tris=tris(hydroxymethyl)aminomethane
PEG=polyethylene glycol
LiCl=lithium chloride
MES=morpholinoethyl sulfonic acid
MeP=1-methyl-2-pyrrolidinone.
PMSF=phenylmethylsulfonyl fluoride
XMP*=a form of IMP in which the 2-position hydrogen has been replaced with a covalent bond to Cys 331 of IMPDH.
IMPDH/IMP/MPA=IMPDH in complex with IMP and MPA
IMPDH/XMP*/MPA=IMPDH in complex with XMP* and MPA Additional definitions are set forth in the specification where necessary.

In order that the invention described herein may be more fully understood, the following detailed description is set forth.

Applicants have provided crystals comprising IMPDH/XMP*/MPA, which are suitable for X-ray crystallographic analysis. The IMPDH/XMP*/MPA complex is derived from an IMPDH/IMP complex in which a covalent bond has formed between the C2 carbon of IMP and the sulfur atom of Cys 331 (FIGS. 5-7), yielding an oxidized IMP thioimidate intermediate (XMP*) which is trapped by MPA.

Applicants have solved the three-dimensional structure of the IMPDH/XMP*/MPA complex using high resolution X-ray crystallography. Thus, in one embodiment of this invention is provided an IMPDH/XMP*/MPA crystal.

Preferably, the crystal has tetragonal space group P4. More preferably, the crystal comprises rectangular shaped unit cells, each unit cell having the dimensions a=b=110.6±5 Å, and c=111.0±5 Å. Most preferably, the crystallized enzyme is a tetramer.

Importantly, applicants' invention has provided, for the first time, information about the shape and structure of the XMP* and MPA active site binding pocketts of IMPDH.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations will help lead to the design of drugs having more favorable associations with their target receptor or enzyme, and thus, improved biological effects. Therefore, this information is valuable in designing potential inhibitors of IMPDH-like binding pockets.

The term "binding pocket", as used herein, refers to a region of a molecule or molecular complex, that, as a result of its shape, favorably associates with another chemical entity or compound.

The term "IMPDH-like binding pocket" refers to a portion of a molecule or molecular complex whose shape is sufficiently similar to all or any parts of the XMP* and MPA active site binding pockets of IMPDH as to bind common ligands. This commonality of shape is defined by a root mean square deviation from the structure coordinates of the backbone atoms of the amino acids that make up the binding pockets in IMPDH (as set forth in FIG. 1) of not more than 1.5 Å. How this calculation is obtained is described below.

The "active site binding pockets" or "active site" of IMPDH refers to the area on the IMPDH enzyme surface where conversion of IMP to XMP occurs, and where MPA exerts its inhibitory effect. In resolving the crystal structure of Chinese hamster IMPDH type II, applicants have determined that IMPDH amino acids 67, 68, 69, 70, 73, 93, 273, 274, 275, 276, 277, 303, 322, 323, 324, 325, 326, 327, 328, 329, 330, 331, 332, 333, 334, 335, 337, 339, 340, 364, 365, 366, 367, 368, 385, 386, 387, 388, 389, 391, 411, 412, 413, 414, 415, 416, 419, 420, 439, 440, 441, 442, 443, 469, 470, 500, 501, 502, 503, 504, 505, and 506, are situated close enough to either XMP* or MPA (within 7 Å) to interact with these ligands. It will be readily apparent to those of skill in the art that the numbering of amino acids in other isoforms of IMPDH may be different than that isolated from Chinese hamster.

Each of those amino acids is defined by a set of structure coordinates as set forth in FIG. 1. The term "structure coordinates" refers to Cartesian coordinates derived from mathematical equations related to the patterns obtained on diffraction of a monochromatic beam of X-rays by the atoms (scattering centers) of an IMPDH complex in crystal form. The diffraction data are used to calculate an electron density map of the repeating unit of the crystal. The electron density maps are then used to establish the positions of the individual atoms of the IMPDH enzyme or enzyme complex.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The term "associating with" refers to a condition of proximity between a chemical entity or compound, or portions thereof, and an IMPDH molecule or portions thereof. The association may be non-covalent—wherein the juxtaposition is energetically favored by hydrogen bonding or van der Waals or electrostatic interactions—or it may be covalent.

The variations in coordinates discussed above may be generated because of mathematical manipulations of the IMPDH/XMP*/MPA structure coordinates. For example, the structure coordinates set forth in FIG. 1 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same. Thus, for example, a ligand that bound to the active site binding pocket of IMPDH would also be expected to bind to another binding pocket whose structure coordinates defined a shape that fell within the acceptable error. Such modified complexes or the binding pocket(s) thereof are also within the scope of this invention.

Various computational analyses are therefore necessary to determine whether a molecule or the binding pocket portion thereof is sufficiently similar to all or parts of the IMPDH binding pockets described above. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) for all conserved residues between the two structures being compared. We will also consider only rigid fitting operations.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or binding pocket thereof that has a root mean square deviation of conserved residue backbone atoms (N, Cα, C, O) of less than 1.5 Å when superimposed on the relevant backbone atoms described by structure coordinates listed in FIG. 1 are considered identical. More preferably, the root mean square deviation is less than 1.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of IMPDH or a binding pocket portion thereof, as defined by the structure coordinates of IMPDH described herein.

Therefore, according to one embodiment, the present invention provides a molecule or molecular complex comprising all or any parts of the binding pocket defined by structure coordinates of IMPDH amino acids situated within about 7 Å of MPA in the crystal, i.e., amino acids 68, 69, 93, 273, 274, 275, 276, 277, 303, 322, 324, 325, 326, 327, 328, 330, 331, 332, 333, 334, 337, 339, 340, 364, 413, 414, 415, 416, 420, 439, 440, 441, 442, 469, and 470 according to FIG. 1, or a homologue of said molecule or molecular complex, wherein said homologue comprises a binding pocket that has a root mean square deviation from the backbone atoms of said amino acids of not more than 1.5 Å.

Preferably, the binding pocket is defined by structure coordinates of IMPDH amino acids situated within about 5 Å of MPA in the crystal, i.e., amino acids 274, 275, 276, 277, 303, 322, 324, 325, 326, 331, 333, 414, 415, and 441 according to FIG. 1, or a homologue of said molecule or molecular complex, wherein said homologue comprises a binding pocket that has a root mean square deviation from the backbone atoms of said amino acids of not more than 1.5 Å.

More preferably, the binding pocket is defined by structure coordinates of IMPDH amino acids situated within about 3.5 Å of MPA in the crystal, i.e., amino acids 275, 276, 303, 325, 326, 331, 333 and 441 according to FIG. 1, or a homologue of said molecule or molecular complex, wherein said homologue comprises a binding pocket that has a root mean square deviation from the backbone atoms of said amino acids of not more than 1.5 Å.

According to another embodiment, the present invention provides a molecule or molecular complex comprising all or any parts of the binding pocket defined by structure coordinates of IMPDH amino acids situated within about 7 Å of XMP* in the crystal, i.e., amino acids 67, 68, 69, 70, 73, 274, 275, 276, 303, 322, 323, 324, 325, 326, 327, 328, 329, 330, 331, 332, 333, 334, 335, 364, 365, 366, 367, 368, 385, 386, 387, 388, 389, 391, 411, 412, 413, 414, 415, 416, 419, 440, 441, 442, 443, 500, 501, 502, 503, 504, 505, and 506 according to FIG. 1, or a homologue of said molecule or molecular complex, wherein said homologue comprises a binding pocket that has a root mean square deviation from the backbone atoms of said amino acids of not more than 1.5 Å.

Preferably, the binding pocket is defined by structure coordinates of IMPDH amino acids situated within about 5 Å of XMP* in the crystal, i.e., amino acids 68, 69, 70, 303, 322, 326, 327, 328, 329, 330, 331, 332, 333, 335, 364, 365, 366, 367, 385, 386, 387, 388, 411, 413, 414, 415, 416, 419, 441, 442, 443, 501, 502, 503, and 504 according to FIG. 1, or a homologue of said molecule or molecular complex, wherein said homologue comprises a binding pocket that has a root mean square deviation from the backbone atoms of said amino acids of not more than 1.5 Å.

More preferably, the binding pocket is defined by structure coordinates of IMPDH amino acids situated within about 3.5 Å of XMP* in the crystal, i.e., amino acids 68, 70, 322, 328, 329, 331, 332, 335, 364, 366, 387, 388, 411, 413, 414, 415, 441, 442, 501, and 502 according to FIG. 1, or a homologue of said molecule or molecular complex, wherein said homologue comprises a binding pocket that has a root mean square deviation from the backbone atoms of said amino acids of not more than 1.5 Å.

According to another embodiment, the present invention provides a molecule or molecular complex comprising all or any parts of the binding pocket defined by structure coordinates of IMPDH amino acids situated within about 7 Å of either MPA or XMP* in the crystal, i.e., amino acids 67, 68, 69, 70, 73, 93, 273, 274, 275, 276, 277, 303, 322, 323, 324, 325, 326, 327, 328, 329, 330, 331, 332, 333, 334, 335, 337, 339, 340, 364, 365, 366, 367, 368, 385, 386, 387, 388, 389, 391, 411, 412, 413, 414, 415, 416, 419, 420, 439, 440, 441, 442, 443, 469, 470, 500, 501, 502, 503, 504, 505, and 506, according to FIG. 1, or a homologue of said molecule or molecular complex comprising a binding pocket or pockets that has a root mean square deviation from the backbone atoms of said amino acids of not more than 1.5 Å.

Preferably, the binding pocket that is defined by structure coordinates of those IMPDH amino acids situated within about 5 Å of either MPA or XMP* in the crystal, i.e., amino acids 68, 69, 70, 274, 275, 276, 277, 303, 322, 324, 325, 326, 327, 328, 329, 330, 331, 332, 333, 335, 364, 365, 366, 367, 385, 386, 387, 388, 411, 413, 414, 415, 416, 441, 442, 443, 501, 502, 503, and 504 according to FIG. 1, or a homologue of said molecule or molecular complex, wherein said homologue comprises a binding pocket that has a root mean square deviation from the backbone atoms of those amino acids of not more than 1.5 Å.

More preferably, the binding pocket is defined by structure coordinates of IMPDH amino acids situated within about 3.5 Å of MPA or XMP* in the crystal, i.e., amino acids 68, 70, 275, 276, 303, 322, 325, 326, 328, 329, 331, 332, 333, 335, 364, 366, 387, 388, 411, 413, 414, 415, 441, 442, 501, and 502 according to FIG. 1 +/− a root mean square deviation from the backbone atoms of said amino acids of not more than 1.5 Å.

Even more preferred are molecules or molecular complexes that are defined by the entire set of structure coordinates in FIG. 1 +/− a root mean square deviation from the conserved backbone atoms of those amino acids of not more than 1.5 Å. An alternative more preferred embodiment of this invention is a molecular complex that comprises amino acids 1-514 of IMPDH, XMP*, and MPA.

In order to use the structure coordinates generated for the IMPDH/XMP*/MPA complex or one of its binding pockets or homologues thereof, it is sometimes necessary to convert them into a three-dimensional shape. This is achieved through the use of commercially available software that is capable of generating three-dimensional graphical representations of molecules or portions thereof from a set of structure coordinates.

Therefore, according to another embodiment of this invention is provided a machine-readable storage medium comprising a data storage material encoded with machine readable data which, when using a machine programmed with instructions for using said data, is capable of displaying a graphical three-dimensional representation of any of the molecule or molecular complexes of this invention that have been described above.

According to another embodiment, the present invention provides a machine-readable data storage medium, comprising a data storage material encoded with machine readable data which, when using a machine programmed with instructions for using said data, is capable of displaying a graphical three-dimensional representation of a molecule or molecular complex comprising all or any parts of a binding pocket defined by structure coordinates of IMPDH amino acids situated within about 7 Å of MPA in the crystal, i.e., amino acids 68, 69, 93, 273, 274, 275, 276, 277, 303, 322, 324, 325, 326, 327, 328, 330, 331, 332, 333, 334, 337, 339, 340, 364, 413, 414, 415, 416, 420, 439, 440, 441, 442, 469, and 470 according to FIG. 1, or a homologue of said molecule or molecular complex, wherein said homologue comprises a binding pocket that has a root mean square deviation from the backbone atoms of said amino acids of not more than 1.5 Å.

Preferably, the binding pocket defined by structure coordinates of IMPDH amino acids situated within about 5 Å of MPA in the crystal, i.e., amino acids 274, 275, 276, 277, 303, 322, 324, 325, 326, 331, 333, 414, 415, and 441 according to FIG. 1, or a homologue of said molecule or molecular complex, wherein said homologue comprises a binding pocket that has a root mean square deviation from the backbone atoms of said amino acids of not more than 1.5 Å.

More preferably, the binding pocket is defined by structure coordinates of IMPDH amino acids situated within about 3.5 Å of MPA in the crystal, i.e., amino acids 275, 276, 303, 325, 326, 331, 333 and 441 according to FIG. 1, or a homologue of said molecule or molecular complex, wherein said homologue comprises a binding pocket that has a root mean square deviation from the backbone atoms of said amino acids of not more than 1.5 Å.

According to another embodiment, the present invention provides a machine-readable data storage medium, comprising a data storage material encoded with machine readable data which, when using a machine programmed with instructions for using said data, is capable of displaying a graphical three-dimensional representation of a molecule or molecular complex comprising all or ally parts of a binding pocket defined by structure coordinates of IMPDH amino acids situated within about 7 Å of XPM* in the crystal, i.e., amino acids 67, 68, 69, 70, 73, 274, 275, 276, 303, 322, 323, 324, 325, 326, 327, 328, 329, 330, 331, 332, 333, 334, 335, 364, 365, 366, 367, 368, 385, 386, 387, 388, 389, 391, 411, 412, 413, 414, 415, 416, 419, 440, 441, 442, 443, 500, 501, 502, 503, 504, 505, and 506 according to FIG. 1, or a homologue of said molecule or molecular complex, wherein said homologue comprises a binding pocket that has a root mean square deviation from the backbone atoms of said amino acids of not more than 1.5 Å.

Preferably, the binding pocket is defined by structure coordinates of IMPDH amino acids situated within about 5 Å of XMP* in the crystal, i.e., amino acids 68, 69, 70, 303, 322, 326, 327, 328, 329, 330, 331, 332, 333, 335, 364, 365, 366, 367, 385, 386, 387, 388, 411, 413, 414, 415, 416, 419, 441, 442, 443, 501, 502, 503, and 504 according to FIG. 1, or a homologue of said molecule or molecular complex, wherein said homologue comprises a binding pocket that has a root mean square deviation from the backbone atoms of said amino acids of not more than 1.5 Å.

More preferably, the binding pocket is defined by structure coordinates of IMPDH amino acids situated within about 3.5 Å of XMP* in the crystal, i.e., amino acids 68, 70, 322, 328, 329, 331, 332, 335, 364, 366, 387, 388, 411, 413, 414, 415, 441, 442, 501, and 502 according to FIG. 1, or a homologue of said molecule or molecular complex, wherein said homologue comprises a binding pocket that has a root mean square deviation from the backbone atoms of said amino acids of not more than 1.5 Å.

According to another embodiment, the present invention provides a machine-readable storage medium is capable of displaying a graphical three-dimensional representation of a molecule or molecular complex comprising all or any parts of a binding pocket defined by structure coordinates of IMPDH amino acids situated with in about 7 Å of MPA or XMP* in the crystal, i.e., amino acids 67, 68, 69, 70, 73, 93, 273, 274, 275, 276, 277, 303, 322, 323, 324, 325, 326, 327, 328, 329, 330, 331, 332, 333, 334, 335, 337, 339, 340, 364, 365, 366, 367, 368, 385, 386, 387, 388, 389, 391, 411, 412, 413, 414, 415, 416, 419, 420, 439, 440, 441, 442, 443, 469, 470, 500, 501, 502, 503, 504, 505, and 506 according to FIG. 1, or a homologue of said molecule or molecular complex, wherein said homologue comprises a binding pocket that has a root mean square deviation from the backbone atoms of said amino acids of not more than 1.5 Å.

Preferably, the binding pocket is defined by structure coordinates of IMPDH amino acids situated within about 5 Å of MPA or XMP* in the crystal, i.e., amino acids 68, 69, 70, 274, 275, 276, 277, 303, 322, 324, 325, 326, 327, 328, 329, 330, 331, 332, 333, 335, 364, 365, 366, 367, 385, 386, 387, 388, 411, 413, 414, 415, 416, 441, 442, 443, 501, 502, 503, and 504 according to FIG. 1 +/− a root mean square deviation from the backbone atoms of said amino acids of not more than 1.5 Å.

More preferably, the binding pocket is defined by structure coordinates of IMPDH amino acids situated within about 3.5 Å of MPA or XMP* in the crystal, i.e., amino acids 68, 70, 275, 276, 303, 322, 325, 326, 328, 329, 331, 332, 333, 335, 364, 366, 387, 388, 411, 413, 414, 415, 441, 442, 501, and 502 according to FIG. 1 +/− a root mean square deviation from the backbone atoms of said amino acids of not more than 1.5 Å.

Even more preferred is a machine-readable data storage medium that is capable of displaying a graphical three-dimensional representation of a molecule or molecular complex that is defined by the structure coordinates of all of the amino acids in FIG. 1 +/− a root mean square deviation from the backbone atoms of those amino acids of not more than 1.5 Å.

According to an alternate embodiment, the machine-readable data storage medium comprises a data storage material encoded with a first set of machine readable data which comprises the Fourier transform of the structure coordinates set forth in FIG. 1, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

FIG. 9 demonstrates one version of these embodiments. System 10 includes a computer 11 comprising a central processing unit ("CPU") 20, a working memory 22 which may be, e.g, RAM (random-access memory) or "core"memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 10 shows a cross section of a magnetic data storage medium 100 which can be encoded with a machine-readable data that can be carried out by a system such as system 10 of FIG. 9. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 9.

FIG. 11 shows a cross section of an optically-readable data storage medium 110 which also can be encoded with such a machine-readable data, or set of instructions, which can be carried out by a system such as system 10 of FIG. 9. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Thus, in accordance with the present invention, data capable of displaying the three dimensional structure of IMPDH and portions thereof and their structurally similar homologues is stored in a machine-readable storage medium, which is capable of displaying a graphical three-dimensional representation of the structure. Such data may be used for a variety of purposes, such as drug discovery.

For example, the structure encoded by the data may be computationally evaluated for its ability to associate with chemical entities. Chemical entities that associate with IMPDH may inhibit IMPDH, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with any of the molecules or molecular complexes set forth above. This method comprises the steps of: a) employing computational means to perform a fitting operation between the chemical entity and a binding pocket of the molecule or molecular complex; and b) analyzing the results of said fitting operation to quantify the association between the chemical entity and the binding pocket. The term "chemical entity", as used herein, refers to chemical compounds, complexes of at least two chemical compounds, and fragments of such compounds or complexes.

For the first time, the present invention permits the use of molecular design techniques to identify, select and design chemical entities, including inhibitory compounds, capable of binding to IMPDH-like binding pockets.

Applicants' elucidation of the XMP* and MPA binding sites on IMPDH provides the necessary information for designing new chemical entities and compounds that may interact with either or both IMPDH-like binding pockets, in whole or in part. This elucidation also enables the evaluation of structure-activity data for analogs of MPA or other compounds which bind to IMPDH-like binding pockets.

Throughout this section, discussions about the ability of an entity to bind to, associate with or inhibit a IMPDH-like binding pocket refers to features of the entity alone. Assays to determine if a compound binds to IMPDH are well known in the art [B. Magasanik et al., *J. Biol. Chem.*, 226, p. 339 (1957)].

The design of compounds that bind to or inhibit IMPDH-like binding pockets according to this invention generally involves consideration of two factors. First, the entity must be capable of physically and structurally associating with parts or all of the IMPDH-like binding pockets. Non-covalent molecular interactions important in this association include hydrogen bonding, van der Waals interactions, hydrophobic interactions and electrostatic interactions.

Second, the entity must be able to assume a conformation that allows it to associate with the IMPDH-like binding pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the IMPDH-like binding pocket or homologues thereof.

The potential inhibitory or binding effect of a chemical entity on a IMPDH-like binding pocket may be analyzed prior to its actual synthesis and testing by the use of computer modeling techniques. If the theoretical structure of the given entity suggests insufficient interaction and association between it and the IMPDH-like binding pocket, testing of the entity is obviated. However, if computer modeling indicates a strong interaction, the molecule may then be synthesized and tested for its ability to bind to a IMPDH-like binding pocket. This may be achieved by testing the ability of the molecule to inhibit IMPDH using the assays described in Examples 7 and 8. In this manner, synthesis of inoperative compounds may be avoided.

A potential inhibitor of a IMPDH-like binding pocket may be computationally evaluated by means of a series of steps in which chemical entities or fragments are screened and selected for their ability to associate with the IMPDH-like binding pockets.

One skilled in the art may use one of several methods to screen chemical entities or fragments for their ability to associate with a IMPDH-like binding pocket. This process may begin by visual inspection of, for example, a IMPDH-like binding pocket on the computer screen based on the IMPDH structure coordinates in FIG. 1 or other coordinates which define a similar shape generated from the machine-readable storage medium. Selected fragments or chemical entities may then be positioned in a variety of orientations, or docked, within that binding pocket as defined supra. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:

1. GRID (P. J. Goodford, "A Computational Procedure for Determining Energetically Favorable Binding Sites on Biologically Important Macromolecules", *J. Med. Chem.*, 28, pp. 849-857 (1985)). GRID is available from Oxford University, Oxford, UK.

2. MCSS (A. Miranker et al., "Functionality Maps of Binding Sites: A Multiple Copy Simultaneous Search Method." *Proteins: Structure, Function and Genetics*, 11, pp. 29-34 (1991)). MCSS is available from Molecular Simulations, San Diego, Calif.

3. AUTODOCK (D. S. Goodsell et al., "Automated Docking of Substrates to Proteins by Simulated Annealing", *Proteins: Structure, Function, and Genetics*, 8, pp. 195-202 (1990)). AUTODOCK is available from Scripps Research Institute, La Jolla, Calif.

4. DOCK (I. D. Kuntz et al., "A Geometric Approach to Macromolecule-Ligand Interactions", *J. Mol. Biol.*, 161, pp. 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of IMPDH. This would be followed by manual model building using software such as Quanta or Sybyl [Tripos Associates, St. Louis, Mo.]

Useful programs to aid one of skill in the art in connecting the individual chemical entities or fragments include:

1. CAVEAT (P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc., 78, pp. 182-196 (1989); G. Lauri and P. A. Bartlett, "CAVEAT: a Program to Facilitate the Design of Organic Molecules", *J. Comput. Aided Mol. Des.*, 8, pp. 51-66 (1994)). CAVEAT is available from the University of California, Berkeley, Calif.

2. 3D Database systems such as ISIS (MDL Information Systems, San Leandro, Calif.) This area is reviewed in Y. C. Martin, "3D Database Searching in Drug Design", *J. Med. Chem.*, 35, pp. 2145-2154 (1992).

3. HOOK (M. B. Eisen et al, "HOOK: A Program for Finding Novel Molecular Architectures that Satisfy the Chemical and Steric Requirements of a Macromolecule Binding Site", *Proteins: Struct., Funct., Genet.,* 19, pp. 199-221 (1994). HOOK is available from Molecular Simulations, San Diego, Calif.

Instead of proceeding to build an inhibitor of a IMPDH-like binding pocket in a step-wise fashion one fragment or chemical entity at a time as described above, inhibitory or other IMPDH binding compounds may be designed as a whole or "de novo" using either an empty binding site or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", *J. Comp. Aid. Molec. Design,* 6, pp. 61-78 (1992)). LUDI is available from Molecular Simulations Incorporated, San Diego, Calif.
2. LEGEND (Y. Nishibata et al., *Tetrahedron,* 47, p. 8985 (1991)). LEGEND is available from Molecular Simulations Incorporated, San Diego, Calif.
3. LeapFrog (available from Tripos Associates, St. Louis, Mo.)
4. SPROUT (V. Gillet et al, "SPROUT: A Program for Structure Generation", *J. Comput. Aided Mol. Design,* 7, pp. 127-153 (1993)). SPROUT is available from the University of Leeds, UK.

Other molecular modeling techniques may also be employed in accordance with this invention (see, e.g., N. C. Cohen et al., "Molecular Modeling Software and Methods for Medicinal Chemistry, *J. Med. Chem.,* 33, pp. 883-894 (1990); see also, M. A. Navia and M. A. Murcko, "The Use of Structural Information in Drug Design", *Current Opinions in Structural Biology,* 2, pp. 202-210 (1992); L. M. Balbes et al., "A Perspective of Modern Methods in Computer-Aided Drug Design", in *Reviews in Computational Chemistry, Vol.* 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology,* 4, pp. 777-781 (1994)].

Once a compound has been designed or selected by the above methods, the efficiency with which that entity may bind to an IMPDH binding pocket may be tested and optimized by computational evaluation. For example, an effective IMPDH binding pocket inhibitor must preferably demonstrate a relatively small difference in energy between its bound and free states (i.e., a small deformation energy of binding). Thus, the most efficient IMPDH binding pocket inhibitors should preferably be designed with a deformation energy of binding of not greater than about 10 kcal/mole, more preferably, not greater than 7 kcal/mole. IMPDH binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to an IMPDH binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. © 1995); AMBER, version 4.1 (P. A. Kollman, University of California at San Francisco, © 1995); QUANTA/CHARMM (Molecular Simulations, Inc., San Diego, Calif. ©1995); Insight II/Discover (Molecular Simulations, Inc., San Diego, Calif. © 1995); DelPhi (Molecular Simulations, Inc., San Diego, Calif. © 1995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach enabled by this invention, is the computational screening of small molecule databases for chemical entities or compounds that can bind in whole, or in part, to a IMPDH binding pocket. In this screening, the quality of fit of such entities to the binding site may be judged either by shape complementarity or by estimated interaction energy [E. C. Meng et al., *J. Comp. Chem.,* 13, pp. 505-524 (1992)].

Thus, enabled by this invention are compounds that inhibit IMPDH by associating directly with the MPA binding site. In one embodiment, such compounds comprise a surrogate for the bicyclic ring portion of MPA and additional functionality which imparts affinity for IMPDH. Preferably, the compounds comprise a substantially hydrophobic core capable of making van der Waals contact with the bound XMP* intermediate and one or more of the following IMPDH residues: Asp 274, Ser 275, Ser 276, Gln 277, Asn 303, Arg 322, Gly 324, Met 325, Gly 326, Thr 333, Met 414, Gly 415 and Gln 441, and further comprise one or more atoms that are substituted via linkers onto the substantially hydrophobic core, wherein the atoms are capable of forming one or more hydrogen bonds with residues such as Asp 274, Thr 333, Gln 441, Gly 326, or nearby residues on IMPDH. Preferably, these linkers form additional van der Waals interactions with residues His 93, Gly 251, Thr 252, His 253, Asp 256, Arg 259, Leu 273, Phe 282, and Gln 283, or nearby residues. More preferably, such compounds have a strain energy of 10 kcal/mol or less. Even more preferably, these compounds contain fewer than three secondary amide bonds. Most preferably, these compounds have a molecular weight of less than 1000.

For example, according to another embodiment, these compounds are those of formula (I):

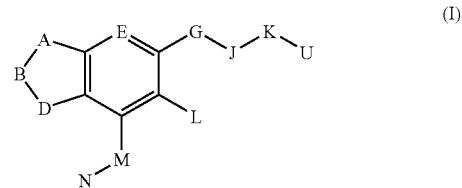

wherein:

A is —C(O)— or —S(O)$_2$—;

B is —O— or —N(R$^1$)—;

D is —CH$_2$— or —CH$_2$CH$_2$—;

E is selected from the group consisting of C(OH), C(SH), C(NH$_2$), C(NHR$^1$), C(F), N and —N(O$^-$)—;

G is a C$_{1-5}$ straight or branched alkyl group or a C$_{2-5}$ straight or branched alkenyl or alkynyl group, wherein any CH$_2$ group is optionally replaced by —O— or —N(H)—;

J is selected from the group consisting of CH$_2$, O , N, S, and a 5-6 membered monocyclic ring system, containing from 0-4 heteroatoms selected from the group consisting of —O—, —N—, and —S—, and optionally containing one or more double bonds, wherein when a heteroatom is attached to at least one —CH$_2$—, the —CH$_2$— is optionally substituted with =O;

K is a $C_{1-5}$ straight or branched alkyl group or a $C_{2-5}$ straight or branched alkenyl or alkynyl group, wherein any $CH_2$ of the alkyl, alkenyl, or alkynyl groups is optionally replaced by —O—, —N(H)—, or —S—;

L is selected from the group consisting of —$R^1$, —OH, —$OR^1$, —$NH_2$, and —N(H) ($R^1$);

M is a $C_{0-3}$ straight or branched alkyl group or a $C_{2-5}$ straight or branched alkenyl group;

N is selected from the group consisting of —OH, —$OR^1$, —$NH_2$, —N(H) ($R^1$), —$CO_2H$, —F, —Cl, —$S(O_2)NH_2$, —$S(O_2)N(H)$ ($R^1$), —$NO_2$, and —CN;

provided that when M is —$CH_2$—, then N is not —OH;

U is a substituent bound to an alkyl carbon atom of K and selected from the group consisting of —OH, —$OR^1$, —$NH_2$, —N(H) ($R^1$), —$CO_2H$, —F, —$S(O_2)NH_2$, —$SO_2N(H)$ ($R^1$), —$NO_2$, and —CN; and $R_1$ is a $C_{1-4}$ straight or branched alkyl.

In another embodiment, this invention provides compounds of formula (II):

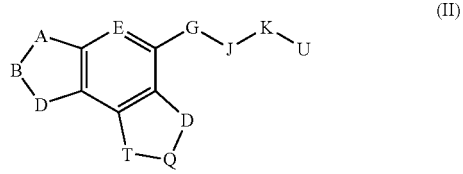

(II)

wherein,

A, B, E, G, J, K and U are as defined above in formula (I);

each D is independently selected from —$CH_2$— or —$CH_2CH_2$—;

Q is selected from the group consisting of —O—, —N(H)—, —N($R^1$)—, and —$CH_2$—; and T is selected from the group consisting of —$CH_2$—, —C(O)— and —$S(O_2)$—.

In another embodiment, this invention provides compounds of formula (III):

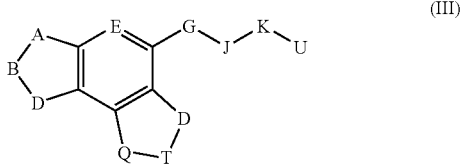

(III)

wherein:

A, B, D, E, G, J, K and U are as defined above in formula (I);

each D is as defined above in formula (II);

Q is selected from the group consisting of —O—, —N(H)—, —N($R^1$)—, and —$CH_2$—; and T is selected from the group consisting of —$CH_2$—, —C(O)—and —$S(O_2)$—.

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The term "immunosuppressant" refers to a compound or drug which possesses immune response inhibitory activity. Examples of such agents include cyclosporin A, FK506, rapamycin, leflunomide, deoxyspergualin, prednisone, azathioprine, mycophenolate mofetil, OKT3, ATAG and mizoribine.

IMPDH-mediated disease refers to any disease state in which the IMPDH enzyme plays a regulatory role in the metabolic pathway of that disease. Examples of IMPDH-mediated disease include transplant rejection and autoimmune diseases, such as rheumatoid arthritis, multiple sclerosis, juvenile diabetes, asthma, and inflammatory bowel disease, as well as cancer, viral replication diseases and vascular diseases.

Pharmaceutical compositions of this invention comprise a compound of formulae I-III or a pharmaceutically acceptable salt thereof; an additional agent selected from an immunosuppressant, an anti-cancer agent, an anti-viral agent, or an anti-vascular hyperproliferation compound; and any pharmaceutically acceptable carrier, adjuvant or vehicle. Alternate compositions of this invention comprise a compound of formulae I-III or a pharmaceutically acceptable salt thereof; and a pharmaceutically acceptable carrier, adjuvant or vehicle. Such composition may optionally comprise an additional agent selected from an immunosuppressant, an anti-cancer agent, an anti-viral agent, or an anti-vascular hyperproliferation compound.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

Dosage levels of between about 0.01 and about 100 mg/kg body weight per day, preferably between about 0.5 and about 75 mg/kg body weight per day of the IMPDH inhibitory compounds described herein are useful in a monotherapy for the prevention and treatment of IMPDH mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of an IMPDH inhibitor of formulae I-III and one or more additional therapeutic or prophylactic agents, both the IMPDH inhibitor and the additional agent should be present at dosage levels of between about 10 to 100%, and more preferably between about 10 to 80% of the dosage normally administered in a monotherapy regimen.

The structure coordinates set forth in FIG. 1 can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a molecule or molecular complex whose structure is unknown comprising the steps of:

a) crystallizing said molecule or molecular complex of unknown structure;

b) generating an X-ray diffraction pattern from said crystallized molecule or molecular complex; and c) applying at least a portion of the structure coordinates set forth in FIG. 1 to the X-ray diffraction pattern to generate a three-dimensional electron density map of the molecule or molecular complex whose structure is unknown.

By using molecular replacement, all or part of the structure coordinates of the IMPDH/XMP*/MPA complex as provided by this invention (and set forth in FIG. 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the IMPDH/XMP*/MPA complex according to FIG. 1 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55-77 (1985); M. G. Rossmann, ed., "The Molecular Replacement Method", *Int. Sci. Rev. Ser.*, No. 13, Gordon & Breach, New York (1972)].

The structure of any portion of any crystallized molecule or molecular complex that is sufficiently homologous to any portion of the IMPDH/XMP*/MPA complex can be resolved by this method.

In a preferred embodiment, the method of molecular replacement is utilized to obtain structural information about a molecule or molecular complex, wherein the complex comprises at least one IMPDH subunit or homologue.

The structure coordinates of IMPDH as provided by this invention are particularly useful in solving the structure of other crystal forms of IMPDH or IMPDH complexes.

Furthermore, the structure coordinates of IMPDH as provided by this invention are useful in solving the structure of IMPDH mutants, which may optionally be crystallized in co-complex with a chemical entity. The crystal structures of a series of such complexes may then be solved by molecular replacement and compared with that of wild-type IMPDH. Potential sites for modification within the various binding sites of the enzyme may thus be identified. This information provides an additional tool for determining the most efficient binding interactions, for example, increased hydrophobic interactions, between IMPDH and a chemical entity or compound.

The structure coordinates are also particularly useful to solve the structure of crystals of IMPDH or IMPDH homologues co-complexed with a variety of chemical entities. This approach enables the determination of the optimal sites for interaction between chemical entities, including candidate IMPDH inhibitors and IMPDH. For example, high resolution X-ray diffraction data collected from crystals exposed to different types of solvent allows the determination of where each type of solvent molecule resides. Small molecules that bind tightly to those sites can then be designed and synthesized and tested for their IMPDH inhibition activity.

All of the complexes referred to above may be studied using well-known X-ray diffraction techniques and may be refined versus 1.5-3 Å resolution X-ray data to an R value of about 0.20 or less using computer software, such as X-PLOR [Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)]. This information may thus be used to optimize known IMPDH inhibitors, and more importantly, to design new IMPDH inhibitors.

In another embodiment of this invention is provided a method for preparing a IMPDH/XMP*/MPA crystal comprising the steps of:

a. forming a complex between IMPDH and IMP;

b. adding NAD and MPA to the complex formed in step a;

c. monitoring the accumulation of the IMPDH/XMP*/MPA complex; and d. crystallizing the complex formed in step c in the presence of MeP.

In order that this invention be more fully understood, the following examples are set forth. These examples are for the purpose of illustration only and are not to be construed as limiting the scope of the invention in any way.

EXAMPLE 1

Purification of IMPDH and Preparation of an IMPDH/XMP*/MPA Complex for Crystallization Chinese hamster IMPDH type II was purified by published methods [H. J. Gilbert et. al., *Biochem. J.*, 183, pp. 481-494 (1979); and T. Ikegami et al., *Life Sci.*, 40, pp. 2277-2282 (1987)] with the following modifications: Typically 100 g of *E. coli* cell paste containing the over-expressed protein was suspended in 5 volumes of Buffer a (50 mM Tris-HCl, 300 mM KCl, 2 mM EDTA, 10 mM BME, 1.5 M urea, pH 8.0 at 4° C.). Protease inhibitors were added (0.2 mM PMSF, and 1 mg/liter each of Pepstatin, Leupeptin, and E-64) and the cells were lysed in a microfluidizer (Microfluidics Corporation) at about 4° C. Cellular debris was removed by centrifugation at 45,000×g for 40 minutes at 4° C. Crystalline ammonium sulfate was added slowly to the supernatant, while stirring at 4° C., to a final concentration of 25 g per 100 ml supernatant. The ammonium sulfate solution was allowed to stabilize for 1 hour at 4° C., whereupon the precipitated IMPDH was harvested by centrifugation, as above. The ammonium sulfate pellets were resuspended in Buffer B (50 mM Tris-HCl, 300 mM KCl, 2 mM EDTA, 10 mM BME, 10% glycerol, pH 8.0 at 4° C.) and loaded (20% at a time while the remainder was stored at −70° C.) onto a column (5×12.5 cm) of IMP-Sepharose, prepared from epoxy-activated Sepharose (Pharmacia) essentially as described by Gilbert et al. (1979). The affinity column was washed with more than 4 column volumes of Buffer B, then the enzyme was eluted from the column with the same buffer containing 10 mM IMP (pH readjusted to 8.0 at 4° C., with KOH).

At this point the protein appeared to be >95% pure, as judged by SDS PAGE, but combined size-exclusion chromatography and light-scattering analyses indicated about 30% of the protein existed as high molecular weight aggregates. The IMPDH-containing fractions were pooled and concentrated by ultra-filtration to about 5 mg/ml (50 ml), then fractionated on a Sephacryl S-300 (Pharmacia) size-exclusion column (5×90 cm, eluting at 3 ml/min in Buffer B, at 4° C.). This step removed the aggregated protein and virtually all of the IMP used to elute the enzyme from the affinity matrix. Aggregated IMPDH did not re-appear upon re-concentration, but some purified samples still contained small quantities of IMP. The residual IMP was removed by exhaustive dialysis, when necessary. SDS PAGE and N-terminal sequence analyses indicated that the IMPDH samples were greater than 99% pure at this point.

Samples for crystallization studies were made as follows. One hundred milligrams of purified apo-IMPDH (2-4 mg/ml) was placed in a stirred ultrafiltration cell with a 30 kDa MW cut-off membrane. A stock of 100 mM MPA in MeP was added to a final concentration of 2 mM MPA. IMP and NAD were then added in a 2-fold molar excess over IMPDH protomers and the solutions were allowed to equilibrate at room temperature for 30 minutes. Samples were concentrated and exchanged into fresh Buffer B containing 2 mM MPA, until no IMP, NAD or NADH was detectable by high-performance capillary electrophoresis (HPCE). The fully inhibited samples were concentrated to 20-60 mg/ml, harvested, and centrifuged at 45,000×g for 20 minutes at 4° C. 100 ml aliquots were stored at −70° C. until use in crystallization experiments.

EXAMPLE 2

Crystallization of the IMPDH/XMP*/MPA Complex

Crystals of inhibited IMPDH were grown by vapor diffusion when protein at 20 mg/ml in Buffer B was mixed with reservoir (10% polyethylene glycol 6000, 1 M LiCl, 100 mM morpholino ethyl sulfonic (MES) acid, 5.4% MeP (v/v), 36 mM BME, pH 5.88) at a 4:2 ratio, and allowed to stand over the reservoir solution at 22° C. Crystals grew within 72 hours to form blocks of approximate dimension 0.15 mm×0.15 mm×0.5 mm. The crystals belong to space group P4, with unit cell dimensions a=b=110.6 Å, c=111.0 Å, and angles $\alpha=\beta=\gamma=90°$. There are two IMDPH/XMP*/MPA complexes per asymmetric unit of the crystal. Analysis of the dissolved crystals showed identical protein composition as the original complex solution.

The addition of MeP was critical in obtaining well-diffracting crystals, and was subsequently identified in electron density maps positioned between two phenylalanine residues in the crystal. It was also critical to use a Chinese hamster form of IMPDH; human type II IMPDH did not yield well-diffracting crystals under conditions which did yield well-diffracting crystals of Chinese hamster type II IMPDH.

Those of skill in the art will appreciate that the aforesaid crystallization conditions can be varied and still produce crystals of IMPDH or IMPDH complexes or homologues suitable for structural analysis. Such variations may be used alone or in combination, and include final protein complex concentrations between 1 mg/ml and 100 mg/ml; any combination of IMPDH/XMP*/MPA complex to precipitant ratios; pH buffer concentrations between 1 mM and 500 mM; any concentration of BME or other sulphur reducing agent between 0 mM and 100 mM; pH ranges between 4.0 and 9.0; polyethylene glycol (PEG) concentrations between 1% and 25% (g/100 ml); PEG weights between 2000 and 20000; LiCl or other salt concentration between 50 and 2000 mM; any concentration or type of detergent; any temperature between −5° C. and 30° C.; and crystallization of IMPDH/XMP*/MPA complexes by batch, liquid bridge, or dialysis method using these conditions or variations thereof.

EXAMPLE 3

Crystal Structure Determination of the IMPDH/XMP*/MPA Complex

Crystals were equilibrated with 10% PEG 6000, 1M LiCl, 100 mM MES, 9% glycerol, 3% MeP, 2mM MPA, pH 5.88 prior to heavy atom derivitization or native data collection, and then transferred to a 15% glycerol version of this stock just before X-ray data collection at −165° C. Native and derivative data sets were collected on frozen crystals by oscillation photography on a Rigaku R-AXIS IIC phosphor imaging area detector mounted on a Rigaku RU200 rotating anode generator (Molecular Structure Corp., Houston, Tex.), operating at 50 kV and 100 mA. Measured intensities were integrated, scaled, and merged using software supplied by the manufacturer (Molecular Structure Corp., Houston, Tex.). Thirty-five heavy atom reagents were tested, and $K_2WO_4$, PCMBS, PbCl, $EuCl_3$, tet-HgCl furan, bis-Hg bithiophene, and bis-Hg benzofuran, were identified as compounds that would bind to IMPDH and be useful to determine initial phase angles for the calculation of electron density maps of the IMPDH/XMP*/MPA complex.

Heavy atom positions were located and confirmed with Patterson or difference Fourier syntheses using PHASES [W. Furey et al., *S. Am. Cryst. Assoc. Mtg. Summ.* 18, p. 73 (1990)]. Heavy atom parameters were refined with PHASES, and used to compute multiple isomorphous replacement (MIR) phases. The mean figure of merit was 0.65 to 4.0 Å. MIR phases were improved and extended by cycles of solvent flattening (B. C. Wang, *Meth. Enzym.* 115, pp. 90-112 (1985)), and phase combination using SIGMAA (R. J. Reed, *Acta Crystallogr., A*42, pp. 140-149 (1986). The initial electron density map revealed the alpha-helices and beta-strands of the barrel cores, but the insertion domain (residues 110-224) in each subunit was poorly seen. The molecular model for IMPDH/XMP*/MPA was built into electron density maps using QUANTA (*Ouanta version* 4.1, Molecular Simulations Inc., Burlington Mass, 1995). Cycles of model building, positional refinement, and simulated annealing using XPLOR-3.1 (A. T. Brunger, *X-PLOR (Version* 3.1), Yale Univ., New Haven (1993)), and phase combination were done until the switch to phases calculated from the model could be made. The current model is consistent with the derived amino-acid sequence of Chinese hamster IMPDH, and the chemical nature of the heavy atom substitutions. The R-factor is 21.7% against X-ray data between 8 and 2.6 Å resolution, with root-mean-square deviation from ideal bond lengths and angles of 0.007 Å and 1.63° respectively. Definitions for Patterson synthesis, Fourier synthesis, R-factor, figure of merit, multiple isomorphous replacement, and other phrases in this section not previously defined can be found in T. L. Blundell and L. N. Johnson, *Protein Crystallography*, Academic Press (1976). Additional data collection and structure determination statistics is listed in Table 1.

EXAMPLE 4

IMP and MPA binding to IMPDH

The crystal structure reveals the interactions between XMP*, MPA and IMPDH that lead to tight-binding of these ligands. This structure reveals that a covalent bond has been formed between the C2 carbon of IMP and the sulfur atom of Cys 331 (FIGS. 5-7), to yield an oxidized IMP thioimidate intermediate (XMP*). Cys 331 has also been shown to form a covalent bond with [8–$^{14}$C] IMP when NAD is present, [J. A. Huete-Perez et al., *Biochemistry*, 34, pp. 13889-13894 (1995)] and with the purine ring of 6-Cl-IMP, which inactivates IMPDH [L. C. Antonino et al., *Biochemistry*, 33, pp. 1760-1765 (1994)]. Together these observations confirm an important role for this residue in catalysis.

Many additional interactions between XMP* and the enzyme are observed (FIGS. 5-7). The XMP* phosphate forms hydrogen bonds to the amide nitrogen atoms of Ser 329, Gly 366, Gly 387 Ser 388, and the side chain hydroxyl groups of Ser 329 and Tyr 411. Two water molecules near Gly 387 are also within hydrogen bonding distance of the phosphate moiety. The hypoxanthine ring makes three hydrogen bonds with IMPDH. The first is between the amide nitrogen of Met 414 and the N7 nitrogen, the second between the C6 carbonyl oxygen and the amide nitrogen of Gly 415, and the third is between the N1 nitrogen and the carbonyl oxygen of Gln 441. The hypoxanthine ring may also be stabilized by an interaction between the N3 nitrogen and a water molecule.

The ribose ring, which adopts a C3'-endo conformation, also contributes significantly to binding. The structure shows that the 02' and 03' hydroxyl groups form a hydrogen-bonding network to Ser 68 and Asp 364. The ribose 03' hydroxyl group accepts a proton from the Ser 68 side chain, and donates a proton to the carboxylate group of Asp 364. Van der Waals contacts between XMP*, Met 70, and Ile 330 are also observed.

Mycophenolic acid is a potent, uncompetitive, inhibitor of Chinese hamster IMPDH, and the structure reveals many interactions between MPA and IMPDH active site residues (FIGS. 5-7). One face of the bicyclic ring system is stacked on the XMP* hypoxanthine ring, while the other makes contact with the main-chain atoms of Ser 276. Together, the hexenoic acid tail, methyl substituent, and methoxy group of MPA make van der Waals contacts with the side chain atoms of Asp 274, Ser 275, Ser 276, Asn 303, Arg 322, and Gln 441. Six hydrogen bonds between the drug and IMPDH are also observed. These include hydrogen bonds between the 02 lactone oxygen and the amide nitrogen of Gly 326, and the Cl carbonyl oxygen and hydroxyl group of Thr 333. The hexenoic acid tail of MPA adopts a bent conformation, unlike the extended conformation seen in NMR studies [G. M. Makara et al., *J. Med. Chem.*, 39, pp. 1236-1242 (1996)] and the crystal structure of free MPA [W. Harrison et al., *J. Chem. Soc., Perkin Trans. II*, pp. 1542-1544 (1972)] allowing the carboxylate group to form hydrogen bonds with the amide nitrogen and side-chain hydroxyl groups of Ser 276 [F. H. Allen et al., *J. Chem. Info. Comp. Sci.* 31, p. 187 (1991)]. Additionally, the C7 phenolic oxygen forms hydrogen bonds to the side chain hydroxyl group of Thr 333 and the side chain amide of Gln 441.

Enzymatic Mechanism of IMPDH and Inhibition by Mycophenolic Acid

Aspects of the IMPDH catalyzed reaction can be addressed with the crystal structure. The IMPDH catalyzed oxidation of IMP results in transfer of hydrogen to the nicotinamide ring of NAD, forming NADH and XMP. Since direct transfer of the hydride is energetically unfavorable, two mechanisms involving activation of IMP at the inosine C2 position have been proposed [L. Hedstrom and C. C. Wang, *Biochemistry*, 29, 849-854 (1990)]. In the first mechanism, water, aided by an active site base to provide OH$^-$ attack, is added in an initial step at C2. Hydride transfer to NAD then occurs from the tetrahedral intermediate thus formed, producing the enol tautomer of XMP. In the second mechanism, nucleophilic attack on IMP occurs from an active site cysteine thiol. This is followed by hydride transfer to NAD, to yield a covalently bound thioimidate intermediate which is hydrolyzed to XMP in a subsequent step. The crystal structure, in combination with recent results that also demonstrate the formation of an IMPDH-substrate covalent adduct [J. A. Huete-Perez et al., *Biochemistry*, 34, pp. 13889-13894 (1995)]; J. 0. Link and K. Straub, *J. Am. Chem. Soc.*, 118, pp. 2091-2092 (1996)], strongly supports the second mechanism. The direct observation of the covalently bound thioimidate as the oxidized IMP intermediate confirms that enzyme-catalyzed oxidation of IMP occurs via attack of Cys 331 at the C2 position, and excludes a general base mechanism where water is added to the inosine ring in an early step.

Other aspects of the IMPDH catalyzed reaction can be addressed with the crystal structure. Although the MPA-inhibited complex does not contain NAD or NADH, a combination of structural and chemical evidence allows the nicotinamide ring to be modeled into the active site. The nicotinamide ring must be oriented to allow hydride transfer from the C2 position of IMP to the C4 position of NAD. Further, hydride transfer occurs more readily if the nicotinamide and hypoxanthine rings are nearly parallel [Y.-D. Wu et al., *J. Am. Chem. Soc.*, 117, pp. 4100-4108 (1995)], consistent with the favorable interactions provided by stacking between the nicotinamide ring and the bound substrate, and as observed in the structures of glutathione reductase (1GET) and NADH peroxidase (2NPX). It is also known that hydride transfer occurs on the beta face of NAD [D. Cooney et al., *Biochim. Biophys. Acta*, pp. 89-93 (1987)]. If no large conformational changes occur between the time NADH leaves and MPA binds, these structural considerations support an earlier prediction [L. Hedstrom and C. C. Wang, *Biochemistry*, 29, pp.849-854 (1990)] that during hydride transfer the nicotinamide of NAD occupies a position similar to the 6,5 ring system of MPA. In this orientation, the nicotinamide amide moiety would form hydrogen bonds with Gly-324, Thr 333, Gly-326 and Asn-303.

The structure of the inhibited complex also indicates that the phenolic hydroxyl group of MPA, which forms hydrogen bonds to Thr 333 and Gln 441, may be a replacement for the catalytic water that hydrolyzes the thioimidate intermediate to produce XMP. In the absence of MPA, a water molecule in the vicinity of the MPA hydroxyl would be stabilized by hydrogen bonds with Thr 333 and Gln 441, and would be properly positioned for nucleophilic attack at the C2 carbon of the thioimidate intermediate. Therefore, structural features of the bound orientation of MPA indicate it is both a nicotinamide ring and a catalytic water mimic. This hypothesis is consistent with a report that des-hydroxy-MPA is at least 1,000-fold less potent in a cellular assay than MPA [Y. S. Or et al., ACS Meeting, Chicago, Poster No. 112 (1995)]. It has also been shown that the presence of a hydroxyl group which is able to mimic a catalytic water molecule can lead to as much as a 10 kcal/mol improvement in binding [R. Wolfenden and W. M. Kati, *Acc. Chem. Res.*, 24, pp. 209-215 (1991)].

Similarity of IMPDH to Other Enzymes

Insight into the structure and mechanism of related enzymes is revealed in part by the IMPDH structure. Sequence database searching identified GMP reductase as the closest IMPDH homologue, with 63% similarity and 37% identity over a region of 150 amino acids that includes the active site cysteine as well as the phosphate binding site. The high level of sequence conservation around the active site suggests that GMP reductase has a similar fold and active site geometry to IMPDH. This is supported by the observation that GMP reductase, like IMPDH, binds substrate before co-factor [T. Spector et al., *J. Biol. Chem.*, 254, pp. 2308-2315 (1979)].

The structure of the IMPDH α/β barrel is similar to that of other flavin and nicotinamide dependent oxidoreductases, including glycolate oxidase, the NADPH-dependent aldo-keto reductases, and triethylamine dehydrogenase. The C-terminally sequence encoded phosphate binding site is also conserved, but in IMPDH this site is occupied by the IMP ribose phosphate rather than by the phosphates of the flavin or NAD(P) cofactors as seen in the other enzymes. This suggests that the NAD binding site in IMPDH is novel, and may help explain the specificity seen with inhibitors that bind in this site, such as MPA and thiazole adenine dinucleotide [H. J. Lee et al., *Cancer Res.*, 45, pp. 5512-5520 (1985); L. Hedstrom and C. C. Wang, *Biochemistry*, 29, pp. 849-854 (1990)]. In contrast, nucleoside analog inhibitors that are competitive with IMP, such as mizoribine and ribavirin phosphate, are more likely to recognize the consensus nucleotide phosphate binding site found in other enzymes, and are thus likely to be less specific than MPA.

FIGS. 2-7 further depict the structure of the IMPDH/XMP*/MPA complex. Thus, FIG. 2 depicts the fold and conformation of IMPDH in three dimensions as determined by x-ray crystallography. The structure is viewed from the C-terminal end of the β-strands that form the α/β barrel. The α-helices on the outside of the barrel are labeled α1 through α8. The portion of the sub-domain that is ordered is shown. Cys 331 is labeled and sits over one end of the barrel. An arrow marks the location of the flap (residues 400-450) that, together with the active site loop, helps form the active site pocket.

FIG. 3 depicts a topological diagram of the IMPDH fold. Secondary structure was assigned using the Kabsch and Sander algorithm, along with visual inspection [W. Kabsch and C. Sander, *Biopolymers*, 22, pp. 2577-2637 (1983)]. The β-strands and α-helices that form the α/β barrel core are labeled β1 through β8 and α1 through α8. The strands and helices that are not part of the barrel are labeled βA through βP and αA through αG. Cys 331 is located on the loop between strand β6 and helix αD. The sub-domain starts after helix α2 and ends at strand β3, and includes strands βF through βI and helices βB and αC. Parts of the structure that were not visible in electron density maps are marked "???". The flap (residues 400-450) between strand β8 and helix α8 includes strands βJ through βN and helix αE. Residue assignments for the strands and helices that form the α/β barrel are as follows: β1, residues 65-68; α1, 76-85; β2, 88-91; α2, 98-109; β3, 245-250; α3, 256-266; β4, 270-274; α4, 281-293; β5, 298-302; α5, 307-316; β6, 320-324; α6, 343-355; β7, 360-364; α7, 370-378; β8, 382-386; and α8, 456-469. Residue assignments for the remaining secondary structural elements are as follows: βA, residues 18-19; βB, 35-38; βC, 40-42; βD, 53-55; βE, 59-61; βF, 114-116; βG, 186-189; βH, 206-212; βI, 220-223; βJ, 400-402; βK, 406-409; βL, 411-413; βM, 438-440; βN, 443-448; βO, 489-492; βP, 509-513; αA, 21-23; αB, 194-200; αC, 225-232; αD, 333-337; αE, 416-420; αF, 476-484; and αG, 495-501.

FIG. 4 depicts a ribbon drawing of the IMPDH tetramer, viewed down the crystallographic four-fold axis [M. Carson, *J. Appl. Cryst.*, 24, pp. 958-961 (1991)]. Most of the tetramer-related contacts are made between adjacent barrels, and the surface area buried at each subunit interface is approximately 4000 Å$^2$. Bound potassium ions are seen adjacent to Cys 331 at each subunit interface. Several other contacts are noteworthy. Residues 41-43 form a beta-strand parallel with residues 279-281 in an adjacent subunit. Residues 502-503 make van der Waals contact with Cys 331 in an adjacent subunit. Residues 507-510 form an anti-parallel beta-strand with residues 444-447 of the active site flap of an adjacent subunit, and these two strands can be seen above the potassium ions.

FIG. 5 depicts a stereo view of the IMPDH active site electron density [M. Carson, *J. Appl. Cryst.*, 24, pp. 958-961 (1991)]. Refined coordinates of the XMP* thioimidate intermediate and MPA are shown in thick bonds superimposed on the SigmaA-weighted [R. J. Read, *Acta Cryst.*, A42, pp. 140-149 (1986)] $2F_{obs}-F_{calc}$ electron density map contoured at 2.0σ. The hypoxanthine ring makes a covalent bond to the sulfur of Cys 331. Some of the side chains that interact with substrate or inhibitor to form the active site pocket are shown using thin bonds. There are only six differences in amino acid sequence between Chinese hamster and human type II IMPDH (R173C, N215D, L265Q, M290I, E292D, and C327S). These are all at least 15 Å away from the active site, except C327S, which is a conservative mutation and points away from the active site pocket. Thus, these interactions should also apply to the human type II form of IMPDH.

FIG. 6 depicts a schematic representation of the XMP*-IMPDH interactions. There is a covalent bond between the sulfur atom of Cys 331 and the C2 carbon of the hypoxanthine ring.

FIG. 7 depicts a schematic representation of the MPA-IMPDH interactions. All proximal water molecules observed in electron density difference maps are labeled "H$_2$O". All distances pertain to non-hydrogen atoms.

EXAMPLE 5

Mutational and Kinetic Analysis of the Active Site

A series of mutants was generated to determine the roles of human type II IMPDH active site residues in catalysis and inhibitor binding (FIG. 8).

Knowledge of the three-dimensional structure which we have determined permits rationalization of the observed phenotype. Mutation of either Cys 331 or Asp 364 to Ala effectively abolished IMPDH activity relative to wild type. The crystal structure shows that these two residues are in direct contact with XMP*. Cys 331 forms a covalent bond to XMP*, confirming its role in catalysis, while the side-chain of Asp 364 forms a hydrogen bond to the ribose moiety of XMP*. Changing Ser 329 to Ala reduces enzyme activity to 13% of the wild type. This side chain forms a hydrogen bond to the phosphate of XMP*. Residues which make direct contact with MPA also were modified. Substituting Thr 333 with Ile, and Gln 441 with Ala, increased the $K_i$ app. of MPA 300-fold and 25-fold respectively. The Thr 333 to Ile mutation is of particular interest, since it has been observed in murine blastoma cells selected for 10,000-fold increased resistance to MPA [S. D. Hodges et al., *J. Biol. Chem.* 264, p. 18137 (1989); T. Lightfoot and F. F. Synder, *Biochem. Biophys. Acta*, 1217, p. 156 (1994)]. The crystal structure shows a hydrogen bond network between Thr 333, Gln 441 and MPA, with the phenolic oxygen in particularly good hydrogen bonding distance and geometry with the side chain hydroxyl of Thr 333 (FIGS. 5-7). The carboxylate group of the hexenoic acid tail of MPA forms two hydrogen bonds with Ser 276. Mutating this residue to Ala disrupts this interaction and leads to a 7-fold increase in $K_i$ app. In contrast, mutations of other active site residues, such as Ser 275, Ser 327 and Gln 368, have little effect on catalytic activity or drug inhibition. The structure indicates these residues do not contact substrate or inhibitor directly.

Kinetic experiments with human IMPDH have revealed that, although IMP can bind to the enzyme in the absence of potassium, this ion is required for the reaction to proceed [B. Xiang et al., *J. Biol. Chem.*, 271, pp. 1435-1440 (1996)]. The crystal structure of this invention explains this observation. We observed a large peak in difference electron density maps that was surrounded by a water molecule and five main-chain carbonyl oxygens, including that of Cys 331 (data not shown). The average distance of the peak center to each of the surrounding ligands was 3.1 Å, and the peak was hexagonally coordinated. The nature and positioning of the ligands suggested a potassium binding site. Thus, potassium may organize protein conformation around the active site, and could help position Cys 331 for catalysis. In addition, three of the carbonyl oxygen ligands reside on residues near the C-terminus of an adjacent IMPDH subunit, suggesting that potassium may also stabilize the tetramer form of IMPDH (FIG. 4).

FIG. 8 depicts the specific activity of IMPDH mutants for IMP substrate. Mutations were made in the human type II IMPDH cDNA cloned into a pT7 blue vector (Novagen) by a four primer PCR method using Pfu DNA polymerase (Stratagen) [A. Rashchian et al., *PCR Methods and Applications*, 2, pp. 124-130 (1992)]. PCR products were digested with appropriate restriction enzymes and cloned into unique sites within IMPDH cDNA. Mutants were sequenced in the area containing PCR products and the surrounding restriction sites. The full length IMPDH cDNA carrying the confirmed mutation was then subcloned into a pSPC27 vector in the IMPDH-deficient *E. coli* strain H712 [H. J. J. Nijkamp and P. G. Haan, *Biochim. Biophys. Acta* 145, pp. 31-40 (1967)]. Cultures (500 ml) were grown at 37° C. for 14 to 16 hours after IPTG induction, and typically yielded 2 grams of cell paste. Cells were resuspended in 50 mM Tris, pH 8.0, 150 mM KCl, 3 mM EDTA, 2 mM DTT buffer containing 10% urea, and then lysed by addition of lysozyme (1 mg/g cell paste) and sonication. IMPDH wild-type and mutant proteins were precipitated from crude lysates by 25% w/v ammonium sulfate. Up to 150 mgs of at least 65%-70% pure IMPDH was obtained by this single purification step. The partially purified IMPDH was resuspended in 50 mM Tris, pH 8.0, 100 mM KCl, 3 mM EDTA, 2 mM DTT, 10% glycerol buffer and used for kinetic analysis. Second order rate constants (k cat/Km, $M^{-1}sec^{-1}$) were calculated from IMP titration data at saturating (400 mM). NAD concentration obtained by monitoring the rate of NADH production at 340 nm at 37° C. FIG. 8 also presents the inhibition of various mutant IMPDH proteins by MPA. $K_i$ app. values for MPA were obtained from the rate vs. inhibitor data of IMPDH mutants at saturating IMP and NAD concentrations. The data were fit to the equation for tight-binding uncompetitive inhibition using the program KineTic 3.0 [D. W. Marquardt, *J. Soc. Ind. Appl. Math.*, 11, pp. 431-441 (1963)].

EXAMPLE 6

Use of IMPDH/XMP*/MPA Coordinates for Inhibitor Design

The coordinates in FIG. 1 are used to design compounds, including inhibitory compounds, that associate with IMPDH or homologues of IMPDH. This process may be aided by using a machine-readable data storage medium encoded with a set of machine-executable instructions, wherein the recorded instructions are capable of displaying a three-dimensional representation of the IMPDH/XMP*/MPA complex or a portion thereof. The graphical representation is used according to the methods described herein to design compounds, including inhibitory compounds, that bind to IMPDH. Such compounds may associate with IMPDH at the active site, in the XMP* binding site, in the MPA binding site, or in parts or all of both sites.

Compounds which Bind at the MPA Binding Site

The process outlined above is used to design a compound that inhibits IMPDH by associating directly with the MPA binding site, and is expected to bind in the MPA binding site. Such compounds will have a surrogate for the bicyclic ring portion of MPA and additional functionality that imparts affinity for IMPDH. The compound comprises a substantially hydrophobic core capable of making van der Waals contact with the bound XMP* intermediate and one or more of the following residues on IMPDH: Asp 274, Ser 275, Ser 276, Gln 277, Asn 303, Arg 322, Gly 324, Met 325, Gly 326, Thr 333, Met 414, Gly 415 and Gln 441. Substituted onto this hydrophobic core is one or more atoms capable of forming one or more hydrogen bonds with residues such as Asp 274, Thr 333, Gln 441, Gly 326, or nearby residues on IMPDH. These hydrogen bonding atoms are connected by linkers to the substantially hydrophobic core. These linkers may form additional van der Waals interactions with residues His 93, Gly 251, Thr 252, His 253, Asp 256, Arg 259, Leu 273, Phe 282, and Gln 283, or nearby residues. In the lowest-energy bound conformation, this molecule will have a strain energy of 10 kcal/mol or less. Further, this molecule will contain fewer than three secondary amide bonds and will have a molecular weight of less than 1000.

EXAMPLE 7

IMPDH Activity Inhibition Assay

IMP dehydrogenase activity was assayed following an adaptation of the method first reported [B. Magasanik et al., *J. Biol. Chem.* 226, p. 339 (1957)]. Enzyme activity was measured spectrophotometrically, by monitoring the increase in absorbance at 340 nm due to the formation of NADH (e340 is 6220 $M^{-1}$ $cm^{-1}$). The reaction mixture contained 0.1 M Tris pH 8.0, 0.1 M KCl, 3 mM EDTA, 2 mM DTT, 0.1 M IMP and enzyme (IMPDH human type II) at a concentration of 15 to 50 nM. This solution is incubated at 37° C. for 10 minutes. The reaction is started by adding NAD to a final concentration of 0.1M and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 µl.

For the analysis of inhibitors, the compound in question is dissolved in DMSO to a final concentration of 20 mM and added to the initial assay mixture for preincubation with the enzyme at a final volume of 2-5% (v/v). The reaction is started by the addition of NAD, and the initial rates measured as above. $K_i$ determinations are made by measuring the initial velocities in the presence of varying amounts of inhibitor and fitting the data using the tight-binding equations of Henderson [P. J. F. Henderson, *Biochem. J.*, 127, p. 321 (1972)].

EXAMPLE 8

Immunosuppression (Mitogenesis)

Assays Cell Source and Culture

Fresh peripheral blood lymphocytes (PBLs) from Leuko-Pak cells or whole blood from random normal blood donors (tested HIV-negative and hepatitis negative) are isolated and separated by density centrifugation over Histopaque 1077 (Sigma Chemical Co., St. Louis, Mo.). The murine CTLL cytotoxic T-cell line and the human Jurkat T-cell line are available from ATCC (CTLL-2 ATCC TIB214, JURKAT CLONE E6-1 ATCC TIB152). The human allogeneic B-cell lines used for activation of the fresh PBLs are EBV-transformed lymphocytes from normal healthy adult donors with two completely different HLA haplotypes. All cell lines are routinely tested for the presence of *Mycoplasma* contamination using the Gibco Mycotect test kit and found to be *Mycoplasma*-free. Culture medium consisted of RPMI 1640 (Gibco, Grand Island, N.Y.) containing penicillin (50 U/ml) and streptomycin (50 µg/ml), L-glutamine 2 mM, BME ($5\times10^{-5}$), 10% heat-inactivated FCS and 10 mM HEPES.

Compound Solutions and Titrations

All chemical stocks are dissolved in DMSO. Titrations of compounds are made into the medium the individual assay are carried out in, i.e., complete RPMI or HB 104 for final diluted concentrations, using multip le three-fold dilutions from 1 µM or 10 µM stock solutions.

Mitogenesis Assays ("PMA" and "OKT3")

The inhibitory effect of test compounds on the proliferation of human PBLs in response to mitogens [W. K. Waithe et al., *Handbook of Experimental Immunology*. 3d Ed., Blackwell Scientific Publications, Oxford (1978); B.B. Mishell et al., *Selected Methods in Cellular Immunology*, W. H. Freeman and Co., San Francisco, Calif. (1980)] are assessed by stimulation of $5\times10^4$ cells with OKT3 ($10^{-4}$ dilution final) or PMA (10 ng/ml) plus ionomycin (250 ng/ml) in the presence or absence of different concentrations of test compounds and control drugs (CsA, FK506, rapamycin) in final volume of 200 µl per well in 96 well round bottomed plates. After 48 h incubation (37° C., 5% $CO_2$), cells are pulsed with 1 µCi of $^3$H-Leucine, harvested 24 h later with a Tom Tek cell harvester, and counted in LKB β-scintillation counter. Results (cpm) are compared with controls with medium alone, and concentrations causing 50% reduction in counts ($IC_{50}$) are calculated.

While we have described a number of embodiments of this invention, it is apparent that our basic examples may be altered to provide other embodiments which utilize the products and processes of this invention. Therefore, it will be appreciated that the scope of this invention is to be defined by the appended claims rather than by the specific embodiments which have been represented by way of example.

We claim:

1. A crystal comprising Chinese hamster type II inosine monophosphate dehydrogenase (IMPDH) in complex with an oxidized inosine monophosphate thioimidate intermediate (XMP*) and mycophenolic acid (MPA), wherein said crystal is characterized with space group P4 and unit cell dimensions of a=b=110.6 Å, c=111.0 Å, and angles $\alpha=\beta=\gamma=90°$.

2. A method for preparing a Chinese hamster type II inosine monophosphate dehydrogenase/oxidized inosine monophosphate thioimidate intermediate/mycophenolic acid (IMPDH/XMP*/MPA) crystal comprising the steps of:
   a. preparing a solution of MPA, 1-methyl-2-pyrrolidinone (MeP), and purified Chinese hamster type II apo-IMPDH;
   b. adding inosine monophosphate (IMP) and nicotinamide adenine dinucleotide (NAD) to the solution of step (a), wherein an IMPDH/XMP*/MPA complex is formed;
   c. concentrating and exchanging the solution of step (b) into buffer containing MPA until no IMP, NAD or NADH is detectable; and
   d. crystallizing said IMPDH/XMP*/MPA complex in the presence of MeP.

* * * * *